(12) United States Patent
Uehara et al.

(10) Patent No.: US 10,745,700 B2
(45) Date of Patent: Aug. 18, 2020

(54) NUCLEIC ACID CONJUGATE

(71) Applicant: Kyowa Kirin Co., Ltd., Tokyo (JP)

(72) Inventors: Keiji Uehara, Tokyo (JP); Yasuhiro Suzuki, Tokyo (JP); Hiroto Iwai, Tokyo (JP); Masakazu Homma, Tokyo (JP); Yuichi Fukuda, Tokyo (JP); Tatsuto Kiuchi, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 21 days.

(21) Appl. No.: 16/073,112

(22) PCT Filed: Jan. 30, 2017

(86) PCT No.: PCT/JP2017/003249
§ 371 (c)(1),
(2) Date: Jul. 26, 2018

(87) PCT Pub. No.: WO2017/131236
PCT Pub. Date: Aug. 3, 2017

(65) Prior Publication Data
US 2019/0055558 A1    Feb. 21, 2019

(30) Foreign Application Priority Data

Jan. 29, 2016 (JP) ................. 2016-016707

(51) Int. Cl.
| | | |
|---|---|---|
| *C12N 15/113* | (2010.01) | |
| *A61K 31/713* | (2006.01) | |
| *C07H 21/00* | (2006.01) | |
| *A61K 31/7088* | (2006.01) | |
| *C07C 237/10* | (2006.01) | |
| *C07C 271/16* | (2006.01) | |
| *C07C 247/04* | (2006.01) | |

(52) U.S. Cl.
CPC ........ *C12N 15/113* (2013.01); *A61K 31/7088* (2013.01); *A61K 31/713* (2013.01); *C07C 237/10* (2013.01); *C07C 247/04* (2013.01); *C07C 271/16* (2013.01); *C07H 21/00* (2013.01); *C12N 2310/14* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | |
|---|---|---|
| 8,106,022 B2 | 1/2012 | Manoharan et al. |
| 8,450,467 B2 | 5/2013 | Manoharan et al. |
| 8,828,956 B2 | 9/2014 | Manoharan et al. |
| 9,127,276 B2 | 9/2015 | Prakash et al. |
| 9,145,558 B2 | 9/2015 | Prakash et al. |
| 9,163,239 B2 | 10/2015 | Prakash et al. |
| 9,181,549 B2 | 11/2015 | Prakash et al. |
| 9,181,550 B2 | 11/2015 | Prakash et al. |
| 9,352,048 B2 | 5/2016 | Manoharan et al. |
| 9,370,581 B2 | 6/2016 | Manoharan et al. |
| 9,370,582 B2 | 6/2016 | Manoharan et al. |
| 9,399,775 B2 | 7/2016 | Rajeev et al. |
| 9,714,421 B2 | 7/2017 | Prakash et al. |
| 9,814,777 B2 | 11/2017 | Manoharan et al. |
| 9,867,882 B2 | 1/2018 | Manoharan et al. |
| 9,932,580 B2 | 4/2018 | Prakash et al. |
| 9,932,581 B2 | 4/2018 | Prakash et al. |
| 9,957,504 B2 | 5/2018 | Prakash et al. |
| 2009/0239814 A1 | 9/2009 | Manoharan et al. |
| 2009/0247608 A1 | 10/2009 | Manoharan et al. |
| 2012/0136042 A1 | 5/2012 | Manoharan et al. |
| 2012/0157509 A1 | 6/2012 | Hadwiger et al. |
| 2013/0178512 A1 | 7/2013 | Manoharan et al. |
| 2013/0210887 A1 | 8/2013 | Cena Callejo et al. |
| 2014/0179761 A1 | 6/2014 | Manoharan et al. |
| 2014/0315835 A1 | 10/2014 | Rajeev et al. |
| 2014/0343123 A1 | 11/2014 | Prakash et al. |
| 2015/0011615 A1 | 1/2015 | Manoharan et al. |
| 2015/0119444 A1 | 4/2015 | Manoharan et al. |

(Continued)

FOREIGN PATENT DOCUMENTS

| | | |
|---|---|---|
| JP | 2013-521328 | 6/2013 |
| JP | 2014-504295 | 2/2014 |

(Continued)

OTHER PUBLICATIONS

Nair J.K. et al., "Multivalent N-Acetylgalactosamine-Conjugated siRNA Localizes in Hepatocytes and Elicits Robust RNAi-Mediated Gene Silencing", Journal of American Chemical Society, Dec. 2014, vol. 136, pp. 16958-16961.

(Continued)

*Primary Examiner* — Tracy Vivlemore

(74) *Attorney, Agent, or Firm* — Wenderoth, Lind & Ponack L.L.P.

(57) ABSTRACT

The present invention relates to a nucleic acid conjugate represented by the following formula 1:

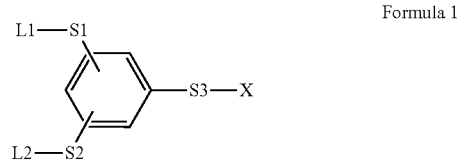

Formula 1 wherein X is an oligonucleotide, L1 and L2 are each independently sugar ligand, and S1, S2 and S3 are each independently a linker.

8 Claims, No Drawings

Specification includes a Sequence Listing.

(56) References Cited

U.S. PATENT DOCUMENTS

| | | |
|---|---|---|
| 2015/0119445 A1 | 4/2015 | Manoharan et al. |
| 2015/0126718 A1 | 5/2015 | Prakash et al. |
| 2015/0126719 A1 | 5/2015 | Prakash et al. |
| 2015/0126720 A1 | 5/2015 | Prakash et al. |
| 2015/0176007 A1 | 6/2015 | Prakash et al. |
| 2016/0017323 A1 | 1/2016 | Prakash et al. |
| 2016/0051691 A1 | 2/2016 | Manoharan et al. |
| 2016/0076030 A1 | 3/2016 | Prakash et al. |
| 2016/0076032 A1 | 3/2016 | Prakash et al. |
| 2016/0090595 A1 | 3/2016 | Prakash et al. |
| 2016/0090596 A1 | 3/2016 | Prakash et al. |
| 2016/0355817 A1 | 12/2016 | Rajeev et al. |
| 2016/0375137 A9 | 12/2016 | Manoharan et al. |
| 2018/0002693 A1 | 1/2018 | Prakash et al. |
| 2018/0044676 A1 | 2/2018 | Prakash et al. |
| 2018/0273952 A1 | 9/2018 | Prakash et al. |
| 2018/0273953 A1 | 9/2018 | Prakash et al. |
| 2018/0326070 A1 | 11/2018 | Manoharan et al. |
| 2019/0055554 A1 | 2/2019 | Prakash et al. |
| 2019/0099493 A1 | 4/2019 | Manoharan et al. |
| 2019/0184018 A1 | 6/2019 | Manoharan et al. |
| 2019/0367914 A1 | 12/2019 | Prakash et al. |

FOREIGN PATENT DOCUMENTS

| | | |
|---|---|---|
| WO | 2009/073809 | 6/2009 |
| WO | 2013/075035 | 5/2013 |
| WO | 2013/165816 | 11/2013 |
| WO | 2013/166121 | 11/2013 |
| WO | 2014/179620 | 11/2014 |
| WO | 2014/179626 | 11/2014 |
| WO | 2014/179627 | 11/2014 |
| WO | 2014/179629 | 11/2014 |
| WO | 2015/042447 | 3/2015 |
| WO | 2015/105083 | 7/2015 |

OTHER PUBLICATIONS

Prakash T.P. et al., "Comprehensive Structure-Activity Relationship of Triantennary N-Acetylgalactosamine Conjugated Antisense Oligonucleotides for Targeted Delivery to Hepatocytes", Journal of Medicinal Chemistry, Feb. 2016, vol. 59, pp. 2718-2733.

NUCLEIC ACID CONJUGATE

TECHNICAL FIELD

The present invention relates to a nucleic acid conjugate and a pharmaceutical composition comprising the nucleic acid conjugate, etc.

BACKGROUND ART

For example, aptamers, antisenses, decoy nucleic acids, ribozymes, siRNA, miRNA and anti-miRNA are known as nucleic acid medicines. Such nucleic acid medicines are expected to be clinically applied to various previously difficult-to-treat diseases, because of their high versatility that permits control of every gene in cells.

Also, the nucleic acid medicines are expected as next-generation medicines following antibody or low-molecular medicines, because of their high target selectivity and activity in cells.

However, a problem of the nucleic acid medicines is difficult delivery to a target tissue.

Use of a conjugate of a targeting compound and a nucleic acid (nucleic acid conjugate) has been reported as one of the methods for effectively delivering the nucleic acid medicines in vivo. Examples of the targeting compound include ligands capable of binding to extracellularly expressed receptors. Among others, there are a plurality of reports on a nucleic acid conjugate that utilizes N-acetyl-D-galactosamine (GalNAc) or the like as a ligand capable of binding to an asialoglycoprotein receptor (ASGPR) very highly expressed on liver cells. In recent years, nucleic acid conjugates containing such ligands bound to siRNAs have been reported to be efficiently delivered to liver cells (Non Patent Literature 1).

Patent Literatures 1 and 2 disclose, for example, the following nucleic acid conjugate as a conjugate of a targeting compound and an oligonucleotide:

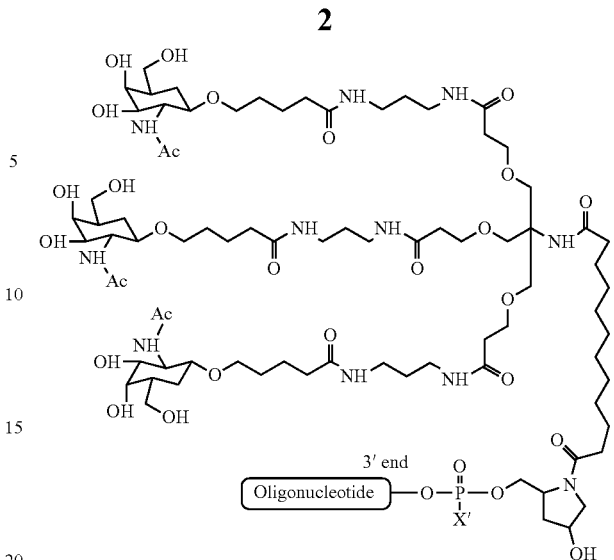

wherein Ac represents an acetyl group; hereinafter, the same holds true for the present specification.

Patent Literature 3 discloses a nucleic acid conjugate having the following structure having a sugar ligand-tether unit similar to that of Patent Literatures 1 and 2:

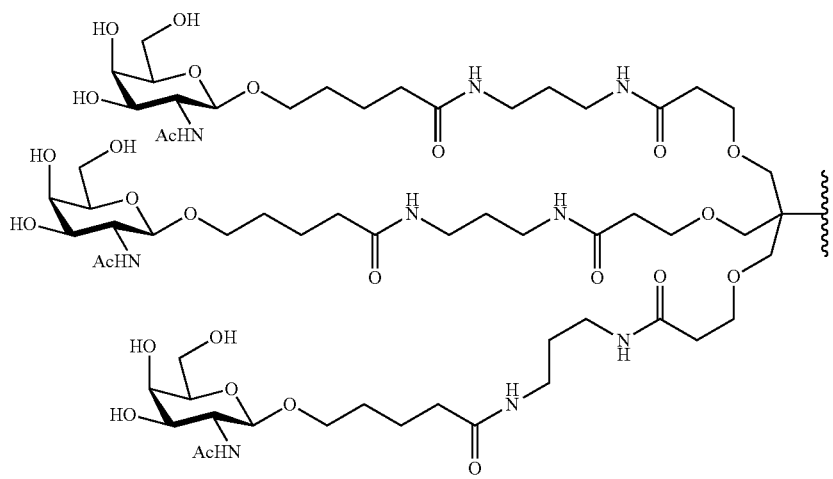

Patent Literature 4 discloses a nucleic acid conjugate having the following structure as a sugar ligand-tether unit:

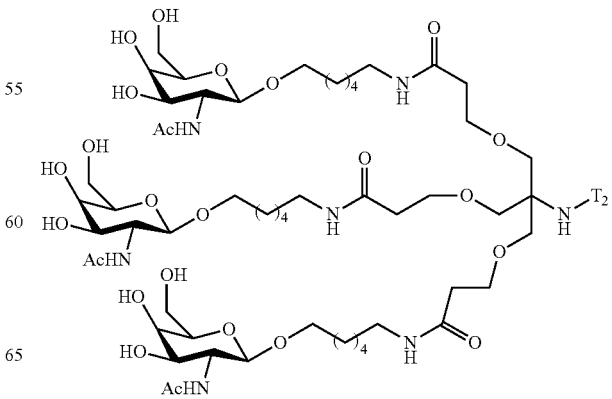

CITATION LIST

Patent Literature

Patent Literature 1: International Publication No. WO 2009/073809
Patent Literature 2: International Publication No. WO 2013/075035
Patent Literature 3: International Publication No. WO 2015/105083
Patent Literature 4: International Publication No. WO 2014/179620

Non Patent Literature

Non Patent Literature 1: Journal of American Chemical Society, 2014, Vol. 136, p. 16958-16961

SUMMARY OF INVENTION

Technical Problem

An object of the present invention is to provide a novel nucleic acid conjugate.

Solution to Problem

The present invention relates to the following (1) to (22):
(1) A nucleic acid conjugate represented by the following formula 1:

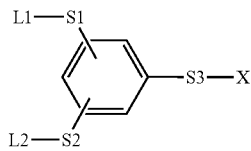

Formula 1 wherein
 X is an oligonucleotide,
 L1 and L2 are each independently a sugar ligand, and
 S1, S2 and S3 are each independently a linker.
(2) The nucleic acid conjugate according to (1), wherein the nucleic acid conjugate has a structure represented by the following formula 2:

Formula 2:

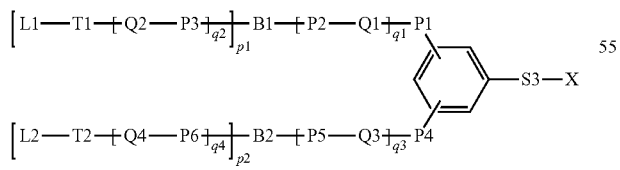

wherein
 X, L1, L2 and S3 are each as defined above,
 P1, P2, P3, P4, P5 and P6, and T1 and T2 are each independently absent, or —CO—, —NH—, —O—, —S—, —O—CO—, —S—CO—, —NH—CO—, —CO—O—, —CO—S— or —CO—NH—, Q1, Q2, Q3 and Q4 are each independently absent, or substituted or unsubstituted alkylene having 1 to 12 carbon atoms or —(CH$_2$CH$_2$O)$_n$—CH$_2$CH$_2$— wherein n is an integer of 0 to 99,
B1 and B2 are each independently a bond, or any structure represented by the following formula 2-1, wherein each of the terminal dots in each structure is a binding site to P2 or P3, or P5 or P6, and m1, m2, m3 and m4 are each independently an integer of 0 to 10:

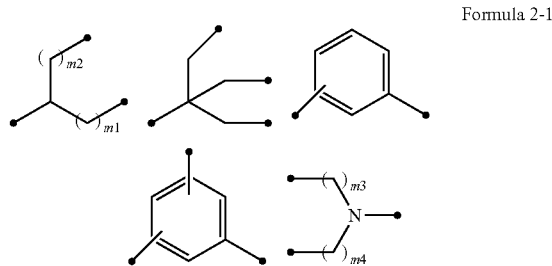

Formula 2-1 p1 and p2 are each independently an integer of 1, 2 or 3, and
q1, q2, q3 and q4 are each independently an integer of 0 to 10,
provided that when each of p1 and p2 is an integer of 2 or 3, each P3 and P6, Q2 and Q4, T1 and T2 or L1 and L2 are the same or different.
(3) The nucleic acid conjugate according to (2), wherein P1 and P4 are each independently —CO—NH—, —NH—CO— or —O—.
(4) The nucleic acid conjugate according to (2) or (3), wherein —(P2-Q1)$_{q1}$- and —(P5-Q3)$_{q3}$- are each independently absent, or any structure represented by the following formulas 3-1 to 3-3:

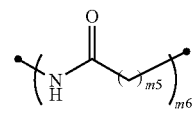

Formula 3-1

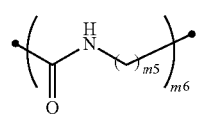

Formula 3-2

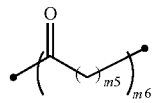

Formula 3-3 wherein
 m5 and m6 are each independently an integer of 0 to 10, and each of the terminal dots in the structures of formulas 3-1 to 3-3 is a binding site to B1 or B2, or P1 or P4.
(5) The nucleic acid conjugate according to any one of (2) to (4), wherein the nucleic acid conjugate has any structure represented by the following formulas 4-1 to 4-9:

Formula 4-1:
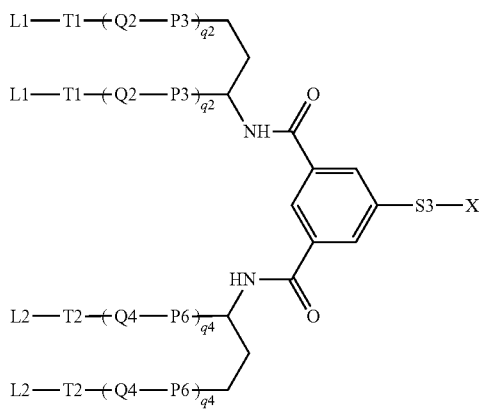
Formula 4-2:
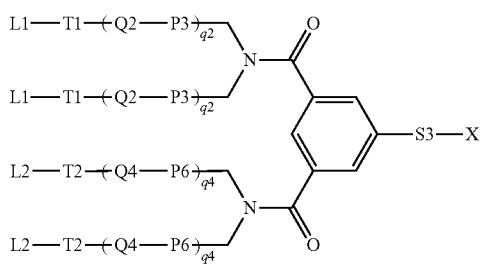
Formula 4-3:
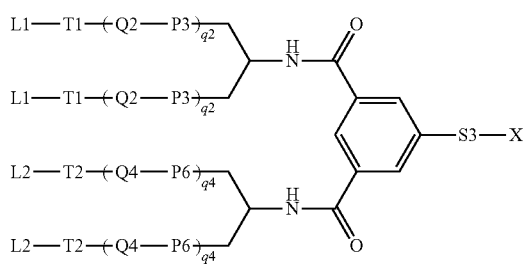
Formula 4-4:
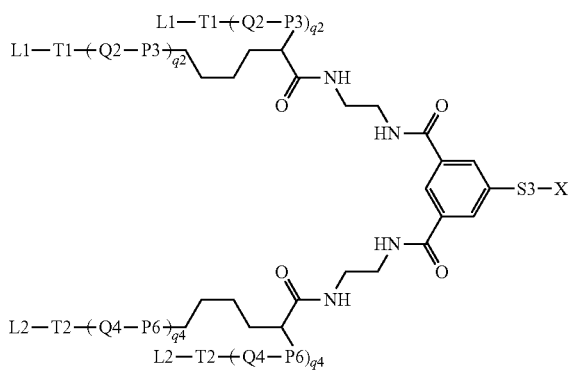
Formula 4-5:
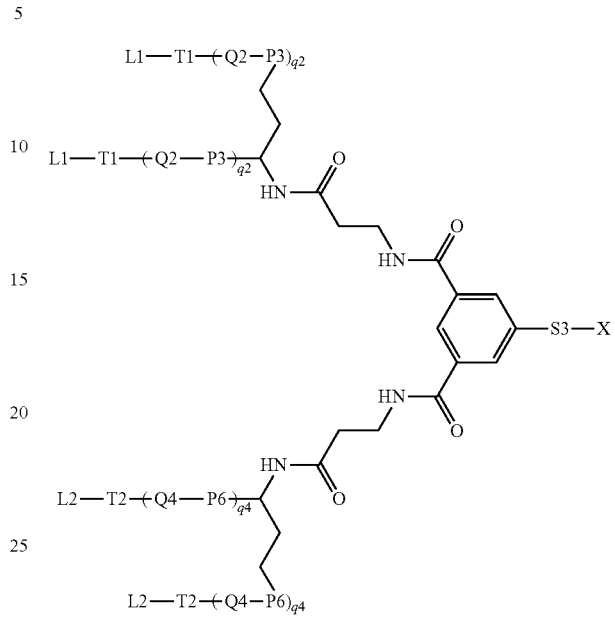
Formula 4-6:
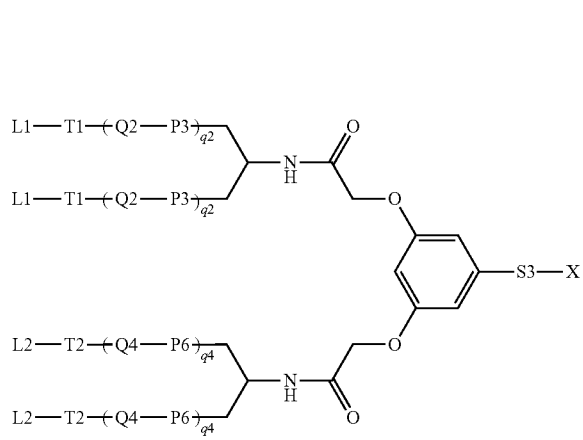
Formula 4-7:
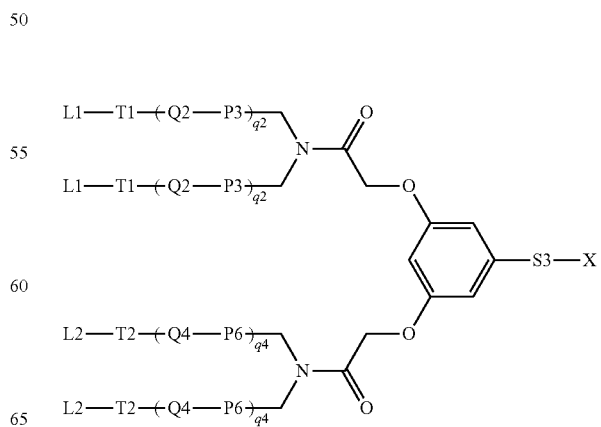

Formula 4-8:

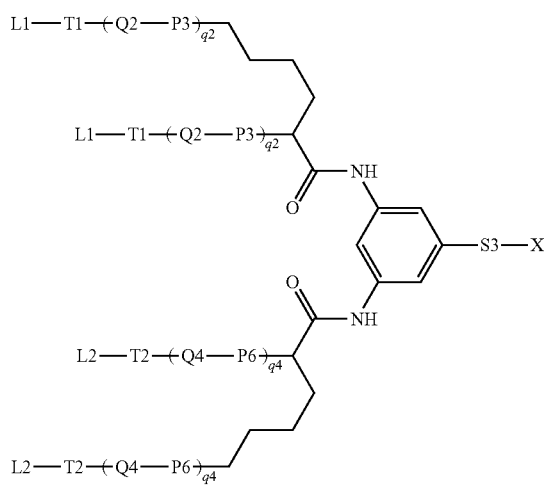

Formula 4-9:

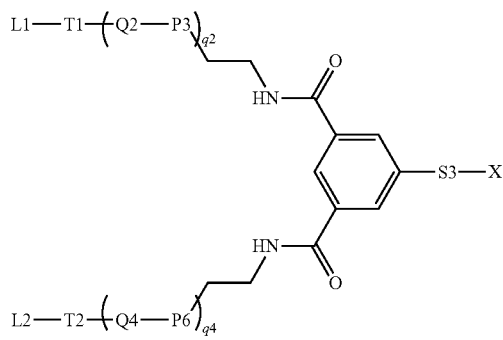

wherein
X, L1, L2, S3, P3, P6, T1, T2, Q2, Q4, q2 and q4 are each as defined above.

(6) The nucleic acid conjugate according to (1), wherein the nucleic acid conjugate has a structure represented by the following formula 5:

Formula 5

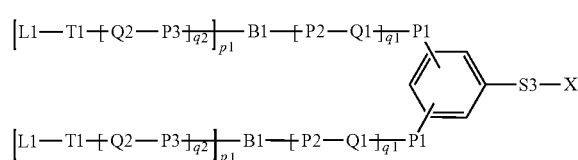

wherein
X, S3, P1, P2, P3, Q1, Q2, B1, T1, L1, p1, q1 and q2 are each as defined above.

(7) The nucleic acid conjugate according to (6), wherein P1 is —CO—NH—, —NH—CO— or —O—.

(8) The nucleic acid conjugate according to (6) or (7), wherein the nucleic acid conjugate has any structure represented by the following formulas 6-1 to 6-9:

Formula 6-1:

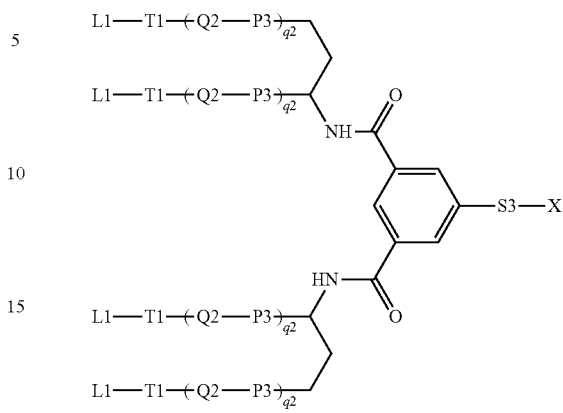

Formula 6-2:

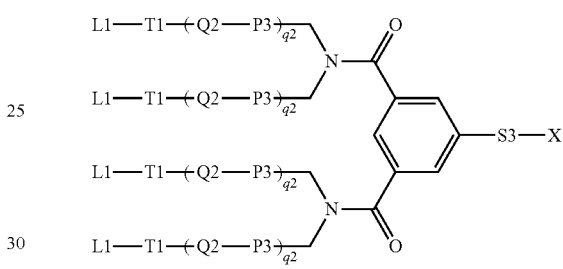

Formula 6-3:

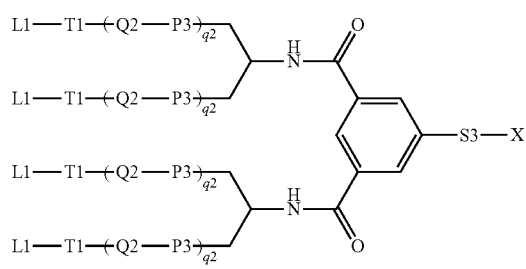

Formula 6-4:

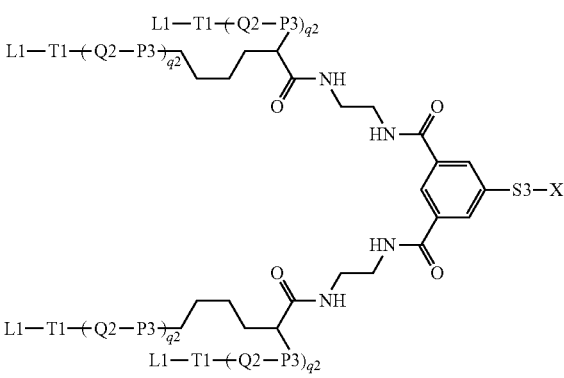

Formula 6-5:
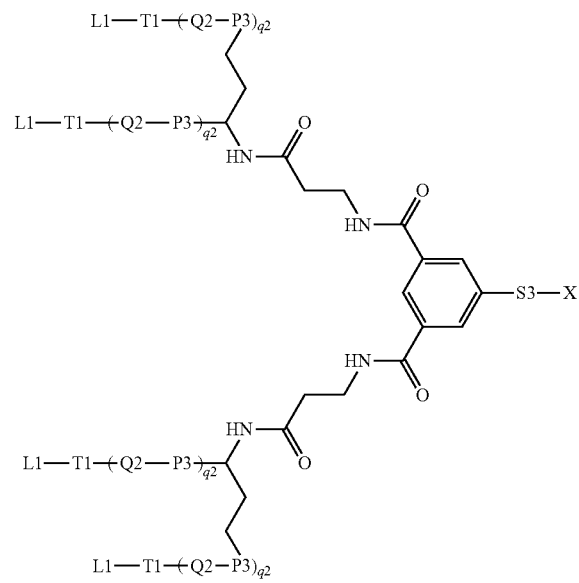
Formula 6-6:
Formula 6-7:
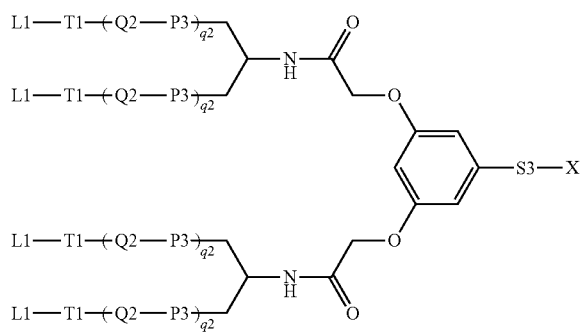
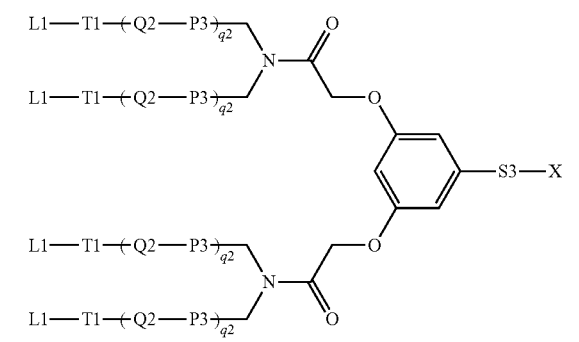
Formula 6-8:
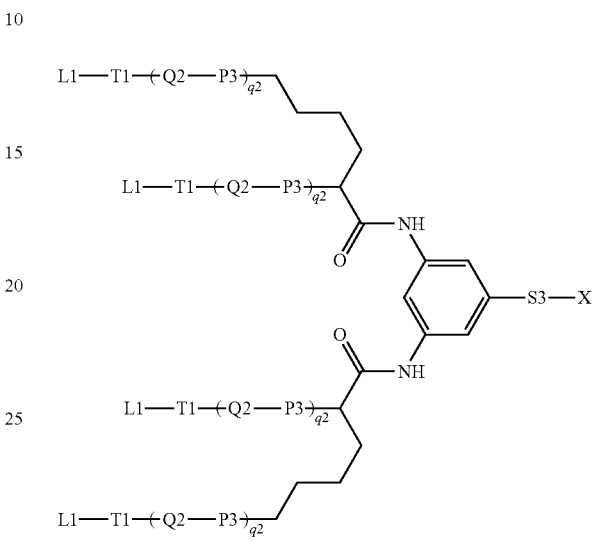
Formula 6-9:
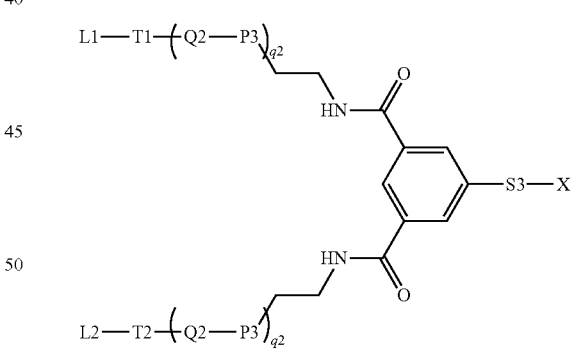
wherein
X, S3, P3, Q2, T1, L1 and q2 are each as defined above.
(9) The nucleic acid conjugate according to any of (2) to (8), wherein the nucleic acid conjugate has any structure represented by the following formulas 7-1 to 7-9:

Formula 7-1
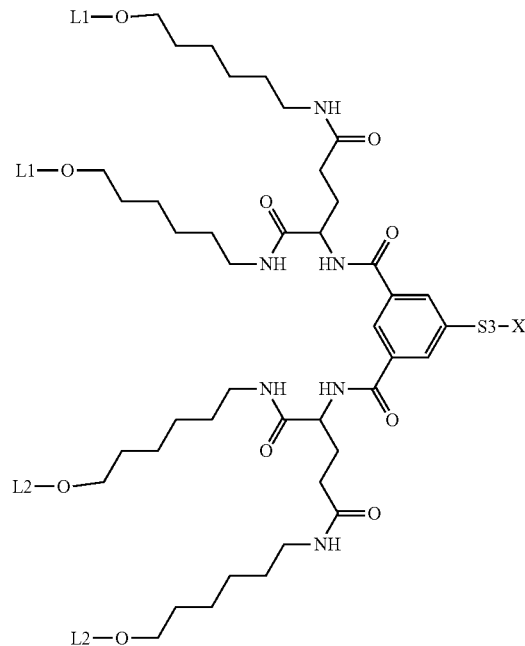
Formula 7-2
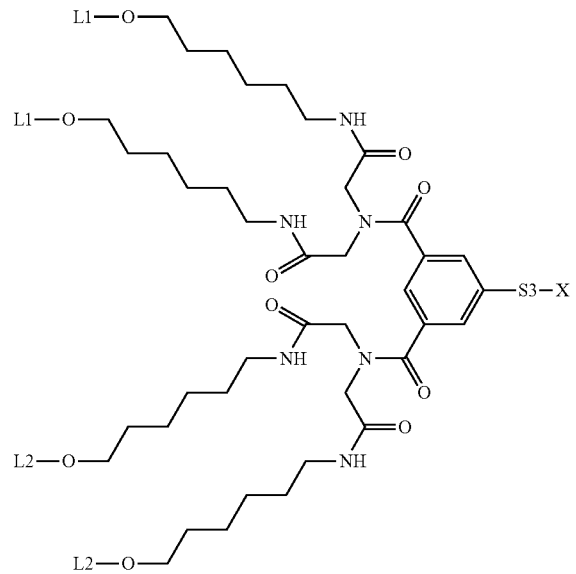
Formula 7-3
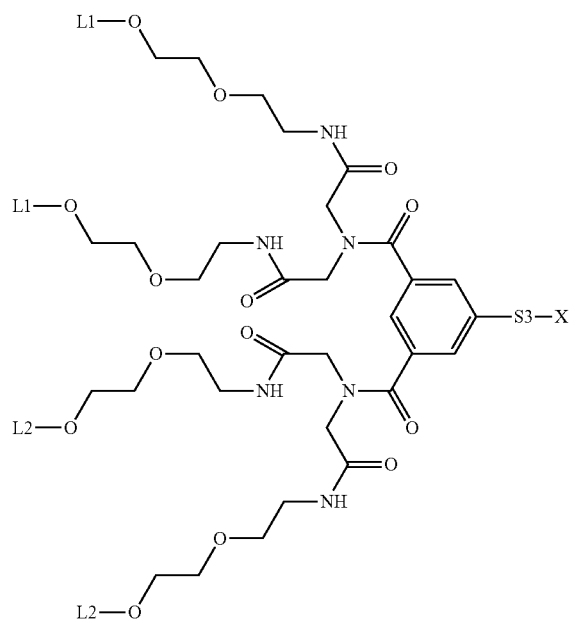
Formula 7-4
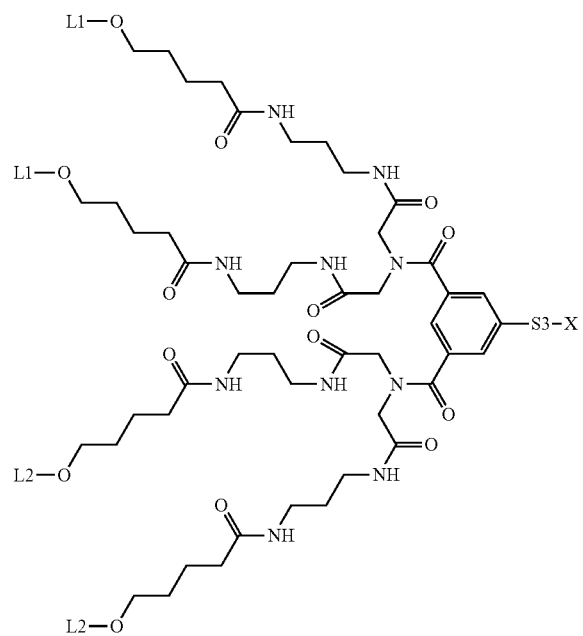

Formula 7-5
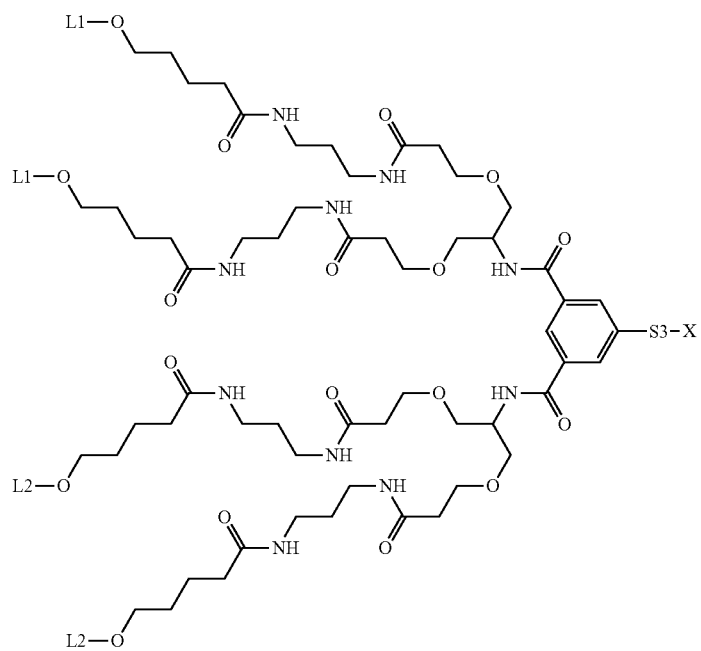
Formula 7-6
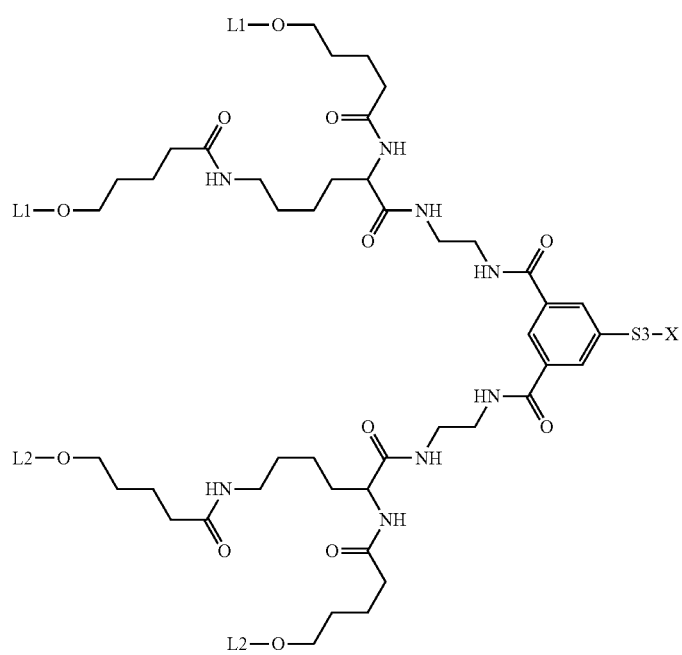

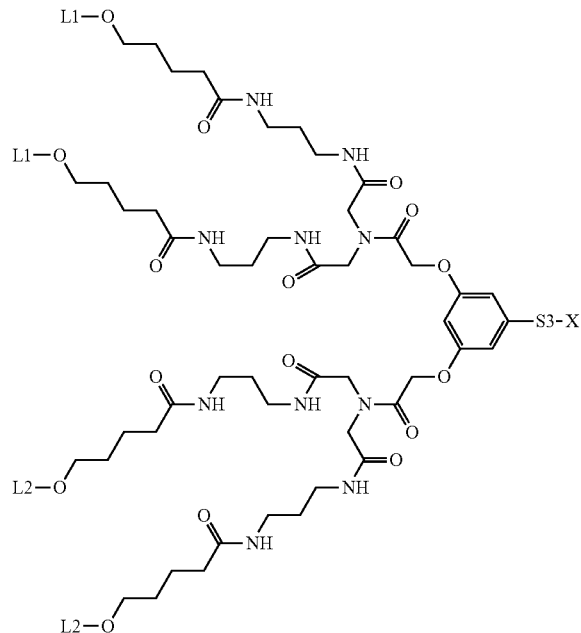
Formula 7-7
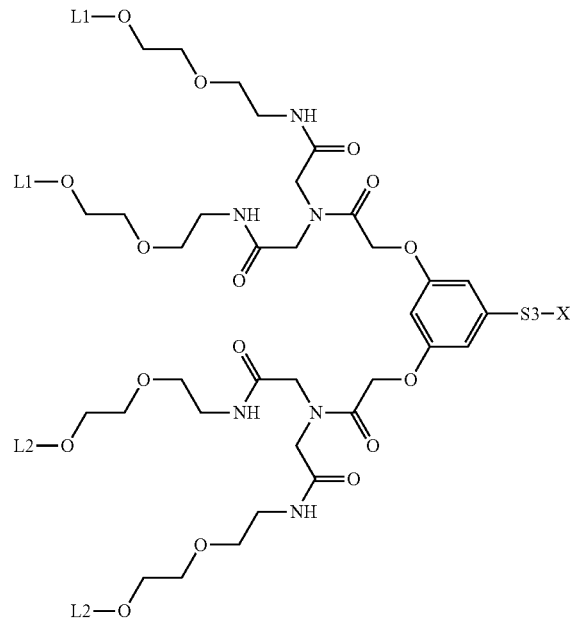
Formula 7-8
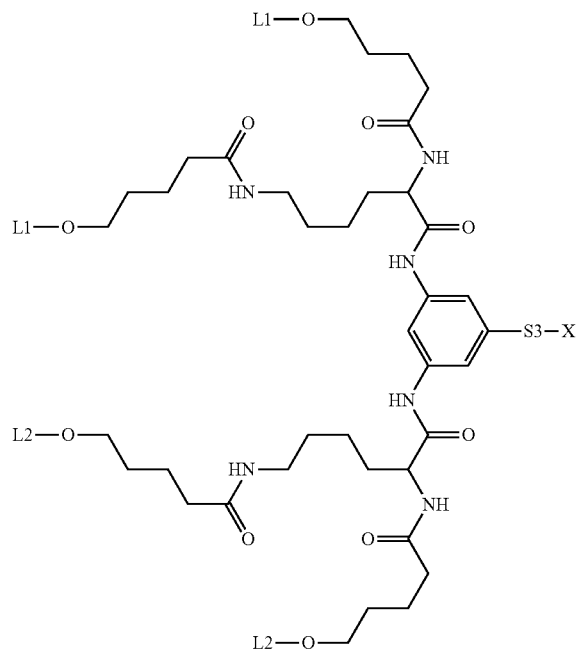
Formula 7-9

(10) The nucleic acid conjugate according to any of (1) to (9), wherein the nucleic acid conjugate has a structure represented by the following formula 11:

Formula 11

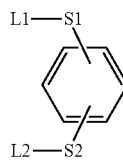

wherein

X, L1, L2, S1 and S2 are each as defined above,

P7 and P8 are each independently absent, or —CO—, —NH—, —O—, —S—, —O—CO—, —S—CO—, —NH—CO—, —CO—O—, —CO—S— or —CO—NH—, Q5, Q6 and Q7 are each independently absent, or substituted or unsubstituted alkylene having 1 to 12 carbon atoms or —(CH$_2$CH$_2$O)$_{n8}$—CH$_2$CH$_2$— wherein n8 is an integer of 0 to 99, B3 is any structure represented by the following formula 11-1, wherein the broken lines respectively mean bonds to Q5 and Q6:

Formula 11-1

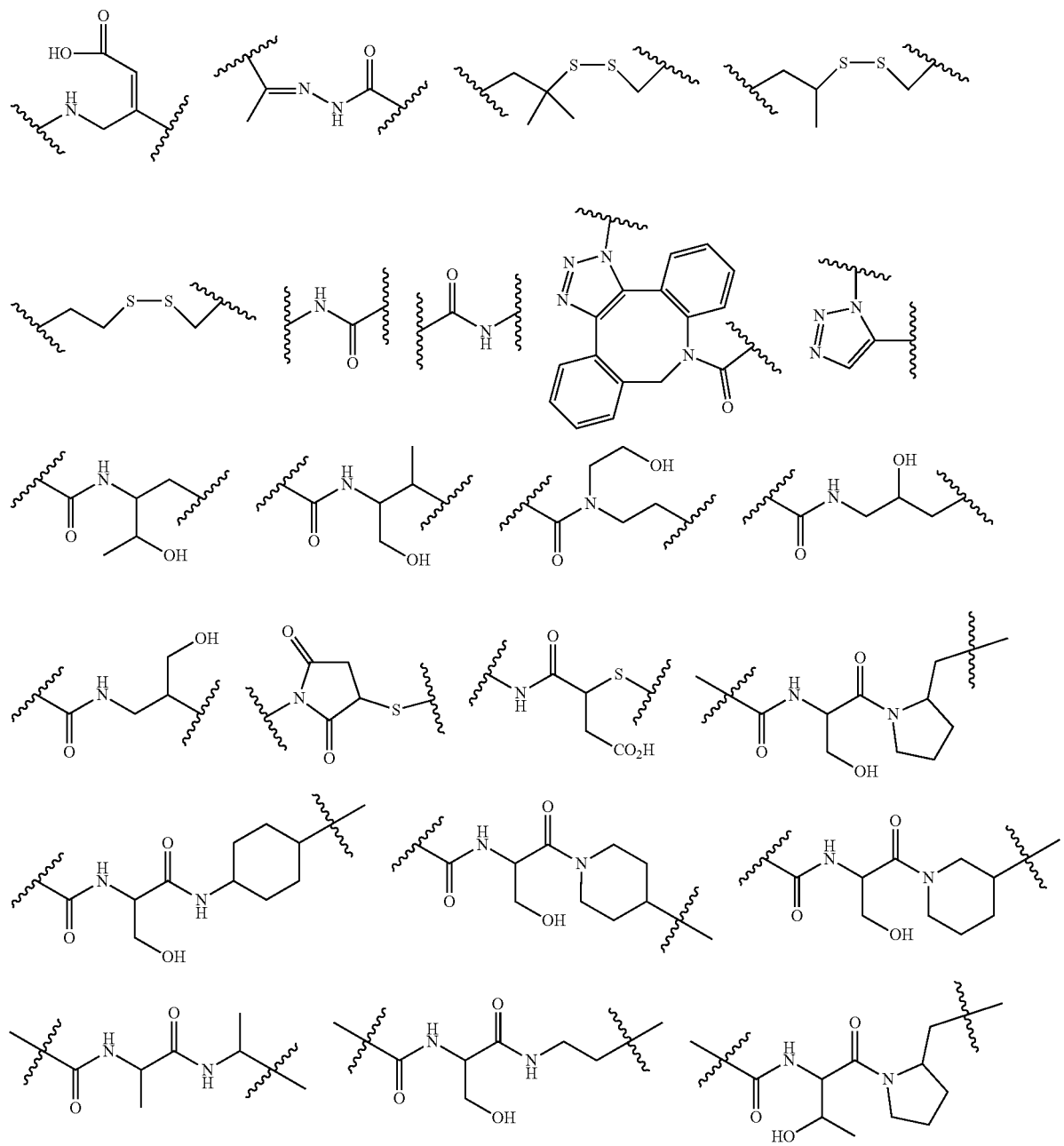

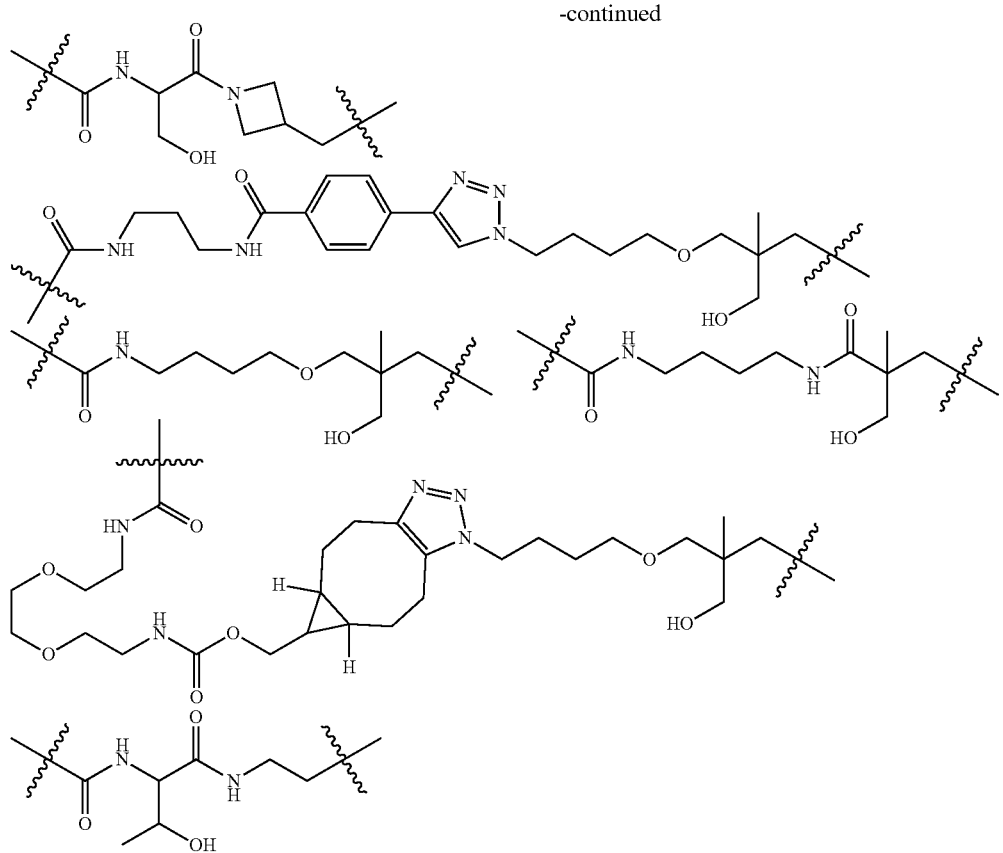
and
q5 and q6 are each independently an integer of 0 to 10.
(11) The nucleic acid conjugate according to any of (1) to (10), wherein the nucleic acid conjugate has any structure represented by the following formulas 12-1 to 12-12:
Formula 12-1
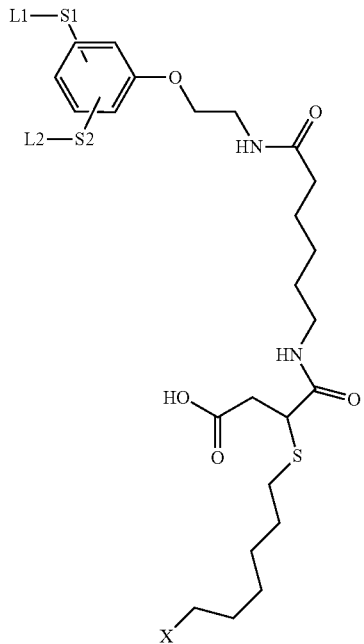
Formula 12-2
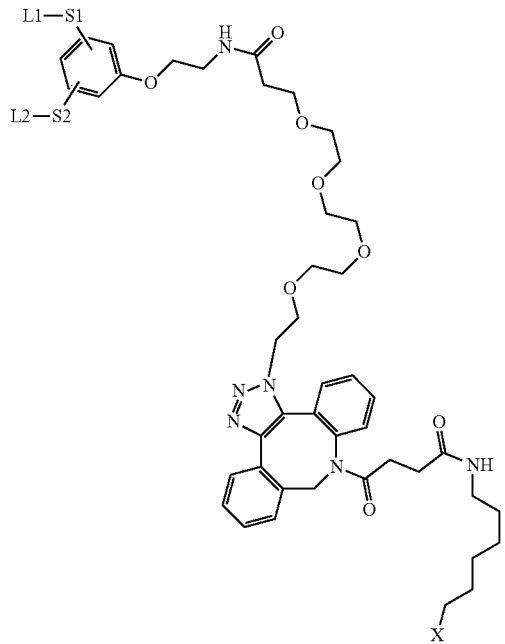

Formula 12-3
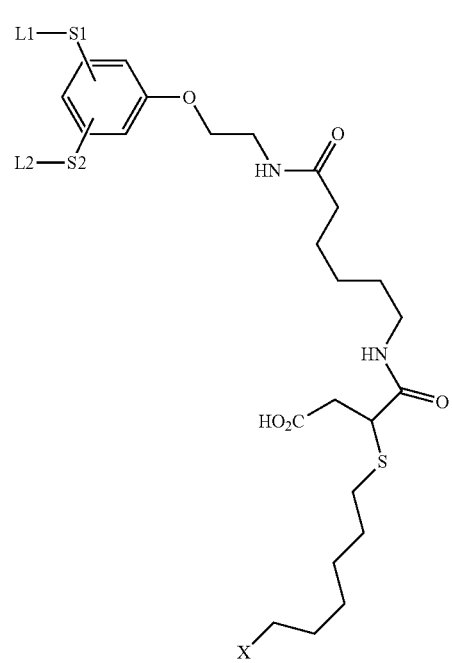
Formula 12-4
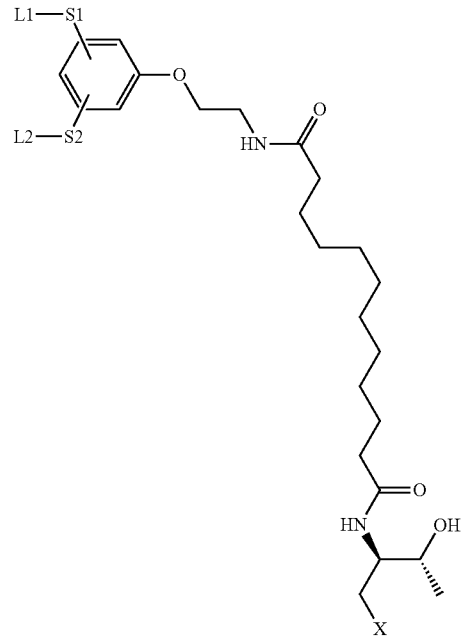
Formula 12-5
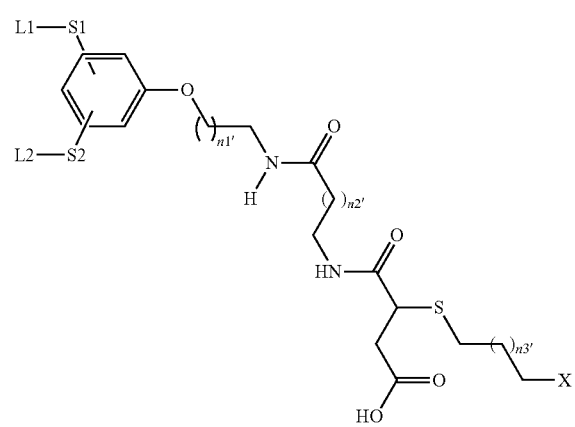
Formula 12-6
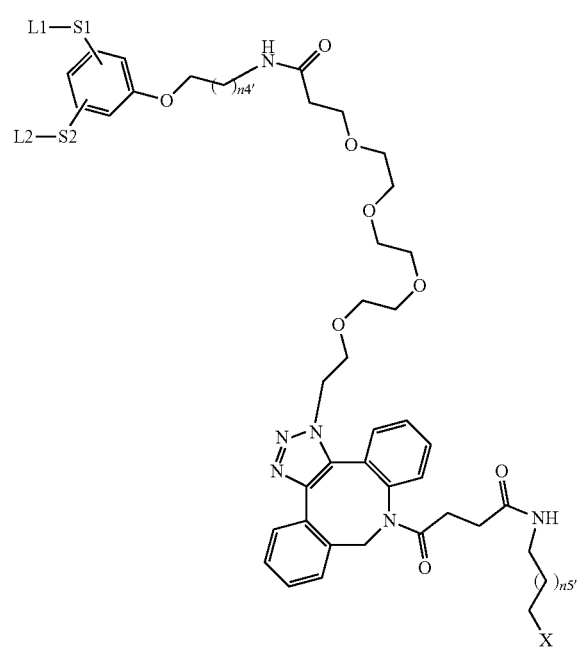

Formula 12-7
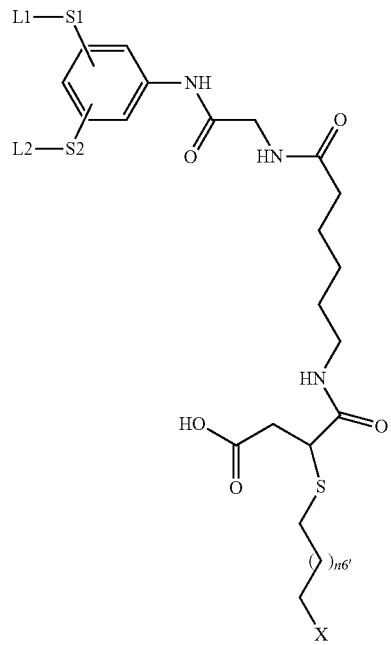
Formula 12-8
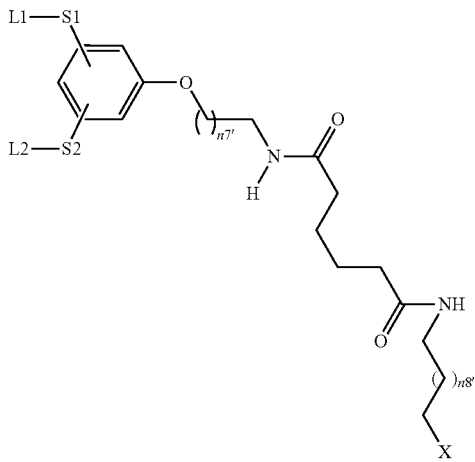
Formula 12-9
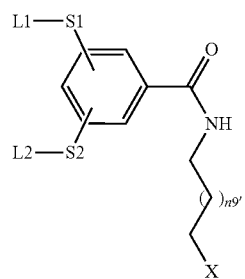
Formula 12-10
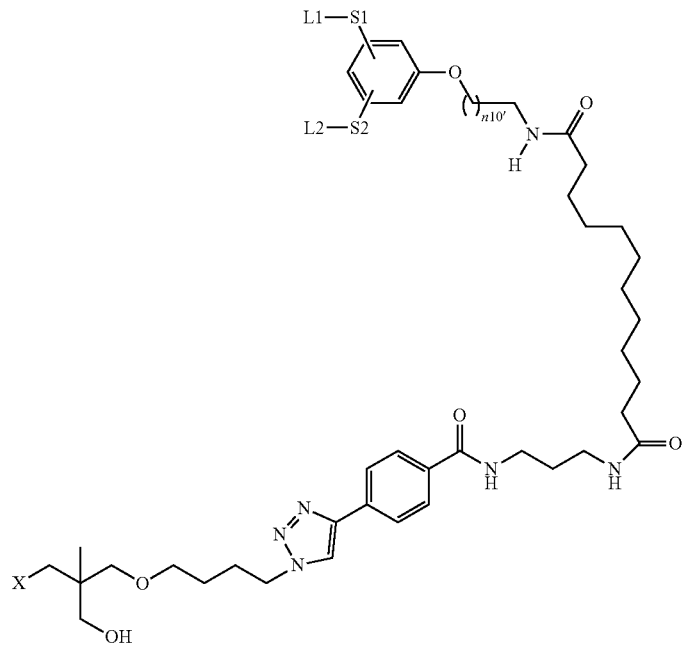

Formula 12-11

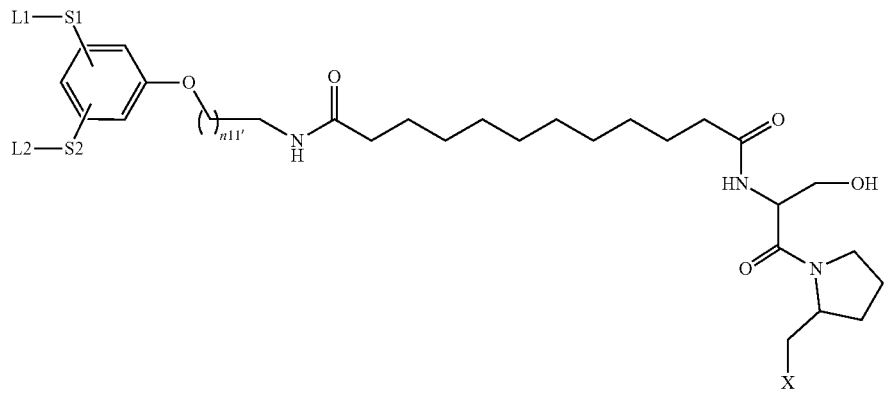

Formula 12-12

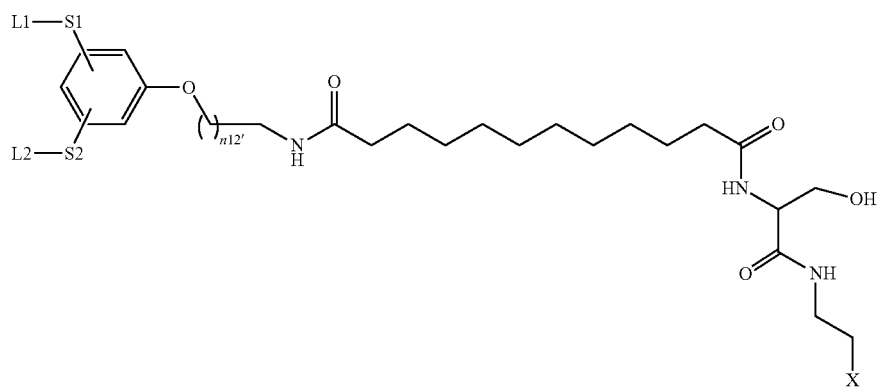

wherein

X, L1, L2, S1 and S2 are each as defined above, and n1' to n12' are each independently an integer of 1 to 10.

(12) The nucleic acid conjugate according to any of (1) to (11), wherein the sugar ligand is mannose or N-acetylgalactosamine.

(13) The nucleic acid conjugate according to any of (1) to (12), wherein the oligonucleotide comprises a modified nucleotide.

(14) A pharmaceutical composition comprising a nucleic acid conjugate according to any of (1) to (13).

(15) The pharmaceutical composition according to (14), wherein the pharmaceutical composition is for transfer into a cell.

(16) The pharmaceutical composition according to (15), wherein the cell is a liver cell.

(17) The pharmaceutical composition according to any of (14) to (16), wherein the pharmaceutical composition is intravenously administered or subcutaneously administered.

(18) A method for treating or preventing a disease, comprising administering a nucleic acid conjugate according to any of (1) to (13) or a pharmaceutical composition according to any of (14) to (17) to a patient in need thereof.

(19) The treatment or prevention method according to (18), wherein the patient is a mammal.

(20) A compound represented by the following formula 8:

Formula 8 wherein

R1 and R2 are each independently a hydrogen atom, a t-butoxycarbonyl group, a benzyloxycarbonyl group, a 9-fluorenylmethyloxycarbonyl group, —CO—R4, or —CO-α4-[(P9-Q8)$_{q7}$-T3-L3]$_{p3}$, P9 and T3 are each independently absent, or —CO—, —NH—, —O—, —S—, —O—CO—, —S—CO—, —NH—CO—, —CO—O—, —CO—S— or —CO—NH—, Q8 is absent, or substituted or unsubstituted alkylene having 1 to 12 carbon atoms or —(CH$_2$CH$_2$O)$_{n1}$—CH$_2$CH$_2$— wherein n1 is an integer of 0 to 99, B4 is a bond, or any structure represented by the following formula 8-1, wherein each of the terminal dots in each structure is a binding site to a carbonyl group or P9, and m7, m8, m9 and m10 are each independently an integer of 0 to 10:

Formula 8-1

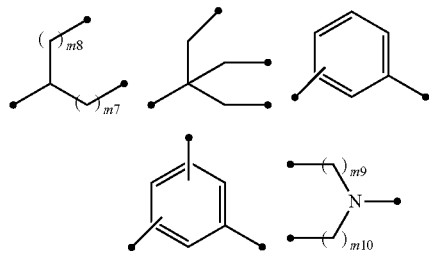

p3 is an integer of 1, 2 or 3,
q7 is an integer of 0 to 10,
L3 is a sugar ligand,
Y is —O—$(CH_2)_{m11}$—NH— or —NH—CO—$(CH_2)_{m12}$—NH— wherein m11 and m12 are each independently an integer of 1 to 10,
R3 is a hydrogen atom, a t-butoxycarbonyl group, a benzyloxycarbonyl group, a 9-fluorenylmethyloxycarbonyl group, —CO—R4, —CO—$(CH_2CH_2O)_{n2}$—$CH_2CH_2$—$N_3$, or —CO-Q9-B5-(Q10-P10)$_{q8}$-X1 wherein n2 is an integer of 0 to 99, P10 is absent, or —CO—, —NH—, —O—, —S—, —O—CO—, —S—CO—, —NH—CO—, —CO—O—, —CO—S— or —CO—NH—,
Q9 and Q10 are each independently absent, or substituted or unsubstituted alkylene having 1 to 12 carbon atoms or —$(CH_2CH_2O)_{n3}$—$CH_2CH_2$— wherein n3 is an integer of 0 to 99,
B5 is any structure represented by the following formula 8-2, wherein the broken lines respectively mean bonds to Q9 and Q10:

Formula 8-2

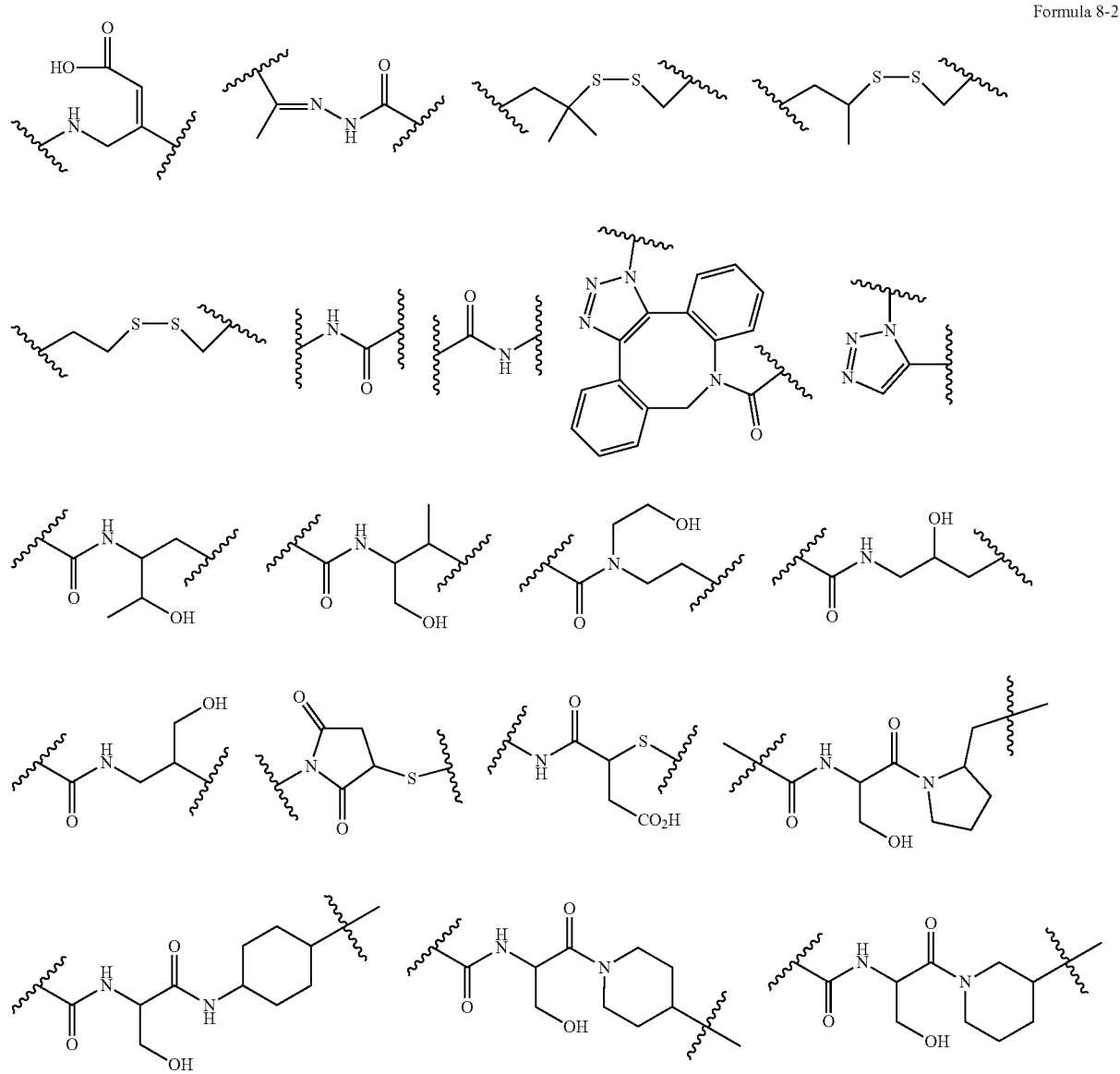

-continued
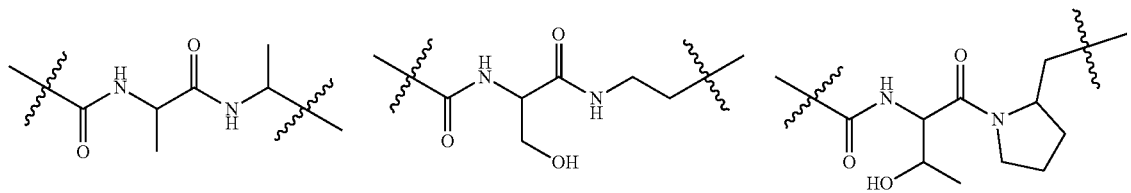
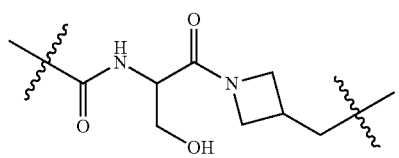
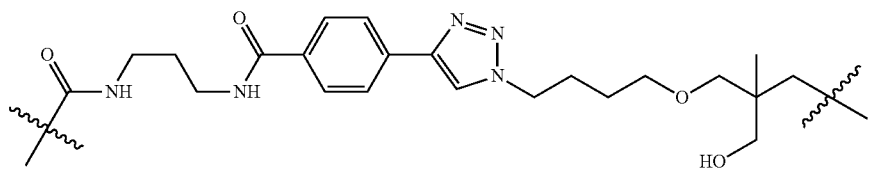
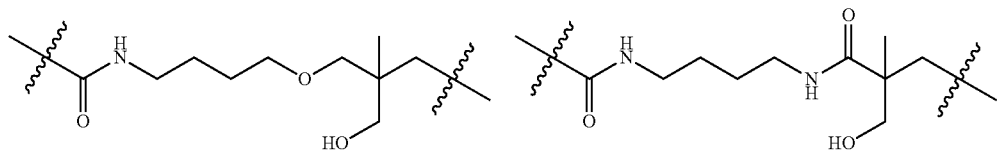
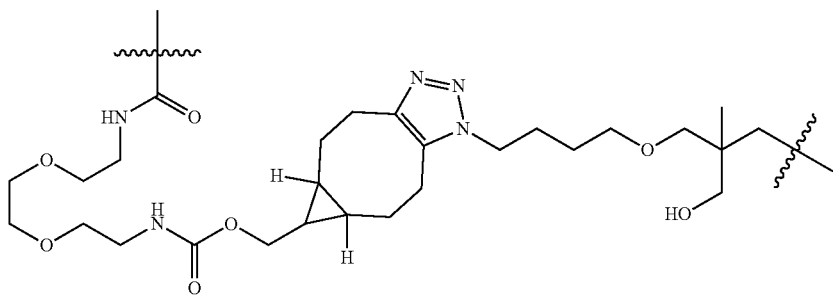
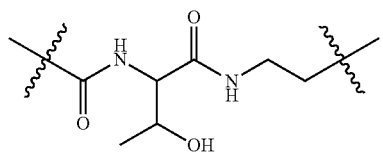

q8 is an integer of 0 to 10,

X1 is a hydrogen atom or a solid-phase support, and

R4 is an alkyl group having 2 to 10 carbon atoms substituted with 1 or 2 substituents selected from the group consisting of an amino group unsubstituted or substituted with a t-butoxycarbonyl group, a benzyloxycarbonyl group or a 9-fluorenylmethyloxycarbonyl group, a carboxy group, a maleimide group, and an aralkyloxycarbonyl group.

(21) A compound represented by the following formula 9:

Formula 9

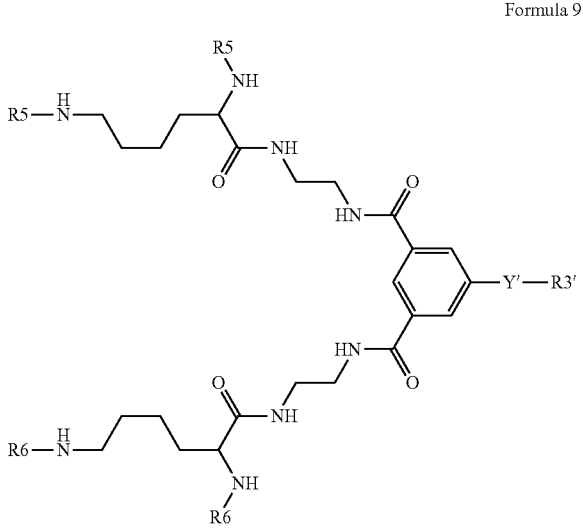

wherein

R5 and R6 are each independently a hydrogen atom, a t-butoxycarbonyl group, a benzyloxycarbonyl group, a 9-fluorenylmethyloxycarbonyl group, —CO—R4', or —CO-Q11-(P11-Q11')$_{q9}$-T4-L4, P11 and T4 are each independently absent, or —CO—, —NH—, —O—, —S—, —O—CO—, —S—CO—, —NH—CO—, —CO—O—, —CO—S— or —CO—NH—, each of Q11 and Q11' is absent, or substituted or unsubstituted alkylene having 1 to 12 carbon atoms or —(CH$_2$CH$_2$O)$_{n4}$—CH$_2$CH$_2$— wherein n4 is an integer of 0 to 99, q9 is an integer of 0 to 10, L4 is a sugar ligand, Y' is —O—(CH$_2$)$_{m11'}$—NH— or —NH—CO—(CH$_2$)$_{m12'}$—NH— wherein m11' and m12' are each independently an integer of 1 to 10, R3' is a hydrogen atom, a t-butoxycarbonyl group, a benzyloxycarbonyl group, a 9-fluorenylmethyloxycarbonyl group, —CO—R4', —CO—(CH$_2$CH$_2$O)$_{n2'}$—CH$_2$CH$_2$—N$_3$, or —CO-Q9'-B5'-(Q10'-P10')$_{q8'}$-X1' wherein n2' is an integer of 0 to 99, P10' is absent, or —CO—, —NH—, —O—, —S—, —O—CO—, —S—CO—, —NH—CO—, —CO—O—, —CO—S— or —CO—NH—, Q9' and Q10' are each independently absent, or substituted or unsubstituted alkylene having 1 to 12 carbon atoms or —(CH$_2$CH$_2$O)$_{n3'}$—CH$_2$CH$_2$— wherein n3' is an integer of 0 to 99, B5' is any structure represented by the following formula 9-1, wherein the broken lines respectively mean bonds to Q9' and Q10':

Formula 9-1

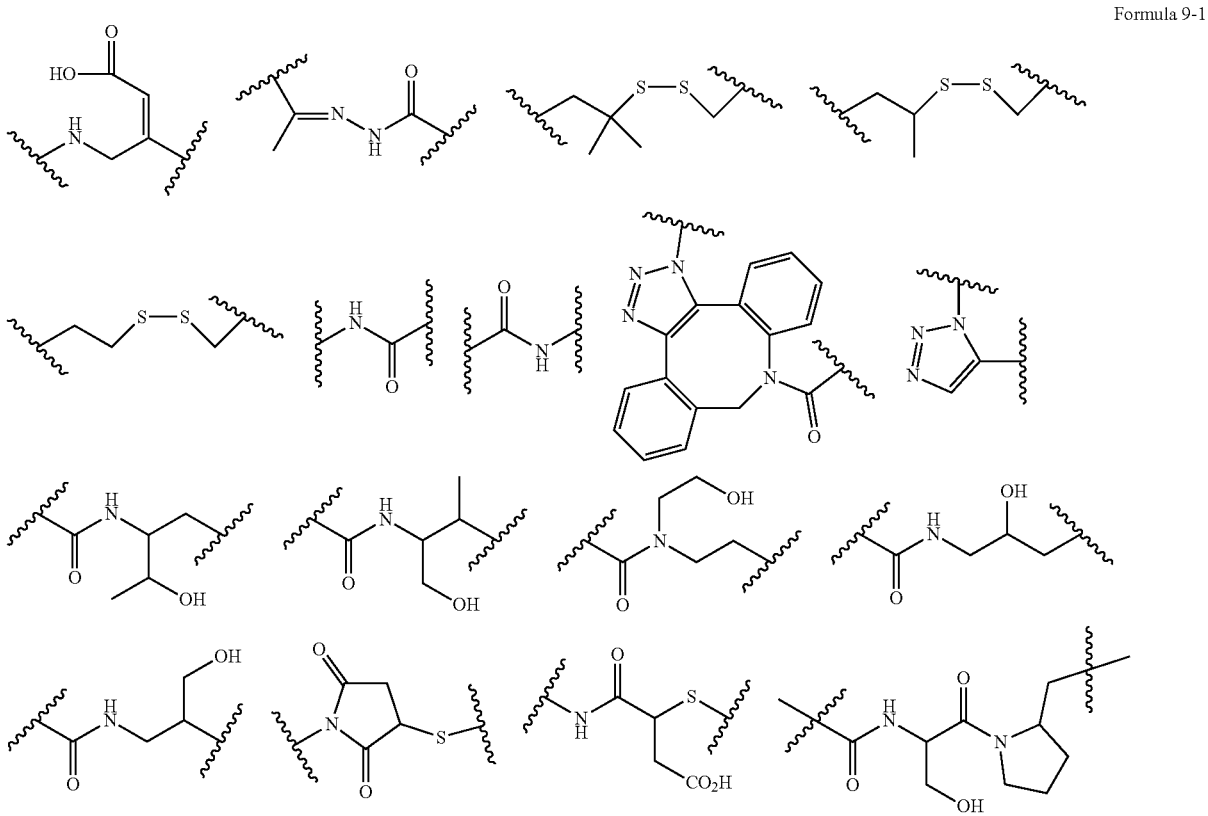

-continued

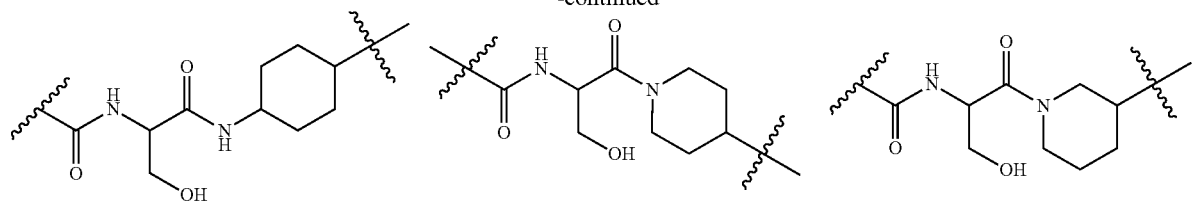

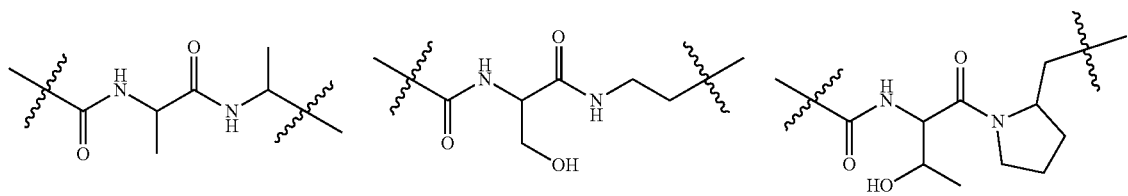

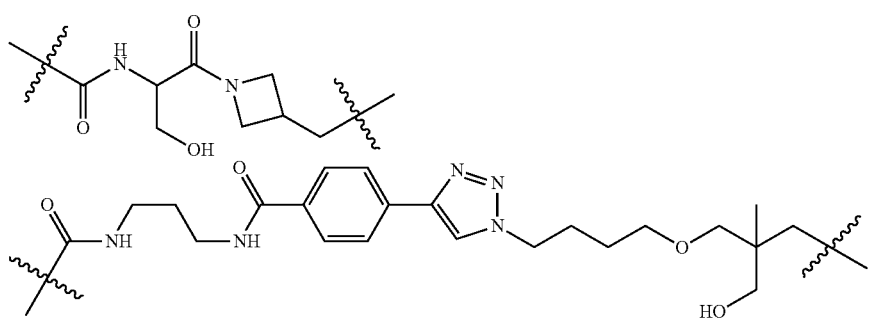

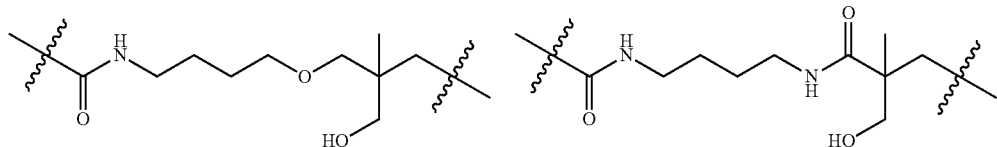

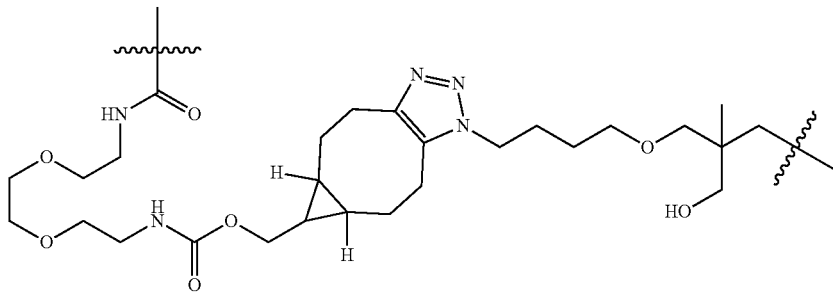

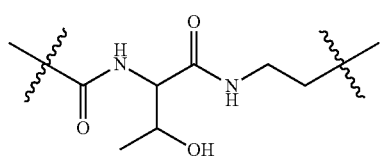

q8' is an integer of 0 to 10,

X1' is a hydrogen atom or a solid-phase support, and

R4' is an alkyl group having 2 to 10 carbon atoms substituted with 1 or 2 substituents selected from the group consisting of an amino group unsubstituted or substituted with a t-butoxycarbonyl group, a benzyloxycarbonyl group or a 9-fluorenylmethyloxycarbonyl group, a carboxy group, a maleimide group, and an aralkyloxycarbonyl group.

(22) A compound represented by the following formula 10:

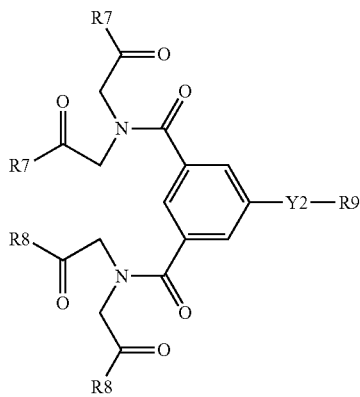

Formula 10 wherein
R7 and R8 are each independently a hydroxy group, a t-butoxy group, a benzyloxy group, —NH—R10, or —NH-Q12-(P12-Q12')$_{q10}$-T5-L5, P12 and T5 are each independently absent, or —CO—, —NH—, —O—, —S—, —O—CO—, —S—CO—, —NH—CO—, —CO—O—, —CO—S— or —CO—NH—, each of Q12 and Q12' is absent, or substituted or unsubstituted alkylene having 1 to 12 carbon atoms or —(CH$_2$CH$_2$O)$_{n5}$—CH$_2$CH$_2$— wherein n5 is an integer of 0 to 99, L5 is a sugar ligand, Y2 is —O—(CH$_2$)$_{m13}$—NH— or —NH—CO—(CH$_2$)$_{m14}$—NH— wherein m13 and m14 are each independently an integer of 1 to 10, q10 is an integer of 0 to 10, R9 is a hydrogen atom, a t-butoxycarbonyl group, a benzyloxycarbonyl group, a 9-fluorenylmethyloxycarbonyl group, —CO—R10, —CO—(CH$_2$CH$_2$O)$_{n6}$—CH$_2$CH$_2$—N$_3$, or —CO-Q13-B6-(Q14-P13)$_{q11}$-X2 wherein n6 is an integer of 0 to 99, P10 is absent, or —CO—, —NH—, —O—, —S—, —O—CO—, —S—CO—, —NH—CO—, —CO—O—, —CO—S— or —CO—NH—, Q13 and Q14 are each independently absent, or substituted or unsubstituted alkylene having 1 to 12 carbon atoms or —(CH$_2$CH$_2$O) n-CH$_2$CH$_2$— wherein n7 is an integer of 0 to 99, B6 is any structure represented by the following formula 10-1, wherein the broken lines respectively mean bonds to 013 and Q14:

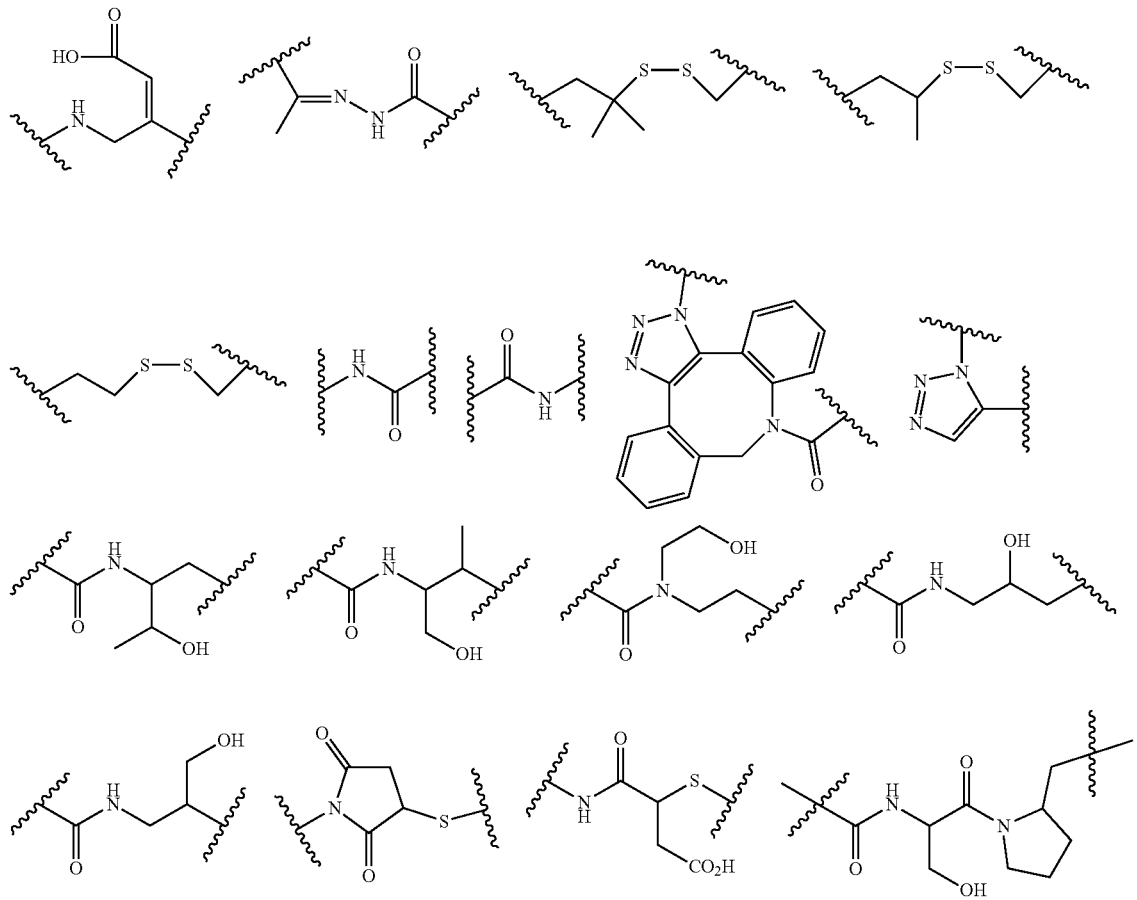

Formula 10-1

-continued

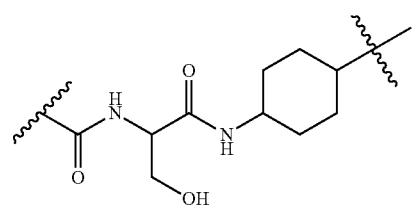 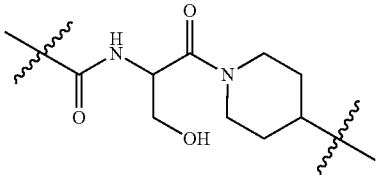 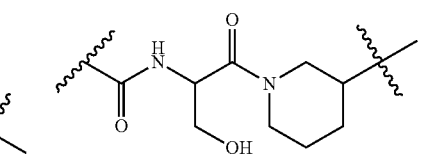

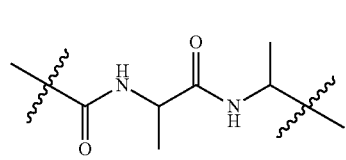 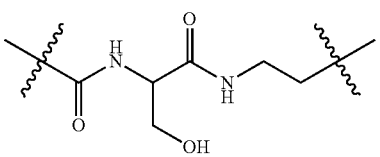

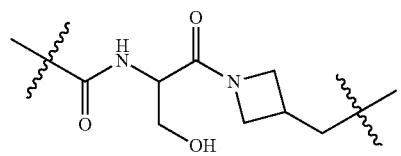

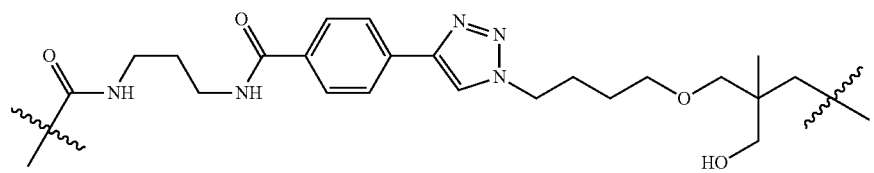

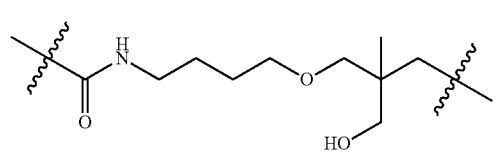 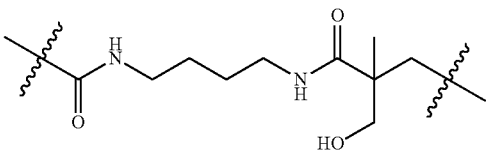

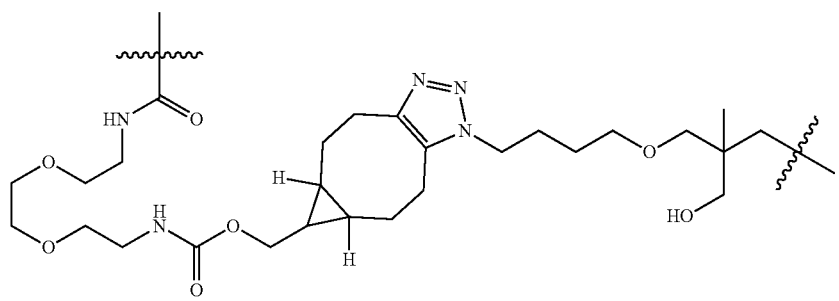

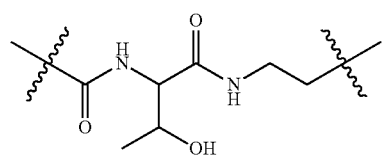

q11 is an integer of 0 to 10,

X2 is a hydrogen atom or a solid-phase support, and

R10 is an alkyl group having 2 to 10 carbon atoms substituted with 1 or 2 substituents selected from the group consisting of an amino group unsubstituted or substituted with a t-butoxycarbonyl group, a benzyloxycarbonyl group or a 9-fluorenylmethyloxycarbonyl group, a carboxy group, a maleimide group, and an aralkyloxycarbonyl group.

Advantageous Effects of Invention

For example, a pharmaceutical composition comprising the nucleic acid conjugate of the present invention can be administered to mammals to treat various related diseases in vivo.

DESCRIPTION OF EMBODIMENTS

The nucleic acid conjugate of the present invention is a nucleic acid conjugate represented by the following formula 1:

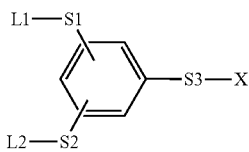

Formula 1

In formula 1,

X is an oligonucleotide,

L1 and L2 are each independently a sugar ligand, and

S1, S2 and S3 are each independently a linker.

In the present invention, S1 and S2 can each be bonded to the benzene ring at an ortho-, meta- or para-position with respect to the substitution position of S3 on the benzene ring. A nucleic acid conjugate represented by formula 1-1 given below is preferred. The bonds of S1 and S2 to the benzene ring in formula 1 mean that the bonds can be at arbitrary positions other than the substitution position of S3 on the benzene ring.

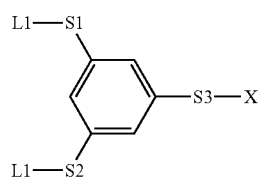

Formula 1-1

In formula 1-1,

X, L1, L2, S1, S2 and S3 are each as defined above.

In the present specification, the phrase "as defined above" means that, when formula 1-1 is taken as an example, each of X, L1, L2, S1 and S2 in formula 1-1 can be the same group as in the definition about each of X, L1, L2, S1 and S2 described above in formula 1.

In the present invention, X is an oligonucleotide, and an oligonucleotide known to be used as a nucleic acid medicine can be used. In the present invention, the nucleic acid medicine means a nucleotide that is used as an aptamer, an antisense, a decoy nucleic acid, a ribozyme, siRNA, miRNA, anti-miRNA or the like.

In the present invention, the oligonucleotide is not only bonded to S3 via position 3' or 5' of a sugar moiety constituting a nucleotide but may be bonded to S3 via a base moiety constituting the nucleotide. In the present invention, the oligonucleotide can be understood as a group having a structure that bonds the oligonucleotide to S3. For example, when the oligonucleotide is bonded to S3 via —O—P(Z)(Z')O— (wherein Z and Z' are each independently an oxygen atom or a sulfur atom), the oligonucleotide represented by X may be understood as —O—P(Z)(Z')O-oligonucleotide.

The oligonucleotide may be a single-stranded or double-stranded oligonucleotide.

Linker S3 and oligonucleotide X are bonded to each other at the 3' or 5' end of the oligonucleotide. When the oligonucleotide is double-stranded, linker S3 is preferably bonded to the 3' or 5' end of a sense strand constituting the double-stranded nucleic acid, though the bond is not limited thereto.

In the present invention, a nucleic acid comprising a nucleotide sequence complementary to target mRNA is also referred to as an antisense nucleotide, and a nucleic acid comprising a nucleotide sequence complementary to the nucleotide sequence of the antisense nucleotide is also referred to as a sense nucleotide.

The oligonucleotide constituting the nucleic acid conjugate used in the present invention can have any shape as long as the oligonucleotide has the ability to control the expression of a target gene when transferred to mammalian cells. A single-stranded oligonucleotide or a double-stranded oligonucleotide is suitably used.

The oligonucleotide can be any molecule which is a polymer of nucleotides or molecules functionally equivalent to nucleotides. Examples thereof include DNA which is a polymer of deoxyribonucleotides, RNA which is a polymer of ribonucleotides, and a chimeric nucleic acid which is a polymer of DNA and RNA. Alternatively, the oligonucleotide may be a nucleotide polymer derived from DNA, RNA or a chimeric nucleic acid by the replacement of at least one nucleotide (deoxyribonucleotide, ribonucleotide, etc.) with a molecule functionally equivalent to the nucleotide. Uracil (U) in RNA and thymine (T) in DNA can be used interchangeably with each other.

Examples of the molecules functionally equivalent to nucleotides include nucleotide derivatives prepared by modifying nucleotides. For example, a modified deoxyribonucleotide or ribonucleotide molecule is suitably used for improving or stabilizing nuclease resistance, for enhancing affinity for a complementary strand nucleic acid, for enhancing cell permeability, or for visualizing the molecule, as compared with DNA or RNA.

Examples of the nucleotide derivatives include nucleotides modified at at least one of a sugar moiety, a phosphodiester bond and a base, such as nucleotides modified at the sugar moiety, nucleotides modified at the phosphodiester bond, and nucleotides modified at the base.

The nucleotide modified at the sugar moiety can be any nucleotide in which a portion or the whole of the chemical structure of its sugar is modified or substituted with an arbitrary substituent or substituted with an arbitrary atom. A 2'-modified nucleotide is preferably used.

Examples of the 2'-modified nucleotide include 2'-modified nucleotides in which the 2'-OH group of ribose is substituted with a substituent selected from the group consisting of OR, R, R'OR, SH, SR, $NH_2$, NHR, $NR_2$, $N_3$, CN, F, Cl, Br and I (R is alkyl or aryl, preferably alkyl having 1 to 6 carbon atoms, and R' is alkylene, preferably alkylene having 1 to 6 carbon atoms). Examples of the 2'-modification preferably include substitution with F, a methoxy group and/or an ethoxy group. Further examples thereof include 2'-modified nucleotides having substitution with a substituent selected from the group consisting of a 2-(methoxy) ethoxy group, a 3-aminopropoxy group, a 2-[(N,N-dimethylamino)oxy]ethoxy group, a 3-(N,N-dimethylamino) propoxy group, a 2-[2-(N,N-dimethylamino)ethoxy]ethoxy group, a 2-(methylamino)-2-oxoethoxy group, a 2-(N-methylcarbamoyl)ethoxy group and a 2-cyanoethoxy group.

Bridged nucleic acid (BNA) having two cyclic structures by the introduction of a bridged structure to the sugar moiety is also suitably used as the nucleotide modified at the sugar moiety. Specific examples thereof include locked nucleic acid (LNA) having the oxygen atom at position 2' and the carbon atom at position 4' bridged via methylene [Tetrahedron Letters, 38, 8735 (1997); and Tetrahedron, 54, 3607 (1998)], ethylene bridged nucleic acid (ENA) [Nucleic Acid Research, 32, e175 (2004)], constrained ethyl (cEt) [The Journal of Organic Chemistry 75, 1569 (2010)], amido-bridged nucleic acid (AmNA) [Chem Bio Chem 13, 2513 (2012)] and 2'-O,4'-C-spirocyclopropylene bridged nucleic acid (scpBNA) [Chem. Commun., 51, 9737 (2015)].

Further examples of the nucleotide modified at the sugar moiety include peptide nucleic acid (PNA) [Acc. Chem. Res., 32, 624 (1999)], oxy-peptide nucleic acid (OPNA) [J. Am. Chem. Soc., 123, 4653 (2001)] and peptide ribonucleic acid (PRNA) [J. Am. Chem. Soc., 122, 6900 (2000)].

The nucleotide modified at the phosphodiester bond can be any nucleotide in which a portion or the whole of the chemical structure of its phosphodiester bond is modified or substituted with an arbitrary substituent or substituted with an arbitrary atom. Examples thereof include a nucleotide resulting from the substitution of the phosphodiester bond with a phosphorothioate bond, a nucleotide resulting from the substitution of the phosphodiester bond with a phosphorodithioate bond, a nucleotide resulting from the substitution of the phosphodiester bond with an alkyl phosphonate bond, and a nucleotide resulting from the substitution of the phosphodiester bond with a phosphoramidate bond and preferably include a nucleotide resulting from the substitution of the phosphodiester bond with a phosphorothioate bond.

The nucleotide modified at the base can be any nucleotide in which a portion or the whole of the chemical structure of its base is modified or substituted with an arbitrary substituent or substituted with an arbitrary atom. Examples thereof include a nucleotide resulting from the substitution of an oxygen atom in the base with a sulfur atom, a nucleotide resulting from the substitution of a hydrogen atom with an alkyl group having 1 to 6 carbon atoms or a halogen group, a nucleotide resulting from the substitution of a methyl group with a hydrogen atom, a hydroxymethyl group or an alkyl group having 2 to 6 carbon atoms, and a nucleotide resulting from the substitution of an amino group with an alkyl group having 1 to 6 carbon atoms, an alkanoyl group having 1 to 6 carbon atoms, an oxo group, a hydroxy group, or the like. In a preferred aspect of the present invention, 5-methylcytosine (5-mC) is also used instead of cytosine (C) as the nucleotide modified at the base.

Examples of the nucleotide derivatives also include nucleotides or nucleotides modified at at least one of a sugar moiety, a phosphodiester bond and a base which contain an additional chemical substance, such as peptide, protein, sugar, lipid, phospholipid, phenazine, folate, phenanthridine, anthraquinone, acridine, fluorescein, rhodamine, coumarin, or a dye, added thereto directly or via a linker, and specifically include 5'-polyamine-added nucleotide derivatives, cholesterol-added nucleotide derivatives, steroid-added nucleotide derivatives, bile acid-added nucleotide derivatives, vitamin-added nucleotide derivatives, Cy5-added nucleotide derivatives, Cy3-added nucleotide derivatives, 6-FAM-added nucleotide derivatives, and biotin-added nucleotide derivatives.

The nucleotide derivative may form a bridged structure, such as an alkylene structure, a peptide structure, a nucleotide structure, an ether structure, an ester structure, and a structure combined with at least one of these structures, with another nucleotide or nucleotide derivative within the nucleic acid.

The oligonucleotide also encompasses molecules in which a portion or the whole of the atoms is substituted with an atom having an atomic mass number different therefrom (isotope).

In the present specification, the term "complementation" means a relationship capable of forming a base pair between two bases via a mild hydrogen bond, for example, the relationship between adenine and thymine or uracil, and the relationship between guanine and cytosine.

In the present specification, the term "complementary" not only means the case where two nucleotide sequences are completely complementary to each other, but means that 0 to 30%, 0 to 20% or 0 to 10% of a mismatch base can be present between the nucleotide sequences, and, for example, an antisense oligonucleotide complementary to target mRNA may contain the substitution of one or more bases in its nucleotide sequence completely complementary to a partial nucleotide sequence of the target mRNA. Specifically, the antisense oligonucleotide may have 1 to 8, preferably 1 to 6, 1 to 4 or 1 to 3, particularly, 2 or 1 mismatch bases for a target sequence of a target gene.

Also, the term "complementary" encompasses the case where two nucleotide sequences, one of which is completely complementary to the other nucleotide sequence, have the addition and/or deletion of one or more bases. For example, target mRNA and the antisense oligonucleotide may have 1 or 2 bulge bases in the antisense strand and/or target mRNA region by the addition and/or deletion of base(s) in the antisense oligonucleotide.

Hereinafter, the term "complementary" is described to also encompass "complementation".

The antisense oligonucleotide used in the present invention is an oligonucleotide complementary to DNA encoding the target gene or a mRNA precursor, mRNA, a microRNA precursor or microRNA transcribed from the DNA encoding the target gene, and inhibits the function of the DNA, the mRNA precursor, the mRNA, the microRNA precursor or the microRNA by forming a duplex with the DNA, the mRNA precursor or the mRNA targeted by the antisense oligonucleotide.

The antisense oligonucleotide includes not only an oligonucleotide completely complementary to its target DNA, mRNA precursor, mRNA, microRNA precursor or microRNA, but an oligonucleotide having one or several mismatches as long as the oligonucleotide can hybridize under stringent conditions to the DNA, the mRNA precursor, the mRNA, the microRNA precursor or the microRNA.

The antisense oligonucleotide may be introduced into the form of a hairpin oligomer or a cyclic oligomer and may contain a structural factor such as an internal or terminal bulge or loop as long as the nucleic acid hybridizes to the target gene.

The length of the antisense oligonucleotide is 8 to 80 bases, preferably 8 to 30 bases. The length can be, for example, 8 to 20 bases, 10 to 20 bases, 13 to 20 bases, 13 to 16 bases, 13 bases, 14 bases, 15 bases, 16 bases, 17 bases, 18 bases, 19 bases, or 20 bases.

The antisense oligonucleotide, when transferred into cells, can bind to its complementary mRNA precursor or mRNA and sterically inhibit the translation thereof into a protein, inhibiting the expression of the target gene.

The antisense oligonucleotide can also bind to its complementary microRNA precursor or microRNA in cells and sterically inhibit the function of the microRNA.

The antisense oligonucleotide may bind to its complementary mRNA or mRNA precursor in cells and cleave the mRNA or the mRNA precursor. Action mediated by RNase H which is an endonuclease that cleaves the RNA strand of a duplex of RNA and DNA is known as such an example. When the antisense oligonucleotide of the present invention in cells forms a duplex with the mRNA or the mRNA precursor, the duplex can be recognized by RNase H, which then enzymatically can degrade the complementary mRNA strand.

An antisense oligonucleotide having 4 to 80 consecutive DNA regions is preferred for inducing the cleavage of the mRNA or the mRNA precursor by RNase H. In this case, the antisense oligonucleotide preferably has 0 to 80%, more preferably 10 to 60%, further preferably 20 to 50%, of a nucleotide modified at the sugar moiety. When the antisense oligonucleotide has a nucleotide modified at the sugar moiety, the number of the consecutive DNA regions is more preferably 4 to 20, further preferably 4 to 15, most preferably 5 to 10. The position of the nucleotide modified at the sugar moiety in the antisense oligonucleotide is preferably near the 5' end and/or near the 3' end and is more preferably a position within 25% of the whole length from the 5' end and/or a position within 25% of the whole length from the 3' end.

The antisense oligonucleotide can also induce the inhibition of the expression of a target gene by forming a duplex with its complementary oligonucleic acid and transferring the double-stranded nucleic acid into cells (see International Publication No. WO 2005/113571). In this case, the position of modification of the double-stranded nucleic acid with a ligand is preferably the 5' or 3' end of the complementary oligonucleic acid.

The antisense oligonucleotide used in the present invention can also increase the expression of a target gene by using a nucleotide sequence complementary to a promoter sequence or the like of the target gene (see International Publication Nos. WO 2013/173601 and WO 2013/173637).

Examples of a method for producing the antisense oligonucleotide include, but are not particularly limited to, methods using chemical synthesis known in the art, and enzymatic transcription methods. Examples of the methods using chemical synthesis known in the art can include a phosphoramidite method, a phosphorothioate method, a phosphotriester method, and a CEM method [Nucleic Acid Research, 35, 3287 (2007)]. The antisense oligonucleotide can be synthesized using, for example, ABI3900 high-throughput nucleic acid synthesizer (manufactured by Applied Biosystems, Inc.). After the completion of synthesis, dissociation from a solid phase, deprotection of a protective group and purification of the compound of interest, etc. are performed. Desirably, an antisense oligonucleotide having a purity of 90% or higher, preferably 95% or higher, is obtained by the purification. Examples of the enzymatic transcription methods for producing the antisense oligonucleotide of the present invention include methods based on transcription using a plasmid or DNA having the nucleotide sequence of interest as a template and phage RNA polymerase, for example, T7, T3, or SP6 RNA polymerase.

The double-stranded oligonucleotide used in the present invention may be constituted by any oligonucleotide or derivative thereof as long as the oligonucleotide or the derivative is a nucleic acid comprising a nucleotide sequence complementary to a partial nucleotide sequence of target mRNA and/or a nucleic acid comprising a nucleotide sequence complementary to the nucleotide sequence of the nucleic acid.

The double-stranded oligonucleotide used in the present invention can have any length as long as the nucleic acid comprising a nucleotide sequence complementary to the target mRNA sequence and the nucleic acid comprising a nucleotide sequence complementary to the nucleotide sequence of the nucleic acid can form a duplex. The sequence length that allows formation of the duplex is usually 11 to 35 bases, preferably 15 to 30 bases, more preferably 17 to 25 bases, further preferably 17 to 23 bases, particularly preferably 19 to 23 bases.

In the present invention, a single-stranded nucleic acid that consists of a nucleic acid comprising a nucleotide sequence complementary to the target mRNA sequence and inhibits the expression of the target protein, or a double-stranded nucleic acid that consists of a nucleic acid comprising a nucleotide sequence complementary to the target mRNA sequence and a nucleic acid comprising a nucleotide sequence complementary to the nucleotide sequence of the nucleic acid and inhibits the expression of the target protein is suitably used as the double-stranded oligonucleotide inhibiting the expression of the target protein.

The double-stranded oligonucleotide can also increase the expression of a target gene by using a molecule consisting of a nucleic acid comprising a nucleotide sequence complementary to a promoter sequence or the like of the target gene and a nucleic acid comprising a nucleotide sequence complementary to the nucleotide sequence of the nucleic acid [Nucleic Acid Research, 41, 10086 (2013); and Hepatology, 59, 216 (2014)].

The double-stranded oligonucleotide refers to nucleotides having a duplex region formed by the pairing of two oligonucleotides. The duplex region refers to a moiety in which nucleotides or derivatives thereof, constituting the two strands have formed a duplex by constituting base pairs. The duplex region is usually 11 to 27 base pairs, preferably 15 to 25 base pairs, more preferably 15 to 23 base pairs, further preferably 17 to 21 base pairs.

Each single-stranded oligonucleotide constituting the double-stranded oligonucleotide usually consists of 11 to 30 bases, preferably 15 to 29 bases, more preferably 15 to 27 bases, further preferably 15 to 25 bases, particularly preferably 17 to 23 bases.

The double-stranded oligonucleotide may have a non-duplex-forming additional nucleotide or nucleotide derivative on the 3' or 5' side subsequent to the duplex region. This non-duplex-forming moiety is referred to as an overhang. When the double-stranded oligonucleotide has an overhang, the nucleotide constituting the overhang may be a ribonucleotide, a deoxyribonucleotide or a derivative thereof.

A double-stranded oligonucleotide having an overhang consisting of 1 to 6 bases, usually 1 to 3 bases, at the 3' or 5' end of at least one of the strands is used as the double-stranded oligonucleotide having the overhang. A double-stranded oligonucleotide having an overhang consisting of 2 bases is preferably used. Examples thereof include double-stranded oligonucleotides having an overhang consisting of dTdT or UU. The overhang can be present in only the antisense oligonucleotide, only the sense oligonucleotide, and both the antisense oligonucleotide and the sense oligonucleotide. A double-stranded oligonucleotide having an overhang in the antisense oligonucleotide is preferably used. The antisense oligonucleotide comprises the duplex region and the overhang subsequent thereto.

A nucleic acid consisting of a sequence identical to the nucleotide sequence of a target gene or the nucleotide sequence of its complementary strand may be used in the double-stranded oligonucleotide. A double-stranded nucleic acid consisting of a nucleic acid derived from the nucleic acid by the truncation of 1 to 4 bases from the 5' or 3' end of at least one strand, and a nucleic acid comprising a nucleotide sequence complementary to the nucleotide sequence of the nucleic acid may be used.

The double-stranded oligonucleotide may be double-stranded RNA (dsRNA) comprising a RNA duplex, double-stranded DNA (dsDNA) comprising a DNA duplex, or a hybrid nucleic acid comprising a RNA-DNA duplex. Alternatively, the double-stranded oligonucleotide may be a chimeric nucleic acid having two strands, one or both of which consists of DNA and RNA. Double-stranded RNA (dsRNA) is preferred.

Preferably, the 2nd nucleotide counted from the 5' end of the antisense oligonucleotide is complementary to the 2nd deoxyribonucleotide counted from the 3' end of the target mRNA sequence. More preferably, the 2nd to 7th nucleotides counted from the 5' end of the antisense oligonucleotide are completely complementary to the 2nd to 7th deoxyribonucleotides counted from the 3' end of the target mRNA sequence. Further preferably, the 2nd to 11th nucleotides counted from the 5' end of the antisense oligonucleotide are completely complementary to the 2nd to 11th deoxyribonucleotides counted from the 3' end of the target mRNA sequence. Also preferably, the 11th nucleotide counted from the 5' end of the antisense oligonucleotide is complementary to the 11th deoxyribonucleotide counted from the 3' end of the target mRNA sequence. More preferably, the 9th to 13th nucleotides counted from the 5' end of the antisense oligonucleotide are completely complementary to the 9th to 13th deoxyribonucleotides counted from the 3' end of the target mRNA sequence. Further preferably, the 7th to 15th nucleotides counted from the 5' end of the antisense oligonucleotide are completely complementary to the 7th to 15th deoxyribonucleotides counted from the 3' end of the target mRNA sequence.

The double-stranded oligonucleotide preferably contains 50 to 100%, more preferably 70 to 100%, further preferably 90 to 100%, of a modified nucleotide with respect to the nucleotides within the double-stranded nucleic acid region.

The double-stranded oligonucleotide can be chemically synthesized and can generally be synthesized by use of a solid-phase oligonucleotide synthesis method (see, for example, Usman et al., U.S. Pat. Nos. 5,804,683; 5,831,071; 5,998,203; 6,117,657; 6,353,098; 6,362,323; 6,437,117; and U.S. Pat. No. 6,469,158; Scaringe et al., U.S. Pat. Nos. 6,111,086; 6,008,400; and 6,111,086).

RNA may be produced enzymatically or by partial or total organic synthesis. A modified ribonucleotide can be introduced enzymatically or by organic synthesis in vitro. In one aspect, each strand is chemically prepared. A method for chemically synthesizing a RNA molecule is known in the art [see Nucleic Acids Research, 32, 936 (1998)].

Examples of the RNA used in the present invention include RNA comprising a sequence of 15 to 30 consecutive bases, preferably 17 to 25 consecutive bases, more preferably 19 to 23 consecutive bases (hereinafter, referred to as sequence X) of mRNA of a target gene, and a sequence of bases complementary (hereinafter referred to as complementary sequence X') to the sequence X, for example, double-stranded RNA consisting of a sense oligonucleotide comprising sequence X and an antisense oligonucleotide comprising complementary sequence X', and RNA having a hairpin structure of the sense oligonucleotide and the antisense oligonucleotide connected via a spacer oligonucleotide.

Examples of the sense oligonucleotide comprising sequence X include RNA comprising only the sequence X as bases (hereinafter, referred to as a sequence X strand), and RNA having 1 to 6, preferably 2 to 4 same or different nucleotides added to the 3' or 5' end, or both, of the sequence X strand.

Examples of the antisense oligonucleotide comprising complementary sequence X' include RNA comprising only the complementary sequence X' as bases (hereinafter, referred to as a complementary sequence X' strand), and double-stranded RNA having 1 to 6, preferably 2 to 4 same or different nucleotides added to the 3' or 5' end, or both, of the complementary sequence X' strand.

The spacer oligonucleotide in the RNA having a hairpin structure of the sense oligonucleotide comprising sequence X and the antisense oligonucleotide comprising complementary sequence X', connected via the spacer oligonucleotide is preferably nucleotides of 6 to 12 bases, and the 5' terminal sequence thereof is preferably UU. Examples of the spacer oligonucleotide include an oligonucleotide consisting of a nucleotide sequence UUCAAGAGA. As for the order of the two RNA strands connected via the spacer oligonucleotide, either of them may be located on the 5' side, and the sense strand comprising sequence X is preferably located on the 5' side.

The nucleotides to be added to the sequence X strand and the complementary sequence X' strand, and the bases of the spacer oligonucleotide may be any one type or plural types selected from guanine, adenine, cytosine, thymine and uracil. A sugar bonded to each base may be ribose, deoxyribose or ribose substituted at the 2'-hydroxy group with a modifying group. The nucleotides to be added are more preferably any one type or two types selected from uridylic acid (U) and deoxythymidylic acid (dT). The sequence of the bases of the nucleotides to be added to the 3' end of the sequence X strand may be the same as the sequence of bases of nucleotides adjacent to sequence X within the mRNA of the target gene. The sequence of the bases of the nucleotides to be added to the 3' end of the complementary sequence X' strand may be complementary to the sequence of bases of nucleotides adjacent to sequence X within the mRNA of the target gene.

More preferred examples of the RNA used in the present invention include (a) double-stranded RNA consisting of a sense oligonucleotide comprising sequence X and an antisense oligonucleotide comprising complementary sequence X', wherein: the sequence X is a sequence of 19 to 21 consecutive bases of the mRNA of the target gene; the sense oligonucleotide consists of a sequence X strand and 2 to 4 same or different nucleotides added to the 3' end of the sequence X strand; and the antisense oligonucleotide consists of a complementary sequence X' strand and 2 to 4 same or different nucleotides added to the 3' end of the complementary sequence X' strand, (b) double-stranded RNA consisting of a sense oligonucleotide comprising sequence X and an antisense oligonucleotide comprising complementary sequence X', wherein: the sequence X is a sequence of 23 to 25 consecutive bases of the mRNA of the target gene; the sense oligonucleotide is a sequence X strand; and the antisense oligonucleotide is a complementary sequence X' strand, and (c) double-stranded RNA consisting of a sense oligonucleotide comprising sequence X and an antisense oligonucleotide comprising complementary sequence X', wherein: the sequence X is a sequence of 23 to 27 consecutive bases of the mRNA of the target gene; the sense oligonucleotide consists of a sequence X strand and 2 to 4 same or different nucleotides added to the 3' end of the sequence X strand; the antisense oligonucleotide consists of a complementary sequence X' strand and 2 to 4 same or different nucleotides added to the 3' end of the complementary sequence X' strand; and the sequence of the bases of the nucleotides to be added to the 3' end of the complementary sequence X' strand is complementary the sequence of the bases of nucleotides adjacent to sequence X within the mRNA of the target gene.

Further examples of the RNA used in the present invention preferably include RNA having an inhibitory effect on the expression of the target gene through the use of RNA interference (RNAi).

The single-stranded oligonucleotide is synthesized by use of a solid-phase phosphoramidite method [see Nucleic Acids Research, 30, 2435 (1993)], deprotected, and desalted on NAP-5 column (Amersham Pharmacia Biotech Ltd., Piscataway, N.J.). The oligomer is purified by ion-exchange high-performance liquid chromatography (IE-HPLC) on Amersham Source 15Q column (1.0 cm, height: 25 cm; Amersham Pharmacia Biotech Ltd., Piscataway, N.J.) using a linear gradient in a 15-minute step. The gradient shifts from buffer solution A:B of 90:10 to buffer solution A:B of 52:48. The buffer solution A is 100 mmol/L Tris, pH 8.5, and the buffer solution B is 100 mmol/L Tris, pH 8.5 (1 mol/L NaCl). A sample is monitored at 260 nm, and a peak corresponding to full-length oligonucleotide species is collected, pooled, desalted on NAP-5 column, and freeze-dried.

The purity of each single-stranded oligonucleotide is determined by capillary electrophoresis (CE) using Beckman PACE 5000 (Beckman Coulter, Inc., Fullerton, Calif.). The CE capillary has an inside diameter of 100 m and contains ssDNA 100R Gel (Beckman-Coulter, Inc.). Typically, approximately 0.6 nmole of the oligonucleotide is injected to the capillary, and CE is carried out in an electric field of 444 V/cm, followed by the detection of UV absorbance at 260 nm. An electrophoresis buffer solution containing modified Tris-borate and 7 mol/L urea is purchased from Beckman Coulter, Inc. A single-stranded oligonucleotide having at least 90% purity evaluated by CE is obtained for use in an experiment mentioned below. Compound identity is verified by matrix-assisted laser desorption/ionization time of flight (MALDI-TOF) mass spectrometry using Voyager DE™ Biospectometry workstation (Applied Biosystems, Inc., Foster City, Calif.) according to manufacturer's recommended protocol. The relative molecular mass of the single-stranded oligonucleotide can be obtained within 0.2% of a predicted molecular mass.

The single-stranded oligonucleotide is resuspended at a concentration of 100 μmol/L in a buffer solution consisting of 100 mmol/L potassium acetate and 30 mmol/L HEPES, pH 7.5. The complementary sense strand and the antisense strand are mixed in equimolar amounts to obtain a final solution of 50 μmol/L double-stranded oligonucleotide. The sample is heated to 95° C. for 5 minutes and cooled to room temperature before use. The double-stranded nucleic acid is preserved at −20° C. The single-stranded oligonucleotide is freeze-dried or stored at −80° C. in nuclease-free water.

L1 and L2 are each independently a sugar ligand.

In the present invention, the sugar ligand means a group derived from a saccharide (monosaccharide, disaccharide, trisaccharide and polysaccharide, etc.) capable of binding to a receptor expressed on a target cell. In the present invention, when the sugar ligand is bonded to linker S1 or S2 through an O— bond, the sugar ligand as a group derived from a saccharide means a sugar ligand-constituting moiety, except for a hydroxy group, involved in the binding of the saccharide.

In the present invention, the sugar ligand can be selected such that the cell is targeted by the oligonucleotide.

Examples of the monosaccharide include allose, aldose, arabinose, cladinose, erythrose, erythrulose, fructose, D-fucitol, L-fucitol, fucosamine, fucose, fuculose, galactosamine, D-galactosaminitol, N-acetylgalactosamine, galactose, glucosamine, N-acetyl-glucosamine, glucosaminitol, glucose, glucose-6-phosphate, gulose, glyceraldehyde, L-glycero-D-manno-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose, and xylulose.

Examples of the disaccharide, the trisaccharide, and the polysaccharide include abequose, acarbose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evemitrose, fructo-oligosaccharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotriose, melicitose, melibiose, muramic acid, mycarose, mycinose, neuraminic acid, sialic acid-containing sugar chains, nigerose, nojirimycin, nobiose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose, xylobiose, and umbelliferose.

Each monosaccharide as the saccharide may be in a D form or a L form and may be a mixture of D and L forms at an arbitrary ratio.

The saccharide may contain deoxysugar (derived by the replacement of an alcoholic hydroxy group with a hydrogen atom), aminosugar (derived by the replacement of an alcoholic hydroxy group with an amino group), thiosugar (derived by the replacement of an alcoholic hydroxy group with thiol, the replacement of C=O with C=S, or the replacement of ring oxygen with sulfur), selenosugar, tellurosugar, azasugar (derived by the replacement of ring carbon with nitrogen), iminosugar (derived by the replacement of ring oxygen with nitrogen), phosphano-sugar (derived by the replacement of ring oxygen with phosphorus), phospha-sugar (derived by the replacement of ring carbon with phosphorus), C-substituted monosaccharide (derived by the replacement of a hydrogen atom on a nonterminal carbon atom with a carbon atom), unsaturated monosaccharide, alditol (derived by the replacement of a carbonyl group with a CHOH group), aldonic acid (derived by the replacement of an aldehyde group with a carboxy group), ketoaldonic acid, uronic acid, aldaric acid, or the like.

Examples of the aminosugar include amino monosaccharides as the saccharide, such as galactosamine, glucosamine, mannosamine, fucosamine, quinovosamine, neuraminic acid, muramic acid, lactosediamine, acosamine, bacillosamine, daunosamine, desosamine, forosamine, galosamine, kanosamine, kansosamine, mycaminose, mycosamine, perosamine, pneumosamine, purpurosamine, and rhodosamine. The amino group of the aminosugar may be substituted with an acetyl group or the like.

Examples of the sialic acid-containing sugar chains include sugar chains containing NeuAc at their non-reducing ends and include sugar chains containing NeuAc-Gal-GlcNAc, and Neu5Acα(2-6)Galβ(1-3)GlcNAc.

Each monosaccharide as the saccharide may be substituted with a substituent as long as the monosaccharide is capable of binding to a receptor expressed on a target cell. For example, the monosaccharide may be substituted with a hydroxy group, or one or more hydrogen atoms in each monosaccharide may be replaced with azide and/or an optionally substituted aryl group.

The sugar ligand is preferably selected as a sugar ligand binding to a receptor expressed on the surface of a target cell according to each targeted organ. When the target cell is, for example, a liver cell, the sugar ligand is preferably a sugar ligand against a receptor expressed on the surface of the liver cell, more preferably a sugar ligand against an asialoglycoprotein receptor (ASGPR).

The sugar ligand against ASGPR is preferably mannose or N-acetylgalactosamine, more preferably N-acetylgalactosamine.

For example, sugar derivatives described in Bioorganic Medicinal Chemistry, 17, 7254 (2009), and Journal of American Chemical Society, 134, 1978 (2012) are known as sugar ligands having higher affinity for ASGPR, and these sugar derivatives may be used.

In the present invention, each of S1, S2 and S3 is a linker.

S1 and S2 are not particularly limited as long as their structures link sugar ligands L1 and L2 to the benzene ring. A structure known in the art for use in nucleic acid conjugates may be adopted. S1 and S2 may be the same or may be different.

Sugar ligands L1 and L2 are preferably linked to S1 and S2 through glycoside bonds. S1 and S2 may each be linked to the benzene ring, for example, through a —CO—, —NH—, —O—, —S—, —O—CO—, —S—CO—, —NH—CO—, —CO—O—, —CO—S— or —CO—NH— bond.

S3 is not particularly limited as long as its structure links oligonucleotide X to the benzene ring. A structure known in the art for use in nucleic acid conjugates may be adopted.

Oligonucleotide X is preferably linked to S3 through a phosphodiester bond. S3 may be linked to the benzene ring, for example, through a —CO—, —NH—, —O—, —S—, —O—CO—, —S—CO—, —NH—CO—, —CO—O—, —CO—S— or —CO—NH— bond.

For example, structures disclosed in International Publication Nos. WO 2009/073809, WO 2013/075035, WO 2015/105083, WO 2014/179620, and WO 2015/006740 may be adopted as linkers S1, S2 and S3.

In the present invention, the nucleic acid conjugate is preferably a nucleic acid conjugate having a structure represented by the following formula 2:

Formula 2

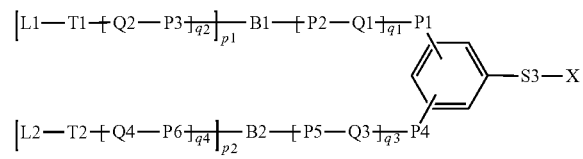

In formula 2,

X, L1, L2 and S3 are each as defined above,

P1, P2, P3, P4, P5 and P6, and T1 and T2 are each independently absent, or —CO—, —NH—, —O—, —S—, —O—CO—, —S—CO—, —NH—CO—, —CO—O—, —CO—S— or —CO—NH—, Q1, Q2, Q3 and Q4 are each independently absent, or substituted or unsubstituted alkylene having 1 to 12 carbon atoms or —(CH$_2$CH$_2$O)$_n$—CH$_2$CH$_2$— wherein n is an integer of 0 to 99, B1 and B2 are each independently a bond, or any structure represented by the following formula 2-1, wherein each of the terminal dots in each structure is a binding site to P2 or P3, or P5 or P6, and m1, m2, m3 and m4 are each independently an integer of 0 to 10:

Formula 2-1

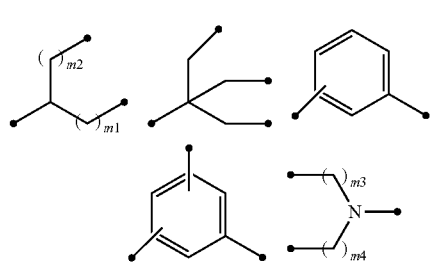

p1 and p2 are each independently an integer of 1, 2 or 3, and q1, q2, q3 and q4 are each independently an integer of 0 to 10, provided that when each of p1 and p2 is an integer of 2 or 3, each P3 and P6, Q2 and Q4, T1 and T2 or L1 and L2 are the same or different.

P1 and P4 are each independently absent, or —CO—, —NH—, —O—, —S—, —O—CO—, —S—CO—, —NH—CO—, —CO—O—, —CO—S— or —CO—NH— and are each preferably —O—, —O—CO—, —NH—CO— or —CO—NH—, more preferably —O—, —NH—CO— or —CO—NH—, further preferably —NH—CO—.

When P1 or P4 is, for example, —NH—CO—, a substructure —NH—CO-benzene ring is present.

Q1, Q2, Q3 and Q4 are each independently absent, or substituted or unsubstituted alkylene having 1 to 12 carbon atoms or —(CH$_2$CH$_2$O)$_n$—CH$_2$CH$_2$— wherein n is an integer of 0 to 99, and are each preferably substituted or unsubstituted alkylene having 1 to 12 carbon atoms, more preferably unsubstituted alkylene having 1 to 12 carbon atoms, further preferably unsubstituted alkylene having 1 to 6 carbon atoms, still further preferably unsubstituted alkylene having 1 to 4 carbon atoms.

P2 and P5 are each independently absent, or —CO—, —NH—, —O—, —S—, —O—CO—, —S—CO—, —NH—CO—, —CO—O—, —CO—S— or —CO—NH— and are each preferably absent, —CO—O— or —CO—NH—, more preferably absent or —CO—NH—. When each of P2 and P5 is, for example, —CO—NH—, substructures B1-CO—NH-Q1 and B2-CO—NH-Q3 are present.

—(P2-Q1)$_{q1}$- and —(P5-Q3)$_{q3}$- are each independently preferably absent, or any structure represented by the following formulas 3-1 to 3-3:

Formula 3-1

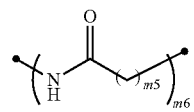

Formula 3-2

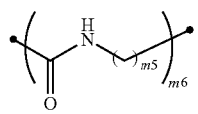

Formula 3-3

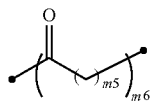

In formulas 3-1 to 3-3,
m5 and m6 are each independently an integer of 0 to 10, and each of the terminal dots in the structures of formulas 3-1 to 3-3 is a binding site to B1 or B2, or P1 or P4.

B1 and B2 are each independently a bond, or any structure represented by the following formulas, wherein each of the terminal dots in each structure is a binding site to P2 or P3, or P5 or P6, and m1, m2, m3 and m4 are each independently an integer of 0 to 10:

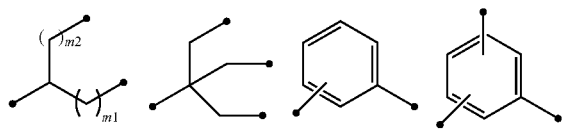

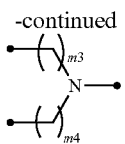

Each of B1 and B2 is preferably a group derived from an amino acid such as glutamic acid, aspartic acid, lysine, including non-natural amino acids such as iminodiacetic acid, or an amino alcohol such as 1,3-propanediol. When B1 and B2 are groups derived from glutamic acid or aspartic acid, it is preferred that the amino group of each glutamic acid or aspartic acid should be bonded while P2 and P5 should be —NH—CO— bonds. When B1 and B2 are groups derived from lysine, it is preferred that the carboxyl group of each lysine should be bonded while P2 and P5 should be —CO—NH— bonds. When B1 and B2 are groups derived from iminodiacetic acid, it is preferred that the amino group of each iminodiacetic acid should be bonded while P2 and P5 should be —CO— bonds.

In the present invention, the nucleic acid conjugate is preferably a nucleic acid conjugate having any structure represented by the following formulas 4-1 to 4-9:

Formula 4-1

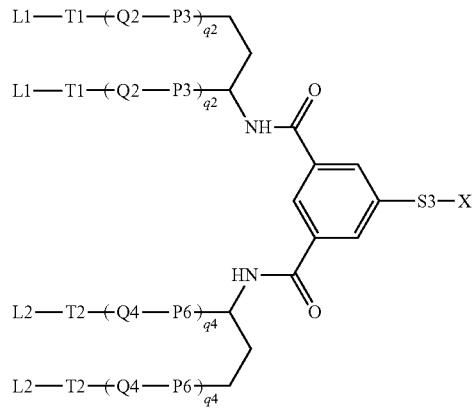

Formula 4-2

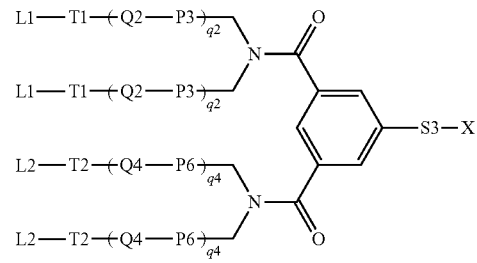

Formula 4-3

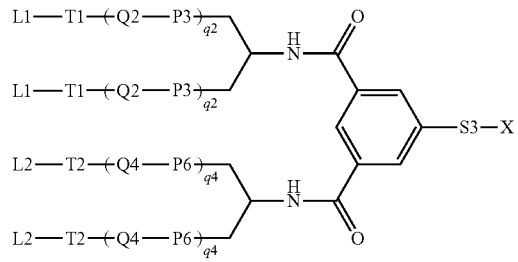

Formula 4-4

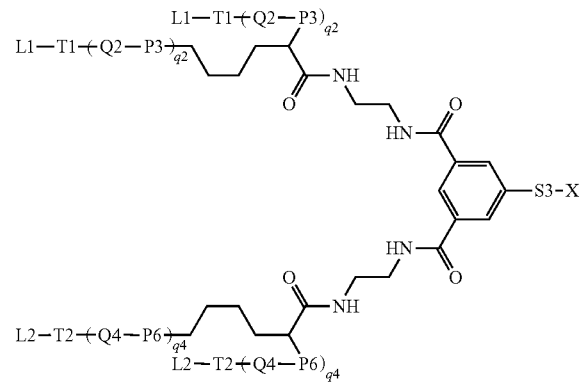

Formula 4-5
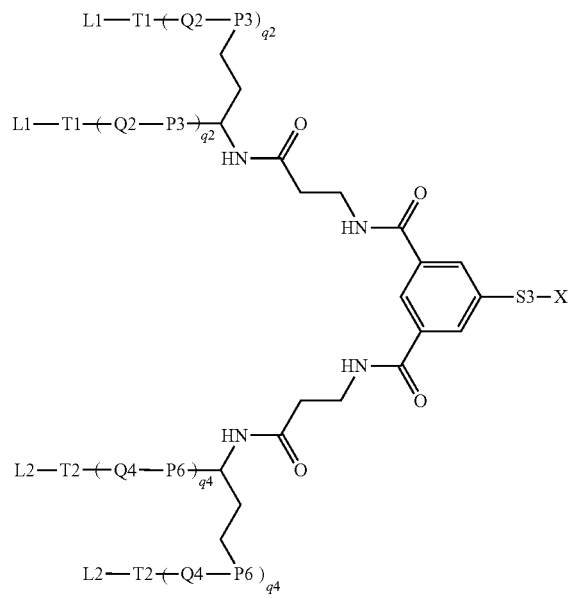
Formula 4-6
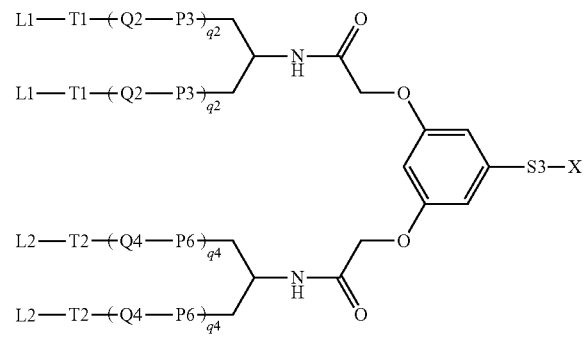
Formula 4-7
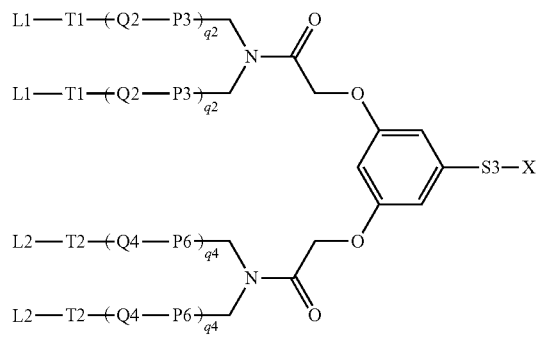
Formula 4-8
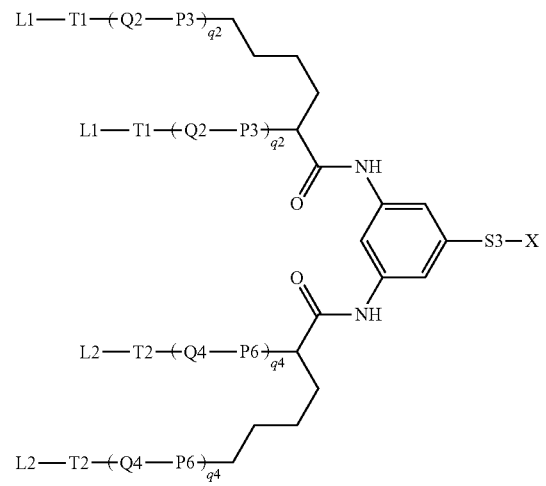
Formula 4-9
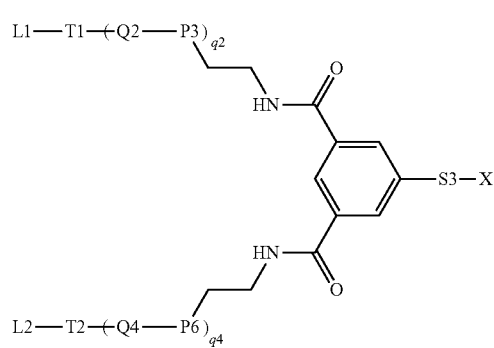

In formulas 4-1 to 4-9,

X, L1, L2, S3, P3, P6, T1, T2, Q2, Q4, q2 and q4 are each as defined above.

P3 and P6 are each independently absent, or —CO—, —NH—, —O—, —S—, —O—CO—, —S—CO—, —NH—CO—, —CO—O—, —CO—S— or —CO—NH— and are each preferably —O—CO— or —NH—CO—, more preferably —NH—CO—. When each of P3 and P6 is, for example, —NH—CO—, substructures B1-NH—CO-Q2 and B2-NH—CO-Q4 are present.

T1 and T2 are each independently absent, or —CO—, —NH—, —O—, —S—, —O—CO—, —S—CO—, —NH—CO—, —CO—O—, —CO—S— or —CO—NH— and are each preferably —O— or —S—, more preferably —O—.

In the present invention, the nucleic acid conjugate is preferably a nucleic acid conjugate having a structure represented by formula 5 given below.

In formula 5, P1 and P4 in formula 2 are the same; P2 and P5 in formula 2 are the same; P3 and P6 in formula 2 are the same; Q1 and Q3 in formula 2 are the same; Q2 and Q4 in formula 2 are the same; B1 and B2 in formula 2 are the same; T1 and T2 in formula 2 are the same; L1 and L2 in formula 2 are the same; p1 and p2 in formula 2 are the same; q1 and q3 in formula 2 are the same; and q2 and q4 in formula 2 are the same.

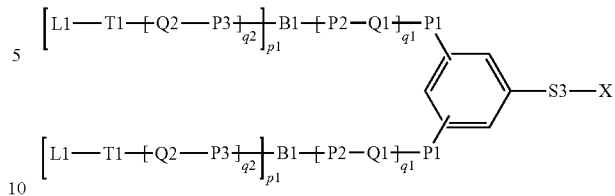

Formula 5

In formula 5,

X, S3, P1, P2, P3, Q1, Q2, B1, T1, L1, p1, q1 and q2 are each as defined above.

X, S3, P1, P2, P3, Q1, Q2, B1, T1, L1, p1, q1 and q2 in formula 5 can each be any of the preferred groups mentioned above. P1 is preferably —CO—NH—, —NH—CO— or —O—.

$(P2-Q1)_{q1}$- in formula 5 is preferably absent, or any structure represented by formulas 3-1 to 3-3 described above.

In the present invention, the nucleic acid conjugate is preferably a nucleic acid conjugate having any structure represented by the following formulas 6-1 to 6-9:

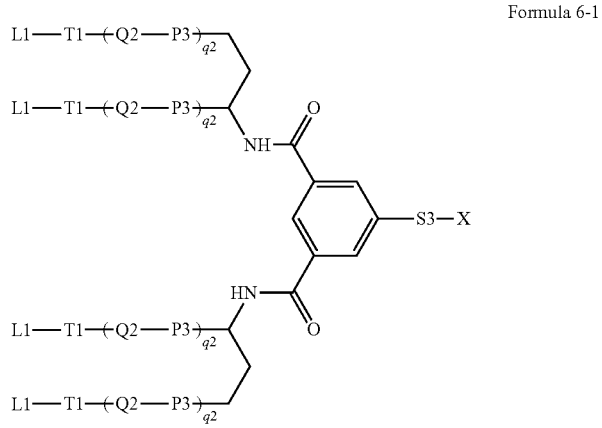

Formula 6-1

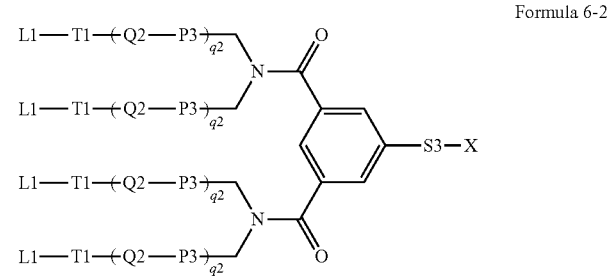

Formula 6-2

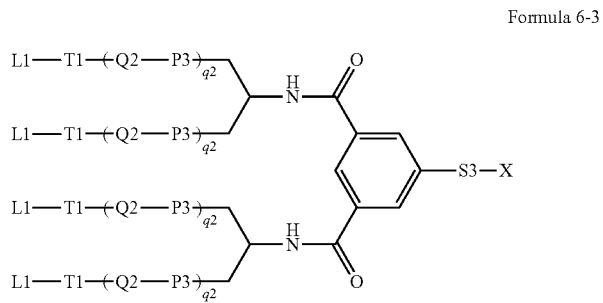

Formula 6-3

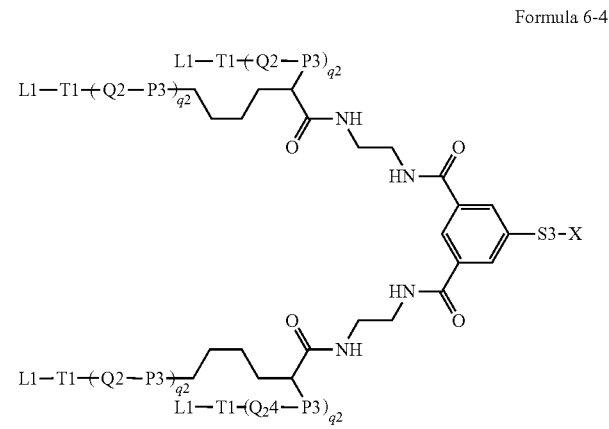

Formula 6-4

Formula 6-5
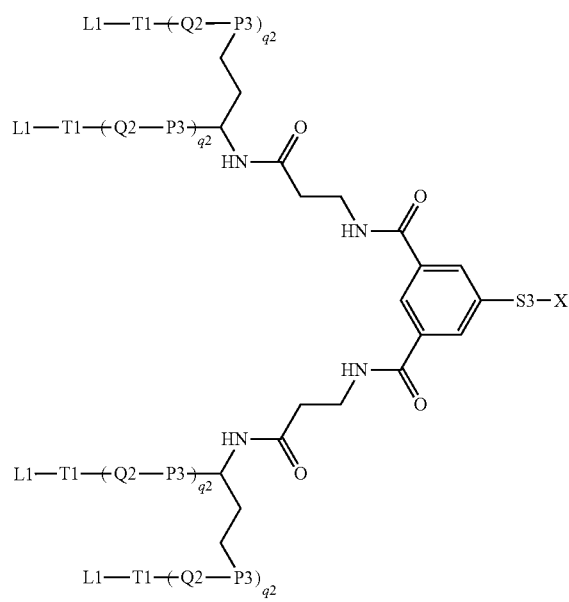
Formula 6-6
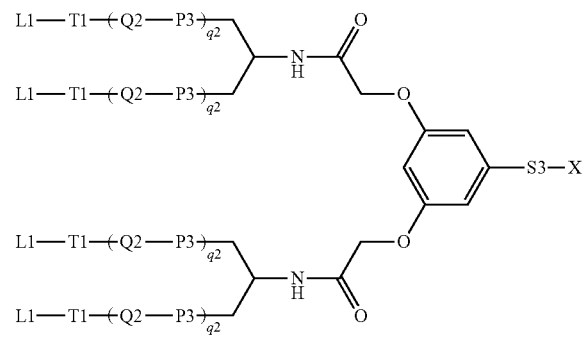
Formula 6-7
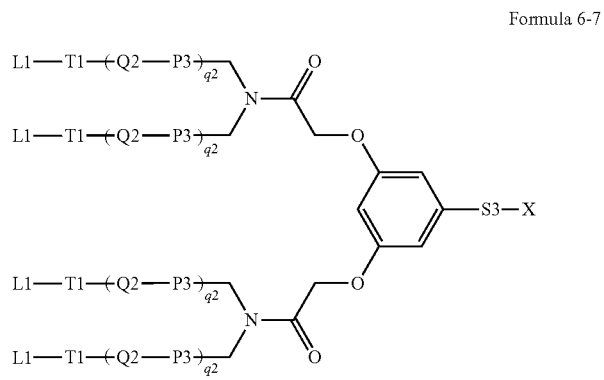
Formula 6-8
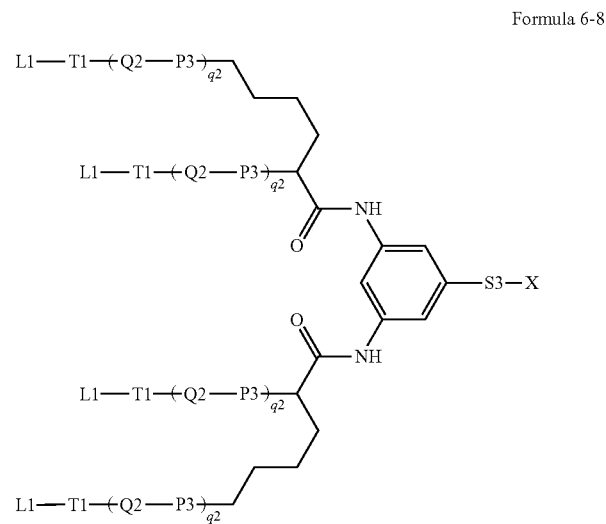
Formula 6-9
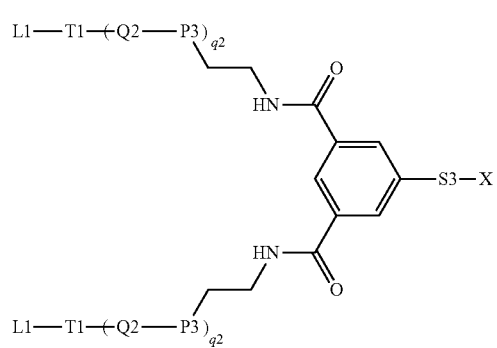

In formulas 6-1 to 6-9,
X, S3, P3, Q2, T1, and L1 are each as defined above.
In the present invention, the nucleic acid conjugate is preferably a nucleic acid conjugate having any structure represented by the following formulas 7-1 to 7-9:
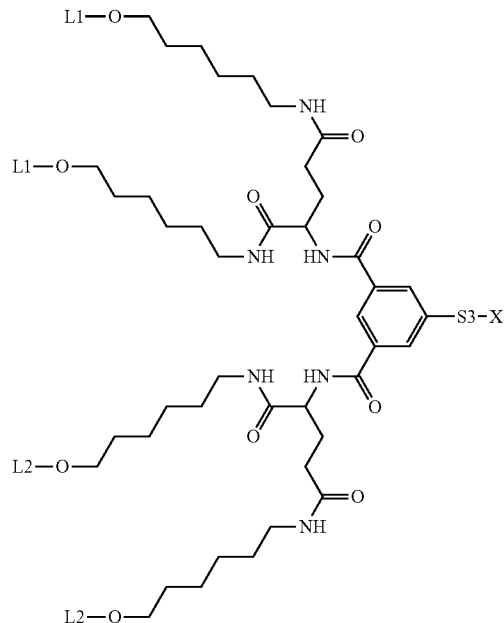
Formula 7-1
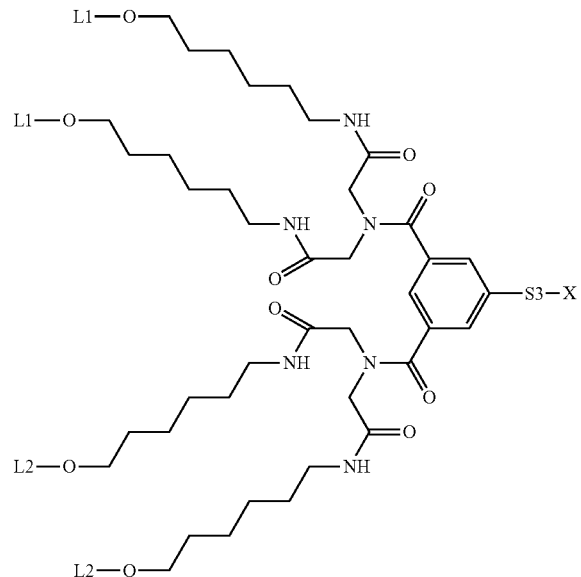
Formula 7-2
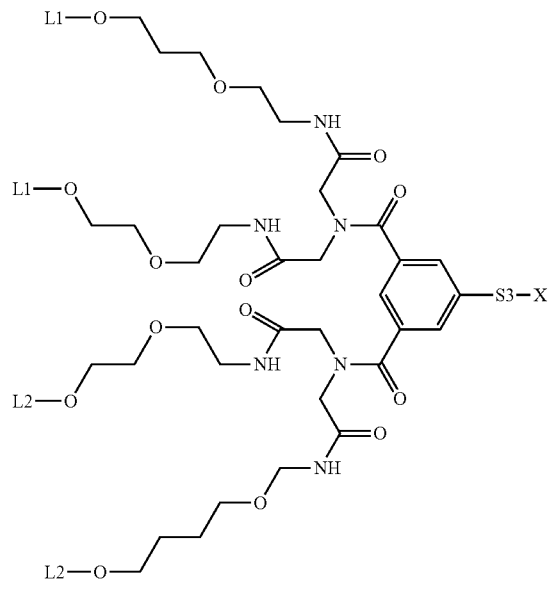
Formula 7-3
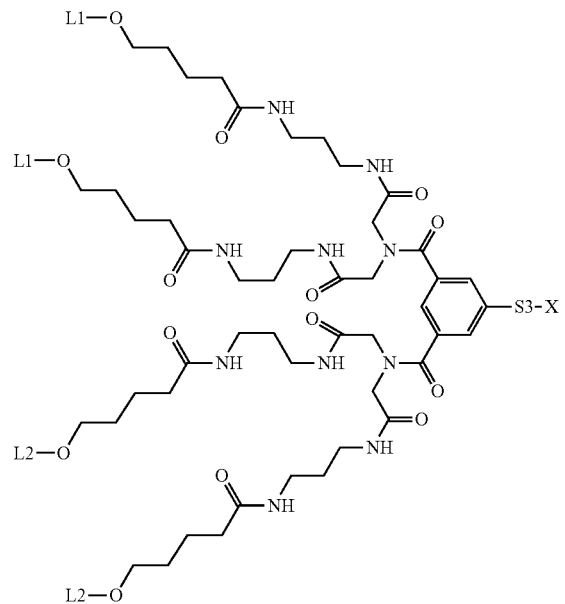
Formula 7-4

Formula 7-5
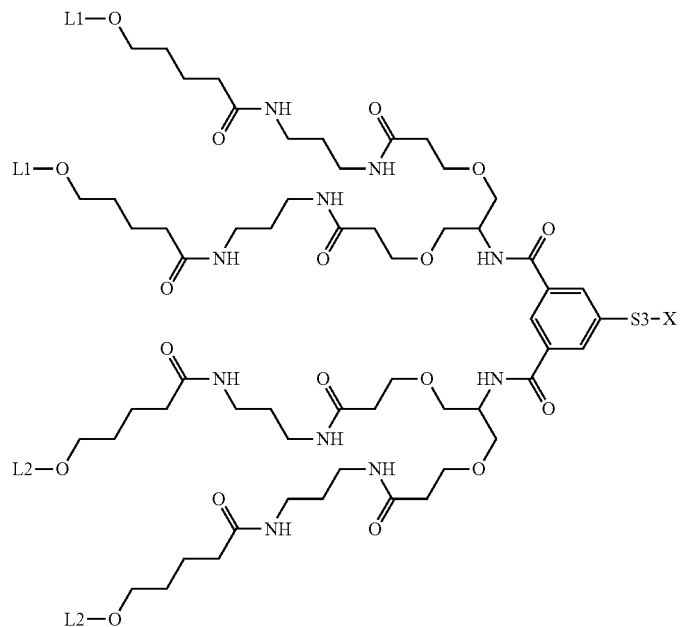
Formula 7-6
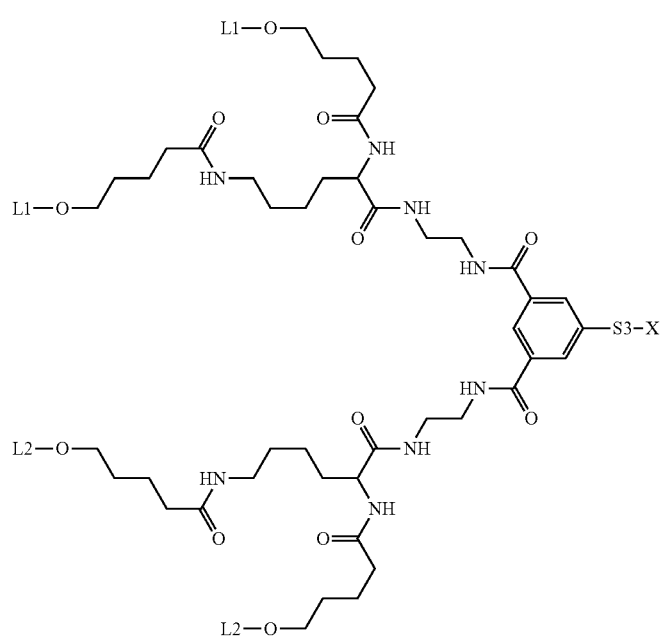

-continued

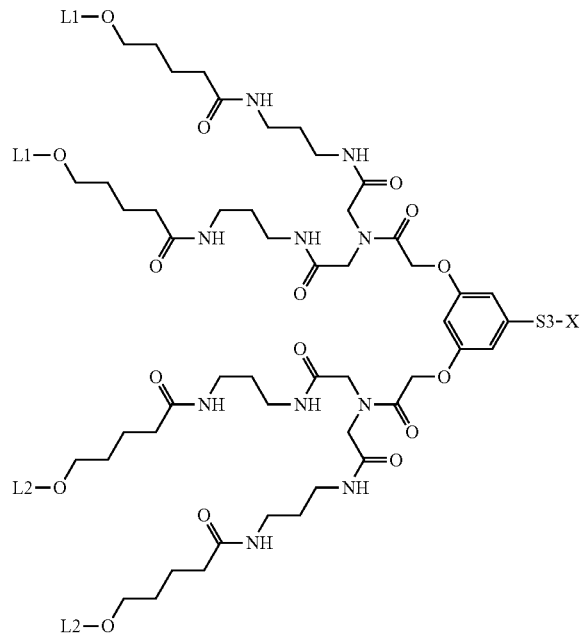

Formula 7-8

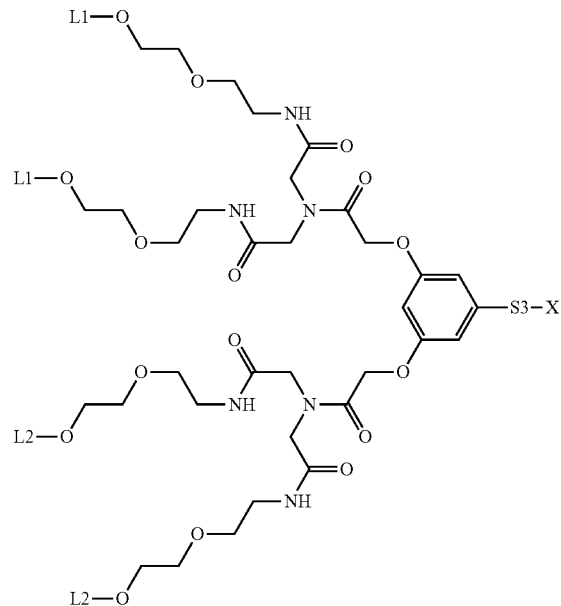

Formula 7-9

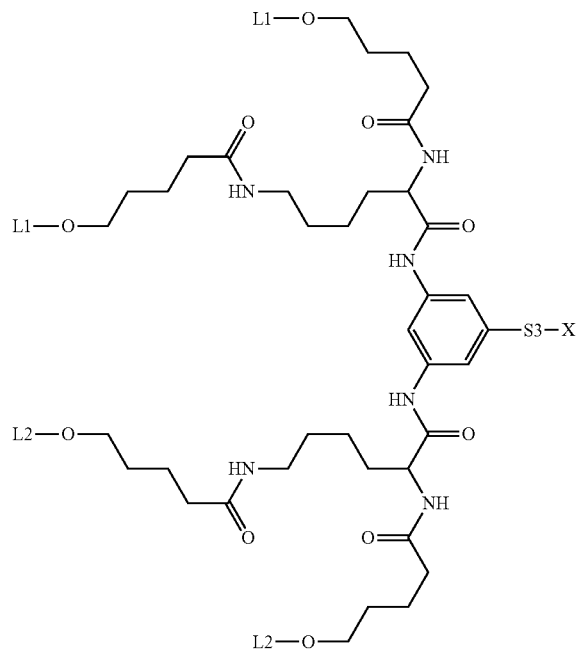

In formulas 7-1 to 7-9,

X, L1, L2 and S3 are each as defined above. L1 and L2 may be the same or may be different and is preferably the same.

A nucleic acid derivative other than the nucleic acid conjugate having any structure represented by formulas 7-1 to 7-9 can also be produced by introducing alkylene chains differing in chain length as each alkylene group moiety in formulas 7-1 to 7-9, or by replacing an amide bond or the like with another bond.

In the present invention, the nucleic acid conjugate is preferably a nucleic acid conjugate having a structure represented by the following formula 11:

Formula 11

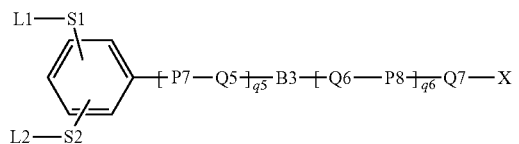

In formula 11,

L1, L2, S1 and S2 are each as defined above,

P7 and P8 are each independently absent, or —CO—, —NH—, —O—, —S—, —O—CO—, —S—CO—, —NH—CO—, —CO—O—, —CO—S— or —CO—NH—, Q5, Q6 and Q7 are each independently absent, or substituted or unsubstituted alkylene having 1 to 12 carbon atoms or —(CH$_2$CH$_2$O)$_{n8}$—CH$_2$CH$_2$— wherein n8 is an integer of 0 to 99, B3, which is referred to as a brancher unit in the present specification, is any structure represented by the following formula 11-1, wherein the broken lines respectively mean bonds to Q5 and Q6:

Formula 11-1

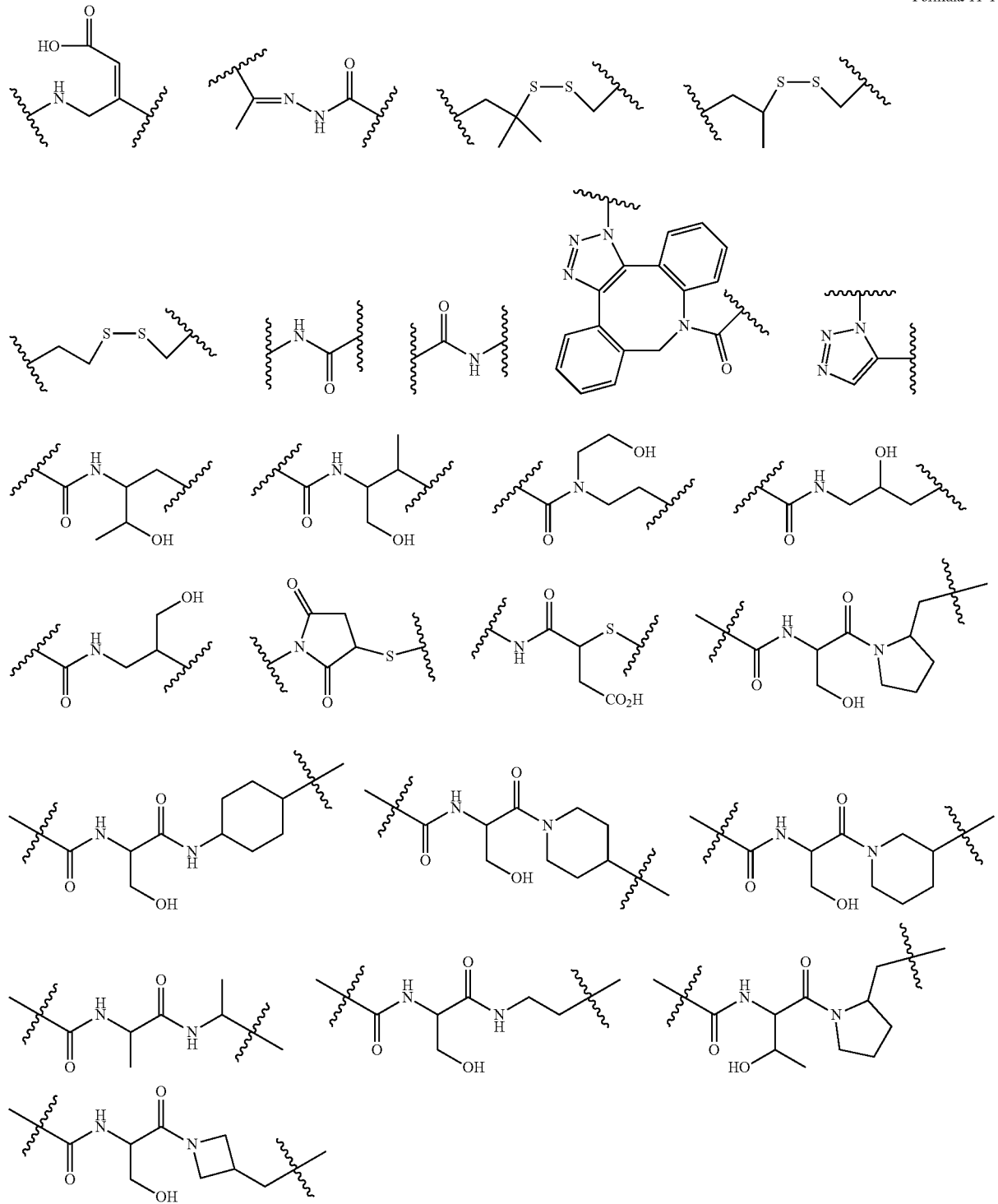

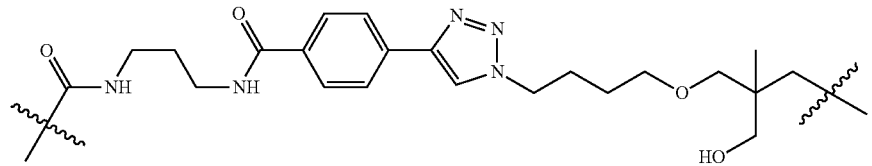

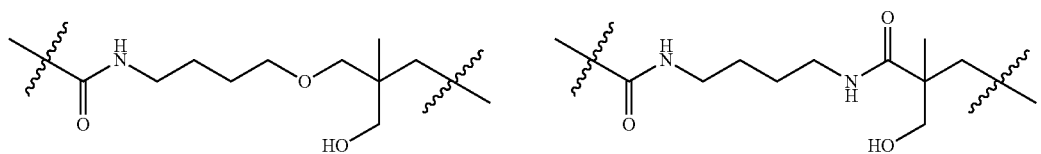

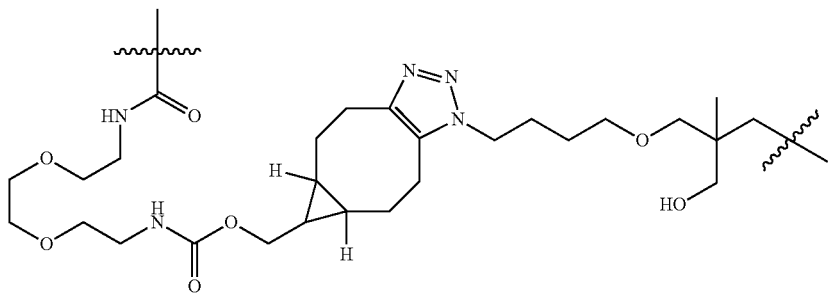

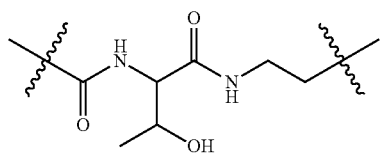

and q5 and q6 are each independently an integer of 0 to 10.

P7 is absent, or —CO—, —NH—, —O—, —S—, —O—CO—, —S—CO—, —NH—CO—, —CO—O—, —CO—S— or —CO—NH— and is preferably —O—, —NH—CO— or —CO—NH—, more preferably —O— or —NH—CO—. When P7 is, for example, —O—, a substructure benzene ring-O— is present.

P8 is absent, or —CO—, —NH—, —O—, —S—, —O—CO—, —S—CO—, —NH—CO—, —CO—O—, —CO—S— or —CO—NH—. When P8 is present, P8 is preferably —CO—O— or —CO—NH—, more preferably —CO—NH—. When P8 is, for example, —CO—NH—, a substructure Q6-CO—NH— is present.

Q5, Q6 and Q7 are each independently absent, or substituted or unsubstituted alkylene having 1 to 12 carbon atoms or —(CH$_2$CH$_2$O)ne-CH$_2$CH$_2$— wherein n8 is an integer of 0 to 99, and are each preferably substituted or unsubstituted alkylene having 1 to 12 carbon atoms, more preferably unsubstituted alkylene having 1 to 12 carbon atoms, further preferably unsubstituted alkylene having 1 to 6 carbon atoms, still further preferably unsubstituted alkylene having 1 to 4 carbon atoms.

Preferably, —(P7-Q5)$_{q5}$- is —O—(CH$_2$)$_{m15}$—NH— or —NH—CO—(CH$_2$)$_{m16}$—NH—, and m15 and m16 are each independently an integer of 1 to 10.

In the present invention, the nucleic acid conjugate is preferably a nucleic acid conjugate having any structure represented by the following formulas 12-1 to 12-12:

Formula 12-1
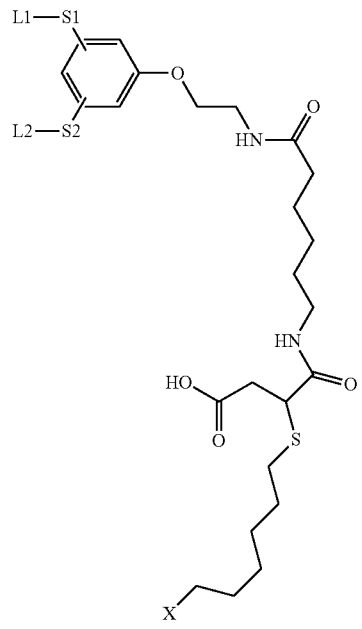
Formula 12-2
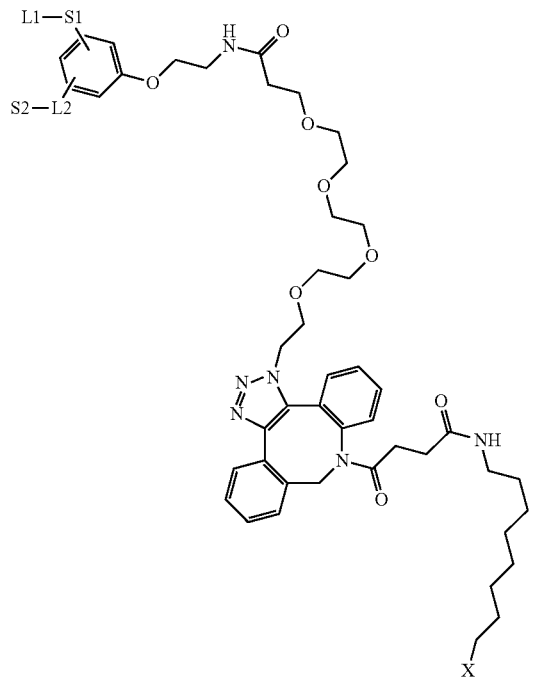
Formula 12-3
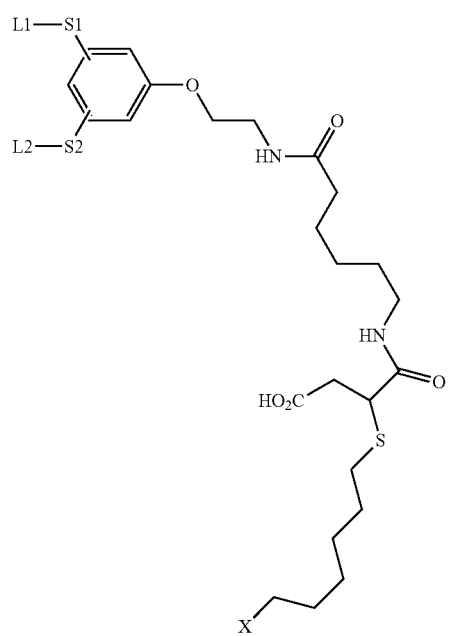
Formula 12-4
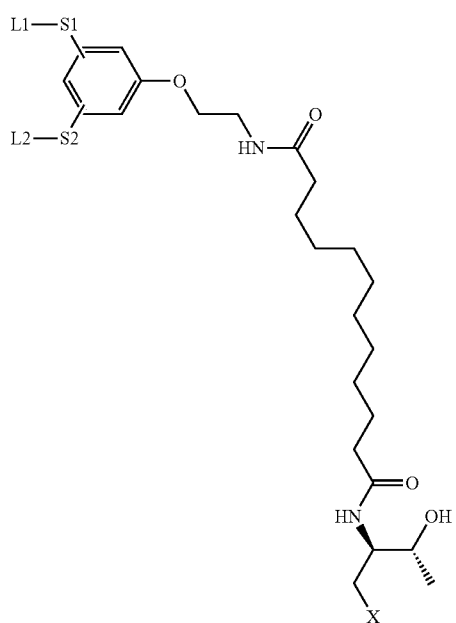

Formula 12-5
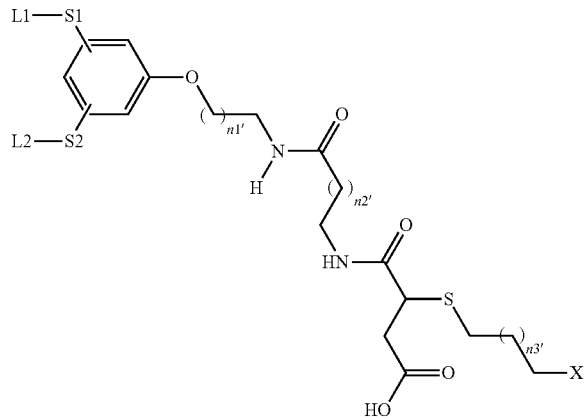
Formula 12-6
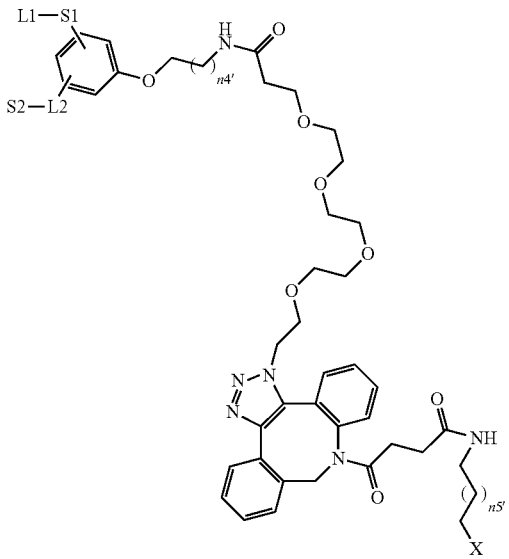
Formula 12-7
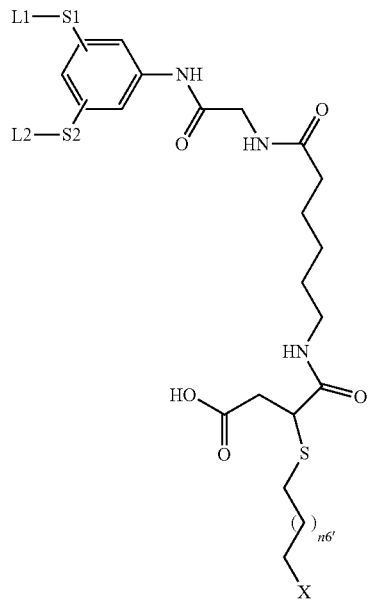
Formula 12-8
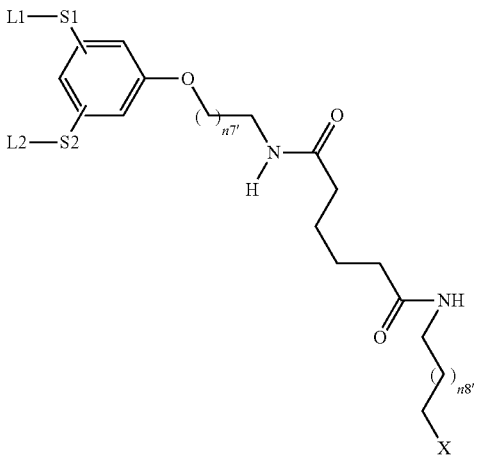
Formula 12-9
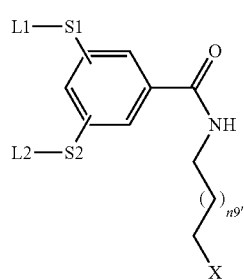

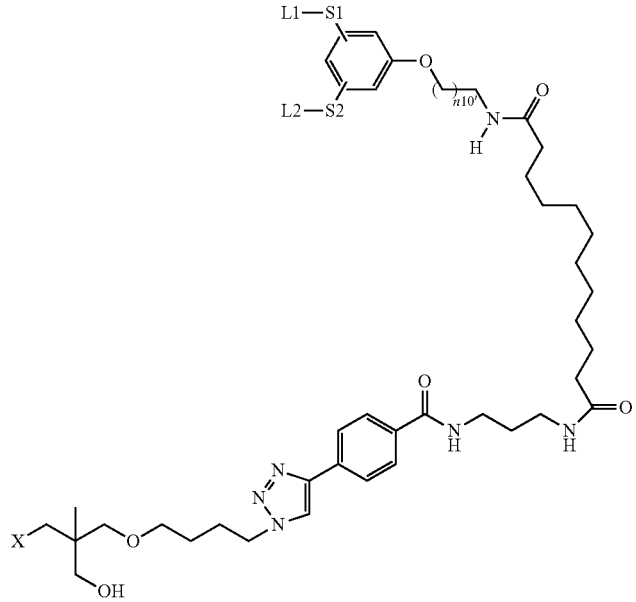

Formula 12-10

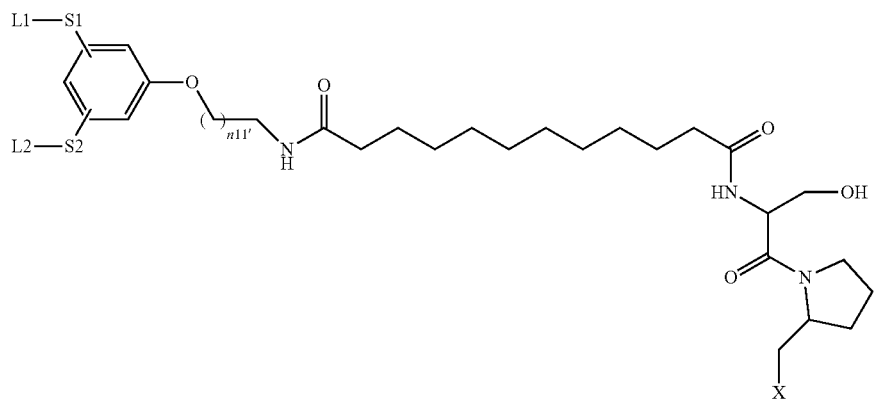

Formula 12-11

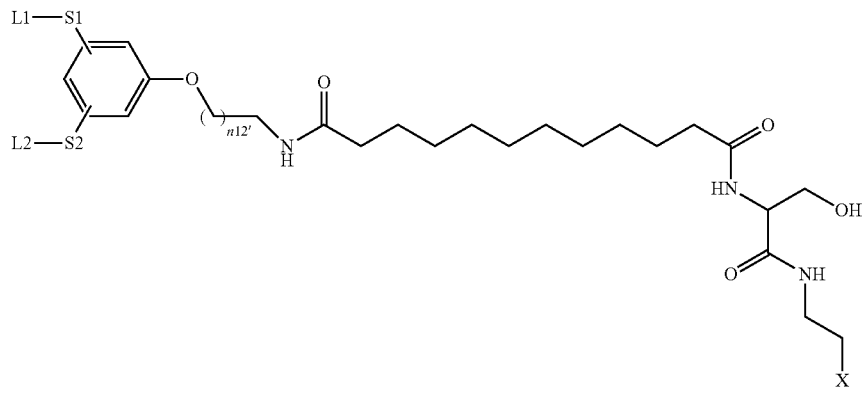

Formula 12-12

In formulas 12-1 to 12-12,

X, L1, L2, S1 and S2 are each as defined above, and n1' to n12' are each independently an integer of 1 to 10.

The nucleic acid conjugate of the present invention is preferably a nucleic acid conjugate having both the structures of formula 2 and formula 11 as the nucleic acid conjugate represented by formula 1. The nucleic acid conjugate has the structure of formula 11, and formula 2 may be any of formulas 4-1 to 4-9, may be any of formulas 6-1 to 6-9, or may be any of formulas 7-1 to 7-9. When formula 2 is any of formulas 4-1 to 4-9, formulas 6-1 to 6-9, or formulas 7-1 to 7-9, formula 11 may be any of formulas 12-1 to 12-12. The nucleic acid conjugate of the present invention is more preferably a nucleic acid conjugate having both of any one structure of formulas 4-1 to 4-9 and any one structure of formulas 12-1 to 12-12, a nucleic acid conjugate having both of any one structure of formulas 6-1 to 6-9 and any one structure of formulas 12-1 to 12-12, or a nucleic acid conjugate having both of any one structure of formulas 7-1 to 7-9 and any one structure of formulas 12-1 to 12-12, as the nucleic acid conjugate represented by formula 1.

The nucleic acid conjugate of the present invention may form a salt with a pharmaceutically acceptable anion when hydrogen ions are coordinated to a lone pair of electrons on any nitrogen atom.

In the present invention, examples of the pharmaceutically acceptable anion include: inorganic ions such as chloride ions, bromide ions, nitrate ions, sulfate ions, and phosphate ions; and organic acid ions such as acetate ions, oxalate ions, maleate ions, fumarate ions, citrate ions, benzoate ions, and methanesulfonate ions.

A method for producing the nucleic acid conjugate of the present invention will be described. In the production methods given below, if defined groups react under conditions of the production methods or are unsuitable for carrying out the production methods, the compounds of interest can be produced by use of methods for introducing and removing protective groups commonly used in organic synthetic chemistry [e.g., methods described in Protective Groups in Organic Synthesis, third edition, T. W. Greene, John Wiley & Sons Inc. (1999)] or the like. If necessary, the order of reaction steps including substituent introduction and the like may be changed.

The nucleic acid polymer represented by formula 1 can also be synthesized by solid-phase synthesis.

The nucleic acid polymer represented by formula 1 can be synthesized with reference to a method for synthesizing a linker structure known in the art for nucleic acid conjugates.

The synthesis of a L1-benzene ring unit having linker S1 or a L2-benzene ring unit having linker S2 in the nucleic acid conjugate represented by formula 1 will be described by taking the nucleic acid conjugate represented by formula 2 as an example.

The L1-benzene ring unit and the L2-benzene ring unit in the nucleic acid conjugate represented by formula 2 has linkages by P1, P2, P3, P4, P5, and P6, and T1 and T2.

The —CO—, —NH—, —O—, —S—, —O—CO—, —S—CO—, —NH—CO—, —CO—O—, —CO—S— or —CO—NH— bond represented by P1, P2, P3, P4, P5, and P6, and T1 and T2 can be appropriately synthesized by selecting a starting material suitable for forming the structure represented by formula 2 with reference to methods for binding reaction described in, for example, The Fourth Series of Experimental Chemistry 19, "Synthesis of Organic Compound I", Maruzen Co., Ltd. (1992) and The Fourth Series of Experimental Chemistry 20, "Synthesis of Organic Compound II", Maruzen Co., Ltd. (1992).

A substructure of the L1-benzene ring unit can be produced by sequentially bonding a compound having Q1 as a substructure and a compound having B1 as a substructure to the benzene ring.

The L1-benzene ring unit structure can be produced by separately synthesizing a compound having L1 and Q2 as a substructure, and bonding the compound having L1 and Q2 as a substructure to a compound having a substructure of a L1-benzene ring unit having the benzene ring, Q1 and B1 as a substructure.

Likewise, a substructure of the L2-benzene ring unit can be produced by sequentially bonding a compound having Q3 as a substructure and a compound having B2 as a substructure to the benzene ring.

The L2-benzene ring unit structure can be produced by separately synthesizing a compound having L2 and Q4 as a substructure, and bonding the compound having L2 and Q4 as a substructure to a compound having a substructure of a L2-benzene ring unit having the benzene ring, Q3 and B2 as a substructure.

Examples of the compound having Q1 as a substructure and the compound having Q3 as a substructure include compounds having a hydroxy group, a carboxyl group, an amino group, and/or a thiol group at both ends of alkylene having 1 to 10 carbon atoms or —(CH$_2$CH$_2$O)$_n$—CH$_2$CH$_2$—.

Examples of the compound having B1 as a substructure and the compound having B2 as a substructure include compounds having any structure represented by the following formula 2-1 and having a hydroxy group, a carboxyl group, an amino group, or a thiol group at each of the terminal dots in each structure:

Formula 2-1

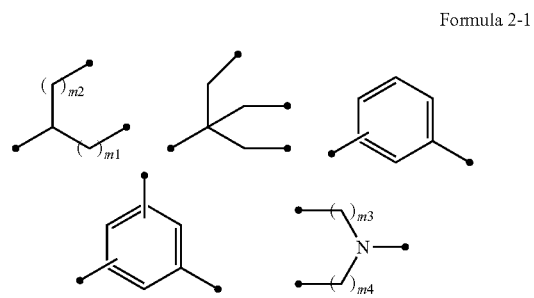

Specific examples of the compound having B1 as a substructure and the compound having B2 as a substructure include glycol, glutamic acid, aspartic acid, lysine, Tris, iminodiacetic acid, and 2-amino-1,3-propanediol. Glutamic acid, aspartic acid, lysine, or iminodiacetic acid are preferred.

The L1-benzene ring unit structure may be produced by synthesizing a compound having L1, Q2 and B1 as a substructure and then bonding this compound to a compound having Q1 and the benzene ring.

The L2-benzene ring unit structure may be produced by synthesizing a compound having L2, Q4 and B2 as a substructure and then bonding this compound to a compound having Q3 and the benzene ring.

In the present invention, the substructure [L1-T1-(Q2-P3)$_{q2}$-]$_{p1}$-B1-(P2-Q1)$_{q1}$-P1- and the substructure [L2-T2-(Q3-P6)$_{q4}$-]$_{p2}$-B2-(P5-Q3)$_{q3}$-P2- may be the same or different and are preferably the same.

Examples of the unit corresponding to L1-T1-Q2 in the sugar ligand include L3-T1-Q2-COOH and L3-T1-(Q2-P3)$_{q2-1}$-Q2-NH$_2$. Specific examples thereof include L3-O-alkylene having 1 to 12 carbon atoms-COOH and L3-alkylene having 1 to 12 carbon atoms-CO—NH-alkylene having 2 to 12 carbon atoms-NH$_2$.

L3 is not particularly limited as long as L3 is a sugar ligand derivative that is converted to L1 by deprotection. The substituent on the sugar ligand is not particularly limited as long as the substituent is routinely used in the field of carbohydrate chemistry. An Ac group is preferred.

Specifically, the L1-benzene ring unit having linker S1 or the L2-benzene ring unit having linker S2 can be synthesized by appropriately increasing or decreasing the number of carbon atoms of an alkylene chain, and using a compound with a terminal amino group or a terminal carboxyl group converted to a group capable of forming a —CO—, —NH—, —O—, —S—, —O—CO—, —S—CO—, —NH—CO—, —CO—O—, —CO—S— or —CO—NH— bond, with reference to a method described in Examples. Mannose or N-acetylgalactosamine is taken as an example of sugar ligand L1 in Examples. However, sugar ligand L1 may be changed to other sugar ligands for the practice.

The synthesis of an X-benzene ring unit having linker S3 in the nucleic acid conjugate represented by formula 1 will be described by taking the nucleic acid conjugate represented by formula 11 as an example.

The X-benzene ring unit in the nucleic acid conjugate represented by formula 11 has bonds represented by P7 and P8 in addition to the bond of the oligonucleotide.

The —CO—, —NH—, —O—, —S—, —O—CO—, —S—CO—, —NH—CO—, —CO—O—, —CO—S— or —CO—NH— bond represented by P7 and P8 can be appropriately synthesized by selecting a starting material suitable for forming the structure represented by formula 11 with reference to methods for binding reaction described in, for example, The Fourth Series of Experimental Chemistry 19, "Synthesis of Organic Compound I", Maruzen Co., Ltd. (1992) and The Fourth Series of Experimental Chemistry 20, "Synthesis of Organic Compound II", Maruzen Co., Ltd. (1992).

A substructure of the X-benzene ring unit can be produced by sequentially bonding a compound having Q5 as a substructure and a compound having B3 as a substructure to the benzene ring.

The X-benzene ring unit structure can be produced by separately synthesizing a compound having X and Q7 as a substructure or a compound having X and Q6 as a substructure, and bonding the compound having X and Q7 as a substructure or the compound having X and Q6 as a substructure to a compound having a substructure of a X-benzene ring unit having the benzene ring and Q5 as a substructure to construct the B3 moiety.

Specifically, the case of having an azide group at the end of the compound having a substructure of an X-benzene ring unit having the benzene ring and Q5 as a substructure will be taken as an example. The X-benzene ring unit structure can be produced by reacting an oligonucleotide allowed to have a terminal binding functional group as disclosed in Examples so that a triazole ring is formed by cycloaddition to construct the B3 moiety.

Examples of the compound having Q5 as a substructure, the compound having Q6 as a substructure, and the compound having Q7 as a substructure include compounds having a hydroxy group, a carboxyl group, an amino group, and/or a thiol group at both ends of alkylene having 1 to 10 carbon atoms or —(CH$_2$CH$_2$O)$_{n8}$—CH$_2$CH$_2$—.

The L1-benzene ring unit structure, the L2-benzene ring unit structure, and the X-benzene ring unit structure can be sequentially produced. It is preferred to synthesize the L1-benzene ring unit structure and the L2-benzene ring unit structure and then bond the X-benzene ring unit structure thereto. Particularly, it is preferred to introduce X having the oligonucleotide moiety into the compound near the final step of sugar ligand conjugate synthesis.

In the present invention, a compound represented by the following formulas 8 to 10 is obtained as an intermediate of synthesis:

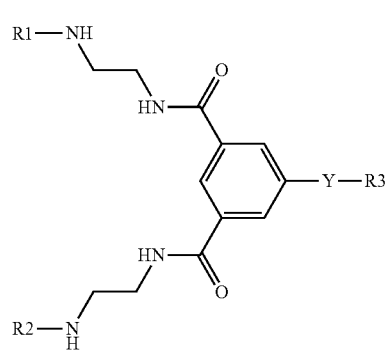

Formula 8 wherein
R1 and R2 are each independently a hydrogen atom, a t-butoxycarbonyl group (Boc group), a benzyloxycarbonyl group (Z group), a 9-fluorenylmethyloxycarbonyl group (Fmoc group), —CO—R4, or —CO—B4-[(P9-Q8)$_{q7}$-T3-L3]$_{p3}$, P9 and T3 are each independently absent, or —CO—, —NH—, —O—, —S—, —O—CO—, —S—CO—, —NH—CO—, —CO—O—, —CO—S— or —CO—NH—, Q8 is absent, or substituted or unsubstituted alkylene having 1 to 12 carbon atoms or —(CH$_2$CH$_2$O)$_{n1}$—CH$_2$CH$_2$— wherein n1 is an integer of 0 to 99, B4 is a bond, or any structure represented by the following formula 8-1, wherein each of the terminal dots in each structure is a binding site to a carbonyl group or P9, and m7, m8, m9 and m10 are each independently an integer of 0 to 10:

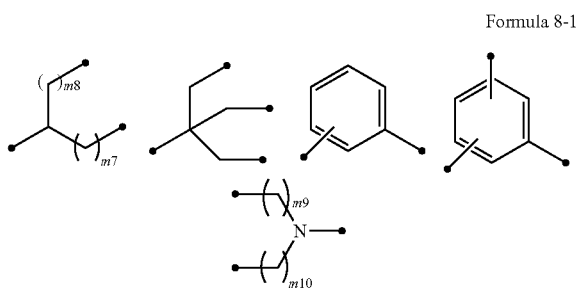

Formula 8-1 p3 is an integer of 1, 2 or 3,
q7 is an integer of 0 to 10,
L3 is a sugar ligand,
Y is —O—(CH$_2$)$_{m11}$—NH— or —NH—CO—(CH$_2$)$_{m12}$—NH— wherein m11 and m12 are each independently an integer of 1 to 10,
R3 is a hydrogen atom, a t-butoxycarbonyl group, a benzyloxycarbonyl group, a 9-fluorenylmethyloxycarbonyl group, —CO—R4, —CO— (CH$_2$CH$_2$O)$_{n2}$—CH$_2$CH$_2$—N$_3$, or —CO-Q9-B5-(Q10-P10)$_{q8}$-X1 wherein n2 is an integer of 0 to 99,
P10 is absent, or —CO—, —NH—, —O—, —S—, —O—CO—, —S— CO—, —NH—CO—, —CO—O—, —CO—S— or —CO—NH—,
Q9 and Q10 are each independently absent, or substituted or unsubstituted alkylene having 1 to 12 carbon atoms or —(CH$_2$CH$_2$O)$_{n3}$—CH$_2$CH$_2$— wherein n3 is an integer of 0 to 99, B5 is any structure represented by the following formula 8-2, wherein the broken lines respectively mean bonds to Q9 and Q10:
Formula 8-2
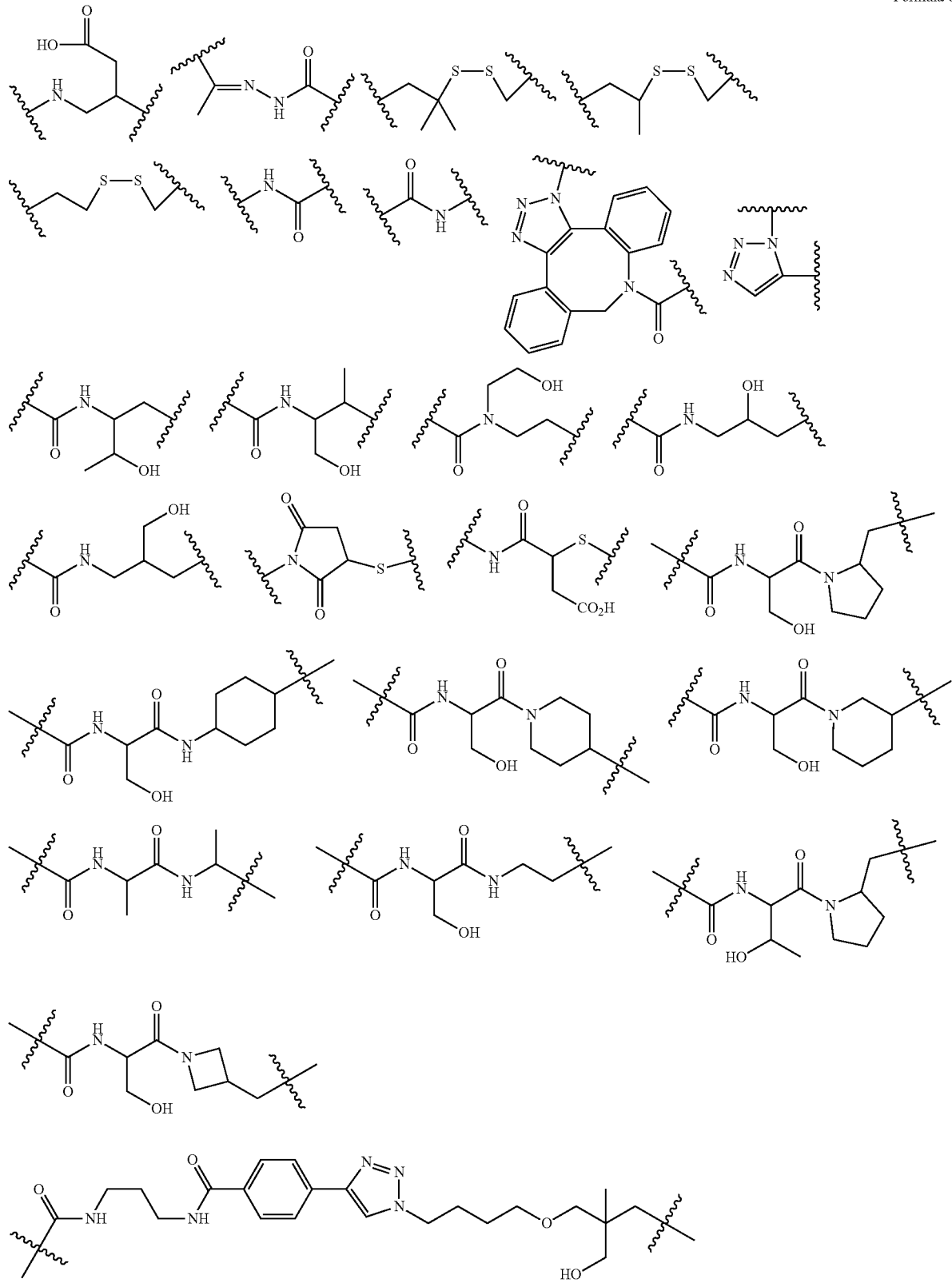

-continued

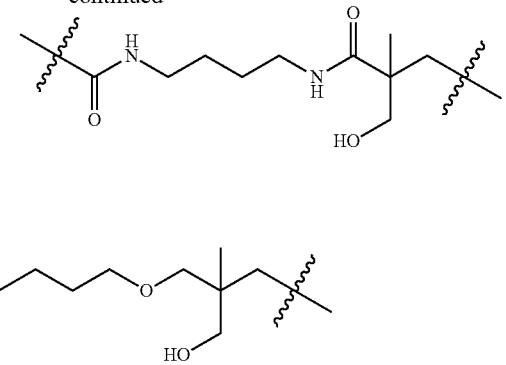

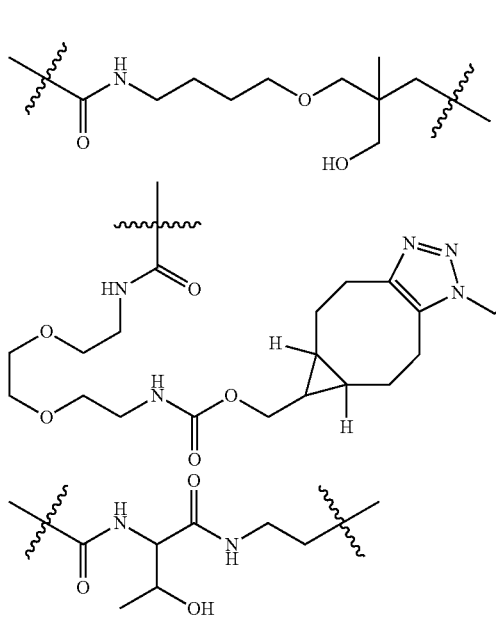

q8 is an integer of 0 to 10,

X1 is a hydrogen atom or a solid-phase support, and

R4 is an alkyl group having 2 to 10 carbon atoms substituted with 1 or 2 substituents selected from the group consisting of an amino group unsubstituted or substituted with a t-butoxycarbonyl group, a benzyloxycarbonyl group or a 9-fluorenylmethyloxycarbonyl group, a carboxy group, a maleimide group, and an aralkyloxycarbonyl group.

In the present invention, a compound represented by the following formula 9 is obtained as an intermediate of synthesis:

Formula 9

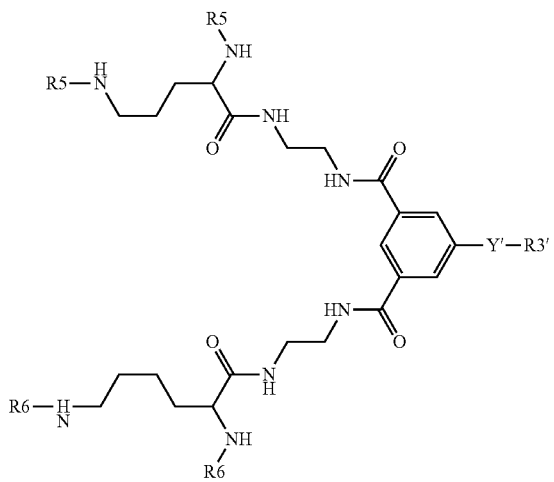

wherein

R5 and R6 are each independently a hydrogen atom, a t-butoxycarbonyl group, a benzyloxycarbonyl group, a 9-fluorenylmethyloxycarbonyl group, —CO—R4', or —CO-Q11-(P11-Q11')$_{q9}$-T4-L4, P11 and T4 are each independently absent, or —CO—, —NH—, —O—, —S—, —O—CO—, —S—CO—, —NH—CO—, —CO—O—, —CO—S— or —CO—NH—, each of Q11 and Q11' is absent, or substituted or unsubstituted alkylene having 1 to 12 carbon atoms or —(CH$_2$CH$_2$O)$_{n4}$—CH$_2$CH$_2$— wherein n4 is an integer of 0 to 99, q9 is an integer of 0 to 10, L4 is a sugar ligand, Y' is —O—(CH$_2$)$_{n11'}$—NH— or —NH—CO—(CH$_2$)$_{m12'}$*—NH— wherein m11' and m12' are each independently an integer of 1 to 10, R3' is a hydrogen atom, a t-butoxycarbonyl group, a benzyloxycarbonyl group, a 9-fluorenylmethyloxycarbonyl group, —CO—R4', —CO— (CH$_2$CH$_2$O)$_{n2'}$—CH$_2$CH$_2$—N$_3$ or —CO-Q9'-B5'-(Q10'-P10')$_{q8'}$—X1' wherein n2' is an integer of 0 to 99, P10' is absent, or —CO—, —NH—, —O—, —S—, —O—CO—, —S— CO—, —NH—CO—, —CO—O—, —CO—S— or —CO—NH—, Q9' and Q10' are each independently absent, or substituted or unsubstituted alkylene having 1 to 12 carbon atoms or —(CH$_2$CH$_2$O)$_{n3'}$—CH$_2$CH$_2$— wherein n3' is an integer of 0 to 99, B5' is any structure represented by the following formula 9-1, wherein the broken lines respectively mean bonds to Q9' and Q10':

Formula 9-1

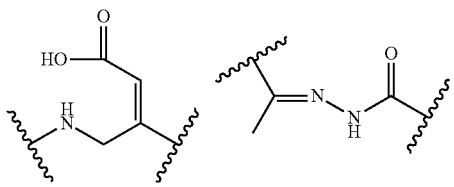

-continued
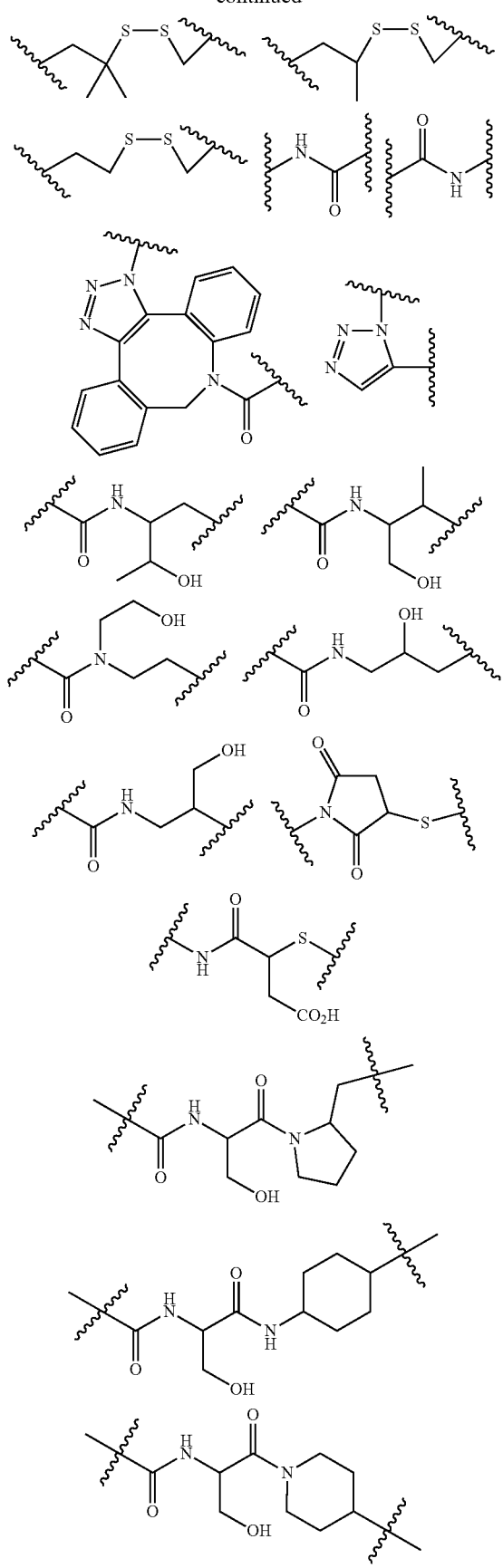
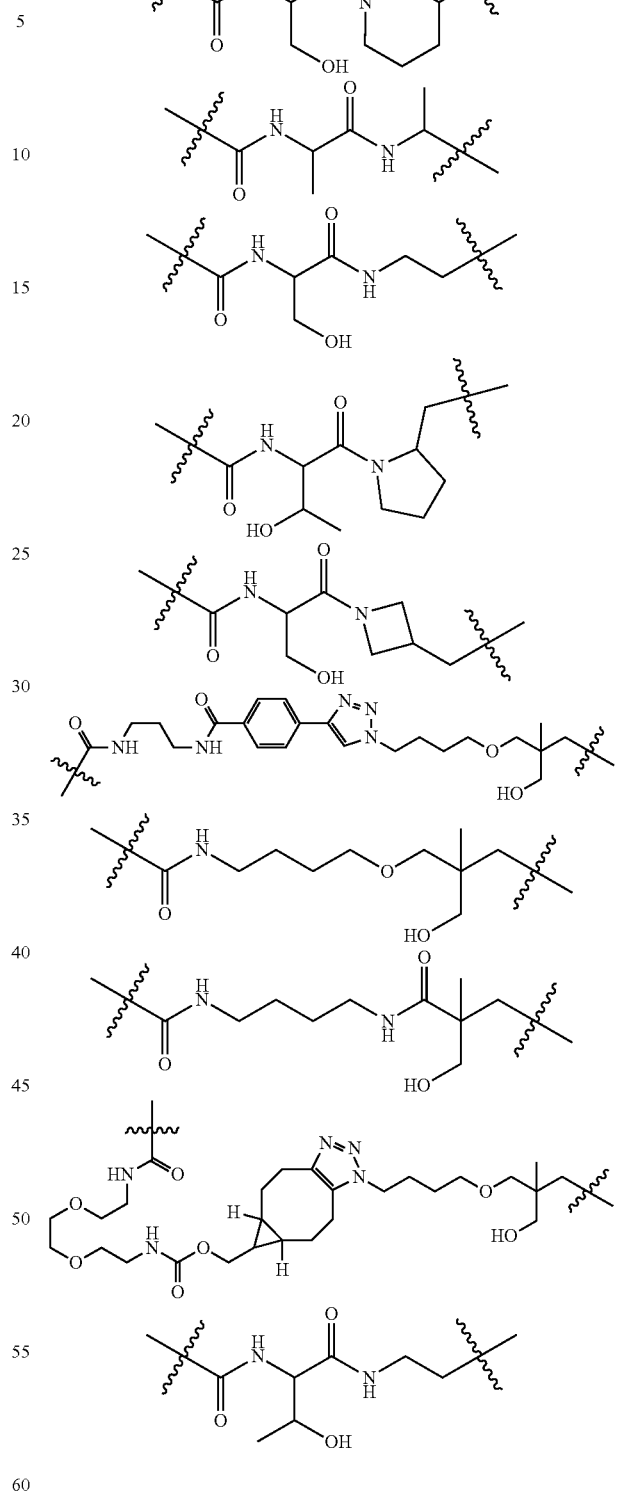
q8' is an integer of 0 to 10,
X1' is a hydrogen atom or a solid-phase support, and
R4' is an alkyl group having 2 to 10 carbon atoms substituted with 1 or 2 substituents selected from the group consisting of an amino group unsubstituted or substituted with a t-butoxycarbonyl group, a benzyloxycarbonyl group or a 9-fluorenylmethyloxycarbonyl group, a carboxy group, a maleimide group, and an aralkyloxycarbonyl group.

In the present invention, a compound represented by the following formula 10 is obtained as an intermediate of synthesis:

Formula 10

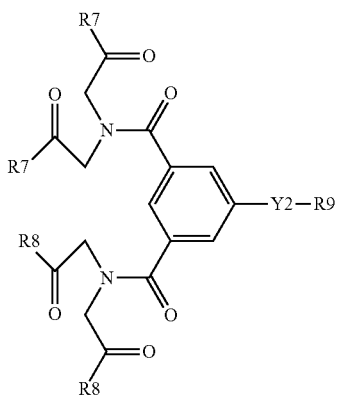

wherein
- R7 and R8 are each independently a hydroxy group, a t-butoxy group, a benzyloxy group, —NH—R10, or —NH-Q12-(P12-Q12')$_{q10}$-T4-L4,
- P12 and T4 are each independently absent, or —CO—, —NH—, —O—, —S—, —O—CO—, —S—CO—, —NH—CO—, —CO—O—, —CO—S— or —CO—NH—,
- each of Q12 and Q12' is absent, or substituted or unsubstituted alkylene having 1 to 12 carbon atoms or —(CH$_2$CH$_2$O)$_{n2}$—CH$_2$CH$_2$— wherein n2 is an integer of 0 to 99,
- L4 is a sugar ligand,
- Y2 is —O—(CH$_2$)$_{m9}$—NH— or —NH—CO—(CH$_2$)$_{m10}$—NH— wherein m9 and m10 are each independently an integer of 1 to 10,
- q10 is an integer of 0 to 10,
- R9 is a hydrogen atom, a t-butoxycarbonyl group, a benzyloxycarbonyl group, a 9-fluorenylmethyloxycarbonyl group, —CO—R10, —CO—(CH$_2$CH$_2$O)$_{n6}$—CH$_2$CH$_2$—N$_3$, or —CO-Q13-B6-(Q14-P13)$_{q11}$—X2 wherein n6 is an integer of 0 to 99,
- P13 is absent, or —CO—, —NH—, —O—, —S—, —O—CO—, —S—CO—, —NH—CO—, —CO—O—, —CO—S— or —CO—NH—,
- Q13 and Q14 are each independently absent, or substituted or unsubstituted alkylene having 1 to 12 carbon atoms or —(CH$_2$CH$_2$O)$_{n7}$—CH$_2$CH$_2$— wherein n7 is an integer of 0 to 99,
- B6 is any structure represented by the following formula 10-1, wherein the broken lines respectively mean bonds to Q13 and Q14:

Formula 10-1

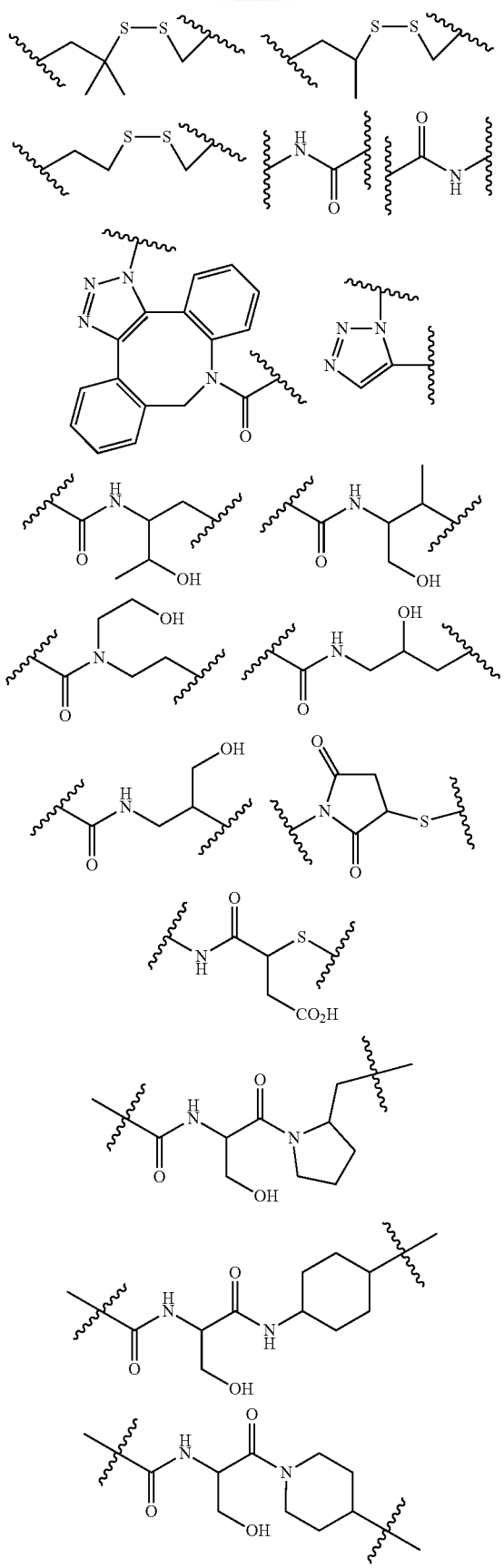

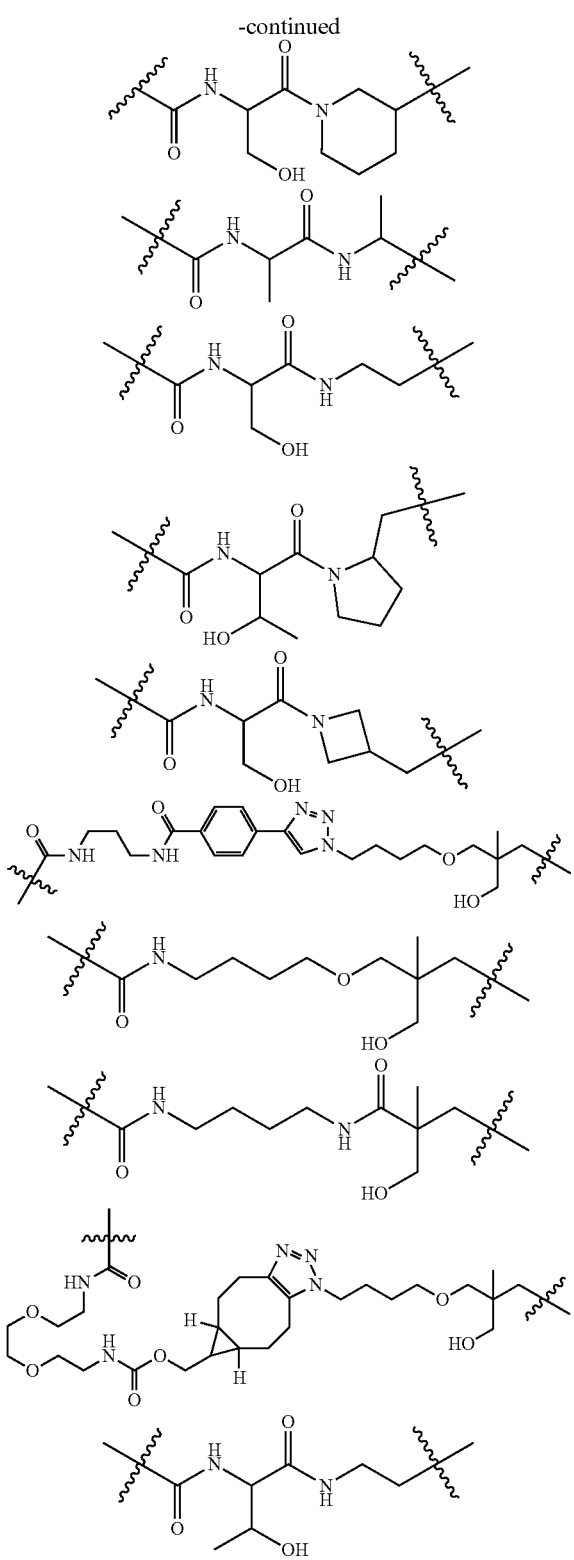

q11 is an integer of 0 to 10,

X2 is a hydrogen atom or a solid-phase support, and

R10 is an alkyl group having 2 to 10 carbon atoms substituted with 1 or 2 substituents selected from the group consisting of an amino group unsubstituted or substituted with a t-butoxycarbonyl group, a benzyloxycarbonyl group or a 9-fluorenylmethyloxycarbonyl group, a carboxy group, a maleimide group, and an aralkyloxycarbonyl group.

Hereinafter, exemplary production methods will be given in relation to the present invention. In the description about production methods 1 to 17 given below, the same symbols as those representing groups in the compounds represented by formulas 1 to 12 in the nucleic acid derivative, etc. of the present invention may be used. These symbols in production methods 1 to 17 should be understood separately from those in the compounds represented by formulas 1 to 12. The present invention should not be restrictively interpreted by the description of the groups about production methods 1 to 12. For the nucleic acid derivative according to the present invention, X representing the oligonucleotide is described as —O—X in production methods 1 to 17.

Production Method 1

For the nucleic acid derivative according to the present invention, the production method can be taken as an example of a method for producing a compound having a substructure represented by formula (I'):

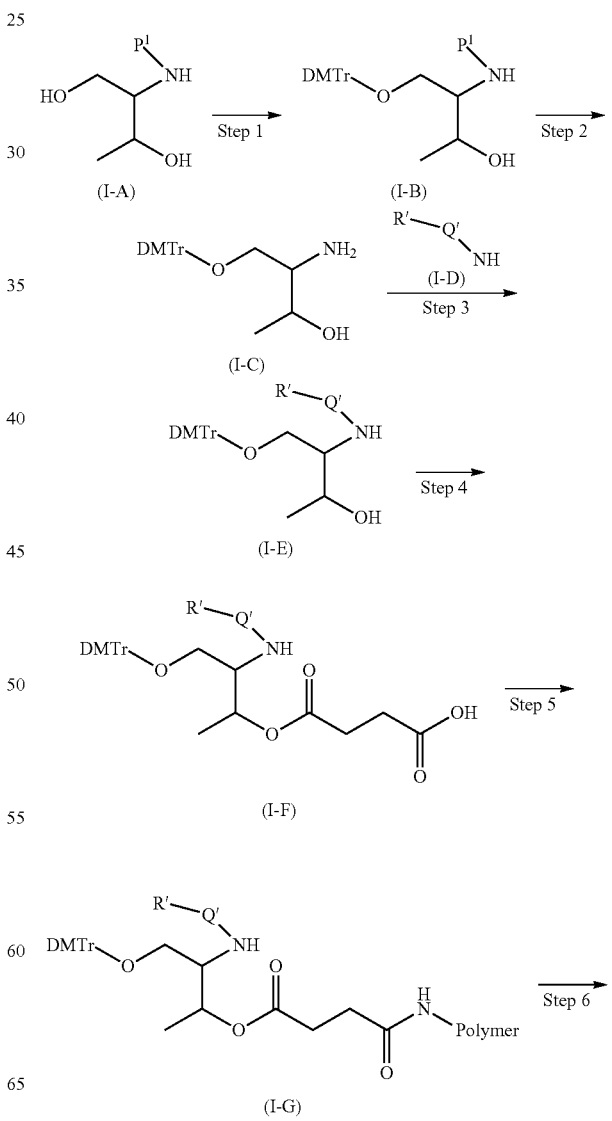

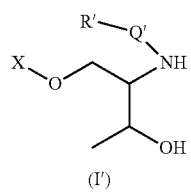

(I')

wherein P1 is a base-deprotectable protective group such as Fmoc, DMTr represents a p,p'-dimethoxytrityl group, R represents a sugar ligand-tether unit, R' represents a group in which each hydroxy group of the sugar ligand in R is protected with a base-deprotectable protective group such as an acetyl group, Polymer represents a solid-phase support, and Q' is —CO—.

Step 1

Compound (I-B) can be produced by reacting compound (I-A) with p,p'-dimethoxytrityl chloride at a temperature between 0° C. and 100° C. for 5 minutes to 100 hours in a solvent such as pyridine, if necessary, in the presence of a cosolvent.

Examples of the cosolvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide (DMF), N,N-dimethylacetamide, N-methylpyrrolidone, pyridine, and water. These cosolvents may be used alone or as a mixture.

Step 2

Compound (I-C) can be produced by reacting compound (I-B) at a temperature between room temperature and 200° C. for 5 minutes to 100 hours in the presence of 1 to 1000 equivalents of a secondary amine without a solvent or in a solvent.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide (DMF), N,N-dimethylacetamide, N-methylpyrrolidone, pyridine, and water. These solvents may be used alone or as a mixture.

Examples of the secondary amine include diethylamine and piperidine.

Step 3

Compound (1-E) can be produced by reacting compound (I-C) with compound (I-D) at a temperature between room temperature and 200° C. for 5 minutes to 100 hours in the presence of 1 to 30 equivalents of a base, a condensing agent and, if necessary, 0.01 to 30 equivalents of an additive without a solvent or in a solvent.

Examples of the solvent include those listed in step 2.

Examples of the base include cesium carbonate, potassium carbonate, potassium hydroxide, sodium hydroxide, sodium methoxide, potassium tert-butoxide, triethylamine, diisopropylethylamine, N-methylmorpholine, pyridine, 1,8-diazabicyclo[5.4.0]-7-undecene (DBU), and N,N-dimethyl-4-aminopyridine (DMAP).

Examples of the condensing agent include 1,3-dicyclohexanecarbodiimide (DCC), 1-ethyl-3-(3-dimethylaminopropyl)carbodiimide hydrochloride (EDC), carbonyldiimidazole, benzotriazol-1-yloxytris(dimethylamino)phosphonium hexafluorophosphate, (benzotriazol-1-yloxy)tripyrrolidinophosphonium hexafluorophosphate, O-(7-azabenzotriazol-1-yl)-N,N,N',N'-tetramethyluronium hexafluorophosphate (HATU), O-(benzotriazol-1-yl)-N,N, N',N'-tetramethyluronium hexafluorophosphate (HBTU), and 2-chloro-1-methylpyridinium iodide.

Examples of the additive include 1-hydroxybenzotriazole (HOBt) and 4-dimethylaminopyridine (DMAP).

Compound (I-D) can be obtained by a method known in the art (see, for example, Journal of American Chemical Society, 136, 16958, (2014) or a method equivalent thereto.

Step 4

Compound (I-F) can be produced by reacting compound (I-E) with succinic anhydride at a temperature between room temperature and 200° C. for 5 minutes to 100 hours in the presence of 1 to 30 equivalents of a base in a solvent.

Examples of the solvent include those listed in step 2.

Examples of the base include those listed in step 3.

Step 5

Compound (I-G) can be produced by reacting compound (I-F) with a terminally aminated solid-phase support at a temperature between room temperature and 200° C. for 5 minutes to 100 hours in the presence of 1 to 30 equivalents of a base, a condensing agent and, if necessary, 0.01 to 30 equivalents of an additive without a solvent or in a solvent, and then reacting the resultant with a solution of acetic anhydride in pyridine at a temperature between room temperature and 200° C. for 5 minutes to 100 hours.

Examples of the solvent include those listed in step 2.

Examples of the base, the condensing agent and the additive include those respectively listed in step 3.

Examples of the aminated solid-phase support include long-chain alkylamine controlled pore glass (LCAA-CPG). Such an aminated solid-phase support can be obtained as a commercially available product.

Step 6

The nucleic acid conjugate having the sugar ligand-tether-brancher unit represented by formula (I') can be produced by elongating a corresponding nucleotide strand by a chemical oligonucleotide synthesis method known in the art using compound (I-G), followed by dissociation from the solid phase, deprotection of the protective group and purification.

Examples of the chemical oligonucleotide synthesis method known in the art can include a phosphoramidite method, a phosphorothioate method, a phosphotriester method, and a CEM method (see Nucleic Acids Research, 35, 3287 (2007)). The nucleotide strand can be synthesized using, for example, ABI3900 high-throughput nucleic acid synthesizer (manufactured by Applied Biosystems, Inc.).

The dissociation from the solid phase and the deprotection can be performed by treatment with a base at a temperature between –80° C. and 200° C. for 10 seconds to 72 hours in a solvent or without a solvent after the chemical oligonucleotide synthesis.

Examples of the base include ammonia, methylamine, dimethylamine, ethylamine, diethylamine, isopropylamine, diisopropylamine, piperidine, triethylamine, ethylenediamine, 1,8-diazabicyclo[5.4.0]-7-undecene (DBU), and potassium carbonate.

Examples of the solvent include water, methanol, ethanol, and THF.

The oligonucleotide can be purified using a C18 reverse-phase column or an anion-exchange column, preferably these two approaches in combination. The purity of the nucleic acid conjugate thus purified is desirably 90% or higher, preferably 95% or higher.

In step 3 described above, if necessary, compound (I-D) may be divided into two units and condensed with compound (I-C) at two separate stages. Specifically, when R-Q' is, for example, R—NH—CO-Q4'-CO— (Q4' is substituted or unsubstituted alkylene having 1 to 12 carbon atoms), in step 3, compound (I-C) and CH₃CH₂—O—CO-Q4'-CO—OH (Q4' is as defined above) are condensed in the same way as in step 3, and ethyl ester of the obtained compound can be hydrolyzed with a base such as lithium hydroxide in a solvent such as ethanol or water, followed by further condensation with R'—NH₂ (R' is as defined above) to obtain the compound of interest. CH₃CH₂—O—CO-Q4'-CO—OH (Q4' is as defined above) and R'—NH₂ (R' is as defined above) can be obtained by a method known in the art (see, for example, Journal of American Chemical Society, 136, 16958 (2014)) or a method equivalent thereto. In this context, the substituent and the alkylene moiety in the substituted or unsubstituted alkylene having 1 to 12 carbon atoms, represented by Q4' are as defined above.

Although the case where Q is —CO— is taken as an example above, a compound in which Q is not —CO— can also be prepared according to the same method as above or a method known in the art, or a combination thereof by appropriately changing the structure of Q and appropriately changing the reaction conditions.

Production Method 2

For the nucleic acid derivative according to the present invention, the production method can be taken as an example of a method for producing a compound having a substructure represented by formula (II'):

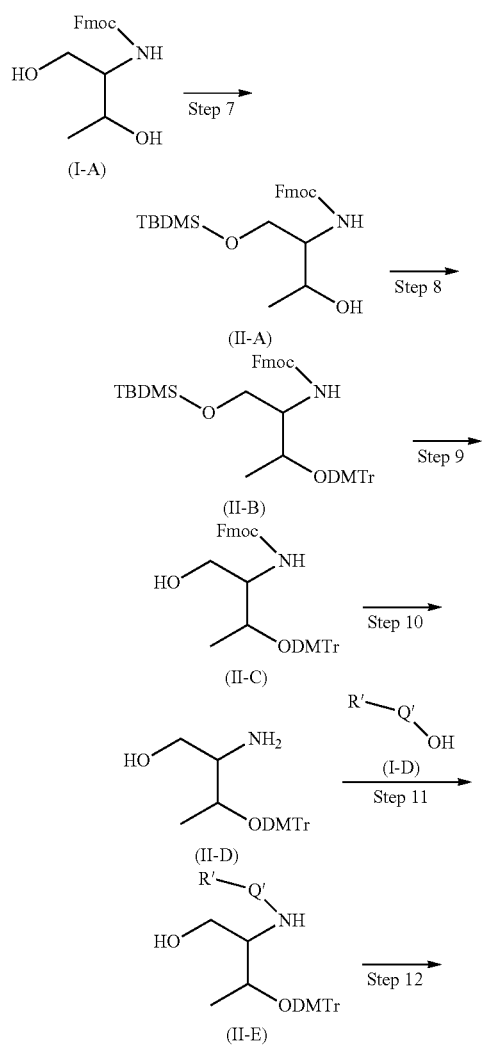

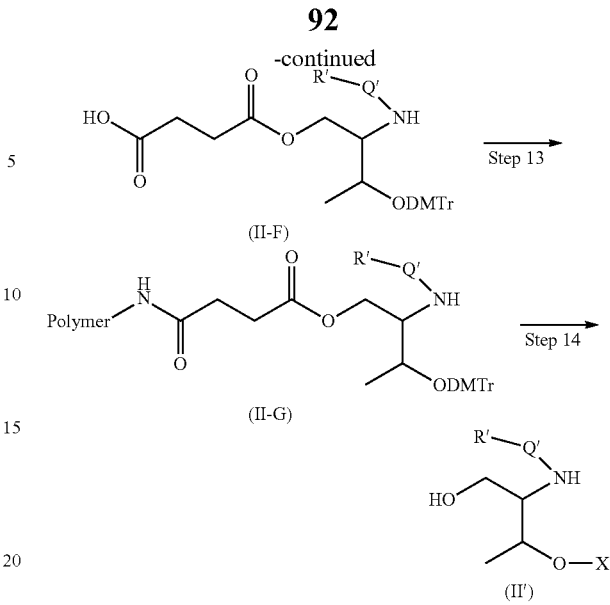

wherein DMTr, R, R', X, Q', and Polymer are as defined above, TBDMS represents a t-butyldimethylsilyl group, and Fmoc represents a 9-fluorenylmethyloxycarbonyl group.

Step 7

Compound (II-A) can be produced by reacting compound (I-A) with t-butyldimethylsilyl chloride and dimethylaminopyridine at a temperature between 0° C. and 100° C. for 5 minutes to 100 hours in a solvent such as N,N-dimethylformamide (DMF), preferably in the presence of 2 equivalents of a base.

Examples of the base include those listed in step 3 of production method 1.

Step 8

Compound (II-B) can be produced under the same conditions as in step 1 of production method 1 using compound (II-A).

Step 9

Compound (II-C) can be produced by reacting compound (II-B) with n-tetrabutylammonium fluoride (TBAF) at a temperature between room temperature and 200° C. for 5 minutes to 100 hours in a solvent.

Examples of the solvent include those listed in step 2.

Step 10

Compound (II-D) can be produced under the same conditions as in step 2 of production method 1 using compound (II-C).

Step 11

Compound (II-E) can be produced under the same conditions as in step 3 of production method 1 using compound (II-D) and compound (I-D).

Steps 12 to 14

Compound (II') can be produced under the same conditions as in steps 4 to 6 of production method 1 using compound (II-E).

In step 11 described above, if necessary, compound (I-D) may be divided into two units and condensed with compound (II-C) at two separate stages. Specifically, when R-Q' is, for example, R—NH—CO-Q4'-CO— (Q4' is substituted or unsubstituted alkylene having 1 to 12 carbon atoms), in step 11, compound (II-C) and CH₃CH₂—O—CO-Q4'-CO—OH (Q4' is as defined above) are condensed in the same way as in step 11, and ethyl ester of the obtained compound can be hydrolyzed with a base such as lithium hydroxide in a solvent such as ethanol or water, followed by further condensation with R'—NH₂ (R' is as defined above) to obtain the compound of interest. CH₃CH₂—O—CO-Q4'-CO—OH (Q4' is as defined above) and R'—NH₂ (R' is as defined above) can be obtained by a method known in the art (see, for example, Journal of American Chemical Society, 136, 16958 (2014)) or a method equivalent thereto.

Although the case where Q is —CO— is taken as an example above, a compound in which Q is not —CO— can also be prepared according to the same method as above or a method known in the art, or a combination thereof by appropriately changing the structure of Q and appropriately changing the reaction conditions.

Production Method 3

For the nucleic acid derivative according to the present invention, the production method can be taken as an example of a method for producing a compound having a substructure represented by formula (III'):

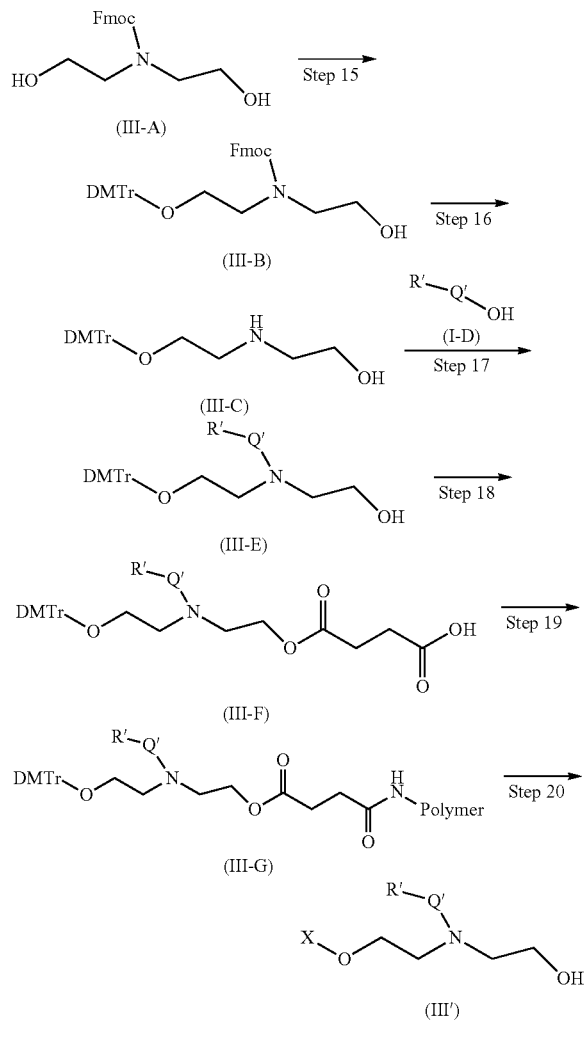

wherein DMTr, Fmoc, R, R', Q', X and Polymer are as defined above.

Compound (III') can be produced under the same conditions as in steps 1 to 6 of production method 1 using compound (III-A). Compound (III-A) can be obtained as a commercially available product.

Step 15

Compound (III-B) can be produced under the same conditions as in step 1 of production method 1 using compound (III-A).

Compound (III-A) can be purchased as a commercially available product.

Step 16

Compound (III-C) can be produced under the same conditions as in step 2 of production method 1 using compound (III-B).

Step 17

Compound (III-E) can be produced under the same conditions as in step 3 of production method 1 using compound (III-C).

Steps 18 to 20

Compound (III') can be produced under the same conditions as in steps 4 to 6 of production method 1 using compound (III-E).

In step 17 described above, if necessary, compound (I-D) may be divided into two units and condensed with compound (III-C) at two separate stages. Specifically, when R-Q' is, for example, —NH—CO-Q4'-CO— (Q4' is substituted or unsubstituted alkylene having 1 to 12 carbon atoms), in step 17, compound (III-C) and CH₃CH₂—O—CO-Q4'-CO—OH (Q4' is as defined above) are condensed in the same way as in step 17, and ethyl ester of the obtained compound can be hydrolyzed with a base such as lithium hydroxide in a solvent such as ethanol or water, followed by further condensation with R'—NH₂ (R' is as defined above) to obtain the compound of interest. CH₃CH₂—O—CO-Q4'-CO—OH (Q4' is as defined above) and R'—NH₂ (R' is as defined above) can be obtained by a method known in the art (see, for example, Journal of American Chemical Society, 136, 16958 (2014)) or a method equivalent thereto.

Although the case where Q is —CO— is taken as an example above, a compound in which Q is not —CO— can also be prepared according to the same method as above or a method known in the art, or a combination thereof by appropriately changing the structure of Q and appropriately changing the reaction conditions.

Production Method 4

For the nucleic acid derivative according to the present invention, the production method can be taken as an example of a method for producing a compound having a substructure represented by formula (IV'):

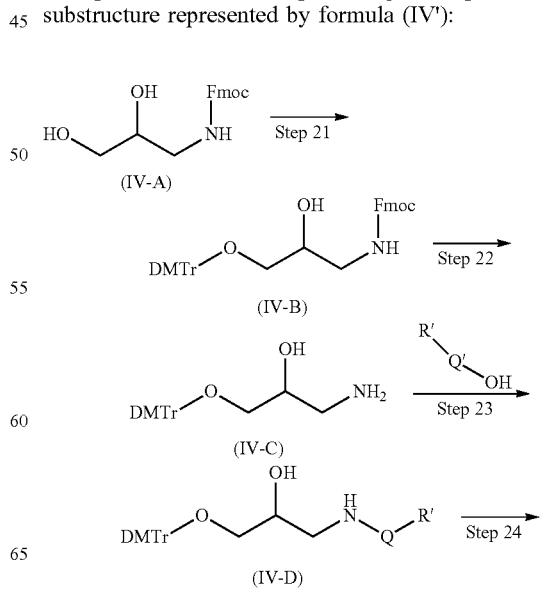

-continued

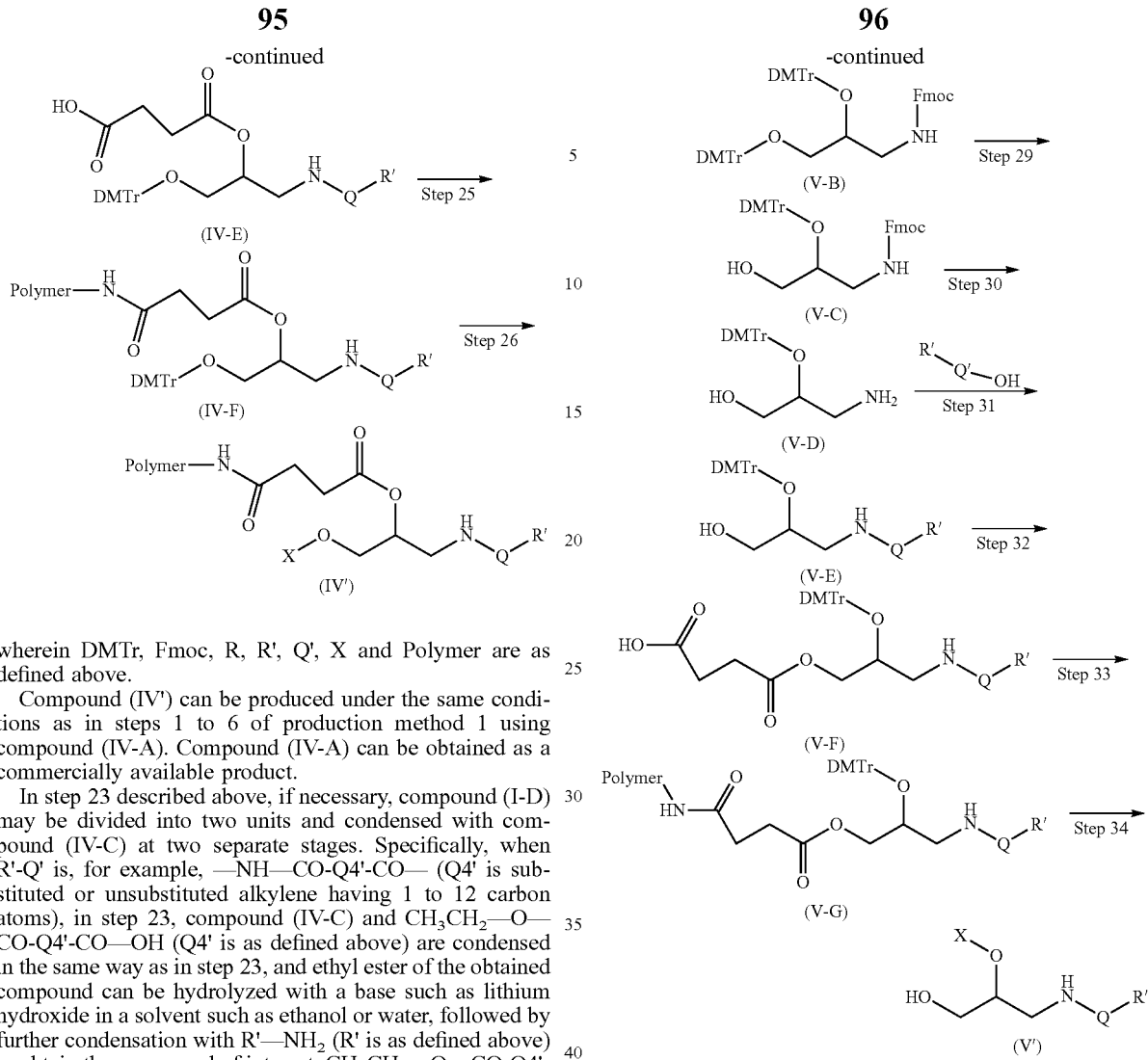

wherein DMTr, Fmoc, R, R', Q', X and Polymer are as defined above.

Compound (IV') can be produced under the same conditions as in steps 1 to 6 of production method 1 using compound (IV-A). Compound (IV-A) can be obtained as a commercially available product.

In step 23 described above, if necessary, compound (I-D) may be divided into two units and condensed with compound (IV-C) at two separate stages. Specifically, when R'-Q' is, for example, —NH—CO-Q4'-CO— (Q4' is substituted or unsubstituted alkylene having 1 to 12 carbon atoms), in step 23, compound (IV-C) and CH₃CH₂—O—CO-Q4'-CO—OH (Q4' is as defined above) are condensed in the same way as in step 23, and ethyl ester of the obtained compound can be hydrolyzed with a base such as lithium hydroxide in a solvent such as ethanol or water, followed by further condensation with R'—NH₂ (R' is as defined above) to obtain the compound of interest. CH₃CH₂—O—CO-Q4'-CO—OH (Q4' is as defined above) and R'—NH₂ (R' is as defined above) can be obtained by a method known in the art (see, for example, Journal of American Chemical Society, 136, 16958 (2014)) or a method equivalent thereto.

Although the case where Q is —CO— is taken as an example above, a compound in which Q is not —CO— can also be prepared according to the same method as above or a method known in the art, or a combination thereof by appropriately changing the structure of Q and appropriately changing the reaction conditions.

Production Method 5

For the nucleic acid derivative according to the present invention, the production method can be taken as an example of a method for producing a compound having a substructure represented by formula (V'):

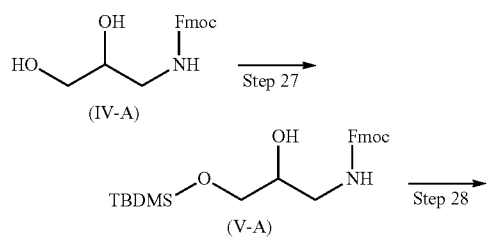

wherein DMTr, R, R', X, Q', TBDMS, Fmoc and Polymer are as defined above.

Compound (V') can be produced under the same conditions as in steps 1 to 7 of production method 2 using compound (IV-A). Compound (IV-A) can be obtained as a commercially available product.

In step 31 described above, if necessary, compound (I-D) may be divided into two units and condensed with compound (V-D) at two separate stages. Specifically, when R'-Q' is, for example, —NH—CO-Q4'-CO— (Q4' is substituted or unsubstituted alkylene having 1 to 12 carbon atoms), in step 31, compound (V-D) and CH₃CH₂—O—CO-Q4'-CO—OH (Q4' is as defined above) are condensed in the same way as in step 31, and ethyl ester of the obtained compound can be hydrolyzed with a base such as lithium hydroxide in a solvent such as ethanol or water, followed by further condensation with R'—NH₂ (R' is as defined above) to obtain the compound of interest. CH₃CH₂—O—CO-Q4'-CO—OH (Q4' is as defined above) and R'—NH₂ (R' is as defined above) can be obtained by a method known in the art (see, for example, Journal of American Chemical Society, 136, 16958 (2014)) or a method equivalent thereto.

Although the case where Q is —CO— is taken as an example above, a compound in which Q is not —CO— can also be prepared according to the same method as above or a method known in the art, or a combination thereof by appropriately changing the structure of Q-OH and appropriately changing the reaction conditions.

Production Method 6

An exemplary method for producing the nucleic acid conjugate of the present invention in which a sugar ligand-tether-brancher unit is bonded to the 5' end of the oligonucleotide will be given below.

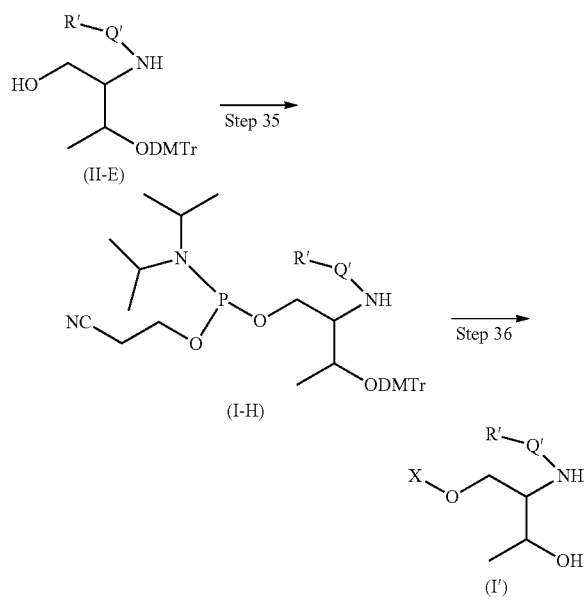

wherein R, R', Q', DMTr and X are as defined above.

Step 35

Compound (I-H) can be produced by reacting compound (II-E) with 2-cyanoethyl-N,N,N',N'-tetraisopropylphosphodiamidite at a temperature between room temperature and 200° C. for 5 minutes to 100 hours in the presence of a base and a reaction accelerator without a solvent or in a solvent.

Examples of the solvent include those listed in step 2 of production method 1.

Examples of the base include those listed in step 3 of production method 1.

Examples of the reaction accelerator include 1H-tetrazole, 4,5-dicyanoimidazole, 5-ethylthiotetrazole, and 5-benzylthiotetrazole. These reaction accelerators can be purchased as commercially available products.

Step 36

Compound (I'') can be produced by elongating an oligonucleotide strand and finally modifying the 5' end of the oligonucleotide with a sugar ligand-tether-brancher unit using compound (I-H), followed by dissociation from the solid phase, deprotection of the protective group and purification. In this context, the dissociation from the solid phase, the deprotection of the protective group and the purification can each be performed in the same way as in step 7 of production method 1.

Production Method 7

An exemplary method for producing the nucleic acid conjugate of the present invention in which a sugar ligand-tether-brancher unit is bonded to the 5' end of the oligonucleotide will be given below.

The nucleic acid conjugate can be produced under the same conditions as in steps 35 and 36 of production method 6.

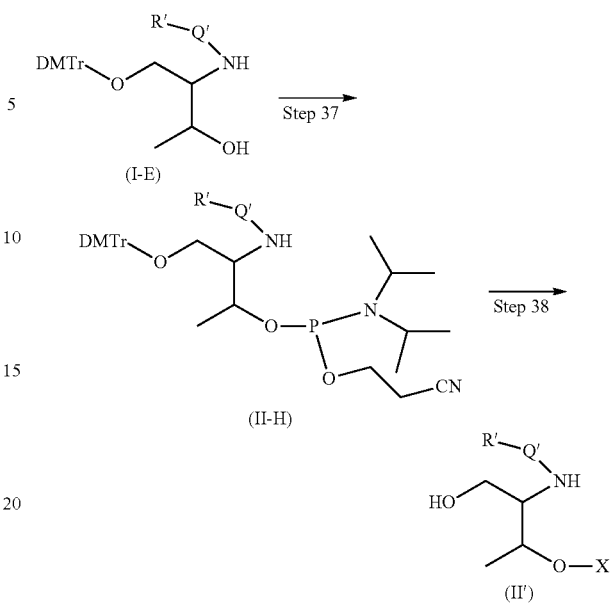

wherein R, R', Q', DMTr and X are as defined above.

Production Method 8

An exemplary method for producing the nucleic acid conjugate of the present invention in which a sugar ligand-tether-brancher unit is bonded to the 5' end of the oligonucleotide will be given below.

The nucleic acid conjugate can be produced under the same conditions as in steps 35 and 36 of production method 6.

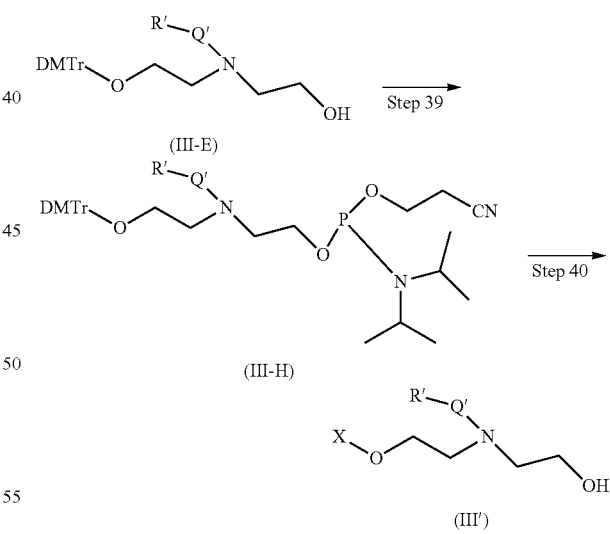

wherein R, R', Q', DMTr and X are as defined above.

Production Method 9

An exemplary method for producing the nucleic acid conjugate of the present invention in which a sugar ligand-tether-brancher unit is bonded to the 5' end of the oligonucleotide will be given below.

The nucleic acid conjugate can be produced under the same conditions as in steps 35 and 36 of production method 6.

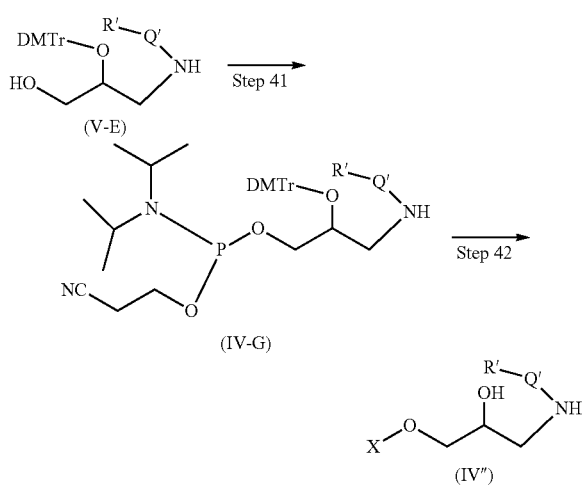

wherein R, R', Q', DMTr and X are as defined above.

Production Method 10

An exemplary method for producing the nucleic acid conjugate of the present invention in which a sugar ligand-tether-brancher unit is bonded to the 5' end of the oligonucleotide will be given below.

The nucleic acid conjugate can be produced under the same conditions as in steps 35 and 36 of production method 6.

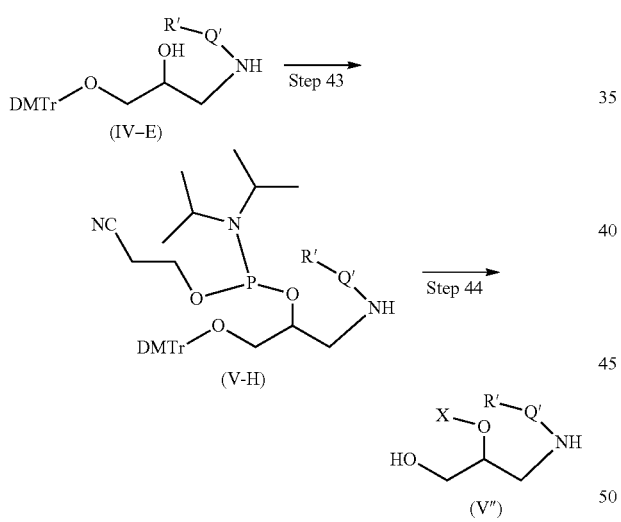

wherein R, R', Q', DMTr and X are as defined above.

Production Method 11

A nucleic acid conjugate having a double-stranded nucleic acid can be obtained by dissolving each of a sense strand having a sugar ligand-tether-brancher unit at the 3' or 5' end of a sense strand constituting the double-stranded nucleic acid, and an antisense strand constituting the double-stranded nucleic acid, in water or an appropriate buffer solution, and mixing the solutions.

Examples of the buffer solution include acetate buffer solutions, Tris buffer solutions, citrate buffer solutions, phosphate buffer solutions, and water. These buffer solutions are used alone or as a mixture.

The mixing ratio between the sense strand and the antisense strand is preferably 0.5 to 2 equivalents, more preferably 0.9 to 1.1 equivalents, further preferably 0.95 equivalents to 1.05 equivalents, of the antisense strand with respect to 1 equivalent of the sense strand.

The sense strand and the antisense strand thus mixed may be appropriately subjected to annealing treatment. The annealing treatment can be performed by heating the mixture of the sense strand and the antisense strand to preferably 50 to 100° C., more preferably 60 to 100° C., further preferably 80 to 100° C., followed by slow cooling to room temperature.

The antisense strand can be obtained in conformity to the aforementioned oligonucleotide synthesis method known in the art.

Production Method 12

For the nucleic acid derivative according to the present invention, the production method can be taken as an example of a method for producing a compound having a substructure represented by formula (VI'):

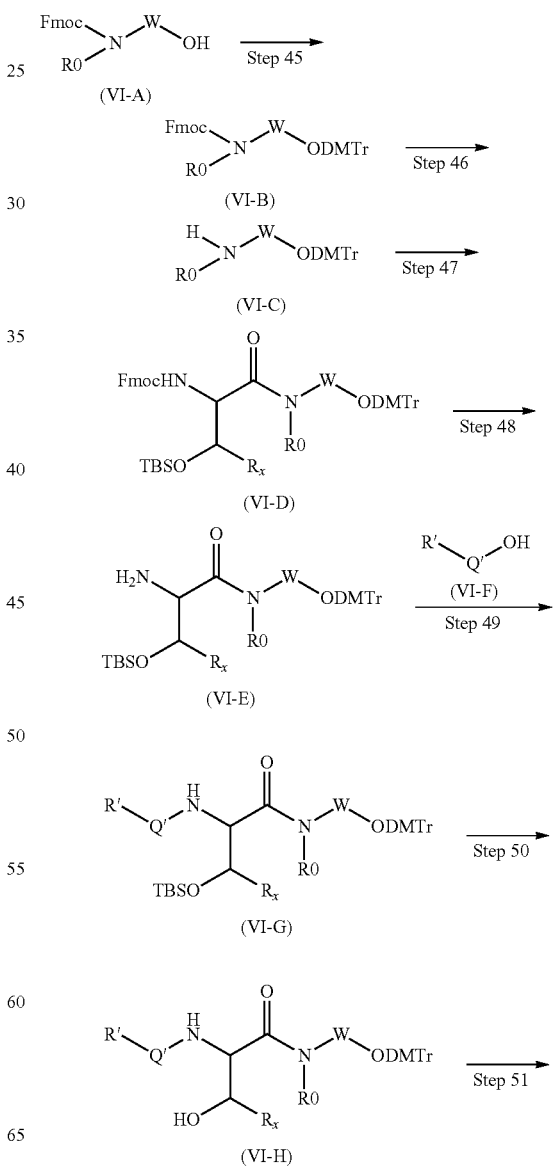

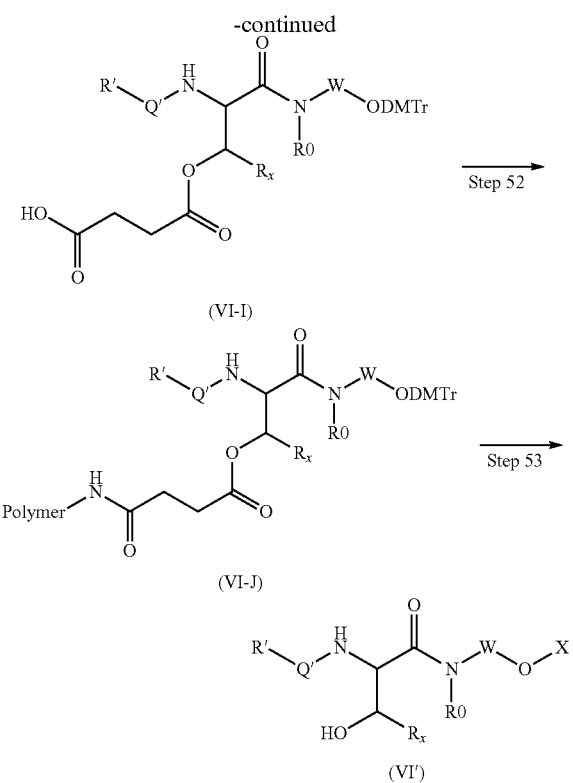

(VI-I), (VI-J), (VI')

wherein DMTr, R, R', X, Q', Polymer, TBS and Fmoc are as defined above, R0 and Rx are the same or different and each represent a hydrogen atom, C1-C10 alkylene or C3-C8 cycloalkylene, and W is C1-C10 alkylene or C3-C8 cycloalkylene or may form a C4-C8 nitrogen-containing heterocyclic ring together with R0.

Step 45

Compound (VI-B) can be produced under the same conditions as in step 1 of production method 1 using compound (VI-A).

Compound (VI-A) can be obtained as a commercially available product, or by a method known in the art (e.g., Bioorganic & Medicinal Chemistry Letters, Vol. 11, p. 383-386) or a method equivalent thereto.

Step 46

Compound (VI-C) can be produced under the same conditions as in step 2 of production method 1 using compound (VI-B).

Step 47

Compound (VI-D) can be produced under the same conditions as in step 3 of production method 1 using compound (VI-C).

Step 48

Compound (VI-E) can be produced under the same conditions as in step 2 of production method 1 using compound (VI-D).

Step 49

Compound (VI-G) can be produced under the same conditions as in step 3 of production method 1 using compound (VI-E) and compound (VI-F).

Step 50

Compound (VI-H) can be produced under the same conditions as in step 9 of production method 2 using compound (VI-G).

Steps 51 to 53

Compound (VI') can be produced under the same conditions as in steps 4 to 6 of production method 1 using compound (VI-H), compound (VI-I) and compound (VI-J).

Steps 45 to 53 can also be carried out by a method known in the art (e.g., a method described in International Publication No. WO 2015/105083) or a method equivalent thereto.

Compound (VI-F) can be obtained by a method known in the art (e.g., a method described in Journal of American Chemical Society, Vol. 136, p. 16958, 2014) or a method equivalent thereto.

Production Method 13

A sugar ligand-tether unit in which each of P1 and P4 in formula 2 is —NH—CO—, —O—CO— or —S—CO— can be produced by the following method.

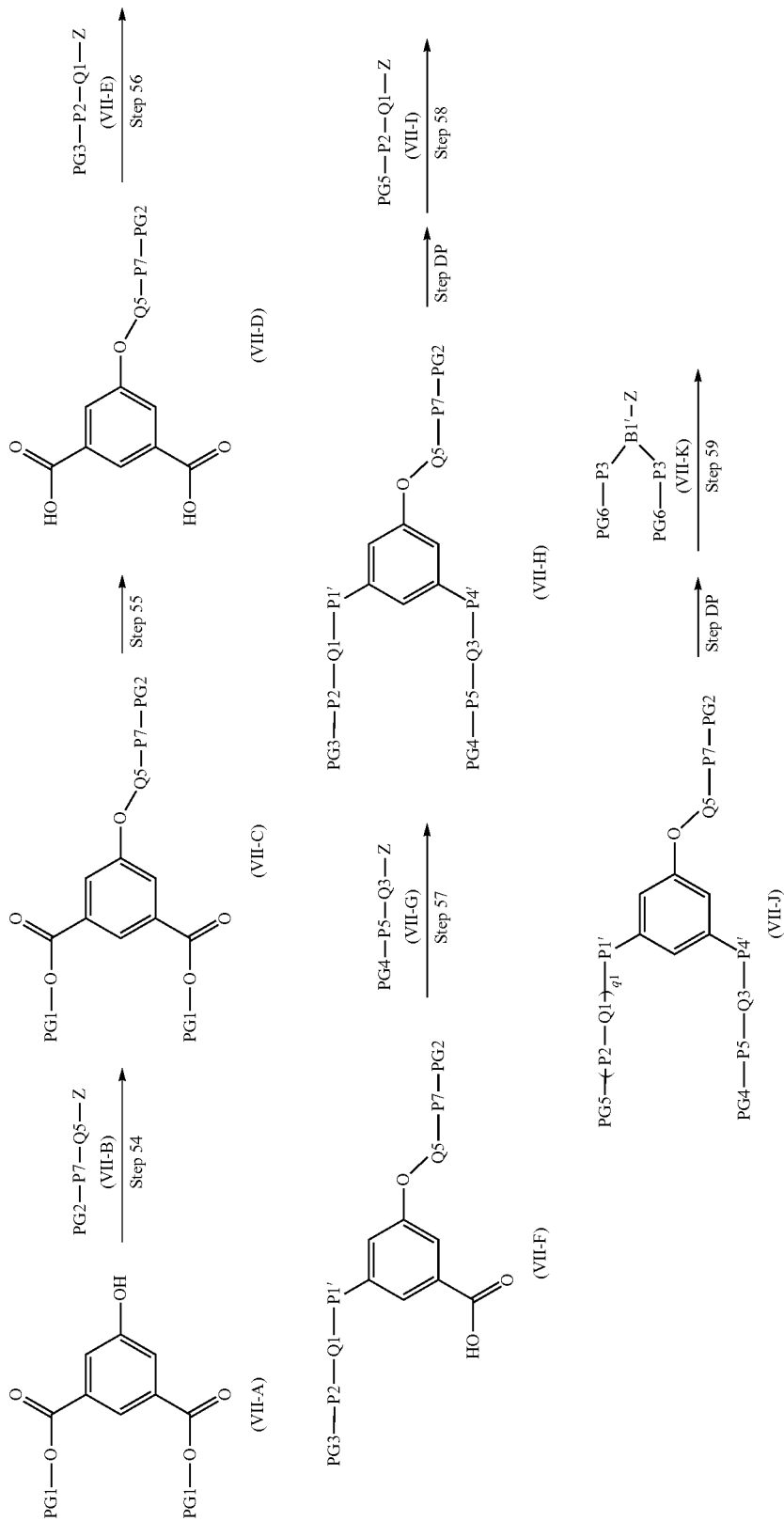

-continued
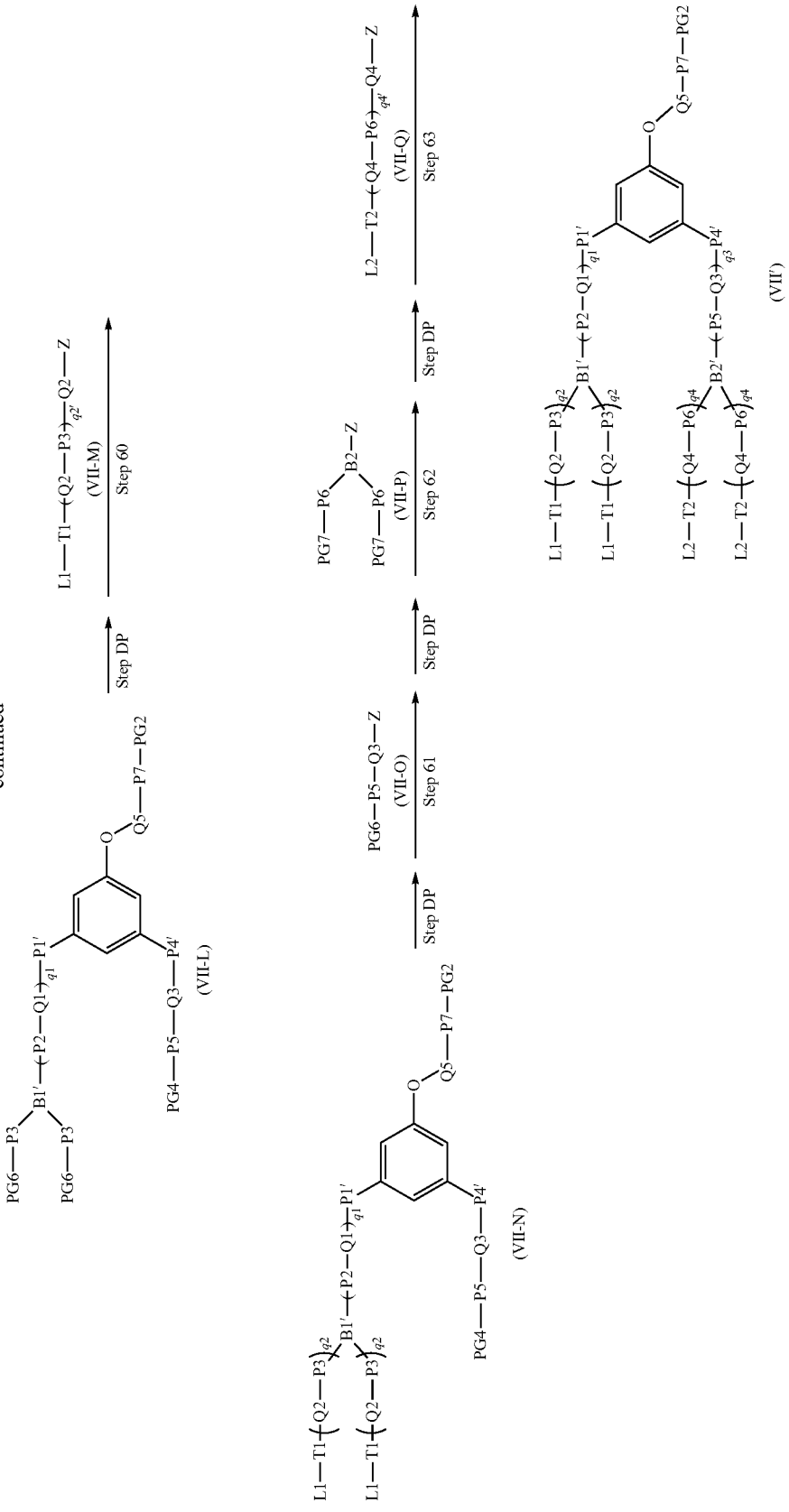

wherein Q1, Q2, Q3, Q4, Q5, P2, P3, P5, P6, P7, T1, T2, L1, L2, q1, q2, q3 and q4 are each as defined above, q1' represents an integer smaller by 1 than q1, q2' represents an integer smaller by 1 than q2, P1' and P4' each independently represent —CO—O—, —CO—NH— or —CO—S—, Z represents H, OH, NH$_2$, SH, a chlorine atom, a bromine atom, an iodine atom, methanesulfonyloxy, p-toluenesulfonyloxy or carboxylic acid, B1' and B2' each represent any one structure of the following formulas, and PG1, PG2, PG3, PG4, PG5, PG6 and PG7 each represent an appropriate protective group.

Formulas

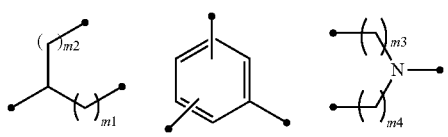

m1, m2, m3 and m4 each independently represent an integer of 0 to 10.

Step 54

Compound (VII-C) can be produced by adding polymer-supported triphenylphosphine to compound (VII-A) with compound (VII-B) in a solvent such as tetrahydrofuran, and reacting the mixture with a solution of diisopropyl azodicarboxylate in toluene under ice cooling.

Examples of the solvent include those listed in step 2 of production step 1.

Compound (VII-A) can be obtained as a commercially available product.

Step 55

Compound (VII-D) can be produced by reacting compound (VII-C) under ice cooling in the presence of a base in a solvent such as methanol.

Examples of the solvent include those listed in step 2 of production step 1.

Examples of the base include those listed in step 3 of production step 1.

Step 56

Compound (VII-F) can be produced under the same conditions as in step 3 of production step 1 using compound (VII-D) and compound (VII-E).

Step 57

Compound (VII-H) can be produced under the same conditions as in step 3 of production step 1 using compound (VII-F) and compound (VII-G).

Step 58

Compound (VII-J) can be produced under the same conditions as in step 3 of production step 1 using compound (VII-H) and compound (VII-I).

Step 59

Compound (VII-L) can be produced under the same conditions as in step 3 of production step 1 using compound (VII-J) and compound (VII-K).

Step 60

Compound (VII-N) can be produced under the same conditions as in step 3 of production step 1 using compound (VII-L) and compound (VII-M).

Steps 61 to 63

Compound (VII') can be produced under the same conditions as in step 3 of production step 1 using compound (VII-O), compound (VII-P) and compound (VII-Q).

Step DP

A method commonly used in organic synthetic chemistry [e.g., a method described in Protective Groups in Organic Synthesis, third edition, T. W. Greene, John Wiley & Sons Inc. (1999)] can be appropriately used in production.

Compound (VII-B), compound (VII-E), compound (VII-G), compound (VII-I), compound (VII-K), compound (VII-M), compound (VII-O), compound (VII-P) and compound (VII-Q) can be obtained as commercially available products, or by methods described in "The Fourth Series of Experimental Chemistry, Organic Synthesis, p. 258, Maruzen Co., Ltd. (1992)" and "March's Advanced Organic Chemistry: Reactions, Mechanisms, and Structure, 7$^{th}$ Edition" in combination or methods equivalent thereto.

Production Method 14

A unit in which P7 in formula 4 is —O— can be produced by the following method.

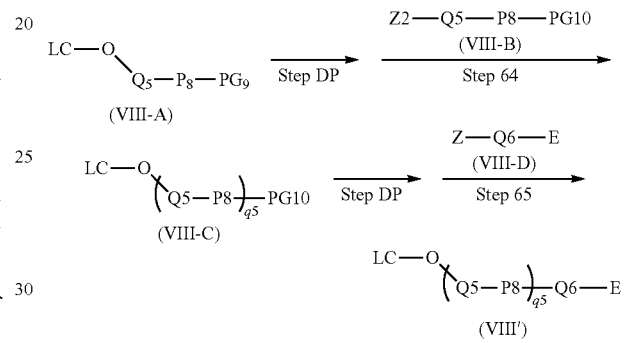

wherein Q5, Q6, P8 and q5 are each as defined above, Z2 represents H, OH, NH$_2$ or SH, PG9 and PG10 each represent an appropriate protective group, LC represents a sugar ligand-tether unit, and E represents carboxylic acid or maleimide.

Step 64

Compound (VIII-C) can be produced under the same conditions as in step 3 of production step 1 using compound (VIII-A) and compound (VIII-B).

Compound (VIII-B) can be obtained as a commercially available product, or by methods described in "The Fourth Series of Experimental Chemistry, Organic Synthesis, p. 258, Maruzen Co., Ltd. (1992)" and "March's Advanced Organic Chemistry: Reactions, Mechanisms, and Structure, 7th Edition" in combination or methods equivalent thereto.

Step 65

Compound (VIII') can be produced under the same conditions as in step 3 of production step 1 using compound (VIII-C) and compound (VIII-D).

Compound (VIII-D) can be obtained as a commercially available product, or by methods described in "The Fourth Series of Experimental Chemistry, Organic Synthesis, p. 258, Maruzen Co., Ltd. (1992)" and "March's Advanced Organic Chemistry: Reactions, Mechanisms, and Structure, 7$^{th}$ Edition" in combination or methods equivalent thereto.

Step DP

A method commonly used in organic synthetic chemistry [e.g., a method described in Protective Groups in Organic Synthesis, third edition, T. W. Greene, John Wiley & Sons Inc. (1999)] can be appropriately used in production.

Production Method 15

A sugar ligand-tether unit in which each of P1 and P4 in formula 2 is —O— can be produced by the following method.

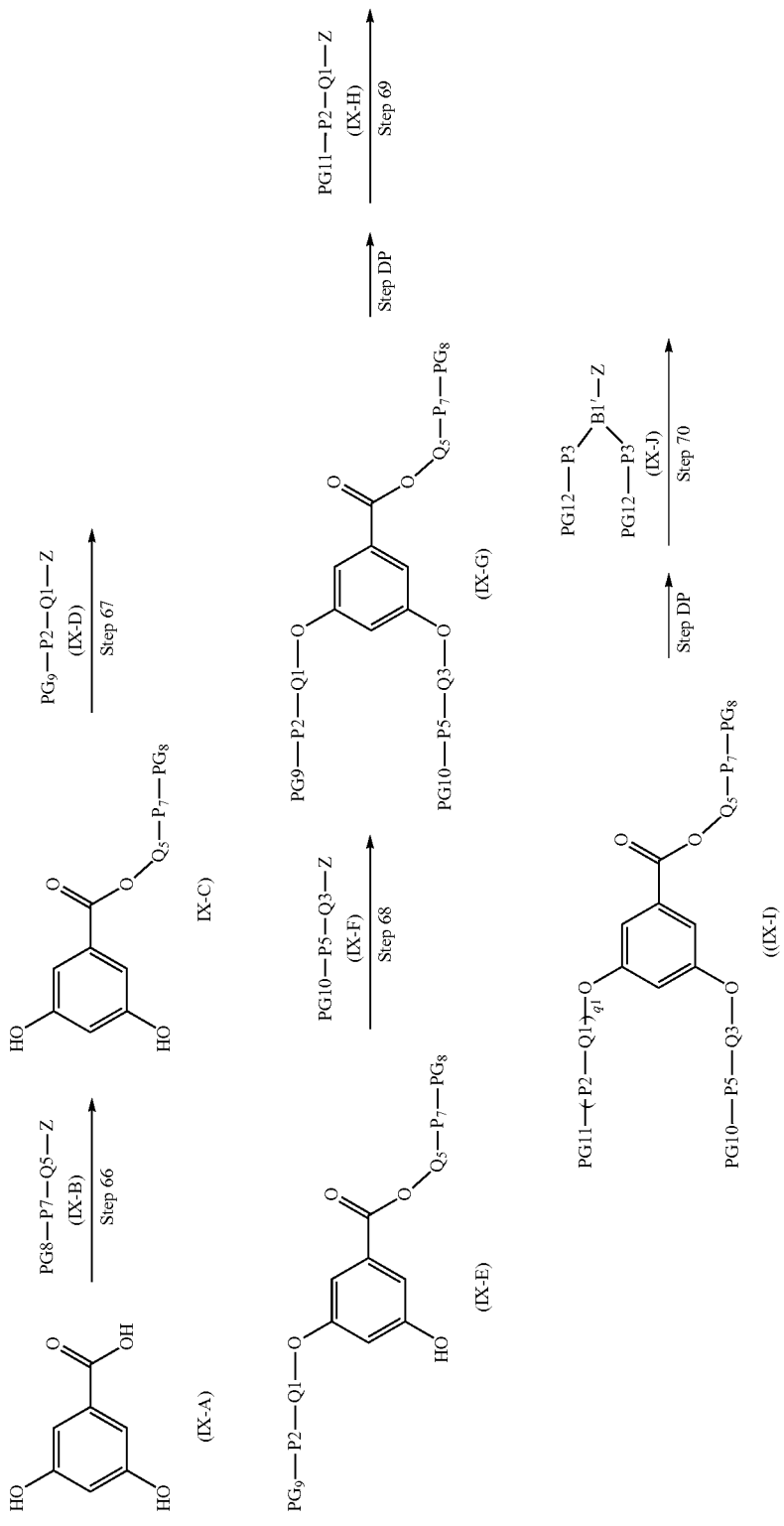

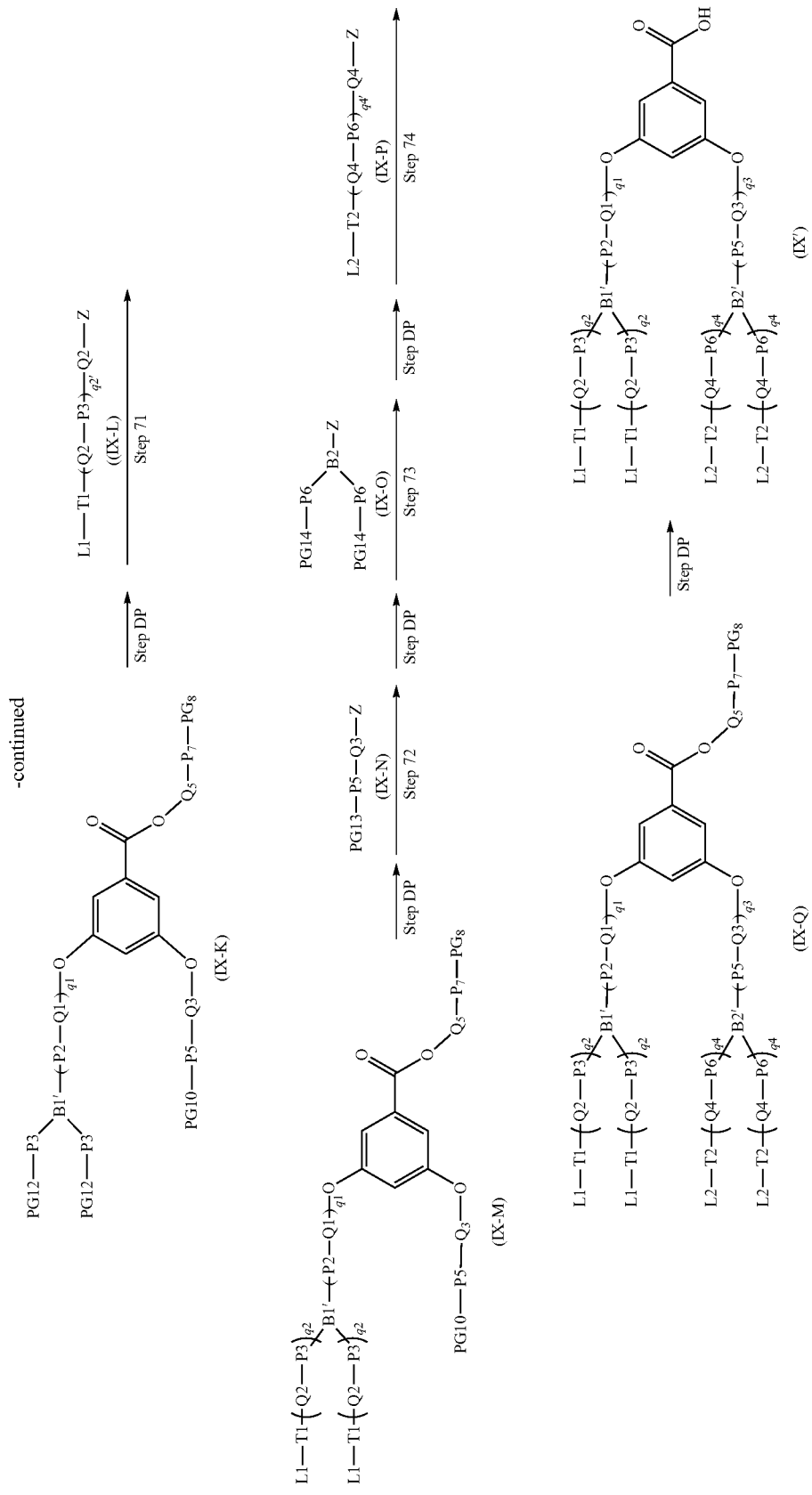

wherein Q1, Q2, Q3, Q4, P2, P3, P5, P6, T1, T2, L1, L2, q1, q2, q3, q4, Z, B1' and B2' are each as defined above, q1' represents an integer smaller by 1 than q1, q2' represents an integer smaller by 1 than q2, and PG8, PG9, PG10, PG11, PG12, PG13 and PG14 each represent an appropriate protective group.

Formulas

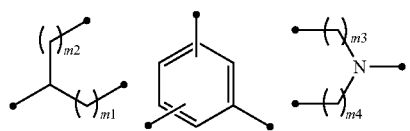

m1, m2, m3 and m4 are as defined above.

Step 66

Compound (IX-C) can be produced by dissolving compound (IX-A) and compound (IX-B) in a solvent such as N,N'-dimethylformamide, adding a base such as potassium bicarbonate to the solution, and reacting the mixture at room temperature to 200° C. for 5 minutes to 100 hours.

Examples of the solvent include those listed in step 2 of production step 1.

Examples of the base include those listed in step 3 of production step 1.

Step 67

Compound (IX-E) can be produced by dissolving compound (IX-C) and compound (IX-D) in a solvent such as N,N'-dimethylformamide, adding a base such as potassium bicarbonate to the solution, and reacting the mixture at room temperature to 200° C. for 5 minutes to 100 hours.

Examples of the solvent include those listed in step 2 of production step 1.

Examples of the base include those listed in step 3 of production step 1.

Compound (IX-A) can be obtained as a commercially available product.

Step 68

Compound (IX-G) can be produced under the same conditions as in step 3 of production step 1 using compound (IX-E) and compound (IX-F).

Step 69

Compound (IX-I) can be produced under the same conditions as in step 3 of production step 1 using compound (IX-G) and compound (IX-H).

Step 70

Compound (IX-K) can be produced under the same conditions as in step 3 of production step 1 using compound (IX-I) and compound (IX-J).

Step 71

Compound (IX-M) can be produced under the same conditions as in step 3 of production step 1 using compound (IX-K) and compound (IX-L).

Steps 72 to 74

Compound (IX') can be produced under the same conditions as in step 3 of production step 1 using compound (IX-M), compound (IX-N), compound (IX-O) and compound (IX-P).

Step DP

A method commonly used in organic synthetic chemistry [e.g., a method described in Protective Groups in Organic Synthesis, third edition, T. W. Greene, John Wiley & Sons Inc. (1999)] can be appropriately used in production.

Compound (IX'-B), compound (IX'-D), compound (IX'-F), compound (IX'-H), compound (IX'-J), compound (IX'-L), compound (IX'-N), compound (IX'-O) and compound (IX'-P) can be obtained as commercially available products, or by methods described in "The Fourth Series of Experimental Chemistry, Organic Synthesis, p. 258, Maruzen Co., Ltd. (1992)" and "March's Advanced Organic Chemistry: Reactions, Mechanisms, and Structure, 7$^{th}$ Edition" in combination or methods equivalent thereto.

Production Method 16

The following method can also be used as a method for producing the nucleic acid conjugates of formulas 1 to 7.

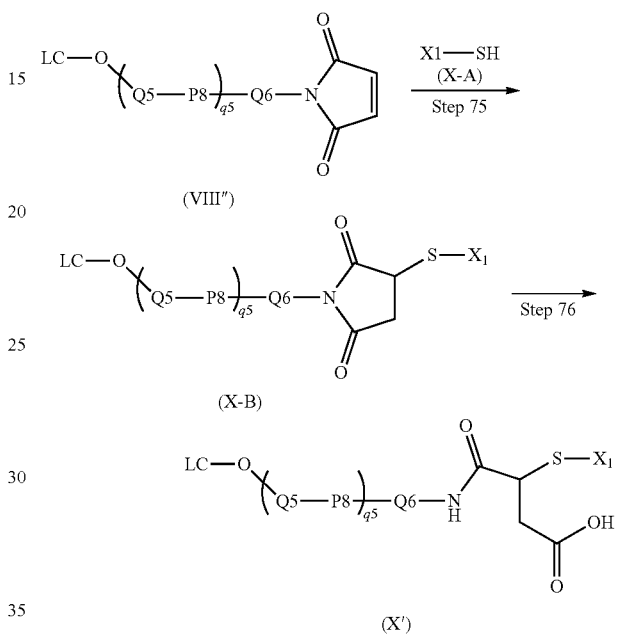

wherein LC, Q5, P8 and Q6 are as defined above, and X1-SH represents an oligonucleotide having a terminal structure containing a SH-substituted C1-C10 alkyl group.

Step 75

Compound (X-B) can be produced by reacting compound (VIII") with compound (X-A) at 0° C. to 100° C. for 10 seconds to 100 hours in a solvent.

Examples of the solvent include water, phosphate buffer solutions, sodium acetate buffer solutions, and dimethyl sulfoxide. These solvents may be used alone or as a mixture.

Compound (VIII') can be obtained by use of production method 14.

Compound (X-B) can also be obtained by a method known in the art (e.g., Bioconjugate Chemistry, Vol. 21, p. 187-202, 2010; and Current Protocols in Nucleic Acid Chemistry, September 2010; CHAPTER: Unit 4.41) or a method equivalent thereto.

Step 76

Compound (X') can be produced by reacting compound (X-B) at a temperature between room temperature and 200° C. for 5 minutes to 100 hours under conditions of pH 8 or higher such as in an aqueous sodium carbonate solution or ammonia water.

Production Method 17

The following method can also be used as a method for producing the nucleic acid conjugates of formulas 1 to 7.

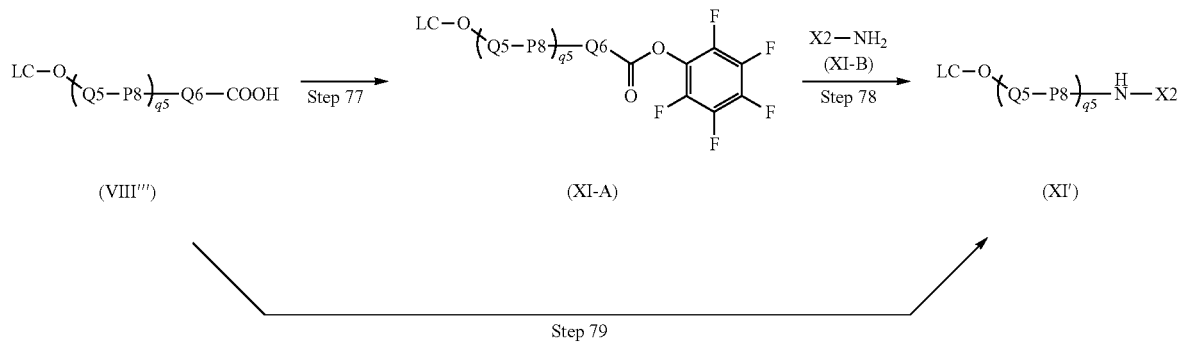

(VIII''')  (XI-A)  (XI')

wherein LC, Q5, P8 and Q6 are as defined above, and X2-NH₂ represents an oligonucleotide having a terminal structure containing a NH₂-substituted C1-C10 alkyl group.

Step 77

Compound (XI-A) can be obtained by using compound (VIII''') and a method known in the art (e.g., a method described in Bioconjugate Chemistry, Vol. 26, p. 1451-1455, 2015) or a method equivalent thereto.

Compound (VIII''') can be obtained by use of production method 14.

Step 78

Compound (XI') can be obtained by using compound (XI-B) and a method known in the art (e.g., a method described in Bioconjugate Chemistry, Vol. 26, p. 1451-1455, 2015) or a method equivalent thereto.

Step 79

In another method, compound (XI') can be obtained directly from compound (XI-A) by a method known in the art (see, for example, Bioconjugate Chemistry, Vol. 22, p. 1723-1728, 2011) or a method equivalent thereto.

The nucleic acid conjugate described in the present specification may be obtained as a salt, for example, an acid-addition salt, a metal salt, an ammonium salt, an organic amine-addition salt, or an amino acid-addition salt.

Examples of the acid-addition salt include: inorganic acid salts such as hydrochloride, sulfate, and phosphate; and organic acid salts such as acetate, maleate, fumarate, citrate, and methanesulfonate. Examples of the metal salt include: alkali metal salts such as sodium salt and potassium salt; alkaline earth metal salts such as magnesium salt and calcium salt; and aluminum salt and zinc salt. Examples of the ammonium salt include salts of ammonium, tetramethylammonium, and the like. Examples of the organic amine-addition salt include addition salts of morpholine, piperidine, and the like. Examples of the amino acid-addition salt include addition salts of lysine, glycine, phenylalanine, and the like.

In the case of preparing the salt of the nucleic acid conjugate described in the present specification, the conjugate obtained in the form of the desired salt can be purified directly, or the conjugate obtained in a free form can be dissolved or suspended in an appropriate solvent, and a corresponding acid or base is added to the solution or the suspension, followed by isolation or purification. In order to convert counter ions forming the conjugate salt to different counter ions, the conjugate salt can be dissolved or suspended in an appropriate solvent, and then, several equivalents to a large excess of an acid, a base and/or a salt (e.g., an inorganic salt such as sodium chloride or ammonium chloride) is added to the solution or the suspension, followed by isolation or purification.

Some nucleic acid conjugates described in the present specification may have stereoisomers such as geometric isomers and optical isomers, tautomers, or the like. All possible isomers and mixtures thereof are also encompassed in the present invention.

The nucleic acid conjugate described in the present specification may be present in the form of an adduct with water or various solvents. These adducts are also encompassed in the present invention.

The nucleic acid conjugate of the present invention further encompasses molecules in which a portion or the whole of the atoms is substituted with an atom having an atomic mass number different therefrom (isotope) (e.g., a deuterium atom).

The pharmaceutical composition of the present invention comprises the nucleic acid conjugate represented by formula 1. The nucleic acid conjugate of the present invention, owing to having sugar ligands L1 and L2, is recognized by a target cell and transferred into the cell.

The nucleic acid conjugate of the present invention can be used in the treatment of diseases related to a target gene by inhibiting (reducing or silencing) the expression of the target gene in vivo when administered to a mammal.

In the case of using the nucleic acid conjugate of the present invention as a therapeutic agent or a prophylactic agent, the administration route is not particularly limited, and an administration route most effective for treatment is desirably used. Examples thereof include intravenous administration, subcutaneous administration and intramuscular administration.

Intravenous administration is preferred. The dose differs depending on the pathological condition or age of the recipient, the administration route, etc. The dose can be, for example, a daily dose of 0.1 μg to 1000 mg, more preferably 1 to 100 mg, in terms of the amount of the double-stranded oligonucleotide.

Examples of the preparation appropriate for intravenous administration or intramuscular administration include injections. A prepared liquid formulation may be used directly in the form of, for example, an injection. Alternatively, the liquid formulation may be used after removal of the solvent by, for example, filtration or centrifugation, or the liquid formulation may be used after being freeze-dried and/or may be used after being supplemented with, for example, an excipient such as mannitol, lactose, trehalose, maltose, or glycine and then freeze-dried.

In the case of an injection, the liquid formulation or the solvent-free or freeze-dried composition is preferably mixed with, for example, water, an acid, an alkali, various buffer solutions, physiological saline, or an amino acid transfusion, to prepare the injection. Alternatively, the injection may be prepared by the addition of, for example, an antioxidant such as citric acid, ascorbic acid, cysteine, or EDTA or a tonicity agent such as glycerin, glucose or sodium chloride. Also, the injection can also be cryopreserved by the addition of a cryopreserving agent such as glycerin.

EXAMPLES

Next, the present invention will be specifically described with reference to Reference Examples, Examples and Test Examples. However, the present invention is not limited by these Examples and Test Examples. Proton nuclear magnetic resonance spectra ($^1$H NMR) shown in Examples and Reference Examples were measured at 270 MHz, 300 MHz or 400 MHz, and no exchangeable proton may be clearly observed depending on compounds and measurement conditions. Signal multiplicity is indicated as usually used, and br means broad and represents an apparently broad signal.

UPLC analysis employed the following conditions:
Mobile phase A: aqueous solution containing 0.1% formic acid, B: acetonitrile solution
Gradient: linear gradient from 10% to 90% of mobile phase B (3 min)
Column: ACQUITY UPLC BEH C18 manufactured by Waters Corp. (1.7 μm, inside diameter: 2.1×50 mm)
Flow rate: 0.8 mL/min
PDA detection wavelength: 254 nm (detection range: 190 to 800 nm)

Reference Example 1 Synthesis of Sugar Ligand Unit the reaction mixture, and the solvent was distilled off under reduced pressure. The obtained mixture was dissolved in N,N'-dimethylformamide (DMF). To the solution, 2-aminoethyl maleimide bromate (0.6479 g, 2.5491 mmol) and diisopropylethylamine (1.7 mL, 9.7835 mmol) were added, and then, the mixture was stirred overnight at room temperature. The solvent in the reaction solution was distilled off under reduced pressure, followed by elution by reverse-phase column chromatography (water/methanol=80/20) to obtain compound 2 (0.8502 g, yield: 76%).

ESI-MS m/z: 570 (M+H)$^+$;
$^1$H-NMR (DMSO-D$_6$) δ: 1.45-1.56 (4H, m), 1.78 (3H, s), 1.90 (3H, s), 1.97 (2H, t, J=7.0 Hz), 2.00 (3H, s), 2.11 (3H, s), 3.18-3.19 (2H, m), 3.38-3.45 (3H, m), 3.64-3.71 (1H, m), 3.85-3.89 (1H, m), 4.01-4.04 (3H, m), 4.48 (1H, d, J=8.6 Hz), 4.95-4.98 (1H, m), 5.21 (1H, d, J=3.5 Hz), 6.99 (2H, s), 7.81-7.87 (2H, m).

Synthesis of Compound 4
Step 2
Compound 1 (0.9602 g, 2.1460 mmol) described in step 1 was dissolved in N,N'-dimethylformamide (10 mL). To the solution, N-Boc-ethylenediamine (manufactured by Sigma-Aldrich Co. LLC, 0.6877 g, 4.292 mmol), diisopropylethylamine (1.90 mL, 10.87 mmol), and 2-(1H-benzotriazol-1-yl)-1,1,3,3-tetramethyluronium hexafluorophosphate (manufactured by Wako Pure Chemical Industries, Ltd., 1.6437 g, 4.3229 mmol) were added, and the mixture was stirred overnight at room temperature. Water was added to the reaction solution, followed by extraction with chloroform twice. Then, the organic layer was washed with saturated saline and dried over anhydrous magnesium sulfate. The solvent was distilled off under reduced pressure to obtain a crude product of compound 3.

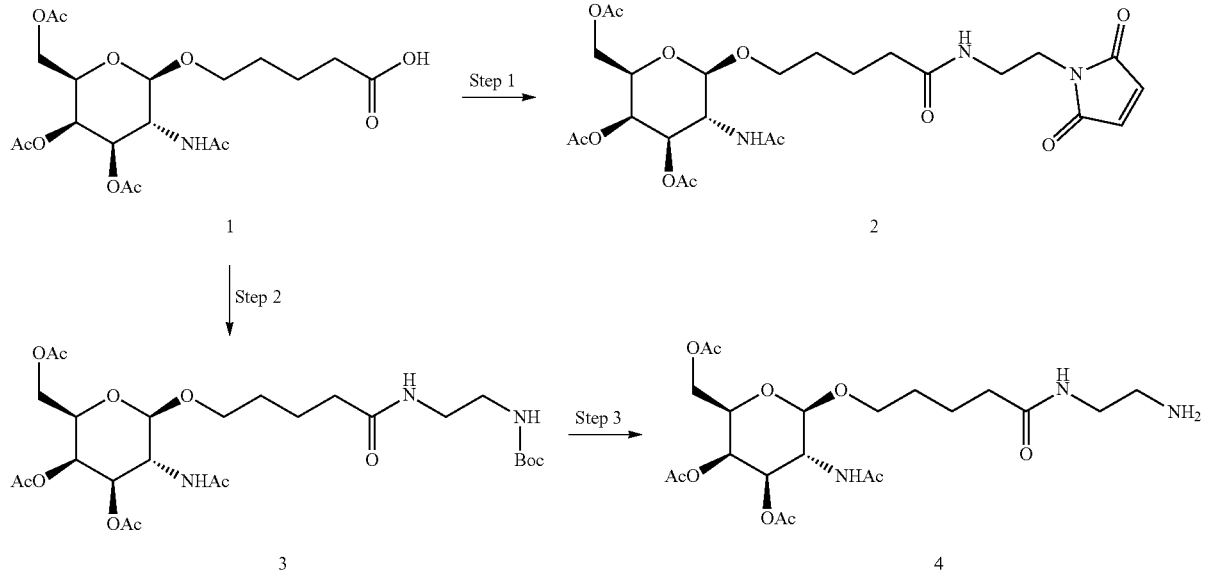

Synthesis of Compound 2
Step 1
Compound 1 (0.8755 g, 1.9567 mmol) synthesized by the method described in Journal of American Chemical Society, Vol. 136, p. 16958-16961, 2014 was dissolved in tetrahydrofuran (10 mL). To the solution, 1,3-dicyclohexanecarbodiimide (DCC, 0.4247 g, 2.0584 mmol) and N-hydroxysuccinimide (0.2412 g, 2.0958 mmol) were stirred overnight at room temperature. A precipitated solid was removed from ESI-MS m/z: 590 (M+H)$^+$
Step 3
Compound 3 (1.2654 g, 2.1460 mmol) synthesized in step 2 was dissolved in dichloromethane (15 mL). To the solution, trifluoroacetic acid (4 mL) was added, and the mixture was stirred overnight at room temperature. Water was added to the reaction solution, followed by extraction with ethyl acetate. Then, the organic layer was washed with saturated saline and dried over anhydrous magnesium sulfate. The solvent was distilled off under reduced pressure, followed by elution by reverse-phase column chromatography (water/methanol=80/20) to obtain compound 4 (0.3879 g, yield: 37%).

ESI-MS m/z: 490 (M+H)$^+$;

$^1$H-NMR (DMSO-D$_6$) δ: 1.46-1.52 (4H, m), 1.78 (3H, s), 1.90 (3H, s), 2.00 (3H, s), 2.08 (2H, t, J=7.4 Hz), 2.11 (3H, s), 2.85 (2H, t, J=6.3 Hz), 3.27 (2H, dd, J=12.3, 6.2 Hz), 3.67-3.69 (1H, m), 3.68-3.73 (1H, m), 3.86-3.90 (1H, m), 4.01-4.04 (3H, m), 4.49 (1H, d, J=8.4 Hz), 4.97 (1H, dd, J=11.3, 3.4 Hz), 5.22 (1H, d, J=3.5 Hz), 7.86 (1H, d, J=9.1 Hz), 7.95-8.02 (1H, m).

Reference Example 2 Synthesis of Brancher Unit
Synthesis of Compound 7

Step 4

(9H-Fluoren-9-yl)methyl ((2R,3R)-1,3-dihydroxybutan-2-yl)carbamate (compound 5, manufactured by Chem-Impex International, Inc., 1.50 g, 4.58 mmol) was dissolved in pyridine (20 mL). To the solution, 4,4'-dimethoxytrityl chloride (manufactured by Tokyo Chemical Industry Co., Ltd., 1.71 g, 5.04 mmol) was added under ice cooling, and then, the mixture was stirred at room temperature for 2 hours. The reaction solution was ice-cooled, and a 10% aqueous citric acid solution was added thereto, followed by extraction with ethyl acetate. Then, the organic layer was washed with saturated saline and dried over anhydrous magnesium sulfate. The solvent was distilled off under reduced pressure, and the residue was purified by silica gel column chromatography (hexane/ethyl acetate=90/10) to obtain compound 6 (1.07 g, yield: 37%).

ESI-MS m/z: 630 (M+H)$^+$

Step 5

Compound 6 (1.07 g, 1.699 mmol) synthesized in step 4 was dissolved in N,N-dimethylformamide (10 mL). To the solution, piperidine (0.336 mL, 3.40 mmol) was added at room temperature, and the mixture was stirred for 3 hours. Water was added to the reaction solution, followed by extraction with ethyl acetate. Then, the organic layer was washed with saturated saline and dried over anhydrous magnesium sulfate. The solvent was distilled off under reduced pressure, and the residue was purified by amino silica gel column chromatography (chloroform/methanol=90/10) to obtain compound 7 (0.59 g, yield: 85%).

ESI-MS m/z: 408 (M+H)$^+$

Example 1 Synthesis of Tether Unit—1

Synthesis of Compound 16

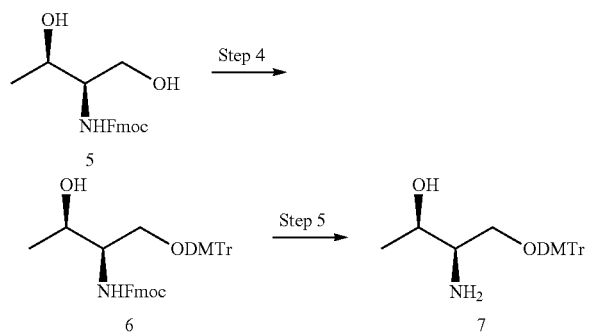

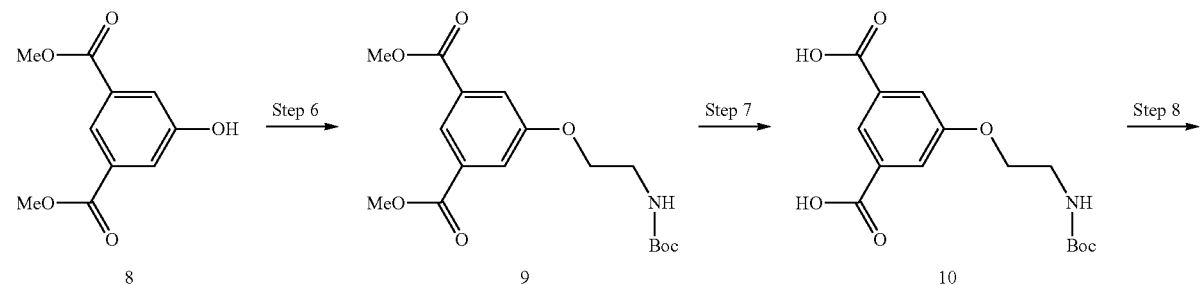

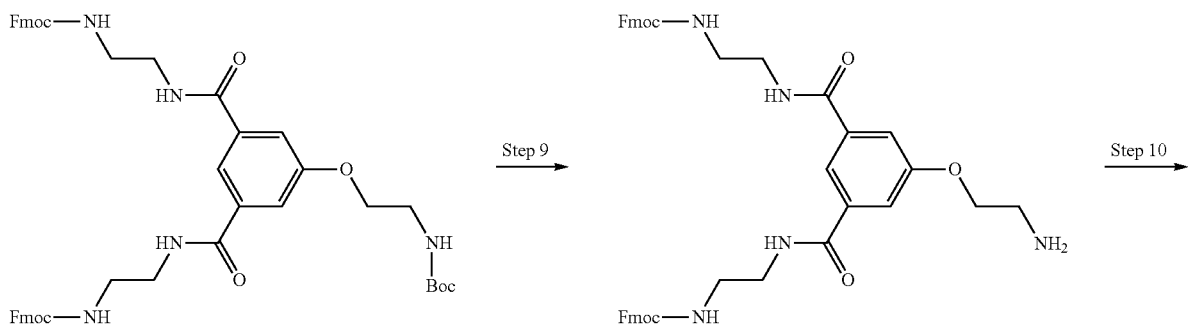

-continued
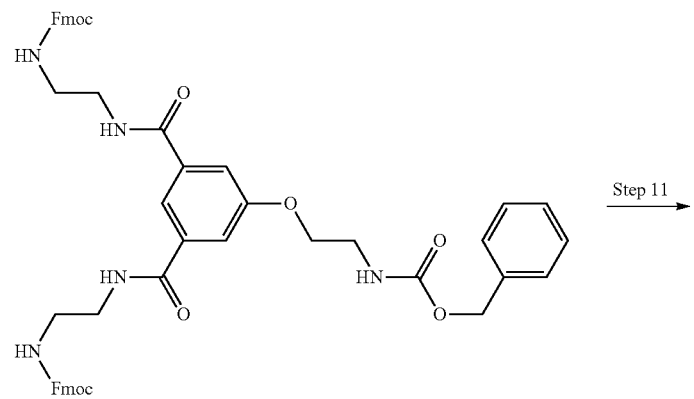
13
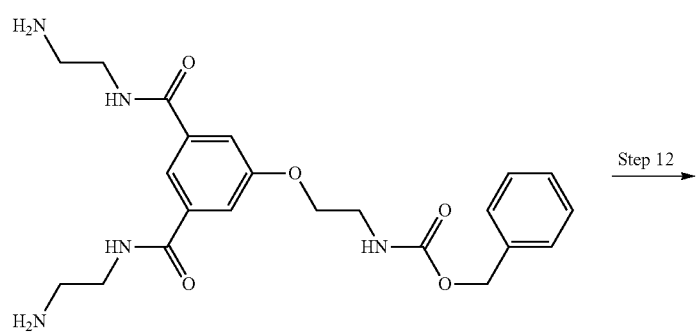
14
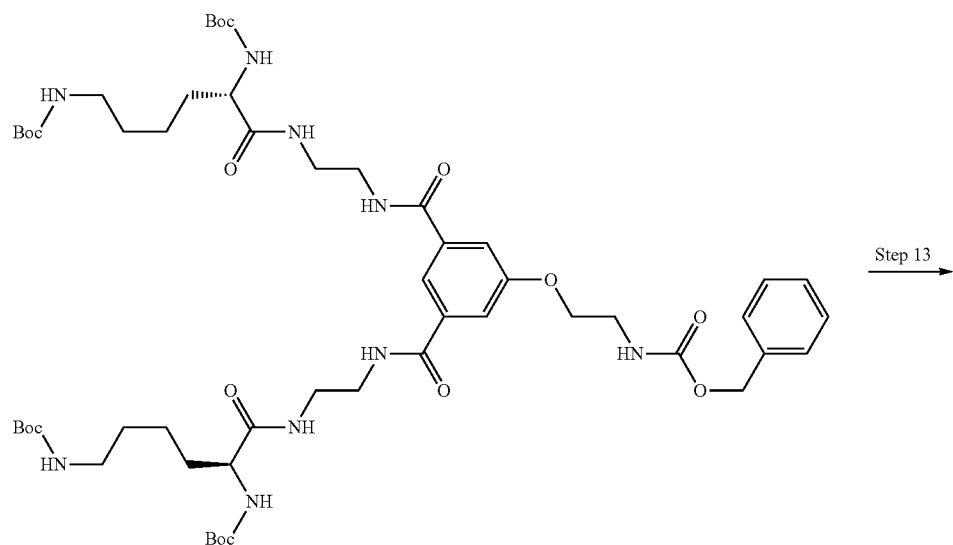
15

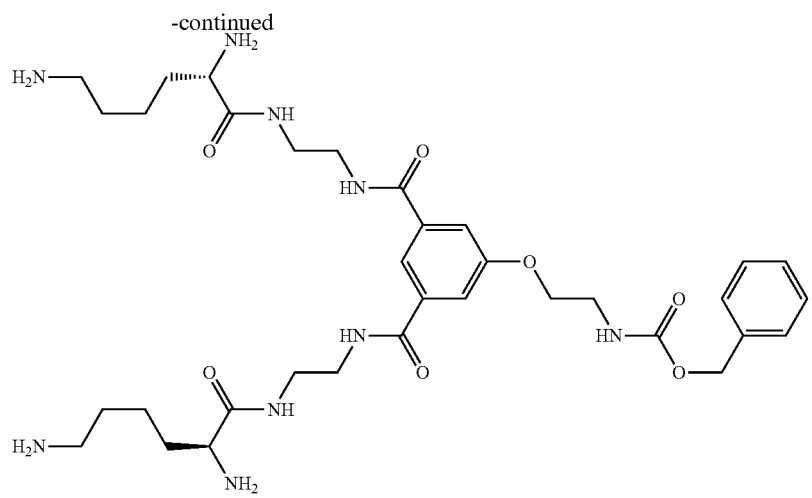

16

Step 6

Dimethyl 5-hydroxyisophthalate (compound 8, manufactured by Wako Pure Chemical Industries, Ltd., 5.0443 g, 24 mmol) was dissolved in tetrahydrofuran (manufactured by Wako Pure Chemical Industries, Ltd., 25 mL). To the solution, 2-(tert-butoxycarbonylamino)-1-ethanol (manufactured by Tokyo Chemical Industry Co., Ltd., 4.0343 g, 25.03 mmol), and polymer-supported triphenylphosphine (manufactured by Sigma-Aldrich Co. LLC, 6.61 g, 25.2 mmol) were added, then a 40% solution of diisopropyl azodicarboxylate (DIAD) in toluene (manufactured by Tokyo Chemical Industry Co., Ltd., 13.26 mL, 25.2 mmol) was added under ice cooling, and the mixture was stirred overnight at room temperature. The reaction solution was filtered, and the solvent in the filtrate was distilled off under reduced pressure. Then, the residue was purified by amino silica gel column chromatography (hexane/ethyl acetate=95/5 to 80/20) to obtain compound 9 (5.3071 g, yield: 63%).

ESI-MS m/z: 254 (M+H)$^+$, detected as a Boc-deprotected form

Step 7

Compound 9 (5.3071 g, 15.02 mmol) synthesized in step 6 was dissolved in methanol (25 mL). To the solution, a 2 mol/L aqueous sodium hydroxide solution (manufactured by Wako Pure Chemical Industries, Ltd., 13 mL) was added under ice cooling, and the mixture was stirred at room temperature for 4 hours. The reaction solution was ice-cooled, and a 10% aqueous citric acid solution was added thereto, followed by extraction with ethyl acetate. Then, the organic layer was washed with saturated saline and dried over anhydrous magnesium sulfate. The solvent was distilled off under reduced pressure to quantitatively obtain compound 10.

ESI-MS m/z: 324 (M−H)$^-$

Step 8

Compound 10 (1.9296 g, 5.93 mmol) synthesized in step 7 was dissolved in N,N'-dimethylformamide (70 mL). To the solution, N-1-(9H-fluoren-9-ylmethoxycarbonyl)-ethylenediamine hydrochloride (3.3493 g, 11.86 mmol), diisopropylethylamine (5.18 mL, 29.7 mmol), and 2-(1H-benzotriazol-1-yl)-1,1,3,3-tetramethyluronium hexafluorophosphate (4.5168 g, 11.88 mmol) were added, and the mixture was stirred at room temperature for 4 hours. The reaction solution was ice-cooled, and a 10% aqueous citric acid solution was added thereto, followed by extraction with chloroform. Then, the organic layer was washed with a saturated aqueous solution of sodium bicarbonate and saturated saline and dried over anhydrous magnesium sulfate. The solvent was distilled off under reduced pressure, and the residue was purified by silica gel column chromatography (chloroform/methanol) to obtain compound 11 (3.4407 g, yield: 68%).

ESI-MS m/z: 898 (M+HCOO)$^-$

Step 9

Compound 11 (1.6087 g, 1.884 mmol) synthesized in step 8 was dissolved in dichloromethane (20 mL). To the solution, trifluoroacetic acid (5 mL, 64.9 mmol) was added under ice cooling, and the mixture was stirred at room temperature for 4 hours. The solvent in the reaction solution was distilled off under reduced pressure to quantitatively obtain compound 12 (2.4079 g).

ESI-MS m/z: 798 (M+HCOO)$^-$

Step 10

Compound 12 (386 mg, 0.512 mmol) synthesized in step 9 was dissolved in tetrahydrofuran (10 mL). To the solution, benzoyl chloride (175 mg, 1.024 mmol) was added under ice cooling, and the mixture was stirred at room temperature for 1 hour. The solvent in the reaction solution was distilled off under reduced pressure, and the residue was purified by silica gel column chromatography (chloroform/methanol) to obtain compound 13 (373 mg, yield: 82%).

ESI-MS m/z: 888 (M+H)$^+$

Step 11

Compound 13 (108 mg, 0.122 mmol) synthesized in step 10 was dissolved in dichloromethane (5 mL). To the solution, diethylamine (0.5 mL, 4.8 mmol) was added at room temperature, and the mixture was stirred for 1 hour. The solvent was distilled off under reduced pressure to quantitatively obtain compound 14 (54.9 mg).

ESI-MS m/z: 444 (M+H)$^+$

Step 12

Compound 14 (180 mg, 0.406 mmol) synthesized in step 11, Nα,Nε-bis(tert-butoxycarbonyl)-L-lysine (manufactured by Novabiochem/Merck Millipore, 295 mg, 0.852 mmol), diisopropylethylamine (0.354 mL, 2.029 mmol), and 2-(1H-benzotriazol-1-yl)-1,1,3,3-tetramethyluronium hexafluorophosphate (324 mg, 0.852 mmol) were added, and the mixture was stirred overnight at room temperature. The reaction solution was ice-cooled, and a 10% aqueous citric acid solution was added thereto, followed by extraction with chloroform. Then, the organic layer was washed with saturated saline and dried over anhydrous magnesium sulfate. The solvent was distilled off under reduced pressure, and the residue was purified by amino silica gel column chromatography (chloroform/methanol) to quantitatively obtain compound 15 (450 mg).

ESI-MS m/z: 1101 (M+H)+

Step 13

Compound 15 (2.1558 g, 1.9593 mmol) synthesized in step 12 was dissolved in dichloromethane (20 mL). To the solution, trifluoroacetic acid (5 mL) was added under ice cooling, and the mixture was stirred at room temperature for 4 hours. The solvent in the reaction solution was distilled off under reduced pressure to quantitatively obtain compound 16.

ESI-MS m/z: 700 (M+H)+

Example 2 Synthesis of Tether Unit—2

Synthesis of Compound 20

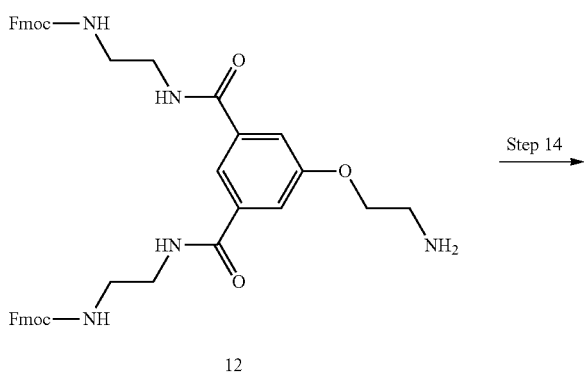

12

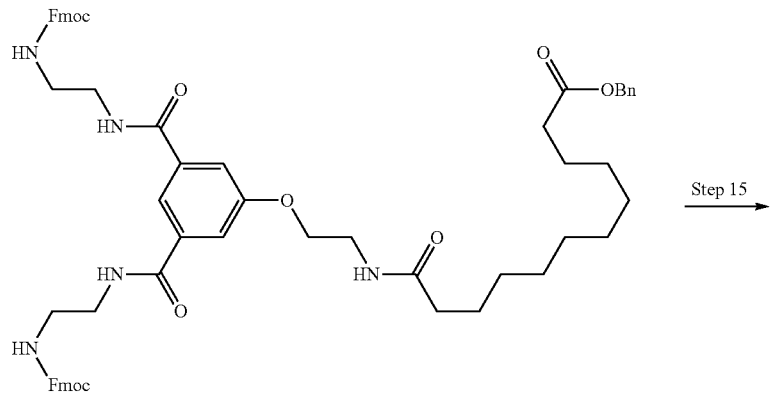

17

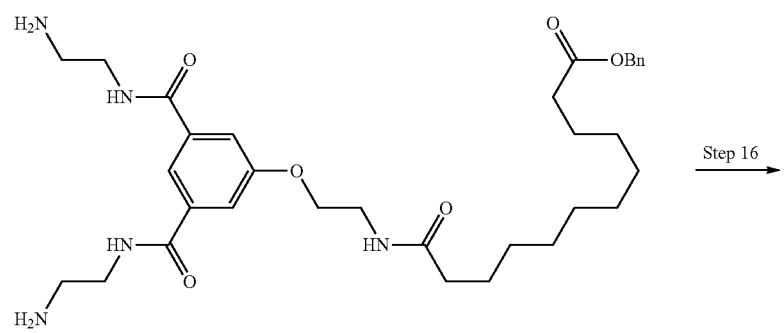

18

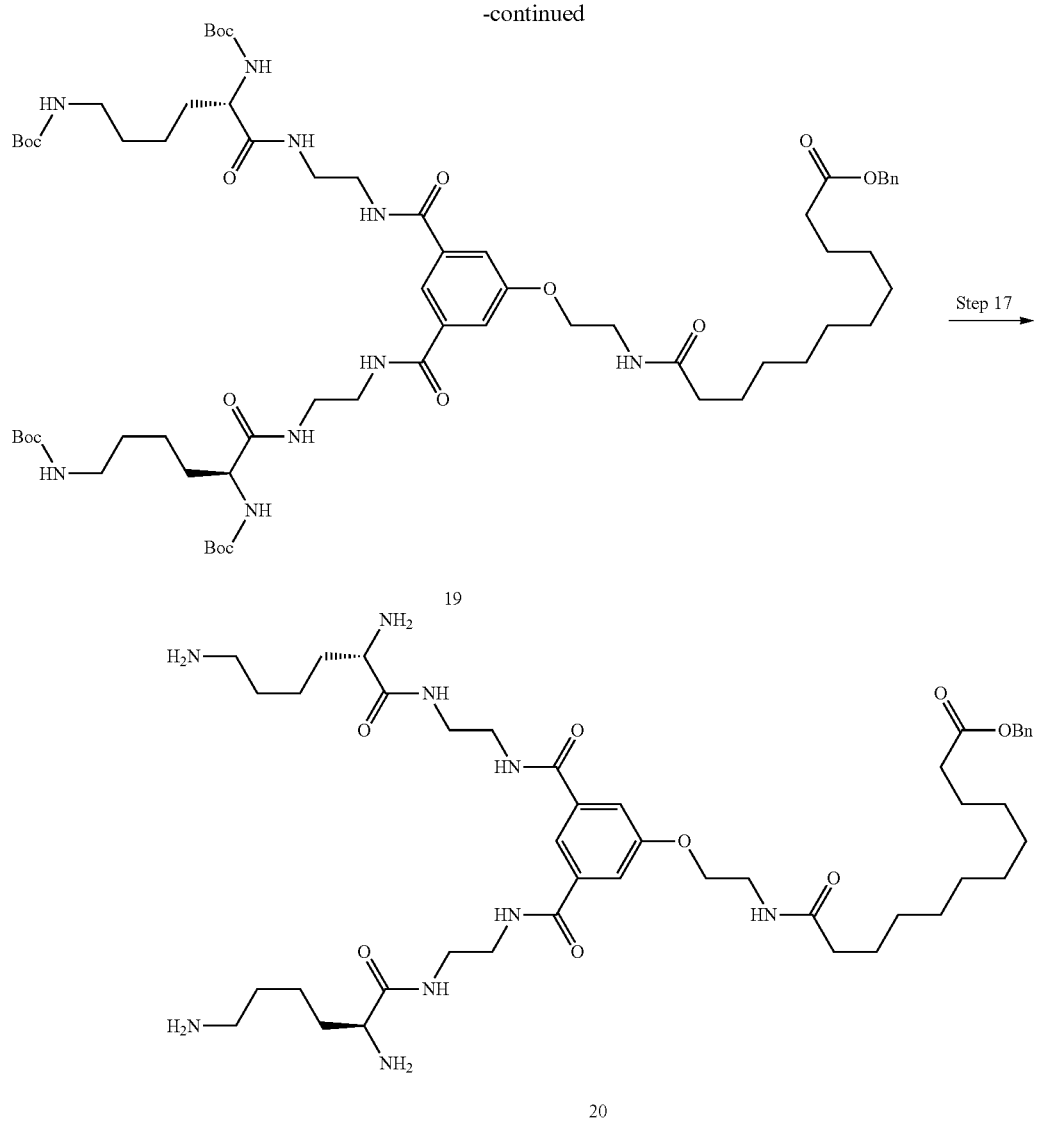

Step 14

Compound 12 (0.5716 g, 0.7582 mmol) synthesized in step 9, dodecanoic acid monobenzyl ester (0.4859 mg, 1.5164 mmol) synthesized by the method described in Bioconjugate Chemistry, Vol. 22, p. 690-699, 2011, diisopropylethylamine (0.662 mL, 3.79 mmol), and 2-(1H-benzotriazol-1-yl)-1,1,3,3-tetramethyluronium hexafluorophosphate (0.5766 g, 1.516 mmol) were dissolved in N,N-dimethylformamide (12 mL). The solution was stirred at room temperature for 1 hour. The reaction solution was ice-cooled, and a saturated aqueous solution of citric acid was added thereto, followed by extraction with chloroform. Then, the organic layer was washed with saturated saline and dried over anhydrous magnesium sulfate. The solvent was distilled off under reduced pressure, and the residue was purified by silica gel column chromatography (chloroform/methanol) to obtain compound 17 (0.88 g, yield: 84%).

ESI-MS m/z: 1057 (M+H)$^+$

Step 15

Compound 17 (0.7545 g, 0.714 mmol) synthesized in step 14 was dissolved in dichloromethane-tetrahydrofuran (20 mL). To the solution, diethylamine (5 mL, 47.9 mmol) was added at room temperature, and the mixture was stirred overnight. The solvent was distilled off under reduced pressure to quantitatively obtain compound 18.

ESI-MS m/z: 612 (M+H)$^+$

Step 16

Compound 18 (0.437 g, 0.7143 mmol) synthesized in step 15, Nα,Nε-bis(tert-butoxycarbonyl)-L-lysine (manufactured by Novabiochem/Merck Millipore, 0.5483 g, 1.583 mmol), diisopropylethylamine (0.624 mL, 3.57 mmol), and 2-(1H-benzotriazol-1-yl)-1,1,3,3-tetramethyluronium hexafluorophosphate (0.5703 g, 1.5 mmol) were added, and the mixture was stirred room at temperature for 2 hours. A 10% aqueous citric acid solution was added to the reaction solution, followed by extraction with ethyl acetate. Then, the organic layer was washed with saturated saline and dried over anhydrous magnesium sulfate. The solvent was distilled off under reduced pressure to obtain a crude product of compound 19.

ESI-MS m/z: 1269 (M+H);

Step 17

Compound 19 (0.906 g, 0.7143 mmol) synthesized in step 16 was dissolved in dichloromethane (12 mL). To the solution, trifluoroacetic acid (3 mL, 38.9 mmol) was added under ice cooling, and the mixture was stirred at room temperature for 4 hours. The solvent in the reaction solution was distilled off under reduced pressure to obtain a crude product of compound 20.

ESI-MS m/z: 869 (M+H)$^+$

Example 3 Synthesis of Tether Unit—3

Synthesis of Compound 23

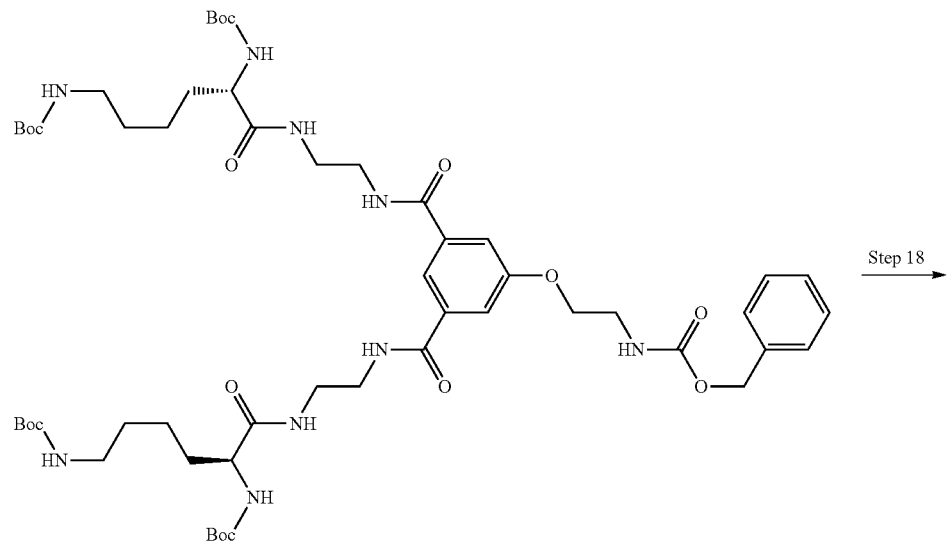

15

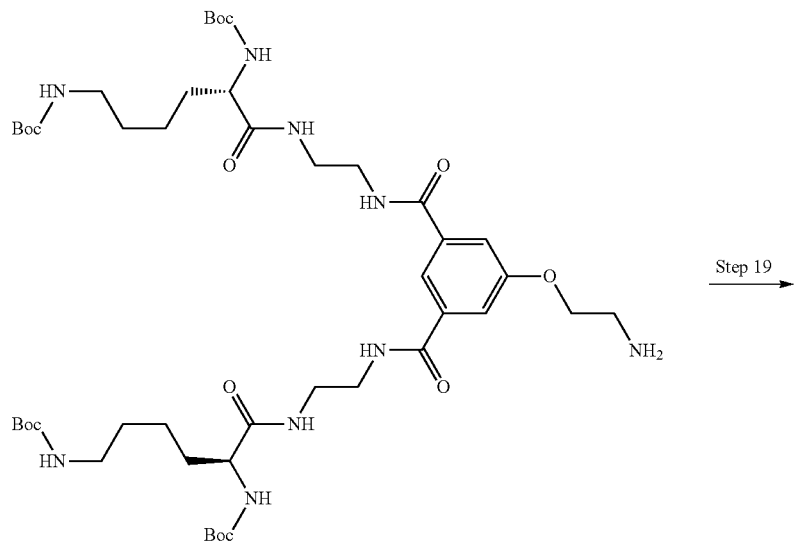

21

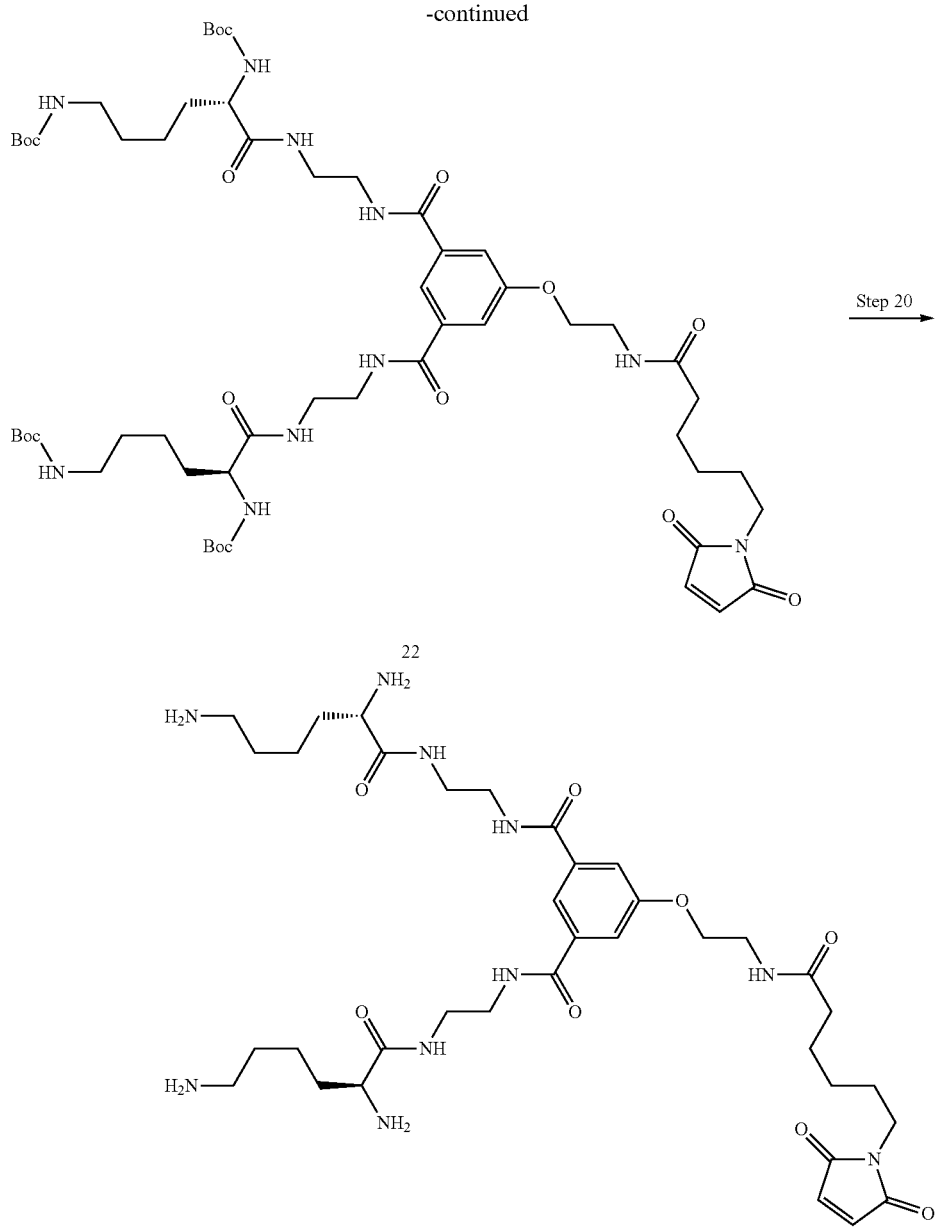

Step 18

Compound 15 (100 mg, 0.091 mmol) synthesized in step 12 was dissolved in methanol (3 mL). To the solution, acetic acid (2 μL) was added, followed by catalytic hydrogen reduction using palladium/carbon. The solvent in the obtained solution fraction was distilled off under reduced pressure to quantitatively obtain compound 21.

ESI-MS m/z: 967 (M+H)$^+$

Step 19

Compound 21 (50 mg, 0.052 mmol) synthesized in step 18 and N-(6-maleimidocaproyloxy)succinimide (48 mg, 0.155 mmol) were dissolved in tetrahydrofuran (2 mL). To the solution, diisopropylethylamine (0.045 mL, 0.259 mmol) was added, and the mixture was stirred overnight at room temperature. The solvent was distilled off under reduced pressure, and the residue was purified by silica gel column chromatography (chloroform/methanol) to obtain compound 22 (18 mg, yield: 30%).

ESI-MS m/z: 1160 (M+H)$^+$

Step 20

Compound 22 (18 mg, 0.016 mmol) synthesized in step 19 was dissolved in dichloromethane (2 mL). To the solution, trifluoroacetic acid (0.2 mL, 2.6 mmol) was added under ice cooling, and the mixture was stirred overnight at room temperature. The solvent in the reaction solution was distilled off under reduced pressure, and the residue was crystallized from diethyl ether to obtain compound 23 (7.5 mg, yield: 64%) as a white solid.

ESI-MS m/z: 759 (M+H)$^+$

Example 4 Synthesis of Tether Unit—4
Synthesis of Compound 29
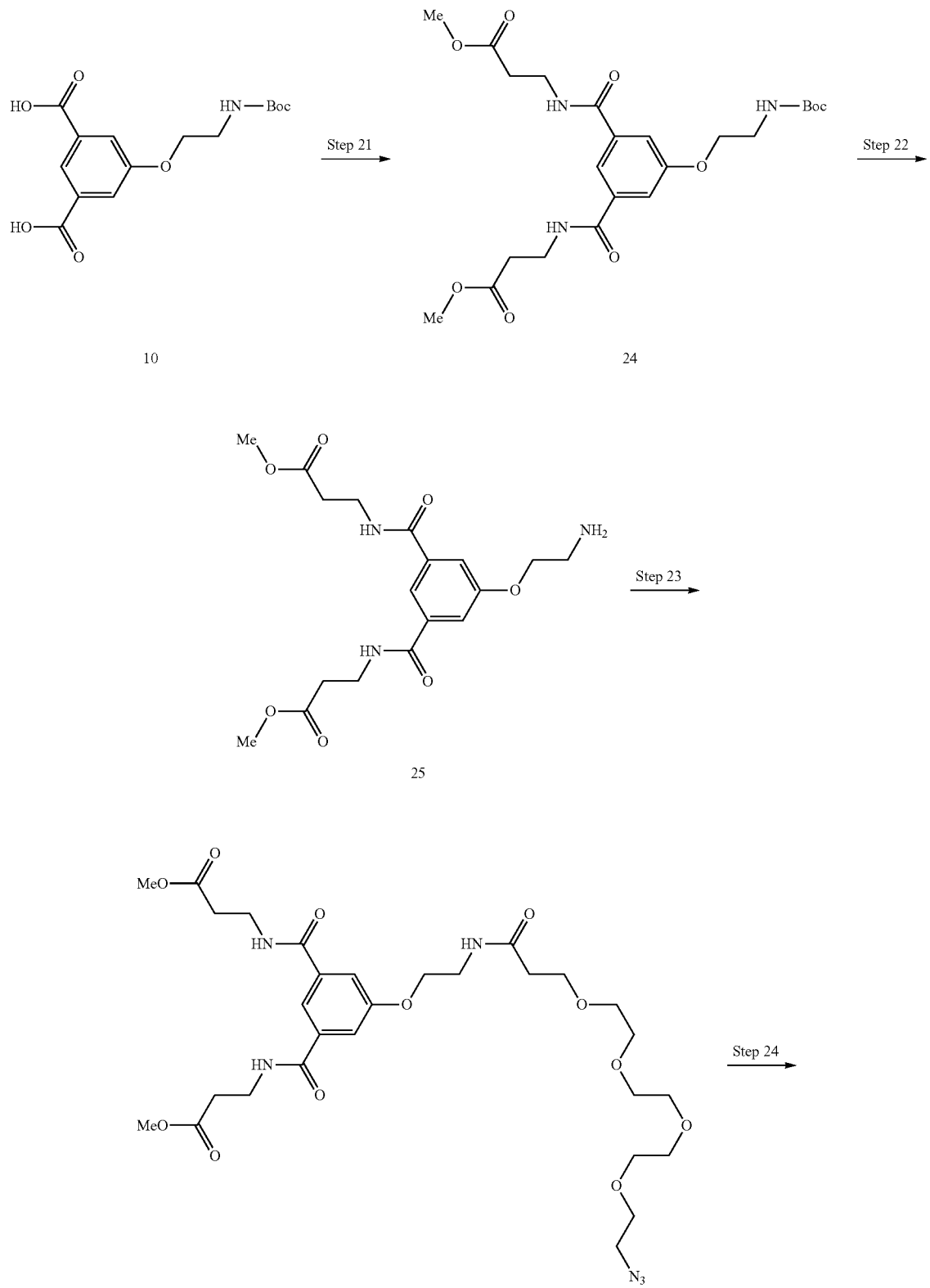

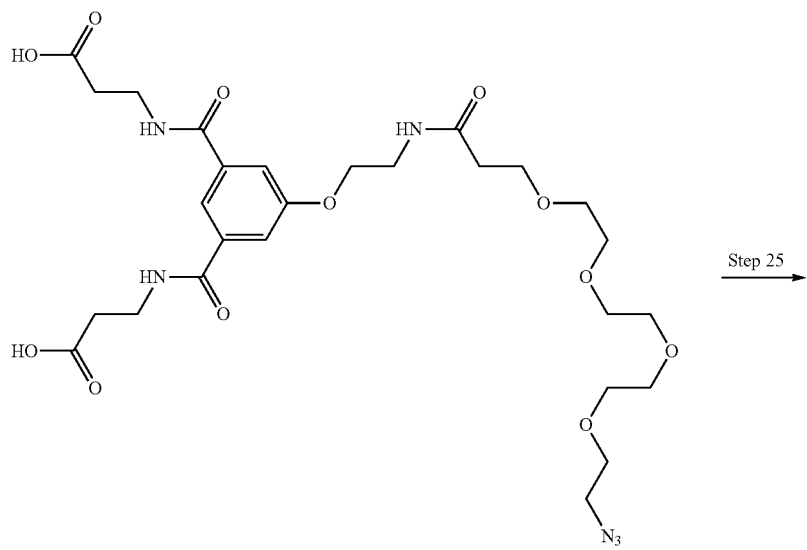
27
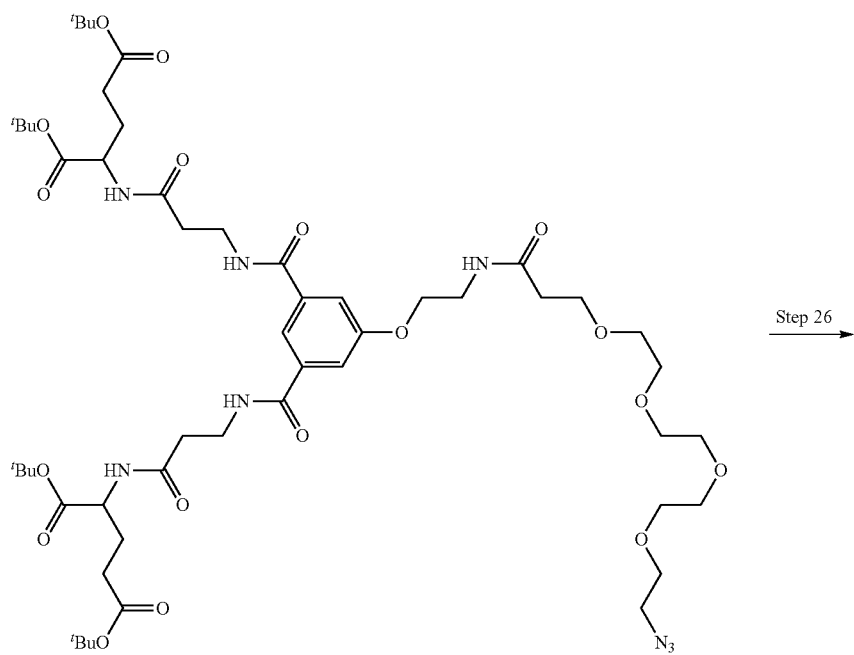
28

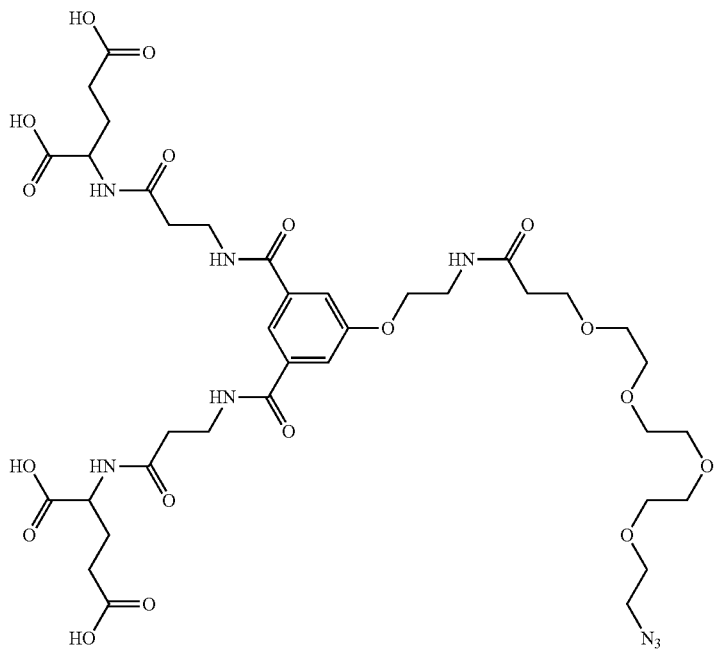

29

Step 21

Compound 24 was quantitatively obtained in the same way as in step 8 of Example 1 using compound 10 (0.9372 g, 2.8809 mmol) synthesized in step 7 and β-alanine methyl ester hydrochloride (manufactured by Tokyo Chemical Industry Co., Ltd., 0.8082 g, 5.7902 mmol).

ESI-MS m/z: 495 (M+H)$^+$

Step 22

Compound 25 was quantitatively obtained in the same way as in step 9 of Example 1 using compound 24 (0.9622 g, 1.952 mmol) synthesized in step 21.

ESI-MS m/z: 396 (M+H)$^+$

Step 23

Compound 26 was quantitatively obtained in the same way as in step 19 of Example 3 using compound 25 (0.1146 g, 0.290 mmol) synthesized in step 22 and N-succinimidyl 15-azido-4,7,10,13-tetraoxapentadecanoic acid (N3-PEG4-NHS, manufactured by Tokyo Chemical Industry Co., Ltd., 0.0750 g, 0.1931 mmol).

ESI-MS m/z: 669 (M+H)$^+$

Step 24

Compound 27 was quantitatively obtained in the same way as in step 7 of Example 1 using compound 26 (0.1291 g, 0.193 mmol) synthesized in step 23.

ESI-MS m/z: 641 (M+H)$^+$

Step 25

Compound 28 (0.0521 g, yield: 24%) was obtained in the same way as in step 8 of Example 1 using compound 27 (0.1252 g, 0.193 mmol) synthesized in step 24 and L-glutamic acid di-tert-butyl ester (manufactured by Watanabe Chemical Industries, Ltd., 0.1180 g, 0.399 mmol).

ESI-MS m/z: 1124 (M+H)$^+$

Step 26

Compound 29 (36 mg, yield: 86%) was obtained in the same way as in step 9 of Example 1 using compound 28 (0.0521 g, 0.0464 mmol) synthesized in step 25.

ESI-MS m/z: 899 (M+H)$^+$

Example 5 Synthesis of Sugar Ligand-Benzene Ring Unit—1
Synthesis of Compound 31
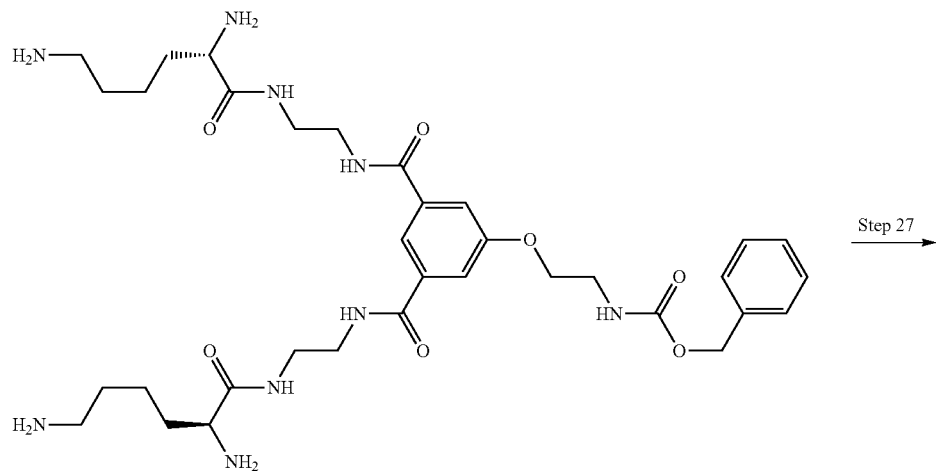
16
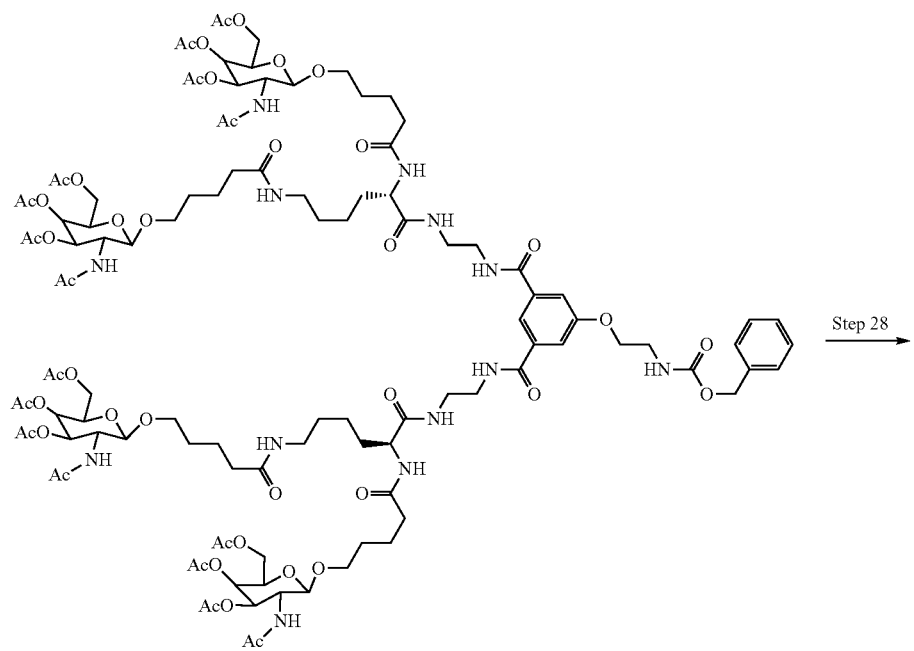
30

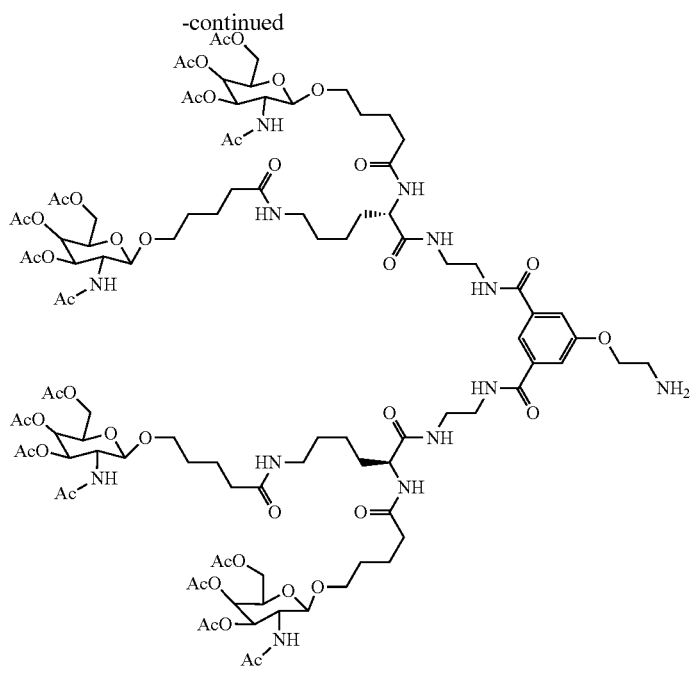

31

Step 27

Compound 30 (0.5272 g, yield: 61%) was obtained in the same way as in step 8 of Example 1 using compound 16 (0.2586 g, 0.3695 mmol) synthesized in step 13 and compound 1 (0.8559 g, 1.7927 mmol) synthesized by the method described in Journal of American Chemical Society, Vol. 136, p. 16958-16961, 2014.

ESI-MS m/z: 2418 (M+H)$^+$

Step 28

Compound 31 (0.1524 g, yield: 61%) was obtained in the same way as in step 21 of Example 3 using compound 30 (0.2653 g, 0.1097 mmol) synthesized in step 27.

ESI-MS m/z: 2284 (M+H)$^+$

Example 6 Synthesis of Sugar Ligand-Tether Unit—2

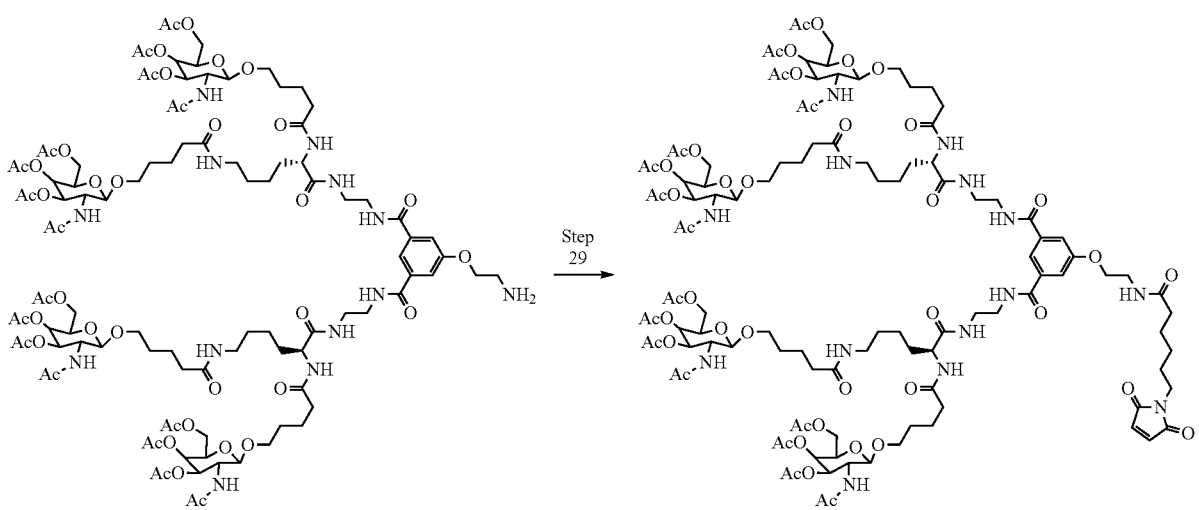

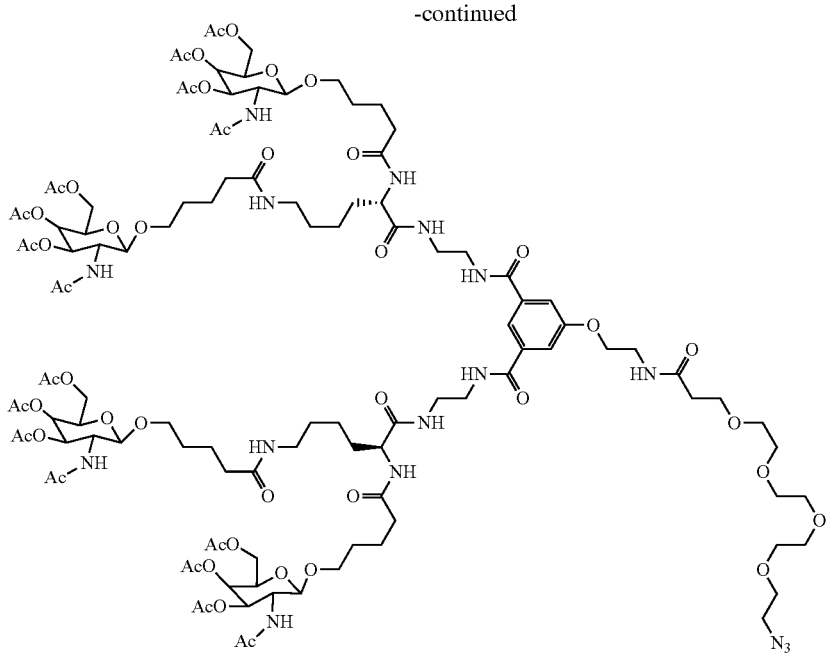

33

Synthesis of Compound 32

Step 29

Compound 32 (0.0077 g, yield: 47%) was obtained in the same way as in step 19 of Example 3 using compound 31 (0.0152 g, 0.006657 mmol) synthesized in step 28.

ESI-MS m/z: 1239 (M+2H)$^{2+}$

1H-NMR (DMSO-D$_6$) δ: 1.11-1.66 (34H, m), 1.77 (12H, d, J=1.5 Hz), 1.89 (12H, s), 2.01-2.14 (10H, m), 2.01 (12H, s), 2.10 (12H, s), 2.92-2.99 (4H, m), 3.16-3.54 (14H, m), 3.65-3.74 (4H, m), 3.81-3.91 (4H, m), 3.98-4.08 (14H, m), 4.11-4.24 (4H, m), 4.48 (4H, dd, J=8.4, 1.8 Hz), 4.93-5.00 (4H, m), 5.21 (4H, d, J=3.5 Hz), 6.99 (2H, s), 7.52 (2H, s), 7.66-7.75 (2H, m), 7.78-7.87 (6H, m), 7.91 (1H, br s), 8.01-8.08 (3H, br m), 8.54-8.60 (2H, br m).

Synthesis of Compound 33

Step 30

Compound 33 (0.0062 g, yield: 37%) was obtained in the same way as in step 23 of Example 4 using compound 31 (0.0150 g, 0.00657 mmol) synthesized in step 28.

ESI-MS m/z: 1279 (M+2H)$^{2+}$ $^1$H-NMR (DMSO-D$_6$) δ: 1.11-1.66 (30H, m), 1.77 (12H, s), 1.89 (12H, s), 2.01-2.14 (8H, m), 2.01 (12H, s), 2.10 (12H, s), 2.33-2.38 (2H, m), 2.92-2.99 (4H, m), 3.16-3.54 (14H, m), 3.58-3.63 (16H, m), 3.65-3.74 (4H, m), 3.81-3.91 (4H, m), 3.98-4.08 (12H, m), 4.11-4.24 (4H, m), 4.48 (4H, dd, J=8.4, 1.8 Hz), 4.93-5.00 (4H, m), 5.21 (4H, d, J=3.5 Hz), 7.52 (2H, s), 7.66-7.75 (2H, m), 7.78-7.87 (6H, m), 7.91 (1H, br s), 8.01-8.08 (3H, br m), 8.54-8.60 (2H, br m).

Example 7 Synthesis of Sugar Ligand-Tether Unit—3

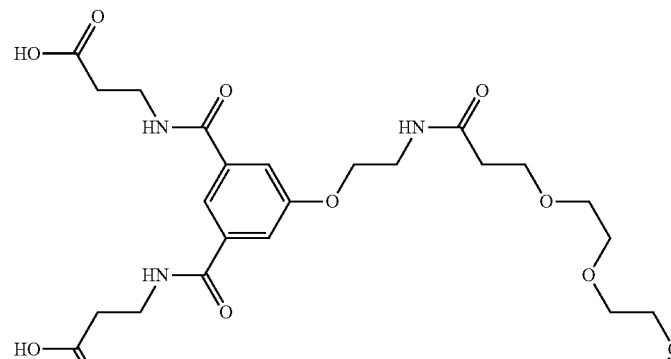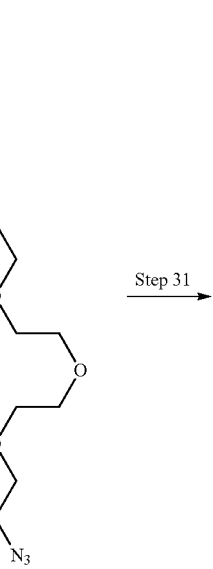

27

-continued
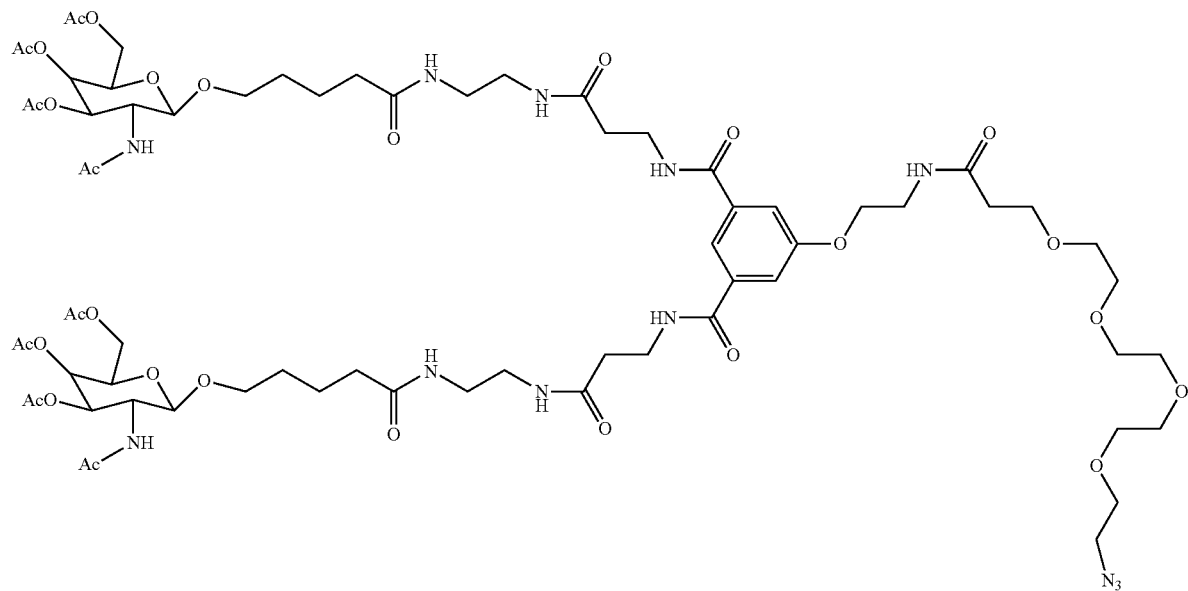
34
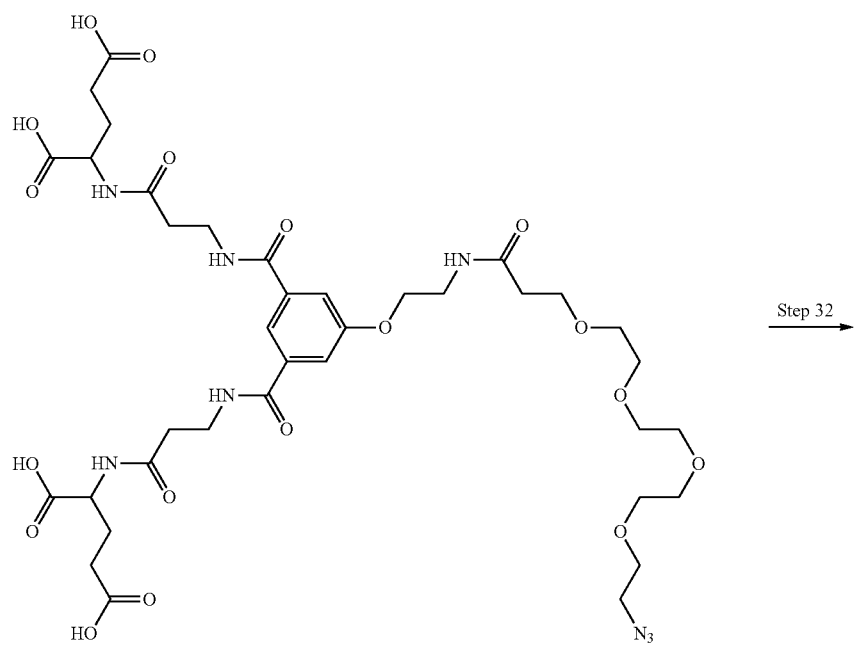
29
Step 32

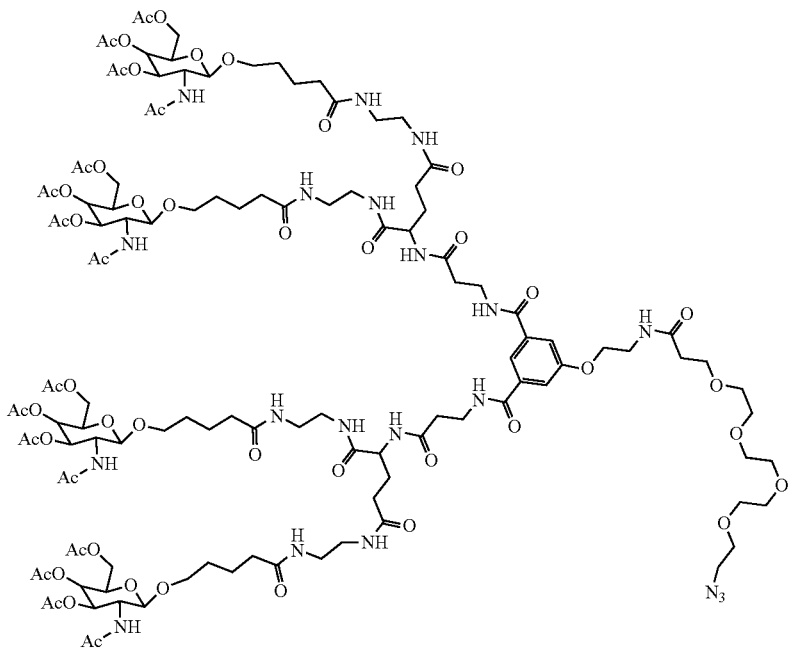

35

Synthesis of Compound 34

Step 31

A crude product of compound 34 was obtained in the same way as in step 8 of Example 1 using compound 27 (0.00436 g, 0.00681 mmol) synthesized in step 24 and compound 4 (0.010 g, 0.020 mmol) synthesized in step 3 of Reference Example 1.

ESI-MS m/z: 1584 (M+H)$^+$

Synthesis of Compound 35

Step 32

Compound 35 (0.0223 g, yield: 72%) was obtained in the same way as in step 8 of Example 1 using compound 29 (0.0100 g, 0.01112 mmol) synthesized in step 26.

ESI-MS m/z: 1393 (M+2H)$^{2+}$

Example 8 Synthesis of Sugar Ligand-Tether-Brancher Unit

Synthesis of Compound 40

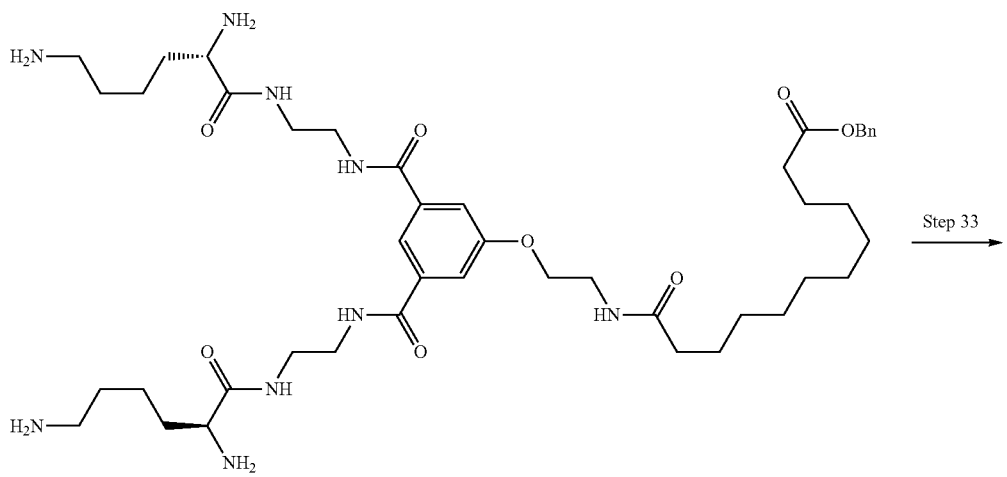

20

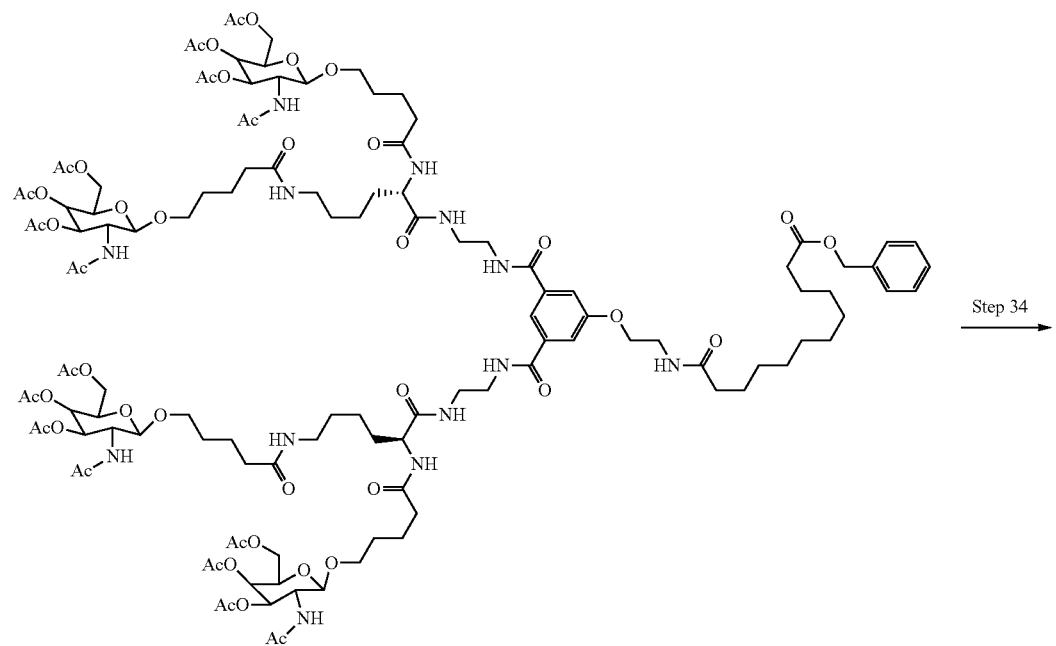
36
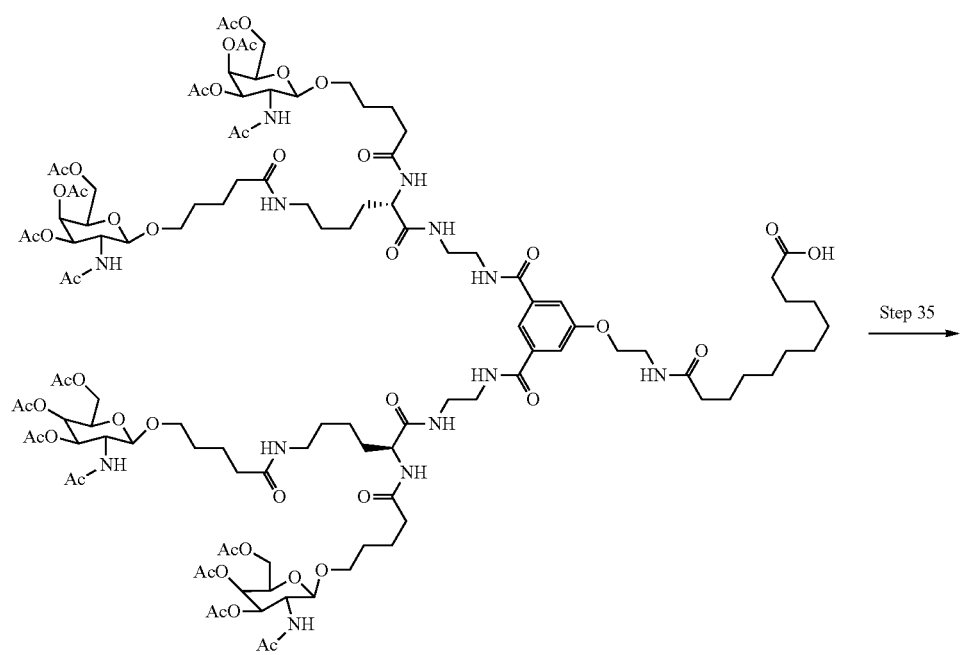
37

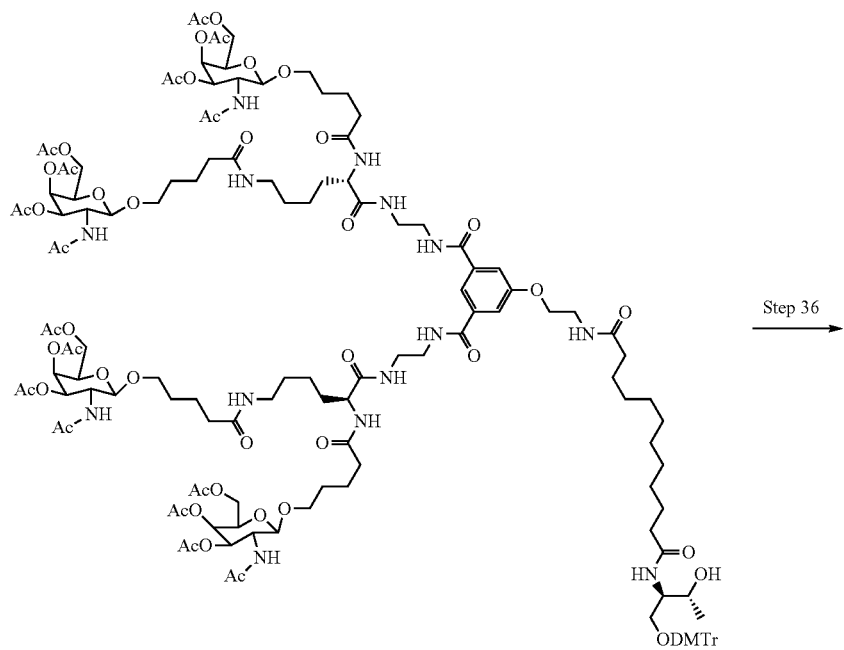
38
Step 36 →
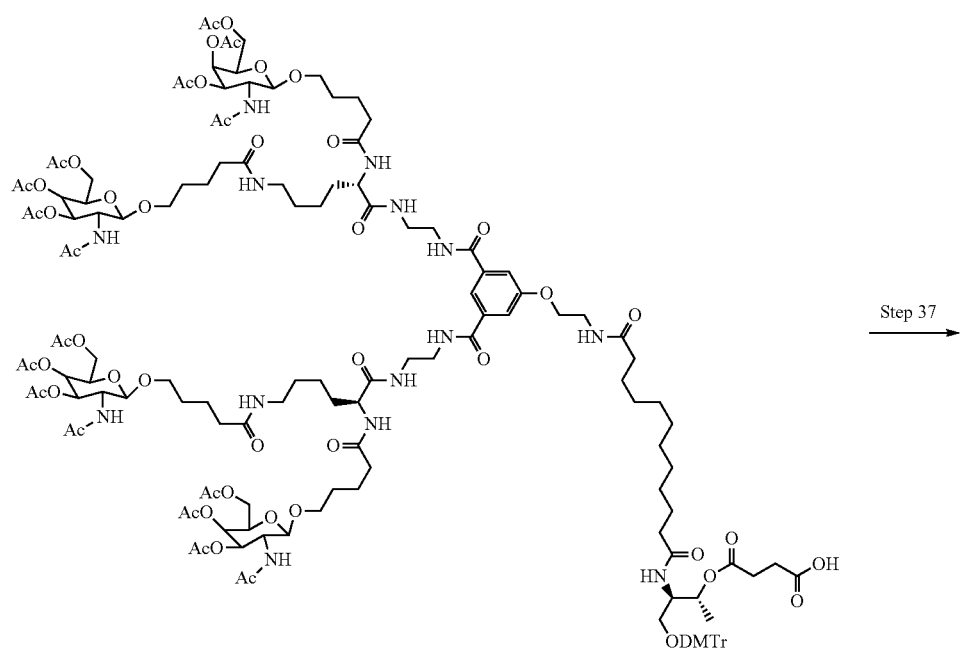
39
Step 37 →

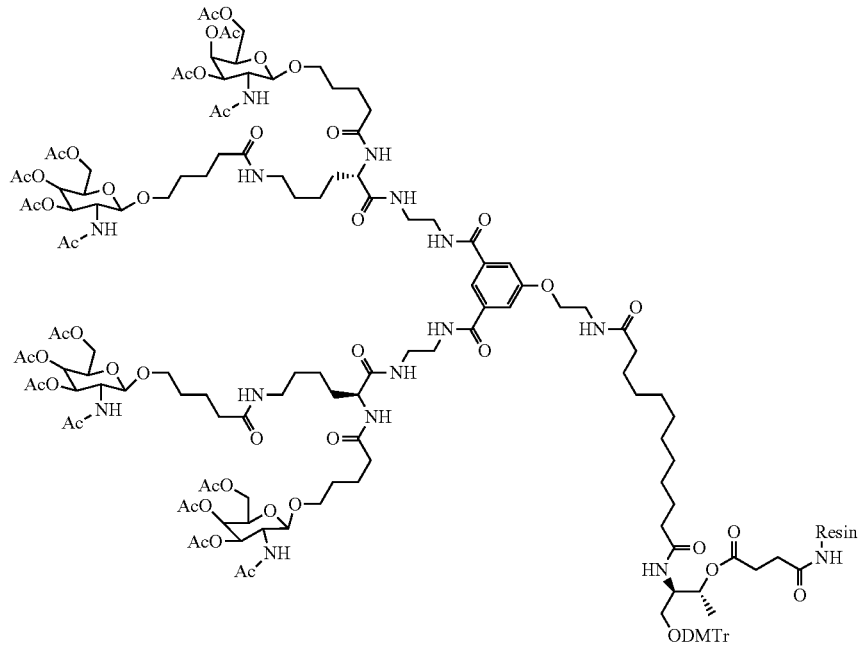

40

Step 33

Compound 36 (334.8 mg, yield: 58%) was obtained in the same way as in step 8 of Example 1 using compound 20 (0.1952 g, 0.225 mmol) synthesized in step 17 and compound 1 (0.4162 g, 0.93 mmol) synthesized by the method described in Journal of American Chemical Society, Vol. 136, p. 16958-16961, 2014.

ESI-MS m/z: 1294 $(M+2H)^{2+}$

Step 34

Compound 37 (112 mg, yield: 80%) was obtained in the same way as in step 18 of Example 3 using compound 36 (0.1459 g, 0.056 mmol) synthesized in step 33.

ESI-MS m/z: 1249 $(M+2H)^{2+}$ $^{1}$H-NMR (DMSO-D$_{6}$) δ: 1.11-1.66 (44H, m), 1.77 (12H, d, J=1.5 Hz), 1.89 (12H, s), 2.01-2.20 (12H, m), 2.01 (12H, s), 2.10 (12H, s), 2.92-2.99 (4H, m), 3.16-3.54 (10H, m), 3.58-3.64 (4H, m), 3.65-3.74 (4H, m), 3.81-3.91 (4H, m), 3.98-4.08 (12H, m), 4.11-4.24 (4H, m), 4.48 (4H, dd, J=8.4, 1.8 Hz), 4.93-5.00 (4H, m), 5.21 (4H, d, J=3.5 Hz), 6.99 (2H, s), 7.52 (2H, s), 7.66-7.75 (2H, m), 7.78-7.87 (6H, m), 7.91 (1H, br s), 8.01-8.08 (3H, br m), 8.54-8.60 (2H, br m).

Step 35

Compound 38 was obtained as a crude product in the same way as in step 8 of Example 1 using compound 37 (0.1091 g, 0.044 mmol) synthesized in step 34 and compound 7 (0.0748 g, 0.184 mmol) produced in step 5 of Reference Example 2.

ESI-MS m/z: 1292 $(M+2H)^{2i}$, detected as a DMTr-deprotected form

Step 36

Compound 38 (0.161 g, 0.05586 mmol) synthesized in step 35 was dissolved in dichloromethane (5 mL). To the solution, succinic anhydride (manufactured by Tokyo Chemical Industry Co., Ltd., 0.1182 g, 1.181 mmol), N,N-dimethylaminopyridine (0.0224 g, 0.183 mmol), and triethylamine (0.55 mL, 3.95 mmol) were added, and the mixture was stirred overnight at room temperature. The reaction solution was ice-cooled, and water was added thereto, followed by extraction with ethyl acetate twice. Then, the organic layer was washed with saturated saline and dried over anhydrous magnesium sulfate. The solvent was distilled off under reduced pressure to obtain a crude product of compound 39.

ESI-MS m/z: 1342 $(M+2H)^{2+}$, detected as a DMTr-deprotected form

Step 37

Compound 39 (0.0816 g, 0.02734 mmol) synthesized in step 36, O-(benzotriazol-1-yl)-N,N,N',N'-tetramethyluronium hexafluorophosphate (0.0221 g, 0.05827 mmol), and diisopropylethylamine (0.02 mL, 0.1094 mmol) were dissolved in N,N-dimethylformamide (4 mL). To the solution, LCAA-CPG (manufactured by ChemGenes Corp., 0.4882 g) was added, and the mixture was stirred overnight at room temperature. The mixture was collected by filtration, washed with dichloromethane, a 10% solution of methanol in dichloromethane, and diethyl ether in this order and then allowed to act on a solution of acetic anhydride in pyridine to obtain compound 40 (49.5 munol/g, yield: 89%). The yield was calculated from the rate of introduction to a solid-phase support which can be calculated from absorption derived from a DMTr group by adding a 1% solution of trifluoroacetic acid in dichloromethane to the form supported by the solid phase.

Example 9 Synthesis of Nucleic Acid Conjugate—1
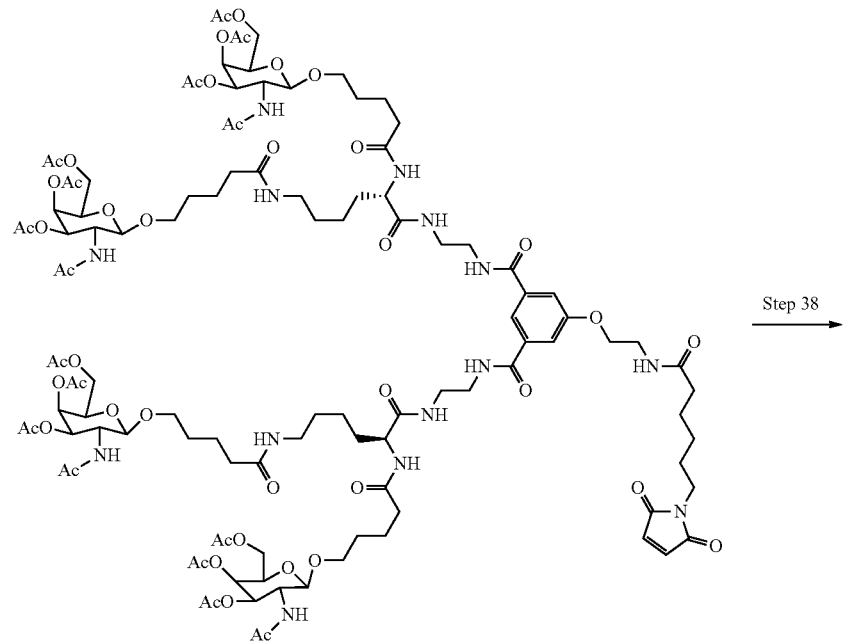
32
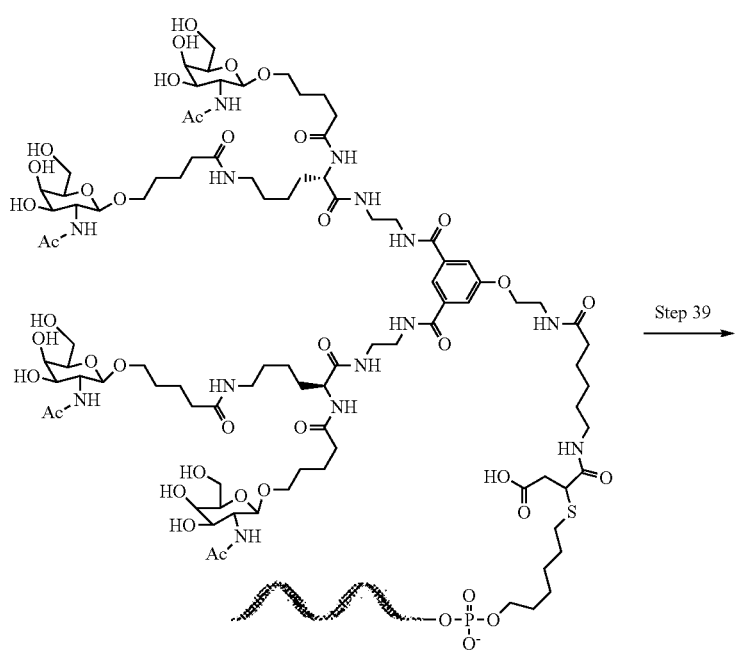
41

-continued

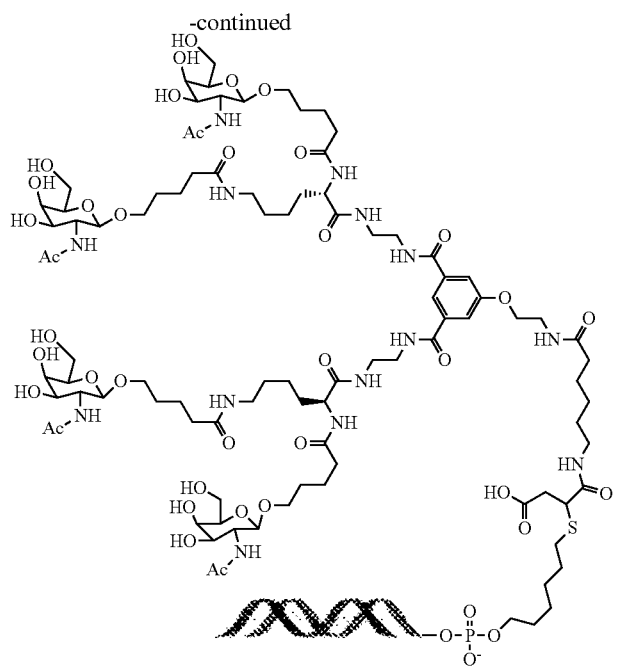

42

Synthesis of Nucleic Acid Conjugate 41

Step 38

Compound 32 synthesized in step 29 and a terminally mercapto group-modified oligonucleotide synthesized by the method described in Molecules, Vol. 17, p. 13825-13843, 2012 were added and left standing at room temperature for 4 hours. Sodium carbonate was added to the reaction mixture, and the mixture was left standing overnight at 4° C. Three types of single-stranded nucleic acid conjugates 41 differing in oligonucleotide were obtained by purification by any method of anion-exchange chromatography (GE Healthcare Japan Corp., Mono Q 5/50 GL, 10 μm, 5.0 mm×50 mm, solution A: 10 mmol/L Tris buffer solution/30% acetonitrile, solution B: gradient with 10 mmol/L Tris buffer solution/30% acetonitrile/1 mol/L NaBr) and reverse-phase liquid chromatography (Waters Corp., X Bridge C18, 5 pun, 4.6 mm×250 mm, 0.1 mol/L triethylammonium acetate buffer solution, solution B: gradient with acetonitrile).

The sequences and mass spectrometry results of the nucleic acid conjugates synthesized in this Example are shown in Table 1.

In the table, n represents DNA; N(M) represents 2'—O-methyl-modified RNA; N(F) represents 2'-fluorine-modified RNA; N(L) represents LNA; 5(L) represents LNAmC; ^ represents phosphorothioate modification; ss represents a sense strand; as represents an antisense strand; an underlined number represents a modifying group corresponding to compound No. in Example. The same holds true for each table described below.

Synthesis of Nucleic Acid Conjugate 42

Step 39

Single-stranded nucleic acid conjugate 41_3'-AT3-ssRNA synthesized in step 38 was concentration-adjusted (50 μmol/L) with a mixed buffer solution (100 mmol/L potassium acetate, 30 mmol/L 2-[4-(2-hydroxyethyl)piperazin-1-yl] ethanesulfonic acid, HEPES)-KOH (pH 7.4), 2 mmol/L magnesium acetate). The sense strand mentioned above and an antisense strand (50 μmol/L) were mixed in equal amounts and left standing at 80° C. for 10 minutes. The antisense strand sequence is as described in Table 2. The temperature was gradually decreased, and the resultant was left standing at 37° C. for 1 hour to obtain double-stranded nucleic acid conjugate 42.

TABLE 1

| Compound | Sequence (5' to 3') | | Theoretical molecular weight | Found |
|---|---|---|---|---|
| ApoBASO | G(L)^5(L)^a^t^t^g^g^t^a^t^T(L)^5(L)^A(L) | | — | — |
| 41_3'-ApoBASO | G(L)^5(L)^a^t^t^g^g^t^a^t^T(L)^5(L)^A(L) | 41 | 6514 | 6512 |
| 41_5'-ApoBASO | 41 G(L)^5(L)^a^t^t^g^g^t^a^t^T(L)^5(L)^A(L) | | 6514 | 6511 |
| 41_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 41 | 8971 | 8971 |

The sequence of the nucleic acid conjugate synthesized in this Example is shown in Table 2.
TABLE 2
| Compound | Single strand name | Sequence (5' to 3') |
|---|---|---|
| 42_3'-AT3-siRNA | 41_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) 41 |
| | AT3-asRNA | U(M)^U(F)^G(M)A(F)A(M)G(F)U(M)A(F)A(M)A(F)<br>U(M)G(M)G(M)U(F)G(M)U(F)U(M)A(F)A(M)C(F)C(M)^A(M)^G(M) |
Example 10 Synthesis of Nucleic Acid Conjugate—2
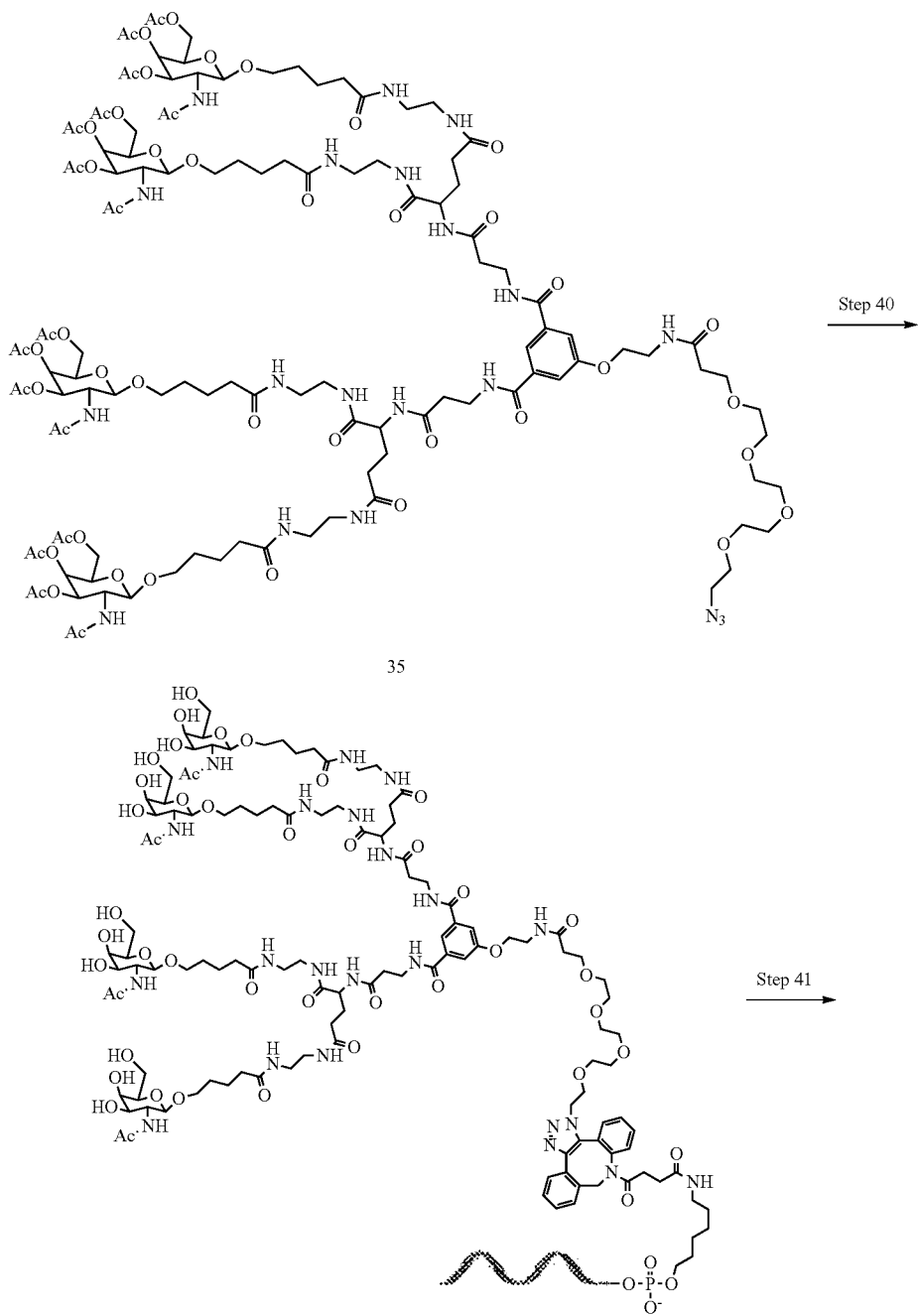

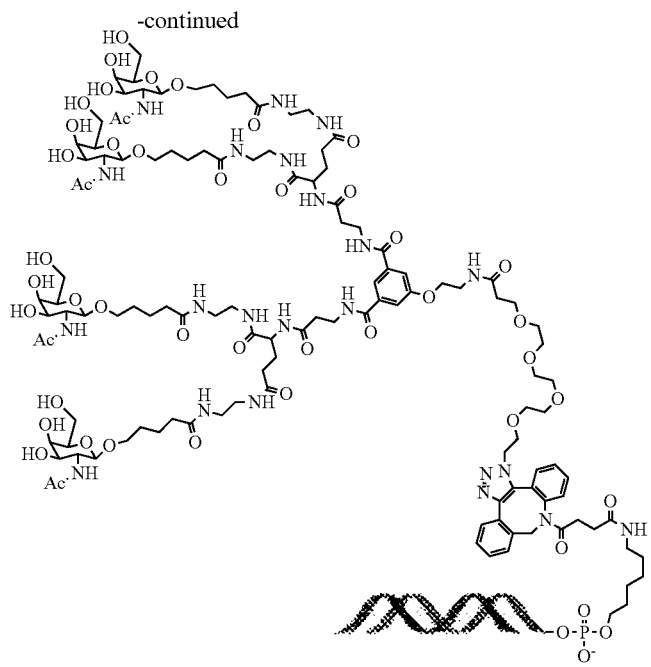

44

Synthesis of Nucleic Acid Conjugate 43
Step 40
Single-stranded nucleic acid conjugate 43 was obtained using the same reaction conditions and procedures as in step 38 of Example 9 using compound 35 synthesized in step 32 and an oligonucleotide synthesized by the method described in ACS Nano, Vol. 9, p. 9652-9664, 2015.

The sequence and mass spectrometry results of the nucleic acid conjugate synthesized in this Example are shown in Table 3.

TABLE 3

| Compound | Sequence (5' to 3') | Theoretical molecular weight | Found |
|---|---|---|---|
| 43_5'-B2M-ssRNA | 43 A(F)G(M)G(F)A(M)C(F)U(M)G(F)G(M)U(F)C(M) U(F)U(F)U(M)C(F)U(M)A(F)U(M)C(F)U(M)^C(F)^U(M) | 9529 | 9528 |

Synthesis of Nucleic Acid Conjugate 44
Step 41
Double-stranded nucleic acid conjugate 44 was obtained in the same way as in step 39 of Example 9.

The sequence of the nucleic acid conjugate synthesized in this Example is shown in Table 4.

TABLE 4

| Compound | Single strand name | Sequence (5' to 3') |
|---|---|---|
| 44_3'-B2M-siRNA | 43 5'-B2M-ssRNA | 43 A(F)G(M)G(F)A(M)C(F)U(M)G(F)G(M)U(F)C(M) U(F)U(F)U(M)C(F)U(M)A(F)U(M)C(F)U(M)^C(F)^U(M) |
| | B2M-as-RNA | A(F)^G(M)^A(F)G(M)A(F)U(M)A(F)G(M)A(F)A(M)A(M) G(F)A(M)C(F)C(M)A(F)G(M)U(F)C(M)C(F)U(M)^U(F)^G(M) |

Example 11 Synthesis of Nucleic Acid Conjugate—3
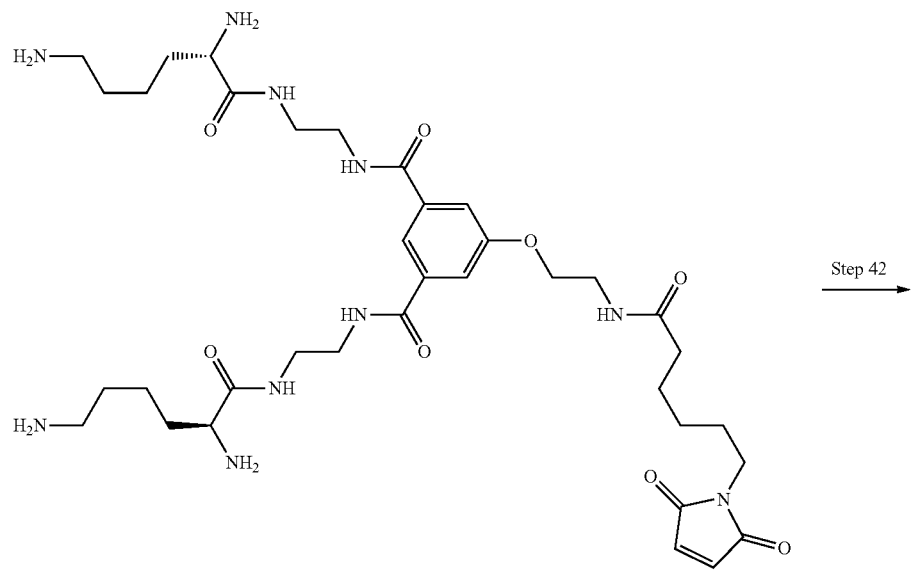
23
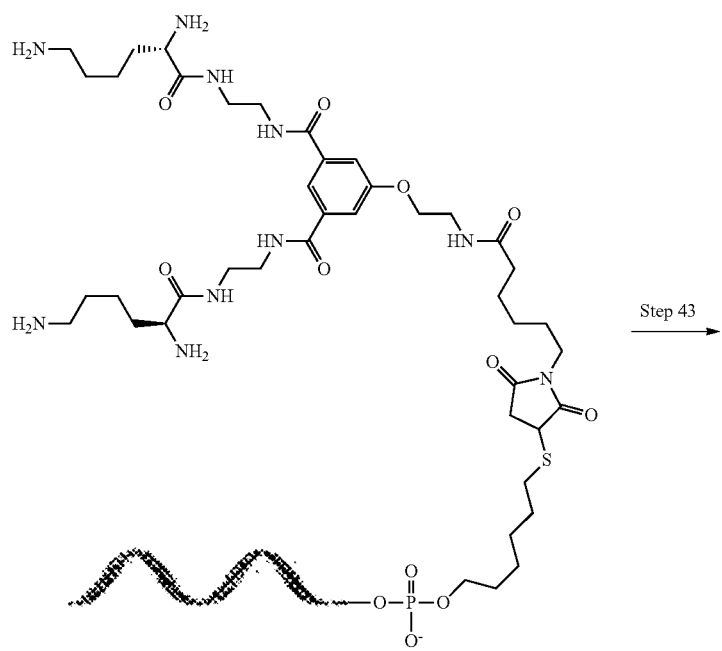
45

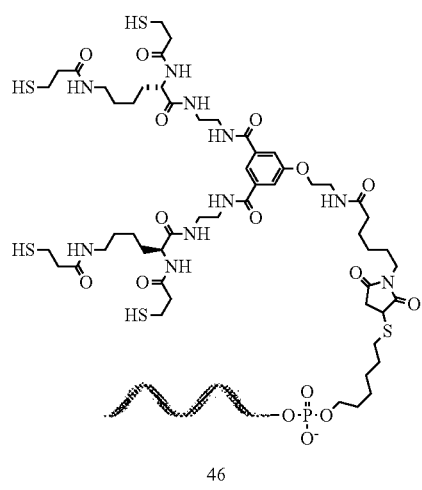

46

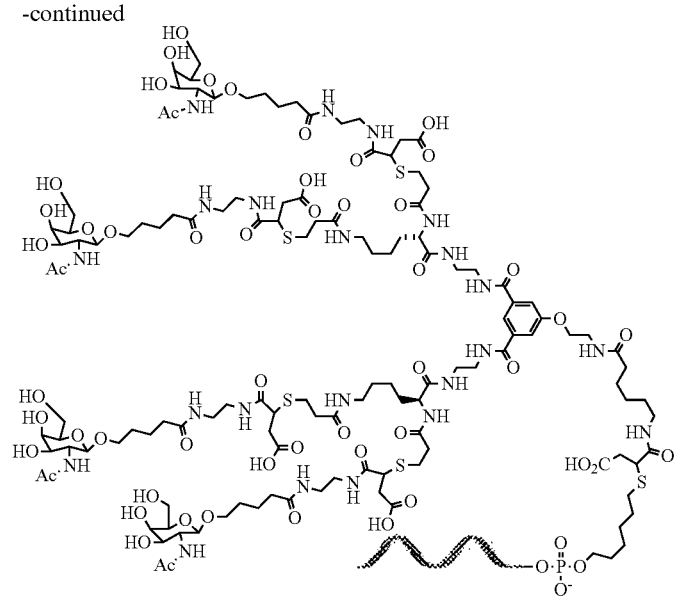

Step 44

47

Step 45

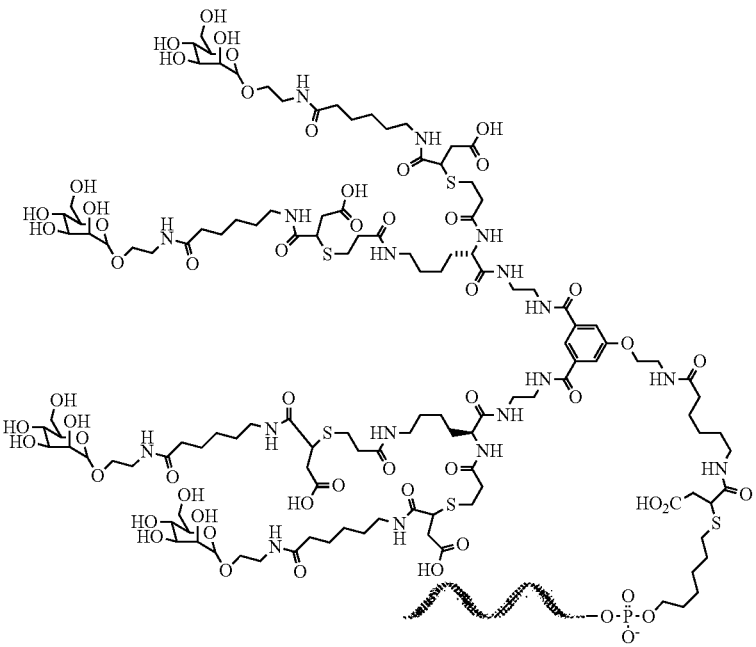

48

Synthesis of Nucleic Acid Conjugate 45

Step 42

Nucleic acid conjugate 45 was obtained in the same way as in step 38 of Example 9 using compound 23 (648 nmol) synthesized in step 20 and a terminally mercapto group-modified oligonucleotide (216 nmol) synthesized by the method described in Molecules, Vol. 17, p. 13825-13843, 2012.

Synthesis of Nucleic Acid Conjugate 46

Step 43

To compound 45 (100 nmol) synthesized in step 42, a solution of N-succinimidyl-3-(2-pyridyldithio)propionate (6.3 mg, 20 μmol) in dimethyl sulfoxide was added, and the mixture was left standing at room temperature for 4 hours in a phosphate buffer solution. Dithiothreitol (15.4 mg, 100 μmol) was added to the reaction solution, and the mixture was left standing overnight at room temperature. The mixture was subjected to gel filtration treatment (Nap column, manufactured by GE Healthcare Japan Corp., elution solvent: 20 mmol/L acetic acid/sodium acetate buffer solution (pH 5.0)) and ultrafiltration to obtain nucleic acid conjugate 46.

Synthesis of Nucleic Acid Conjugate 47
Step 44
Single-stranded nucleic acid conjugate 47 was obtained in the same way as in step 38 of Example 9 using compound 46 synthesized in step 43 and compound 2 synthesized in step 1 of Reference Example 1.

Synthesis of Nucleic Acid Conjugate 48
Step 45
Single-stranded nucleic acid conjugate 48 was obtained in the same way as in step 38 of Example 9 using compound 46 synthesized in step 43 and a mannose maleimide adduct synthesized by the method described in Bioconjugate Chemistry, Vol. 14, p. 232-238, 2003.

The sequences and mass spectrometry results of the nucleic acid conjugates synthesized in this Example are shown in Table 5.

TABLE 5

| Compound | Sequence (5' to 3') | Theoretical molecular weight | Found |
|---|---|---|---|
| 45_5'-CD45-ASO 45 | C(L)^C(L)^A(L)^A(L)^a^t^g^c^c^a^a^g^A(L)^G(L)^C(L)^T(L) | 6479 | 6479 |
| 46_5'-CD45-ASO 46 | C(L)^C(L)^A(L)^A(L)^a^t^g^c^c^a^a^g^A(L)^G(L)^C(L)^T(L) | 6832 | 6832 |
| 47_5'-CD45-ASO 47 | C(L)^C(L)^A(L)^A(L)^a^t^g^c^c^a^a^g^A(L)^G(L)^C(L)^T(L) | 8695 | 8696 |
| 48_5'-CD45-ASO 48 | C(L)^C(L)^A(L)^A(L)^a^t^g^c^c^a^a^g^A(L)^G(L)^C(L)^T(L) | 8587 | 8585 |

Example 12 Synthesis of Nucleic Acid Conjugate—4

Synthesis of Nucleic Acid Conjugate 49

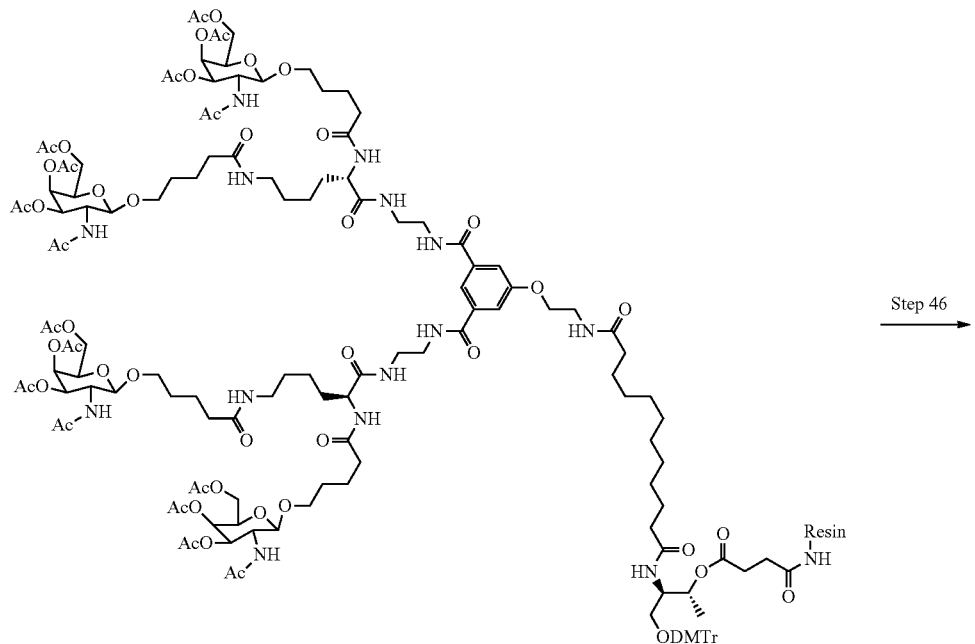

Step 46

-continued

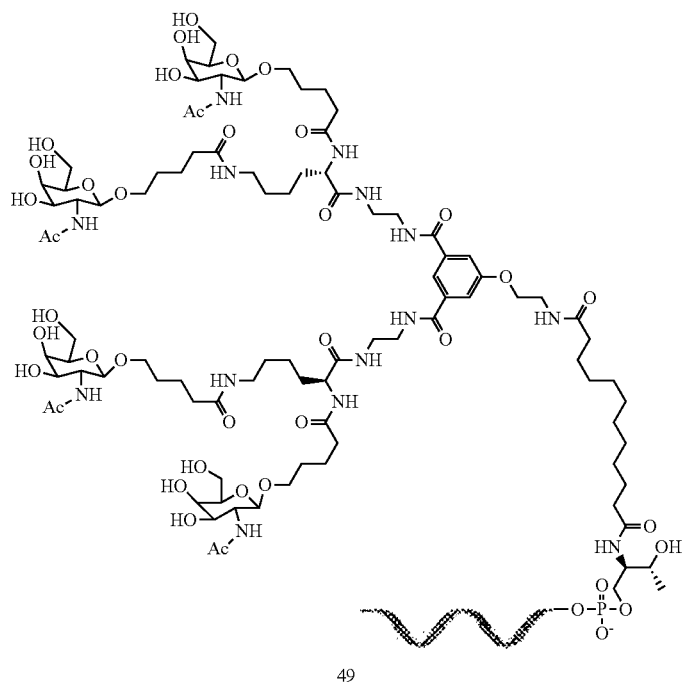

49

Step 46

Oligonucleotide conjugates having a GalNAc group at the 3' end of an antisense strand were synthesized (each referred to as G-CH1179-s, G-CH0099-s, and G-CH1180-s) on a scale of 0.2 μmol using a nucleic acid synthesis apparatus (Ultra Fast Parallel Synthesizer, manufactured by Sigma-Aldrich Co. LLC; hereinafter, referred to as UFPS). Compound 40 synthesized in step 37 was used as a solid-phase support. Dimethoxytrityl dT phosphoramidite (SAFC-PROLIGO/Sigma-Aldrich Co. LLC) was adjusted to 0.06 mol/L with acetonitrile. Condensation reaction was performed with each time set to 10 minutes using 5-benzylthio-1H-tetrazole (SAFC-PROLIGO/Sigma-Aldrich Co. LLC) as a phosphoramidite activator and a 0.06 mol/L solution of dT phosphoramidite in acetonitrile. After the reaction, the resultant was dipped in a 28% ammonia solution and left at 55° C. for 4 hours. After concentration under reduced pressure, the reaction was terminated by the addition of 1-butanol. Single-stranded nucleic acid conjugate 49 was obtained by purification using reverse-phase liquid chromatography (Shiseido Co., Ltd., CAPSELL PAK C18, SG300, 6.0 mm×75 mm, 5% acetonitrile/0.1% triethylammonium acetate buffer solution, solution B: gradient with 50% acetonitrile/water).

The sequence and mass spectrometry results of the nucleic acid conjugate synthesized in this Example are shown in Table 6.

TABLE 6

| Compound | Sequence (5' to 3') | Theoretical molecular weight | Found |
|---|---|---|---|
| 49_3'-dT10 | Tttttttttt 49 | 5120 | 5120 |

Comparative Example 1 Synthesis of Nucleic Acid Conjugate
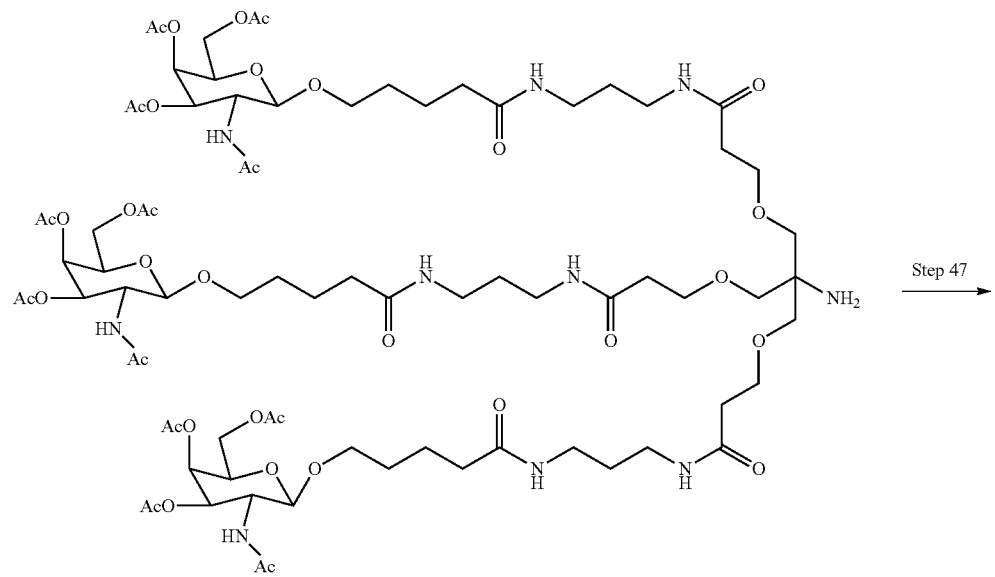
50
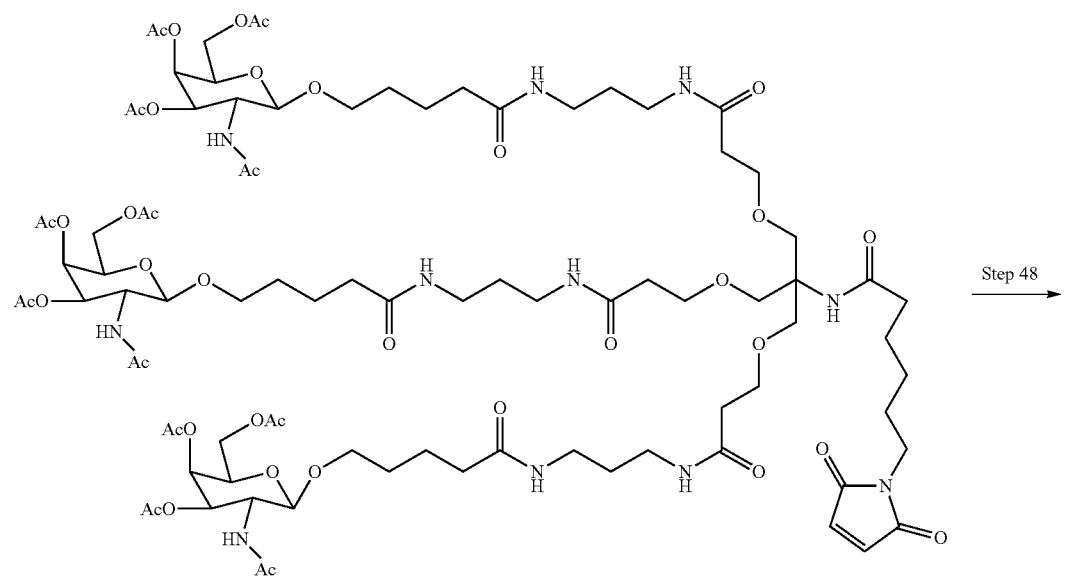
51

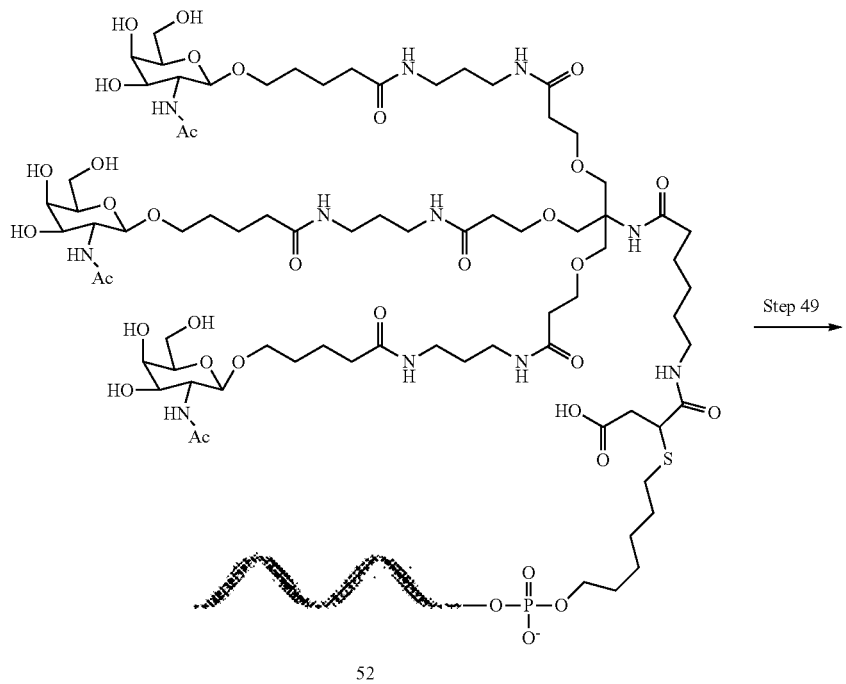

52

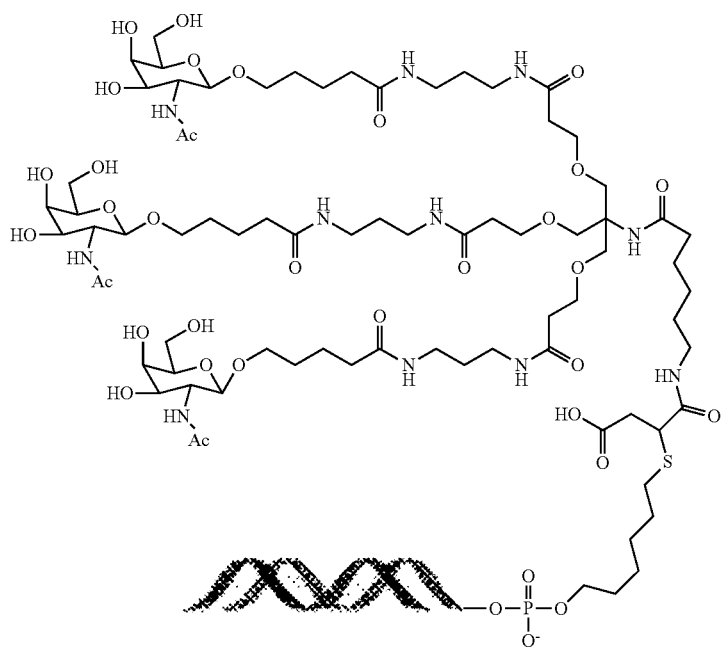

53

Synthesis of Nucleic Acid Conjugate 52
Step 47

Compound 51 (0.014 g, yield: 19%) was obtained in the same way as in step 29 of Example 6 using compound 50 (0.0796 g, 0.044 mmol) synthesized by the method described in Journal of American Chemical Society, Vol. 136, p. 16958-16961, 2014.

ESI-MS m/z: 994 (M+2H)$^{2+}$

Step 48

Three types of single-stranded nucleic acid conjugates 52 differing in oligonucleotide were obtained in the same way as in step 38 of Example 9 using compound 51 synthesized in step 47.

The sequences and mass spectrometry results of the nucleic acid conjugates synthesized in this Example are shown in Table 7.

TABLE 7

| Compound | Sequence (5' to 3') | Theoretical molecular weight | Found |
|---|---|---|---|
| 52_3'-ApoBASO | G(L)^5(L)^a^t^t^g^g^t^a^t^T(L)^5(L)^A(L) 52 | 6148 | 6147 |
| 52_5'-ApoBASO | 52 G(L)^5(L)^a^t^t^g^g^t^a^t^T(L)^5(L)^A(L) | 6148 | 6148 |
| 52_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) 52 | 8564 | 8564 |

Synthesis of Nucleic Acid Conjugate 53

Step 49

Double-stranded nucleic acid conjugate 53 was obtained in the same way as in step 39 of Example 9 using compound 52_3'-AT3-ssRNA synthesized in step 48.

The sequence of the nucleic acid conjugate synthesized in this Example is shown in Table 8.

TABLE 8

| Compound | Single strand name | Sequence (5' to 3') |
|---|---|---|
| 53_3'-AT3-siRNA | 52_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) 52 |
| | AT3-asRNA | U(M)^U(F)^G(M)A(F)A(M)G(F)U(M)A(F)A(M)A(F) U(M)G(M)G(M)U(F)G(M)U(F)U(M)A(F)A(M)C(F)C(M)^A(M)^G(M) |

Comparative Example 2 Synthesis of Nucleic Acid Conjugate

Synthesis of Nucleic Acid Conjugate 54

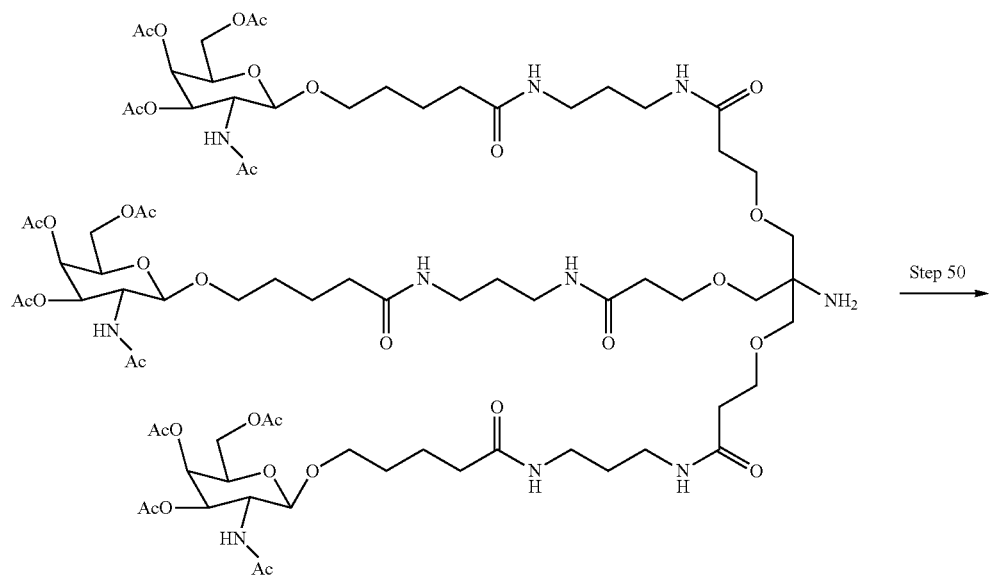

Step 50

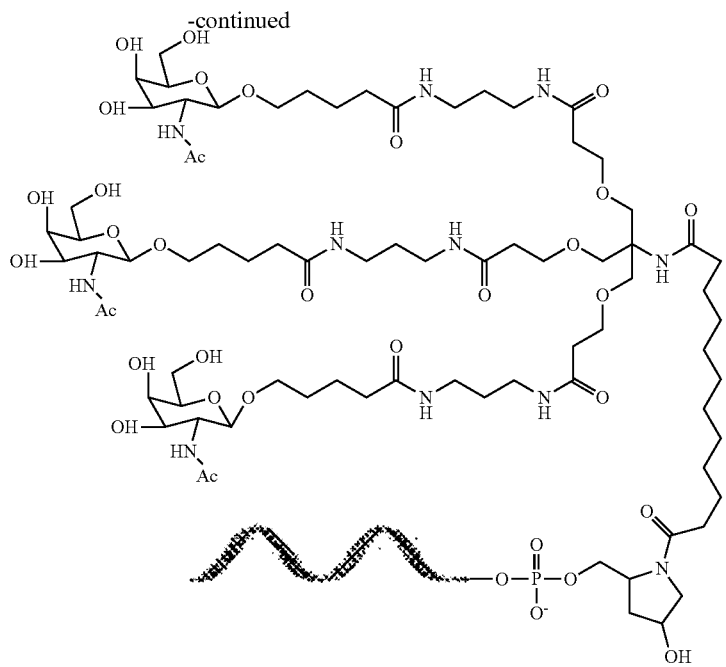

54

Single-stranded nucleic acid conjugate 54 having ApoBASO (see Table 1) was obtained by the method described in Journal of American Chemical Society, Vol. 136, p. 16958-16961, 2014.

Test Example 1 In Vitro Activity of Nucleic Acid Conjugate Against Mouse Primary Liver Cell Among the nucleic acid conjugates synthesized in Example 9, Comparative Example 1 and Comparative Example 2, ApoBASO (test substance 1), nucleic acid conjugate 54 (test substance 2), 52_3'-ApoBASO (test substance 3), 52_5'-ApoBASO (test substance 4), 41_3'-ApoBASO (test substance 5), and 41_5'-ApoBASO (test substance 6) were each transferred to CD-1-derived mouse primary liver cells (manufactured by Life Technologies Corp., Catalog No. MSCP10) by the following method.

Each nucleic acid conjugate diluted with Opti-MEM (Gibco/Thermo Fisher Scientific Inc., 31985) such that the final concentration was 30, 10 or 3 nmol/L was dispensed at 20 μL/well to a 96-well culture plate. Then, mouse primary liver cells suspended in William's E Medium (manufactured by Life Technologies Corp., Catalog No. A12176-01) containing Primary Hepatocyte Thawing and Plating Supplements (manufactured by Life Technologies Corp., Catalog No. CM3000) were inoculated at 12500 cells/80 μL/well thereto and cultured at 37° C. for 6 hours under 5% $CO_2$ conditions. Then, the culture supernatant was carefully removed, and William's E Medium containing Primary Hepatocyte Maintenance Supplements (manufactured by Life Technologies Corp., Catalog No. CM4000) was added thereto. Untreated cells were inoculated as a negative control group.

The cells harboring each preparation were cultured at 37° C. for 18 hours in a 5% C02 incubator and washed with ice-cooled phosphate-buffered saline. The recovery of total RNA and the preparation of cDNA through reverse-transcription reaction using the obtained total RNA as a template were performed using SuperPrep Cell Lysis & RT Kit for qPCR (manufactured by Toyobo Co., Ltd., Catalog No. SCQ-201) according to the method described in the instruction attached to the product.

The obtained cDNA was used as a template in PCR reaction using TaqMan® Gene Expression Assays Probe (manufactured by Applied Biosystems, Inc.) as a probe and QuantStudio 12K Flex Real-Time PCR System (manufactured by Applied Biosystems, Inc.) according to the method described in the attached instruction manual to amplify apolipoprotein B (also called apolipoprotein-B100/apolipoprotein-B48; hereinafter, referred to as apob) gene and a constitutively expressed gene D-glyceraldehyde-3-phosphate dehydrogenase (hereinafter, referred to as gapdh) gene. Their respective mRNA amplification levels were measured, and the semi-quantitative value of apob mRNA was calculated with the amplification level of gapdh mRNA as an internal control. The expression rate of apob mRNA was determined from the semi-quantitative value of apob mRNA when the semi-quantitative value of apob mRNA in the negative control measured in the same way as above was defined as 1. The obtained results about the expression rate of apob mRNA are shown in Tables 9 and 10 as an inhibition rate vs. the apob mRNA expression rate of the negative control. Each table shows the results of each individual test.

TABLE 9

| Test substance | Test substance 1 | | | Test substance 2 | | |
|---|---|---|---|---|---|---|
| Dose [nmol/L] | 30 | 10 | 3 | 30 | 10 | 3 |
| apob mRNA level [inhibition rate %] | 20.89 | 1.46 | 7.22 | 98.65 | 85.96 | 47.78 |

| Test substance | Test substance 3 | | | Test substance 4 | | |
|---|---|---|---|---|---|---|
| Dose [nmol/L] | 30 | 10 | 3 | 30 | 10 | 3 |
| apob mRNA level [inhibition rate %] | 98.46 | 71.13 | 37.32 | 99.99 | 97.23 | 73.02 |

TABLE 10

| Test substance | Test substance 1 | | | Test substance 2 | | |
|---|---|---|---|---|---|---|
| Dose [nmol/L] | 30 | 10 | 3 | 30 | 10 | 3 |
| apob mRNA level [inhibition rate %] | 34.28 | 12.17 | 4.67 | 96.85 | 89.07 | 65.24 |

| Test substance | Test substance 5 | | | Test substance 6 | | |
|---|---|---|---|---|---|---|
| Dose [nmol/L] | 30 | 10 | 3 | 30 | 10 | |
| apob mRNA level [inhibition rate %] | 98.55 | 94.13 | 74.47 | 99.16 | 98.22 | |

As is evident from Tables 9 and 10, the nucleic acid conjugate of the present invention inhibited the mRNA expression of the apob gene after transfer to mouse primary liver cells.

Test Example 2 In Vivo Activity of Nucleic Acid Conjugate Against Mouse

Among the nucleic acid conjugates synthesized in Example 9, Comparative Example 1 and Comparative Example 2, ApoBASO (test substance 1), nucleic acid conjugate 54 (test substance 2), 52_3'-ApoBASO (test substance 3), 52_5'-ApoBASO (test substance 4), 41_3'-ApoBASO (test substance 5), and 41_5'-ApoBASO (test substance 6) were each subjected to an in vivo evaluation test by the following method. Each nucleic acid conjugate used was diluted with Dulbecco's phosphate-buffered saline (DPBS) (manufactured by Nacalai Tesque, Inc.) according to the test. After acclimatization of mice (BALB/cA, obtained from CLEA Japan Inc.), each nucleic acid conjugate was administered at 0.75 mg/kg or 0.25 mg/kg to the mice by subcutaneous injection. For a control group, DPBS alone was administered to the mice by subcutaneous injection. Three days after the administration, serum was collected from the superficial temporal veins. Then, the animals were euthanized, and the livers were collected and cryopreserved in liquid nitrogen. From the cryopreserved liver samples, total RNA was recovered using TRIzol® RNA Isolation Reagents (manufactured by Life Technologies Corp., Catalog No. 15596026) and RNeasy Mini Kit (manufactured by Qiagen N.V., Catalog No. 74106) according to the methods described in the instructions attached to the products. cDNA was further prepared through reverse-transcription reaction with the obtained total RNA as a template using Transcriptor First Strand cDNA Synthesis Kit (manufactured by F. Hoffmann-La Roche, Ltd., Catalog No. 04897030001) according to the method described in the instruction attached to the product.

The obtained cDNA was used as a template in PCR reaction using TaqMan® Gene Expression Assays Probe (manufactured by Applied Biosystems, Inc.) as a probe and QuantStudio 12K Flex Real-Time PCR System (manufactured by Applied Biosystems, Inc.) according to the method described in the attached instruction manual to amplify apob gene and gapdh gene. Their respective mRNA amplification levels were measured, and the semi-quantitative value of apob mRNA was calculated with the amplification level of gapdh mRNA as an internal control. The expression rate of apob mRNA was determined from the semi-quantitative value of apob mRNA when the semi-quantitative value of apob mRNA in the control group measured in the same way as above was defined as 1. Also, a total cholesterol concentration in the serum was measured using LabAssay Cholesterol (manufactured by Wako Pure Chemical Industries, Ltd., Catalog No. 294-65801) according to the method described in the attached instruction manual. The obtained inhibition rate of expression of apob mRNA and total cholesterol concentration in the serum are shown in Tables 11 and 12.

TABLE 11

| | Test substance | | | | |
|---|---|---|---|---|---|
| | Test substance 1 | Test substance 2 | Test substance 3 | Test substance 4 | Control |
| Dose [mg/kg] | 0.75 | 0.75 | 0.75 | 0.75 | — |
| apob mRNA level in liver [inhibition rate %] | 56.46 | 94.07 | 90.21 | 97.74 | — |
| Total cholesterol concentration in serum [mg/dL] | 83.36 | 45.37 | 48.98 | 41.70 | 116.06 |

TABLE 12

| | Test substance | | | | |
|---|---|---|---|---|---|
| | Test substance 1 | | Test substance 2 | | Control |
| Dose [mg/kg] | 0.75 | 0.25 | 0.75 | 0.25 | — |
| apob mRNA level in liver [inhibition rate %] | 75.28 | 24.23 | 95.78 | 74.39 | — |
| Total cholesterol concentration in serum [mg/dL] | 95.68 | 100.35 | 46.45 | 102.85 | 98.53 |

| | Test substance | | | |
|---|---|---|---|---|
| | Test substance 5 | | Test substance 6 | |
| Dose [mg/kg] | 0.75 | 0.25 | 0.75 | 0.25 |
| apob mRNA level in liver [inhibition rate %] | 98.12 | 82.10 | 99.27 | 96.05 |
| Total cholesterol concentration in serum [mg/dL] | 34.61 | 61.55 | 25.24 | 39.65 |

As is evident from Tables 11 and 12, the nucleic acid conjugate of the present invention (test substances 5 and 6) reduced the expression of the apob gene and decreased the total cholesterol concentration in blood in vivo.

Test Example 3 In Vitro Activity of Nucleic Acid Conjugate Against Mouse Primary Liver Cell Among the nucleic acid conjugates obtained in Example 9 and Comparative Example 1, 53_3'-AT3-siRNA (test substance 7) and 42_3'-AT3-siRNA (test substance 8) were each transferred to CD-1-derived mouse primary liver cells (manufactured by Life Technologies Corp., Catalog No. MSCP10) by the following method.

Each nucleic acid conjugate diluted with Opti-MEM (Gibco/Thermo Fisher Scientific Inc., 31985) such that the final concentration was 300, 100 or 30 nmol/L was dispensed at 20 µL/well to a 96-well culture plate. Then, mouse primary liver cells suspended in William's E Medium (manufactured by Life Technologies Corp., Catalog No. A12176-01) containing Primary Hepatocyte Thawing and Plating Supplements (manufactured by Life Technologies Corp., Catalog No. CM3000) were inoculated at 12500 cells/80 µL/well thereto and cultured at 37° C. for 6 hours under 5% CO$_2$ conditions. Then, the culture supernatant was carefully removed, and William's E Medium containing Primary Hepatocyte Maintenance Supplements (manufactured by Life Technologies Corp., Catalog No. CM4000) was added thereto. Untreated cells were inoculated as a negative control group.

The cells harboring each preparation were cultured at 37° C. for 18 hours in a 5% CO$_2$ incubator and washed with ice-cooled phosphate-buffered saline. The recovery of total RNA and the preparation of cDNA through reverse-transcription reaction using the obtained total RNA as a template were performed using SuperPrep Cell Lysis & RT Kit for qPCR (manufactured by Toyobo Co., Ltd., Catalog No. SCQ-201) according to the method described in the instruction attached to the product.

The obtained cDNA was used as a template in PCR reaction using TaqMan® Gene Expression Assays Probe (manufactured by Applied Biosystems, Inc.) as a probe and QuantStudio 12K Flex Real-Time PCR System (manufactured by Applied Biosystems, Inc.) according to the method described in the attached instruction manual to amplify serpin peptidase inhibitor, clade C (antithrombin), member 1 (also called antithrombin III; hereinafter, referred to as AT3) gene and a constitutively expressed gene D-glyceraldehyde-3-phosphate dehydrogenase (hereinafter, referred to as gapdh) gene. Their respective mRNA amplification levels were measured, and the semi-quantitative value of AT3 mRNA was calculated with the amplification level of gapdh mRNA as an internal control. The expression rate of AT3 mRNA was determined from the semi-quantitative value of AT3 mRNA when the semi-quantitative value of AT3 mRNA in the negative control measured in the same way as above was defined as 1. The obtained results about the expression rate of AT3 mRNA are shown in Table 13 as an inhibition rate vs. the AT3 mRNA expression rate of the negative control.

TABLE 13

| | Test substance | | | | | |
|---|---|---|---|---|---|---|
| | Test substance 7 | | | Test substance 8 | | |
| Dose [nmol/L] | 300 | 100 | 30 | 300 | 100 | 30 |
| AT3 mRNA level [inhibition rate %] | 11.906 | 3.0612 | −6.657 | 94.428 | 92.451 | 88.378 |

As is evident from Table 13, the nucleic acid conjugate of the present invention (test substance 8) inhibited the mRNA expression of the AT3 gene after transfer to mouse primary liver cells.

Test Example 4 In Vivo Activity of Nucleic Acid Conjugate Against Mouse

Among the nucleic acid conjugates obtained in Example 9 and Comparative Example 1, 53_3'-AT3-siRNA (test substance 7) and 42_3'-AT3-siRNA (test substance 8) were each subjected to an in vivo evaluation test by the following method. Each nucleic acid conjugate used was diluted with Dulbecco's phosphate-buffered saline (DPBS) (manufactured by Nacalai Tesque, Inc.) according to the test. After acclimatization of mice (BALB/cA, obtained from CLEA Japan Inc.), each nucleic acid conjugate was administered at 1.5 mg/kg or 0.5 mg/kg to the mice by subcutaneous injection. For a control group, PBS alone was administered to the mice by subcutaneous injection. Three days after the administration, blood was collected from the postcaval vein under isoflurane anesthesia. The collected blood was mixed with an anticoagulant solution containing 3.2 M sodium citrate and 5 mmol/L D-glucose at a volume ratio of 9:1, and a supernatant after centrifugation was recovered to obtain plasma. After the blood collection, the animals were euthanized, and the livers were collected and cryopreserved in liquid nitrogen. From the cryopreserved liver samples, total RNA was recovered using TRIzol® RNA Isolation Reagents (manufactured by Life Technologies Corp., Catalog No. 15596026) and RNeasy Mini Kit (manufactured by Qiagen N.V., Catalog No. 74106) according to the methods described in the instructions attached to the products. cDNA was further prepared through reverse-transcription reaction with the obtained total RNA as a template using Transcriptor First Strand cDNA Synthesis Kit (manufactured by F. Hoffmann-La Roche, Ltd., Catalog No. 04897030001) according to the method described in the instruction attached to the product.

The obtained cDNA was used as a template in PCR reaction using TaqMan® Gene Expression Assays Probe (manufactured by Applied Biosystems, Inc.) as a probe and QuantStudio 12K Flex Real-Time PCR System (manufactured by Applied Biosystems, Inc.) according to the method described in the attached instruction manual to amplify AT3 gene and gapdh gene. Their respective mRNA amplification levels were measured, and the semi-quantitative value of AT3 mRNA was calculated with the amplification level of AT3 mRNA as an internal control. The expression rate of AT3 mRNA was determined from the semi-quantitative value of AT3 mRNA when the semi-quantitative value of AT3 mRNA in the control group measured in the same way as above was defined as 1. Also, an AT3 protein concentration in the plasma was measured using Antithrombin III Mouse ELISA Kit (manufactured by Abcam Inc., Catalog No. ab108800) according to the method described in the attached instruction manual. The obtained inhibition rate of expression of AT3 mRNA and AT3 protein concentration in the plasma are shown in Table 14.

TABLE 14

| | Test substance | | | | |
|---|---|---|---|---|---|
| | Control | Test substance 7 | | Test substance 8 | |
| Dose [mg/kg] | — | 1.5 | 0.5 | 1.5 | 0.5 |
| AT3 mRNA level in liver [inhibition rate %] | — | −13.90 | 2.63 | 47.76 | 31.37 |
| AT3 protein concentration in plasma [μg/mL] | 287.32 | 263.03 | 287.42 | 147.54 | 235.68 |

As is evident from Table 14, the nucleic acid conjugate of the present invention (test substance 8) reduced the expression of the AT3 gene and decreased the AT3 protein concentration in blood in vivo.

Reference Example 3 Synthesis of Sugar Ligand Unit

Synthesis of Compound 56

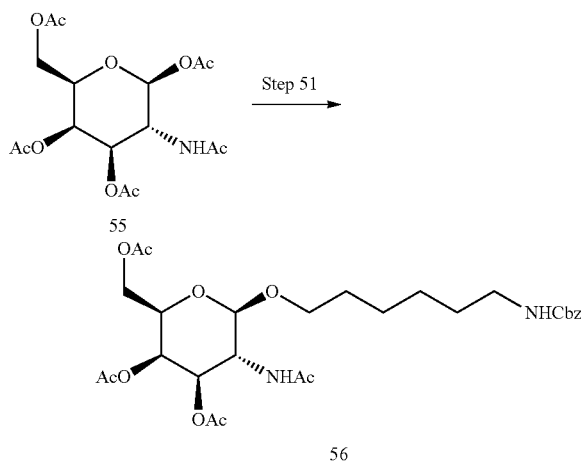

Step 51

Compound 56 (1.050 g, yield: 50%) was synthesized from compound 55 (1.200 g, 3.640 mmol) by the method described in Journal of Medicinal Chemistry, Vol. 59, p. 2718-2733, 2016.

ESI-MS m/z: 582 (M+H)$^+$

Synthesis of Compound 57

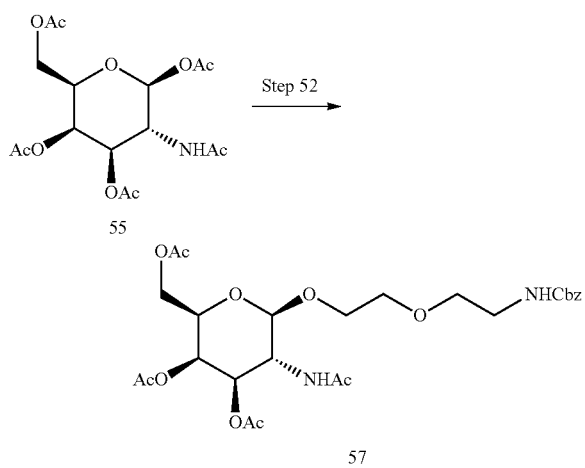

Step 52

Compound 55 (4.000 g, 10.27 mmol) was dissolved in dichloromethane (60 mL). To the solution, benzyl-2-(2-hydroxyethoxy)ethyl carbamate (2.700 g, 11.30 mmol) and trifluoromethanesulfonic acid (0.1360 mL, 1.541 mmol) were added, and the mixture was stirred overnight under reflux conditions. A 10 wt % aqueous potassium carbonate solution was added to the reaction solution, and the mixture was separated into aqueous and organic layers with dichloromethane. Then, the organic layer was washed with water and dried over anhydrous sodium sulfate. The solvent was distilled off under reduced pressure, and the residue was solvent-replaced with 2-methyltetrahydrofuran and concentrated. The residue was added dropwise to heptane, and the obtained crystals were filtered to obtain compound 57 (5.130 g, yield: 88%).

ESI-MS m/z: 570 (M+H)$^+$

Synthesis of Compound 58

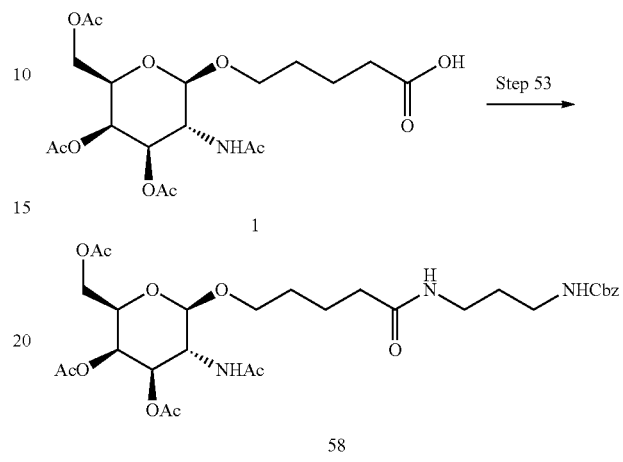

Step 53

Compound 1 (898.0 mg, 2.007 mmol) described in step 1 was dissolved in dichloromethane (15 mL). To the solution, 1-hydroxybenzotriazole monohydrate (338.0 mg, 2.208 mmol), 1-(3-dimethylaminopropyl)-3-ethylcarbodiimide hydrochloride (343 mg, 2.208 mmol), and N-1-Z-1,3-diaminopropane hydrochloride (0.4910 mL, 2.208 mmol) were added, and the mixture was stirred at room temperature for 3 hours. Water was added to the reaction solution, and the mixture was separated into aqueous and organic layers with dichloromethane. Then, the organic layer was washed with a saturated aqueous solution of sodium bicarbonate and dried over anhydrous sodium sulfate. The solvent was distilled off under reduced pressure, and the residue was purified by silica gel column chromatography (chloroform/methanol=90/10) to obtain compound 58 (873.0 mg, yield: 68%).

ESI-MS m/z: 639 (M+H)$^+$

Synthesis of Compound 60

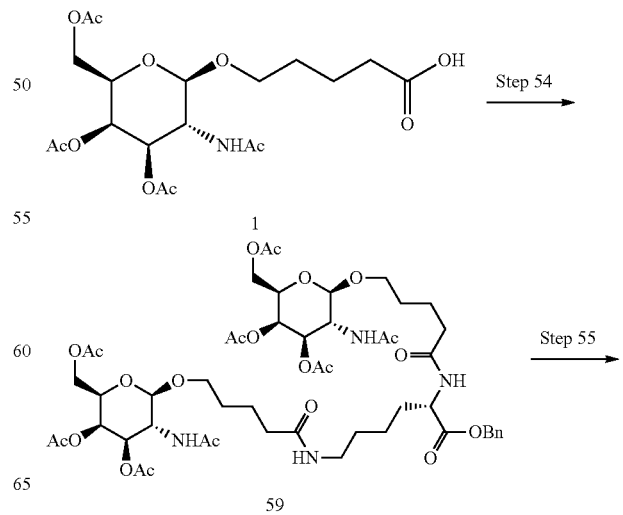

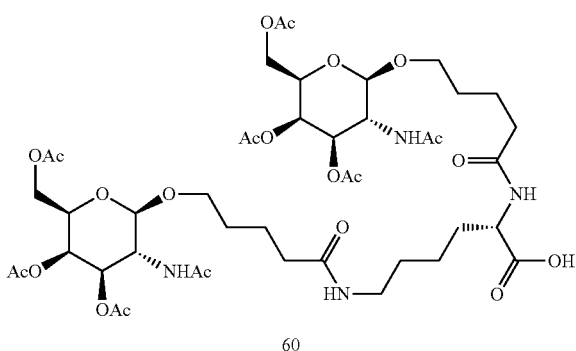

60

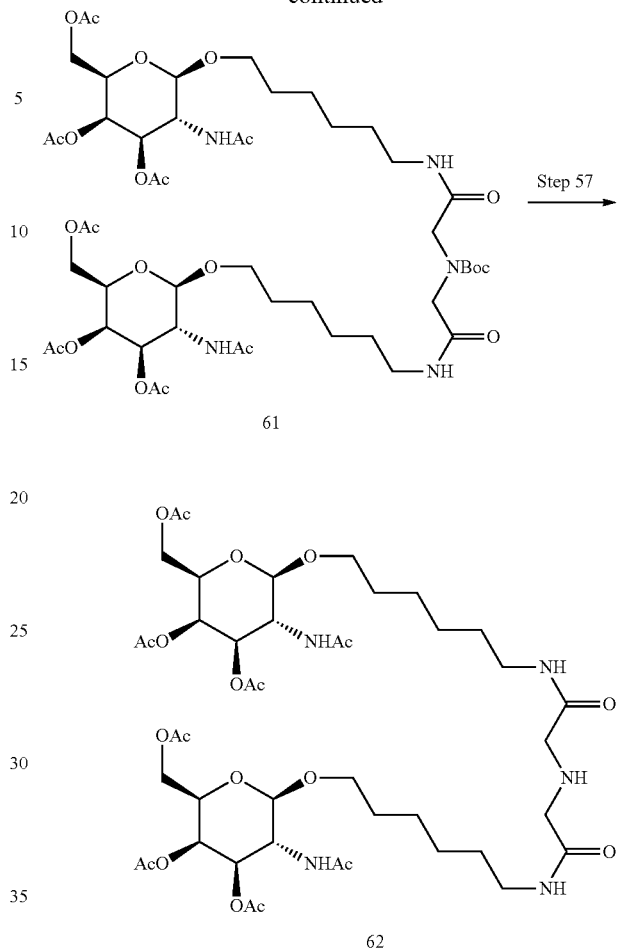

61

62

Step 54

Compound 1 (3.00 g, 6.70 mmol) described in step 1 was dissolved in dichloromethane (60 mL). To the solution, L-lysine benzyl ester di-p-toluenesulfonate (1.75 g, 3.02 mmol), triethylamine (0.935 mL, 6.70 mmol), 1-(3-dimethylaminopropyl)-3-ethylcarbodiimide hydrochloride (1.29 g, 6.70 mmol), and 1-hydroxybenzotriazole monohydrate (103 mg, 0.670 mmol) were added at room temperature, and the mixture was stirred for 2.5 hours. The reaction solution was washed with water and a saturated aqueous solution of sodium bicarbonate and dried over anhydrous sodium sulfate. The solvent was distilled off under reduced pressure, and the residue was purified by silica gel column chromatography (chloroform/methanol=90/10) to quantitatively obtain compound 59.

ESI-MS m/z: 1096 (M+H)$^+$

Step 55

Compound 59 (2.30 g, 2.10 mmol) synthesized in step 54 was dissolved in tetrahydrofuran (46 mL). To the solution, a 10% palladium-carbon powder (water-containing product, 54.29%; 424 mg) was added at room temperature, and the mixture was stirred overnight in a hydrogen atmosphere. The reaction solution was filtered, and the solvent was distilled off under reduced pressure to quantitatively obtain compound 60.

ESI-MS m/z: 1006 (M+H)$^+$

Synthesis of Compound 62

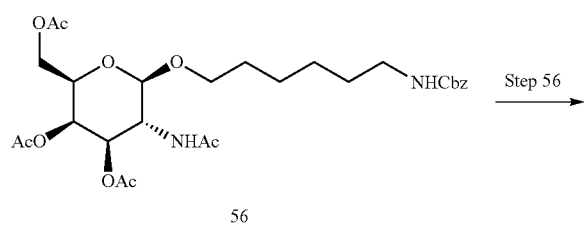

56

Step 56

Iminodiacetic acid (manufactured by Tokyo Chemical Industry Co., Ltd., 1.5 g, 6.43 mmol) was dissolved in methylene chloride (30 mL). To the solution, pentafluorotrifluoroacetic acid (manufactured by Tokyo Chemical Industry Co., Ltd., 2.75 mL, 16.08 mmol) and triethylamine (4.48 mL, 32.2 mmol) were added, and the mixture was stirred for 4 hours. A 10% aqueous citric acid solution was added to the reaction solution, followed by extraction with chloroform. Then, the organic layer was washed with saturated saline and dried over anhydrous magnesium sulfate. A solution of compound 56 (2 g, 3.45 mmol) synthesized in step 51, dissolved in a mixed solution of ethyl acetate (10 mL) and acetonitrile (10 mL) was added to the residue, followed by catalytic hydrogen reduction using palladium/carbon. The solvent in the obtained solution portion was distilled off under reduced pressure to obtain a crude product of compound 61.

ESI-MS m/z: 1091 (M+H)$^+$

Step 57

Compound 62 was quantitatively obtained in the same way as in step 3 of Reference Example 1 using compound 61 (1.5 g, 1.37 mmol) synthesized in step 56.

ESI-MS m/z: 990 (M+H)$^+$

Synthesis of Compound 64

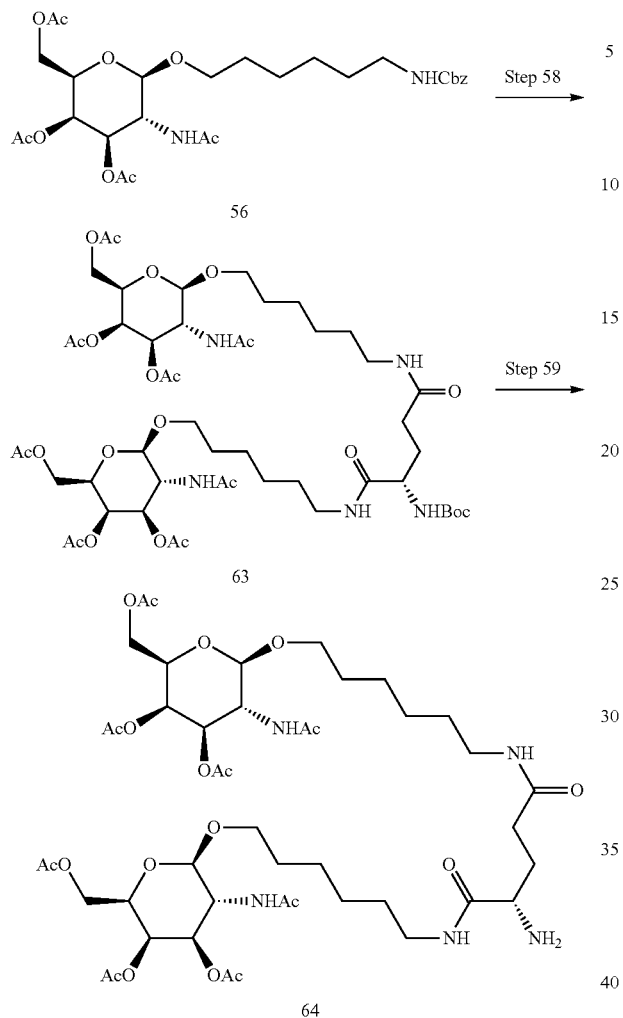

Step 58
A crude product of compound 63 was obtained in the same way as in step 56 of Reference Example 3 using N-(t-butoxycarbonyl)-L-glutamic acid (manufactured by Tokyo Chemical Industry Co., Ltd.) and compound 56 (1.855 g, 3.19 mmol) synthesized in step 51.
ESI-MS m/z: 1105 (M+H)$^+$

Step 59
Compound 64 was quantitatively obtained in the same way as in step 3 of Reference Example 1 using compound 63 (1.421 g, 1.2866 mmol) synthesized in step 58.
ESI-MS m/z: 1004 (M+H)$^+$

Reference Example 4 Synthesis of Brancher Unit

Synthesis of Compound 66

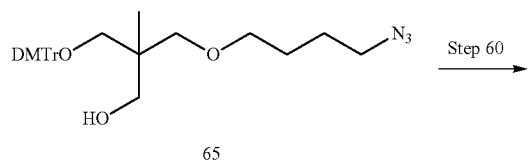

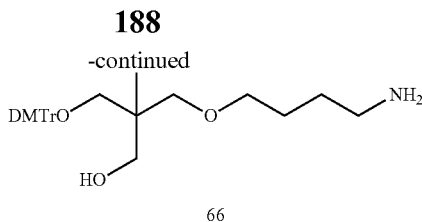

Step 60
Compound 65 (90 mg, 0.173 mmol) synthesized by the method described in Journal of Organic Chemistry, Vol. 74, p. 6837-6842, 2009 was dissolved in tetrahydrofuran (1 mL). To the solution, polymer-supported triphenylphosphine (manufactured by Sigma-Aldrich Co. LLC, 63 mg, 0.189 mmol) was added, and the mixture was stirred for 3 hours under heating to reflux. The reaction solution was filtered, and the solvent was distilled off under reduced pressure to obtain compound 66 (70 mg, yield: 82%).
ESI-MS m/z: 516 (M+Na)$^+$
$^1$H-NMR (400 MHz, CDCl$_3$): δ 0.89 (3H, s), 1.42-1.48 (2H, m), 1.52-1.61 (2H, m), 1.85 (1H, br s), 2.68 (2H, t, J=7.2 Hz), 3.06-3.07 (2H, m), 3.39-3.44 (3H, m), 3.51-3.55 (3H, m), 3.78 (6H, s), 6.80-6.85 (4H, m), 7.17-7.23 (1H, m), 7.27-7.33 (6H, m), 7.41-7.43 (2H, m).

Synthesis of Compound 69

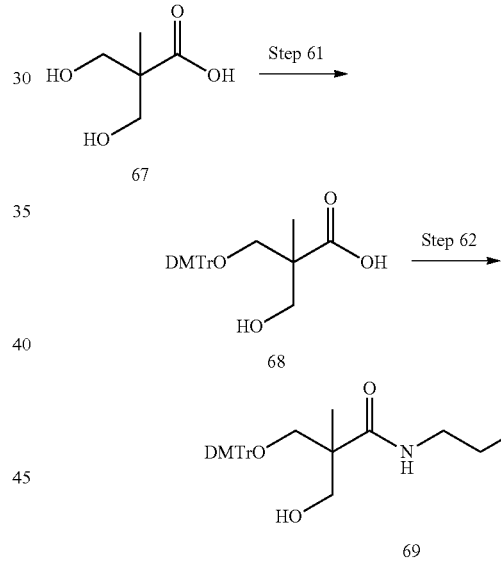

Step 61
A crude product of compound 68 (1.5 g) was obtained in the same way as in step 4 of Reference Example 2 using compound 67 (manufactured by Tokyo Chemical Industry Co., Ltd., 0.500 g, 3.73 mmoL).
ESI-MS m/z: 435 (M−H)$^−$

Step 62
Compound 69 (0.18 g, 2-step yield: 10%) was obtained in the same way as in step 8 of Example 1 using a crude product of compound 68 (1.5 g) synthesized in step 61 and 1,4-diaminobutane (manufactured by Tokyo Chemical Industry Co., Ltd., 3.29 g, 37.3 mmol).
ESI-MS m/z: 551 (M+HCOO)$^−$
$^1$H-NMR (400 MHz, MeOD): δ 1.09 (3H, s), 1.45-1.52 (4H, m), 2.80 (2H, t, J=7.2 Hz), 2.91 (2H, s), 3.05 (1H, d, J=8.8 Hz), 3.12-3.16 (4H, m), 3.24 (1H, s), 3.43 (1H, d, J=10.8 Hz), 3.62-3.66 (7H, m), 6.71-6.76 (4H, m), 7.05-7.11 (1H, m), 7.12-7.20 (6H, m), 7.28-7.32 (2H, m).

Synthesis of Compound 71

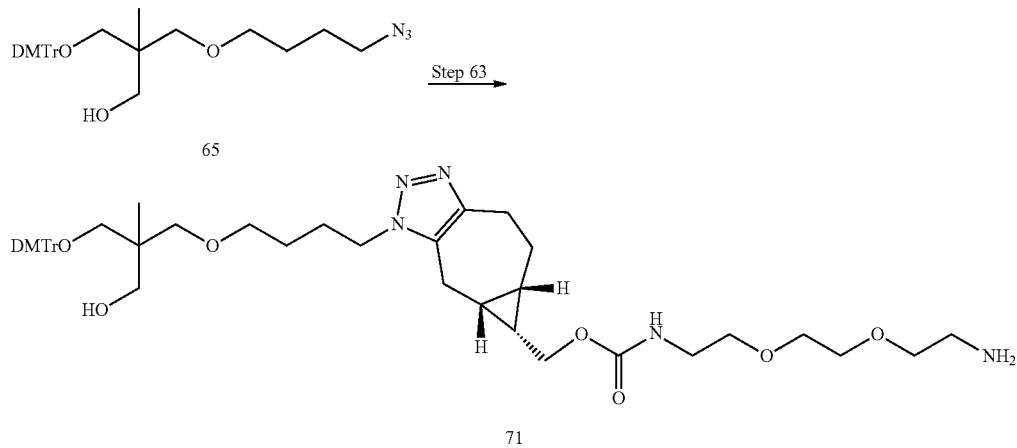

Step 63

Compound 65 (110 mg, 0.212 mmol) synthesized by the method described in Journal of Organic Chemistry, Vol. 74, p. 6837-6842, 2009 was dissolved in tetrahydrofuran (2 mL). To the solution, N-(1R,8S,9s)-bicyclo[6.1.0]non-4-yn-9-ylmethyloxycarbonyl-1,8-diamino-3,6-dioxaoctane (manufactured by Tokyo Chemical Industry Co., Ltd., 72 mg, 0.222 mmol) was added, and the mixture was stirred at room temperature for 1 hour. Water was added to the reaction solution, followed by extraction with chloroform. Then, the organic layer was washed with saturated saline and dried over anhydrous magnesium sulfate. The solvent was distilled off under reduced pressure, and the residue was purified by amino silica gel column chromatography (chloroform/methanol=90/10) to obtain compound 71 (160 mg, yield: 90%). ESI-MS m/z: 845 (M+H)$^+$ $^1$H-NMR (400 MHz, CDCl$_3$): δ 0.88 (3H, s), 0.91-1.09 (3H, m), 1.20-1.25 (1H, m), 1.52-1.59 (4H, m), 1.80-1.85 (2H, m), 2.19-2.25 (4H, m), 2.59-2.68 (1H, m), 2.84-2.90 (4H, m), 3.02-3.11 (3H, m), 3.35-3.44 (5H, m), 3.49-3.53 (5H, m), 3.54-3.58 (2H, m), 3.62 (5H, s), 3.78 (6H, s), 4.13 (2H, d, J=6.4 Hz), 4.21 (2H, t, J=7.2 Hz), 6.79-6.84 (4H, m), 7.18-7.21 (1H, m), 7.24-7.27 (2H, m), 7.28-7.32 (4H, m), 7.39-7.44 (2H, m).

Synthesis of Compound 75

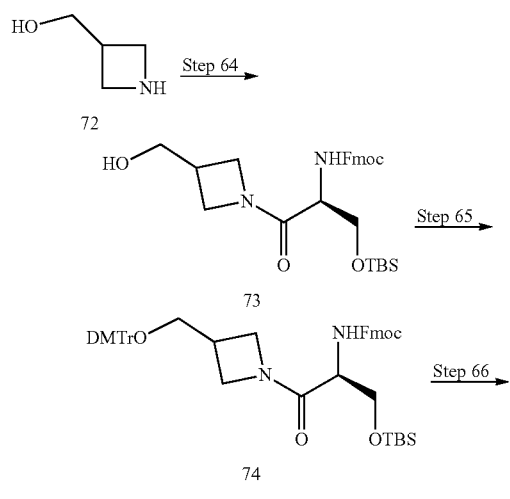

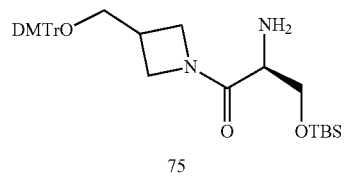

Step 64

Compound 73 (410 mg, yield: 70%) was obtained in the same way as in step 8 of Example 1 using compound 72 (manufactured by AstaTech Inc., 100 mg, 1.148 mmol) and Fmoc-Ser(tBuMe2Si)—OH (manufactured by Watanabe Chemical Industries, Ltd., 532 mg, 1.205 mmol).

ESI-MS m/z: 511 (M+H)$^+$ $^1$H-NMR (400 MHz, CDCl$_3$): δ 0.06 (6H, s), 0.90 (9H, s), 2.76-2.85 (1H, m), 3.65-3.86 (5H, m), 4.02-4.23 (3H, m), 4.32-4.40 (4H, m), 5.55 (1H, d, J=8.0 Hz), 7.31 (2H, t, J=7.6 Hz), 7.40 (2H, t, J=7.6 Hz), 7.59 (2H, d, J=7.6 Hz), 7.76 (2H, d, J=7.6 Hz).

Step 65

A crude product of compound 74 (680 mg) was obtained in the same way as in step 4 of Reference Example 2 using compound 73 (410 mg, 0.803 mmol) synthesized in step 64.

ESI-MS m/z: 814 (M+H)$^+$

Step 66

Compound 75 (330 mg, 2-step yield: 70%) was obtained in the same way as in step 5 of Reference Example 2 using a crude product of compound 74 (680 mg) synthesized in step 65.

ESI-MS m/z: 519 (M+H)$^+$ $^1$H-NMR (400 MHz, CDCl$_3$): δ 0.02-0.09 (6H, m), 0.89 (9H, d, J=28.8 Hz), 2.84-2.94 (1H, m), 3.24-3.30 (2H, m), 3.46 (1H, t, J=7.2 Hz), 3.52-3.68 (2H, m), 3.75-3.80 (1H, m), 3.82 (6H, d, J=2.4 Hz), 3.89-3.96 (1H, m), 4.05-4.17 (1H, m), 4.27-4.37 (1H, m), 6.82-6.89 (4H, m), 7.22-7.27 (1H, m), 7.29-7.34 (6H, m), 7.41-7.45 (2H, m)

Synthesis of Compound 78

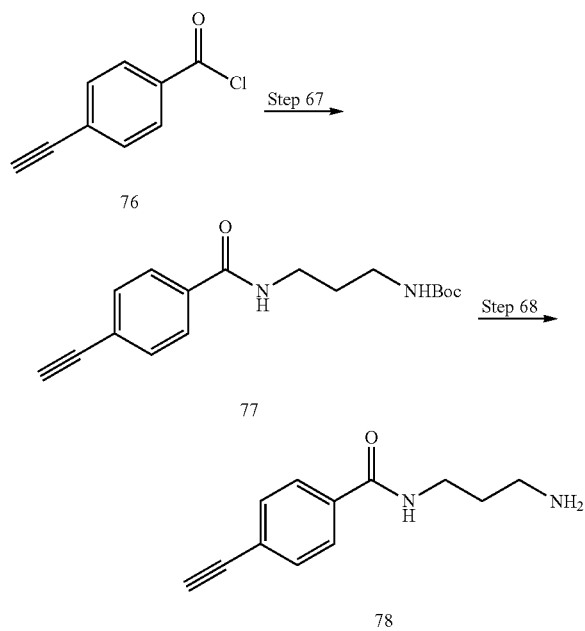 [SMILES: C#Cc1ccc(C(=O)Cl)cc1 ; C#Cc1ccc(C(=O)NCCCNC(=O)OC(C)(C)C)cc1 ; C#Cc1ccc(C(=O)NCCCN)cc1]

Step 67

N-(tert-Butoxycarbonyl)-1,3-diaminopropane (manufactured by Tokyo Chemical Industry Co., Ltd., 1.788 g, 10.26 mmol) was dissolved in dichloromethane (22.8 mL). To the solution, triethylamine (1.907 mL, 13.68 mmol) was added, and the mixture was stirred at room temperature for 15 minutes. A solution of compound 76 (1.126 g, 6.84 mmol) synthesized by the method described in Organic Letter, Vol. 16, p. 6318-6321, 2014 in dichloromethane (5 mL) was added dropwise to the reaction solution, and the mixture was stirred at room temperature for 2 hours. Water was added to the reaction solution, followed by extraction with chloroform. Then, the organic layer was washed with saturated saline and dried over anhydrous magnesium sulfate. The solvent was distilled off under reduced pressure, and the residue was purified by silica gel column chromatography (heptane/ethyl acetate=35/65) to obtain compound 77 (1.65 g, yield: 80%).

ESI-MS m/z: 303 (M+H)$^+$

Step 68

Compound 78 (1.10 g, yield: 100%) was obtained in the same way as in step 3 of Reference Example 1 using compound 77 (1.65 g, 5.46 mmol) synthesized in step 67.

ESI-MS m/z: 203 (M+H)$^+$ $^1$H-NMR (400 MHz, CDCl$_3$): δ 1.74 (2H, dt, J=12.0, 6.0 Hz), 2.95 (2H, t, J=6.0 Hz), 3.18 (1H, s), 3.60 (2H, td, J=6.0, 5.2 Hz), 7.54 (2H, dt, J=8.4, 1.8 Hz), 7.76 (2H, dt, J=8.4, 1.8 Hz), 7.97 (1H, br s).

Synthesis of Compound 82

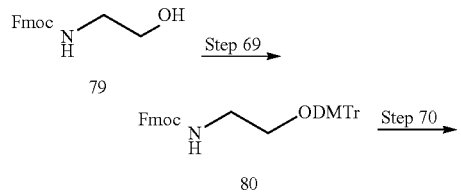

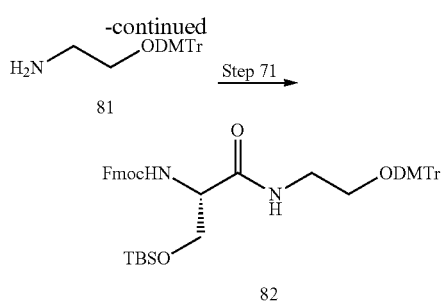

Step 69

A crude product of compound 79 was obtained in the same way as in step 4 of Reference Example 2 using compound 79 (manufactured by Tokyo Chemical Industry Co., Ltd., 1.2 g, 4.24 mmol).

ESI-MS m/z: 608 (M+Na)$^+$

Step 70

Compound 81 (1.34 g, 2-step yield: 52%) was obtained by the method described in step 5 of Reference Example 2 or step 11 of Example 1 using a crude product of compound 80 synthesized in step 69.

ESI-MS m/z: 386 (M+Na)$^+$

1H-NMR (400 MHz, CDCl$_3$): δ 3.34 (2H, t, J=6.4 Hz), 3.47 (2H, t, J=6.4 Hz), 3.79 (6H, s), 6.78-6.84 (4H, m), 7.17-7.21 (1H, m), 7.27-7.35 (6H, m), 7.42-7.46 (2H, m).

Step 71

Compound 82 (560 mg, yield: 31%) was obtained in the same way as in step 8 of Example 1 using compound 81 (1.15 g, 3.16 mmol) synthesized in step 70 and Fmoc-Ser(tBuMe2Si)—OH (manufactured by Watanabe Chemical Industries, Ltd., 1.677 g, 3.8 mmol).

1H-NMR (400 MHz, CDCl$_3$) δ: 0.00-0.07 (6H, m), 0.83-0.89 (9H, m), 3.18-3.26 (2H, m), 3.39-3.46 (2H, m), 3.61-3.68 (1H, m), 3.76 (6H, s), 3.89 (1H, dd, J=10.0, 4.0 Hz), 4.03 (1H, dd, J=10.0, 4.0 Hz), 4.15-4.20 (1H, m), 4.22-4.28 (1H, m), 4.32-4.40 (2H, m), 5.65-5.88 (1H, m), 6.76-6.85 (4H, m), 7.16-7.23 (1H, m), 7.25-7.34 (8H, m), 7.36-7.44 (4H, m), 7.50-7.64 (2H, m), 7.72-7.79 (2H, m).

Synthesis of Compounds 88 to 94

The compounds described in Table 16 were obtained in the same way as in steps 69 to 71 using the compounds described in Table 15 and Fmoc-Ser(tBuMe2Si)—OH and Fmoc-Thr(tBuMe2Si)—OH.

NMR analysis data on the compounds synthesized in this Example are shown in Table 17.

TABLE 15

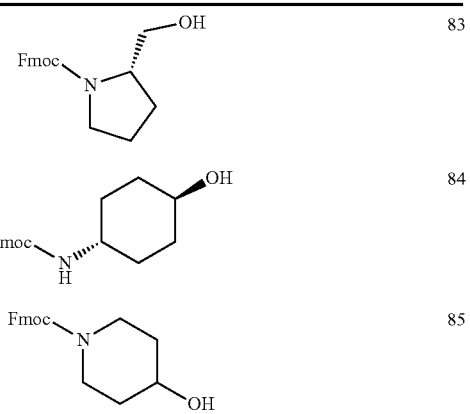

TABLE 15-continued

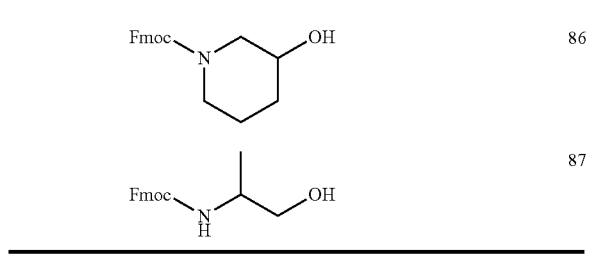

| | |
|---|---|
| | 86 |
| | 87 |

TABLE 16

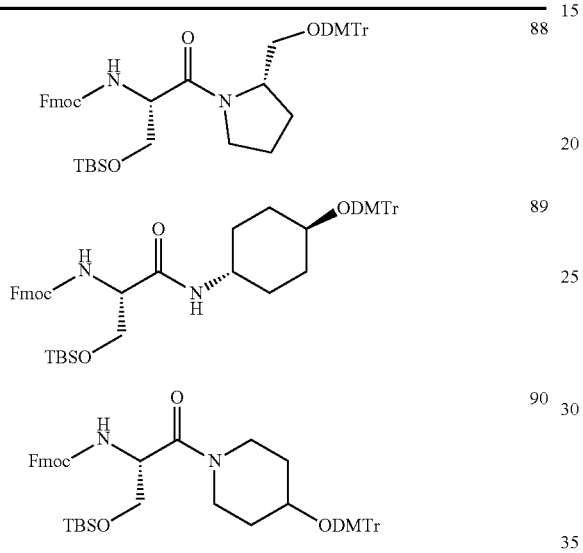

| | |
|---|---|
| | 88 |
| | 89 |
| | 90 |

TABLE 16-continued

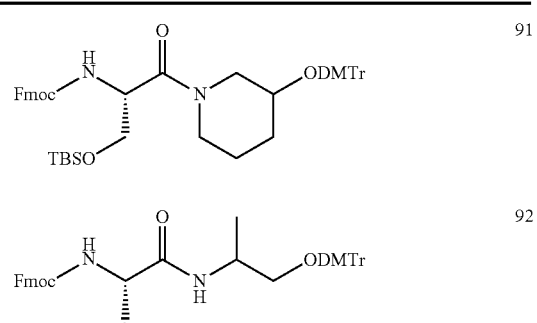

| | |
|---|---|
| | 91 |
| | 92 |
| | 93 |
| | 94 |

TABLE 17

| Compound | NMR |
|---|---|
| 88 | $^1$H-NMR (400 MHz, CDCl$_3$): δ0.07-0.03 (6H, m), 0.89-0.87 (9H, m H), 2.04-1.65 (4H, m), 3.86-3.58 (11H, m), 4.37-4.18 (4H, m), 4.69-4.68 (1H, m), 5.67-5.65 (1H, m), 6.84-6.80 (4H, m), 7.18-7.16 (3H, m), 7.33-7.25 (7H, m), 7.42-7.38 (3H, m), 7.60-7.58 (2H, m), 7.78-7.75 (2H, m). |
| 89 | $^1$H-NMR (400 MHz, CDCl$_3$): δ0.11-0.05 (6H, m), 0.91-0.87 (9H, m), 1.43-1.19 (4H, m), 2.00-1.80 (3H, m), 3.74-3.36 (2H, m), 3.81-3.75 (6H, m), 4.41-3.96 (5H, m), 5.71-5.64 (1H, m), 6.37-6.36 (1H, m), 6.84-6.80 (4H, m), 7.20-7.16 (2H, m), 7.42-7.25 (10H, m), 7.59-7.48 (3H, m), 7.78-7.75 (2H, m). |
| 90 | $^1$H-NMR (400 MHz, CDCl$_3$): δ0.08-0.03 (6H, m), 0.98-0.81 (9H, m), 1.20-1.07 (2H, m), 1.39-1.30 (2H, m), 1.42-1.40 (1H, m), 1.71-1.50 (2H, m), 3.36-3.14 (1H, m), 3.73-3.60 (3H, m), 3.80-3.77 (6H, m), 4.33-4.18 (1H, m), 4.35-4.34 (2H, m), 4.78-4.77 (1H, m), 5.75-5.74 (1H, m), 6.83-6.81 (4H, m), 7.35-7.26 (5H, m), 7.39-7.37 (6H, m), 7.50-7.48 (2H, m), 7.61-7.57 (2H, m), 7.77-7.74 (2H, m) |
| 91 | $^1$H-NMR (400 MHz, CDCl$_3$): δ0.04-0.00 (6H, m), 0.87-0.80 (9H, m), 1.47-1.11 (3H, m), 1.92-1.61 (1H, m), 4.83-2.99 (16H, m), 5.88-5.72 (1H, m), 6.89-6.82 (4H, m), 7.21-7.14 (1H, m), 7.49-7.28 (12H, m), 7.62-7.59 (2H, m), 7.77-7.75 (2H, m) |
| 92 | $^1$H-NMR (400 MHz, CDCl$_3$): δ0.01-0.05 (6H, m), 0.66-0.92 (9H, m), 1.11-1.12 (3H, m), 3.02-3.06 (1H, m), 3.55-3.62 (1H, m), 3.69-3.75 (6H, m), 3.91-4.35 (6H, m), 5.62 (1H, s), 6.74-6.78 (4H, m), 7.10-7.12 (2H, m), 7.14-7.27 (7H, m), 7.30-7.36 (4H, m), 7.43-7.53(2H, m), 7.68-7.71 (2H, m). |
| 93 | $^1$H-NMR (400 MHz, CDCl$_3$): δ0.14-0.08 (6H, m), 1.10-0.87 (9H, m), 1.56-1.55 (3H, m), 3.48-3.41 (2H, m), 3.81-3.73 (7H, m), 4.25-4.14 (2H, m), 4.45-4.39 (3H, m), 5.77-5.76 (1H, m), 6.84-6.79 (4H, m), 7.18-7.16 (3H, m), 7.42-7.26 (10H, m), 7.61-7.56 (2H, m), 7.78-7.74 (2H, m). |
| 94 | $^1$H-NMR (400 MHz, CDCl$_3$): δ-0.10-0.00 (6H, m), 0.81-0.72 (9H, m), 1.12-1.11 (3H, m), 1.47-1.54 (1H, m), 1.83-1.77 (3H, m), 3.71-3.47 (9H, m), 4.39-4.00 (6H, m), 5.55-5.53 (1H, m), 6.74-6.71 (4H, m), 7.08-7.06 (3H, m), 7.32-7.16 (10H, m), 7.52-7.48 (2H, m), 7.67-7.65 (2H, m). |

Synthesis of Compound 95

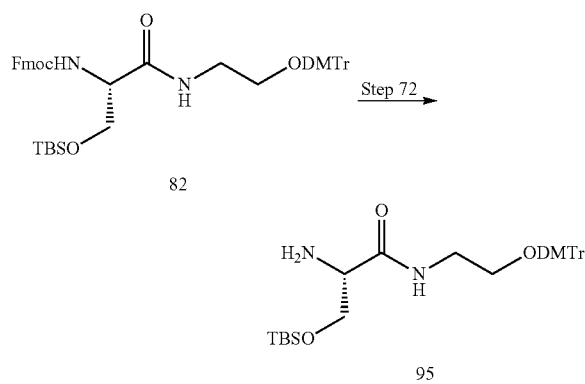

Step 72

Compound 95 (1.2 g, yield: 67%) was obtained in the same way as in step 5 of Reference Example 2 using compound 82 (2.487 g, 3.16 mmol) synthesized in step 71.

ESI-MS m/z: 587 (M+Na)$^+$

1H-NMR (400 MHz, CDCl$_3$): δ −0.01-0.07 (6H, m), 0.86-0.90 (9H, m), 3.15-3.21 (2H, m), 3.41-3.48 (3H, m), 3.72 (1H, dd, J=10.0, 6.4 Hz), 3.79 (6H, s), 3.84 (1H, dd, J=10.0, 4.8 Hz), 6.79-6.84 (4H, m), 7.18-7.23 (1H, m), 7.27-7.33 (6H, m), 7.40-7.44 (2H, m), 7.72-7.75 (1H, br m).

Synthesis of Compounds 96 to 102

The compounds described in Table 18 were obtained in the same way as in step 72 using the compounds described in Table 16.

The mass spectrometry results of the compounds synthesized in this Example are shown in Table 19.

TABLE 18

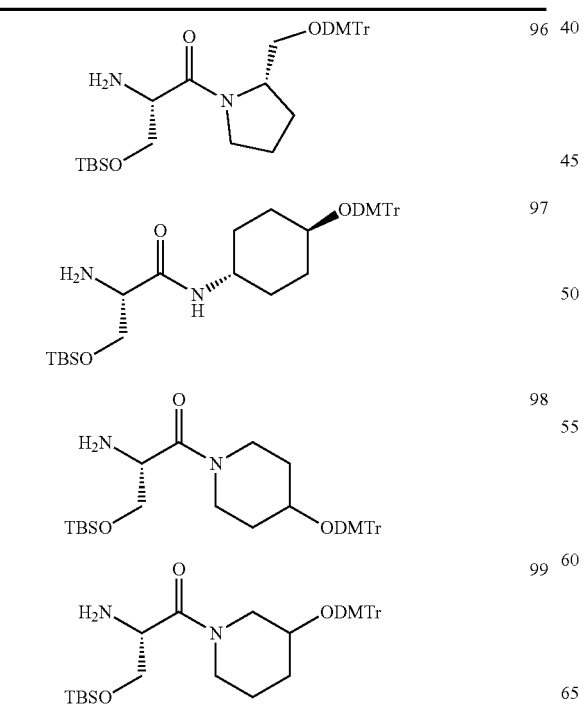

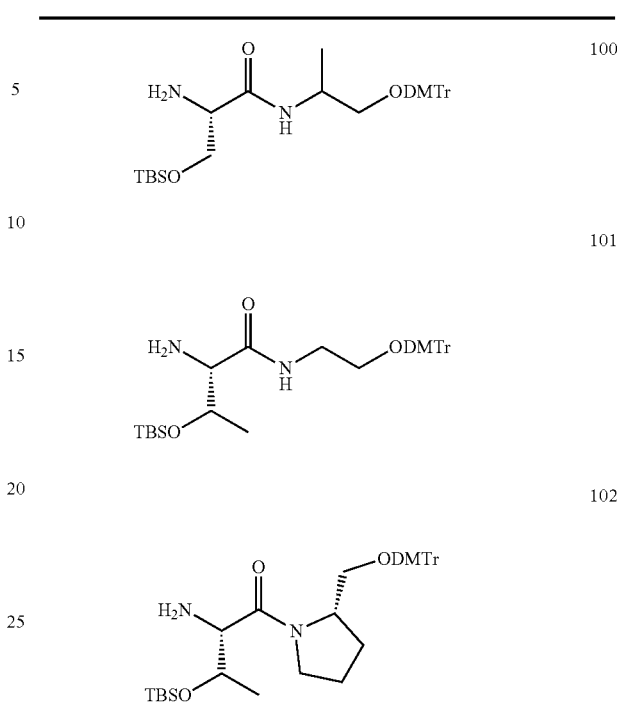

TABLE 19

| Compound | ESI-MS m/z |
|---|---|
| 96 | 605(M + H)$^+$ |
| 97 | 619(M + H)$^+$ |
| 98 | 303(M + H)$^+$, DMTr-deprotected product detected |
| 99 | 649(M + HCOOH)$^-$ |
| 100 | 577(M − H)$^-$ |
| 101 | 623(M + HCOOH)$^-$ |
| 102 | 317(M + H)$^+$, DMTr-deprotected product detected |

Example 13 Synthesis of Tether Unit

Synthesis of Compound 107

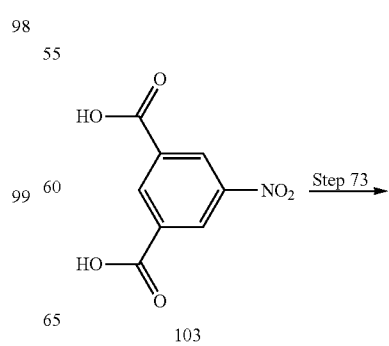

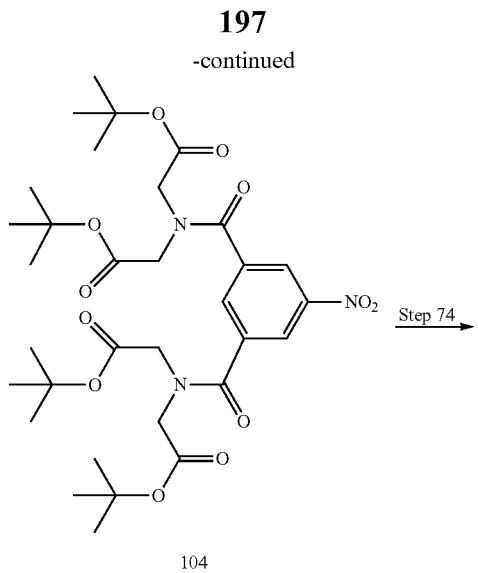

104

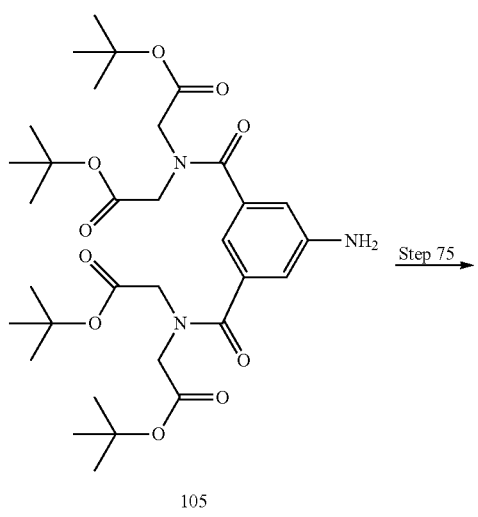

105

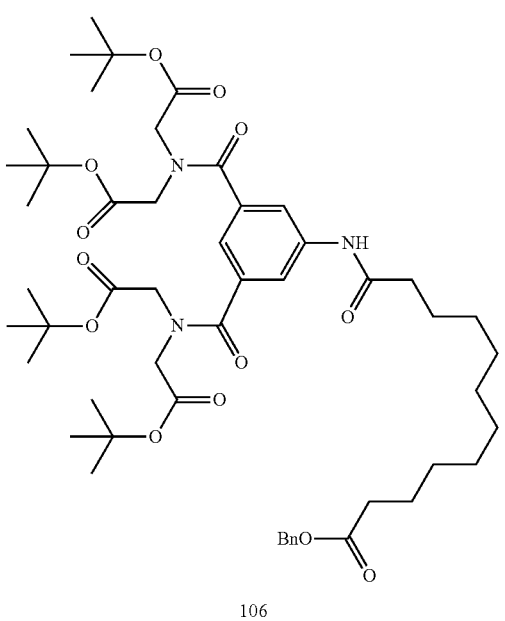

106

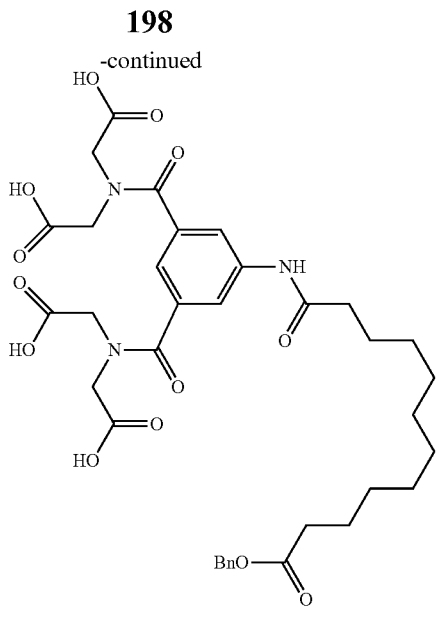

107

Step 73

Compound 103 (2.00 g, 9.47 mmol) was dissolved in N,N'-dimethylformamide (40 mL). To the solution, iminodiacetic acid di-tert-butyl ester (5.11 g, 20.84 mmol), 1-(3-dimethylaminopropyl)-3-ethylcarbodiimide hydrochloride (4.00 g, 20.84 mmol), and 1-hydroxybenzotriazole monohydrate (145 mg, 0.947 mmol) were added at room temperature, and the mixture was stirred for 2 hours. Water was added to the reaction solution, followed by extraction with ethyl acetate. Then, the organic layer was washed with a saturated aqueous solution of sodium bicarbonate and saturated saline and dried over anhydrous sodium sulfate. The solvent was distilled off under reduced pressure, and the residue was purified by silica gel column chromatography (heptane/ethyl acetate=50/50). The purified product was further slurry-purified with methanol to obtain compound 104 (4.07 g, yield: 65%).

ESI-MS m/z: 664 (M–H)⁻

Step 74

Compound 104 (2.66 g, 4.00 mmol) synthesized in step 73 was dissolved in tetrahydrofuran (53 mL). To the solution, a 10% palladium-carbon powder (water-containing product, 54.29%; 490 mg) was added at room temperature, and the mixture was stirred for 3 hours in a hydrogen atmosphere. The reaction solution was filtered, and the solvent was distilled off under reduced pressure to obtain compound 105 (2.86 g, yield: 113%).

ESI-MS m/z: 634 (M–H)⁻

Step 75

Compound 105 (871.0 mg, 1.370 mmol) synthesized in step 74 was dissolved in N,N'-dimethylformamide (17 mL). To the solution, O-(7-azabenzotriazol-1-yl)-N,N,N',N'-tetramethyluronium hexafluorophosphate (625.0 mg, 1.644 mmol), diisopropylethylamine (0.5730 mL, 3.290 mmol), and dodecanedioic acid monobenzyl ester (527.0 mg, 1.644 mmol) were added, and the mixture was stirred overnight at room temperature. Water was added to the reaction solution, followed by extraction with ethyl acetate. Then, the organic layer was washed with a saturated aqueous solution of sodium bicarbonate and saturated saline and dried over anhydrous sodium sulfate. The solvent was distilled off under reduced pressure, and the residue was purified by silica gel column chromatography (heptane/ethyl acetate=60/40) to obtain compound 106 (1.030 g, yield: 80%).

ESI-MS m/z: 939 (M+H)$^+$

Step 76

Compound 106 (1.030 g, 1.098 mmol) synthesized in step 75 was dissolved in dichloromethane (10 mL). To the solution, trifluoroacetic acid (10.00 mL, 130.0 mmol) was added, and the mixture was stirred at room temperature for 1 hour. The solvent was distilled off under reduced pressure to obtain a crude product of compound 107.

ESI-MS m/z: 713 (M−H)$^-$

Synthesis of Compound 113

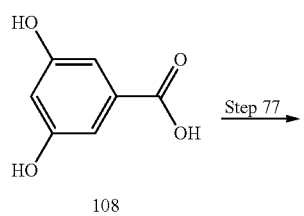
108

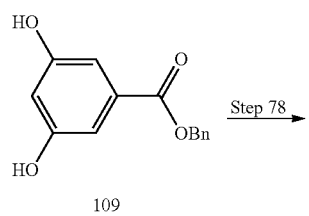
109

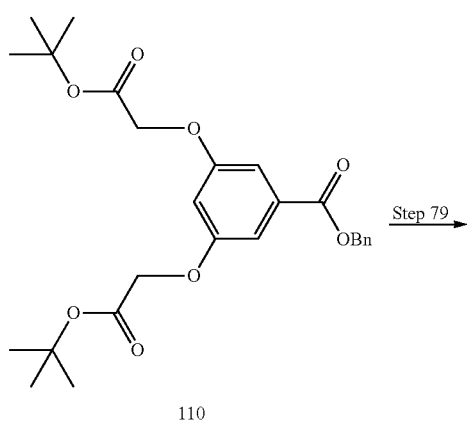
110

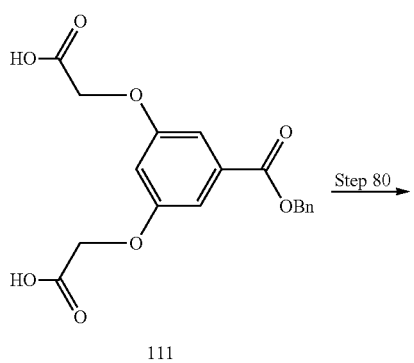
111

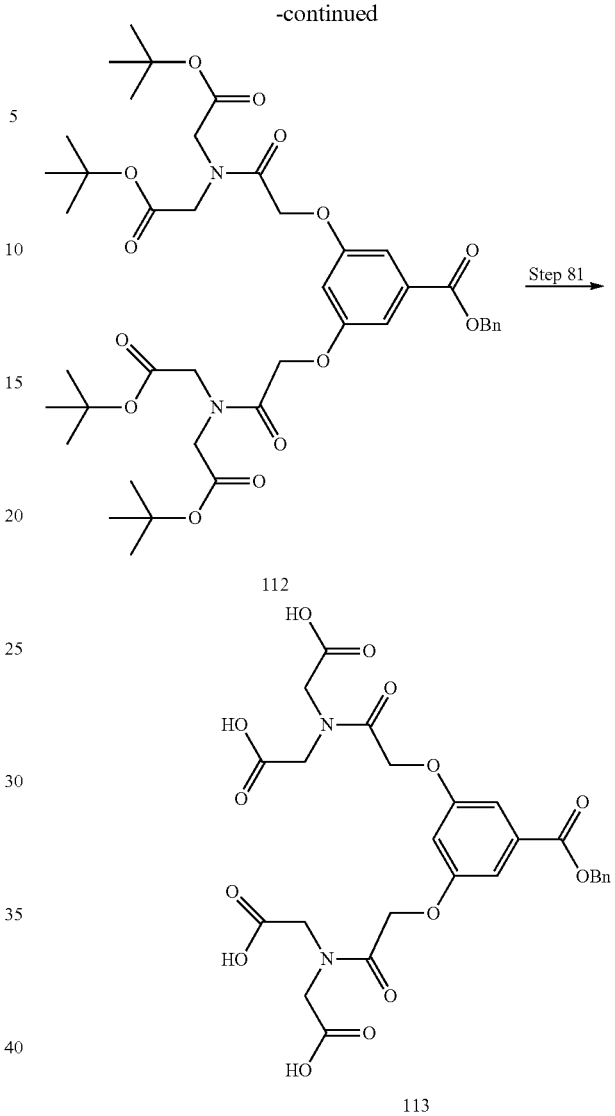
112

113

Step 77

Compound 108 (2.000 g, 12.98 mmol) was dissolved in N,N'-dimethylformamide (30 mL). To the solution, potassium bicarbonate (1.559 g, 15.57 mmol) and benzyl chloride (2.328 mL, 19.47 mmol) were added, and the mixture was stirred at room temperature for 4 hours. Saturated ammonium chloride was added to the reaction solution, followed by extraction with dichloromethane. Then, the organic layer was washed with water and dried over anhydrous sodium sulfate. The solvent was distilled off under reduced pressure, and the residue was purified by silica gel column chromatography (heptane/ethyl acetate=50/50) to obtain compound 109 (2.850 g, yield: 90%).

ESI-MS m/z: 243 (M−H)$^-$

Step 78

Compound 109 (2.500 g, 10.24 mmol) synthesized in step 77 was dissolved in N,N'-dimethylformamide (30 mL). To the solution, potassium carbonate (5.660 g, 40.90 mmol) and tert-butyl bromoacetic acid (3.300 mL, 22.52 mmol) were added, and the mixture was stirred at 90° C. for 4 hours. Saturated ammonium chloride was added to the reaction solution, followed by extraction with dichloromethane. Then, the organic layer was washed with saturated saline and dried over anhydrous sodium sulfate. The solvent was distilled off under reduced pressure, and the residue was purified by silica gel column chromatography (heptane/ethyl acetate=75/25) to obtain compound 110 (4.300 g, yield: 89%).

ESI-MS m/z: 472 (M−H)⁻

Step 79

Compound 110 (1.000 g, 2.116 mmol) synthesized in step 78 was dissolved in dichloromethane (10 mL). To the solution, trifluoroacetic acid (10.00 mL, 130.0 mmol) was added, and the mixture was stirred at room temperature for 6 hours. The solvent was distilled off under reduced pressure to obtain a crude product of compound 111.

ESI-MS m/z: 359 (M−H)⁻

Step 80

Compound 111 (350.0 mg, 0.9710 mmol) synthesized in step 79 was dissolved in N,N'-dimethylformamide (7 mL). To the solution, 1-hydroxybenzotriazole monohydrate (327.0 mg, 2.137 mmol), 1-(3-dimethylaminopropyl)-3-ethylcarbodiimide hydrochloride (410.0 mg, 2.137 mmol), and iminodiacetic acid di-tert-butyl ester (524.0 mg, 2.137 mmol) were added, and the mixture was stirred at room temperature for 5 hours. Water was added to the reaction solution, followed by extraction with ethyl acetate. Then, the organic layer was washed with a saturated aqueous solution of sodium bicarbonate and saturated saline and dried over anhydrous sodium sulfate. The solvent was distilled off under reduced pressure, and the residue was purified by silica gel column chromatography (heptane/ethyl acetate=60/40) to obtain compound 112 (617.0 mg, yield: 78%).

ESI-MS m/z: 814 (M−H)⁻

Step 81

Compound 112 (610.0 mg, 0.7490 mmol) synthesized in step 80 was dissolved in dichloromethane (6 mL). To the solution, trifluoroacetic acid (6 mL, 78.00 mmol) was added, and the mixture was stirred at room temperature for 1 hour. The solvent was distilled off under reduced pressure to obtain a crude product of compound 113.

ESI-MS m/z: 590 (M+H)⁺

Synthesis of Compound 116

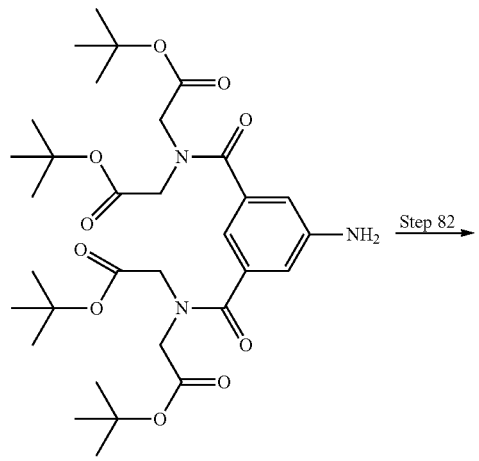

114

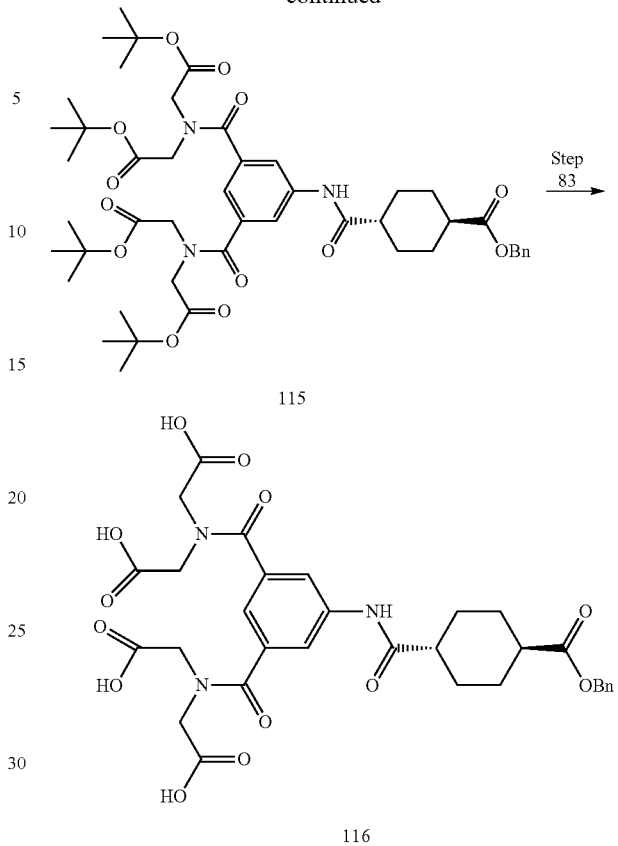

115

116

Step 82

Compound 114 (474 mg, 0.744 mmol) synthesized in step 74 was dissolved in N,N'-dimethylformamide (10 mL). To the solution, trans-cyclohexane-1,4-dicarboxylic acid monobenzyl ester (0.234 mg, 0.893 mmol) synthesized by the method described in Journal of Medicinal Chemistry, Vol. 54, p. 2433-2446, 2011, diisopropylethylamine (0.312 mL, 1.79 mmol), and O-(7-azabenzotriazol-1-yl)-N,N,N',N'-tetramethyluronium hexafluorophosphate (339 mg, 0.893 mmol) were added at room temperature, and the mixture was stirred for 6 hours. Water was added to the reaction solution, followed by extraction with ethyl acetate. Then, the organic layer was washed with a saturated aqueous solution of sodium bicarbonate and saturated saline and dried over anhydrous sodium sulfate. The solvent was distilled off under reduced pressure, and the residue was purified by silica gel column chromatography (heptane/ethyl acetate=50/50) to obtain compound 115 (448 mg, yield: 68%).

ESI-MS m/z: 879 (M−H)⁻

Step 83

Compound 115 (341 mg, 0.387 mmol) synthesized in step 82 was dissolved in dichloromethane (3.4 mL). To the solution, trifluoroacetic acid (3.4 mL) was added at room temperature, and the mixture was stirred overnight. The reaction solution was concentrated under reduced pressure and subjected to azeotropy with ethyl acetate, and the residue was slurry-purified with heptane to obtain compound 116 (254 mg, yield: 100%).

ESI-MS m/z: 656 (M+H)⁺

Synthesis of Compound 120

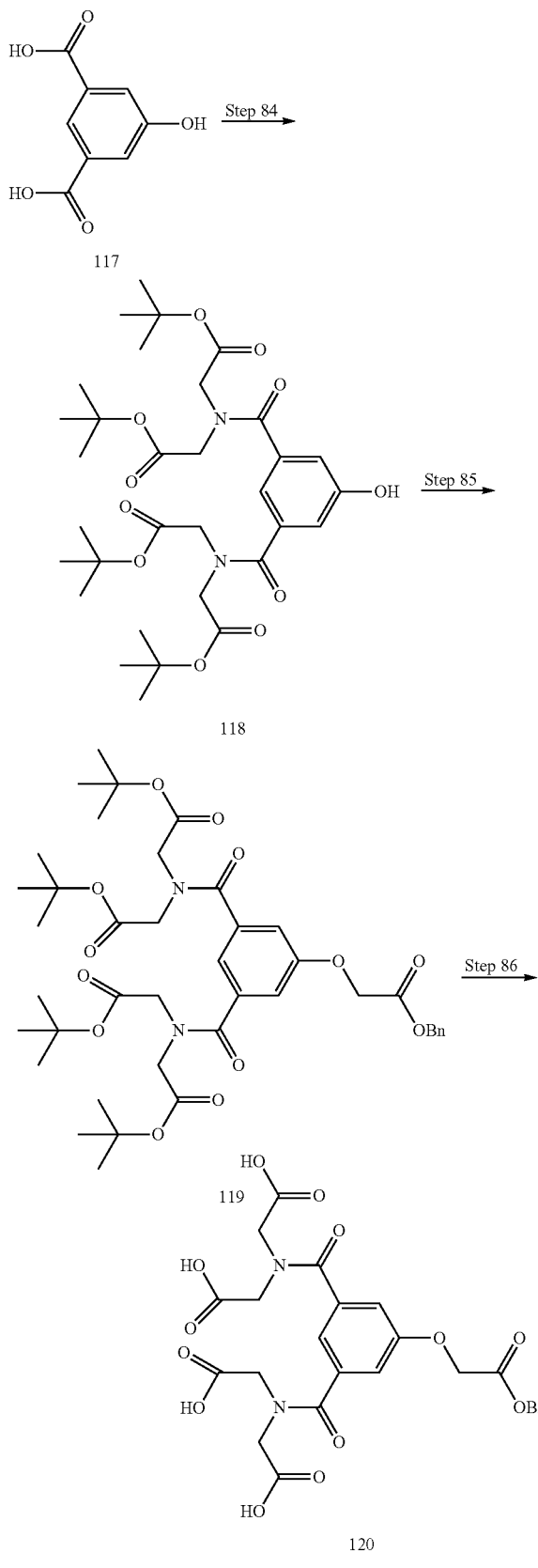

Step 84

Compound 117 (500 mg, 2.75 mmol) was dissolved in N,N'-dimethylformamide (10 mL). To the solution, iminodiacetic acid di-tert-butyl ester (1.48 g, 6.04 mmol), 1-(3-dimethylaminopropyl)-3-ethylcarbodiimide hydrochloride (1.16 g, 6.04 mmol), and 1-hydroxybenzotriazole monohydrate (42.0 mg, 0.275 mmol) were added at room temperature, and the mixture was stirred for 4 hours. Water was added to the reaction solution, followed by extraction with ethyl acetate. Then, the organic layer was washed with saturated saline and dried over anhydrous sodium sulfate. The solvent was distilled off under reduced pressure, and the residue was purified by silica gel column chromatography (heptane/ethyl acetate=50/50) to obtain compound 118 (329 mg, yield: 19%).

ESI-MS m/z: 635 (M−H)⁻

Step 85

Compound 118 (323 mg, 0.507 mmol) synthesized in step 84 was dissolved in N,N'-dimethylformamide (6.5 mL). To the solution, potassium carbonate (84.0 mg, 0.609 mmol) and benzyl bromoacetate (139 mg, 0.609 mmol) were added at room temperature, and the mixture was stirred for 3 hours. Water was added to the reaction solution, followed by extraction with ethyl acetate. Then, the organic layer was washed with saturated saline and dried over anhydrous sodium sulfate. The solvent was distilled off under reduced pressure, and the residue was purified by silica gel column chromatography (heptane/ethyl acetate=50/50) to obtain compound 119 (313 mg, yield: 79%).

ESI-MS m/z: 783 (M−H)⁻

Step 86

Compound 119 (312 mg, 0.398 mmol) synthesized in step 85 was dissolved in dichloromethane (3.1 mL). To the solution, trifluoroacetic acid (3.1 mL) was added at room temperature, and the mixture was stirred overnight. The reaction solution was concentrated under reduced pressure and subjected to azeotropy with ethyl acetate to obtain compound 120 (252 mg, yield: 113%).

ESI-MS m/z: 561 (M+H)⁺

Synthesis of Compound 125

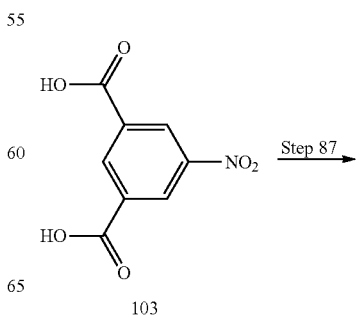

205
-continued

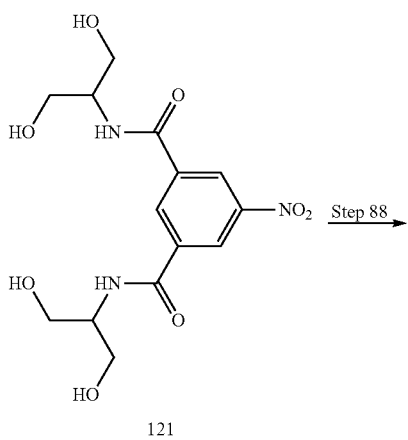

206
-continued

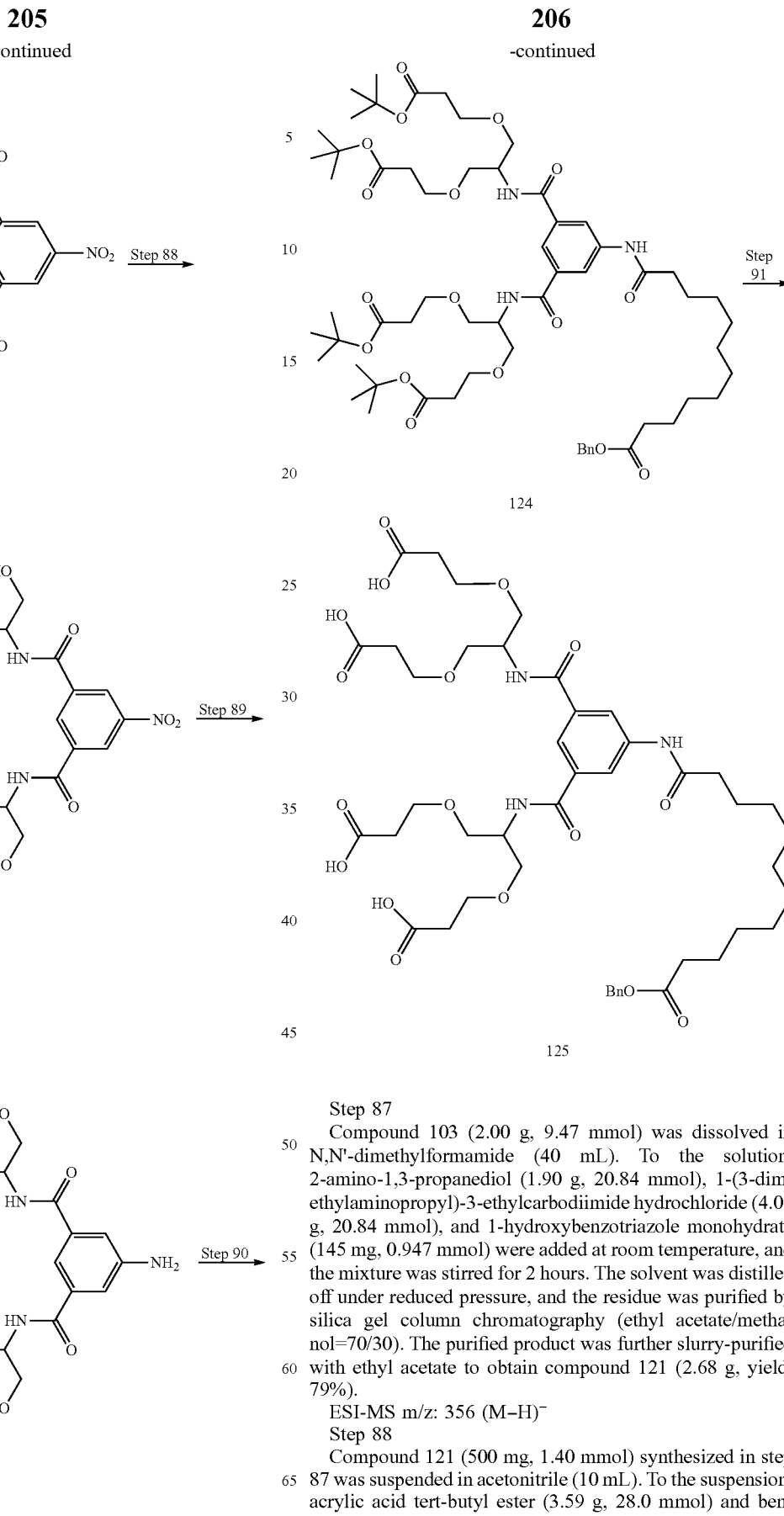

Step 87

Compound 103 (2.00 g, 9.47 mmol) was dissolved in N,N'-dimethylformamide (40 mL). To the solution, 2-amino-1,3-propanediol (1.90 g, 20.84 mmol), 1-(3-dimethylaminopropyl)-3-ethylcarbodiimide hydrochloride (4.00 g, 20.84 mmol), and 1-hydroxybenzotriazole monohydrate (145 mg, 0.947 mmol) were added at room temperature, and the mixture was stirred for 2 hours. The solvent was distilled off under reduced pressure, and the residue was purified by silica gel column chromatography (ethyl acetate/methanol=70/30). The purified product was further slurry-purified with ethyl acetate to obtain compound 121 (2.68 g, yield: 79%).

ESI-MS m/z: 356 (M−H)⁻

Step 88

Compound 121 (500 mg, 1.40 mmol) synthesized in step 87 was suspended in acetonitrile (10 mL). To the suspension, acrylic acid tert-butyl ester (3.59 g, 28.0 mmol) and benzyltrimethylammonium hydroxide (40% aqueous solution;

1.76 mL, 702 mmol) were added at room temperature, and the mixture was stirred overnight. The solvent was distilled off under reduced pressure, and water was added to the residue, followed by extraction with ethyl acetate. Then, the organic layer was washed with saturated saline and dried over anhydrous sodium sulfate. The solvent was distilled off under reduced pressure, and the residue was purified by silica gel column chromatography (heptane/ethyl acetate=50/50) to obtain compound 122 (300 mg, yield: 24%).

ESI-MS m/z: 871 (M+H)$^+$

Step 89

Compound 122 (340 mg, 0391 mmol) synthesized in step 88 was dissolved in tetrahydrofuran (6.8 mL). To the solution, a 10% palladium-carbon powder (water-containing product, 54.29%; 31.3 mg) was added at room temperature, and the mixture was stirred for 6 hours in a hydrogen atmosphere. The reaction solution was filtered, and the solvent was distilled off under reduced pressure. The residue was purified by silica gel column chromatography (heptane/ethyl acetate=30/70) to obtain compound 123 (235 mg, yield: 72%).

ESI-MS m/z: 841 (M+H)$^+$

Step 90

Compound 123 (232 mg, 0.276 mmol) synthesized in step 89 was dissolved in N,N'-dimethylformamide (4.6 mL). To the solution, dodecanoic acid monobenzyl ester (0.133 mg, 0.414 mmol), diisopropylethylamine (0.145 mL, 0.829 mmol), and O-(7-azabenzotriazol-1-yl)-N,N,N',N'-tetramethyluronium hexafluorophosphate (158 mg, 0.414 mmol) were added at room temperature, and the mixture was stirred overnight. Water was added to the reaction solution, followed by extraction with ethyl acetate. Then, the organic layer was washed with a saturated aqueous solution of sodium bicarbonate and saturated saline and dried over anhydrous sodium sulfate. The solvent was distilled off under reduced pressure, and the residue was purified by silica gel column chromatography (heptane/ethyl acetate=30/70) to obtain compound 124 (274 mg, yield: 87%).

ESI-MS m/z: 1141 (M−H)$^−$

Step 91

Compound 124 (273 mg, 0.239 mmol) synthesized in step 90 was dissolved in dichloromethane (2.7 mL). To the solution, trifluoroacetic acid (2.7 mL) was added at room temperature, and the mixture was stirred overnight. The reaction solution was concentrated under reduced pressure and subjected to azeotropy with ethyl acetate to obtain compound 125 (231 mg, yield: 105%).

ESI-MS m/z: 919 (M+H)$^+$

Synthesis of Compound 128

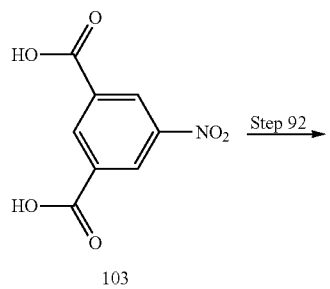

103

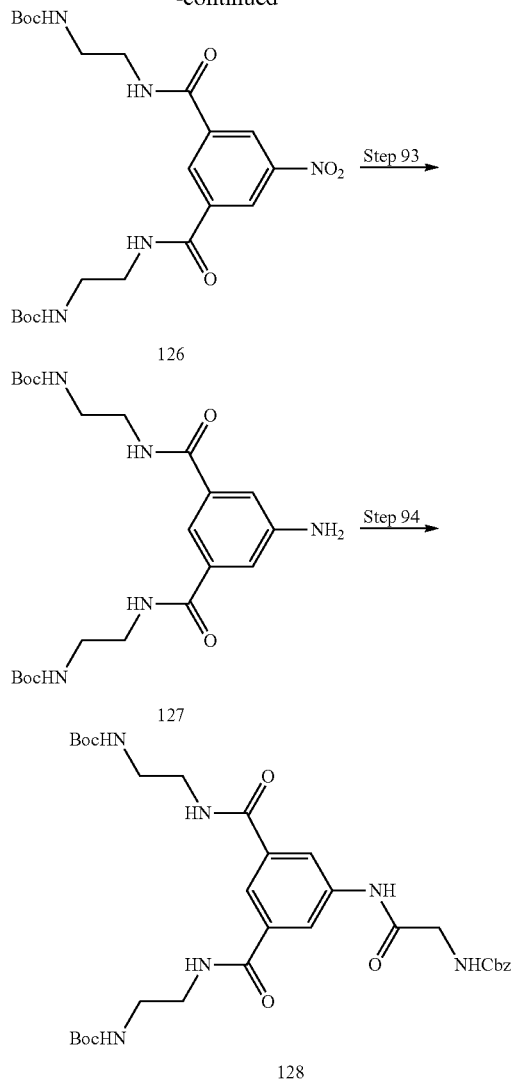

126

127

128

Step 92

4-Nitroisophthalic acid 103 (500 mg, 2.37 mmol) and N-Boc-ethylenediamine (808 mg, 5.21 mmol) were dissolved in N,N'-dimethylformamide (10 mL). To the solution, triethylamine (0.90 mL, 7.11 mmol), 1-hydroxybenzotriazole monohydrate (703 mg, 5.21 mmol) and 1-(3-dimethylaminopropyl)-3-ethylcarbodiimide hydrochloride (1.36 g, 7.11 mmol) were added at room temperature, and the mixture was stirred for 16 hours. The reaction solution was aftertreated, and the crude product was purified by silica gel column chromatography to obtain compound 126 (650 mg, yield: 55%).

Step 93

Compound 126 (500 mg, 1.01 mmol) synthesized in step 92 and a zinc powder (330 mg, 5.05 mmol) were suspended in methanol (3.5 mL) and tetrahydrofuran (3.5 mL). To the suspension, an aqueous solution of ammonium chloride (378 mg, 7.07 mmol) was added dropwise at 0° C., and the mixture was stirred at room temperature for 24 hours. The reaction solution was aftertreated, and the crude product was purified by silica gel column chromatography to obtain compound 127 (160 mg, yield: 34%).

Step 94

Compound 127 (200 mg, 0.430 mmol) synthesized in step 93 and N-Cbz-glycine (90.0 mg, 0.430 mmol) were dissolved in N,N'-dimethylformamide (2.0 mL). To the solution, diisopropylethylamine (0.220 mL, 1.29 mmol) and O-(7-azabenzotriazol-1-yl)-N,N,N',N'-tetramethyluronium hexafluorophosphate (245 mg, 0.645 mmol) were added at room temperature, and the mixture was stirred for 16 hours. The reaction solution was aftertreated, and the crude product was purified by silica gel column chromatography to obtain compound 128 (180 mg, yield: 64%).

ESI-MS m/z: 657 (M+H)$^+$

Synthesis of Compound 130

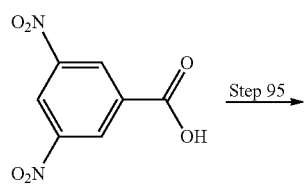

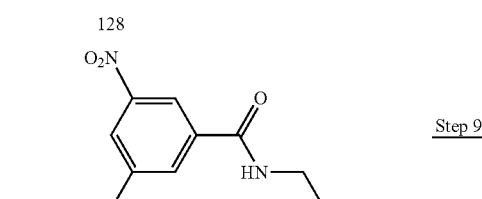

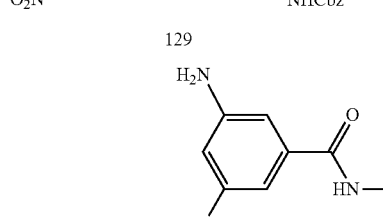

Step 95

3,5-Dinitrobenzoic acid 128 (500 mg, 2.36 mmol) and N-Cbz-ethylenediamine (588 mg, 2.83 mmol) were dissolved in N,N'-dimethylformamide (5.0 mL). To the solution, triethylamine (0.65 mL, 4.72 mmol), 1-hydroxybenzotriazole monohydrate (380 mg, 2.83 mmol) and 1-(3-dimethylaminopropyl)-3-ethylcarbodiimide hydrochloride (675 mg, 3.54 mmol) were added at room temperature, and the mixture was stirred for 16 hours. The reaction solution was aftertreated, and the crude product was purified by silica gel column chromatography to obtain compound 129 (445 mg, yield: 48%).

Step 96

Compound 129 (200 mg, 0.515 mmol) synthesized in step 95 was dissolved in ethanol (5.0 mL). To the solution, tin(II) chloride (584 mg, 3.09 mmol) and concentrated hydrochloric acid (0.2 mL) were added at room temperature, and the mixture was stirred at 80° C. for 16 hours. The reaction solution was aftertreated to obtain compound 130 (180 mg, yield: 106%).

ESI-MS m/z: 329 (M+H)$^+$

Synthesis of Compound 133

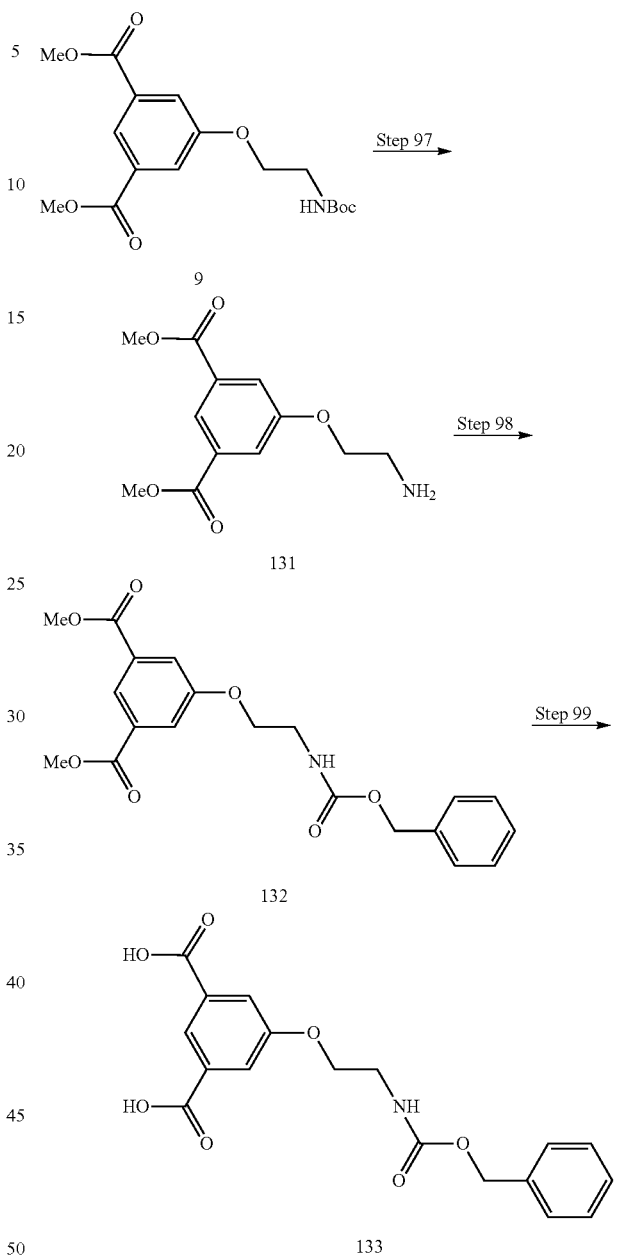

Step 97

Compound 131 (3.7 g, yield: 63%) was obtained in the same way as in step 9 of Example 1 using compound 9 (8.17 g, 23.12 mmol) synthesized in step 6 of Example 1.

ESI-MS m/z: 254 (M+H)$^+$

Step 98

Compound 132 (3.82 g, yield: 67%) was obtained in the same way as in step 10 of Example 1 using compound 131 (3.7 g, 14.63 mmol) obtained in step 97.

ESI-MS m/z: 432 (M+HCOO)$^-$

Step 99

Compound 133 (3.08 g, yield: 87%) was obtained in the same way as in step 7 of Example 1 using compound 132 (3.82 g, 9.86 mmol) obtained in step 98.

ESI-MS m/z: 360 (M+H)$^+$

Synthesis of Compound 135

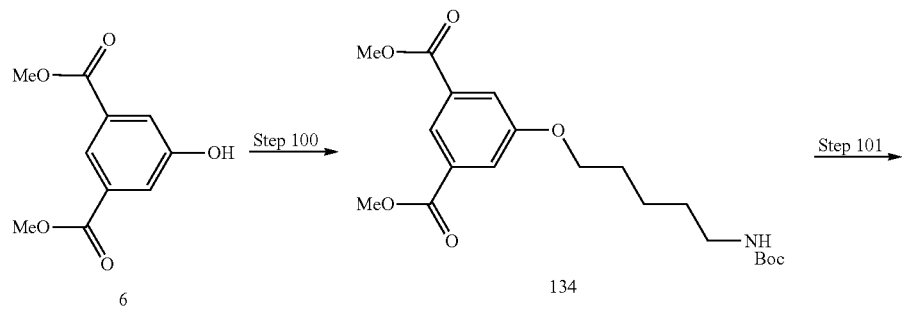

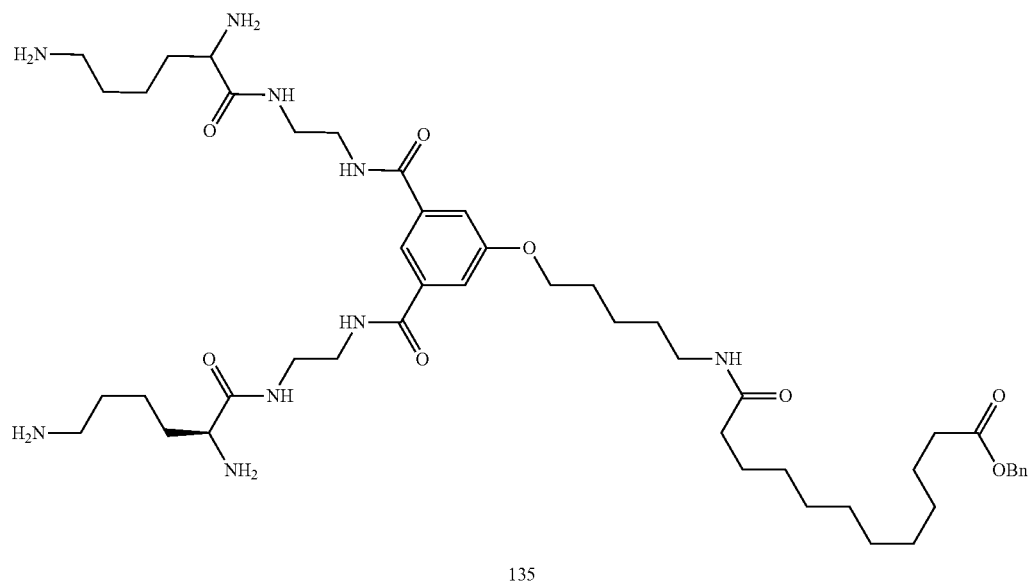

Step 100

Compound 134 (2.40 g, yield: 63%) was obtained in the same way as in step 6 of Example 1 using compound 8 (2 g, 9.53 mmol) and tert-butoxycarbonylamino)-1-pentanol (manufactured by Tokyo Chemical Industry Co., Ltd., 2 g, 10 mmol).

ESI-MS m/z: 296 (M+H)$^+$, detected as a Boc-deprotected form

Step 101

Compound 135 (1.579 g, yield: 21%) was obtained in the same way as in steps 7 to 9 and 14 to 17 of Example 1 using compound 134 synthesized in step 100.

ESI-MS m/z: 910 (M+H)$^+$

Example 14 Synthesis of Sugar Ligand-Tether Unit

Synthesis of Compound 137

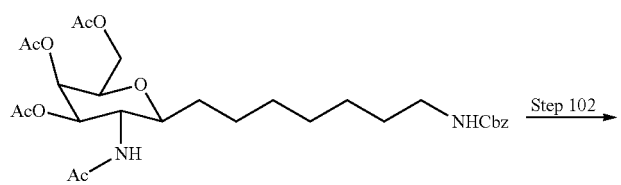

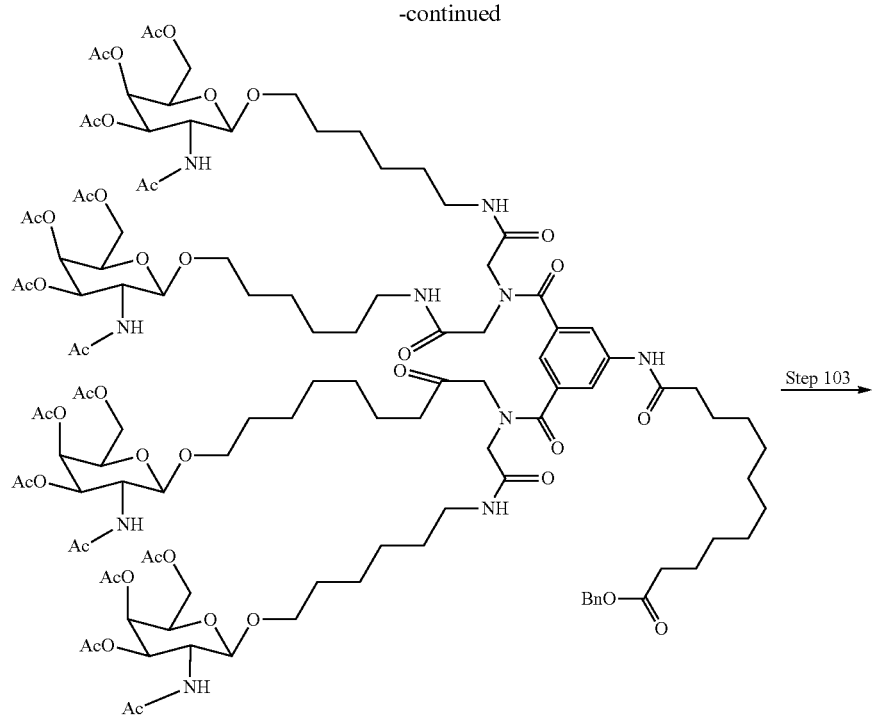

136

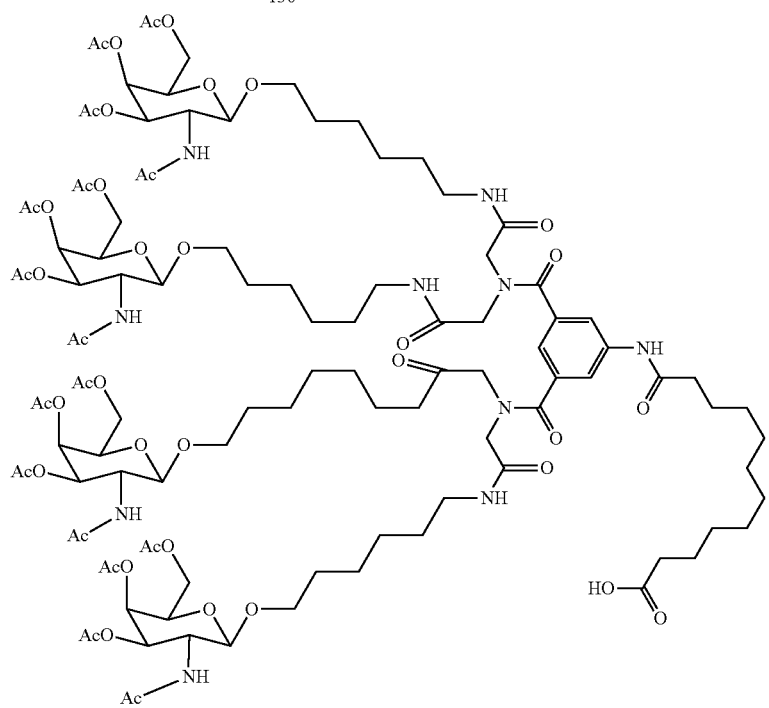

137

Step 102

Compound 56 (1.015 g, 1.748 mol) synthesized in step 51 was dissolved in N,N'-dimethylformamide (12 mL). To the solution, a 10% palladium-carbon powder (water-containing product, 54.29%; 187 mg) was added at room temperature, and the mixture was stirred for 6 hours in a hydrogen atmosphere. The reaction solution was filtered. Compound 107 (250.0 mg, 0.350 mmol) synthesized in step 76, 1-hydroxybenzotriazole monohydrate (26.80 mg, 0.1750 mmol), and 1-(3-dimethylaminopropyl)-3-ethylcarbodiimide hydrochloride (402.0 mg, 2.099 mmol) were added to the filtrate, and the mixture was stirred overnight at room temperature. Water was added to the reaction solution, followed by extraction with ethyl acetate. Then, the organic layer was washed with a saturated aqueous solution of sodium bicarbonate and saturated saline and dried over anhydrous sodium sulfate. The solvent was distilled off under reduced pressure, and the residue was purified by silica gel column chromatography (chloroform/methanol=87/13) to obtain compound 136 (617.0 mg, yield: 88%).

ESI-MS m/z: 1215 (M+2H)$^2$

Step 103

Compound 136 (0.7380 g, 0.3040 mmol) synthesized in step 102 was dissolved in tetrahydrofuran (7 mL). To the solution, a 10% palladium-carbon powder (water-containing product, 54.29%; 135.90 mg) was added at room temperature, and the mixture was stirred overnight in a hydrogen atmosphere. The reaction solution was filtered, and the solvent was distilled off under reduced pressure. The residue was purified by silica gel column chromatography (chloroform/methanol=87/13) to obtain compound 137 (581 mg, yield: 82%).

ESI-MS m/z: 1170 (M+2H)$^{2+}$ $^1$H-NMR (400 MHz, DMSO-d6, δ): 1.12-2.36 (106H, m), 2.91-3.19 (8H, m), 3.23-3.55 (14H, m), 3.60-3.76 (4H, m), 3.78-3.94 (8H, m), 3.95-4.10 (16H, m), 4.47 (4H, d, J=8.8 Hz), 4.92-5.01 (4H, m), 5.17-5.24 (4H, m), 6.98 (1H, s), 7.64 (2H, s), 7.81-7.95 (4H, m), 8.28-8.38 (2H, m), 8.44-8.56 (2H, m), 10.13 (1H, s)

Synthesis of Compound 139

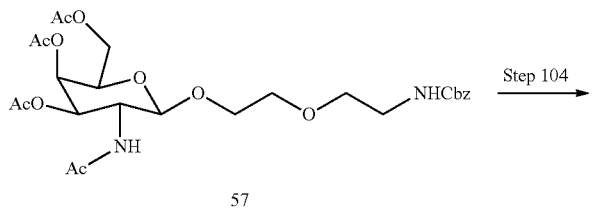

57

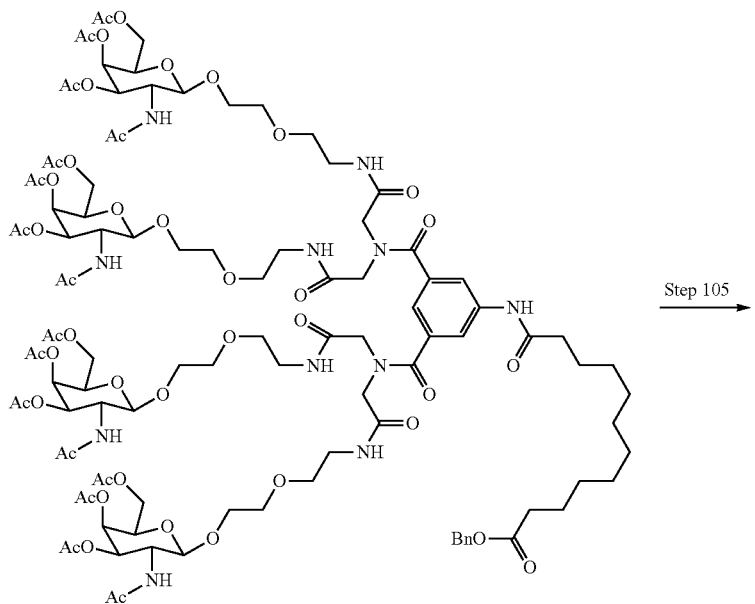

138

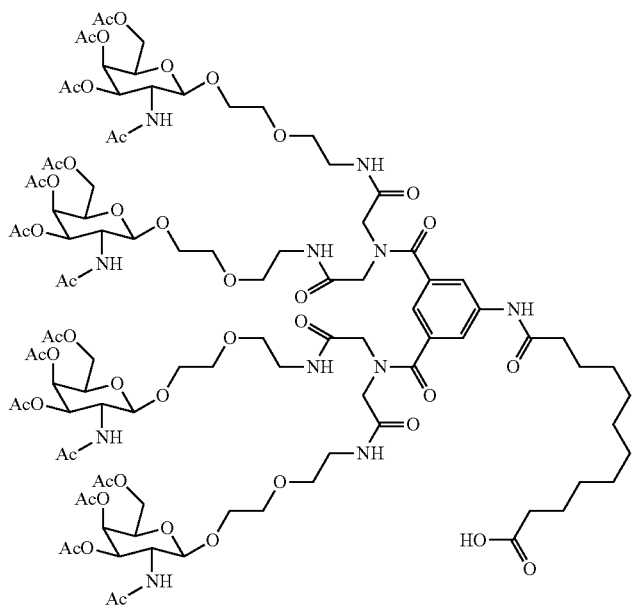

139

Step 104

Compound 57 (500 mg, 0.879 mmol) synthesized in step 52 was dissolved in N,N'-dimethylformamide (6.5 mL). To the solution, a 10% palladium-carbon powder (water-containing product, 54.29%; 94 mg) was added at room temperature, and the mixture was stirred for 4 hours in a hydrogen atmosphere. The reaction solution was filtered. Compound 107 (126.0 mg, 0.176 mmol) synthesized in step 76, 1-hydroxybenzotriazole monohydrate (13.47 mg, 0.088 mmol), and 1-(3-dimethylaminopropyl)-3-ethylcarbodiimide hydrochloride (202.0 mg, 1.055 mmol) were added to the filtrate, and the mixture was stirred overnight at room temperature. The solvent in the reaction solution was distilled off under reduced pressure, and the residue was purified by reverse-phase column chromatography (water/acetonitrile) to obtain compound 138 (249.7 mg, yield: 60%).

ESI-MS m/z: 1191 $(M+2H)^{2+}$

Step 105

Compound 138 (0.242 g, 0.102 mmol) synthesized in step 104 was dissolved in tetrahydrofuran (3.6 mL) and water (1.2 mL). To the solution, a 10% palladium-carbon powder (water-containing product, 54.29%; 45 mg) was added at room temperature, and the mixture was stirred for 4 hours in a hydrogen atmosphere. The reaction solution was filtered, and the solvent was distilled off under reduced pressure to obtain compound 139 (216 mg, yield: 93%).

ESI-MS m/z: 1146 $(M+2H)^{2+}$

1H-NMR (400 MHz, DMSO-d6, δ): 1.15-1.65 (20H, m), 1.68-2.15 (52H, m), 3.13-3.29 (6H, m), 3.40-3.67 (16H, m), 3.71-3.96 (11H, m), 3.98-4.14 (16H, m), 4.55 (4H, t, J=8.8 Hz), 4.93-5.06 (4H, m), 5.12-5.28 (4H, m), 6.56 (1H, s), 6.98 (1H, s), 7.64 (2H, s), 7.77-7.93 (4H, m), 8.26-8.49 (3H, m), 10.10 (1H, s)

Synthesis of Compound 141

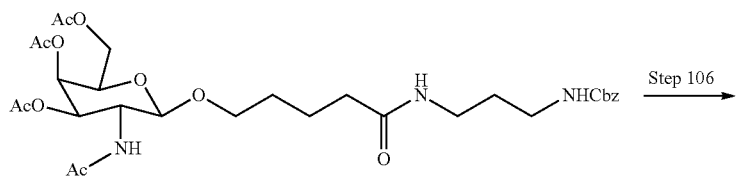

58

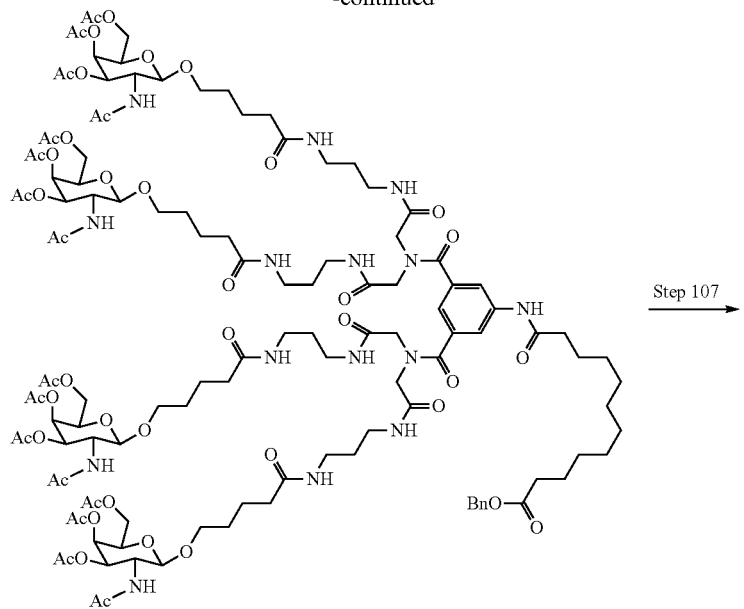

140

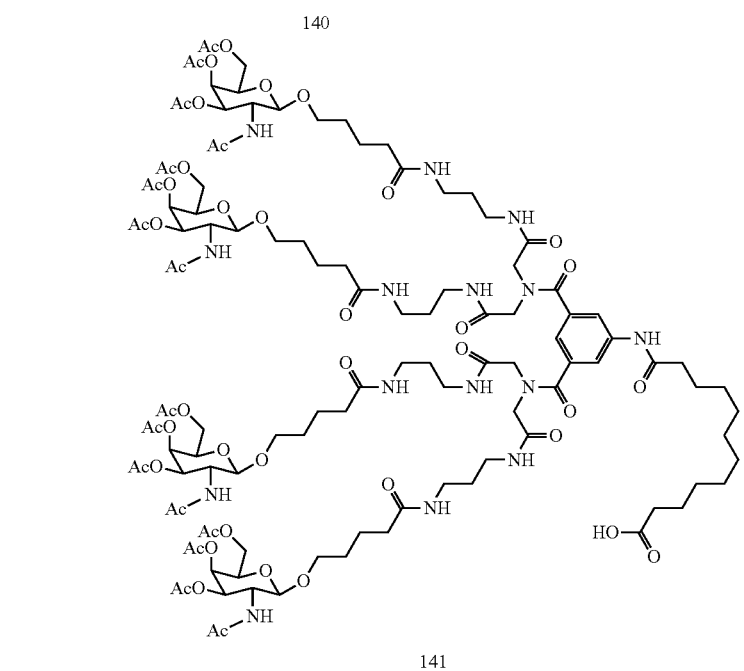

141

Step 106

Compound 58 (430 mg, 0.674 mmol) synthesized in step 53 was dissolved in N,N'-dimethylformamide (6 mL). To the solution, a 10% palladium-carbon powder (water-containing product, 54.29%; 79 mg) was added at room temperature, and the mixture was stirred for 4 hours in a hydrogen atmosphere. The reaction solution was filtered. Compound 107 (105.0 mg, 0.148 mmol), 1-hydroxybenzotriazole monohydrate (11.31 mg, 0.074 mmol), and 1-(3-dimethyl-aminopropyl)-3-ethylcarbodiimide hydrochloride (170.0.0 mg, 0.887 mmol) were added to the filtrate, and the mixture was stirred overnight at room temperature. The solvent in the reaction solution was distilled off under reduced pressure, and the residue was purified by reverse-phase column chromatography (water/acetonitrile) to obtain compound 140 (218.1 mg, yield: 56%).

ESI-MS m/z: 1329 (M+2H)$^{2+}$

Step 107

Compound 140 (0.210 g, 0.079 mmol) synthesized in step 106 was dissolved in tetrahydrofuran (3.1 mL) and water (1.0 mL). To the solution, a 10% palladium-carbon powder (water-containing product, 54.29%; 39 mg) was added at room temperature, and the mixture was stirred for 4 hours in a hydrogen atmosphere. The reaction solution was filtered, and the solvent was distilled off under reduced pressure to obtain compound 141 (192.7 mg, yield: 95%).

ESI-MS m/z: 1284 (M+2H)$^{2+}$

1H-NMR (400 MHz, DMSO-d6, δ): 1.17-1.65 (42H, m), 1.69-2.13 (61H, m), 2.95-3.17 (16H, m), 3.65-3.77 (3H, m), 3.79-3.94 (6H, m), 3.96-4.10 (16H, m), 4.48 (4H, d, J=8.4

Hz), 4.96 (4H, dd, J=2.4, 11.2 Hz), 5.21 (4H, d, J=3.2 Hz), 7.01 (1H, s), 7.64-7.92 (11H, m), 8.26-8.48 (4H, m), 10.14 (1H, s)

Synthesis of Compound 143

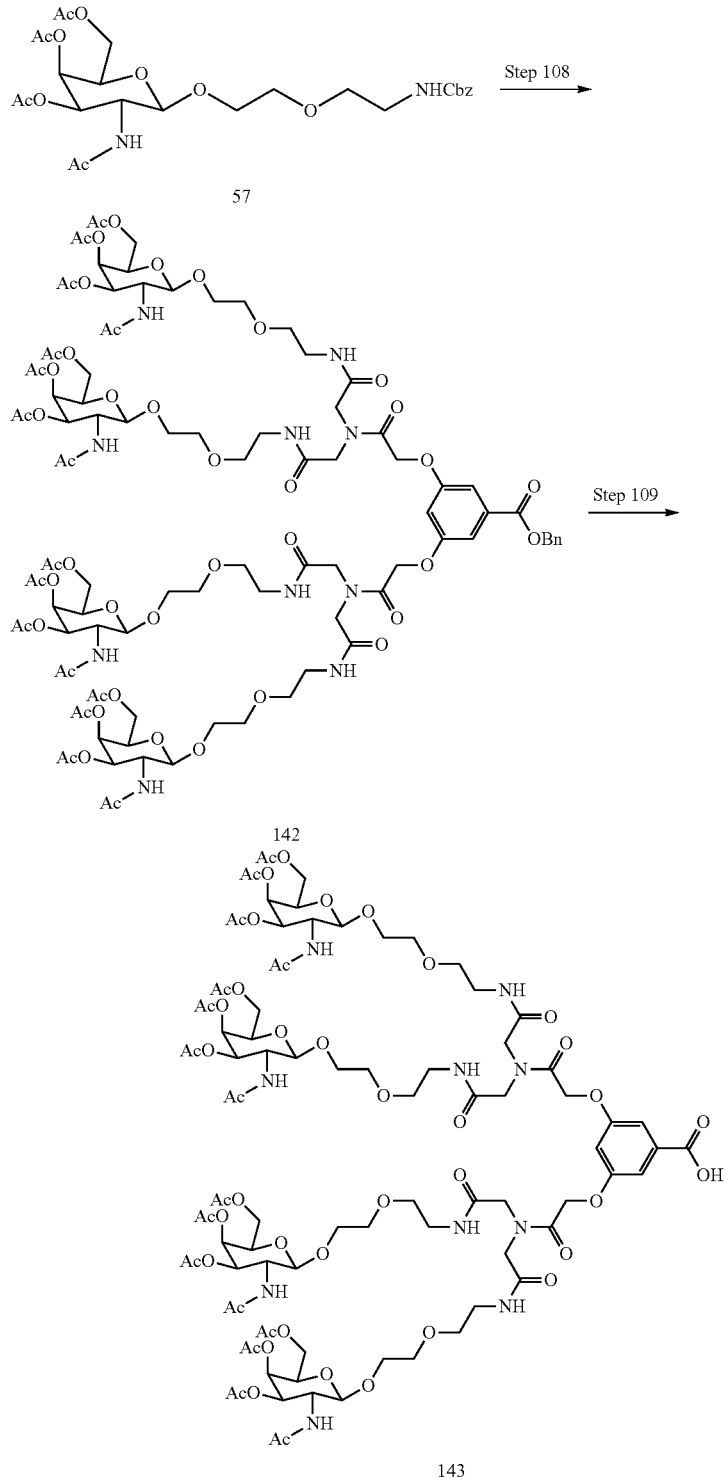

Step 108

Compound 57 (450 mg, 0.791 mmol) synthesized in step 52 was dissolved in N,N'-dimethylformamide (6 mL). To the solution, a 10% palladium-carbon powder (water-containing product, 54.29%; 85 mg) was added at room temperature, and the mixture was stirred for 5 hours in a hydrogen atmosphere. The reaction solution was filtered. Compound 113 (94 mg, 0.158 mmol) synthesized in step 81, 1-hydroxybenzotriazole monohydrate (133.0 mg, 0.871 mmol), and 1-(3-dimethylaminopropyl)-3-ethylcarbodiimide hydrochloride (182.0 mg, 0.950 mmol) were added to the filtrate, and the mixture was stirred overnight at room temperature. The solvent in the reaction solution was distilled off under reduced pressure, and the residue was purified by reverse-phase column chromatography (water/acetonitrile) to obtain compound 142 (99 mg, yield: 28%).

ESI-MS m/z: 1129 (M+2H)$^{2+}$

Step 109

Compound 142 (80 mg, 0.035 mmol) synthesized in step 108 was dissolved in tetrahydrofuran (1.7 mL) and water (0.85 mL). To the solution, a 10% palladium-carbon powder (water-containing product, 54.29%; 26 mg) was added at room temperature, and the mixture was stirred for 2 hours in a hydrogen atmosphere. The reaction solution was filtered, and the solvent was distilled off under reduced pressure to obtain compound 143 (57.5 mg, yield: 75%).

ESI-MS m/z: 1084 (M+2H) 2+

$^1$H-NMR (400 MHz, DMSO-d6, δ): 1.69-2.21 (46H, m), 3.14-3.65 (28H, m), 3.67-4.22 (27H, m), 4.43-4.66 (4H, m), 4.69-4.88 (4H, m), 4.89-5.08 (4H, m), 5.12-5.32 (4H, m), 6.54-6.68 (1H, br), 7.01 (2H, s), 7.78-8.09 (3H, m), 8.13-8.31 (2H, m), 8.58-8.75 (2H, m)

Synthesis of Compound 145

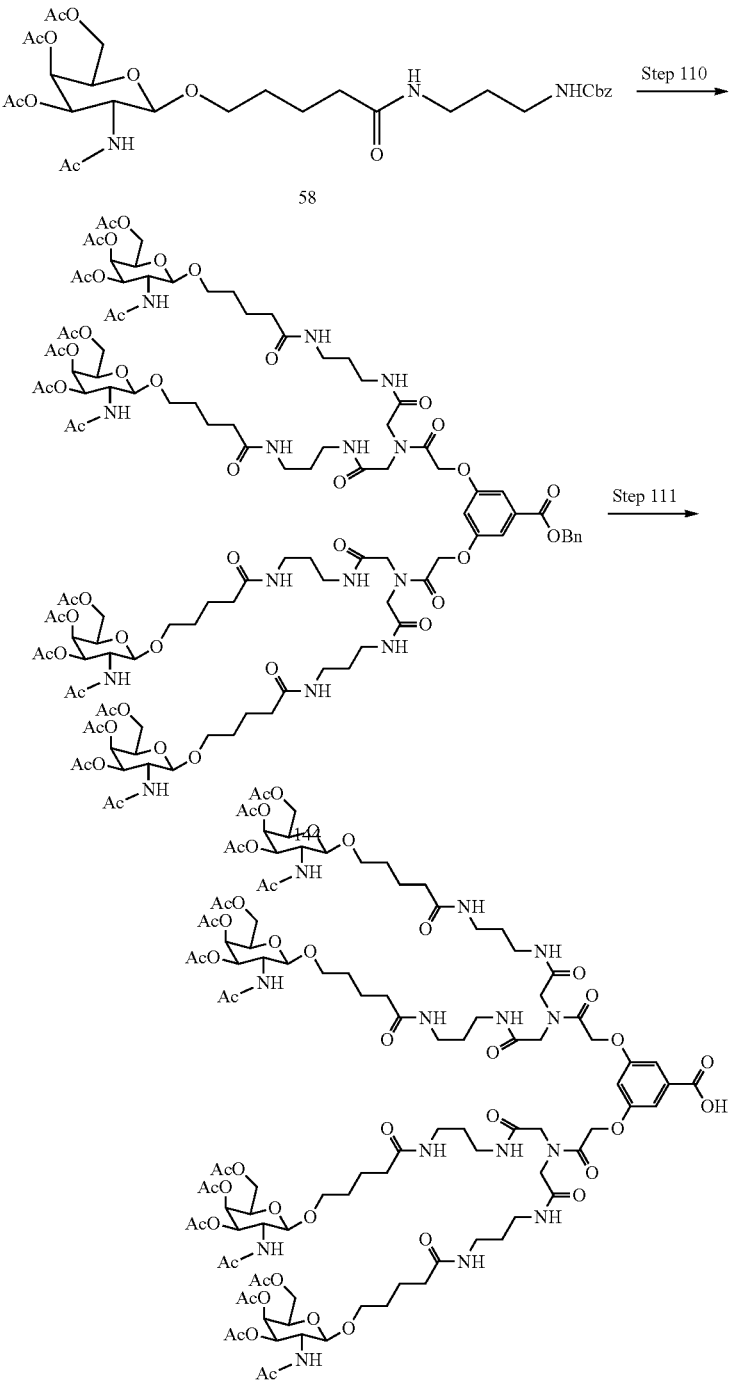

Step 110

Compound 58 (418 mg, 0.655 mmol) synthesized in step 53 was dissolved in N,N'-dimethylformamide (6 mL). To the solution, a 10% palladium-carbon powder (water-containing product, 54.29%; 77 mg) was added at room temperature, and the mixture was stirred for 5 hours in a hydrogen atmosphere. The reaction solution was filtered. Compound 113 (85 mg, 0.144 mmol) synthesized in step 81, 1-hydroxybenzotriazole monohydrate (121.0 mg, 0.791 mmol), and 1-(3-dimethylaminopropyl)-3-ethylcarbodiimide hydrochloride (165.0 mg, 0.863 mmol) were added to the filtrate, and the mixture was stirred overnight at room temperature. The solvent in the reaction solution was distilled off under reduced pressure, and the residue was purified by reverse-phase column chromatography (water/acetonitrile) to obtain compound 144 (99 mg, yield: 28%).

ESI-MS m/z: 1268 (M+2H)$^{2+}$

Step 111

Compound 144 (186 mg, 0.073 mmol) synthesized in step 110 was dissolved in tetrahydrofuran (2.8 mL) and water (0.93 mL). To the solution, a 10% palladium-carbon powder (water-containing product, 54.29%; 40 mg) was added at room temperature, and the mixture was stirred for 2 hours in a hydrogen atmosphere. The reaction solution was filtered, and the solvent was distilled off under reduced pressure to obtain compound 145 (156.7 mg, yield: 87%).

ESI-MS m/z: 1222 (M+2H)$^{2+}$

1H-NMR (400 MHz, DMSO-d6, δ): 1.36-1.62 (27H, m), 1.67-2.17 (64H, m), 2.92-3.21 (15H, m), 3.58-3.77 (2H, m), 3.80-3.95 (7H, m), 3.97-4.13 (15H, m), 4.47 (4H, d, J=8.8 Hz), 4.88-5.02 (7H, m), 5.10-5.24 (3H, m), 6.95-7.00 (1H, m), 7.26-7.31 (2H, m), 7.72-7.88 (8H, m), 8.10-8.20 (2H, m), 8.51-8.60 (2H, m)

Synthesis of Compound 147

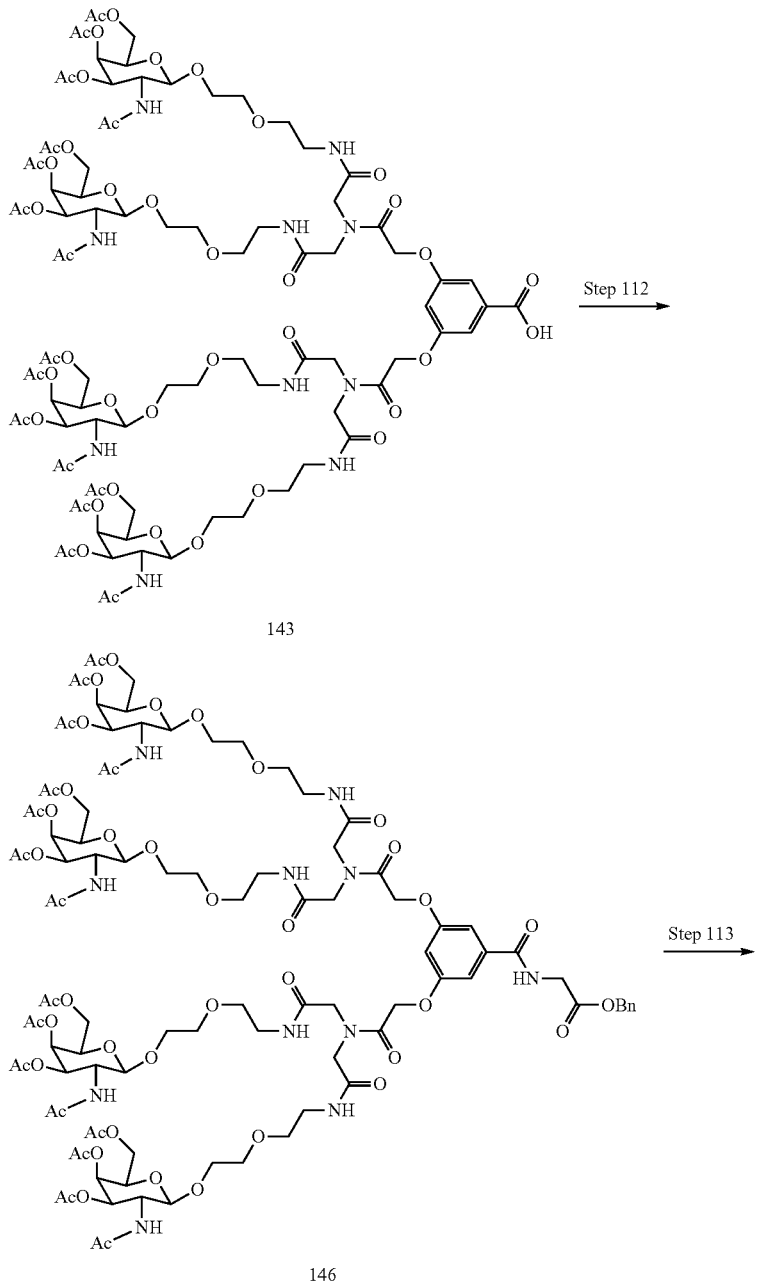

-continued

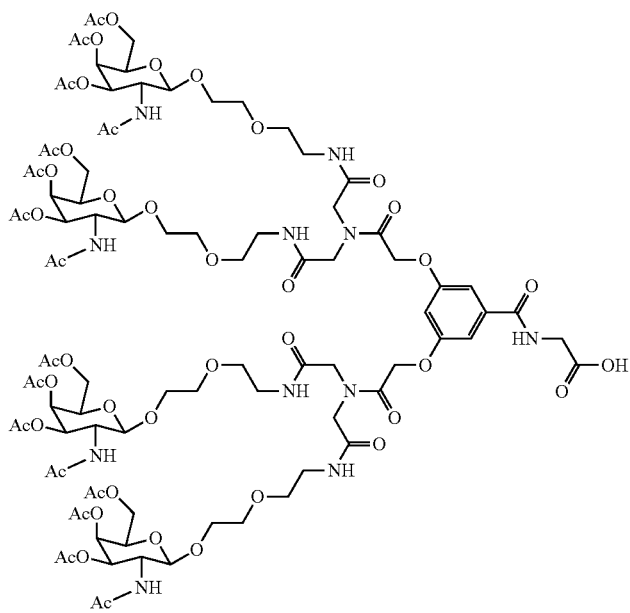

147

Step 112

Compound 143 (171 mg, 0.079 mmol) synthesized in step 109 was dissolved in N,N'-dimethylformamide (3.4 mL). To the solution, glycine benzyl p-toluenesulfonate (32.0 mg, 0.095 mmol), 1-hydroxybenzotriazole monohydrate (12.09 mg, 0.079 mmol), and 1-(3-dimethylaminopropyl)-3-ethylcarbodiimide hydrochloride (18.16 mg, 0.095 mmol) were added, and the mixture was stirred overnight at room temperature. The solvent in the reaction solution was distilled off under reduced pressure, and the residue was purified by reverse-phase column chromatography (water/acetonitrile) to obtain compound 146 (55.7 mg, yield: 31%).

ESI-MS m/z: 1158 $(M+2H)^{2+}$

Step 113

Compound 146 (54 mg, 0.023 mmol) synthesized in step 112 was dissolved in tetrahydrofuran (0.83 mL) and water (0.28 mL). To the solution, a 10% palladium-carbon powder (water-containing product, 54.29%; 18 mg) was added at room temperature, and the mixture was stirred for 2 hours in a hydrogen atmosphere. The reaction solution was filtered, and the solvent was distilled off under reduced pressure to obtain compound 147 (50.1 mg, yield: 97%).

ESI-MS m/z: 1112 $(M+2H)^{2+}$

1H-NMR (400 MHz, DMSO-d6, δ): 0.96-1.06 (3H, m), 1.71-2.20 (54H, m), 3.41-3.64 (15H, m), 3.68-4.20 (32H), 4.55 (4H, d, J=8.4 Hz), 4.81 (4H, s), 4.94-5.02 (4H, m), 5.17-5.25 (4H, m), 6.63-6.76 (2H, m), 6.93-7.02 (2H, m), 7.84-8.00 (3H, m), 8.17-8.30 (2H, m), 8.58-8.70 (2H, m)

Synthesis of Compound 149

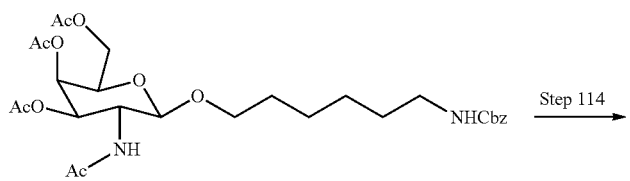

56

Step 114 →

-continued

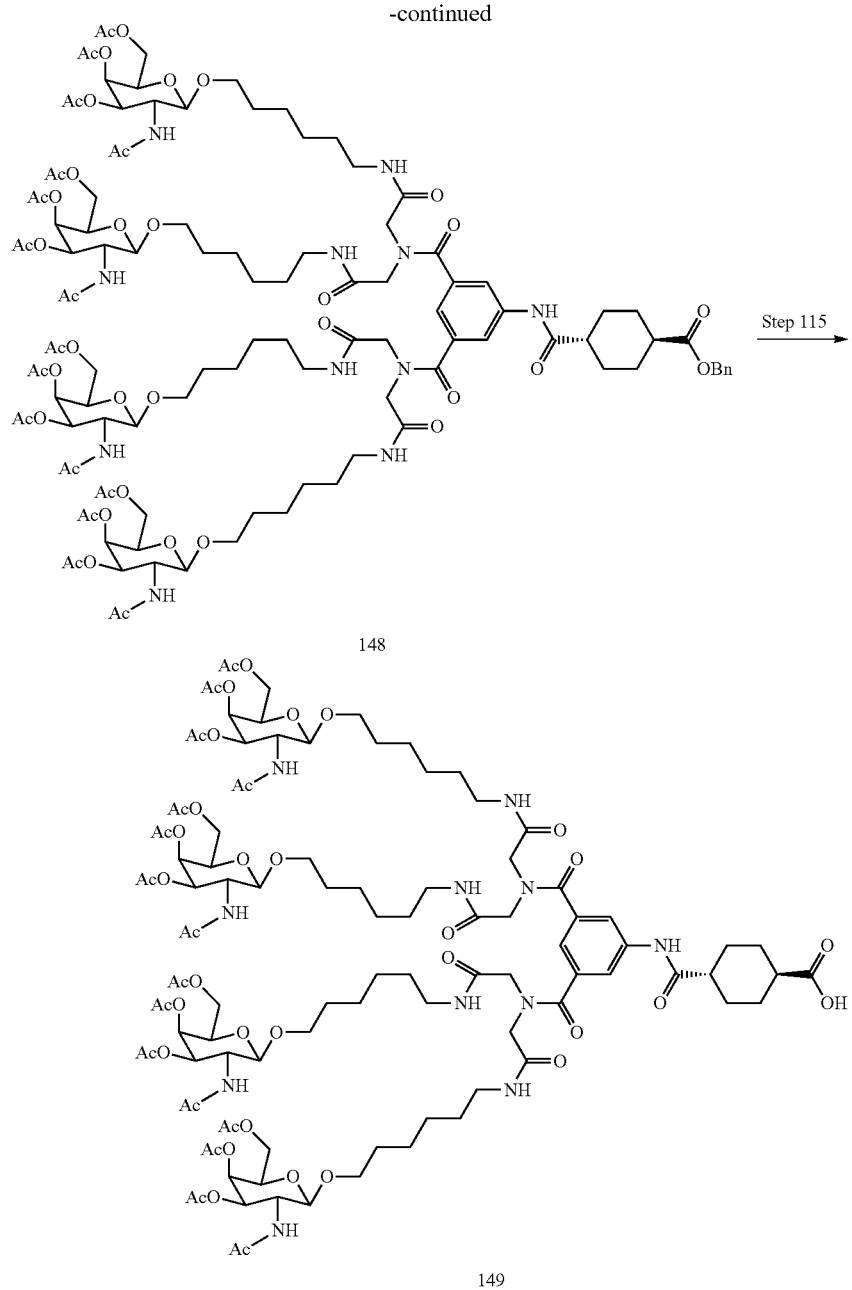

Step 114

Compound 56 (500 mg, 0.861 mmol) was dissolved in N,N'-dimethylformamide (10 mL). To the solution, a 10% palladium-carbon powder (water-containing product, 54.29%; 92.1 mg) was added at room temperature, and the mixture was stirred for 2 hours in a hydrogen atmosphere. Compound 116 (113 mg, 0.172 mmol), 1-(3-dimethylaminopropyl)-3-ethylcarbodiimide hydrochloride (198 mg, 1.03 mmol), and 1-hydroxybenzotriazole monohydrate (13.2 mg, 0.086 mmol) were added thereto at room temperature in an argon atmosphere, and the mixture was stirred overnight. The reaction solution was filtered through celite, and the solvent was distilled off under reduced pressure. The residue was purified by silica gel column chromatography (chloroform/methanol=90/10) and further purified by reverse-phase preparative HPLC (acetonitrile/water) to obtain compound 148 (195 mg, yield: 48%).

ESI-MS m/z: 1186 (M+2H)$^{2+}$

Step 115

Compound 148 (194 mg, 0.082 mmol) synthesized in step 114 was dissolved in tetrahydrofuran (2.9 mg) and water (1.0 mL). To the solution, a 10% palladium-carbon powder (water-containing product, 54.29%; 35.7 mg) was added at room temperature, and the mixture was stirred for 8 hours in a hydrogen atmosphere. The reaction solution was filtered, and the solvent was distilled off under reduced pressure to obtain compound 149 (183 mg, yield: 98%).

ESI-MS m/z: 1141 (M+2H) 2+

$^1$H-NMR (400 MHz, DMSO-d6, δ): 1.21-1.45 (m, 40H), 1.76-2.18 (m, 50H), 3.00-3.09 (m, 8H), 3.40-4.20 (m, 32H), 4.47 (d, J=8.5 Hz, 4H), 4.96 (dd, J=3.1, 11.2 Hz, 4H), 5.21 (d, J=3.1 Hz, 4H), 6.98 (s, 1H), 7.65 (s, 2H), 7.84 (d, J=9.0 Hz, 4H), 8.31 (brs, 1H), 8.44 (brs, 1H), 10.11 (s, 1H).

Synthesis of Compound 151

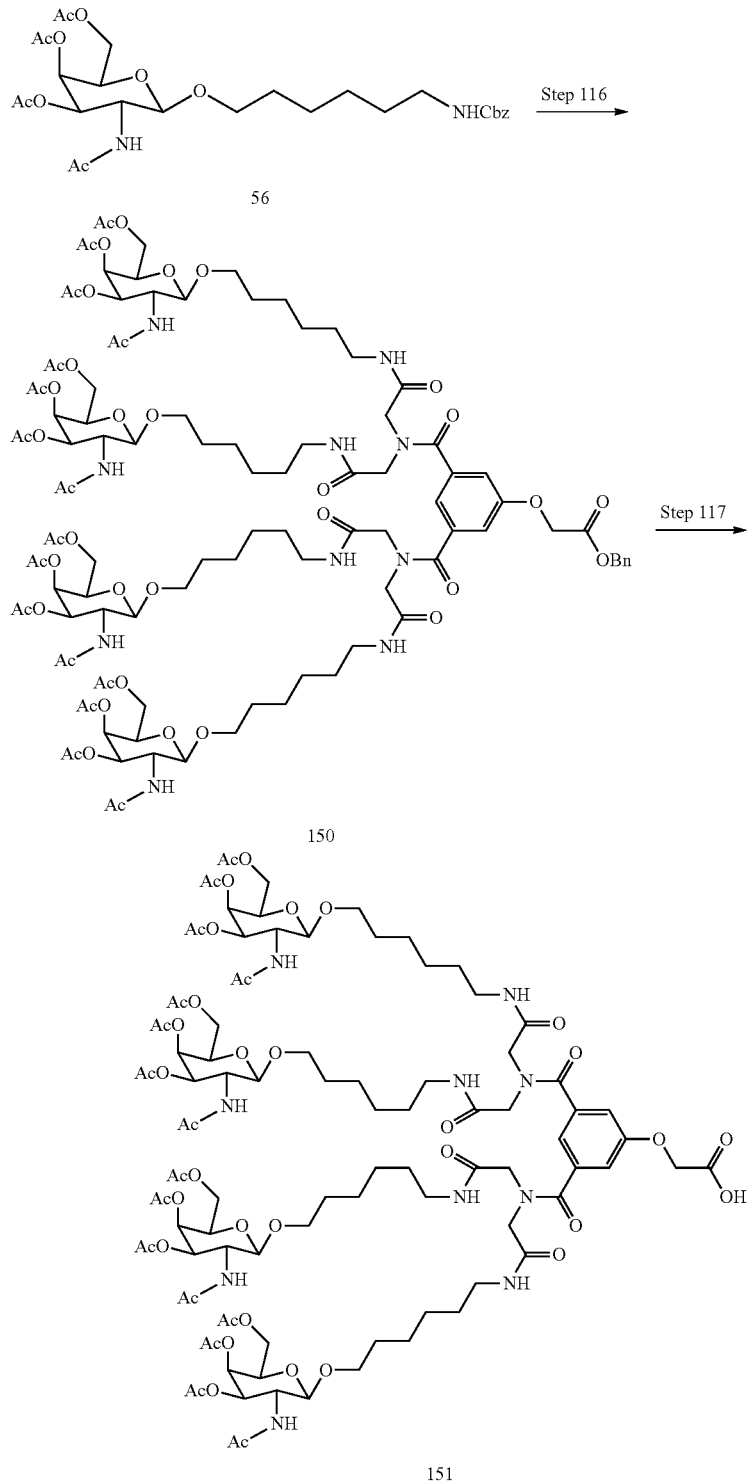

Step 116

Compound 56 (500 mg, 0.861 mmol) was dissolved in N,N'-dimethylformamide (10 mL). To the solution, a 10% palladium-carbon powder (water-containing product, 54.29%; 92.1 mg) was added at room temperature, and the mixture was stirred for 2 hours in a hydrogen atmosphere. Compound 120 (97.0 mg, 0.172 mmol), 1-(3-dimethylaminopropyl)-3-ethylcarbodiimide hydrochloride (198 mg, 1.03 mmol), and 1-hydroxybenzotriazole monohydrate (13.2 mg, 0.086 mmol) were added thereto at room temperature in an argon atmosphere, and the mixture was stirred overnight. The reaction solution was filtered through celite, and the solvent was distilled off under reduced pressure. The residue was purified by silica gel column chromatography (chloroform/methanol=85/15) and further purified by reverse-phase preparative HPLC (acetonitrile/water) to obtain compound 150 (179 mg, yield: 46%).

ESI-MS m/z: 1138 (M+2H)$^{2+}$

Step 117

Compound 150 (175 mg, 0.077 mmol) synthesized in step 116 was dissolved in tetrahydrofuran (2.6 mg) and water (0.9 mL). To the solution, a 10% palladium-carbon powder (water-containing product, 54.29%; 32.4 mg) was added at room temperature, and the mixture was stirred for 1 hour in a hydrogen atmosphere. The reaction solution was filtered, and the solvent was distilled off under reduced pressure to obtain compound 151 (160 mg, yield: 95%).

ESI-MS m/z: 1093 (M+2H)$^{2+}$

1H-NMR (400 MHz, DMSO-d6, δ): 1.23-1.45 (m, 32H), 1.77 (s, 12H), 1.89 (s, 12H), 1.99 (s, 12H), 2.10 (s, 12H), 3.01-3.11 (m, 8H), 3.69-4.02 (m, 34H), 4.47-4.50 (m, 4H), 4.94-4.98 (m, 4H), 5.21 (d, J=3.1 Hz, 4H), 6.92 (s, 1H), 6.94 (s, 2H), 7.87 (d, J=9.4 Hz, 2H), 7.92 (d, J=8.5 Hz, 2H), 8.33 (brs, 2H), 8.50 (brs, 2H).

Synthesis of Compound 153

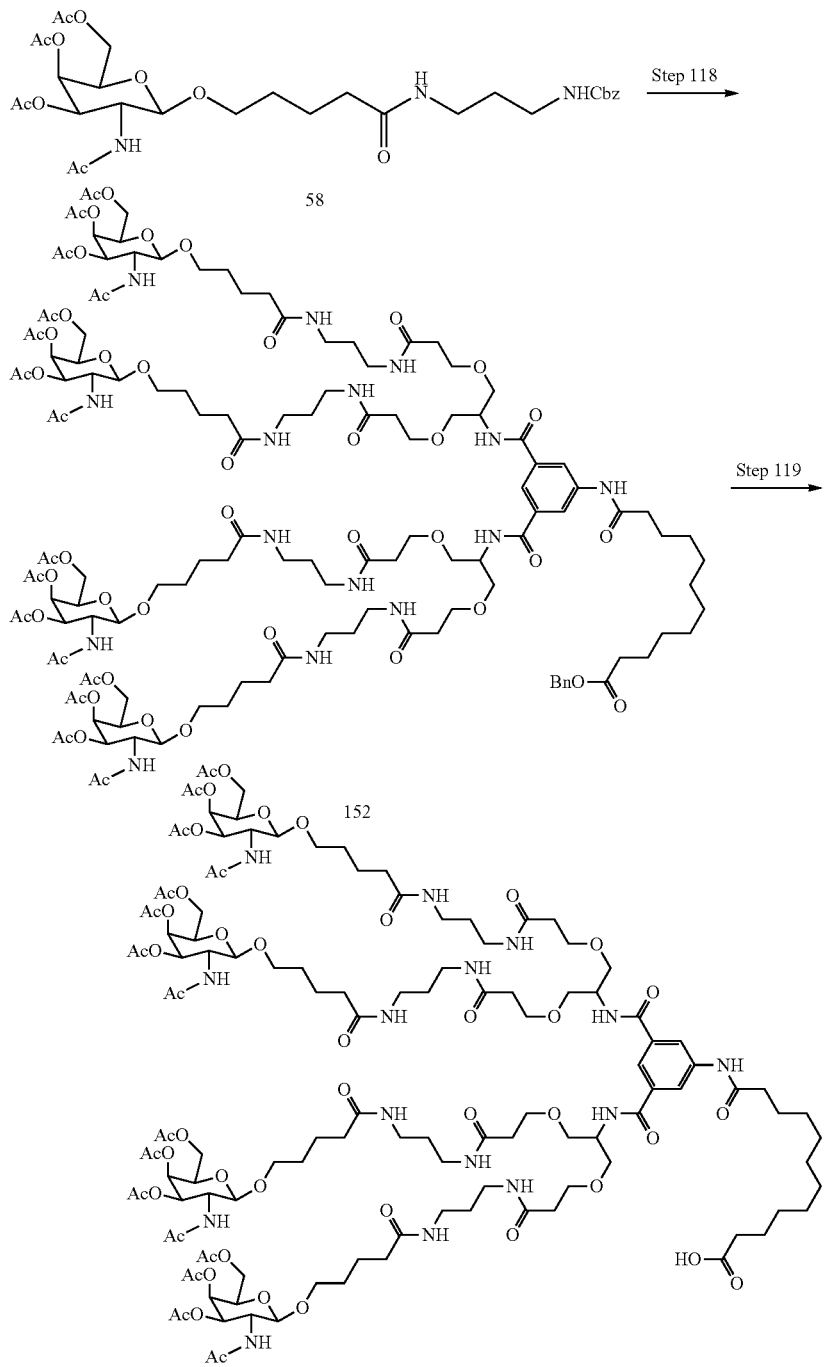

Step 118

Compound 58 (500 mg, 0.784 mmol) was dissolved in N,N'-dimethylformamide (10 mL). To the solution, a 10% palladium-carbon powder (water-containing product, 54.29%; 92.1 mg) was added at room temperature, and the mixture was stirred for 2 hours in a hydrogen atmosphere. Compound 125 (144 mg, 0.157 mmol), 1-(3-dimethylaminopropyl)-3-ethylcarbodiimide hydrochloride (180 mg, 0.941 mmol), and 1-hydroxybenzotriazole monohydrate (12.0 mg, 0.078 mmol) were added thereto at room temperature in an argon atmosphere, and the mixture was stirred overnight. The reaction solution was filtered through celite, and the solvent was distilled off under reduced pressure. The residue was purified by silica gel column chromatography (chloroform/methanol=80/20) and further purified by reverse-phase preparative HPLC (acetonitrile/water) to obtain compound 152 (191 mg, yield: 43%).

ESI-MS m/z: 1431 $(M+2H)^{2+}$

Step 119

Compound 152 (186 mg, 0.065 mmol) synthesized in step 118 was dissolved in tetrahydrofuran (2.8 mg) and water (0.9 mL). To the solution, a 10% palladium-carbon powder (water-containing product, 54.29%; 34.3 mg) was added at room temperature, and the mixture was stirred for 1 hour in a hydrogen atmosphere. The reaction solution was filtered, and the solvent was distilled off under reduced pressure to obtain compound 153 (174 mg, yield: 97%).

ESI-MS m/z: 1386 (M+2H) 2+

$^1$H-NMR (400 MHz, DMSO-d6, δ): 1.25-4.02 (m, 164H), 4.18-4.26 (m, 2H), 4.47 (d, J=8.1 Hz, 4H), 4.96 (dd, J=3.1, 11.2 Hz, 4H), 5.21 (d, J=3.6 Hz, 4H), 7.74-7.91 (m, 13H), 8.18 (s, 2H), 8.36 (d, J=7.2 Hz, 2H), 10.27 (brs, 1H).

Synthesis of Compound 155

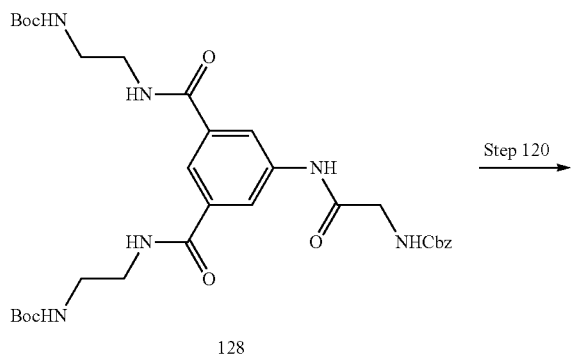

128

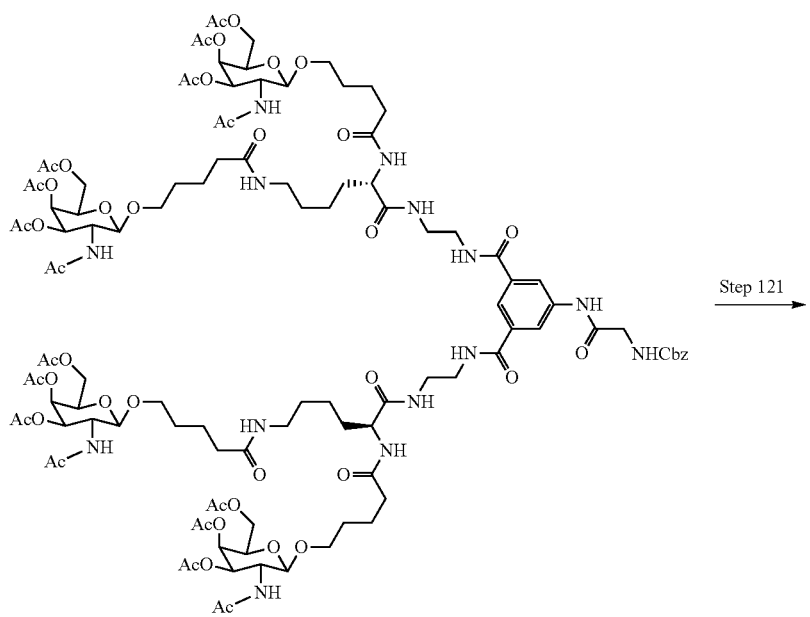

154

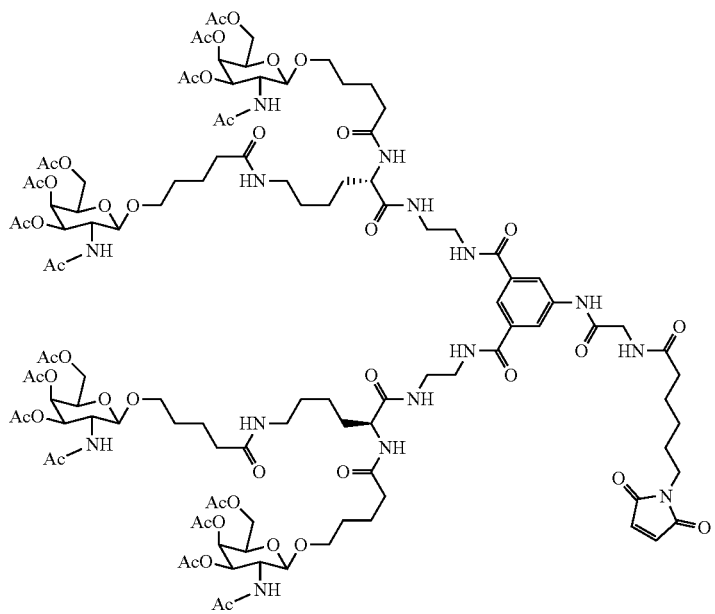

155

Step 120

Compound 128 (150 mg, 0.228 mmol) was dissolved in dichloromethane (1.5 mL). To the solution, trifluoroacetic acid (1.5 mL) was added at room temperature, and the mixture was stirred for 4 hours. The reaction solution was concentrated under reduced pressure and subjected to azeotropy with ethyl acetate. The residue was dissolved in N,N'-dimethylformamide (3 mL). To the solution, compound 7 (574 mg, 0.571 mmol), 1-(3-dimethylaminopropyl)-3-ethylcarbodiimide hydrochloride (109 mg, 0.571 mmol), triethylamine (0.159 mL, 1.14 mmol), and 1-hydroxybenzotriazole monohydrate (3.50 mg, 0.023 mmol) were added at room temperature, and the mixture was stirred overnight. The reaction solution was concentrated under reduced pressure, and the residue was purified by silica gel column chromatography (chloroform/methanol=90/10) and further purified by reverse-phase preparative HPLC (acetonitrile/water) to obtain compound 154 (242 mg, yield: 44%).

ESI-MS m/z: 1216 (M+2H)$^{2+}$

Step 121 Compound 154 (242 mg, 0.100 mmol) was dissolved in tetrahydrofuran/water (4/1; 12 mL). To the solution, a 10% palladium-carbon powder (water-containing product, 54.29%; 44.6 mg) was added at room temperature, and the mixture was stirred for 2 hours in a hydrogen atmosphere. 6-Maleimidohexanoic acid (23.2 mg, 0.110 mmol) and 4-(4,6-dimethoxy-1,3,5-triazin-2-yl)-4-methylmorpholinium chloride (55.2 mg, 0.199 mmol) was added thereto at room temperature in an argon atmosphere, and the mixture was stirred overnight. The reaction solution was filtered through celite, and the solvent was distilled off under reduced pressure. The residue was purified using HP20 resin (acetone/water) to obtain compound 155 (97.4 mg, yield: 39%).

ESI-MS m/z: 1245 (M+2H)$^{2+}$ $^1$H-NMR (400 MHz, DMSO-d6, δ): 1.14-2.16 (100H, m), 2.96-2.98 (4H, m), 3.24-3.41 (18H, m), 3.69-3.73 (4H, m), 3.83-3.91 (6H, m), 4.14-4.16 (2H, m), 4.47 (4H, d, J=8.6 Hz), 4.96 (4H, dd, J=3.6, 11.3 Hz), 5.21 (4H, d, J=3.2 Hz), 7.01 (2H, s), 7.73-7.75 (2H, m), 7.83-7.94 (7H, m), 8.05-8.08 (2H, m), 8.14-8.20 (3H, m), 8.55-8.56 (2H, m), 10.24 (1H, brs).

Synthesis of Compound 157

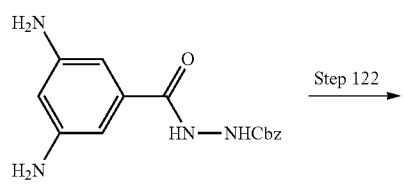

130

-continued

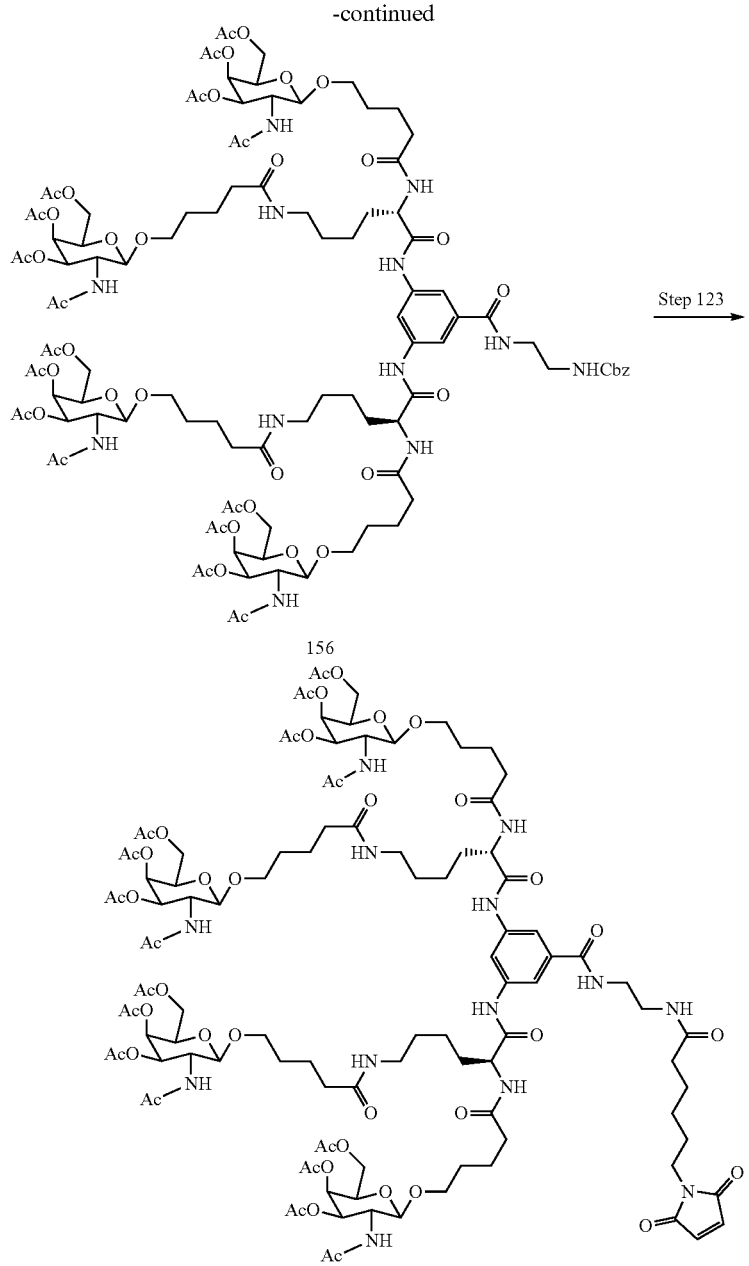

Step 122

Compound 130 (75.0 mg, 0.228 mmol) synthesized in step 96 was dissolved in N,N'-dimethylformamide (3.0 mL). To the solution, compound 60 (574 mg, 0.571 mmol) synthesized in step 55, diisopropylethylamine (0.199 mL, 1.14 mmol), and O-(7-azabenzotriazol-1-yl)-N,N,N',N'-tetramethyluronium hexafluorophosphate (217 mg, 0.571 mmol) were added at room temperature, and the mixture was stirred overnight. The solvent was distilled off under reduced pressure, and the residue was purified by silica gel column chromatography (chloroform/methanol=90/10) and further purified by reverse-phase preparative HPLC (acetonitrile/water) to obtain compound 156 (202 mg, yield: 38%).

ESI-MS m/z: 1152 $(M+2H)^2$

Step 123

Compound 156 (196 mg, 0.085 mmol) synthesized in step 122 was dissolved in tetrahydrofuran/water (4/1; 10 mL). To the solution, a 10% palladium-carbon powder (water-containing product, 54.29%; 36.1 mg) was added at room temperature, and the mixture was stirred for 2 hours in a hydrogen atmosphere. 6-Maleimidohexanoic acid (19.8 mg, 0.094 mmol) and 4-(4,6-dimethoxy-1,3,5-triazin-2-yl)-4-methylmorpholinium chloride (47.0 mg, 0.170 mmol) were added thereto at room temperature in an argon atmosphere, and the mixture was stirred overnight. The reaction solution was filtered through celite, and the solvent was distilled off under reduced pressure. The residue was purified using HP20 resin (acetone/water) to obtain compound 157 (42.4 mg, yield: 21%).

ESI-MS m/z: 1182 $(M+2H)^{2+}$

Synthesis of Compound 158
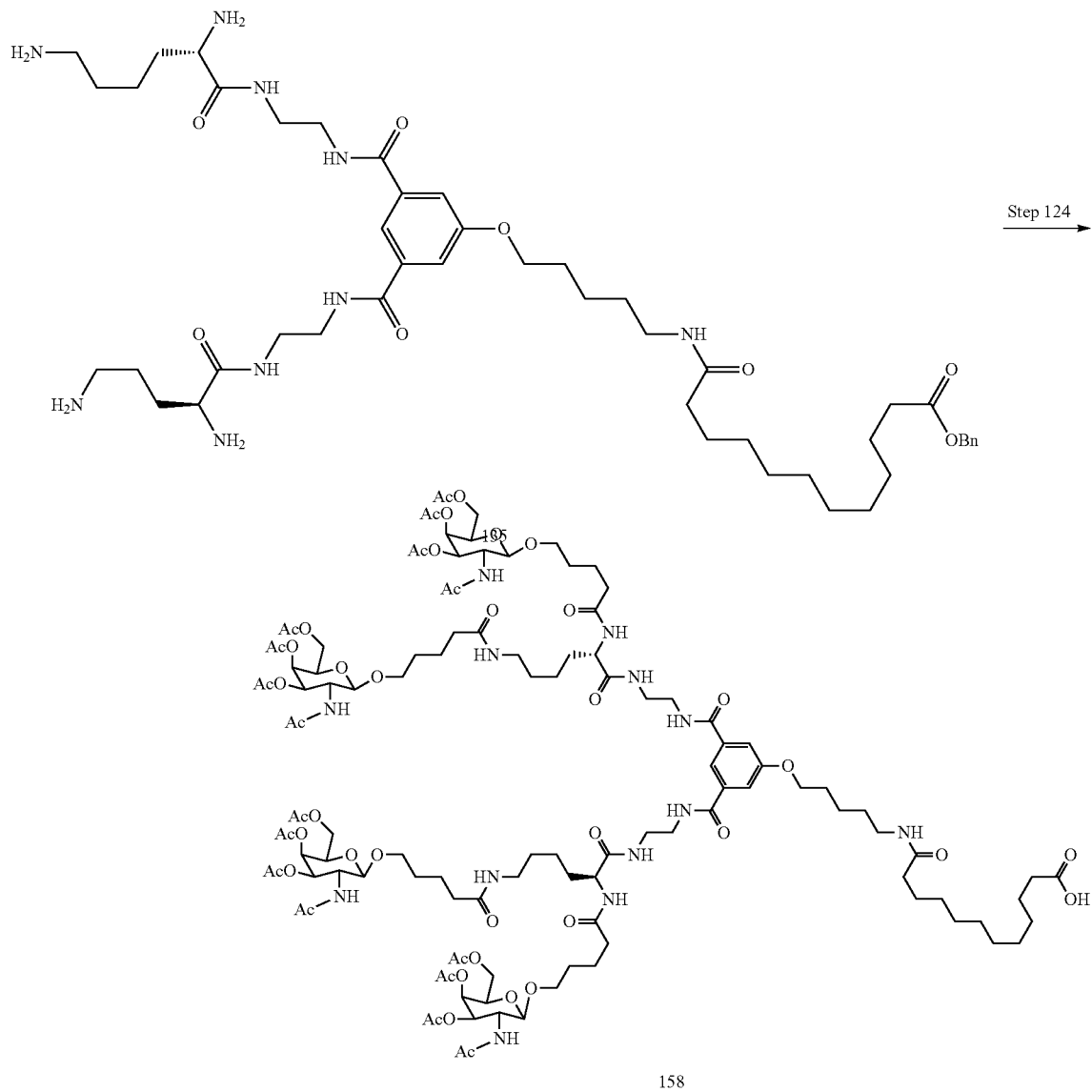
158
Step 124
Compound 158 (2.2 g, yield: 58%) was obtained in the same way as in steps 33 and 34 of Example 8 using compound 135 synthesized in step 101.
ESI-MS m/z: 2437 (M+H)$^+$
Synthesis of Compound 161
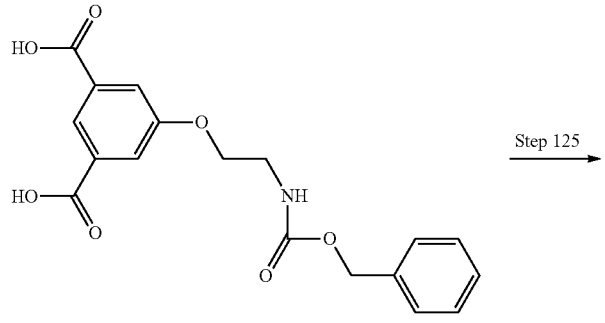
133
Step 125

-continued
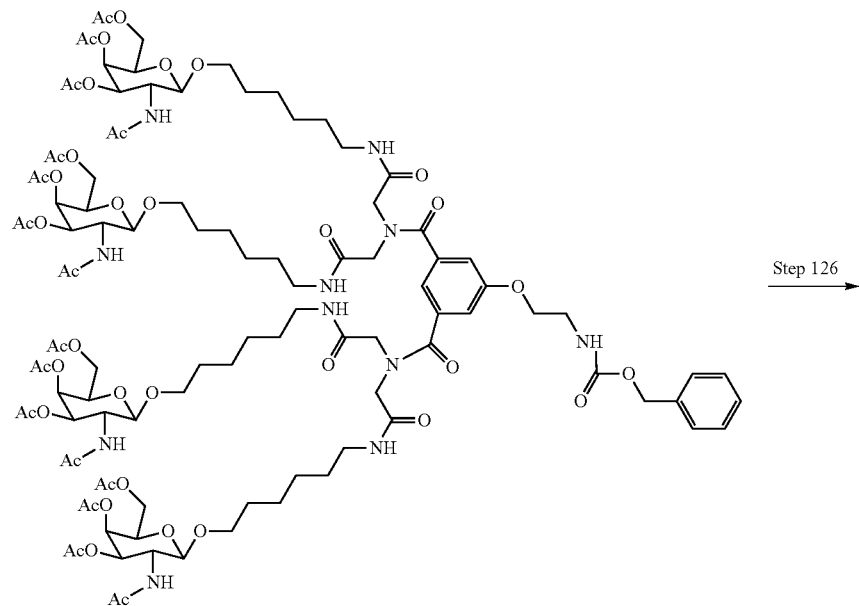
159
Step 126 →
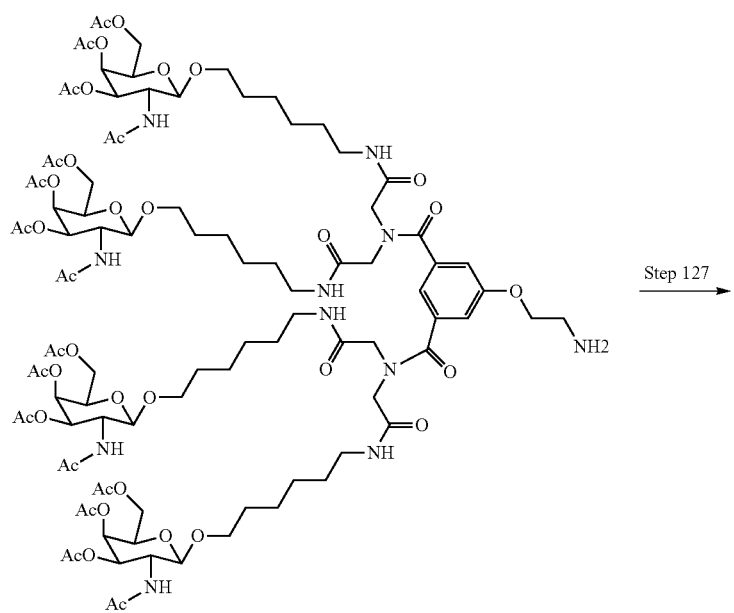
160
Step 127 →

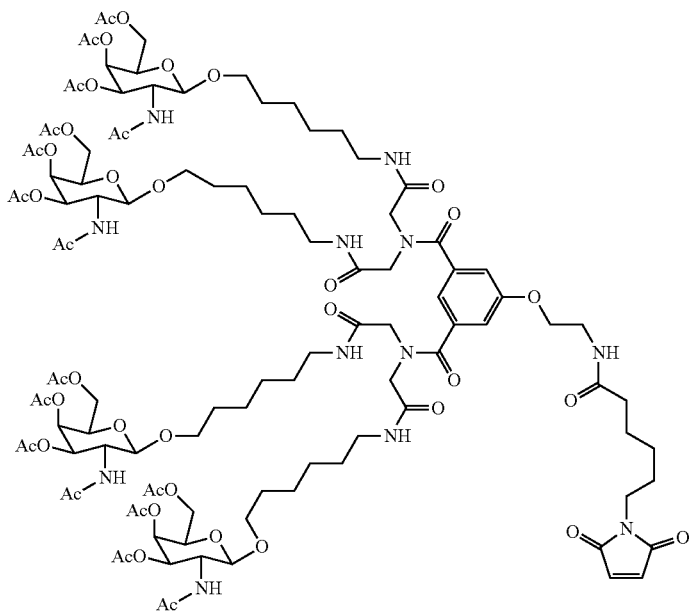

161

Step 125

Compound 159 (0.25 g, yield: 39%) was obtained in the same way as in step 8 of Example 1 using compound 133 (0.101 g, 0.282 mmol) synthesized in step 99 of Example 13 and compound 62 (0.607 g, 0.613 mmol) synthesized in step 57 of Reference Example 3.

ESI-MS m/z: 2304 (M+H)$^+$

Step 126

Compound 160 (0.15 g, yield: 63%) was obtained in the same way as in step 18 of Example 3 using compound 159 (0.255 g, 0.111 mmol) synthesized in step 125.

ESI-MS m/z: 2170 (M+H)$^+$

Step 127

Compound 161 (5.5 mg, yield: 24%) was obtained in the same way as in step 19 of Example 3 using compound 160 (20.8 mg, 9.59 μmol) synthesized in step 126.

ESI-MS m/z: 1182 (M+2H)$^{2+}$

Synthesis of Compound 163

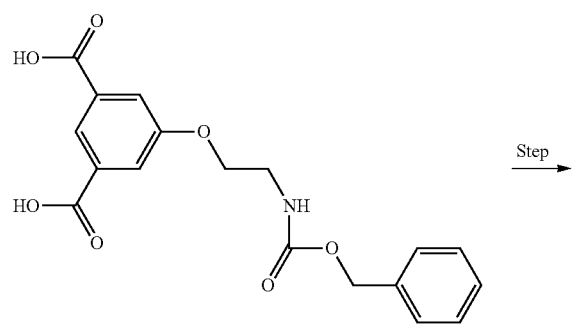

133

Step →

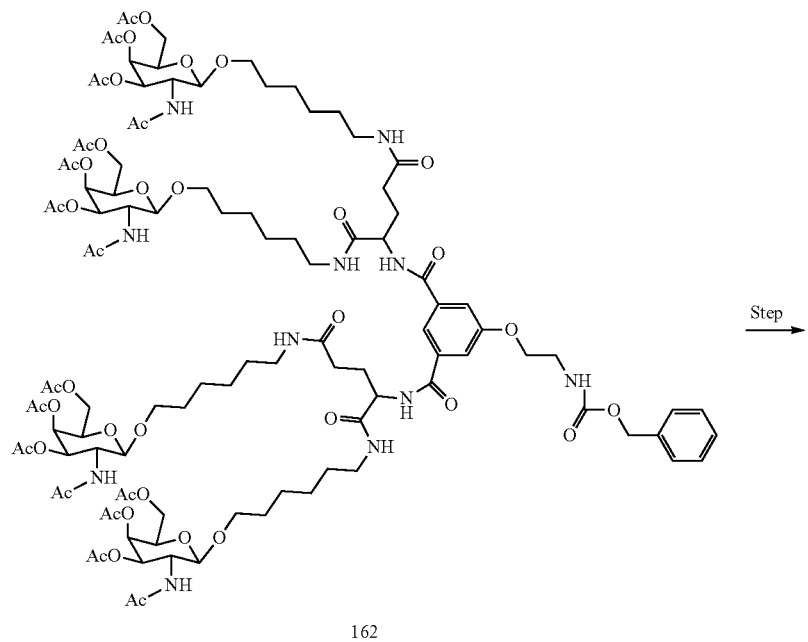
162
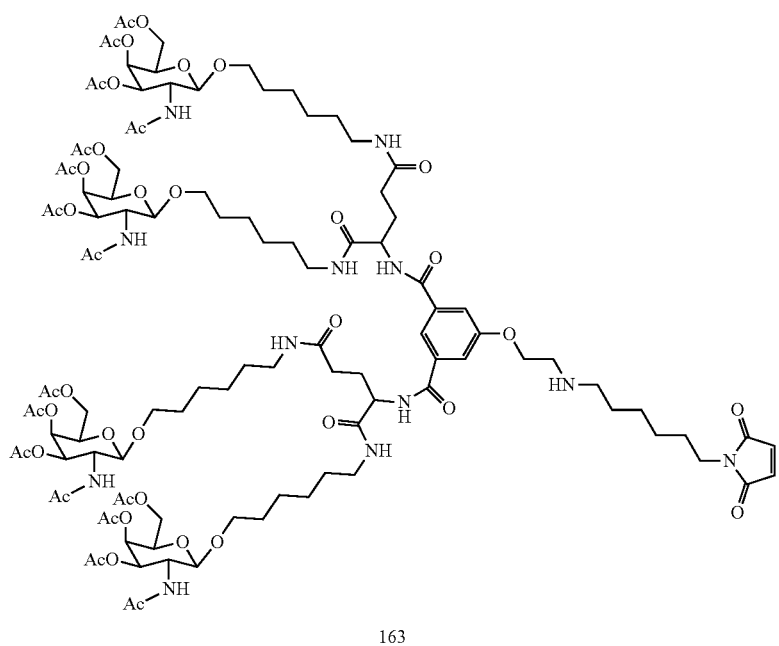
163
Step 128
Compound 162 (0.343 g, yield: 53%) was obtained in the same way as in step 8 of Example 1 using compound 133 (0.099 g, 0.277 mmol) synthesized in step 99 of Example 13 and compound 64 (0.618 g, 0.615 mmol) synthesized in step 59 of Reference Example 3.
ESI-MS m/z: 2333 (M+H)$^+$
Step 129
Compound 163 (6.9 mg, yield: 28%) was obtained in the same way as in steps 18 and 19 of Example 3 using compound 162 synthesized in step 128.
ESI-MS m/z: 2392 (M+H)$^+$ Synthesis of Compound 164
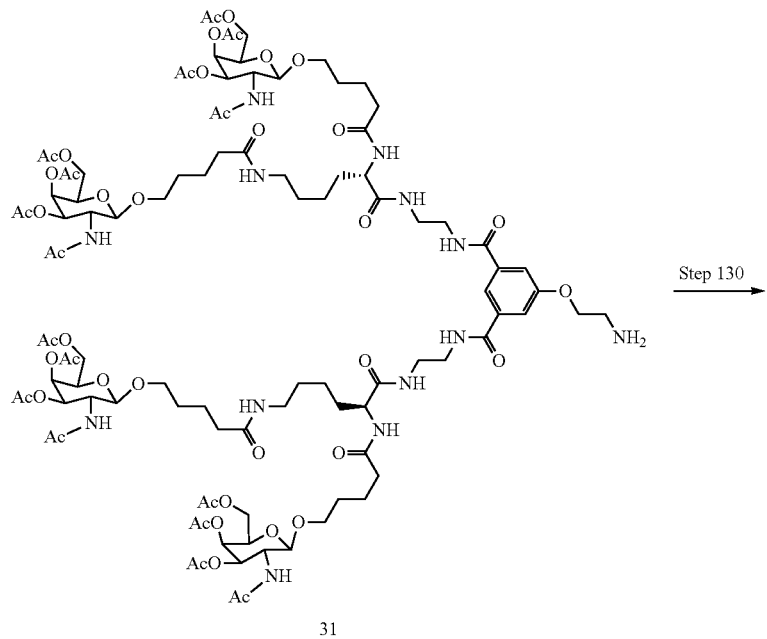
Step 130
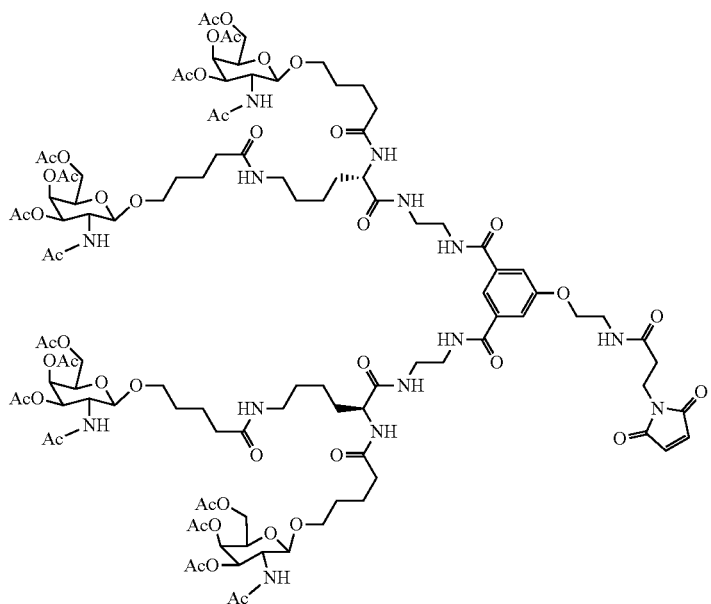
Step 130
Compound 164 (0.040 g, yield: 78%) was obtained in the same way as in step 29 of Example 5 using compound 31 (0.048 g, 0.021 mmol) synthesized in step 28 of Example 5 and N-succinimidyl 3-maleimidopropionate (manufactured by Tokyo Chemical Industry Co., Ltd., 0.017 g, 0.064 mmol).
ESI-MS m/z: 2480 (M+HCOO)$^-$ Synthesis of Compound 165
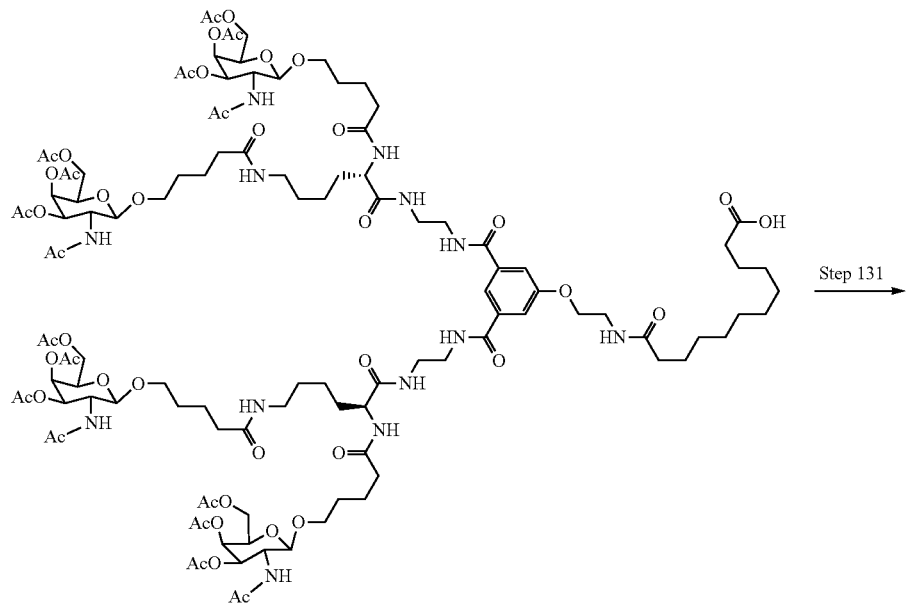
37
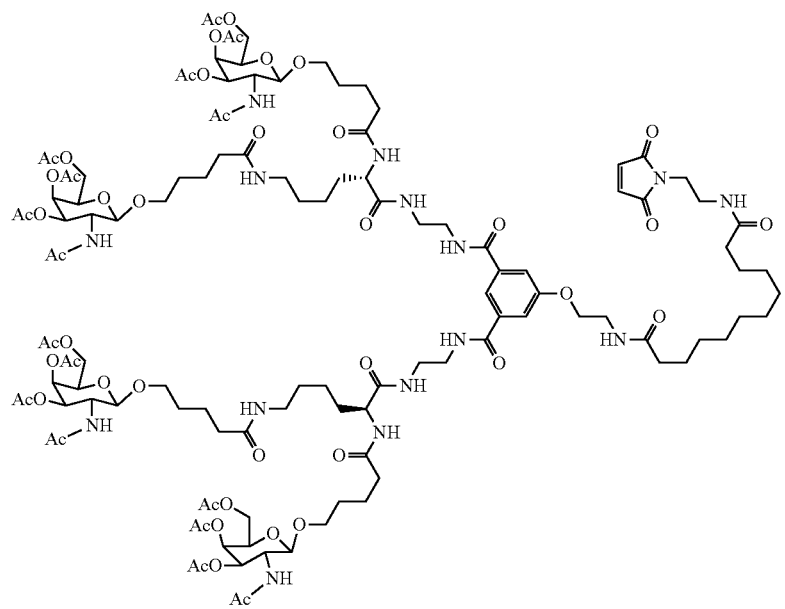
165
Step 131
Compound 165 (9.1 mg, yield: 36%) was obtained in the same way as in step 8 of Example 1 using compound 37 (23.6 mg, 9.46 μmol) synthesized in step 34 of Example 8 and N-(2-aminoethyl)maleimide trifluoroacetate (manufactured by Sigma-Aldrich Co. LLC, 7.21 mg, 0.028 mol).
ESI-MS m/z: 1310 (M+2H)$^{2+}$ Synthesis of Compound 167
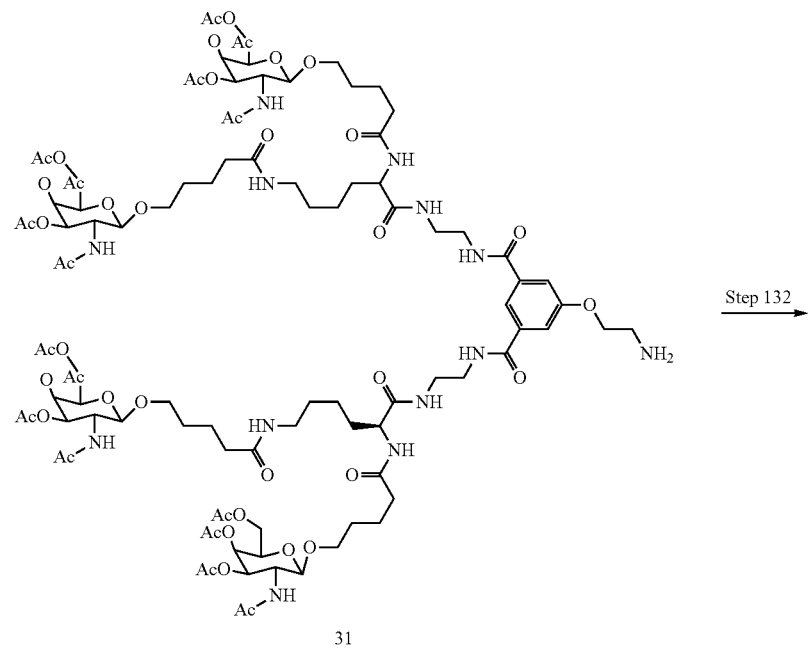
31
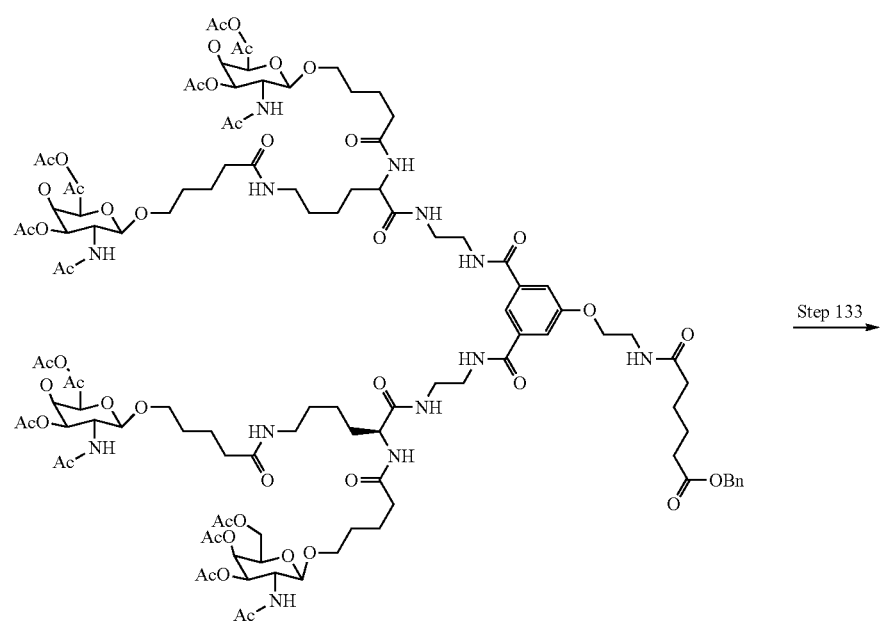
166

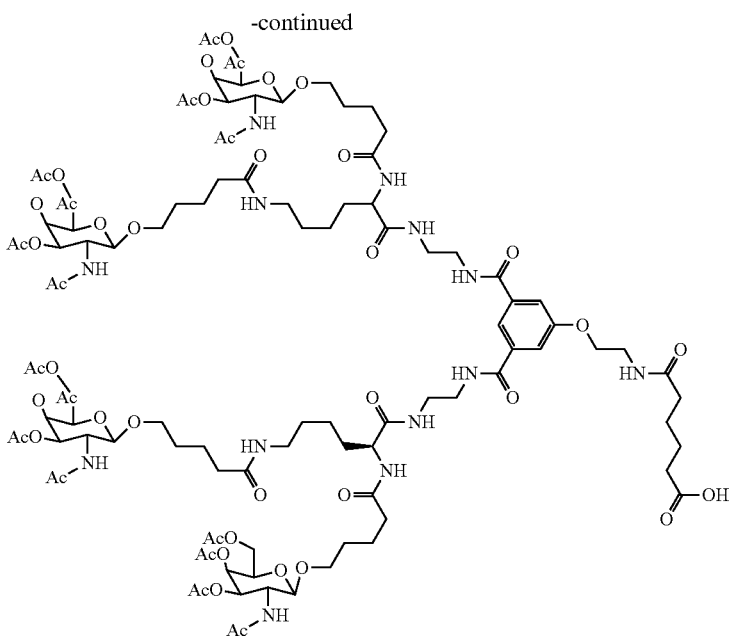

167

Step 132
Compound 166 (0.076 g, yield: 56%) was obtained by the method described in step 14 of Example 2 using hexanoic acid monobenzyl ester synthesized in the same way as in step 14 of Example 2 using compound 31 (0.122 g, 0.054 mmol) synthesized in step 28 of Example 5.
ESI-MS m/z: 2503 (M+H)$^+$

Step 133
Compound 167 (0.030 g, yield: 40%) was obtained in the same way as in step 18 of Example 3 using compound 166 (0.076 g, 0.03 mmol) synthesized in step 132.
ESI-MS m/z: 2412 (M+H)$^+$ Synthesis of Compound 168

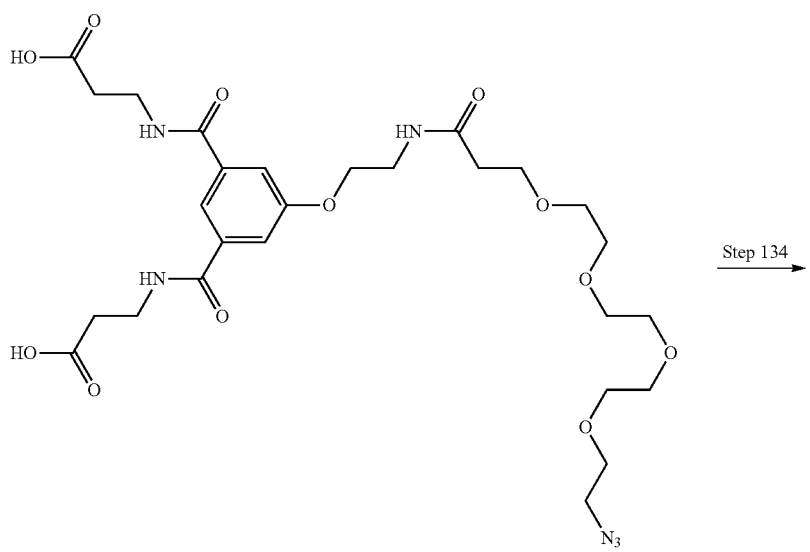

27

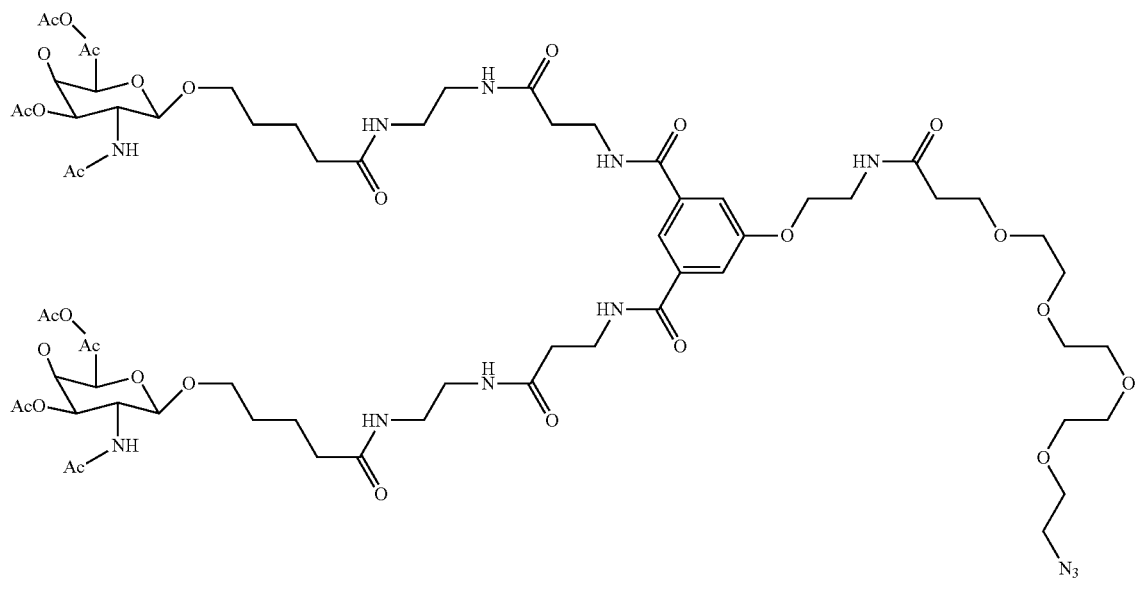
168
Step 134
Compound 168 (7 mg, yield: 65%) was obtained in the same way as in step 12 of Example 1 using compound 27 (4.36 mg, 0.006 mmol) synthesized in step 24 of Example 4 and compound 4 (10 mg, 0.02 mmol) synthesized in step 3 of Reference Example 1.
ESI-MS m/z: 1581 (M−H)⁻
Synthesis of Compound 171
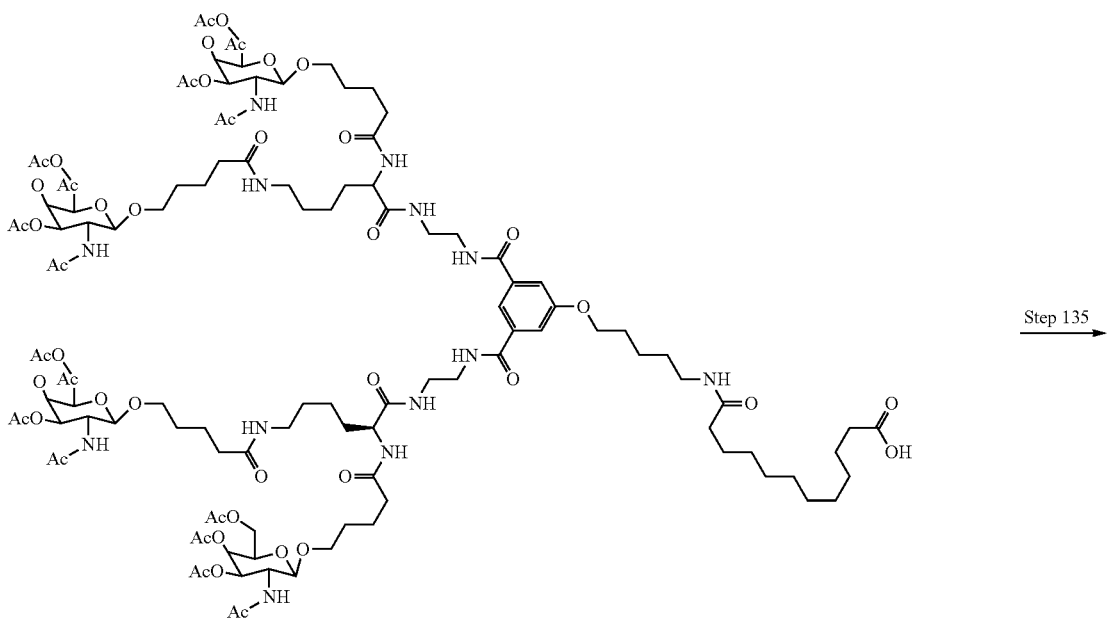
158

-continued
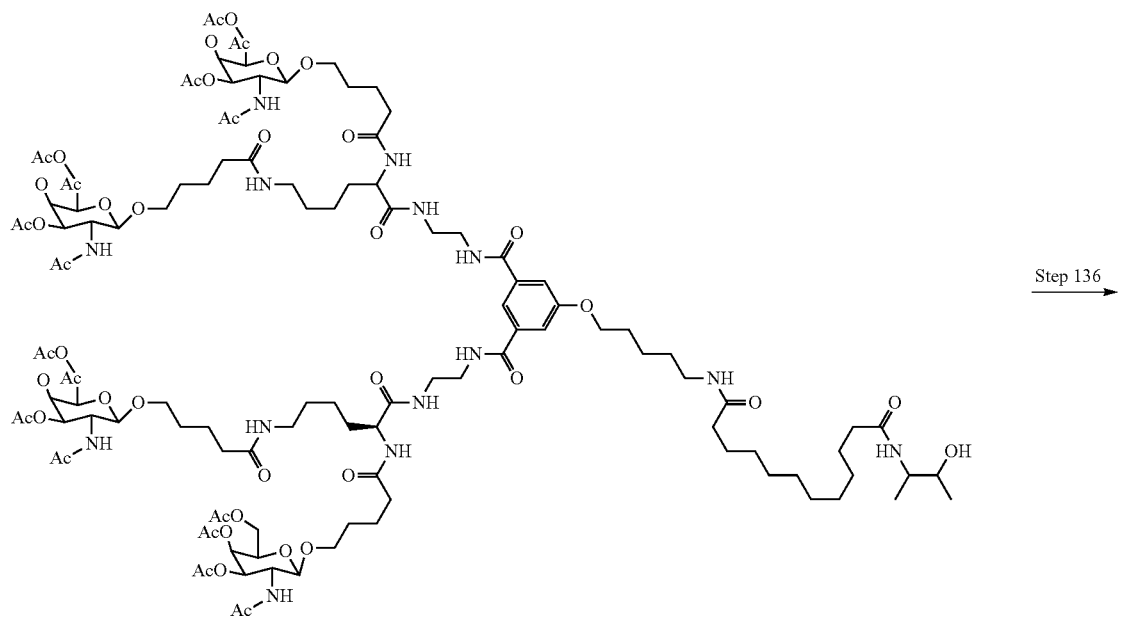
169
Step 136 →
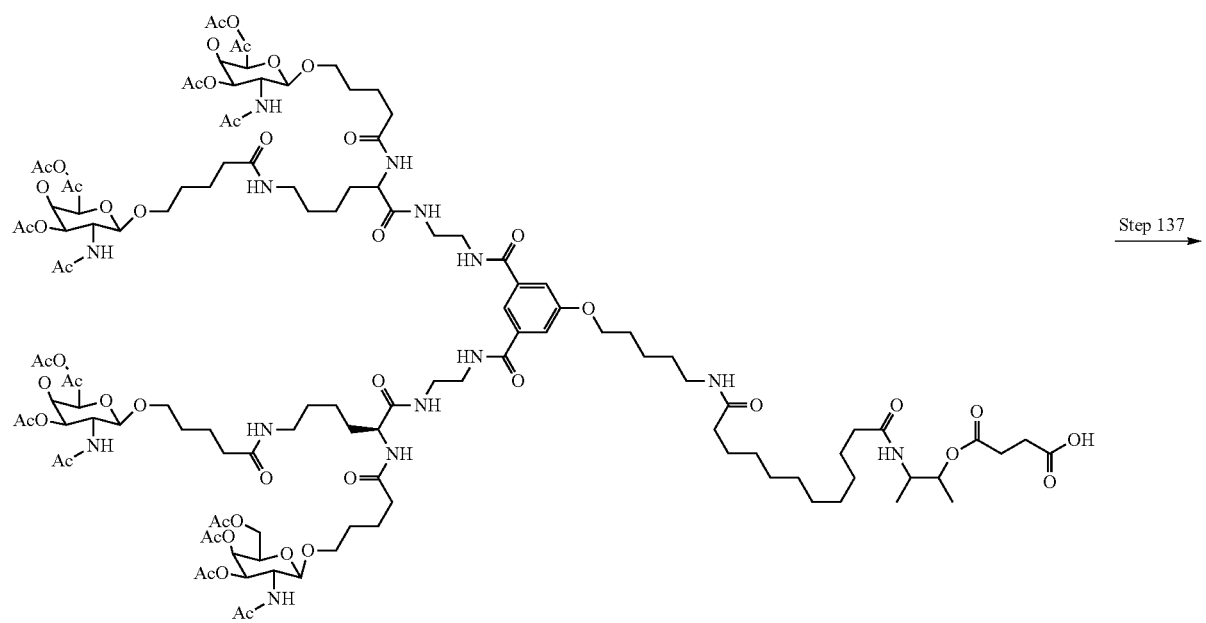
170
Step 137 →

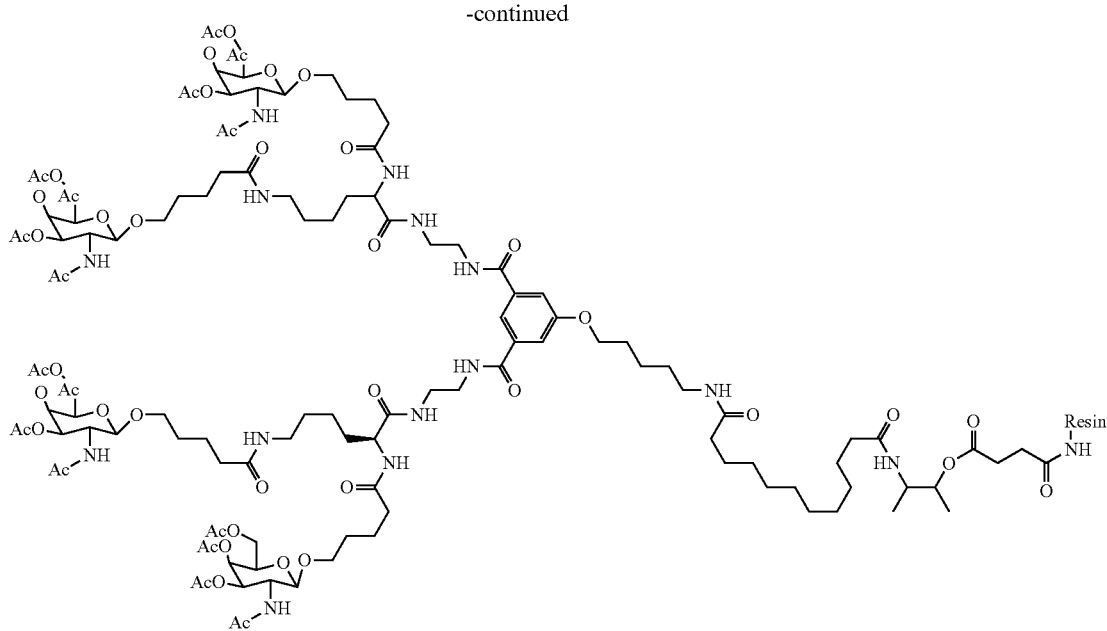

171

Step 135
Compound 169 (0.129 g, yield: 55%) was obtained in the same way as in step 35 of Example 8 using compound 158 (0.2011 g, 0.079 mmol) synthesized in step 124.
ESI-MS m/z: 2972 (M+HCOO)$^-$ Step 136
A crude product of compound 170 was obtained in the same way as in step 36 of Example 8 using compound 169 (0.129 g, 0.044 mmol) synthesized in step 135.
ESI-MS m/z: 1535 (M+HCOOH−2H)$^{2-}$ Step 137

Compound 171 (19.4 µmol/g, yield: 35%) was obtained in the same way as in step 37 of Example 8 using compound 170 (0.0467 g, 0.013 mmol) synthesized in step 136.

Synthesis of Compound 174

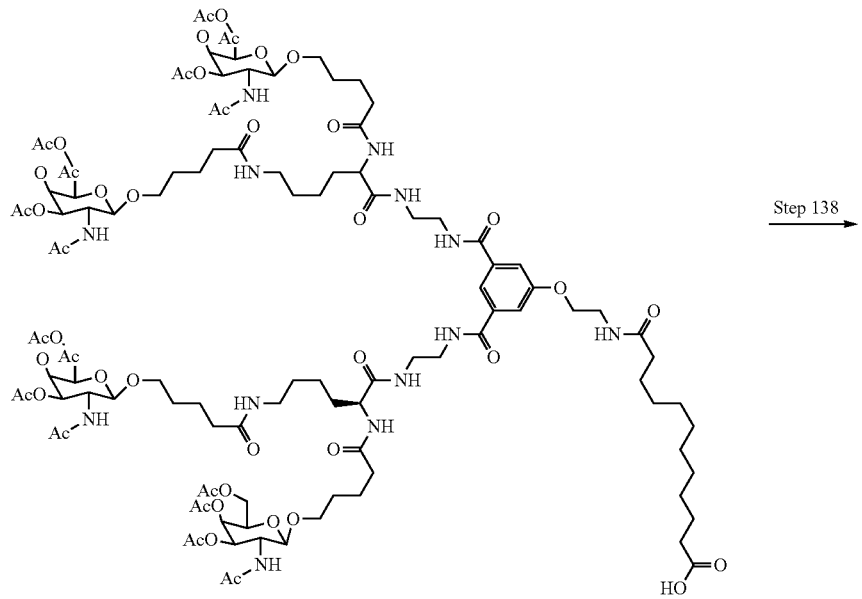

37

-continued
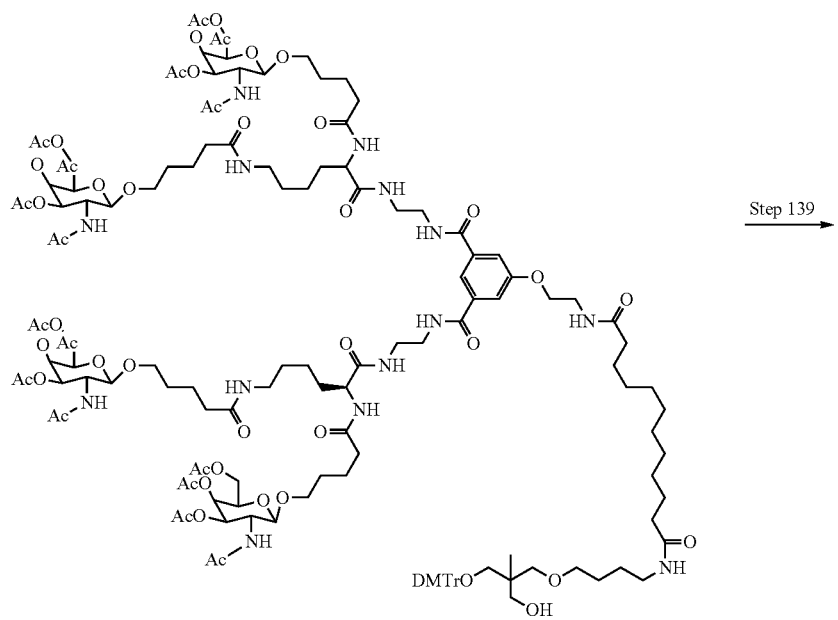
172
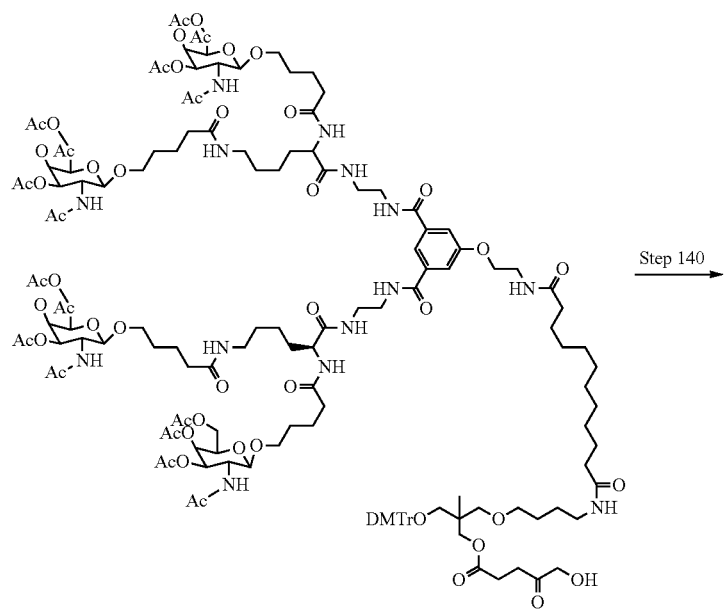
173
Step 139
Step 140

-continued

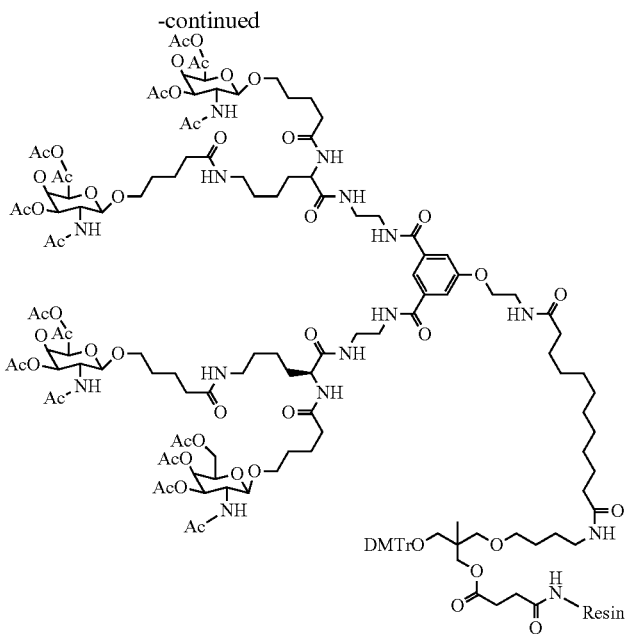

174

Step 138

Compound 172 (90 mg, yield: 76%) was obtained in the same way as in step 35 of Example 8 using compound 37 (100 mg, 0.040 mmol) synthesized in step 35 of Example 8 and compound 66 synthesized in step 60 of Reference Example 4.

ESI-MS m/z: 1335 (M-DMTr+2H)$^{2+}$

Step 139

A crude product of compound 173 was obtained in the same way as in step 36 of Example 8 using compound 172 (90 mg, 0.030 mmol) synthesized in step 138.
ESI-MS m/z: 1558 (M+HCOOH−2H)$^{2-}$ Step 140

Compound 174 (21.5 µmol/g, 2-step yield: 32%) was obtained in the same way as in step 37 of Example 8 using a crude product of compound 173 synthesized in step 139.

Synthesis of Compound 177

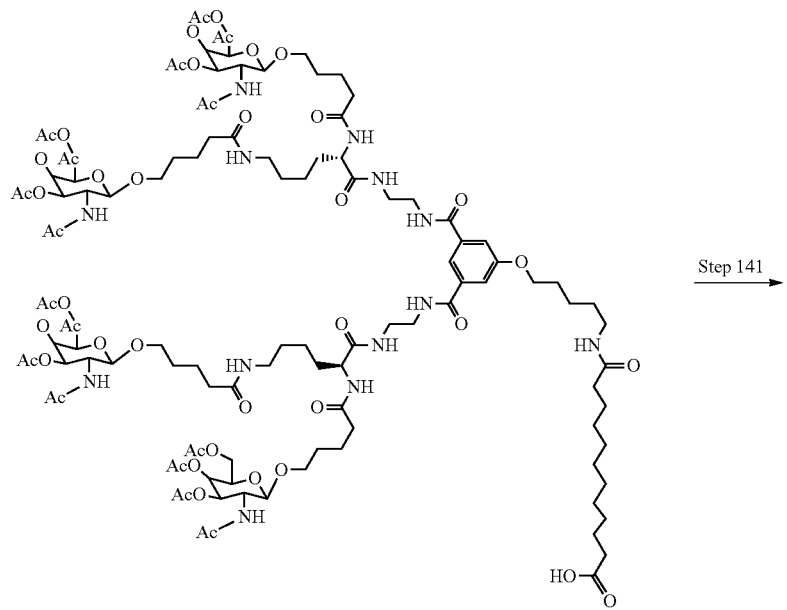

158

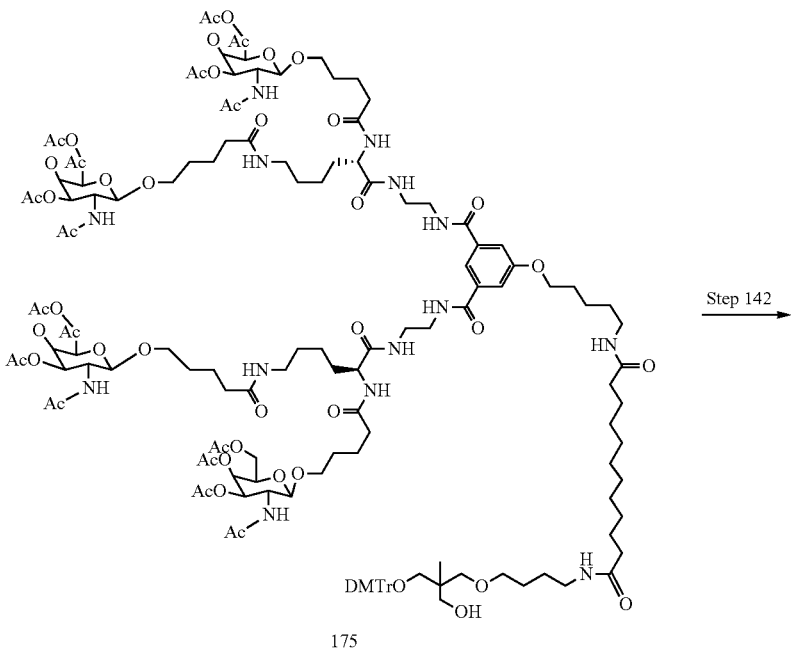
175
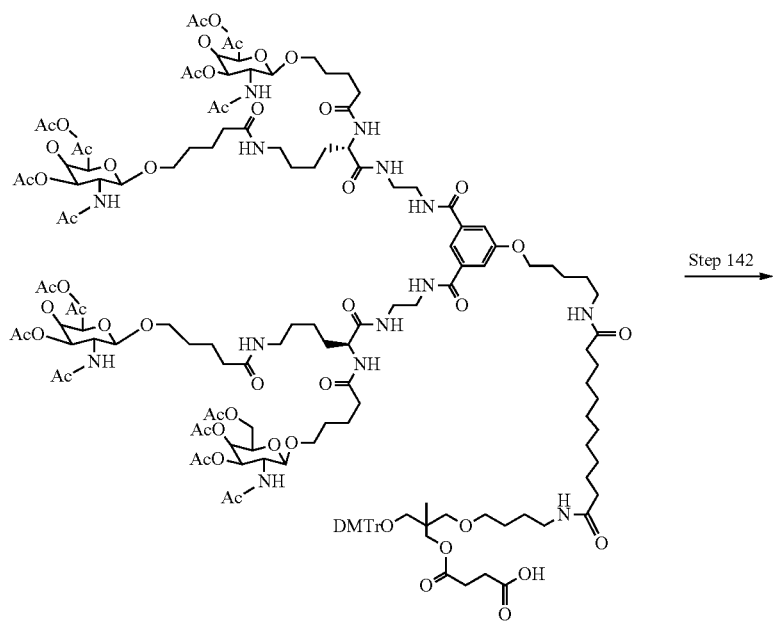
176

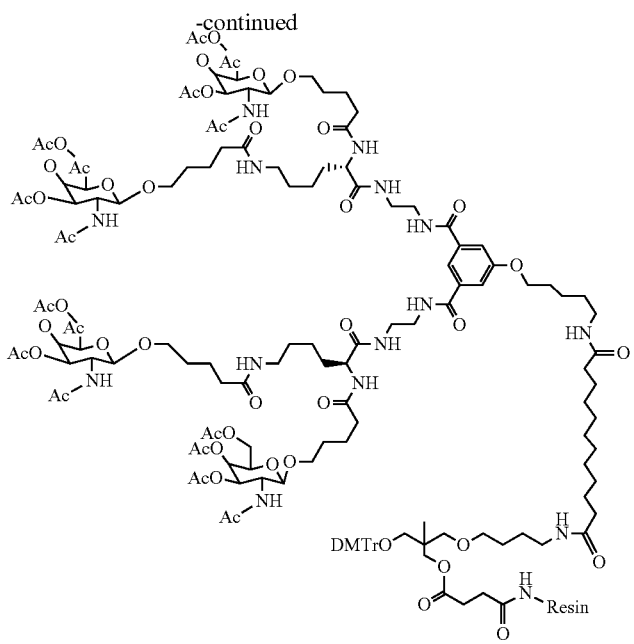

177

Step 141

Compound 175 (90 mg, yield: 76%) was obtained in the same way as in step 35 of Example 8 using compound 158 (100 mg, 0.039 mmol) synthesized in step 124 of Example 14 and compound 66 synthesized in step 60 of Reference Example 4.

ESI-MS m/z: 1356 (M+2H)$^{2+}$ detected as a DMTr-deprotected form

Step 142

A crude product of compound 176 was obtained in the same way as in step 36 of Example 8 using compound 175 (90 mg, 0.030 mmol) synthesized in step 141.

ESI-MS m/z: 1579 (M+HCOOH−2H)$^{2−}$

Step 143

Compound 177 (17.0 μmol/g, 2-step yield: 26%) was obtained in the same way as in step 37 of Example 8 using a crude product of compound 176 synthesized in step 142.

Synthesis of Compound 180

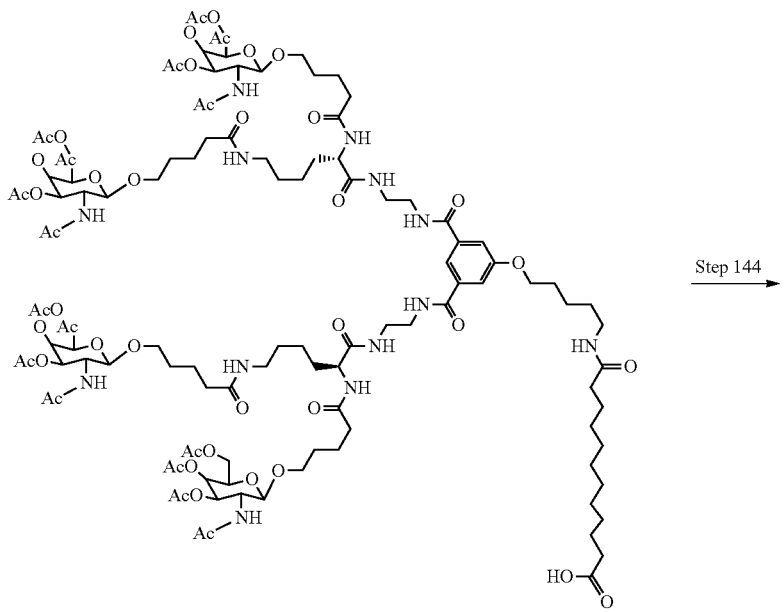

158

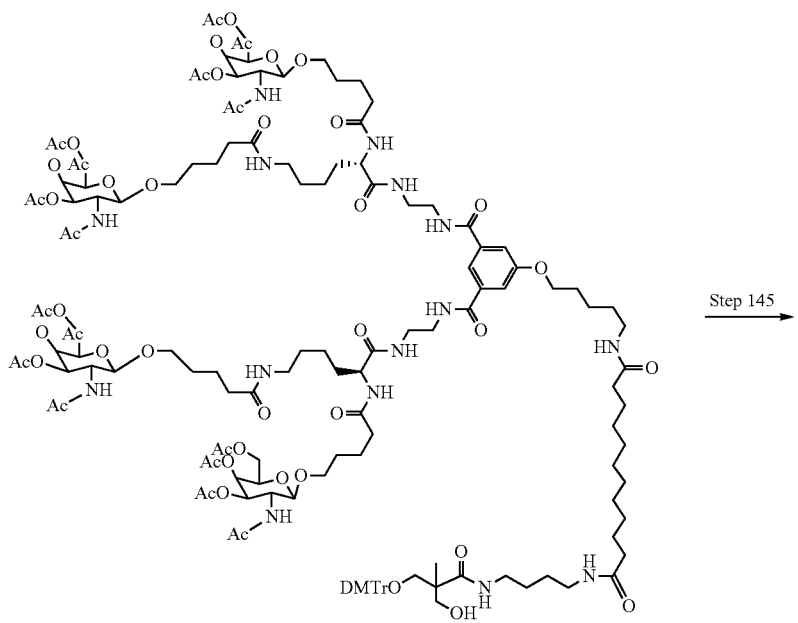
178
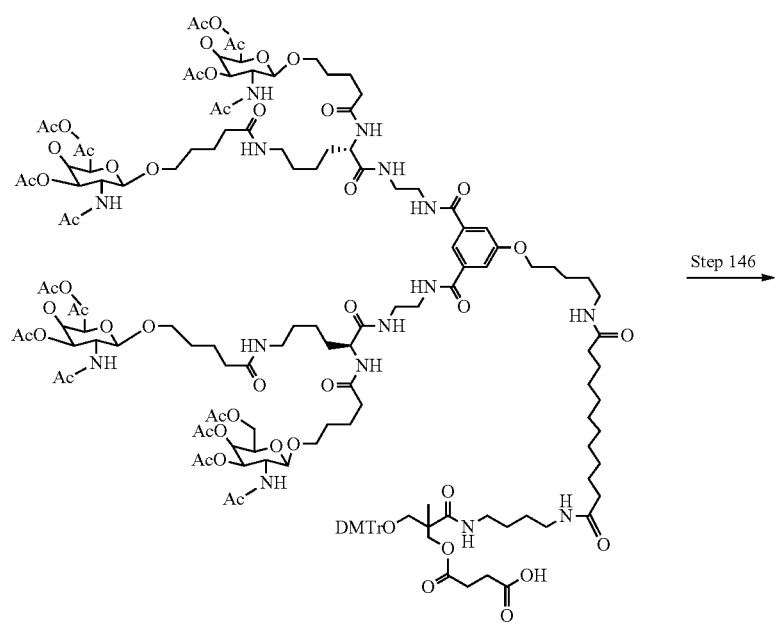
179

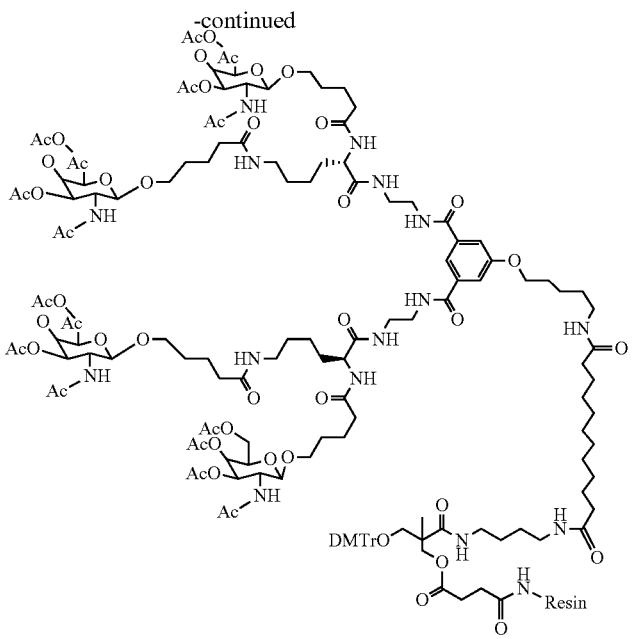

180

Step 144

Compound 178 (50 mg, yield: 42%) was obtained in the same way as in step 35 of Example 8 using compound 158 (100 mg, 0.039 mmol) synthesized in step 124 of Example 14 and compound 69 synthesized in step 62 of Reference Example 4.

ESI-MS m/z: 1363 (M+2H)$^{2+}$ detected as a DMTr-deprotected form

Step 145

A crude product of compound 179 was obtained in the same way as in step 36 of Example 8 using compound 178 (50 mg, 0.017 mmol) synthesized in step 144.

ESI-MS m/z: 1587 (M+HCOOH−2H)$^{2−}$

Step 146

Compound 180 (0.5 μmol/g, 2-step yield: 1%) was obtained in the same way as in step 37 of Example 8 using a crude product of compound 179 synthesized in step 145.

Synthesis of Compound 183

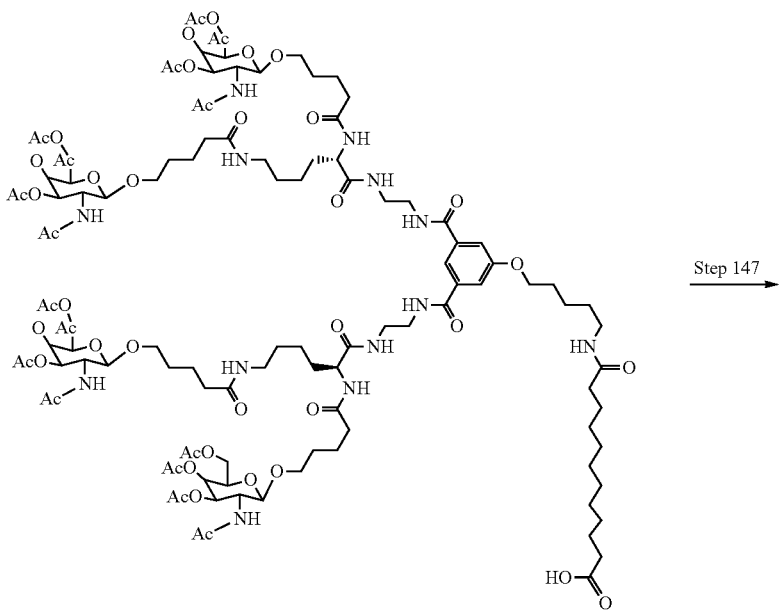

158

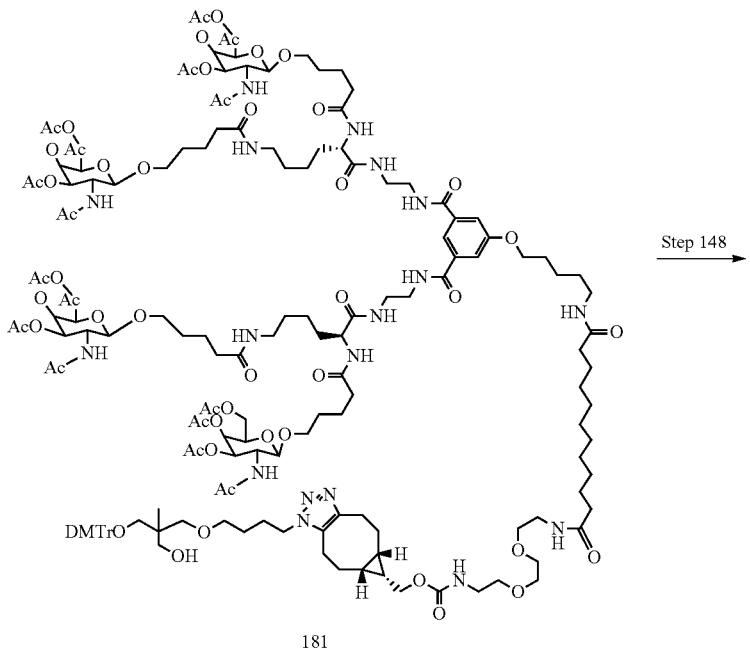
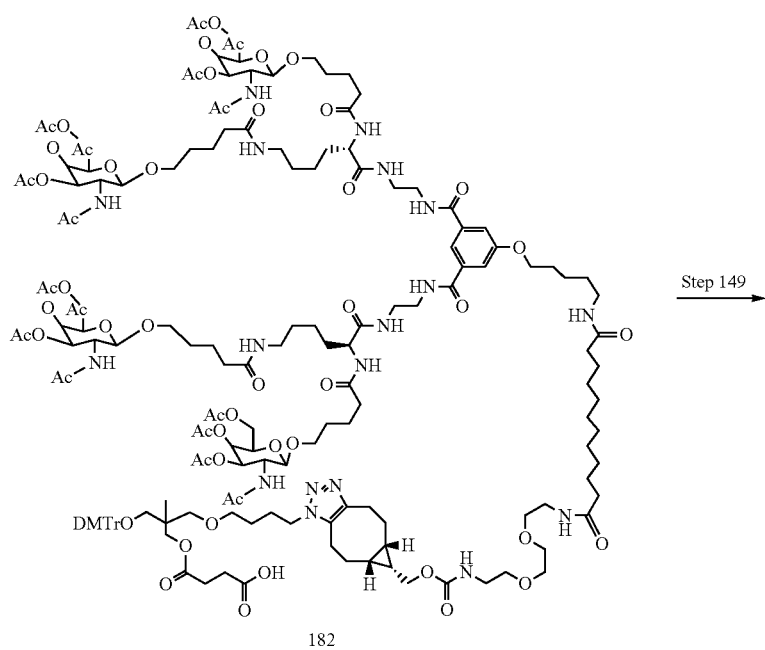

-continued

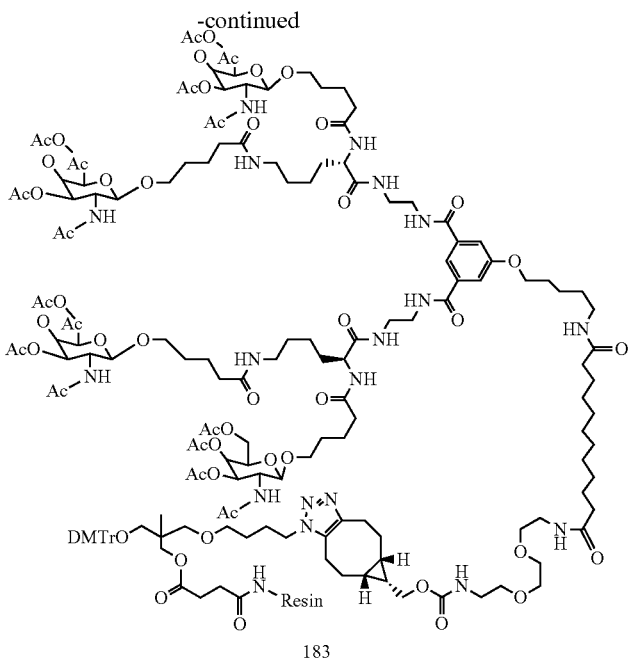

183

Step 147

Compound 181 (40 mg, yield: 30%) was obtained in the same way as in step 35 of Example 8 using compound 158 (100 mg, 0.039 mmol) synthesized in step 124 of Example 14 and compound 71 synthesized in step 63 of Reference Example 4.

ESI-MS m/z: 1532 (M+2H)$^{2+}$ detected as a DMTr-deprotected form

Step 148

A crude product of compound 182 was obtained in the same way as in step 36 of Example 8 using compound 181 (40 mg, 0.012 mmol) synthesized in step 147.

ESI-MS m/z: 1582 (M+2H)$^{2+}$ detected as a DMTr-deprotected form

Step 149

Compound 183 (0.2 μmol/g, 2-step yield: 1%) was obtained in the same way as in step 37 of Example 8 using a crude product of compound 182 synthesized in step 148.

Synthesis of Compound 187

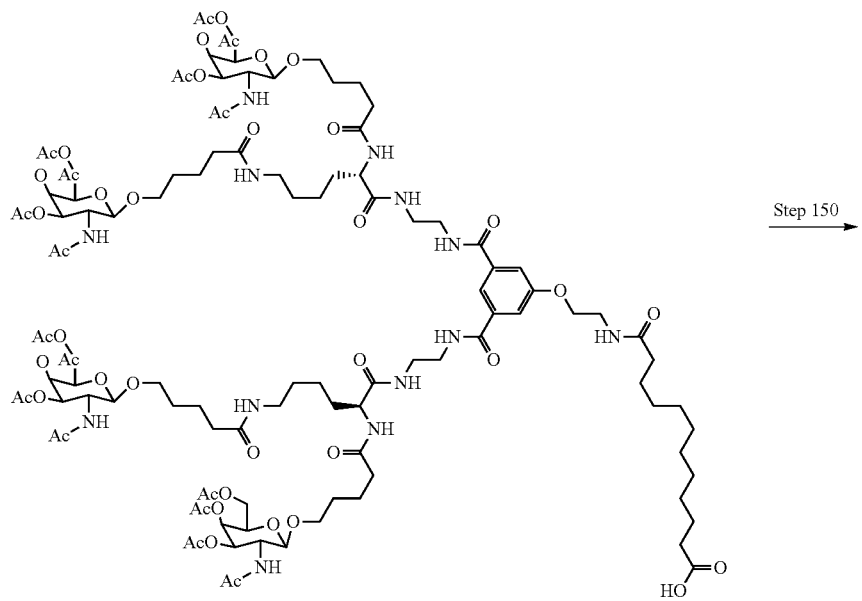

37

-continued
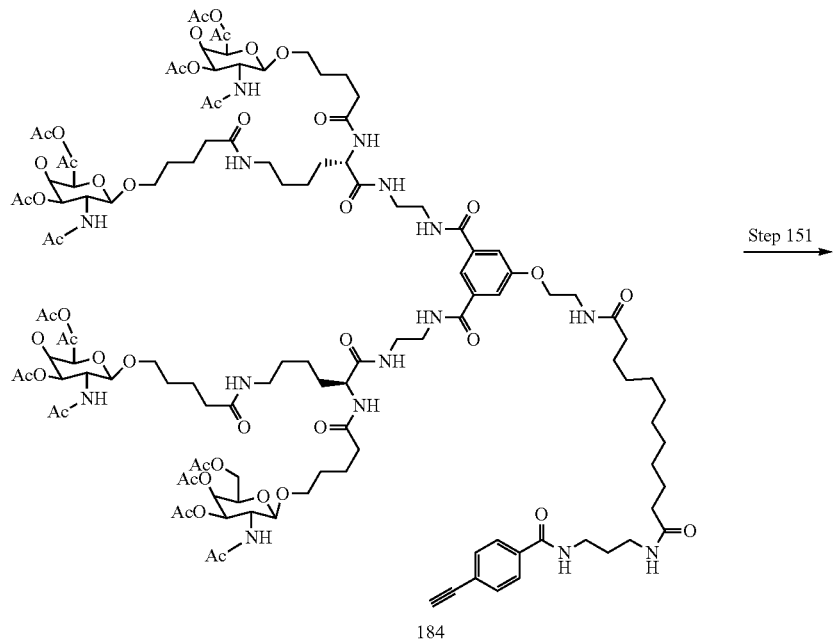
184
Step 151 →
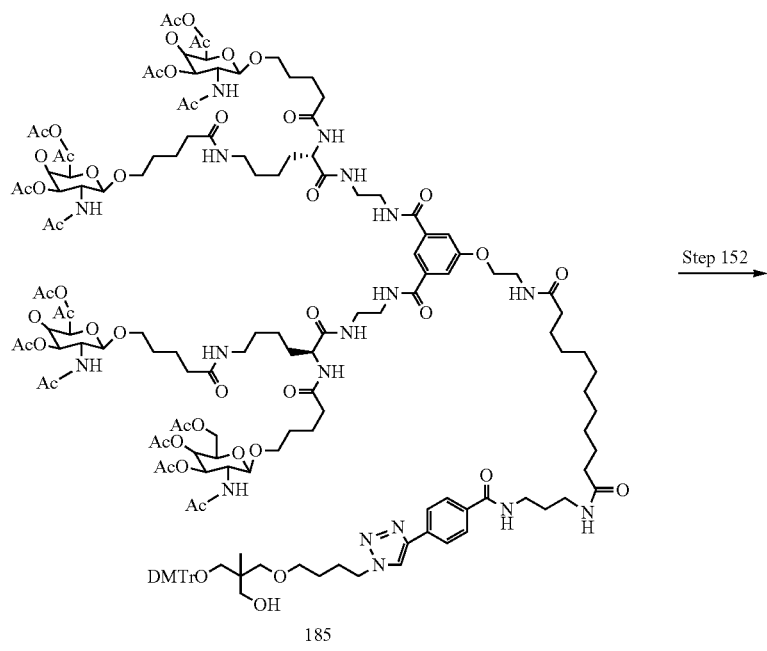
185
Step 152 →

-continued

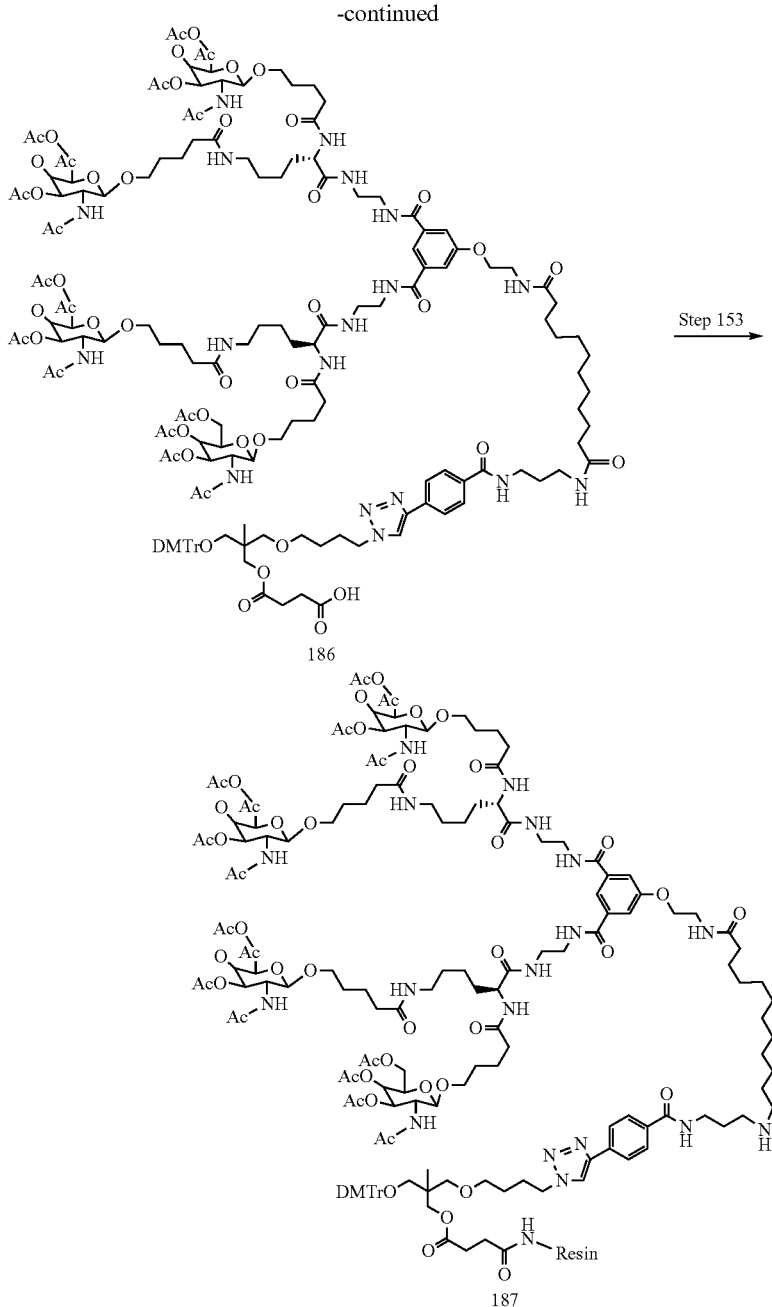

Step 150

Compound 184 (58 mg, yield: 77%) was obtained in the same way as in step 35 of Example 8 using compound 158 (70 mg, 0.028 mmol) synthesized in step 34 of Example 8 and compound 78 synthesized in step 68 of Reference Example 4.

ESI-MS m/z: 1341 (M+2H)$^{2+}$

Step 151

Compound 184 (58 mg, 0.022 mmol) synthesized in step 150 was dissolved in methanol (0.15 mL). To the solution, compound 65 (16.9 mg, 0.032 mmol) synthesized by the method described in Journal of Organic Chemistry, Vol. 74, p. 6837-6842, 2009, a 1 mol/L aqueous sodium L-ascorbate solution (0.022 mL, 0.022 mmol), a 20 mmol/L aqueous copper(II) sulfate solution (0.011 mL, 0.22 μmol), and a 10 mmol/L solution of tris(2-benzimidazolylmethyl)amine in DMSO (0.022 mL, 0.22 μmol) were added, and the mixture was stirred at room temperature for 3 hours. The reaction solution was purified by silica gel column chromatography (chloroform/methanol=80/20) to obtain compound 185 (7 mg, yield: 10%).

ESI-MS m/z: 1450 (M+2H)$^{2+}$ detected as a DMTr-deprotected form

Step 152

A crude product of compound 186 was obtained in the same way as in step 36 of Example 8 using compound 185 (10 mg, 3.13 μmol) synthesized in step 151.

ESI-MS m/z: 1500 (M+2H)$^{2+}$ detected as a DMTr-deprotected form

Step 153
Compound 187 (8.4 μmol/g, yield: 27%) was obtained in the same way as in step 37 of Example 8 using a crude product of compound 186 synthesized in step 152.
Synthesis of Compound 190
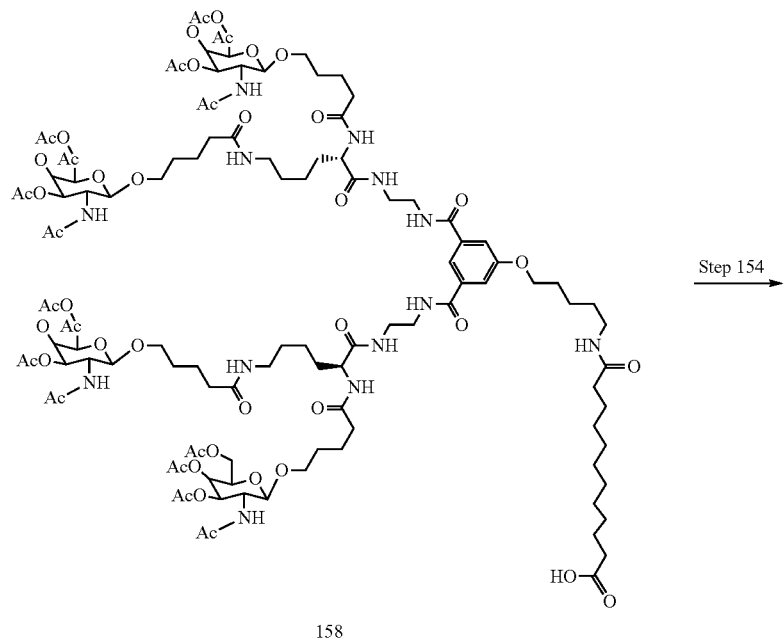
158
Step 154
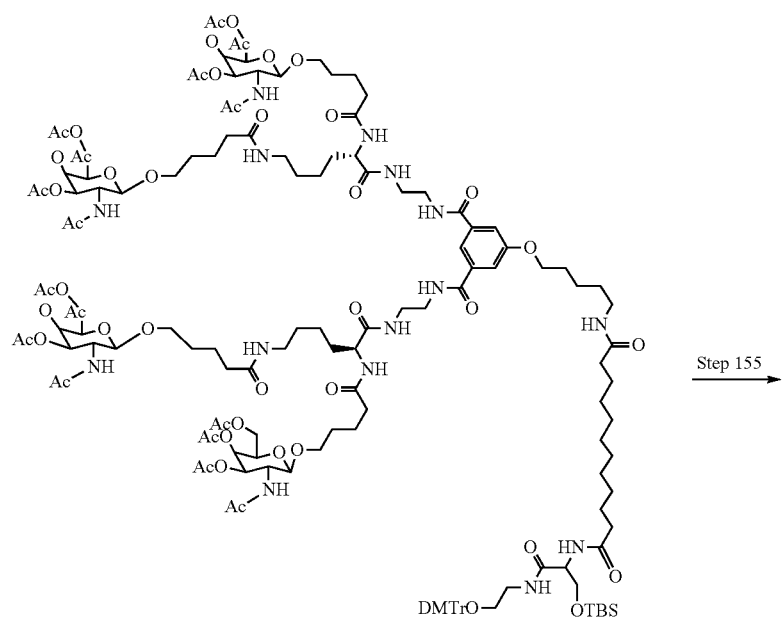
188
Step 155

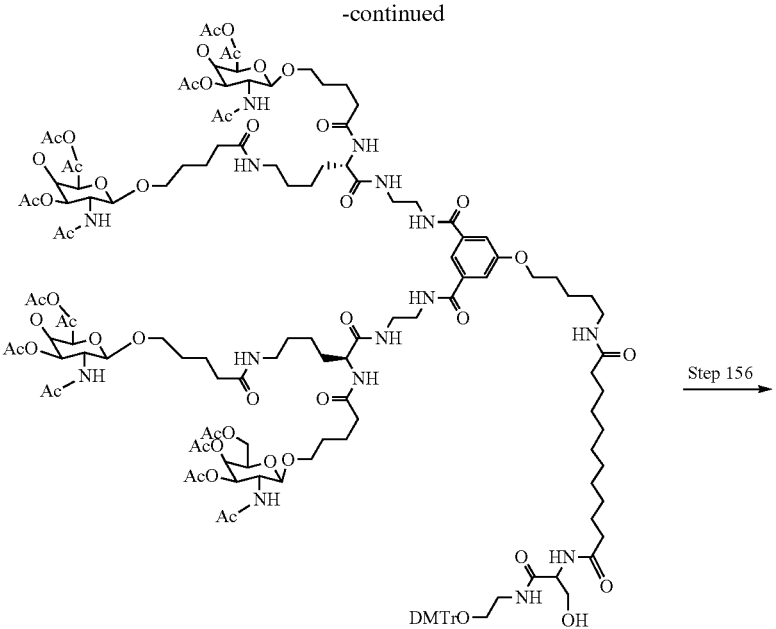

189

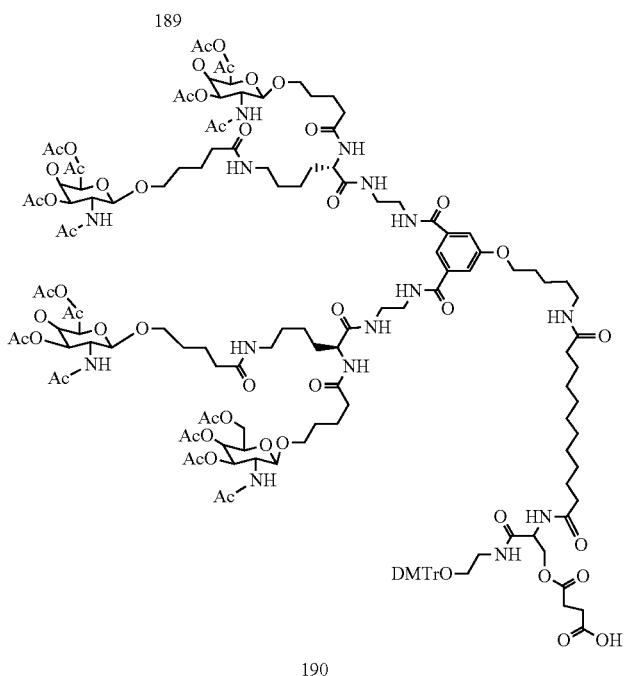

190

Step 154

A crude product of compound 188 was obtained in the same way as in step 8 of Example 1 or by the method described in Bioconjugate Chemistry, Vol. 26, p. 1451-1455, 2015 using compound 158 (74.1 mg, 0.029 mmol) synthesized in step 124 of Example 14 and compound 95 (15 mg, 0.027 mmol) synthesized in step 72 of Example 4. ESI-MS m/z: 1392 (M+H)$^+$, detected as a DMTr-deprotected form Step 155

A crude product of compound 189 was obtained by the method described in a patent literature WO2015105083 using compound 188 (0.083 g, 0.027 mmol) synthesized in step 154.

ESI-MS m/z: 2669 (M+H)$^+$, detected as a DMTr-deprotected form

Step 156

A crude product of compound 190 was obtained in the same way as in step 36 of Example 8 using compound 189 (0.08 g, 0.027 mmol) synthesized in step 155.

ESI-MS m/z: 1556 (M+HOOH−2H)$^{2-}$ $^1$H-NMR (400 MHz, MeOD): δ 1.45-1.86 (48H, m), 1.93 (12H, s), 1.94 (12H, s), 2.02 (12H, s), 2.13 (12H, s), 2.16-2.28 (17H, m), 2.48 (4H, s), 3.10-3.16 (6H, m), 3.36-3.56 (19H, m), 3.77 (6H, s), 3.80-3.89 (6H, m), 3.98-4.35 (30H, m), 4.53-4.59 (4H, m), 4.66-4.72 (1H, m), 5.04-5.10 (4H, m), 5.31-5.36 (4H, m), 6.81-6.88 (4H, m), 7.17-7.23 (1H, m), 7.26-7.32 (6H, m), 7.38-7.44 (2H, m), 7.54 (2H, br s), 7.90 (1H, br s).

Synthesis of Compounds 191 to 199

The compounds described in Tables 20 and 21 were obtained in the same way as in steps 154 and 155 using compound 37 synthesized in step 34 of Example 8, or compound 158 synthesized in step 124 of Example 14 and the structures described in Table 18, or compound 75 synthesized in step 66 of Reference Example 4.

The mass spectrometry results of the compounds synthesized in this Example are shown in Table 22.

TABLE 20

191

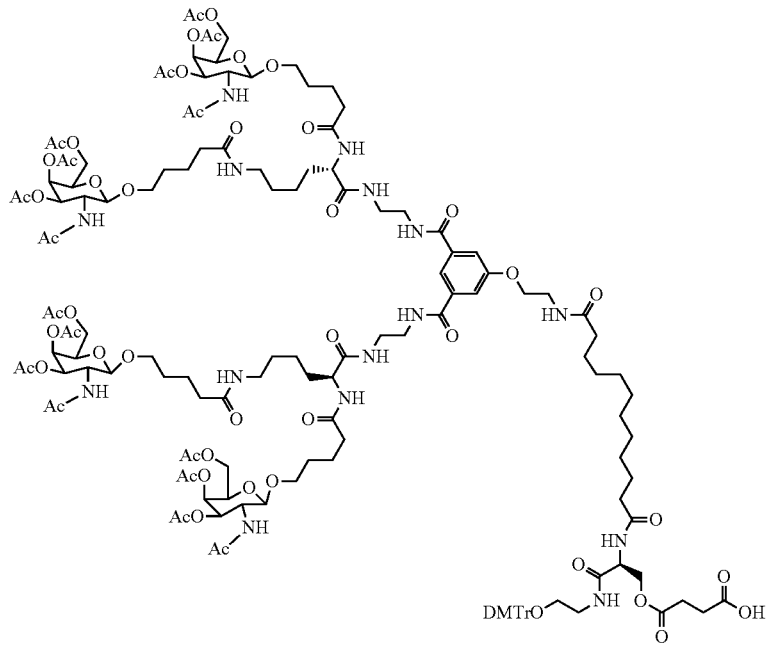

192

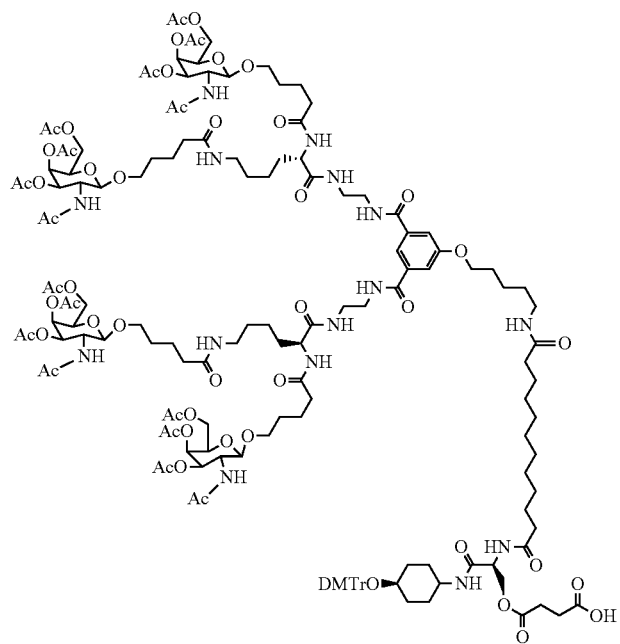

193
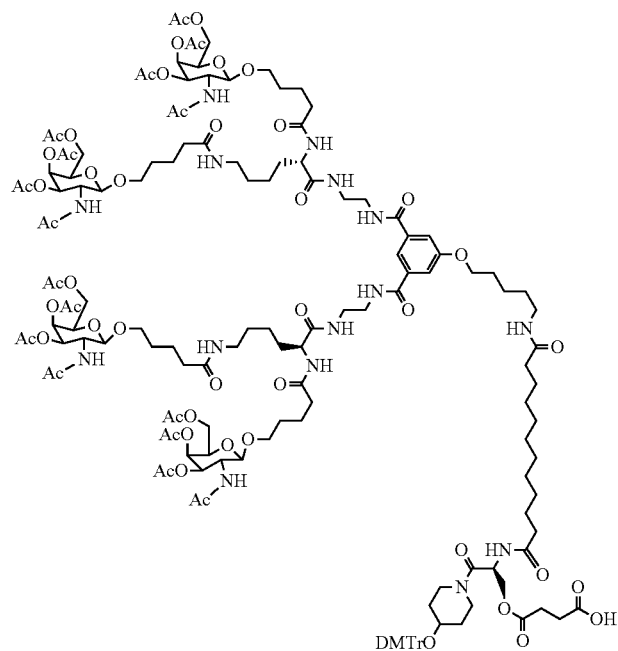
194
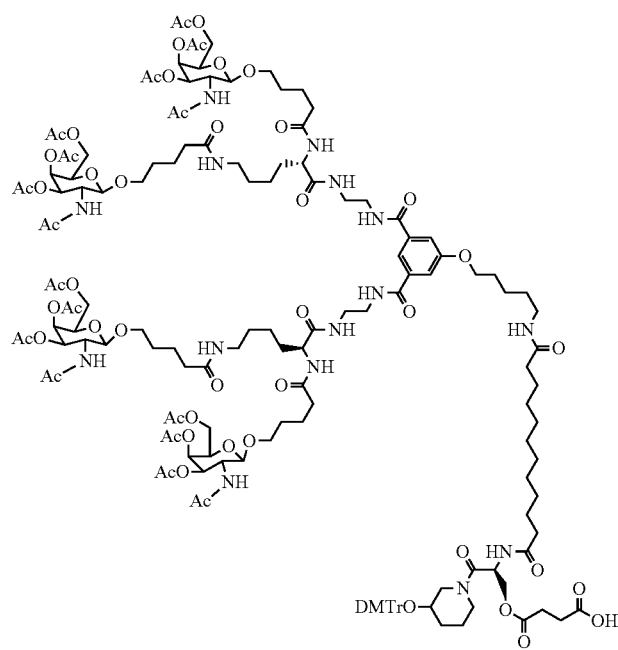

TABLE 20-continued
195
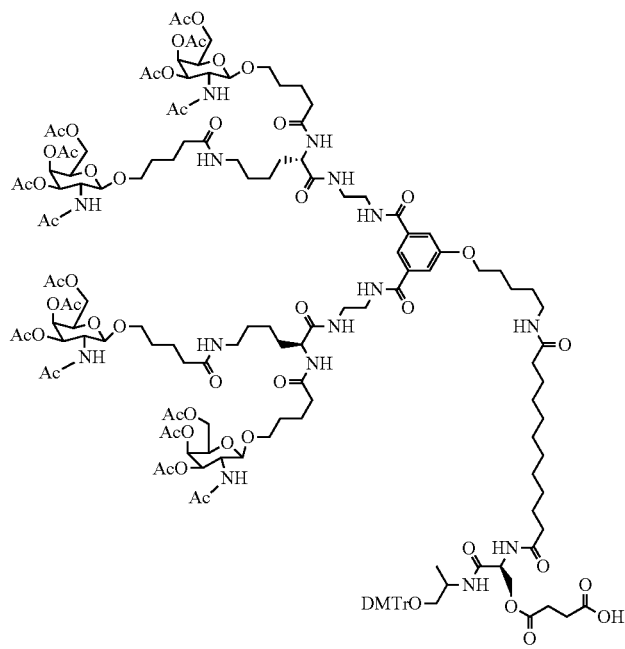
196
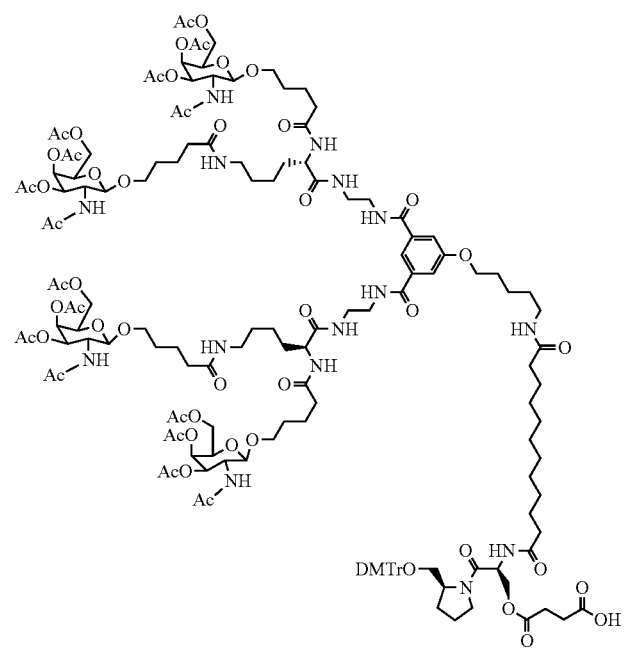

TABLE 21
197
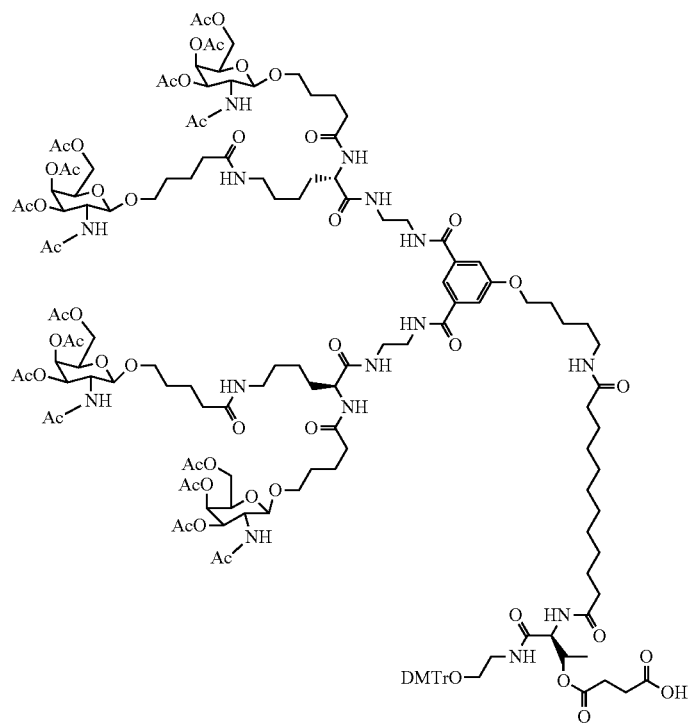
198
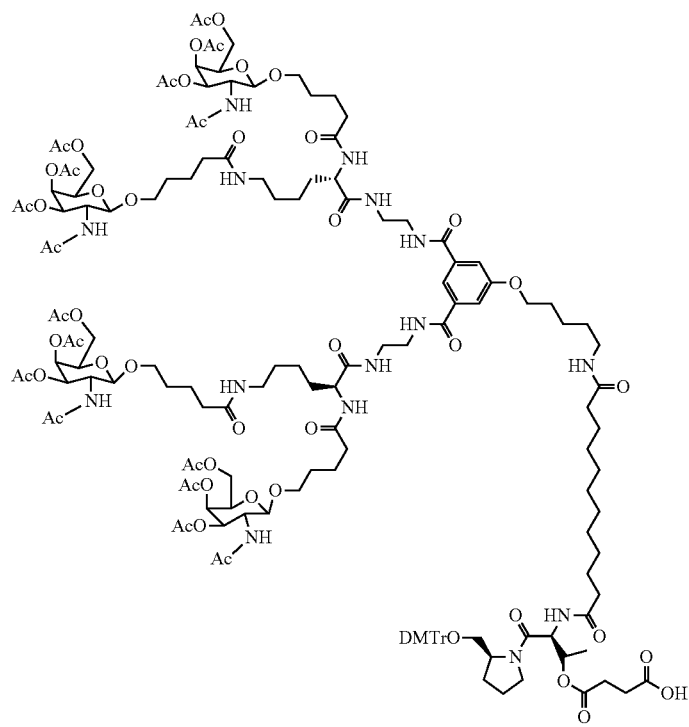

TABLE 21-continued
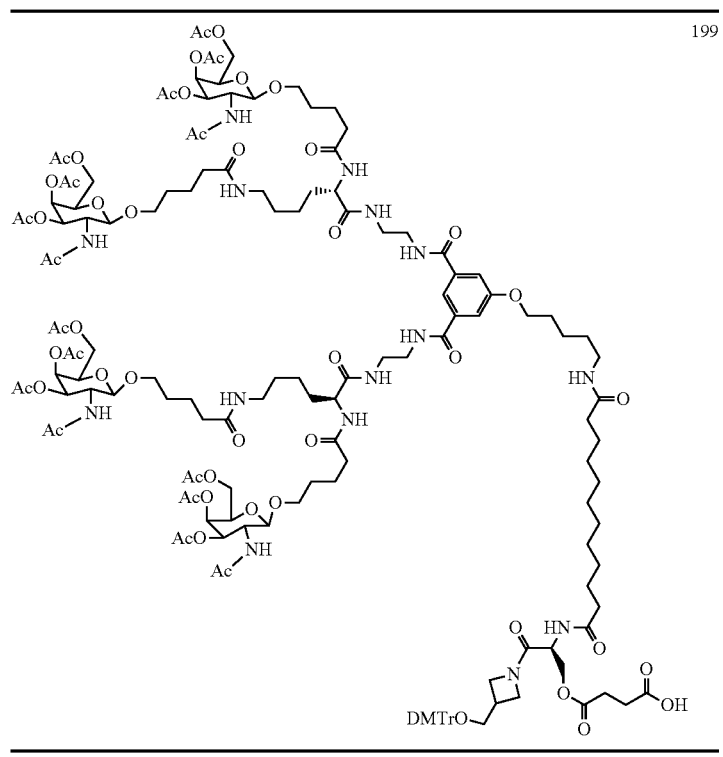
199
TABLE 22
| Compound | ESI-MS m/z |
|---|---|
| 191 | 1537(M + HCOOH)$^{2-}$ |
| 192 | 1584(M + HCOOH)$^{2-}$ |
| 193 | 1577(M + HCOOH)$^{2-}$ |
| 194 | 1577(M + HCOOH)$^{2-}$ |
| 195 | 1564(M + HCOOH)$^{2-}$ |
| 196 | 1578(M + HCOOH)$^{2-}$ |
TABLE 22-continued
| Compound | ESI-MS m/z |
|---|---|
| 197 | 1564(M + HCOOH)$^{2-}$ |
| 198 | 1584(M + HCOOH)$^{2-}$ |
| 199 | 1570(M + 2HCOOH)$^{2-}$ |
Synthesis of Compound 200

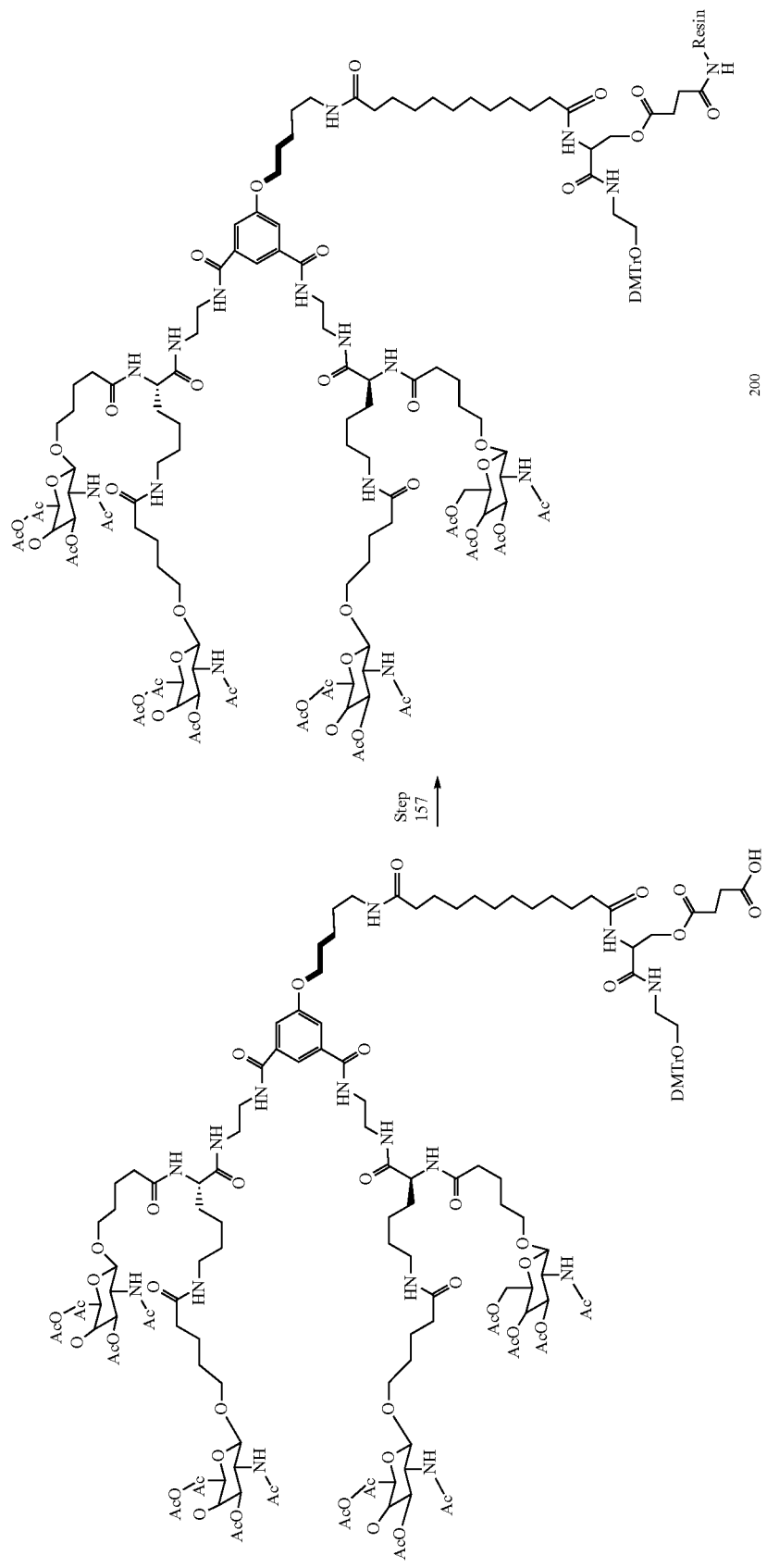

Step 157
Compound 200 (10.0 μmol/g) was obtained in the same way as in step 37 of Example 8 using compound 190 (g, mmol) synthesized in step 156.
Synthesis of compounds 201 to 209
The compounds described in Tables 23 and 24 were obtained in the same way as in step 157 using the compounds described in Tables 20 and 21.
The supported amounts of the compounds synthesized in this Example are shown in Table 25.
TABLE 23
201
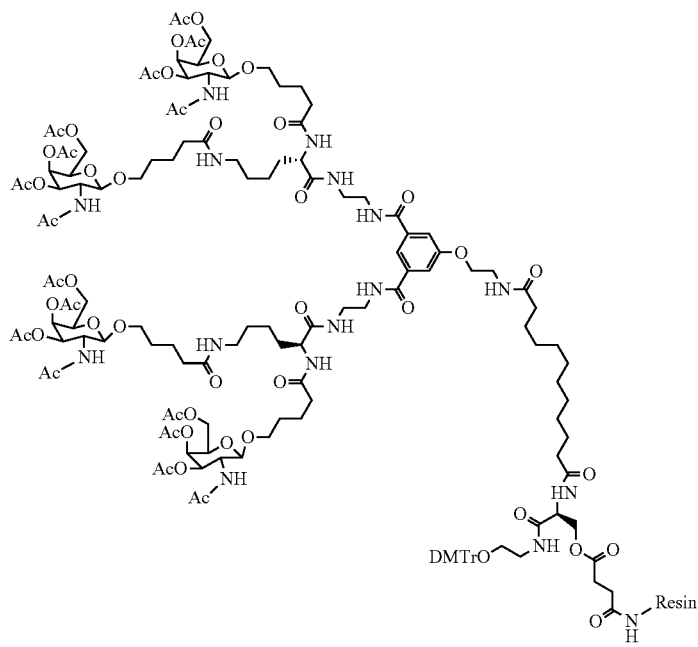
202
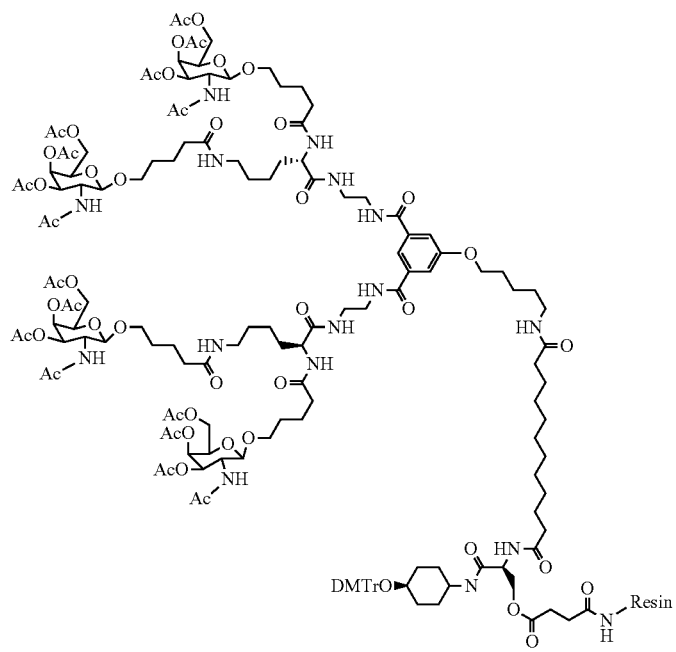

TABLE 23-continued
203
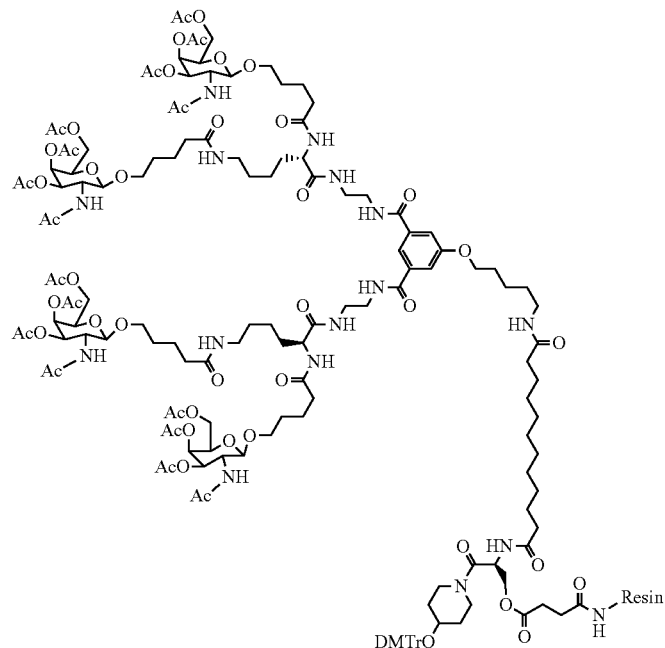
204
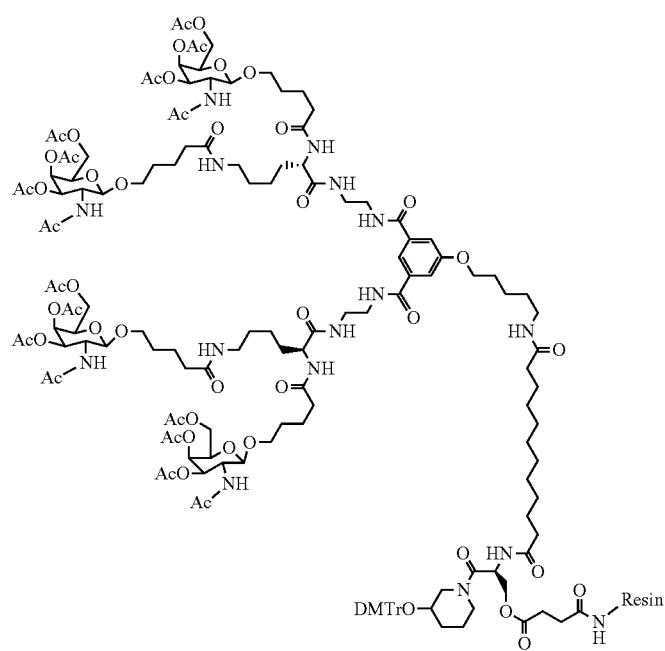

TABLE 23-continued
205
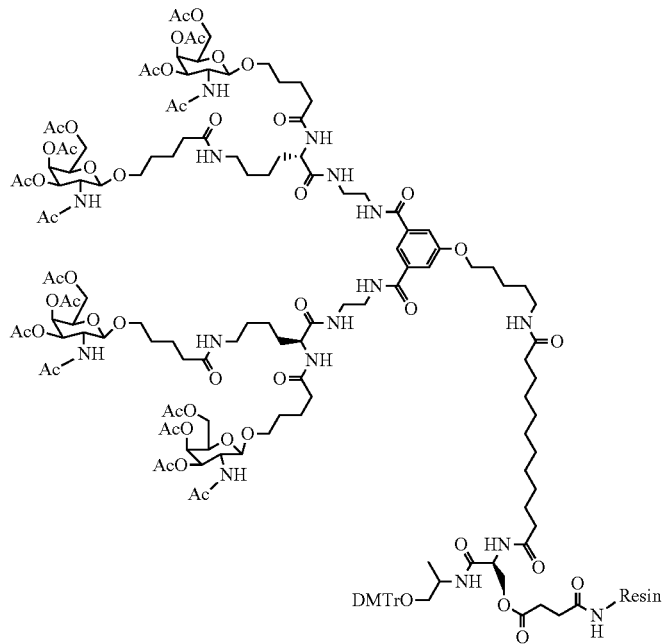
206
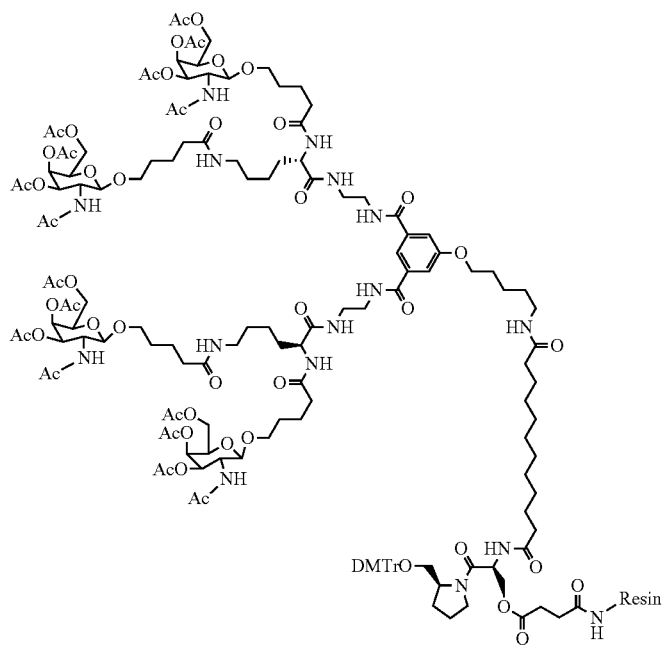

TABLE 24
207
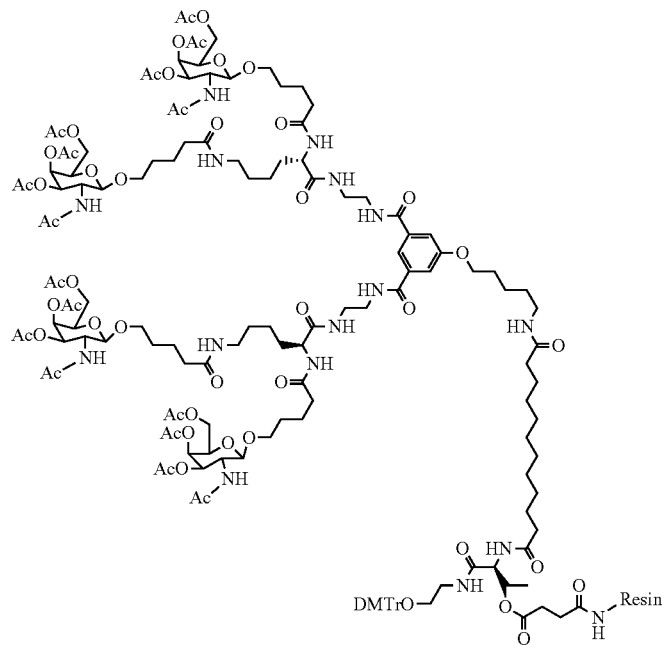
208
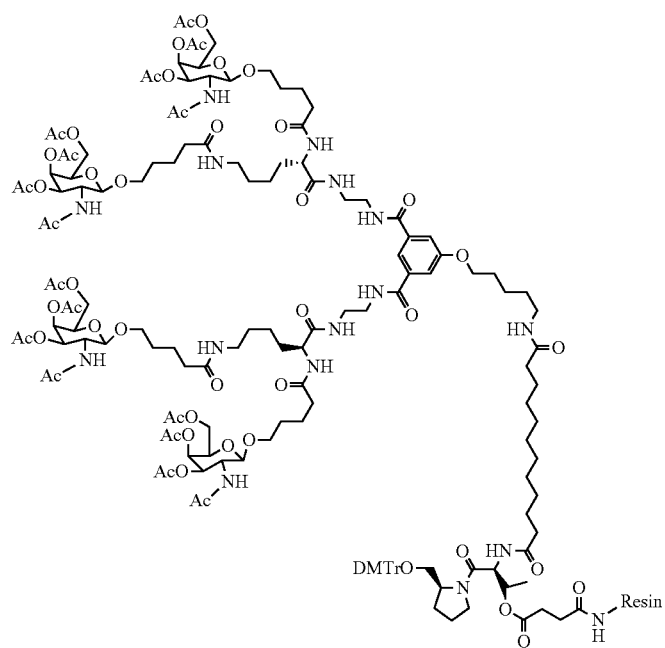

TABLE 24-continued

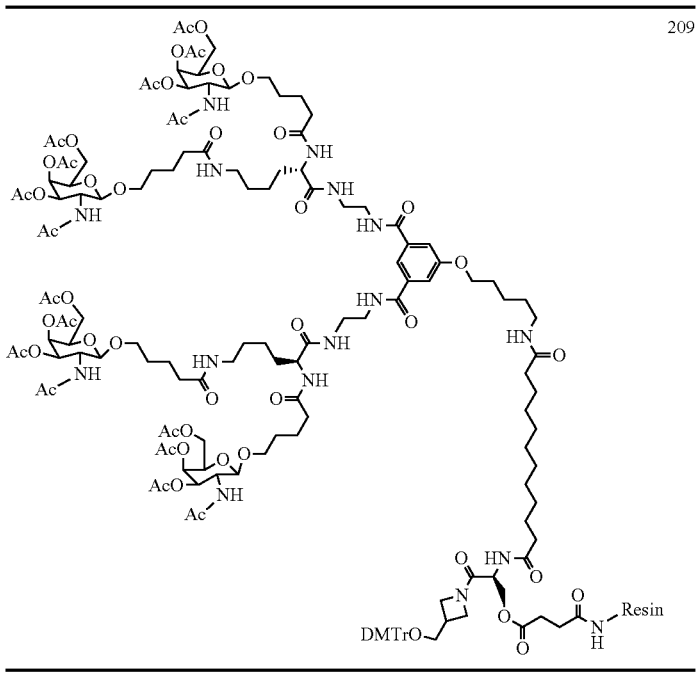

209

TABLE 25

| Compound | Supported amount (μmol/g) |
|---|---|
| 201 | 2.6 |
| 202 | 23.1 |
| 203 | 22.2 |
| 204 | 32.7 |
| 205 | 30.5 |
| 206 | 18.1 |
| 207 | 20.4 |
| 208 | 12.7 |
| 209 | 2.2 |

Example 15 Synthesis of Nucleic Acid Conjugate

Synthesis of Nucleic Acid Conjugates 210 to 218

The single-stranded nucleic acid conjugates described in Tables 27 and 28 were obtained in the same way as in step 38 of Example 9 using the compounds described in Table 26.

The sequences and mass spectrometry results of the nucleic acid conjugates synthesized in this Example are shown in Table 29.

TABLE 26

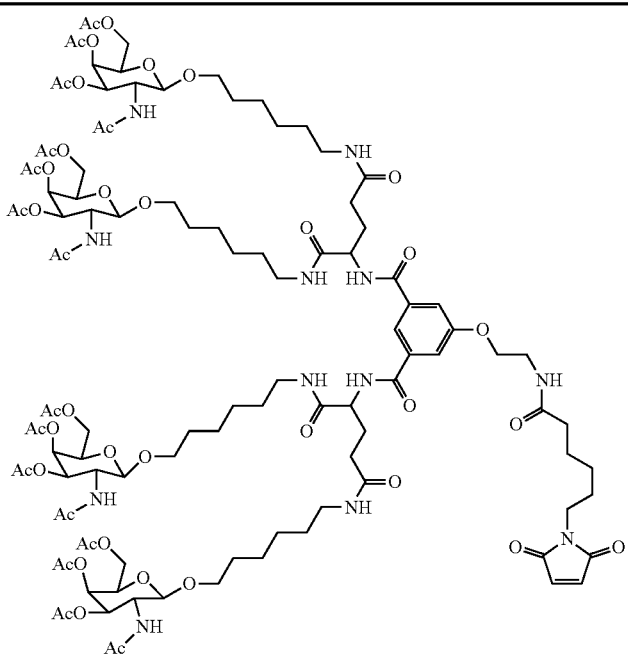

163

TABLE 26-continued
161
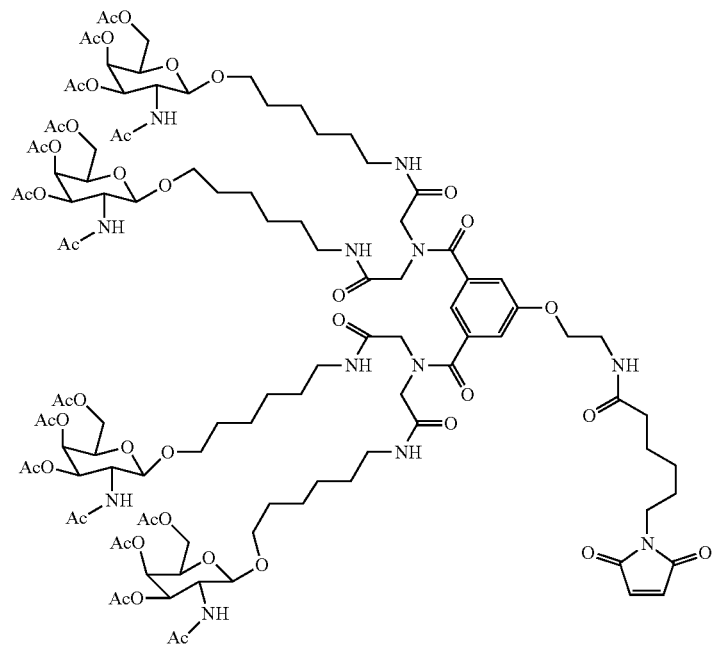 [SMILES: CC(=O)NC1C(OCCCCCCNC(=O)CN(CC(=O)NCCCCCCOC2OC(COC(C)=O)C(OC(C)=O)C(OC(C)=O)C2NC(C)=O)C(=O)c2cc(OCCNC(=O)CCCCCN3C(=O)C=CC3=O)cc(C(=O)N(CC(=O)NCCCCCCOC3OC(COC(C)=O)C(OC(C)=O)C(OC(C)=O)C3NC(C)=O)CC(=O)NCCCCCCOC3OC(COC(C)=O)C(OC(C)=O)C(OC(C)=O)C3NC(C)=O)c2)OC(COC(C)=O)C(OC(C)=O)C1OC(C)=O]
164
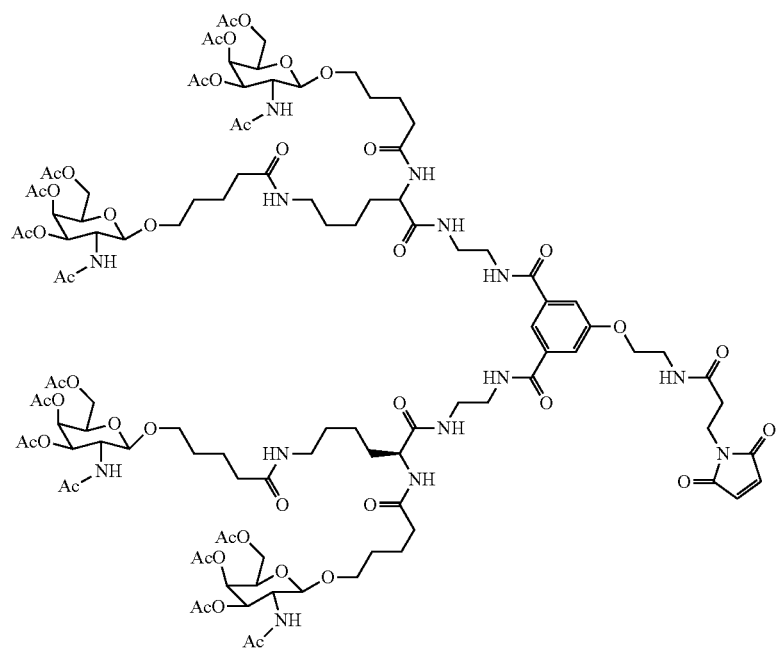 [SMILES: CC(=O)NC1C(OCCCCC(=O)NCCCCC(NC(=O)CCCCOC2OC(COC(C)=O)C(OC(C)=O)C(OC(C)=O)C2NC(C)=O)C(=O)NCCNC(=O)c2cc(OCCNC(=O)CCN3C(=O)C=CC3=O)cc(C(=O)NCCNC(=O)[C@H](CCCCNC(=O)CCCCOC3OC(COC(C)=O)C(OC(C)=O)C(OC(C)=O)C3NC(C)=O)NC(=O)CCCCOC3OC(COC(C)=O)C(OC(C)=O)C(OC(C)=O)C3NC(C)=O)c2)OC(COC(C)=O)C(OC(C)=O)C1OC(C)=O]

TABLE 26-continued
165
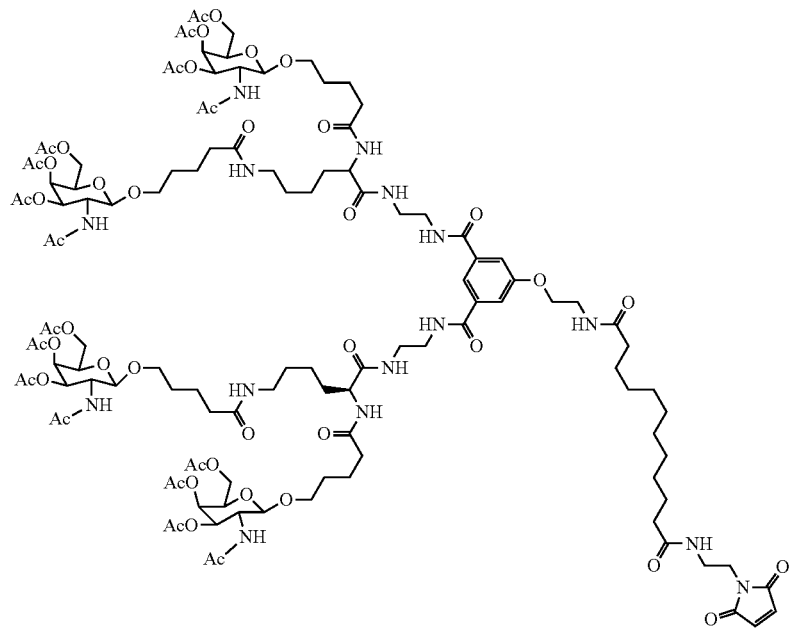 [SMILES: CC(=O)NC1C(OCCCCC(=O)NCCCCC(NC(=O)CCCCOC2OC(COC(C)=O)C(OC(C)=O)C(OC(C)=O)C2NC(C)=O)C(=O)NCCNC(=O)c2cc(OCCNC(=O)CCCCCCCCCCC(=O)NCCN3C(=O)C=CC3=O)cc(C(=O)NCCNC(=O)[C@H](CCCCNC(=O)CCCCOC3OC(COC(C)=O)C(OC(C)=O)C(OC(C)=O)C3NC(C)=O)NC(=O)CCCCOC3OC(COC(C)=O)C(OC(C)=O)C(OC(C)=O)C3NC(C)=O)c2)OC(COC(C)=O)C(OC(C)=O)C1OC(C)=O]
155
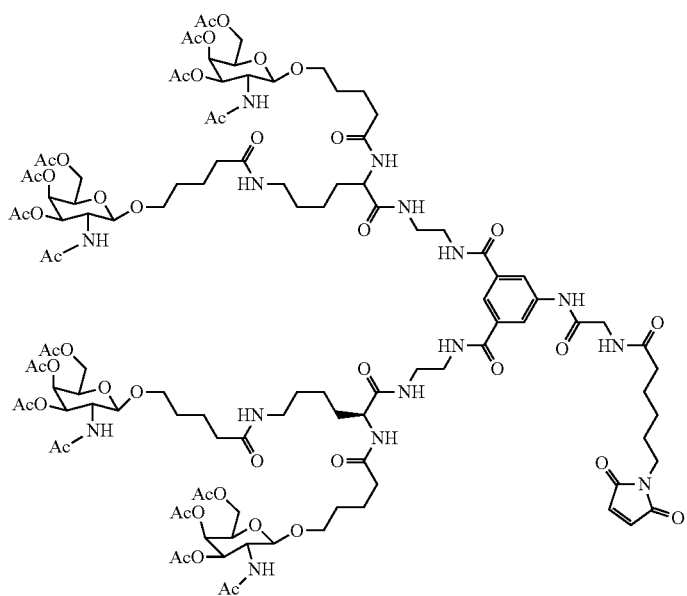 [SMILES: CC(=O)NC1C(OCCCCC(=O)NCCCCC(NC(=O)CCCCOC2OC(COC(C)=O)C(OC(C)=O)C(OC(C)=O)C2NC(C)=O)C(=O)NCCNC(=O)c2cc(NC(=O)CNC(=O)CCCCCN3C(=O)C=CC3=O)cc(C(=O)NCCNC(=O)[C@H](CCCCNC(=O)CCCCOC3OC(COC(C)=O)C(OC(C)=O)C(OC(C)=O)C3NC(C)=O)NC(=O)CCCCOC3OC(COC(C)=O)C(OC(C)=O)C(OC(C)=O)C3NC(C)=O)c2)OC(COC(C)=O)C(OC(C)=O)C1OC(C)=O]

TABLE 26-continued
32
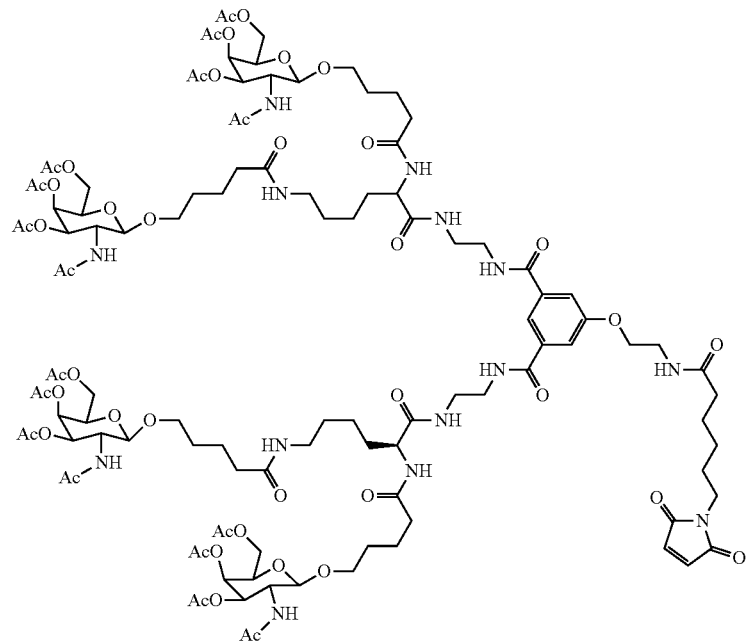 [SMILES: CC(=O)NC1C(OCCCCC(=O)NCCCCC(NC(=O)CCCCOC2OC(COC(C)=O)C(OC(C)=O)C(OC(C)=O)C2NC(C)=O)C(=O)NCCNC(=O)c2cc(OCCNC(=O)CCCCCN3C(=O)C=CC3=O)cc(C(=O)NCCNC(=O)[C@H](CCCCNC(=O)CCCCOC3OC(COC(C)=O)C(OC(C)=O)C(OC(C)=O)C3NC(C)=O)NC(=O)CCCCOC3OC(COC(C)=O)C(OC(C)=O)C(OC(C)=O)C3NC(C)=O)c2)OC(COC(C)=O)C(OC(C)=O)C1OC(C)=O]
157
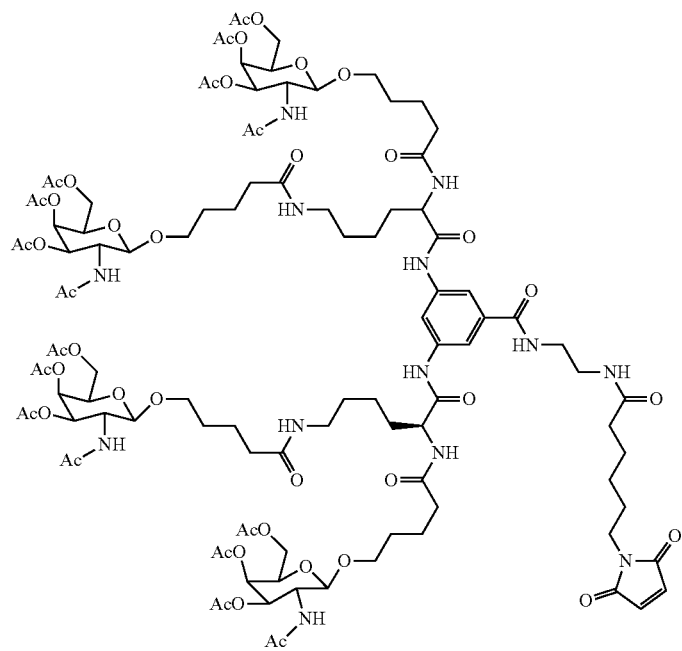 [SMILES: CC(=O)NC1C(OCCCCC(=O)NCCCCC(NC(=O)CCCCOC2OC(COC(C)=O)C(OC(C)=O)C(OC(C)=O)C2NC(C)=O)C(=O)Nc2cc(NC(=O)[C@H](CCCCNC(=O)CCCCOC3OC(COC(C)=O)C(OC(C)=O)C(OC(C)=O)C3NC(C)=O)NC(=O)CCCCOC3OC(COC(C)=O)C(OC(C)=O)C(OC(C)=O)C3NC(C)=O)cc(C(=O)NCCNC(=O)CCCCCN3C(=O)C=CC3=O)c2)OC(COC(C)=O)C(OC(C)=O)C1OC(C)=O]

TABLE 27
210
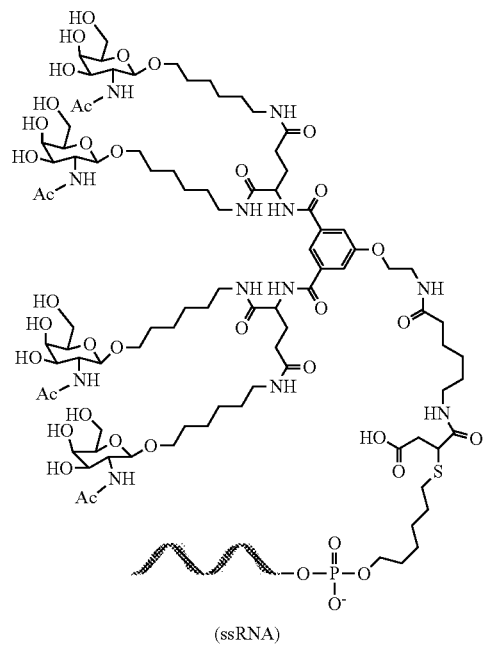 [SMILES: COP(=O)([O-])OCCCCCCSC(CC(=O)O)C(=O)NCCCCCC(=O)NCCOc1cc(C(=O)NC(CCC(=O)NCCCCCCOC2OC(CO)C(O)C(O)C2NC(C)=O)C(=O)NCCCCCCOC2OC(CO)C(O)C(O)C2NC(C)=O)cc(C(=O)NC(CCC(=O)NCCCCCCOC2OC(CO)C(O)C(O)C2NC(C)=O)C(=O)NCCCCCCOC2OC(CO)C(O)C(O)C2NC(C)=O)c1]
211
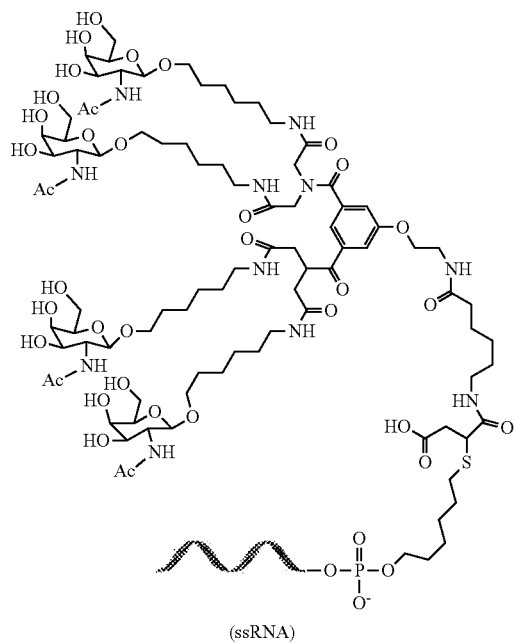 [SMILES: COP(=O)([O-])OCCCCCCSC(CC(=O)O)C(=O)NCCCCCC(=O)NCCOc1cc(C(=O)C(CC(=O)NCCCCCCOC2OC(CO)C(O)C(O)C2NC(C)=O)CC(=O)NCCCCCCOC2OC(CO)C(O)C(O)C2NC(C)=O)cc(C(=O)N(CC(=O)NCCCCCCOC2OC(CO)C(O)C(O)C2NC(C)=O)CC(=O)NCCCCCCOC2OC(CO)C(O)C(O)C2NC(C)=O)c1]

TABLE 27-continued
212
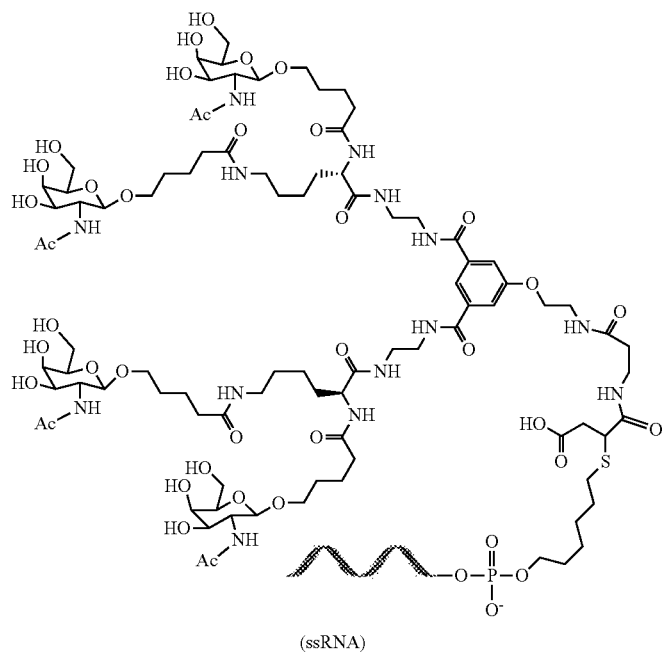 [SMILES: COP(=O)([O-])OCCCCCCSC(CC(=O)O)C(=O)NCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
213
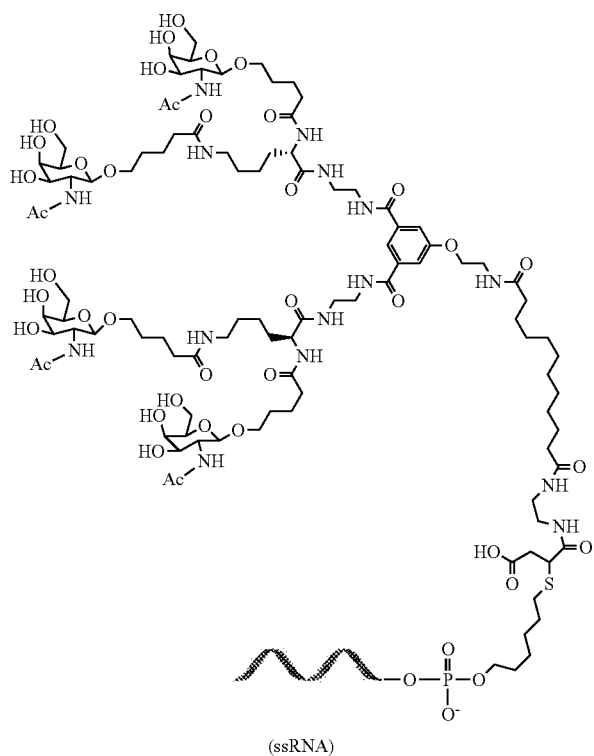 [SMILES: COP(=O)([O-])OCCCCCCSC(CC(=O)O)C(=O)NCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

TABLE 28
214
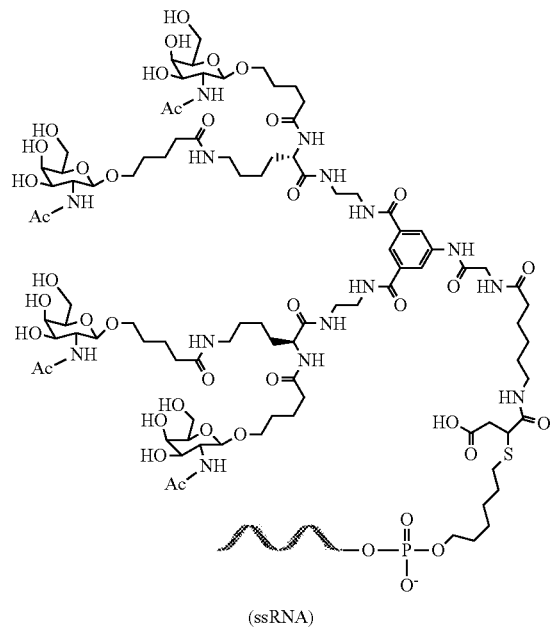 [SMILES: COP(=O)([O-])OCCCCCCSC(CC(=O)O)C(=O)NCCCCCC(=O)NCC(=O)Nc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
215
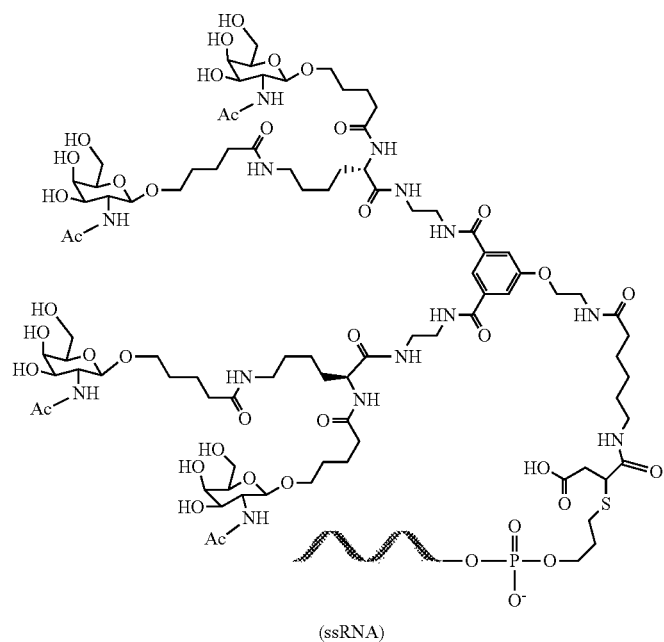 [SMILES: COP(=O)([O-])OCCCSC(CC(=O)O)C(=O)NCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

TABLE 28-continued
216
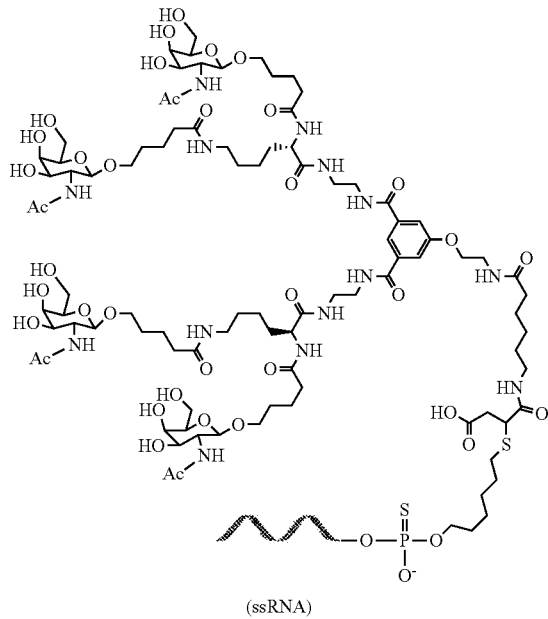 [SMILES: COP([O-])(=S)OCCCCCCSC(CC(=O)O)C(=O)NCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
(ssRNA)
217
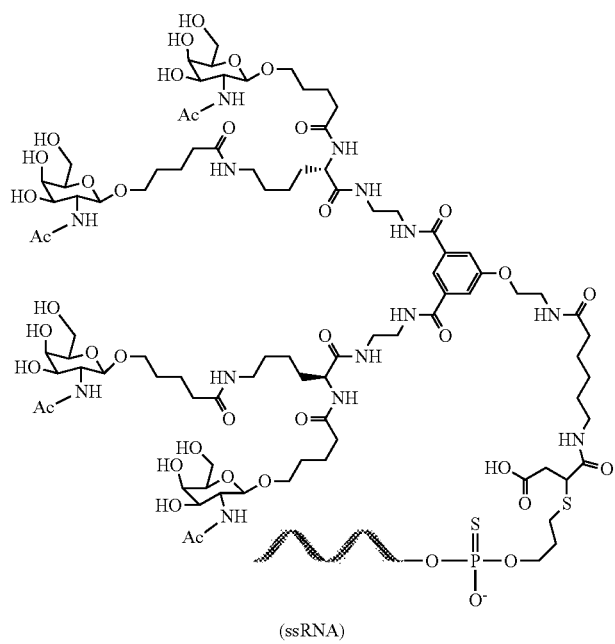 [SMILES: COP([O-])(=S)OCCCSC(CC(=O)O)C(=O)NCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
(ssRNA)

TABLE 28-continued

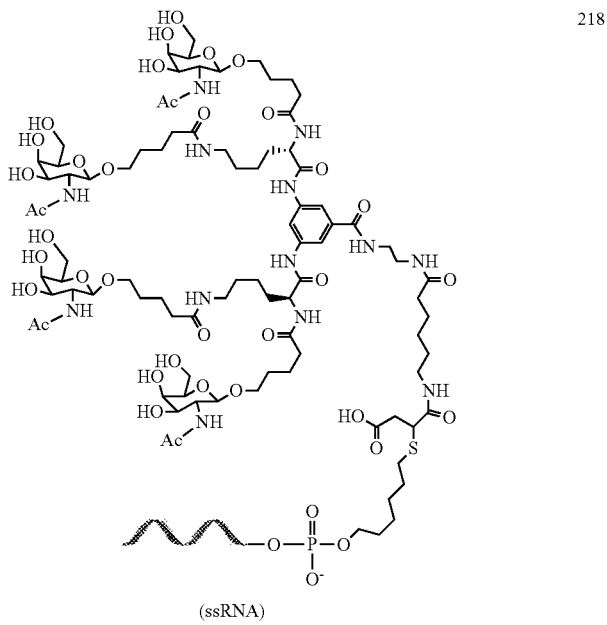

218

(ssRNA)

TABLE 29

| Compound | Sequence (5' to 3') | Theoretical molecular weight | Found |
|---|---|---|---|
| 210_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 210 | 8885 | 8886 |
| 211_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 211 | 8857 | 8857 |
| 212_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 212 | 8929 | 8928 |
| 213_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 213 | 9112 | 9110 |
| 214_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 214 | 8983 | 8982 |
| 215_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 215 | 8929 | 8929 |
| 216_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 216 | 8988 | 8985 |
| 217_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 217 | 8946 | 8943 |
| 218_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 218 | 8854 | 8854 |

Synthesis of Nucleic Acid Conjugate 219
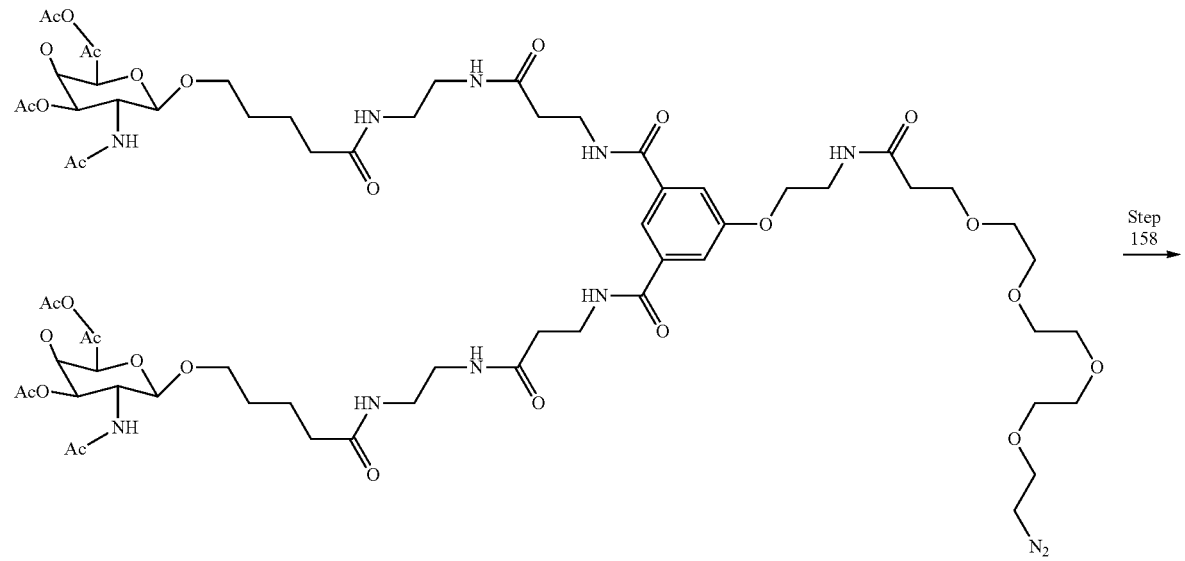
168
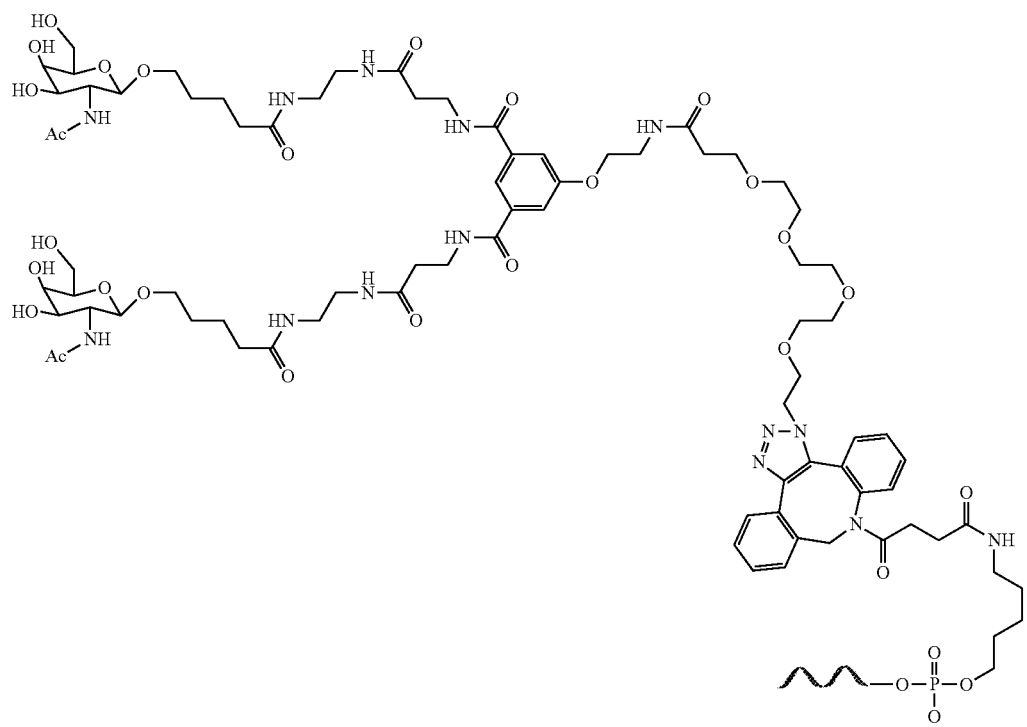
219 (ssRNA)

Step 158

Single-stranded nucleic acid conjugate 219 described in Table 30 was obtained in the same way as in step 40 of Example 10 using compound 168 synthesized in step 134.

The sequence and mass spectrometry results of the nucleic acid conjugate synthesized in this Example are shown in Table 30.

TABLE 30

| Compound | Sequence (5' to 3') | Theoretical molecular weight | Found |
|---|---|---|---|
| 219_5'-B2M-ssRNA | 219 A(F)G(M)G(F)A(M)C(F)U(M)G(F)G(M)U(F)C(M)U(F)U(F)U(M)C(F)U(M)A(F)U(M)C(F)U(M)^C(F)^U(M) | 9529 | 9528 |

Synthesis of Nucleic Acid Conjugate 223

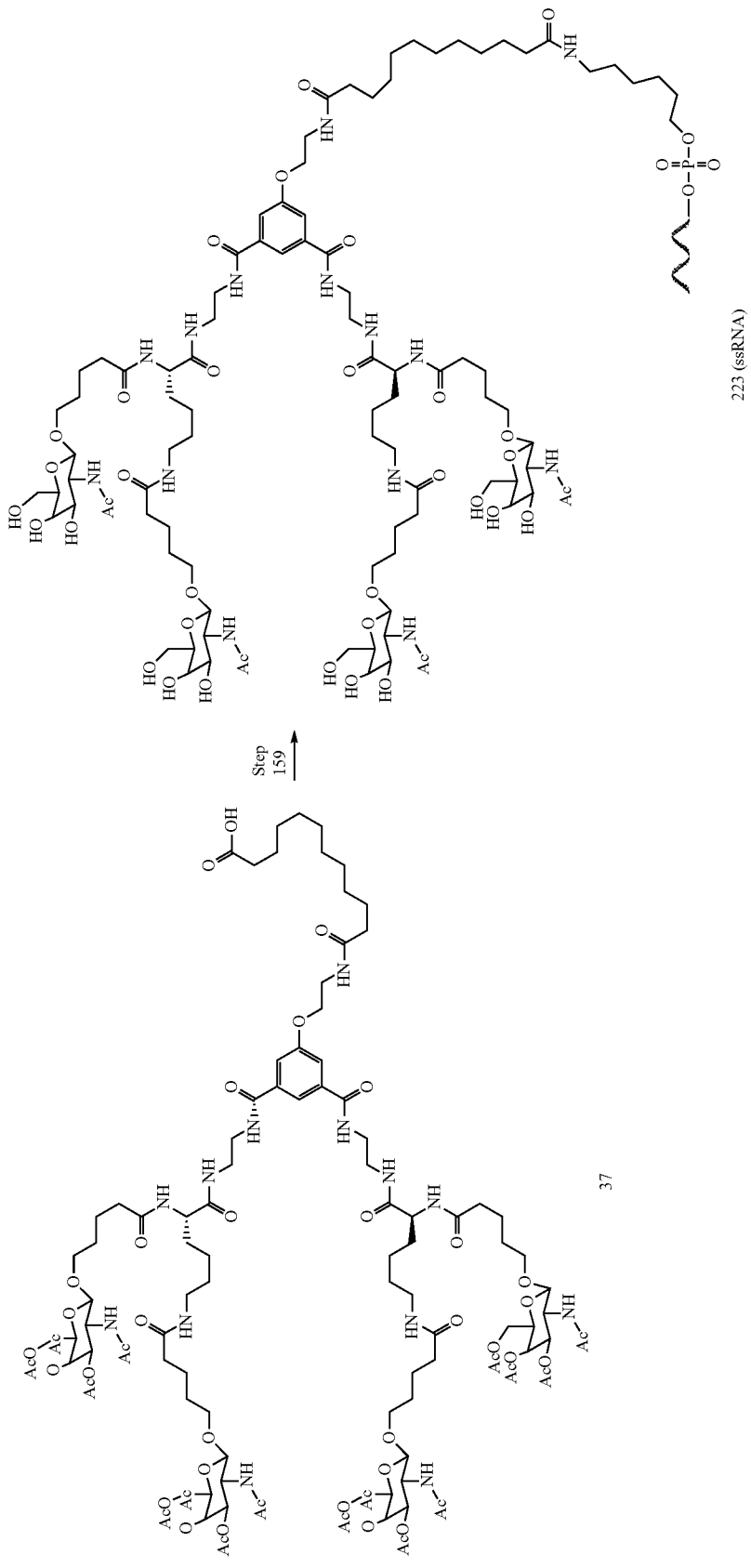

Step 159

Compound 37 synthesized in step 34 of Example 8 and a terminally amino group-modified oligonucleotide synthesized by the method described in Molecules, Vol. 17, p. 13825-13843, 2012 were added and reacted by the method described in Bioconjugate Chemistry, Vol. 22, p. 1723-1728, 2011 or Bioconjugate Chemistry, Vol. 26, p. 1451-1455, 2015. Single-stranded nucleic acid conjugate 223 was obtained by purification by the method described in step 38 of Example 9.

Synthesis of nucleic acid conjugates 220 to 233

The single-stranded nucleic acid conjugates described in Tables 33 to 35 were obtained in the same way as in step 159 of Example 15 using the compounds described in Tables 31 and 32.

The sequences and mass spectrometry results of the nucleic acid conjugates synthesized in this Example are shown in Table 36.

TABLE 31

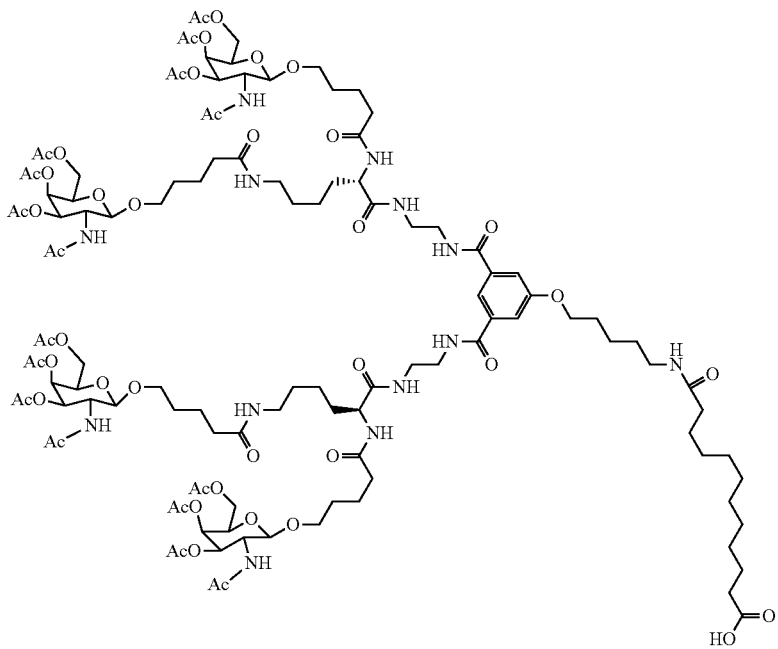 [SMILES: CC(=O)NC1C(OCCCCC(=O)NCCCC[C@H](NC(=O)CCCCOC2OC(COC(C)=O)C(OC(C)=O)C(OC(C)=O)C2NC(C)=O)C(=O)NCCNC(=O)c2cc(OCCCCCNC(=O)CCCCCCCCCCC(=O)O)cc(C(=O)NCCNC(=O)[C@H](CCCCNC(=O)CCCCOC3OC(COC(C)=O)C(OC(C)=O)C(OC(C)=O)C3NC(C)=O)NC(=O)CCCCOC3OC(COC(C)=O)C(OC(C)=O)C(OC(C)=O)C3NC(C)=O)c2)OC(COC(C)=O)C(OC(C)=O)C1OC(C)=O]

158

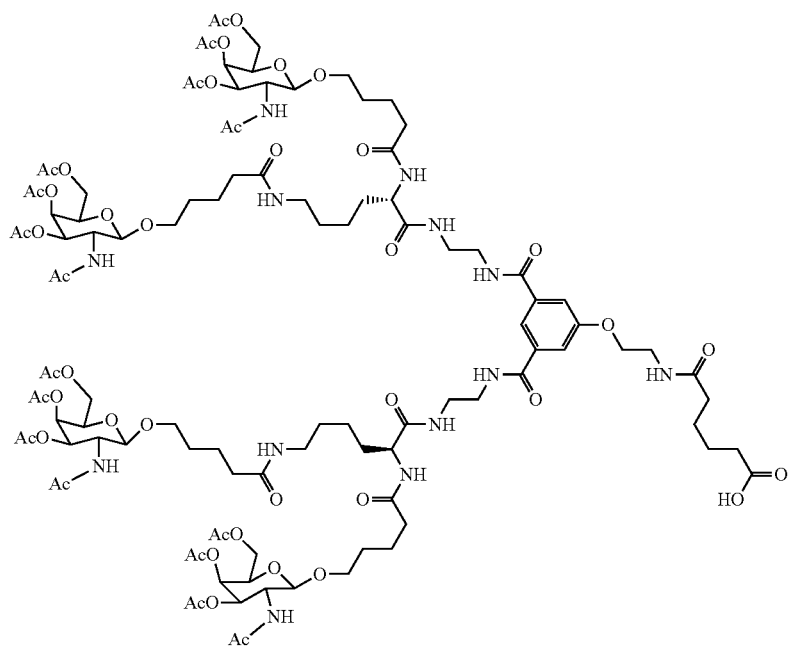 [SMILES: CC(=O)NC1C(OCCCCC(=O)NCCCC[C@H](NC(=O)CCCCOC2OC(COC(C)=O)C(OC(C)=O)C(OC(C)=O)C2NC(C)=O)C(=O)NCCNC(=O)c2cc(OCCNC(=O)CCCCC(=O)O)cc(C(=O)NCCNC(=O)[C@H](CCCCNC(=O)CCCCOC3OC(COC(C)=O)C(OC(C)=O)C(OC(C)=O)C3NC(C)=O)NC(=O)CCCCOC3OC(COC(C)=O)C(OC(C)=O)C(OC(C)=O)C3NC(C)=O)c2)OC(COC(C)=O)C(OC(C)=O)C1OC(C)=O]

167

TABLE 31-continued
137
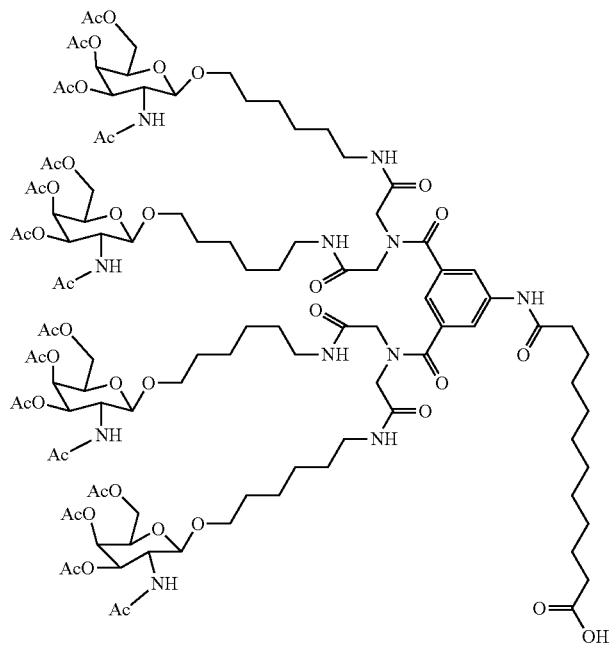 [SMILES: CC(=O)NC1C(OCCCCCCNC(=O)CN(CC(=O)NCCCCCCOC2OC(COC(C)=O)C(OC(C)=O)C(OC(C)=O)C2NC(C)=O)C(=O)c2cc(NC(=O)CCCCCCCCCCC(=O)O)cc(C(=O)N(CC(=O)NCCCCCCOC3OC(COC(C)=O)C(OC(C)=O)C(OC(C)=O)C3NC(C)=O)CC(=O)NCCCCCCOC3OC(COC(C)=O)C(OC(C)=O)C(OC(C)=O)C3NC(C)=O)c2)OC(COC(C)=O)C(OC(C)=O)C1OC(C)=O]
37
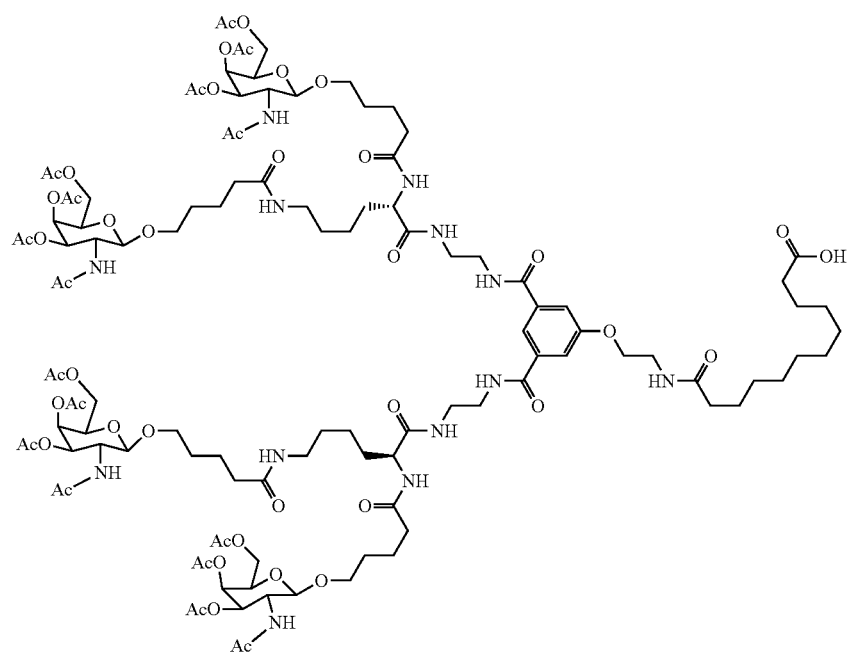 [SMILES: CC(=O)NC1C(OCCCCC(=O)NCCCC[C@H](NC(=O)CCCCOC2OC(COC(C)=O)C(OC(C)=O)C(OC(C)=O)C2NC(C)=O)C(=O)NCCNC(=O)c2cc(OCCNC(=O)CCCCCCCCCCC(=O)O)cc(C(=O)NCCNC(=O)[C@H](CCCCNC(=O)CCCCOC3OC(COC(C)=O)C(OC(C)=O)C(OC(C)=O)C3NC(C)=O)NC(=O)CCCCOC3OC(COC(C)=O)C(OC(C)=O)C(OC(C)=O)C3NC(C)=O)c2)OC(COC(C)=O)C(OC(C)=O)C1OC(C)=O]

TABLE 31-continued
143
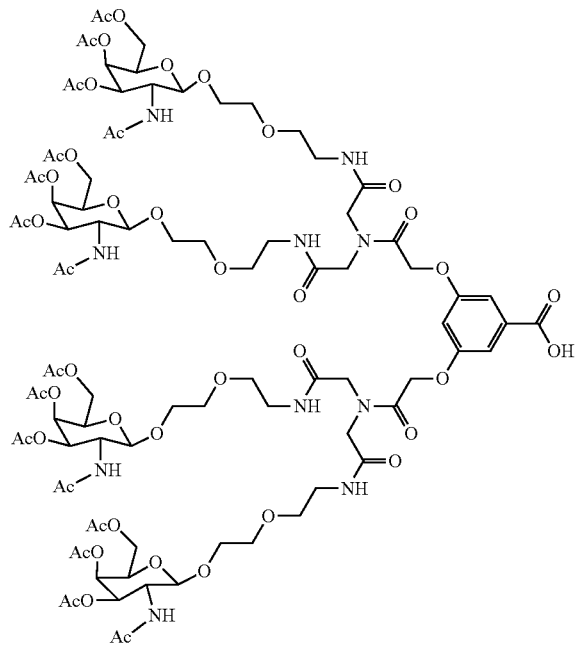 [SMILES: CC(=O)NC1C(OCCOCCNC(=O)CN(CC(=O)NCCOCCOC2OC(COC(C)=O)C(OC(C)=O)C(OC(C)=O)C2NC(C)=O)C(=O)COc2cc(OCC(=O)N(CC(=O)NCCOCCOC3OC(COC(C)=O)C(OC(C)=O)C(OC(C)=O)C3NC(C)=O)CC(=O)NCCOCCOC3OC(COC(C)=O)C(OC(C)=O)C(OC(C)=O)C3NC(C)=O)cc(C(=O)O)c2)OC(COC(C)=O)C(OC(C)=O)C1OC(C)=O]
145
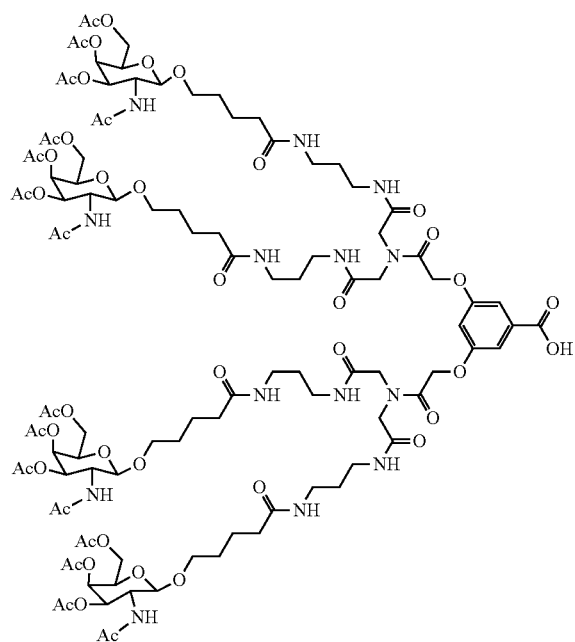 [SMILES: CC(=O)NC1C(OCCCCC(=O)NCCCNC(=O)CN(CC(=O)NCCCNC(=O)CCCCOC2OC(COC(C)=O)C(OC(C)=O)C(OC(C)=O)C2NC(C)=O)C(=O)COc2cc(OCC(=O)N(CC(=O)NCCCNC(=O)CCCCOC3OC(COC(C)=O)C(OC(C)=O)C(OC(C)=O)C3NC(C)=O)CC(=O)NCCCNC(=O)CCCCOC3OC(COC(C)=O)C(OC(C)=O)C(OC(C)=O)C3NC(C)=O)cc(C(=O)O)c2)OC(COC(C)=O)C(OC(C)=O)C1OC(C)=O]

TABLE 32
139
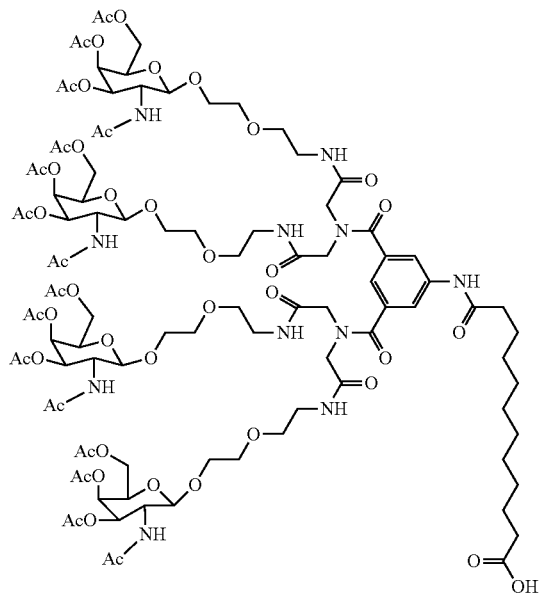 [SMILES: CC(=O)NC1C(OCCOCCNC(=O)CN(CC(=O)NCCOCCOC2OC(COC(C)=O)C(OC(C)=O)C(OC(C)=O)C2NC(C)=O)C(=O)c2cc(NC(=O)CCCCCCCCCCC(=O)O)cc(C(=O)N(CC(=O)NCCOCCOC3OC(COC(C)=O)C(OC(C)=O)C(OC(C)=O)C3NC(C)=O)CC(=O)NCCOCCOC3OC(COC(C)=O)C(OC(C)=O)C(OC(C)=O)C3NC(C)=O)c2)OC(COC(C)=O)C(OC(C)=O)C1OC(C)=O]
141
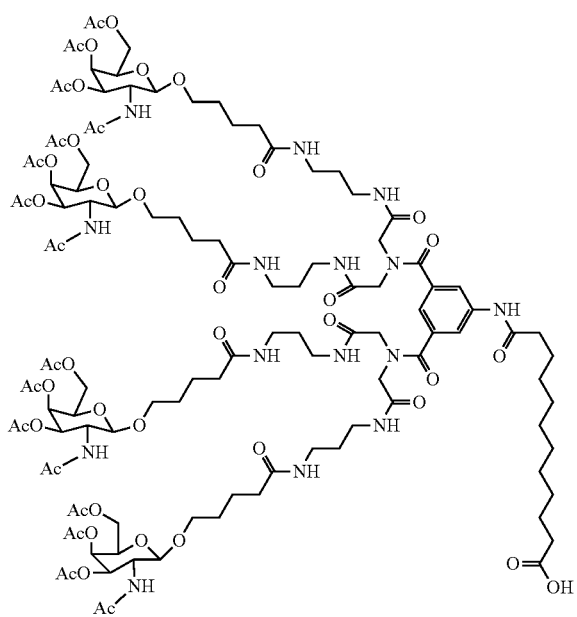 [SMILES: CC(=O)NC1C(OCCCCC(=O)NCCCNC(=O)CN(CC(=O)NCCCNC(=O)CCCCOC2OC(COC(C)=O)C(OC(C)=O)C(OC(C)=O)C2NC(C)=O)C(=O)c2cc(NC(=O)CCCCCCCCCCC(=O)O)cc(C(=O)N(CC(=O)NCCCNC(=O)CCCCOC3OC(COC(C)=O)C(OC(C)=O)C(OC(C)=O)C3NC(C)=O)CC(=O)NCCCNC(=O)CCCCOC3OC(COC(C)=O)C(OC(C)=O)C(OC(C)=O)C3NC(C)=O)c2)OC(COC(C)=O)C(OC(C)=O)C1OC(C)=O]

TABLE 32-continued
149
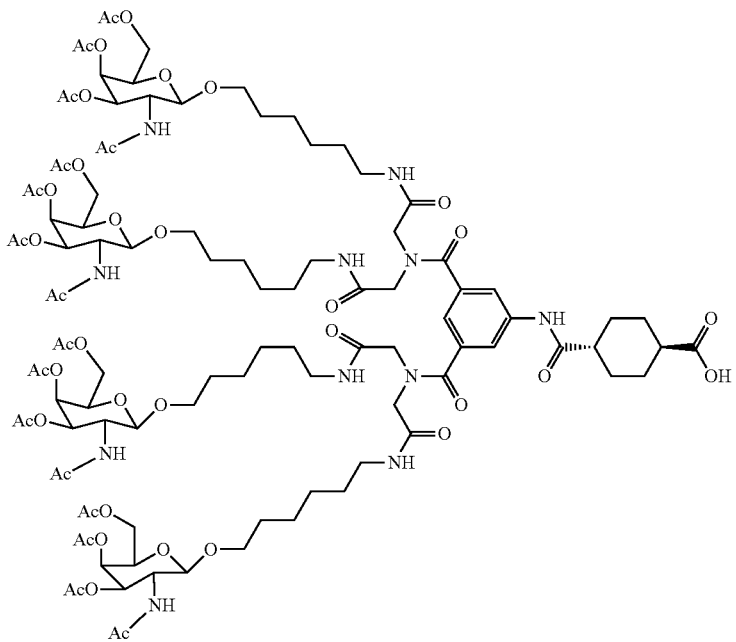 [SMILES: CC(=O)NC1C(OCCCCCCNC(=O)CN(CC(=O)NCCCCCCOC2OC(COC(C)=O)C(OC(C)=O)C(OC(C)=O)C2NC(C)=O)C(=O)c2cc(NC(=O)[C@H]3CC[C@H](C(=O)O)CC3)cc(C(=O)N(CC(=O)NCCCCCCOC3OC(COC(C)=O)C(OC(C)=O)C(OC(C)=O)C3NC(C)=O)CC(=O)NCCCCCCOC3OC(COC(C)=O)C(OC(C)=O)C(OC(C)=O)C3NC(C)=O)c2)OC(COC(C)=O)C(OC(C)=O)C1OC(C)=O]
151
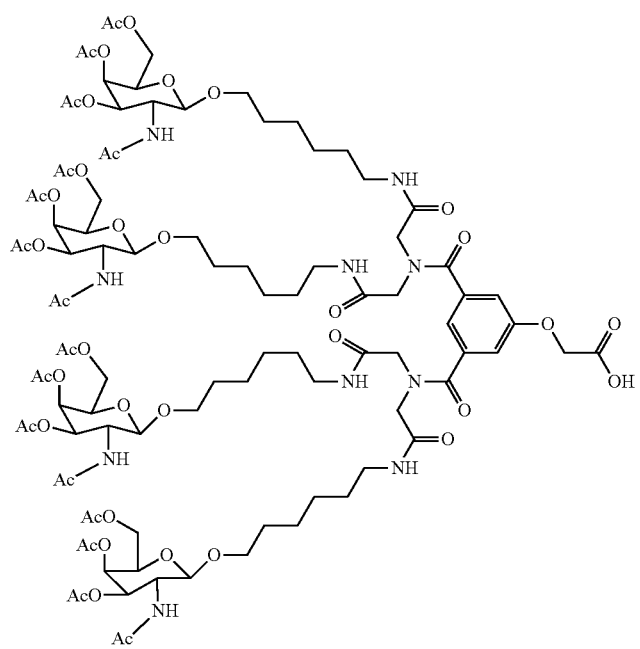 [SMILES: CC(=O)NC1C(OCCCCCCNC(=O)CN(CC(=O)NCCCCCCOC2OC(COC(C)=O)C(OC(C)=O)C(OC(C)=O)C2NC(C)=O)C(=O)c2cc(OCC(=O)O)cc(C(=O)N(CC(=O)NCCCCCCOC3OC(COC(C)=O)C(OC(C)=O)C(OC(C)=O)C3NC(C)=O)CC(=O)NCCCCCCOC3OC(COC(C)=O)C(OC(C)=O)C(OC(C)=O)C3NC(C)=O)c2)OC(COC(C)=O)C(OC(C)=O)C1OC(C)=O]

TABLE 32-continued
153
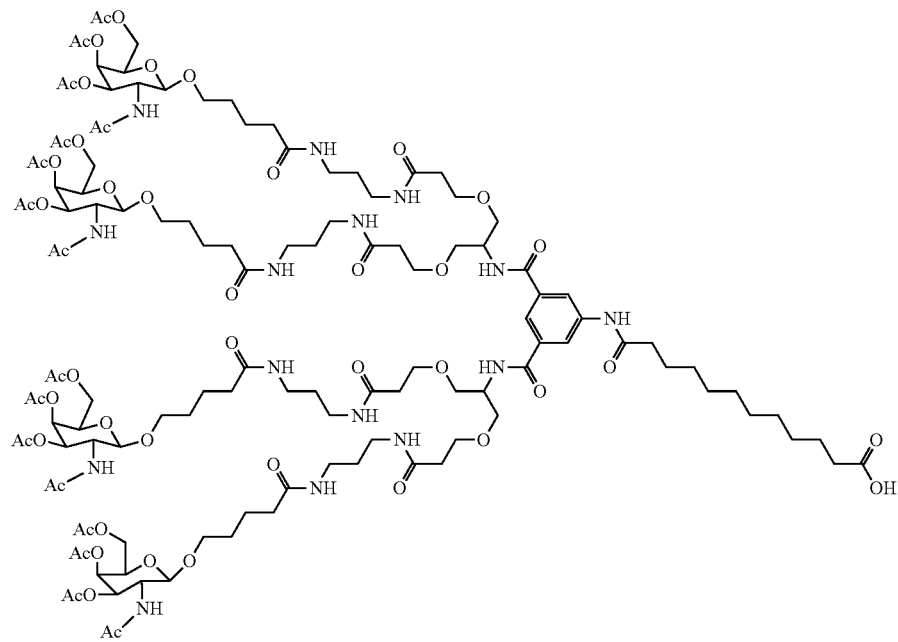 [SMILES: CC(=O)NC1C(OCCCCC(=O)NCCCNC(=O)CCOCC(COCCC(=O)NCCCNC(=O)CCCCOC2OC(COC(C)=O)C(OC(C)=O)C(OC(C)=O)C2NC(C)=O)NC(=O)c2cc(NC(=O)CCCCCCCCCCC(=O)O)cc(C(=O)NC(COCCC(=O)NCCCNC(=O)CCCCOC3OC(COC(C)=O)C(OC(C)=O)C(OC(C)=O)C3NC(C)=O)COCCC(=O)NCCCNC(=O)CCCCOC3OC(COC(C)=O)C(OC(C)=O)C(OC(C)=O)C3NC(C)=O)c2)OC(COC(C)=O)C(OC(C)=O)C1OC(C)=O]
TABLE 33
220
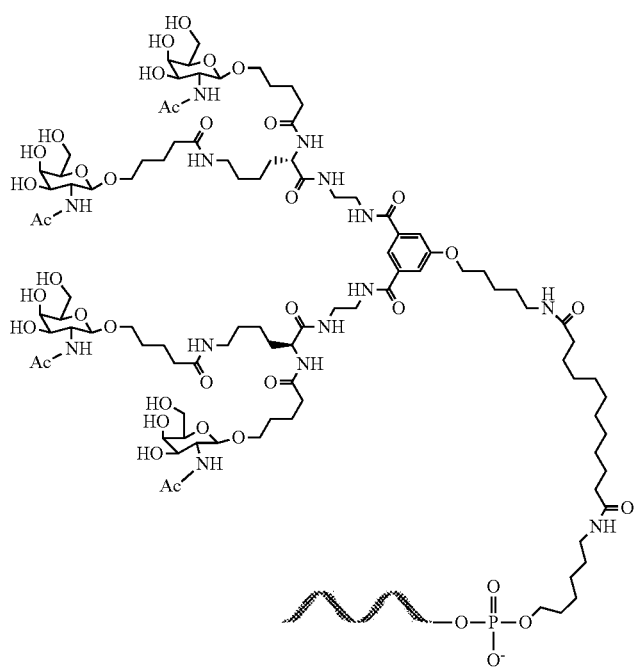
(ssRNA)

TABLE 33-continued
221
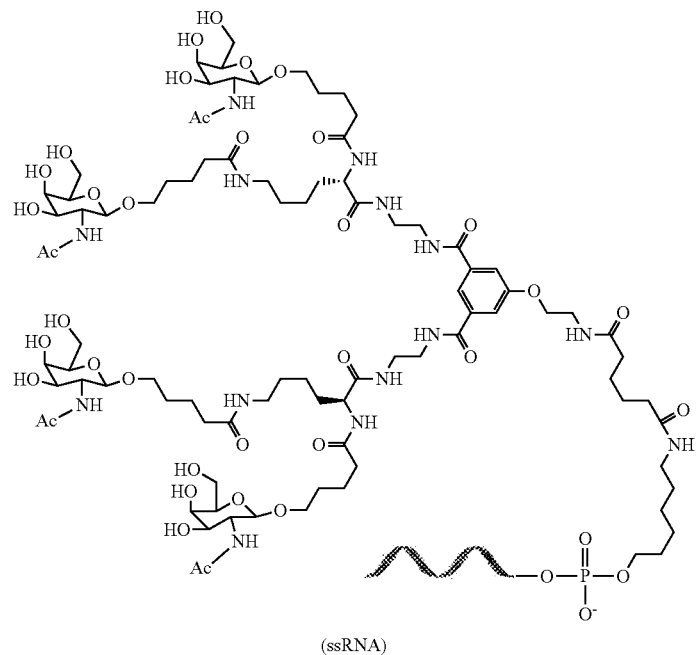 [SMILES: COP(=O)([O-])OCCCCCCNC(=O)CCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
(ssRNA)
222
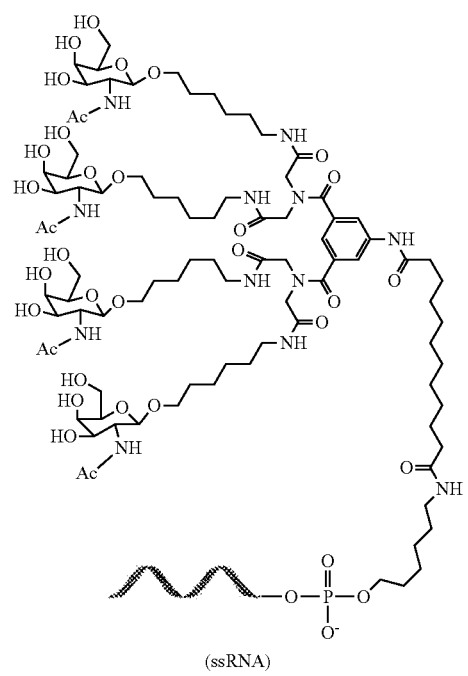 [SMILES: COP(=O)([O-])OCCCCCCNC(=O)CCCCCCCCCCC(=O)Nc1cc(C(=O)N(CC(=O)NCCCCCCOC2OC(CO)C(O)C(O)C2NC(C)=O)CC(=O)NCCCCCCOC2OC(CO)C(O)C(O)C2NC(C)=O)cc(C(=O)N(CC(=O)NCCCCCCOC2OC(CO)C(O)C(O)C2NC(C)=O)CC(=O)NCCCCCCOC2OC(CO)C(O)C(O)C2NC(C)=O)c1]
(ssRNA)

TABLE 33-continued
223
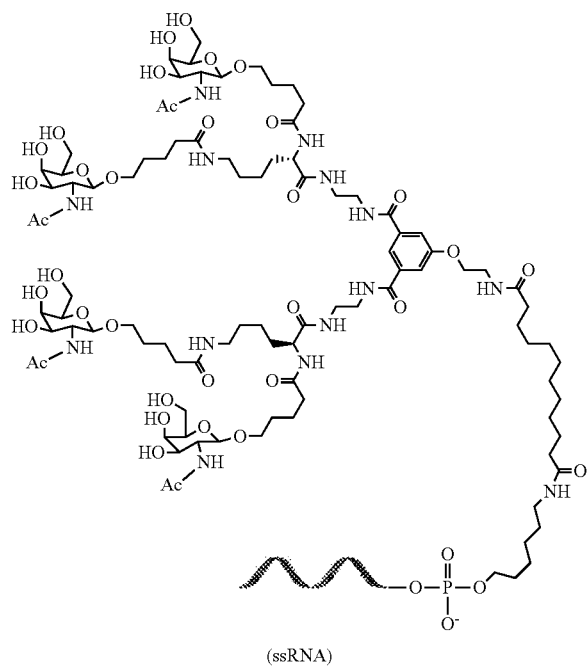 [SMILES: COP(=O)([O-])OCCCCCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
(ssRNA)
TABLE 34
224
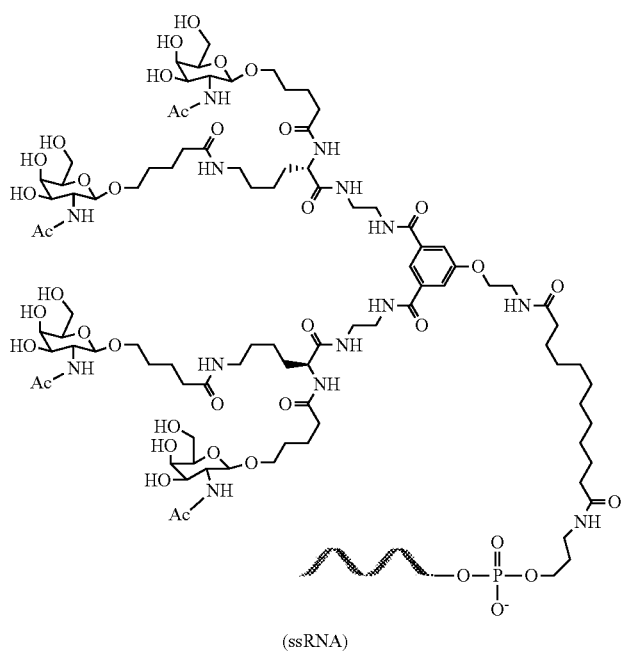 [SMILES: COP(=O)([O-])OCCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
(ssRNA)

TABLE 34-continued
225
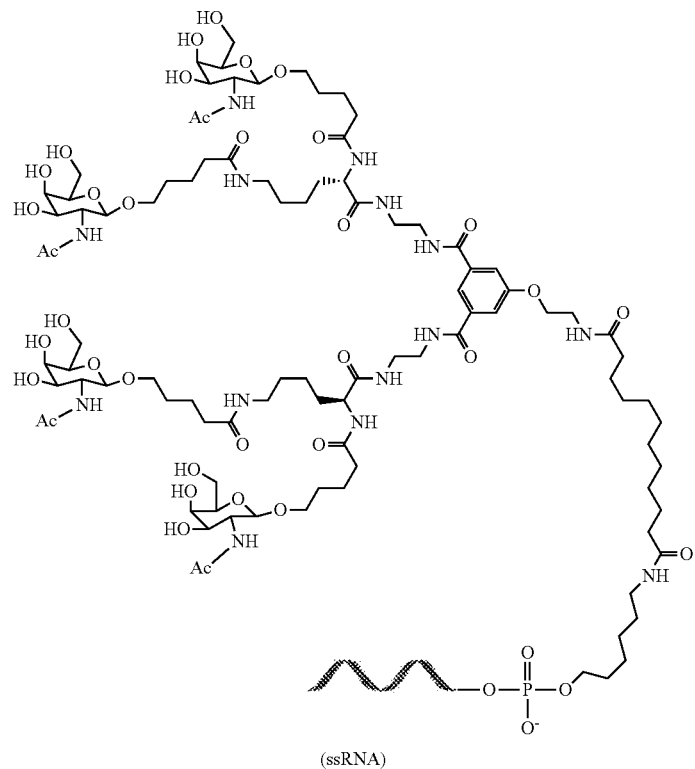 [SMILES: COP(=O)([O-])OCCCCCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
(ssRNA)
226
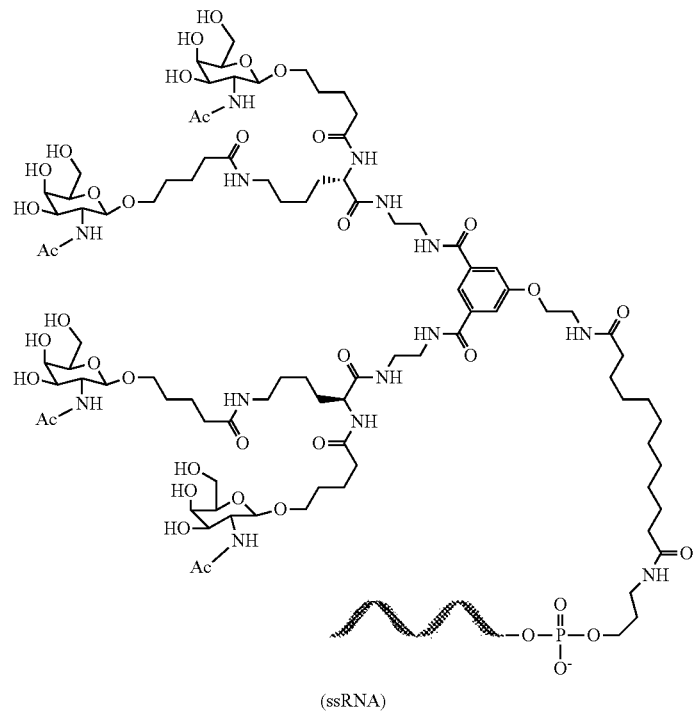 [SMILES: COP(=O)([O-])OCCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
(ssRNA)

TABLE 34-continued
227
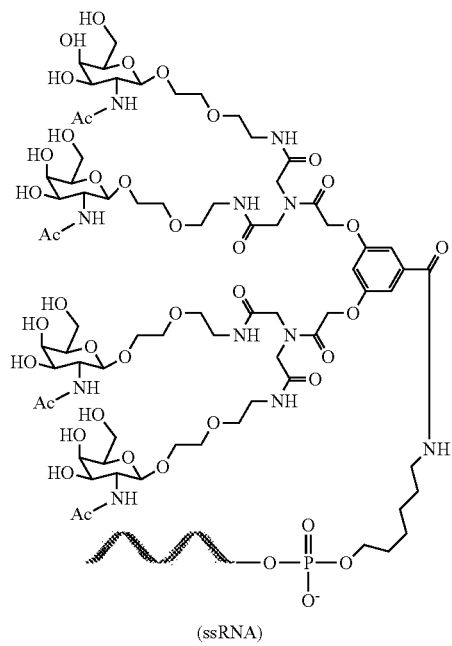 [SMILES: COP(=O)([O-])OCCCCCCNC(=O)c1cc(OCC(=O)N(CC(=O)NCCOCCOC2OC(CO)C(O)C(O)C2NC(C)=O)CC(=O)NCCOCCOC2OC(CO)C(O)C(O)C2NC(C)=O)cc(OCC(=O)N(CC(=O)NCCOCCOC2OC(CO)C(O)C(O)C2NC(C)=O)CC(=O)NCCOCCOC2OC(CO)C(O)C(O)C2NC(C)=O)c1]
(ssRNA)
TABLE 35
228
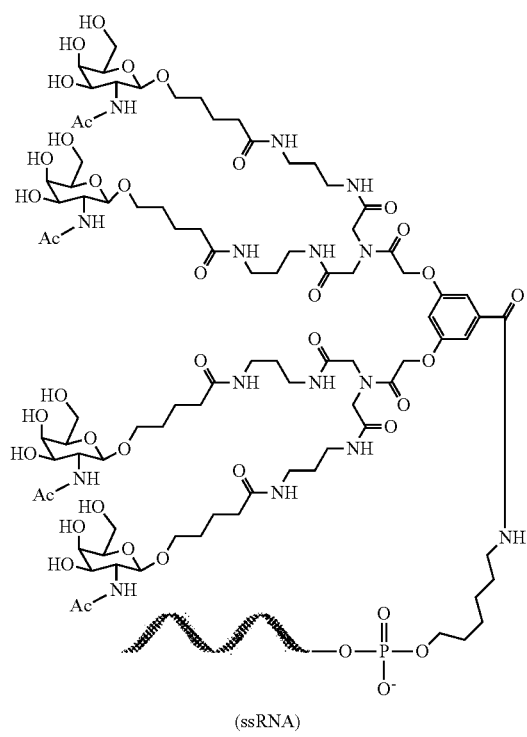 [SMILES: COP(=O)([O-])OCCCCCCNC(=O)c1cc(OCC(=O)N(CC(=O)NCCCNC(=O)CCCCOC2OC(CO)C(O)C(O)C2NC(C)=O)CC(=O)NCCCNC(=O)CCCCOC2OC(CO)C(O)C(O)C2NC(C)=O)cc(OCC(=O)N(CC(=O)NCCCNC(=O)CCCCOC2OC(CO)C(O)C(O)C2NC(C)=O)CC(=O)NCCCNC(=O)CCCCOC2OC(CO)C(O)C(O)C2NC(C)=O)c1]
(ssRNA)

TABLE 35-continued
229
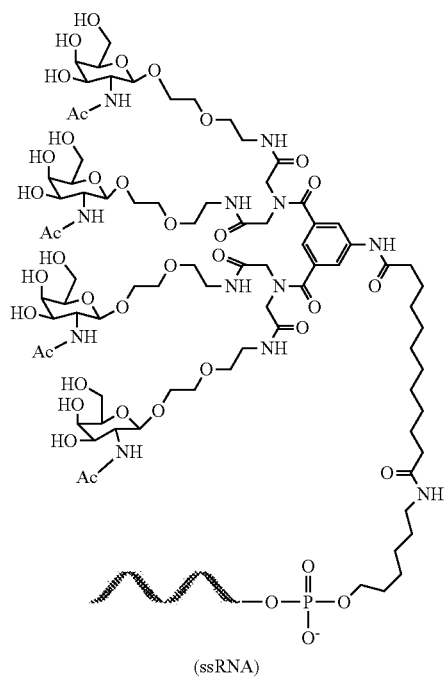 [SMILES: COP(=O)([O-])OCCCCCCNC(=O)CCCCCCCCCCC(=O)Nc1cc(C(=O)N(CC(=O)NCCOCCOC2OC(CO)C(O)C(O)C2NC(C)=O)CC(=O)NCCOCCOC2OC(CO)C(O)C(O)C2NC(C)=O)cc(C(=O)N(CC(=O)NCCOCCOC2OC(CO)C(O)C(O)C2NC(C)=O)CC(=O)NCCOCCOC2OC(CO)C(O)C(O)C2NC(C)=O)c1]
(ssRNA)
230
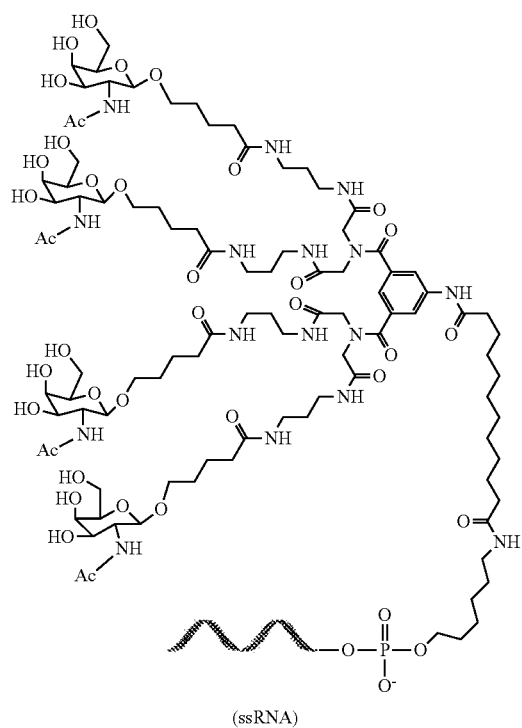 [SMILES: COP(=O)([O-])OCCCCCCNC(=O)CCCCCCCCCCC(=O)Nc1cc(C(=O)N(CC(=O)NCCCNC(=O)CCCCOC2OC(CO)C(O)C(O)C2NC(C)=O)CC(=O)NCCCNC(=O)CCCCOC2OC(CO)C(O)C(O)C2NC(C)=O)cc(C(=O)N(CC(=O)NCCCNC(=O)CCCCOC2OC(CO)C(O)C(O)C2NC(C)=O)CC(=O)NCCCNC(=O)CCCCOC2OC(CO)C(O)C(O)C2NC(C)=O)c1]
(ssRNA)

TABLE 35-continued
231
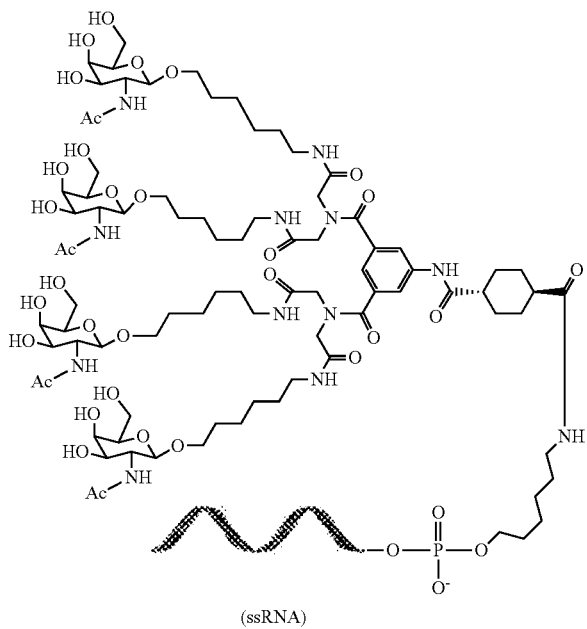 [SMILES: COP(=O)([O-])OCCCCCCNC(=O)[C@H]1CC[C@H](C(=O)Nc2cc(C(=O)N(CC(=O)NCCCCCCOC3OC(CO)C(O)C(O)C3NC(C)=O)CC(=O)NCCCCCCOC3OC(CO)C(O)C(O)C3NC(C)=O)cc(C(=O)N(CC(=O)NCCCCCCOC3OC(CO)C(O)C(O)C3NC(C)=O)CC(=O)NCCCCCCOC3OC(CO)C(O)C(O)C3NC(C)=O)c2)CC1]
232
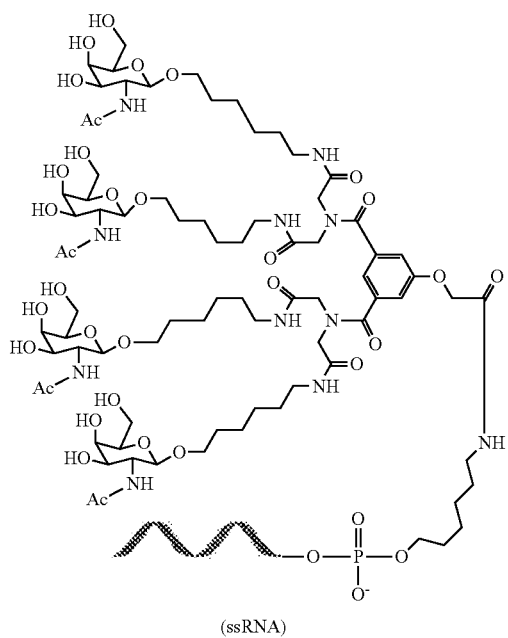 [SMILES: COP(=O)([O-])OCCCCCCNC(=O)COc1cc(C(=O)N(CC(=O)NCCCCCCOC2OC(CO)C(O)C(O)C2NC(C)=O)CC(=O)NCCCCCCOC2OC(CO)C(O)C(O)C2NC(C)=O)cc(C(=O)N(CC(=O)NCCCCCCOC2OC(CO)C(O)C(O)C2NC(C)=O)CC(=O)NCCCCCCOC2OC(CO)C(O)C(O)C2NC(C)=O)c1]

TABLE 35-continued

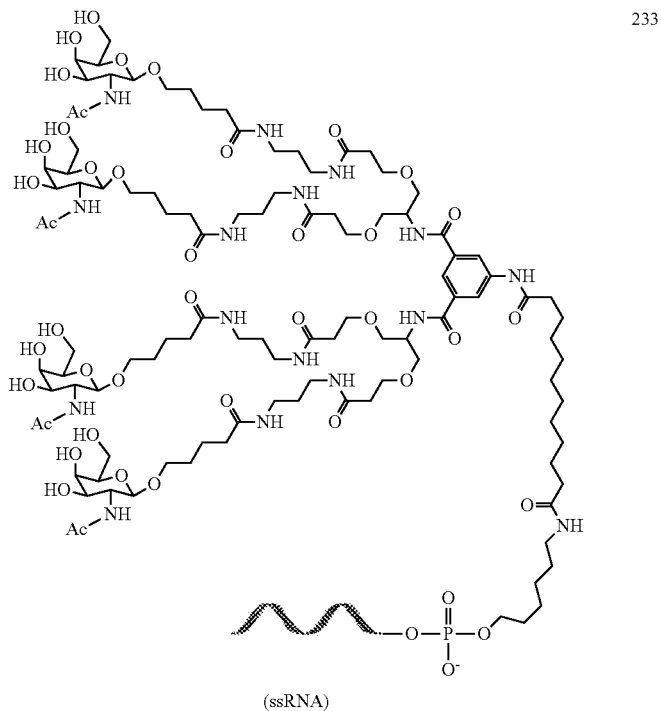

233

(ssRNA)

TABLE 36

| Compound | Sequence (5' to 3') | Theoretical molecular weight | Found |
|---|---|---|---|
| 220_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 220 | 8977 | 8977 |
| 221_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 221 | 8851 | 8851 |
| 222_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 222 | 8778 | 8778 |
| 223_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 223 | 8935 | 8935 |
| 224_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 224 | 8896 | 8893 |
| 225_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 225 | 8954 | 8951 |
| 226_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 226 | 8912 | 8909 |
| 227_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 227 | 8607 | 8606 |
| 228_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 228 | 8883 | 8882 |
| 229_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 229 | 8730 | 8729 |
| 230_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 230 | 9006 | 9005 |
| 231_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 231 | 8719 | 8719 |

TABLE 36-continued

| Compound | Sequence (5' to 3') | Theoretical molecular weight | Found |
|---|---|---|---|
| 232_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 232 | 8624 | 8624 |
| 233_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 233 | 9209 | 9209 |

Synthesis of Nucleic Acid Conjugate 234

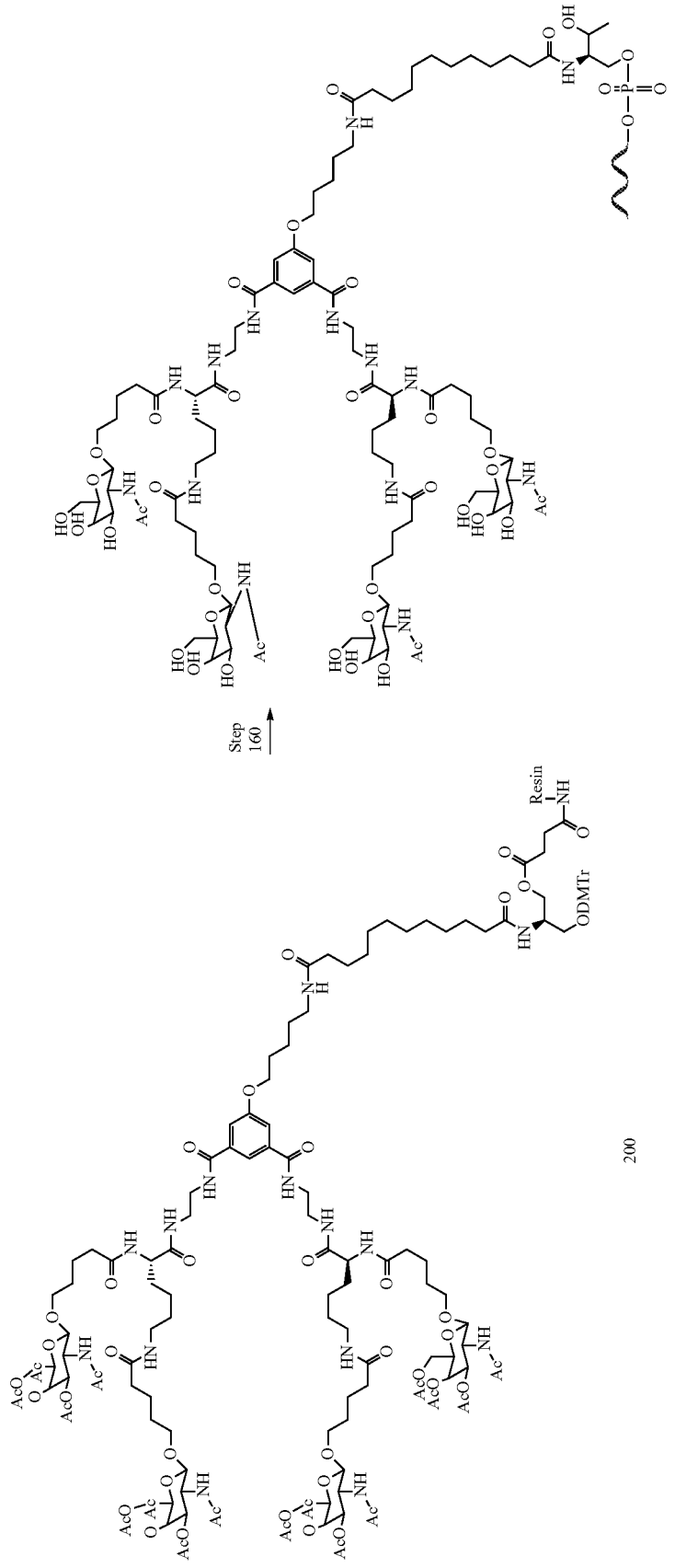

Step 160

Single-stranded nucleic acid conjugate 234 was obtained in the same way as in step 46 of Example 12 using compound 200 synthesized in step 157 of Example 14.

Synthesis of Nucleic Acid Conjugates 235 to 250

The single-stranded nucleic acid conjugates described in Tables 37 to 40 were each obtained in the same way as in step 160 using a corresponding compound selected from compounds 171, 174, 177, 180, 183, 187, and 200 and the compounds described in Tables 23 and 24.

The sequences and mass spectrometry results of the nucleic acid conjugates synthesized in this Example are shown in Table 41.

TABLE 37

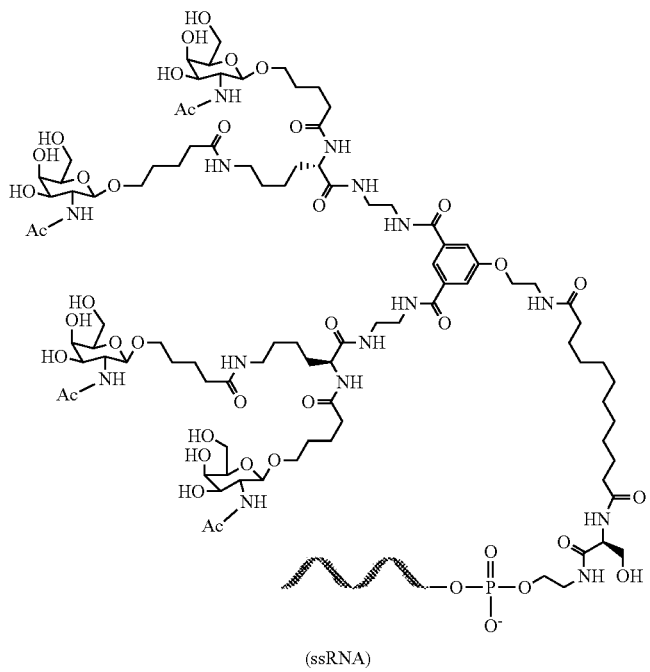 [SMILES: COP(=O)([O-])OCCNC(=O)[C@H](CO)NC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

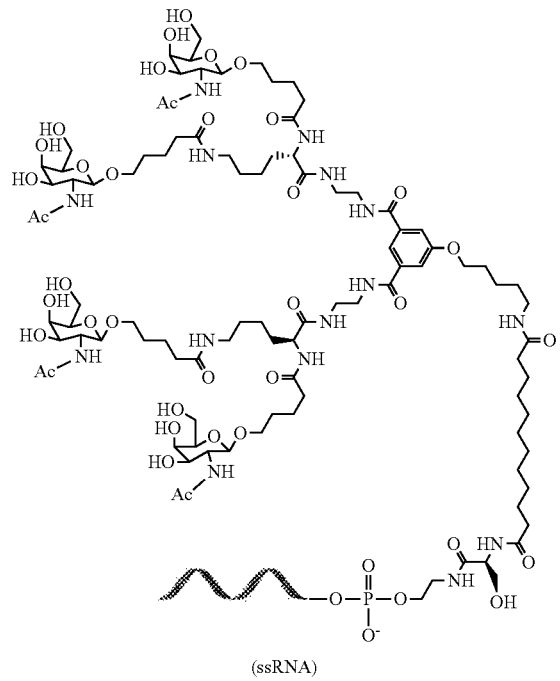 [SMILES: COP(=O)([O-])OCCNC(=O)[C@H](CO)NC(=O)CCCCCCCCCCC(=O)NCCCCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

TABLE 37-continued
237
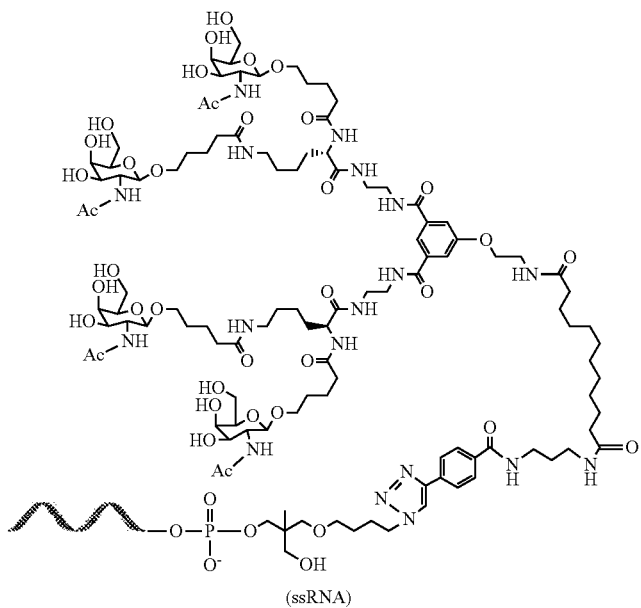 [SMILES: COP(=O)([O-])OCC(C)(CO)COCCCCn1cc(-c2ccc(C(=O)NCCCNC(=O)CCCCCCCCCCC(=O)NCCOc3cc(C(=O)NCCNC(=O)[C@H](CCCCNC(=O)CCCCOC4OC(CO)C(O)C(O)C4NC(C)=O)NC(=O)CCCCOC4OC(CO)C(O)C(O)C4NC(C)=O)cc(C(=O)NCCNC(=O)[C@H](CCCCNC(=O)CCCCOC4OC(CO)C(O)C(O)C4NC(C)=O)NC(=O)CCCCOC4OC(CO)C(O)C(O)C4NC(C)=O)c3)cc2)nn1]
238
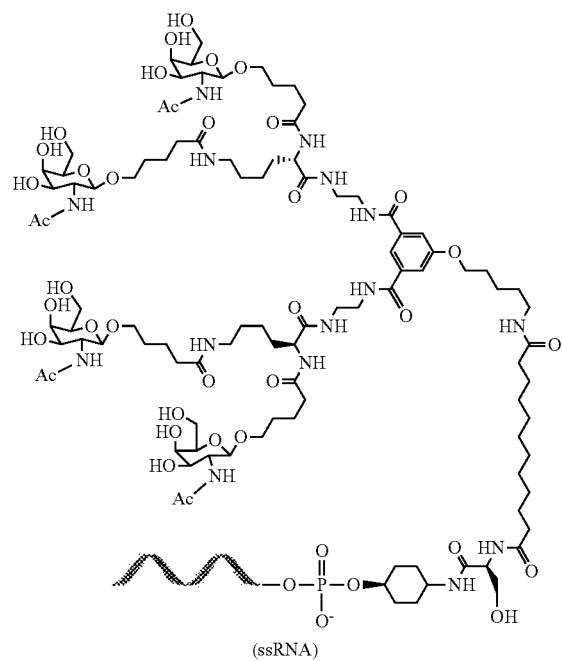

TABLE 38
239
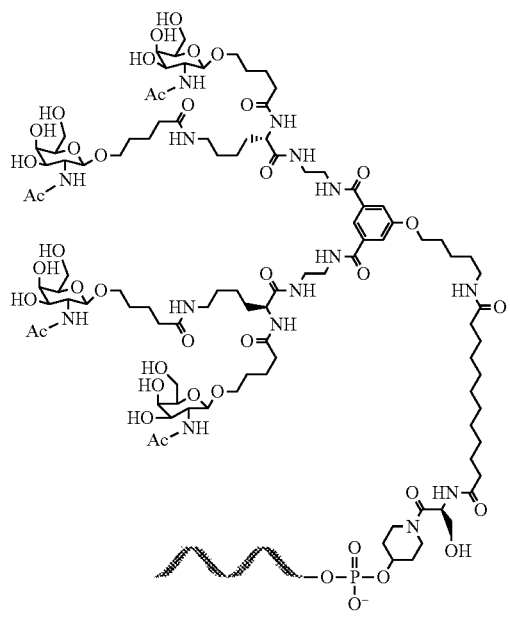
(ssRNA)
240
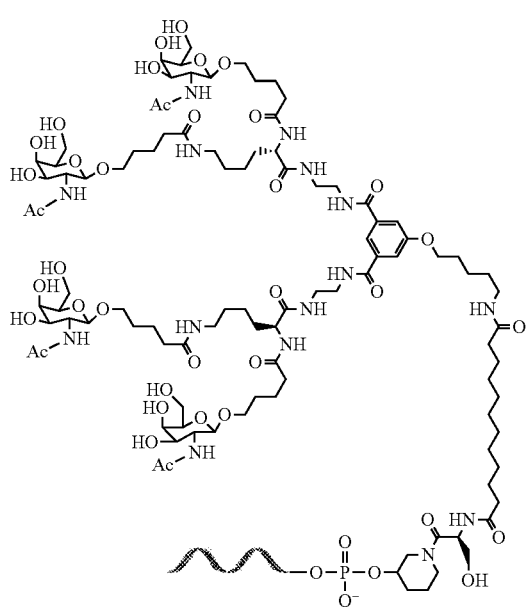
(ssRNA)
TABLE 38-continued
241
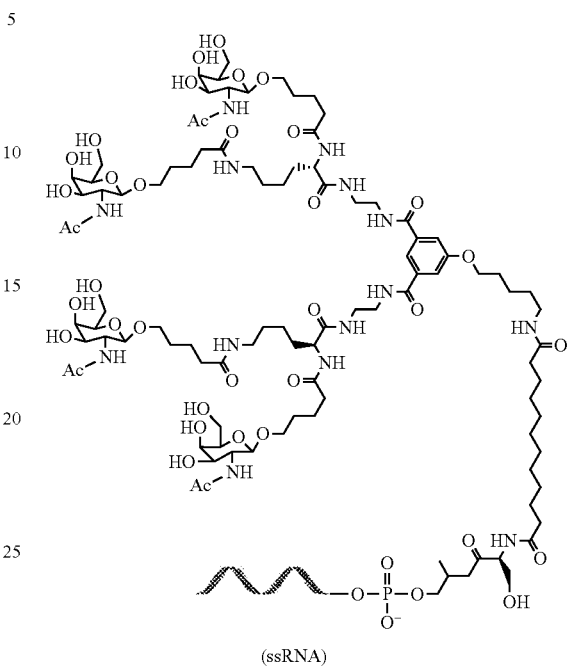
(ssRNA)
242
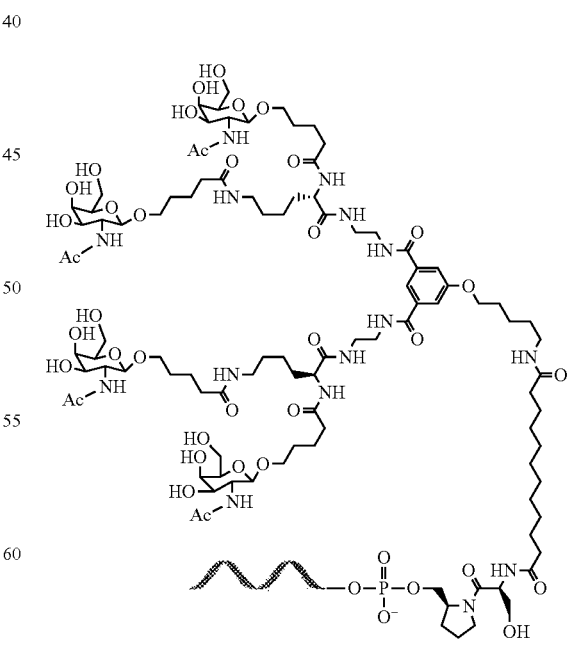
(ssRNA)

TABLE 39
243
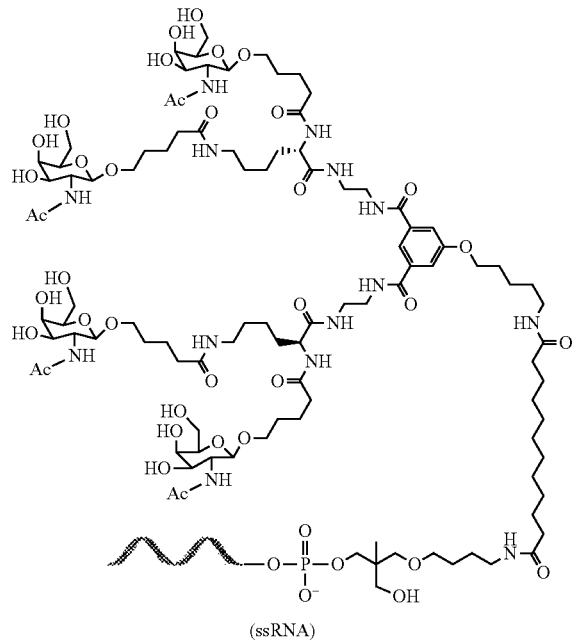 [SMILES: COP(=O)([O-])OCC(C)(CO)COCCCCNC(=O)CCCCCCCCCCC(=O)NCCCCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
244
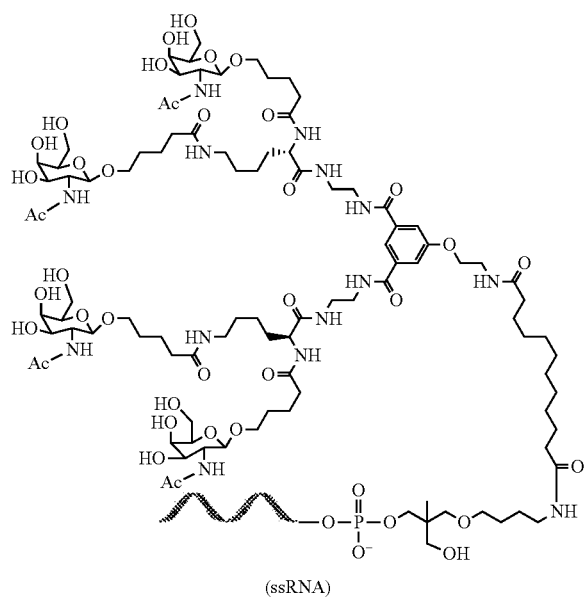 [SMILES: COP(=O)([O-])OCC(C)(CO)COCCCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

TABLE 39-continued
245
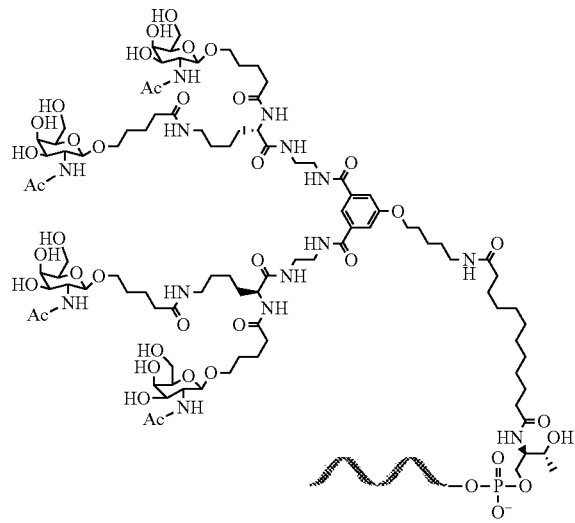
(two types, ssRNA and ssDNA)
246
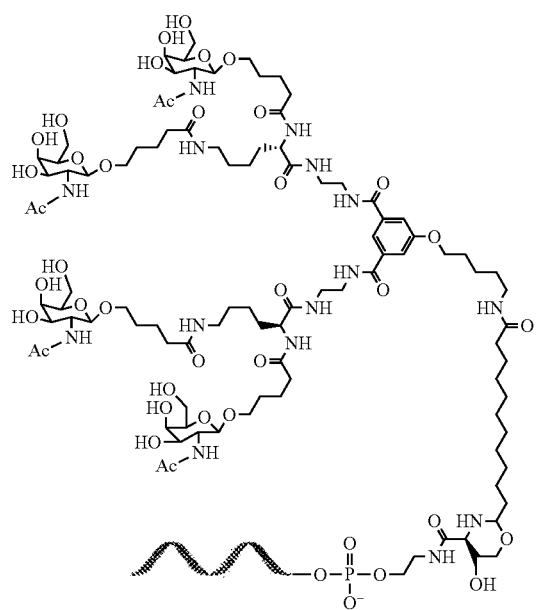
(ssRNA)

TABLE 40
247
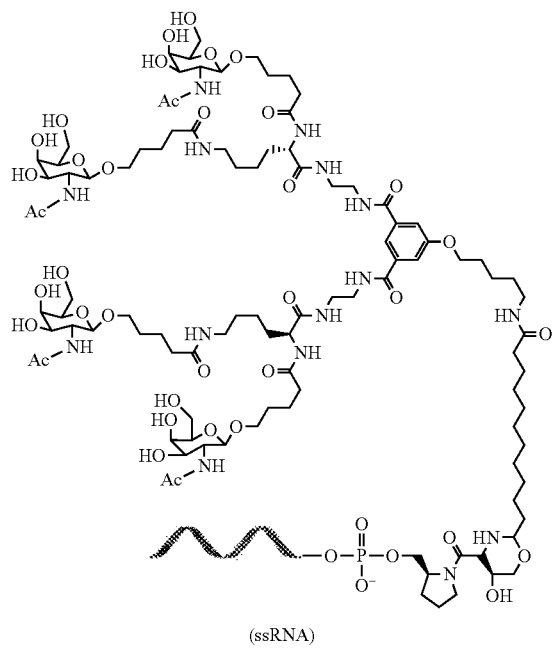
248
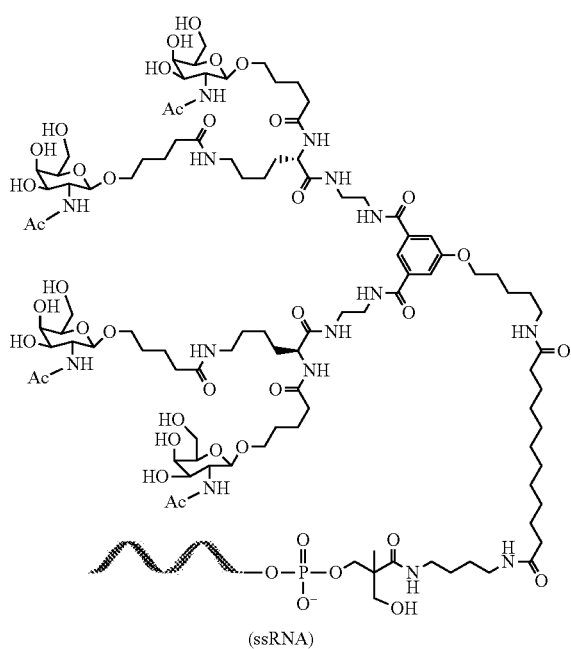 [SMILES: COP(=O)([O-])OCC(C)(CO)C(=O)NCCCCNC(=O)CCCCCCCCCCC(=O)NCCCCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

TABLE 40-continued

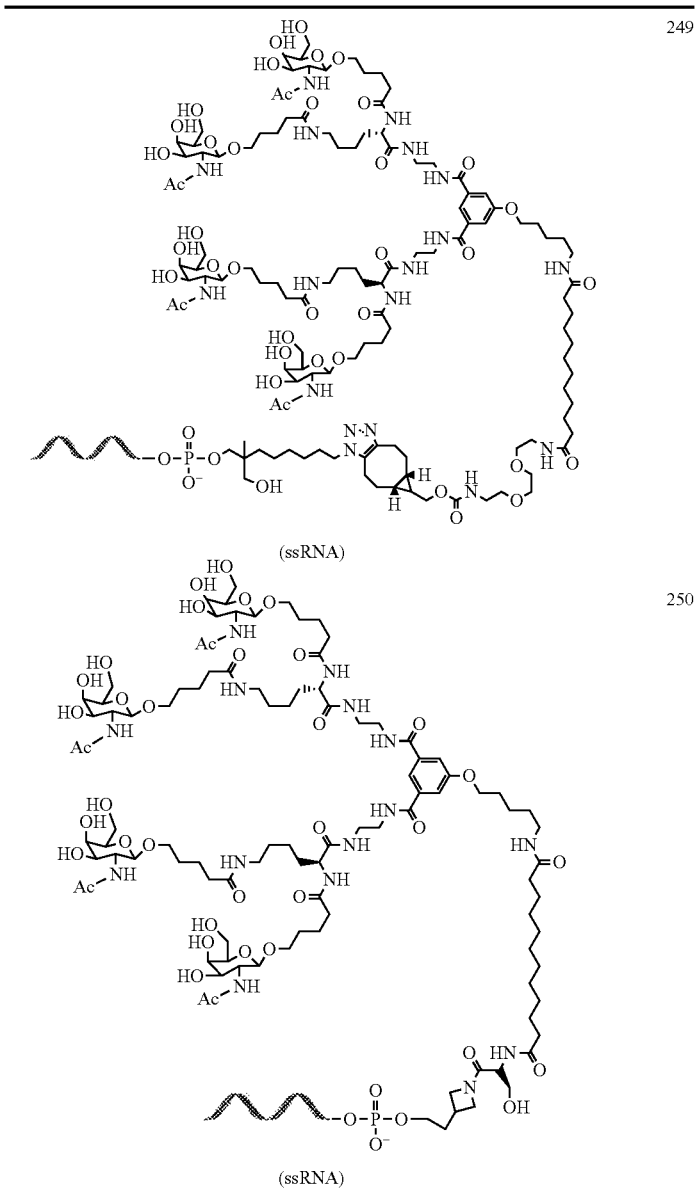

249

250

(ssRNA)

(ssRNA)

TABLE 41

| Compound | Sequence (5' to 3') | | Theoretical molecular weight | Found |
|---|---|---|---|---|
| 235_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 235 | 8967 | 8966 |
| 236_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 236 | 9009 | 9008 |
| 237_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 237 | 9238 | 9238 |
| 238_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 238 | 9063 | 9063 |
| 239_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 239 | 9049 | 9049 |
| 240_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 240 | 9049 | 9048 |

TABLE 41-continued

| Compound | Sequence (5' to 3') | Theoretical molecular weight | Found |
|---|---|---|---|
| 241_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 241 | 9023 | 9022 |
| 242_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 242 | 9049 | 9049 |
| 243_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 243 | 9052 | 9051 |
| 244_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 244 | 9010 | 9009 |
| 245_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 245 | 8966 | 8966 |
| 245_3'-dT10 | Tttttttttt 245 | 5162 | 5161 |
| 246_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 246 | 9024 | 9023 |
| 247_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 247 | 9064 | 9063 |
| 248_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 248 | 9066 | 9064 |
| 249_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 249 | 9403 | 9403 |
| 250_3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 250 | 9036 | 9037 |

Synthesis of nucleic acid conjugates 251 to 287 Double-stranded nucleic acid conjugates 251 to 287 were obtained in the same way as in step 39 of Example 9 using single-stranded nucleic acid conjugates (ssRNA) 210 to 233 and 235 to 247.

The sequences of the nucleic acid conjugates synthesized in this Example are shown in Tables 42, 43, 45, and 47 to 54.

TABLE 42

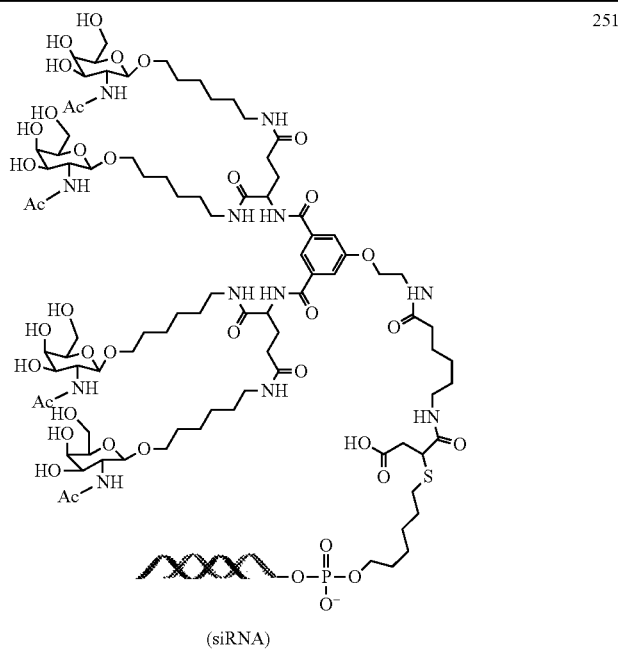

TABLE 42-continued
252
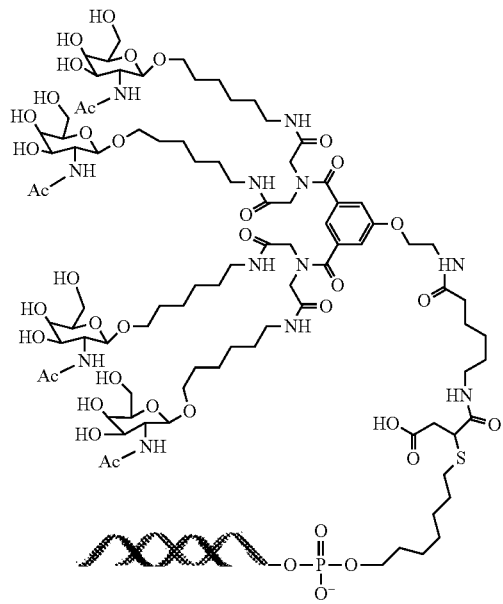
253
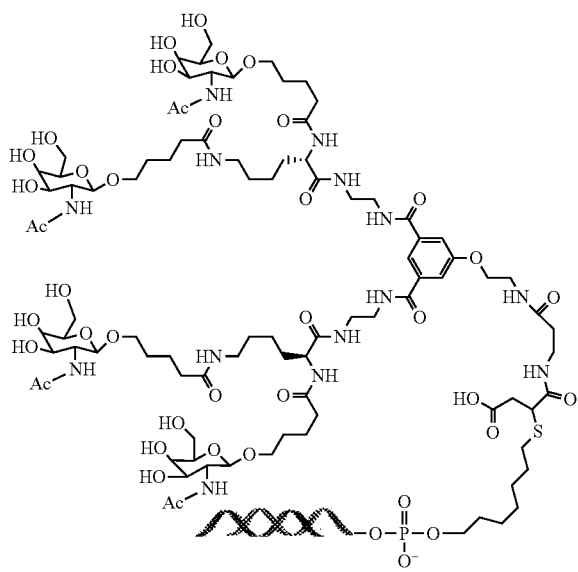

TABLE 42-continued
254
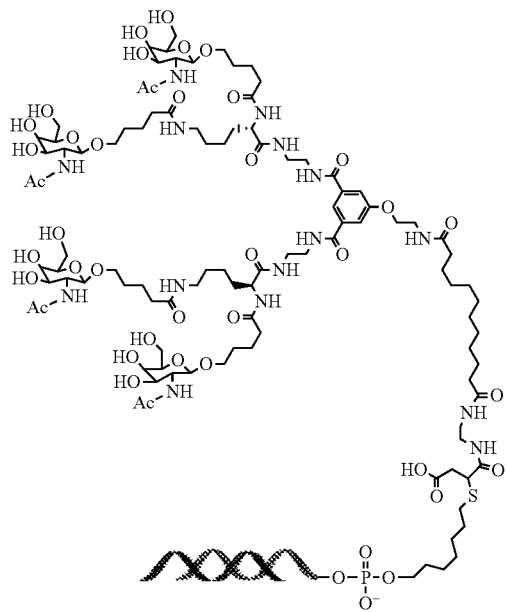
(siRNA)
TABLE 43
255
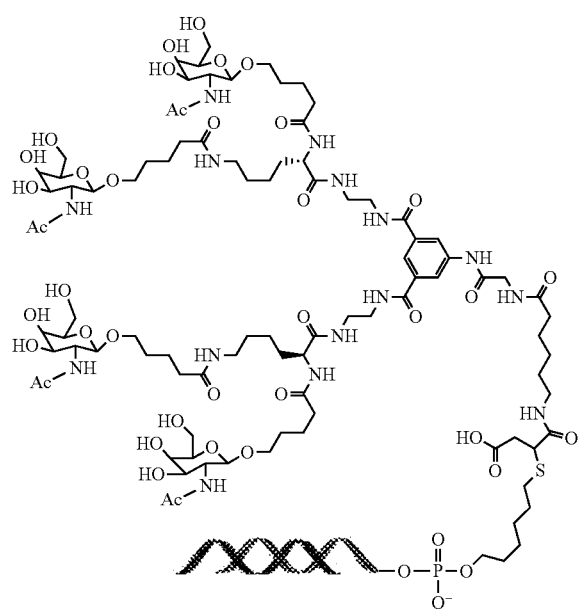
(siRNA)

TABLE 43-continued
256
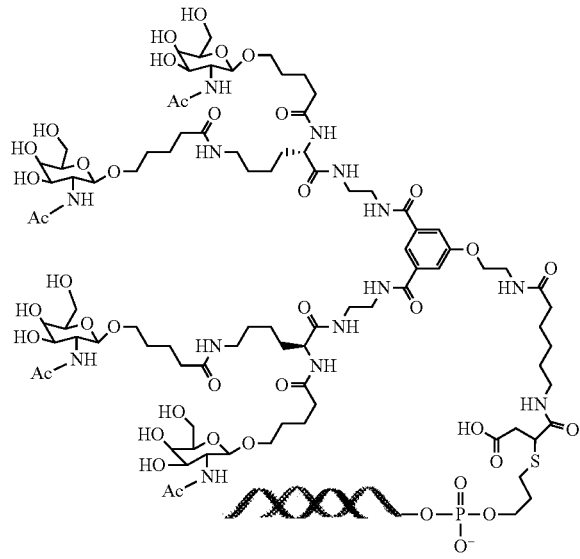
257
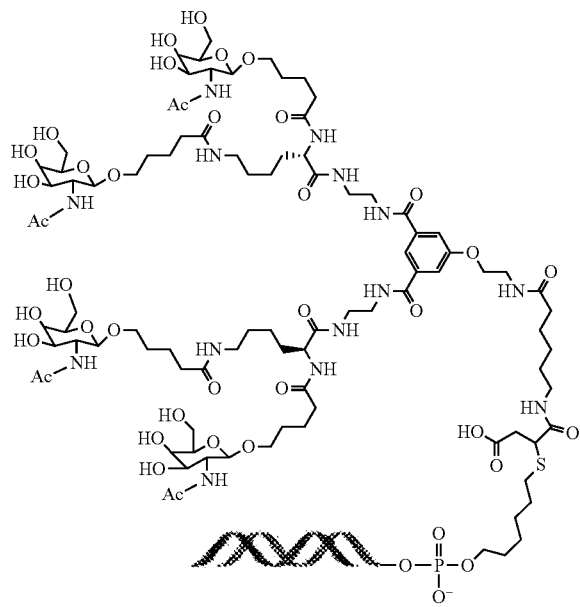

TABLE 43-continued

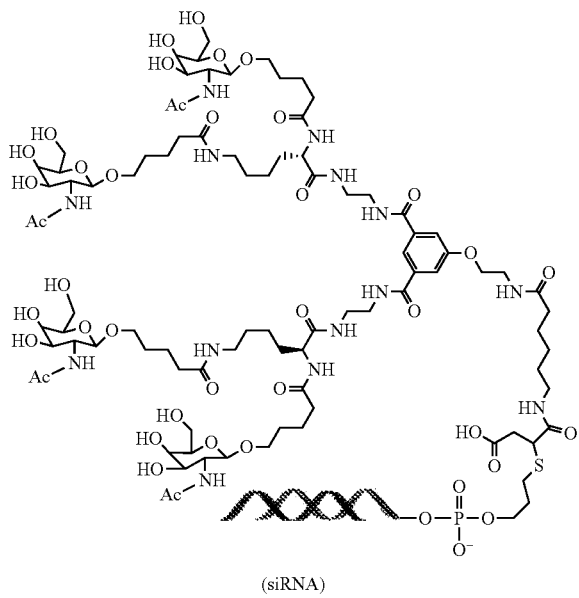 [SMILES: COP(=O)([O-])OCCCSC(CC(=O)O)C(=O)NCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

258

(siRNA)

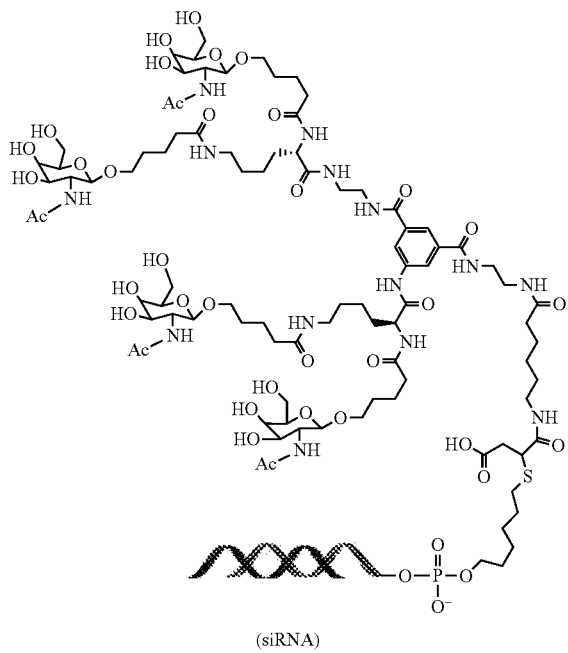 [SMILES: COP(=O)([O-])OCCCCCCSC(CC(=O)O)C(=O)NCCCCCC(=O)NCCNC(=O)c1cc(NC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

259

(siRNA)

TABLE 44

| Compound | Single strand name | Sequence (5' to 3') |
|---|---|---|
| 251_3'-AT3-siRNA | 210_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) 210 |
| 252_3'-AT3-siRNA | 211_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) 211 |
| 253_3'-AT3-siRNA | 212_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) 212 |
| 254_3'-AT3-siRNA | 213_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) 213 |

TABLE 44-continued

| Compound | Single strand name | Sequence (5' to 3') |
|---|---|---|
| 255_3'-AT3-siRNA 214 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 214 |
| 256_3'-AT3-siRNA 215 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 215 |
| 257_3'-AT3-siRNA 216 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 216 |
| 258_3'-AT3-siRNA 217 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 217 |
| 259_3'-AT3-siRNA 218 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 218 |
| — | AT3-asRNA | U(M)^U(F)^G(M)A(F)A(M)G(F)U(M)A(F)A(M)A(F)U(M)G(M)G(M)U(F)G(M)U(F)U(M)A(F)A(M)C(F)C(M)^A(M)^G(M) |

TABLE 45

260

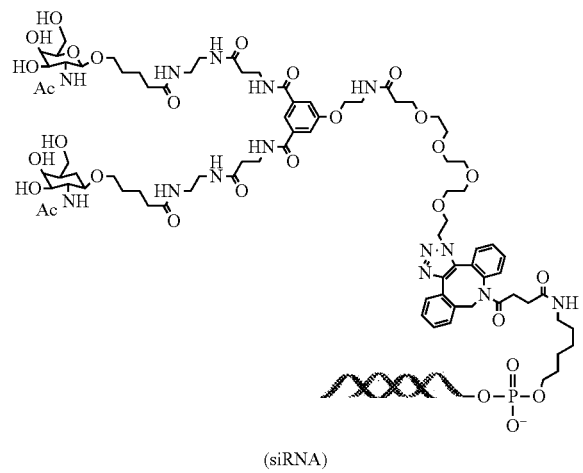 [SMILES: COP(=O)([O-])OCCCCCCNC(=O)CCC(=O)N1Cc2ccccc2-c2nnn(CCOCCOCCOCCOCCC(=O)NCCOc3cc(C(=O)NCCC(=O)NCCNC(=O)CCCCOC4CC(CO)C(O)C(O)C4NC(C)=O)cc(C(=O)NCCC(=O)NCCNC(=O)CCCCOC4OC(CO)C(O)C(O)C4NC(C)=O)c3)c2-c2ccccc21]

(siRNA)

TABLE 46

| Compound | Single strand name | Sequence (5' to 3') |
|---|---|---|
| 260_5'-B2M-siRNA 218 | 5'-B2M-ssRNA | 219 A(F)G(M)G(F)A(M)C(F)U(M)G(F)G(M)U(F)C(M)U(F)U(F)U(M)C(F)U(M)A(F)U(M)C(F)U(M)^C(F)^U(M) |
|  | B2M-asRNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |

TABLE 47
261
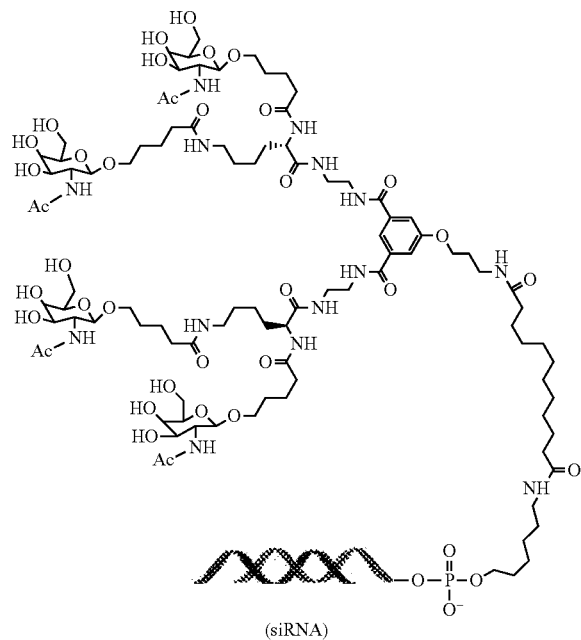 [SMILES: COP(=O)([O-])OCCCCCCNC(=O)CCCCCCCCCCC(=O)NCCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
262
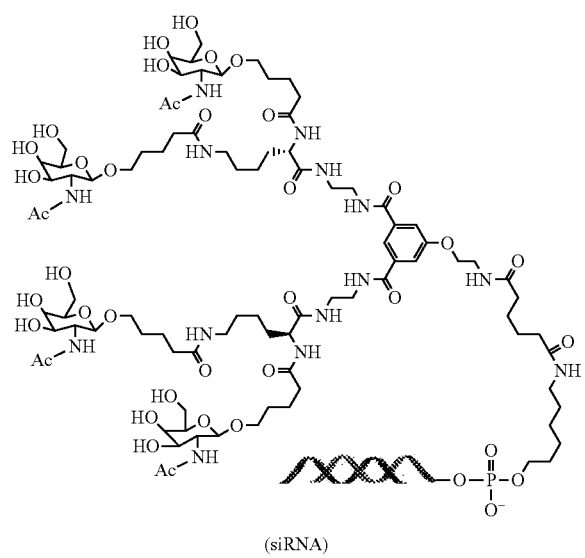 [SMILES: COP(=O)([O-])OCCCCCCNC(=O)CCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

TABLE 47-continued
263
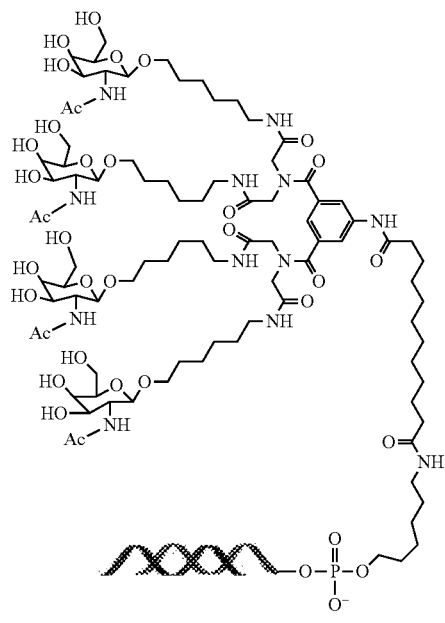
(siRNA)
264
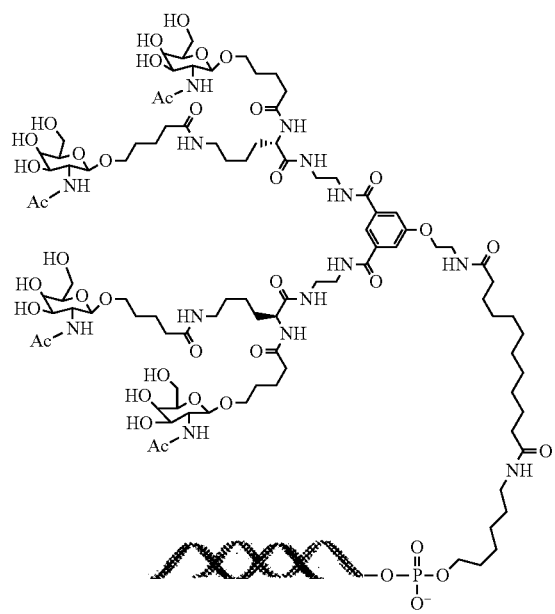
(siRNA)

TABLE 47-continued
265
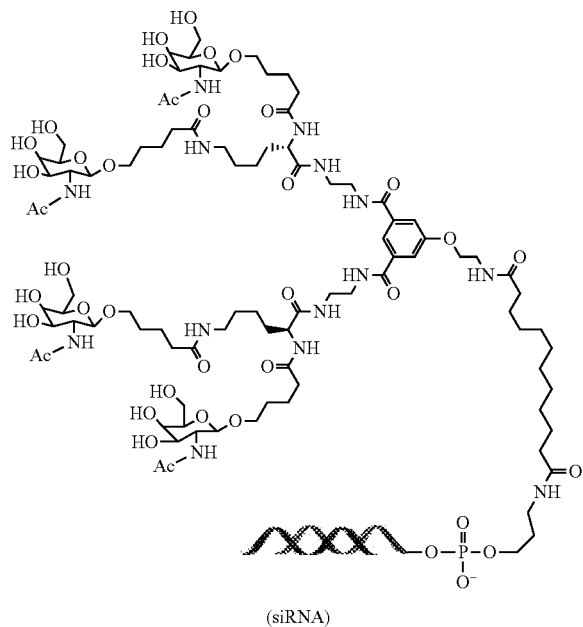 [SMILES: COP(=O)([O-])OCCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
266
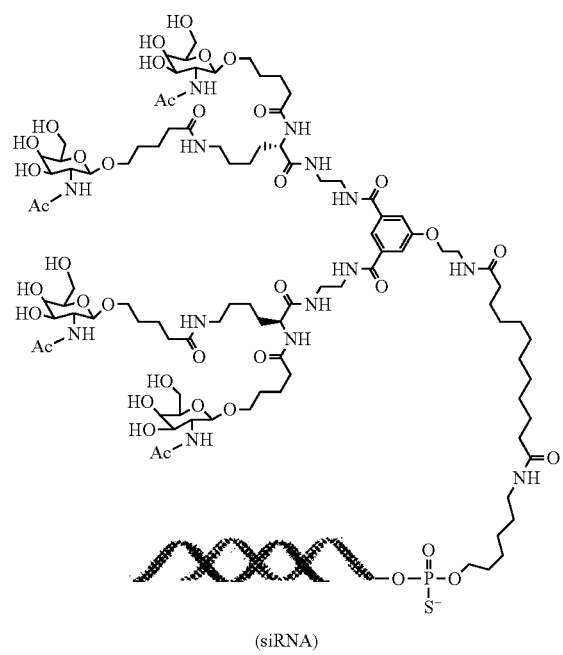 [SMILES: COP(=O)([S-])OCCCCCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]

TABLE 48
267
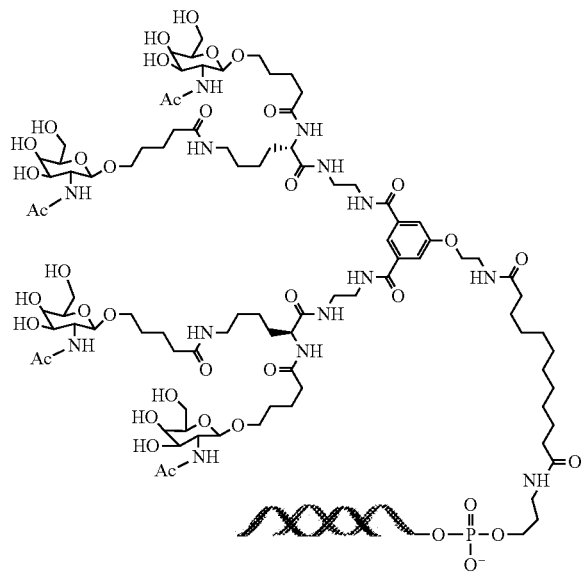
(siRNA)
268
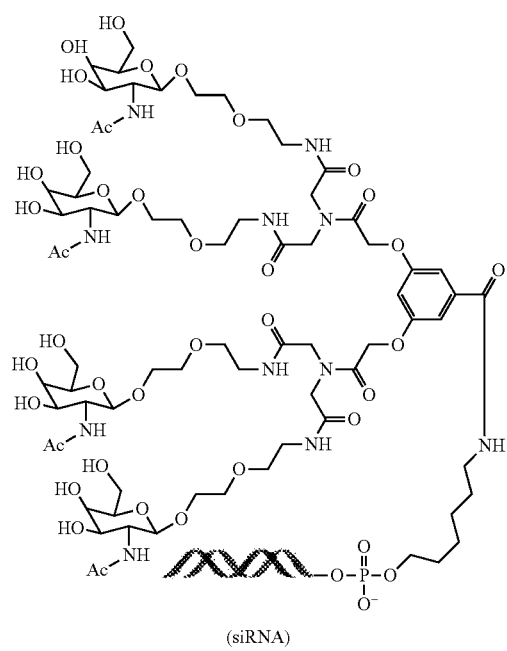 [SMILES: COP(=O)([O-])OCCCCCCNC(=O)c1cc(OCC(=O)N(CC(=O)NCCOCCOC2OC(CO)C(O)C(O)C2NC(C)=O)CC(=O)NCCOCCOC2OC(CO)C(O)C(O)C2NC(C)=O)cc(OCC(=O)N(CC(=O)NCCOCCOC2OC(CO)C(O)C(O)C2NC(C)=O)CC(=O)NCCOCCOC2OC(CO)C(O)C(O)C2NC(C)=O)c1]
(siRNA)

TABLE 48-continued
269
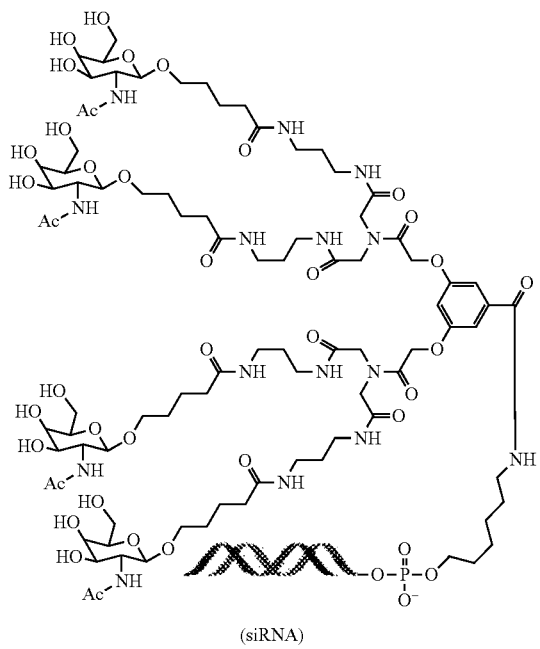 [SMILES: COP(=O)([O-])OCCCCCCNC(=O)c1cc(OCC(=O)N(CC(=O)NCCCNC(=O)CCCCOC2OC(CO)C(O)C(O)C2NC(C)=O)CC(=O)NCCCNC(=O)CCCCOC2OC(CO)C(O)C(O)C2NC(C)=O)cc(OCC(=O)N(CC(=O)NCCCNC(=O)CCCCOC2OC(CO)C(O)C(O)C2NC(C)=O)CC(=O)NCCCNC(=O)CCCCOC2OC(CO)C(O)C(O)C2NC(C)=O)c1]
270
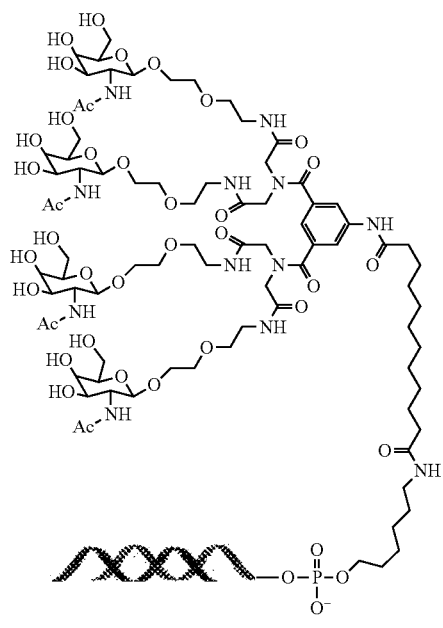

TABLE 49
271
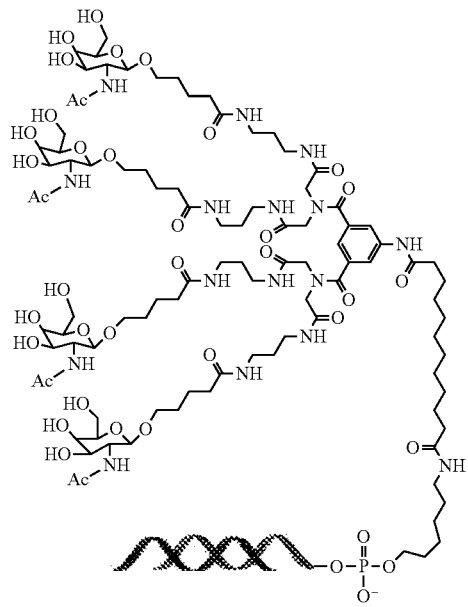
(siRNA)
272
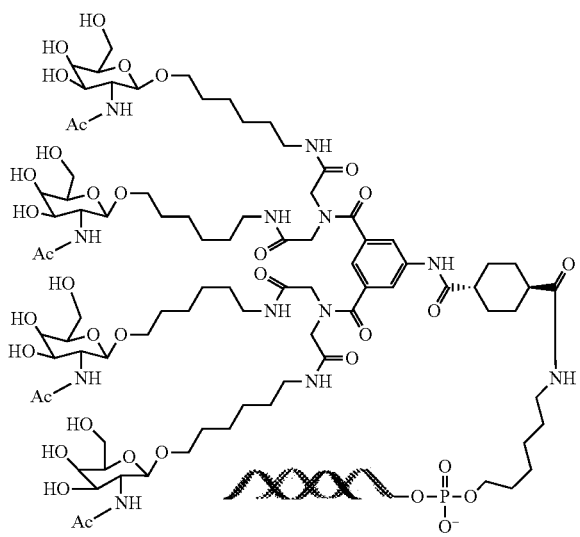
(siRNA)

TABLE 49-continued

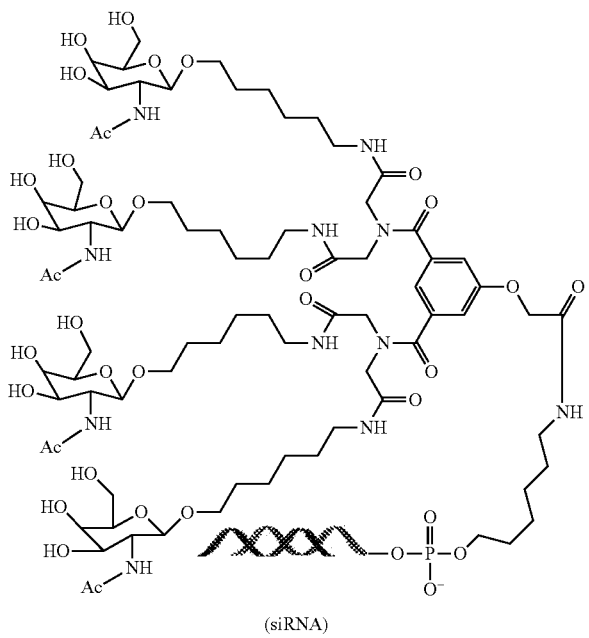 [SMILES: COP(=O)([O-])OCCCCCCNC(=O)COc1cc(C(=O)N(CC(=O)NCCCCCCOC2OC(CO)C(O)C(O)C2NC(C)=O)CC(=O)NCCCCCCOC2OC(CO)C(O)C(O)C2NC(C)=O)cc(C(=O)N(CC(=O)NCCCCCCOC2OC(CO)C(O)C(O)C2NC(C)=O)CC(=O)NCCCCCCOC2OC(CO)C(O)C(O)C2NC(C)=O)c1]

273

(siRNA)

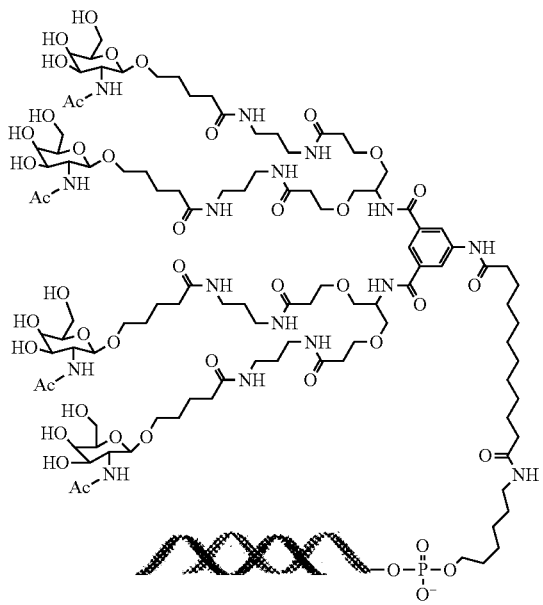

274

(siRNA)

TABLE 50

| Compound | Single strand name | Sequence (5' to 3') | |
|---|---|---|---|
| 261_3'-AT3-siRNA | 220_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 220 |
| 262_3'-AT3-siRNA | 221_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 221 |
| 263_3'-AT3-siRNA | 222_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 222 |
| 264_3'-AT3-siRNA | 223_3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 223 |

TABLE 50-continued

| Compound | Single strand name | Sequence (5' to 3') |
|---|---|---|
| 265_3'-AT3-siRNA 224 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 224 |
| 266_3'-AT3-siRNA 225 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 225 |
| 267_3'-AT3-siRNA 226 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 226 |
| 268_3'-AT3-siRNA 227 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 227 |
| 269_3'-AT3-siRNA 228 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 228 |
| 270_3'-AT3-siRNA 229 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 229 |
| 271_3'-AT3-siRNA 230 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 230 |
| 272_3'-AT3-siRNA 231 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 231 |
| 273_3'-AT3-siRNA 232 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 232 |
| 274_3'-AT3-siRNA 233 | 3'-AT3-ssRNA | G(F)^G(M)^U(F)U(M)A(F)A(M)C(F)A(M)C(F)C(F)A(F)U(M)U(F)U(M)A(F)C(M)U(F)U(M)C(F)A(M)A(F) 233 |
| — | AT3-asRNA | U(M)^U(F)^G(M)A(F)A(M)G(F)U(M)A(F)A(M)A(F)U(M)G(M)G(M)U(F)G(M)U(F)U(M)A(F)A(M)C(F)C(M)^A(M)^G(M) |

TABLE 51

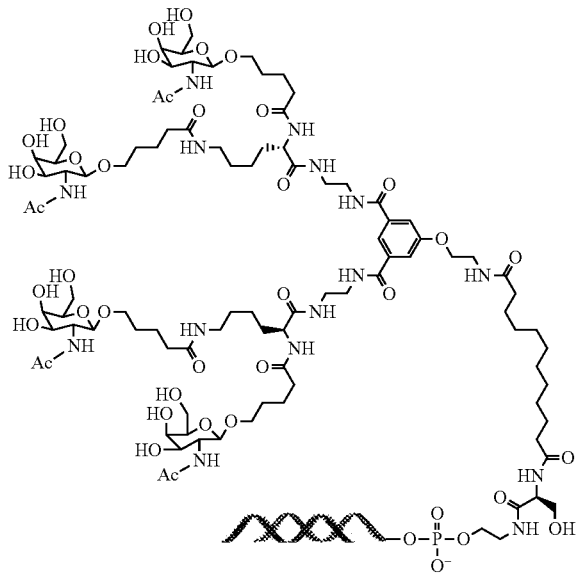

275

(siRNA)

276
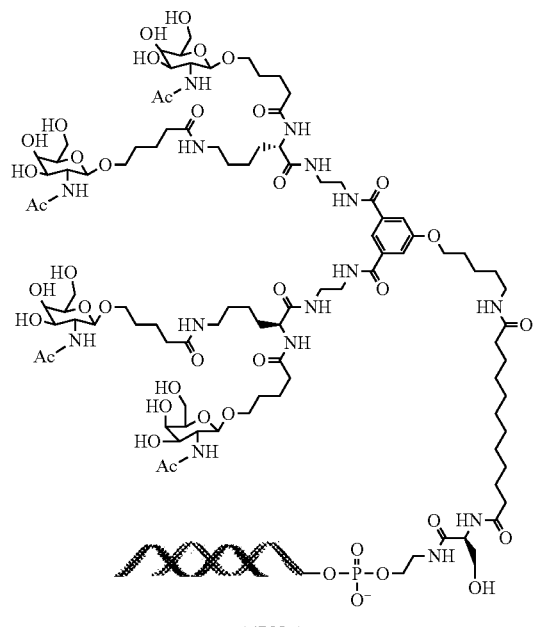
(siRNA)
277
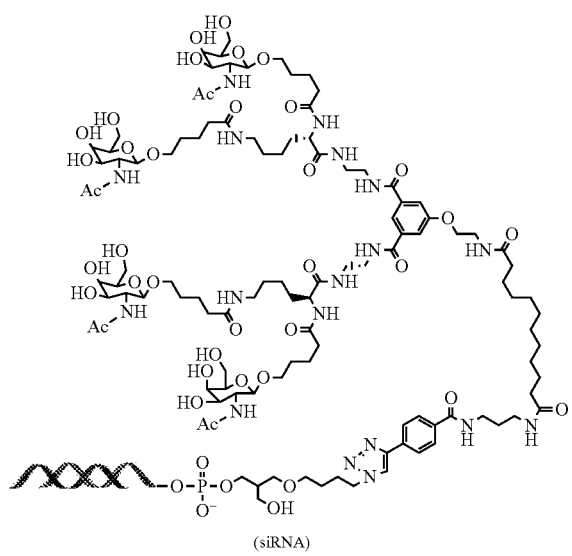
(siRNA)

TABLE 51-continued
278
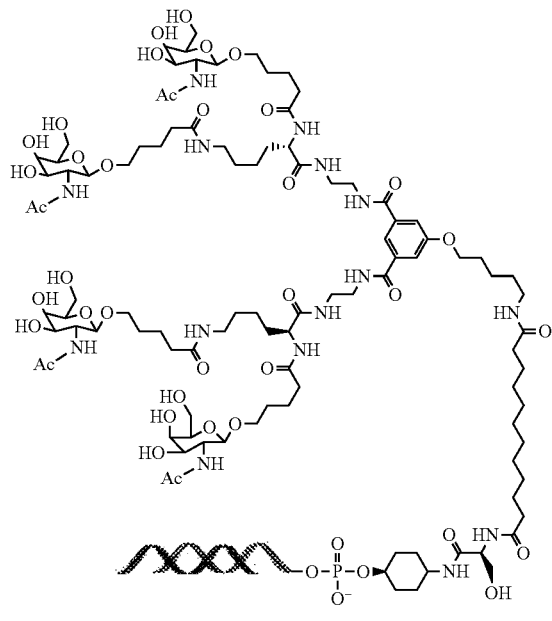
(siRNA)
TABLE 52
279
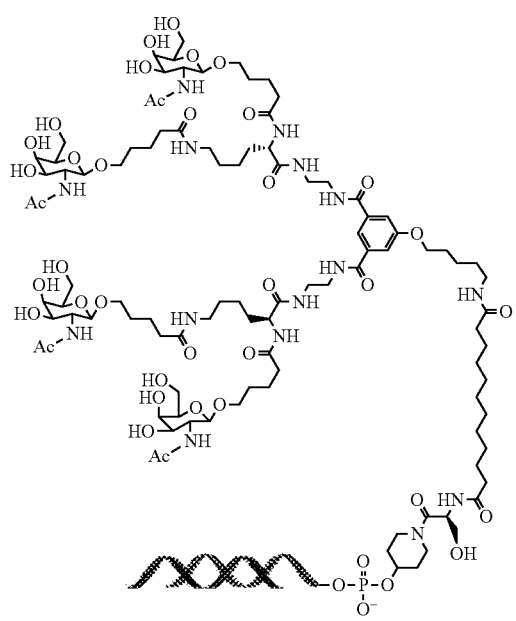
(siRNA)

TABLE 52-continued
280
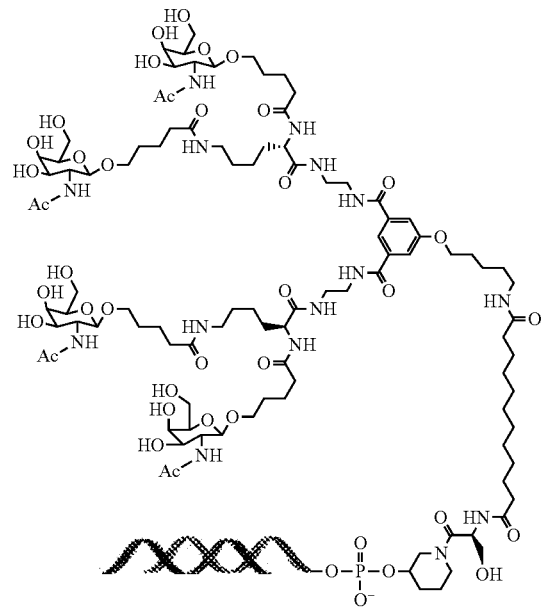
(siRNA)
281
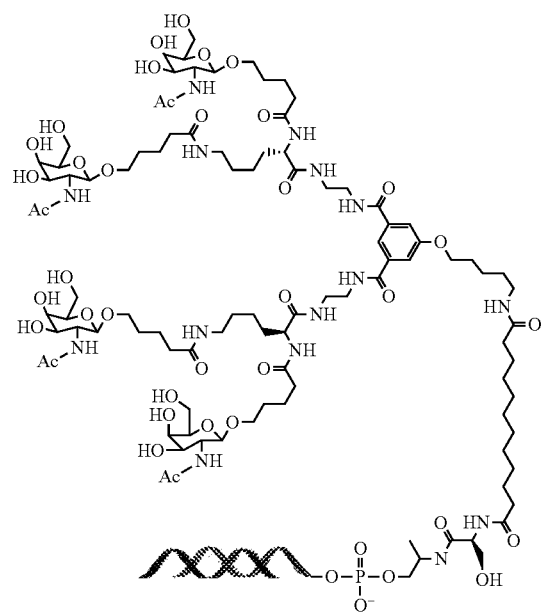
(siRNA)

TABLE 52-continued
282
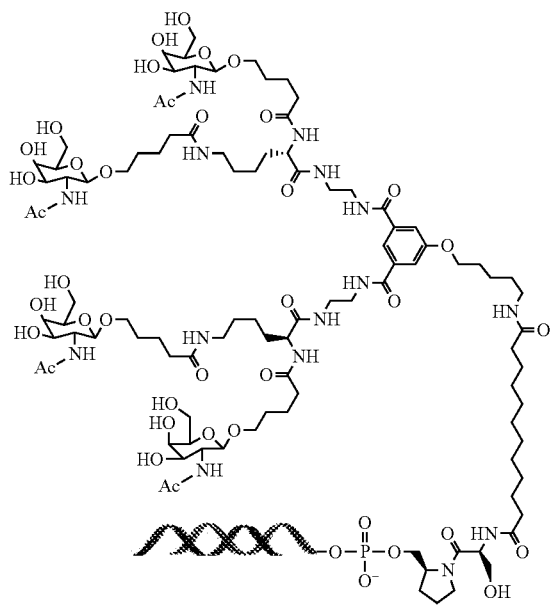
(siRNA)
TABLE 53
283
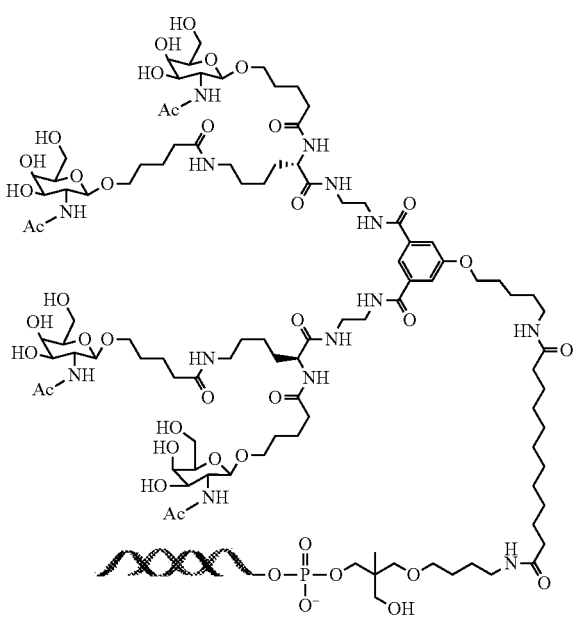
(siRNA)

TABLE 53-continued
284
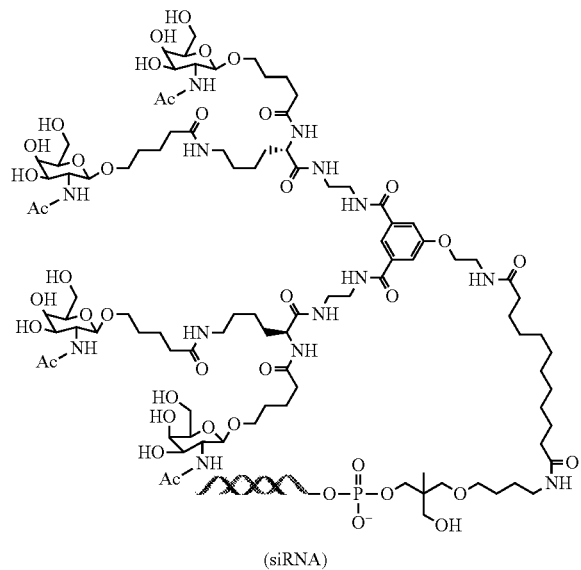 [SMILES: COP(=O)([O-])OCC(C)(CO)COCCCCNC(=O)CCCCCCCCCCC(=O)NCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1]
285
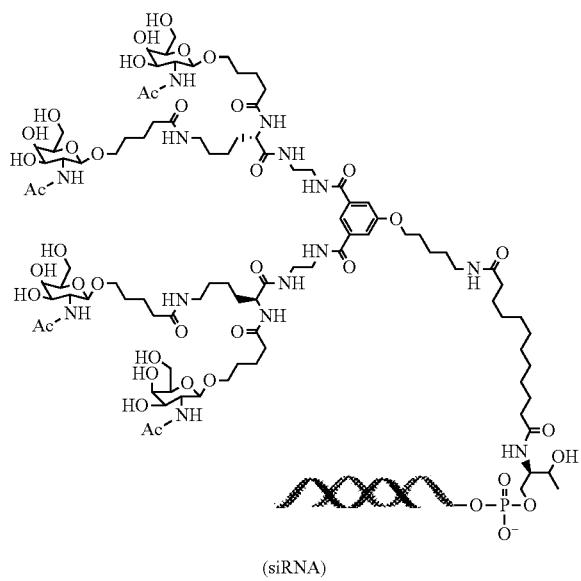 [SMILES: COP(=O)([O-])OC[C@@H](NC(=O)CCCCCCCCCCC(=O)NCCCCCOc1cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)cc(C(=O)NCCNC(=O)[C@H](CCCCNC(=O)CCCCOC2OC(CO)C(O)C(O)C2NC(C)=O)NC(=O)CCCCOC2OC(CO)C(O)C(O)C2NC(C)=O)c1)C(C)O]

TABLE 53-continued
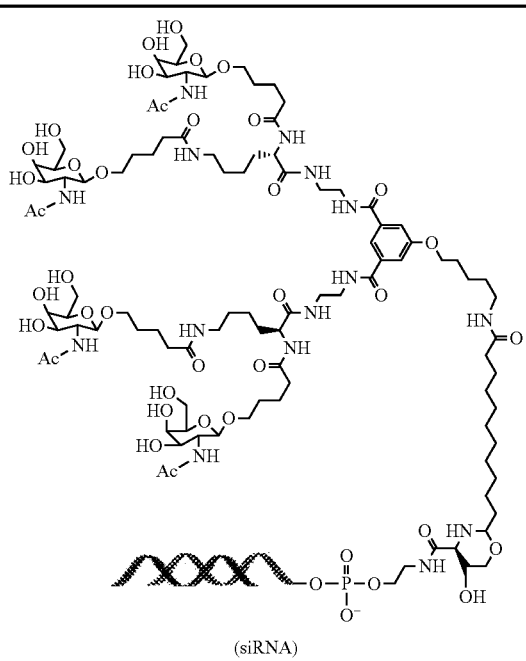
286 (siRNA)
TABLE 54
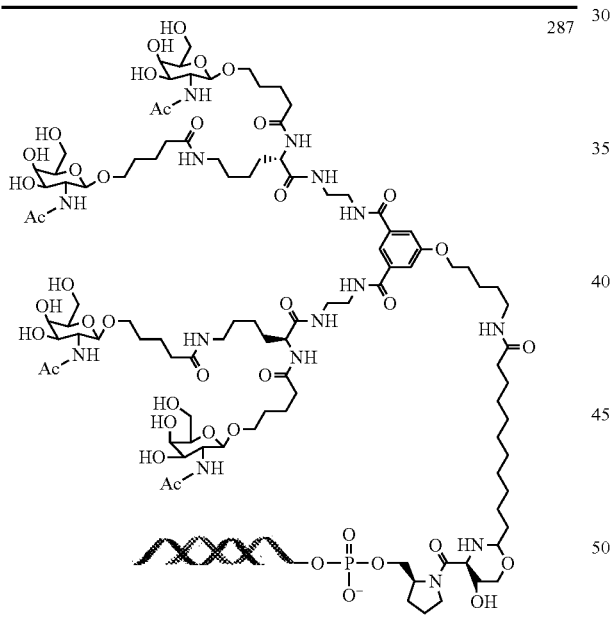
287 (siRNA)
TABLE 55
| Compound | Single strand name | Sequence (5' to 3') | |
|---|---|---|---|
| 275_3'-AT3-siRNA | 235_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 235 |
| 276_3'-AT3-siRNA | 236_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 236 |
| 277_3'-AT3-siRNA | 237_3'-AT3-ssRNA | G(F)^G(M)^U(F)U(M)A(F)A(M)C(F)A(M)C(F)C(F) A(F)U(M)U(F)U(M)A(F)C(M)U(F)U(M)C(F)A(M)A(F) | 237 |

TABLE 55-continued

| Compound | Single strand name | Sequence (5' to 3') | |
|---|---|---|---|
| 278_3'-AT3-siRNA 238 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 238 |
| 279_3'-AT3-siRNA 239 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 239 |
| 280_3'-AT3-siRNA 240 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 240 |
| 281_3'-AT3-siRNA 241 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 241 |
| 282_3'-AT3-siRNA 242 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 242 |
| 283_3'-AT3-siRNA 243 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 243 |
| 284_3'-AT3-siRNA 244 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 244 |
| 285_3'-AT3-siRNA 245 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 245 |
| 286_3'-AT3-siRNA 246 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 246 |
| 287_3'-AT3-siRNA 247 | 3'-AT3-ssRNA | G(F)^G(M)^U(F)U(M)A(F)A(M)C(F)A(M)C(F)C(F)<br>A(F)U(M)U(F)U(M)A(F)C(M)U(F)U(M)C(F)A(M)A(F) | 247 |

Example 16 Synthesis of Sugar Ligand-Tether Unit

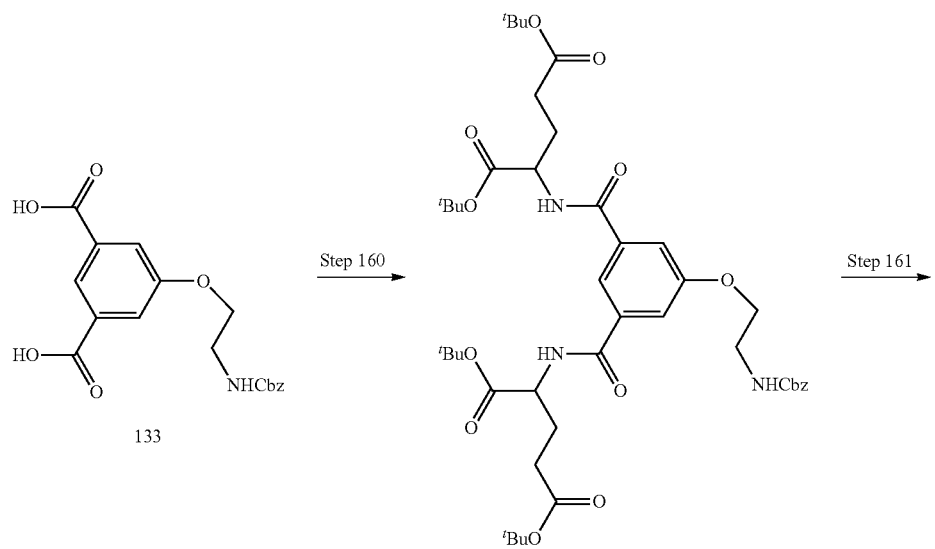

-continued
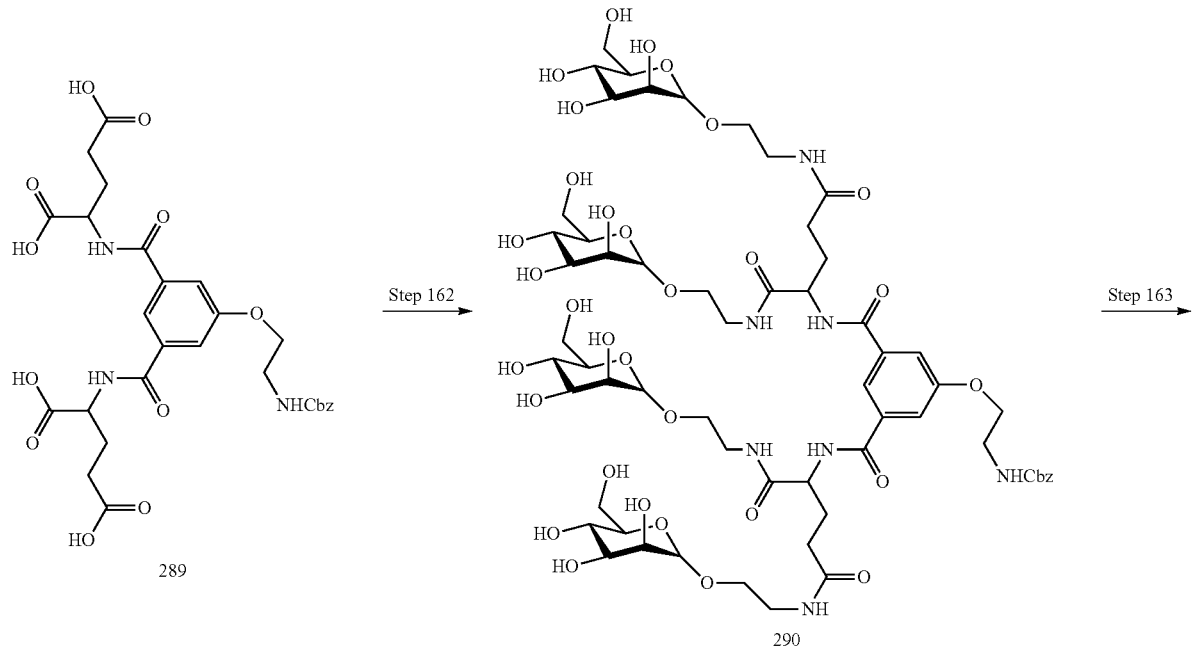
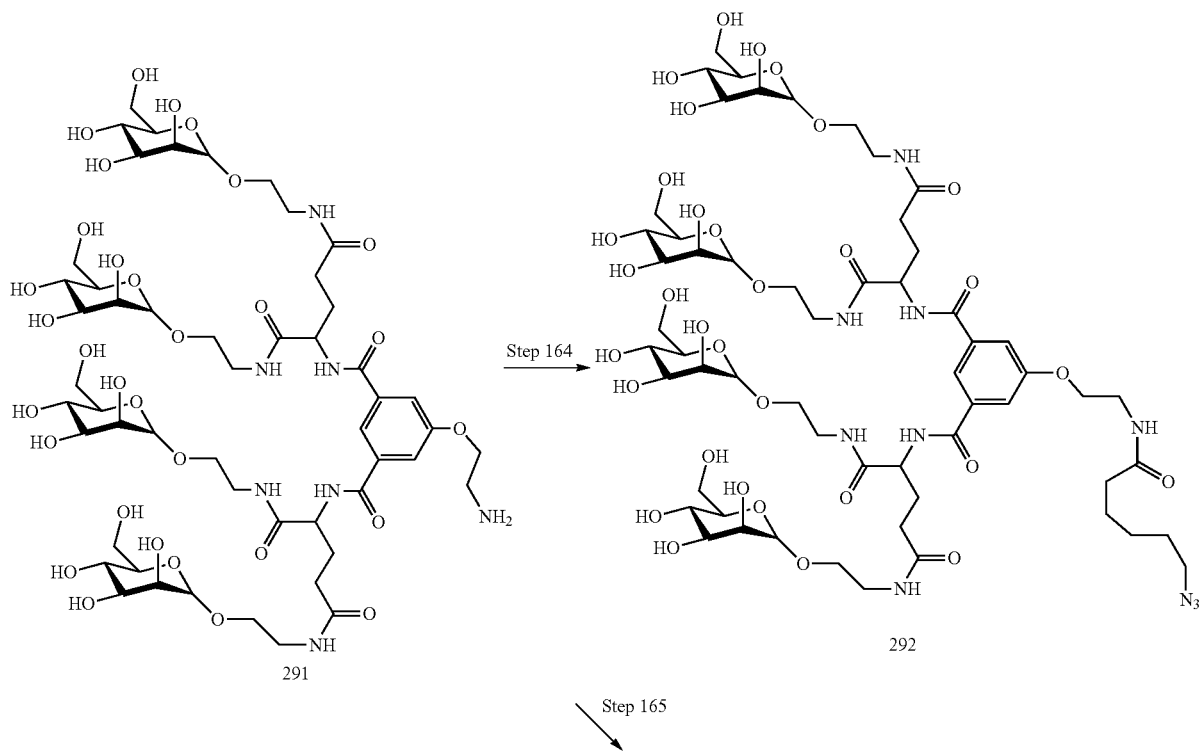

-continued

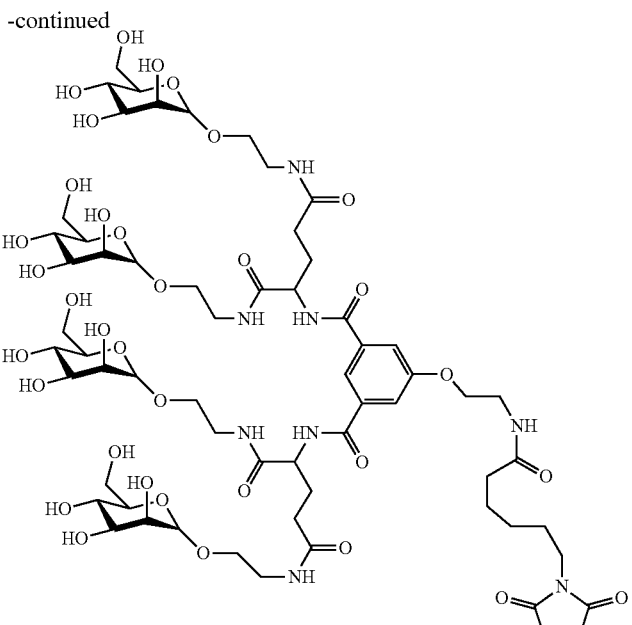

293

Step 160

Compound 288 was obtained as a crude product in the same way as in step 25 of Example 4 using compound 133 (0.5 g, 1.365 mmol) synthesized in step 99 of Example 13.

Step 161

Compound 289 was obtained as a crude product in the same way as in step 26 of Example 4 using compound 288 (0.296 g, 0.247 mmol) synthesized in step 160 of Example 16.

Step 162

Compound 290 (0.110 g, yield: 31%) was obtained in the same way as in step 8 of Example 1 using compound 289 (0.153 g, 0.247 mmol) synthesized in step 161 of Example 16 and 1-(2-azidoethyl)-r-D-mannopyranoside (0.221 g, 0.989 mmol) synthesized by the method described in Inorganic Chemistry, Vol. 83, p. 1000-1007, 2011.

ESI-MS m/z: 720 (M+H)$^+$

Step 163

Compound 291 (0.077 g, yield: 77%) was obtained in the same way as in step 28 of Example 5 using compound 290 (0.110 g, 0.077 mmol) synthesized in step 162 of Example 16.

ESI-MS m/z: 1305 (M+H)$^+$

Step 164

Compound 291 (20 mg, 0.016 mmol) synthesized in step 163 of Example 16 and 2,5-dioxopyrrolidin-1-yl 6-azidohexanoic acid (10 mg, 0.032 mmol) were dissolved in tetrahydrofuran (2 mL). To the solution, diisopropylethylamine (0.027 mL, 0.078 mmol) was added, and the mixture was stirred overnight at room temperature. The mixture was purified by reverse-phase high-performance liquid chromatography (Waters Corp., X Bridge C18, 5 μm, 4.6 mm×250 mm, 0.01% aqueous trifluoroacetic acid solution, solution B: gradient with acetonitrile) to obtain compound 292 (1.7 mg, yield: 8%).

ESI-MS m/z: 1444 (M+H)$^+$

Step 165

Compound 291 (20 mg, 0.016 mmol) synthesized in step 163 of Example 16 and N-(6-maleimidocaproyloxy)succinimide (9.6 mg, 0.031 mmol) were dissolved in tetrahydrofuran (2 mL). To the solution, diisopropylethylamine (0.027 mL, 0.078 mmol) was added, and the mixture was stirred overnight at room temperature. The mixture was purified by reverse-phase high-performance liquid chromatography (Waters Corp., X Bridge C18, 5 μm, 4.6 mm×250 mm, 0.01% aqueous trifluoroacetic acid solution, solution B: gradient with acetonitrile) to obtain compound 293 (1.8 mg, yield: 8%).

ESI-MS m/z: 1498 (M+H)$^+$

Example 17 Synthesis of Nucleic Acid Conjugate 421 422
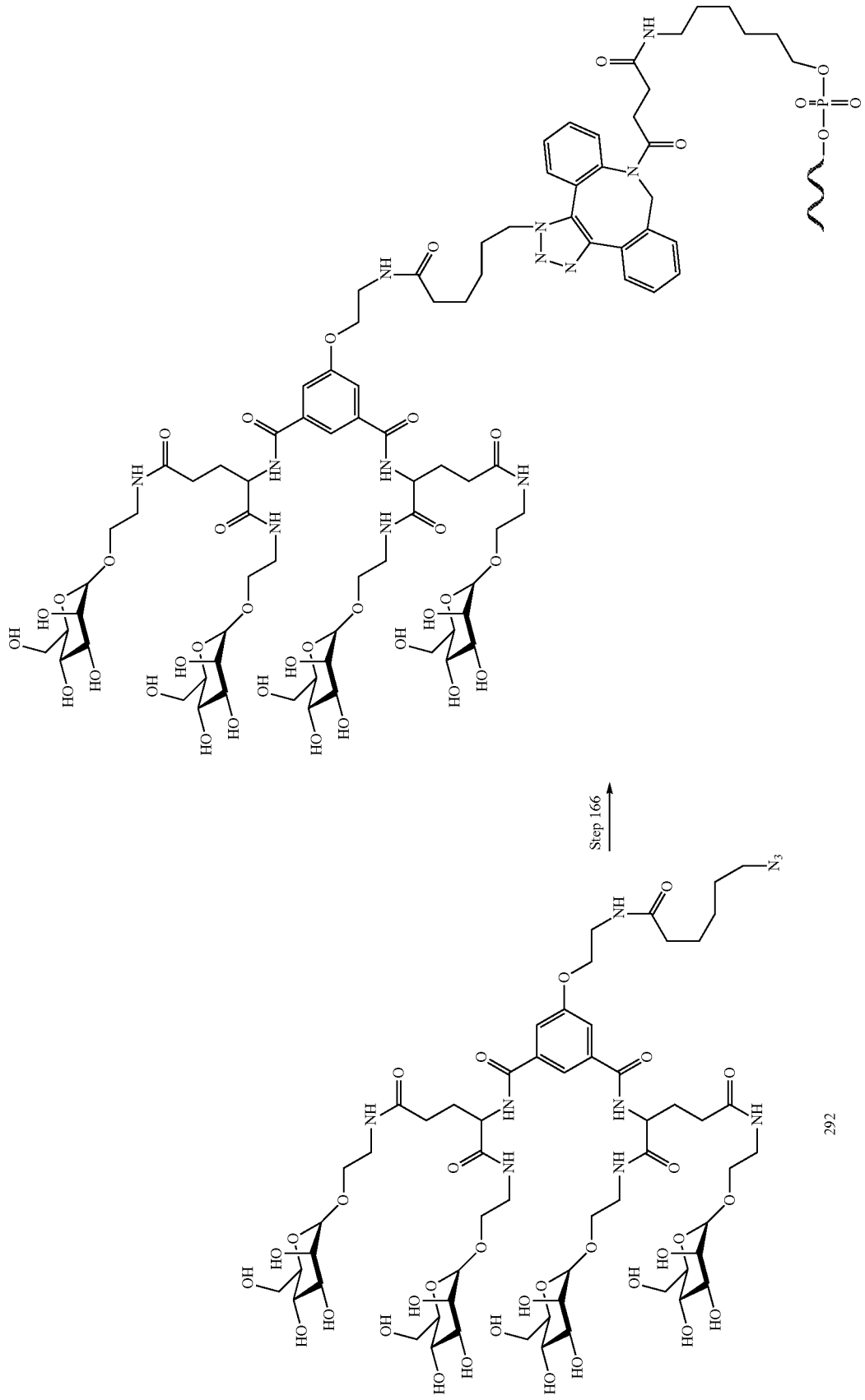

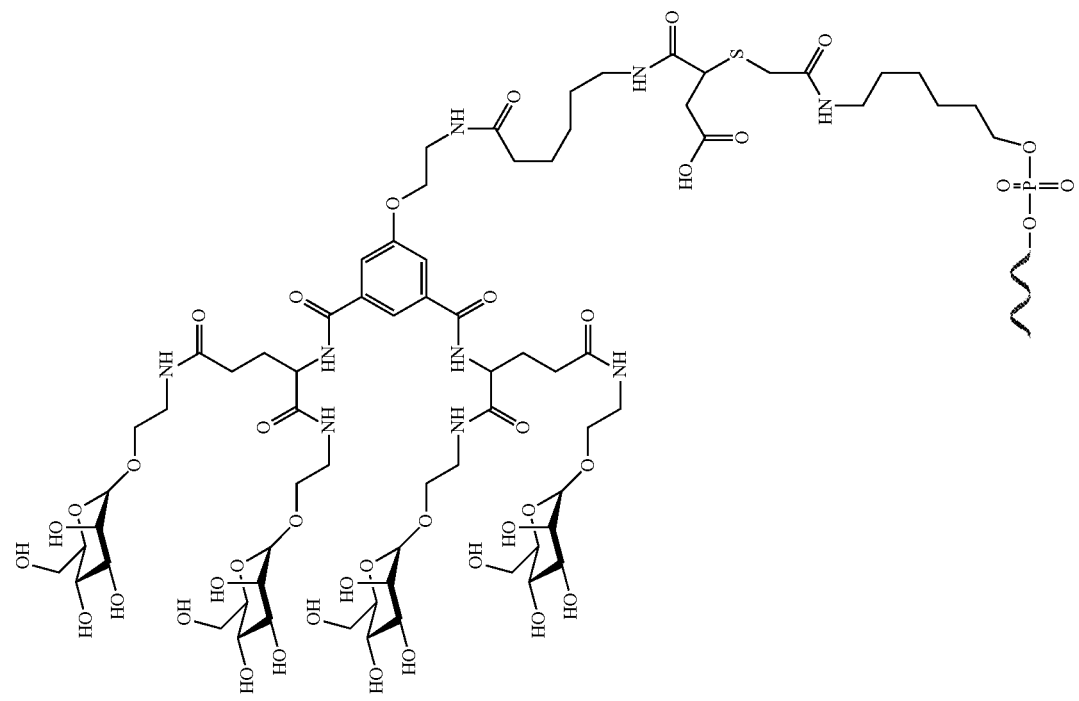
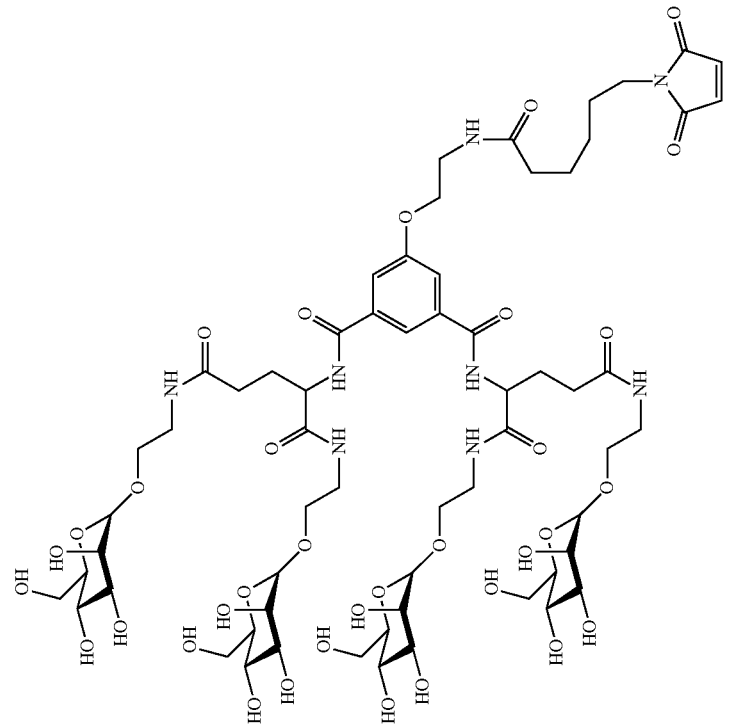

Step 166

Single-stranded nucleic acid conjugate 294 was obtained in the same way as in step 40 of Example 10 using compound 292 synthesized in step 164 of Example 16.

Step 167

Single-stranded nucleic acid conjugate 295 was obtained in the same way as in step 38 of Example 9 using compound 293 synthesized in step 165 of Example 16.

The sequences and mass spectrometry results of the nucleic acid conjugates synthesized in this Example are shown in Table 56.

TABLE 56

| Compound | Sequence (5' to 3') | Theoretical molecular weight | Found |
|---|---|---|---|
| 294_3'-B2M-ssRNA | A(F)G(M)G(F)A(M)C(F)U(M)G(F)G(M)U(F)C(M)U(F)U(F)U(M)C(F)U(M)A(F)U(M)C(F)U(M)^C(F)^U(M) 294 | 8692 | 8691 |
| 295_3'-Hprt1-ssRNA | U(F)C(M)C(F)U(M)A(F)U(M)G(F)A(M)C(F)U(M)G(F)U(M)A(F)G(M)A(F)U(M)U(F)U(M)U(F)A(M)U(F) 295 | 8524 | 8524 |

The double-stranded nucleic acid conjugates described in Table 57 were obtained in the same way as in step 39 of Example 9 using the single-stranded nucleic acid conjugates described in Table 56.

The sequences of the nucleic acid conjugates synthesized in this Example are shown in Table 58.

TABLE 57

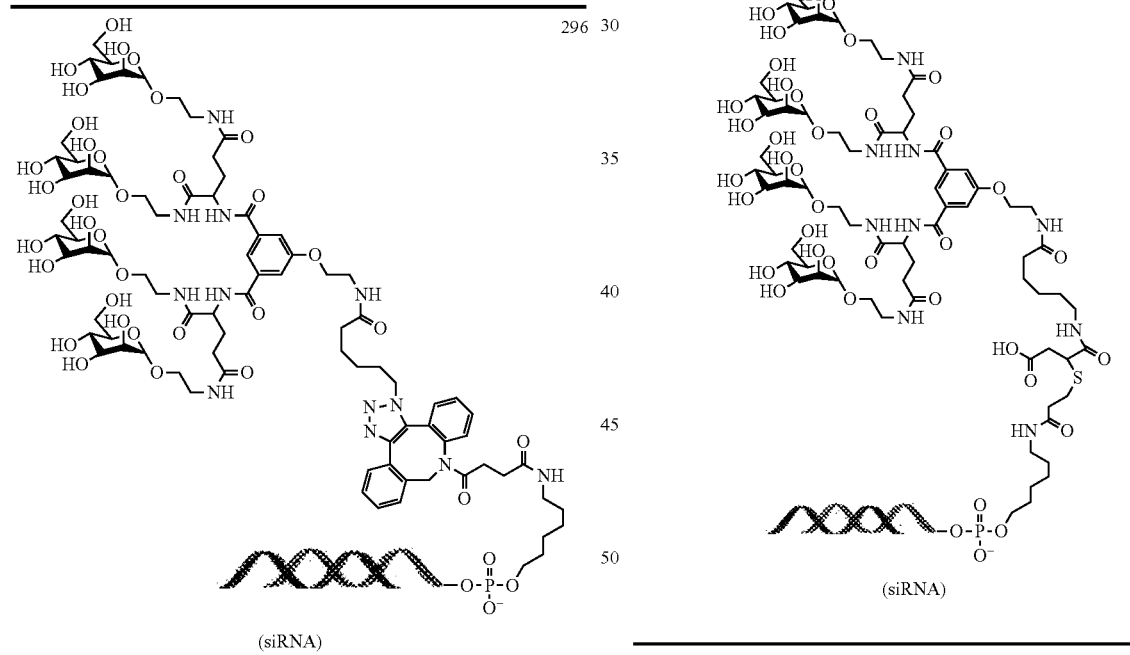

296

(siRNA)

TABLE 57-continued

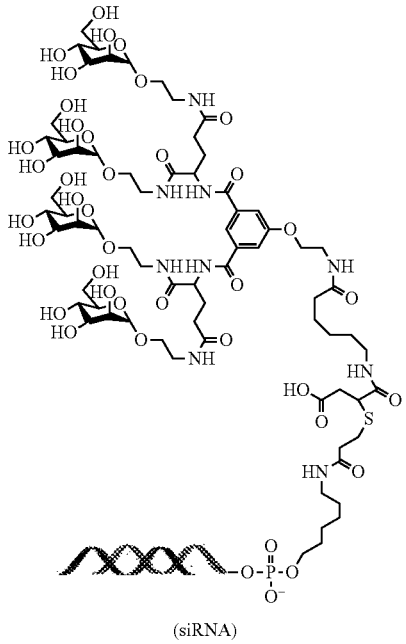

297

(siRNA)

TABLE 58

| Compound | Single strand name | Sequence (5' to 3') |
|---|---|---|
| 296_B2M-siRNA | 294_3'-B2M-ssRNA | A(F)G(M)G(F)A(M)C(F)U(M)G(F)G(M)U(F)C(M)U(F)U(F)U(M)C(F)U(M)A(F)U(M)C(F)U(M)^C(F)^U(M) 294 |
| | B2M-as-RNA | A(F)^G(M)^A(F)G(M)A(F)U(M)A(F)G(M)A(F)A(M)A(M)G(F)A(M)C(F)C(M)A(F)G(M)U(F)C(M)C(F)U(M)^U(F)^G(M) |
| 297_Hprt1-siRNA | 295_3'-Hprt1-ssRNA | U(F)C(M)C(F)U(M)A(F)U(M)G(F)A(M)C(F)U(M)G(F)U(M)A(F)G(M)A(F)U(M)U(F)U(M)U(F)A(M)U(F) 295 |
| | Hprt1-as-RNA | p-A(M)U(F)A(M)A(F)A(M)A(F)U(M)C(F)U(M)A(F)C(M)A(F)G(M)U(F)C(M)A(F)U(M)A(F)G(M)G(F)A(M)^A(F)^U(M) |

Test Example 5 In Vitro Activity of Nucleic Acid Conjugate Against Mouse Primary Liver Cell Among the nucleic acid conjugates obtained in Examples and Comparative Examples, those described in Table 59 were each transferred to CD-1-derived mouse primary liver cells (manufactured by Life Technologies Corp., Catalog No. MSCP10) by the following method.

Each nucleic acid conjugate diluted with Opti-MEM (Gibco/Thermo Fisher Scientific Inc., 31985) such that the final concentration was 30, 10 or 3 nmol/L was dispensed at 20 L/well to a 96-well culture plate. Then, mouse primary liver cells suspended in William's E Medium (manufactured by Life Technologies Corp., Catalog No. A12176-01) containing Primary Hepatocyte Thawing and Plating Supplements (manufactured by Life Technologies Corp., Catalog No. CM3000) were inoculated at 12500 cells/80 μL/well thereto and cultured at 37° C. for 6 hours under 5% $CO_2$ conditions. Then, the culture supernatant was carefully removed, and William's E Medium containing Primary Hepatocyte Maintenance Supplements (manufactured by Life Technologies Corp., Catalog No. CM4000) was added thereto. Untreated cells were inoculated as a negative control group.

The cells harboring each preparation were cultured at 37° C. for 18 hours in a 5% $CO_2$ incubator and washed with ice-cooled phosphate-buffered saline. The recovery of total RNA and the preparation of cDNA through reverse-transcription reaction using the obtained total RNA as a template were performed using SuperPrep Cell Lysis & RT Kit for qPCR (manufactured by Toyobo Co., Ltd., Catalog No. SCQ-201) according to the method described in the instruction attached to the product.

The obtained cDNA was used as a template in PCR reaction using TaqMan® Gene Expression Assays Probe (manufactured by Applied Biosystems, Inc.) as a probe and QuantStudio 12K Flex Real-Time PCR System (manufactured by Applied Biosystems, Inc.) according to the method described in the attached instruction manual to amplify serpin peptidase inhibitor, clade C (antithrombin), member 1 (also called antithrombin III; hereinafter, referred to as AT3) gene and a constitutively expressed gene D-glyceraldehyde-3-phosphate dehydrogenase (hereinafter, referred to as gapdh) gene. Their respective mRNA amplification levels were measured, and the semi-quantitative value of AT3 mRNA was calculated with the amplification level of gapdh mRNA as an internal control. The expression rate of AT3 mRNA was determined from the semi-quantitative value of AT3 mRNA when the semi-quantitative value of AT3 mRNA in the negative control measured in the same way as above was defined as 1. The obtained results about the expression rate of AT3 mRNA are shown in Tables 60 to 66 as an inhibition rate vs. the AT3 mRNA expression rate of the negative control.

TABLE 59

| Test substance No. | Compound No. |
|---|---|
| 1 | AT3-siRNA |
| 2 | 53(3'-AT3-siRNA) |
| 3 | 42(3'-AT3-siRNA) |
| 4 | 264(3'-AT3-siRNA) |
| 5 | 261(3'-AT3-siRNA) |
| 6 | 285(3'-AT3-siRNA) |
| 7 | 251(3'-AT3-siRNA) |
| 8 | 252(3'-AT3-siRNA) |
| 9 | 275(3'-AT3-siRNA) |
| 10 | 276(3'-AT3-siRNA) |
| 11 | 277(3'-AT3-siRNA) |
| 12 | 278(3'-AT3-siRNA) |

TABLE 59-continued

| Test substance No. | Compound No. |
|---|---|
| 13 | 279(3'-AT3-siRNA) |
| 14 | 280(3'-AT3-siRNA) |
| 15 | 281(3'-AT3-siRNA) |
| 16 | 282(3'-AT3-siRNA) |
| 17 | 283(3'-AT3-siRNA) |
| 18 | 284(3'-AT3-siRNA) |
| 19 | 262(3'-AT3-siRNA) |
| 20 | 263(3'-AT3-siRNA) |
| 21 | 255(3'-AT3-siRNA) |
| 22 | 253(3'-AT3-siRNA) |
| 23 | 254(3'-AT3-siRNA) |
| 24 | 257(3'-AT3-siRNA) |
| 25 | 256(3'-AT3-siRNA) |
| 26 | 258(3'-AT3-siRNA) |
| 27 | 266(3'-AT3-siRNA) |
| 28 | 265(3'-AT3-siRNA) |
| 29 | 267(3'-AT3-siRNA) |
| 30 | 268(3'-AT3-siRNA) |
| 31 | 269(3'-AT3-siRNA) |
| 32 | 270(3'-AT3-siRNA) |
| 33 | 271(3'-AT3-siRNA) |
| 34 | 272(3'-AT3-siRNA) |
| 35 | 273(3'-AT3-siRNA) |
| 36 | 274(3'-AT3-siRNA) |
| 37 | 286(3'-AT3-siRNA) |
| 38 | 287(3'-AT3-siRNA) |

TABLE 60

AT3 mRNA level [inhibition rate %]

| Test substance No. | Dose [nmol/L] | | |
|---|---|---|---|
| | 30 | 10 | 3 |
| 1 | 16.24 | −7.51 | 19.07 |
| 2 | −1.77 | −0.39 | 11.50 |
| 3 | 78.72 | 64.66 | 35.07 |
| 4 | 79.29 | 65.43 | 36.90 |
| 5 | 73.61 | 62.53 | 40.42 |

TABLE 61

AT3 mRNA level [inhibition rate %]

| Test substance No. | Dose [nmol/L] | | |
|---|---|---|---|
| | 30 | 10 | 3 |
| 1 | 18.78 | 12.29 | 3.78 |
| 6 | 89.90 | 79.76 | 56.89 |
| 7 | 83.00 | 76.72 | 56.30 |
| 8 | 81.80 | 76.27 | 55.76 |

TABLE 62

AT3 mRNA level [inhibition rate %]

| Test substance No. | Dose [nmol/L] | | |
|---|---|---|---|
| | 30 | 10 | 3 |
| 1 | −4.22 | −9.92 | −6.34 |
| 9 | 96.88 | 91.91 | 73.54 |
| 10 | 96.70 | 93.00 | 80.95 |
| 11 | 97.58 | 95.21 | 86.62 |
| 12 | 97.13 | 94.73 | 82.98 |
| 13 | 97.97 | 94.97 | 83.79 |
| 14 | 97.41 | 93.87 | 82.14 |
| 15 | 97.38 | 93.23 | 79.17 |

TABLE 63

AT3 mRNA level [inhibition rate %]

| Test substance No. | Dose [nmol/L] | | |
|---|---|---|---|
| | 30 | 10 | 3 |
| 1 | −4.23 | 6.14 | 9.84 |
| 16 | 98.66 | 97.09 | 90.01 |
| 17 | 97.26 | 96.22 | 83.87 |
| 18 | 97.90 | 95.52 | 84.55 |

TABLE 64

AT3 mRNA level [inhibition rate %]

| Test substance No. | Dose [nmol/L] | | |
|---|---|---|---|
| | 30 | 10 | 3 |
| 1 | 23.69 | 20.34 | 14.53 |
| 19 | 86.37 | 79.19 | 62.23 |
| 20 | 87.08 | 74.57 | 50.87 |
| 21 | 89.22 | 81.76 | 56.49 |
| 22 | 92.86 | 84.12 | 51.84 |
| 23 | 84.52 | 76.64 | 48.04 |

TABLE 65

AT3 mRNA level [inhibition rate %]

| Test substance No. | Dose [nmol/L] | | |
|---|---|---|---|
| | 30 | 10 | 3 |
| 1 | −0.23 | 8.53 | 2.86 |
| 24 | 96.58 | 92.42 | 78.16 |
| 25 | 94.48 | 89.26 | 72.88 |
| 26 | 94.47 | 92.33 | 71.75 |
| 27 | 96.76 | 93.45 | 76.89 |
| 28 | 95.70 | 92.72 | 68.85 |
| 29 | 96.84 | 93.35 | 78.31 |
| 30 | 94.26 | 89.68 | 71.60 |
| 31 | 95.63 | 91.91 | 71.05 |
| 32 | 95.65 | 91.54 | 72.53 |
| 33 | 94.91 | 91.84 | 79.27 |

TABLE 66

AT3 mRNA level [inhibition rate %]

| Test substance No. | Dose [nmol/L] | | |
|---|---|---|---|
| | 30 | 10 | 3 |
| 1 | −3.22 | 10.06 | −12.88 |
| 34 | 97.67 | 96.70 | 88.26 |
| 35 | 97.18 | 96.13 | 89.84 |
| 36 | 96.80 | 95.47 | 87.56 |
| 37 | 98.10 | 96.09 | 88.26 |
| 38 | 97.55 | 96.19 | 88.25 |

As is evident from Tables 60 to 66, the nucleic acid conjugate of the present invention (test substance Nos. 3 to 38) inhibited the mRNA expression of the AT3 gene after transfer to mouse primary liver cells.

Test Example 6 In Vivo Activity of Nucleic Acid Conjugate Against Mouse

Among the nucleic acid conjugates obtained in Examples and Comparative Examples, those described in Table 59 were each subjected to an in vivo evaluation test by the following method. Each nucleic acid conjugate used was diluted with Dulbecco's phosphate-buffered saline (DPBS) (manufactured by Nacalai Tesque, Inc.) according to the test. After acclimatization of mice (BALB/cA, obtained from CLEA Japan Inc.), each nucleic acid conjugate was administered at 1.5 mg/kg or 0.5 mg/kg to the mice by subcutaneous injection. For a control group, PBS alone was administered to the mice by subcutaneous injection. Three days after the administration, blood was collected from the postcaval vein under isoflurane anesthesia. The collected blood was mixed with an anticoagulant solution containing 3.2 M sodium citrate and 5 mmol/L D-glucose at a volume ratio of 9:1, and a supernatant after centrifugation was recovered to obtain plasma. After the blood collection, the animals were euthanized, and the livers were collected and cryopreserved in liquid nitrogen. From the cryopreserved liver samples, total RNA was recovered using TRIzol® RNA Isolation Reagents (manufactured by Life Technologies Corp., Catalog No. 15596026) and RNeasy Mini Kit (manufactured by Qiagen N.V., Catalog No. 74106) according to the methods described in the instructions attached to the products. cDNA was further prepared through reverse-transcription reaction with the obtained total RNA as a template using Transcriptor First Strand cDNA Synthesis Kit (manufactured by F. Hoffmann-La Roche, Ltd., Catalog No. 04897030001) according to the method described in the instruction attached to the product. The obtained cDNA was used as a template in PCR reaction using TaqMan® Gene Expression Assays Probe (manufactured by Applied Biosystems, Inc.) as a probe and QuantStudio 12K Flex Real-Time PCR System (manufactured by Applied Biosystems, Inc.) according to the method described in the attached instruction manual to amplify AT3 gene and gapdh gene. Their respective mRNA amplification levels were measured, and the semi-quantitative value of AT3 mRNA was calculated with the amplification level of AT3 mRNA as an internal control. The expression rate of AT3 mRNA was determined from the semi-quantitative value of AT3 mRNA when the semi-quantitative value of AT3 mRNA in the control group measured in the same way as above was defined as 1. Also, an AT3 protein concentration in the plasma was measured using Antithrombin III Mouse ELISA Kit (manufactured by Abcam Inc., Catalog No. ab108800) according to the method described in the attached instruction manual. The obtained inhibition rate of expression of AT3 mRNA and AT3 protein concentration in the plasma are shown in Tables 67 to 69.

TABLE 67

| Test substance | AT3 mRNA level in liver [inhibition rate %] Dose [mg/kg] | | AT3 protein concentration in plasma [µg/mL] Dose [mg/kg] | |
|---|---|---|---|---|
| No. | 1.5 | 0.5 | 1.5 | 0.5 |
| Control | — | | 323.05 | |
| 2 | −13.30 | −15.10 | 303.47 | 375.88 |
| 3 | 42.85 | 14.50 | 212.26 | 258.78 |
| 4 | 26.74 | 19.04 | 243.16 | 336.67 |
| 5 | 10.76 | 1.56 | 281.52 | 377.74 |
| 6 | 69.39 | 33.88 | 160.10 | 278.20 |
| 7 | 46.36 | 23.11 | 189.61 | 306.61 |
| 8 | 44.26 | 27.25 | 205.49 | 232.32 |

TABLE 68

| Test substance | AT3 mRNA level in liver [inhibition rate %] Dose [mg/kg] | | AT3 protein concentration in plasma [µg/mL] Dose [mg/kg] | |
|---|---|---|---|---|
| No. | 1.5 | 0.5 | 1.5 | 0.5 |
| Control | — | | 406.25 | |
| 9 | 52.36 | 33.71 | 207.82 | 271.94 |
| 10 | 46.36 | 19.93 | 189.70 | 283.51 |
| 11 | 61.22 | 30.09 | 161.69 | 263.98 |
| 12 | 66.19 | 35.34 | 153.92 | 256.08 |
| 13 | 63.52 | 28.98 | 175.91 | 277.52 |
| 14 | 66.26 | 30.95 | 147.01 | 248.54 |
| 15 | 61.97 | 26.39 | 153.46 | 258.51 |
| 16 | 54.95 | 45.75 | 175.40 | 234.00 |
| 17 | 50.93 | 29.41 | 149.33 | 266.16 |
| 18 | 57.82 | 32.22 | 180.48 | 314.41 |

TABLE 69

| Test substance | AT3 mRNA level in liver [inhibition rate %] Dose [mg/kg] | | AT3 protein concentration in plasma [µg/mL] Dose [mg/kg] | |
|---|---|---|---|---|
| No. | 1.5 | 0.5 | 1.5 | 0.5 |
| Control | — | | 430.38 | |
| 19 | 50.65 | 26.74 | 235.75 | 294.03 |
| 20 | 33.17 | 16.66 | 228.00 | 334.38 |
| 21 | 42.26 | 25.95 | 230.60 | 298.86 |
| 22 | 44.79 | 12.90 | 233.16 | 297.65 |
| 24 | 76.00 | 39.22 | 125.91 | 258.13 |
| 25 | 65.05 | 39.20 | 154.28 | 242.88 |
| 27 | 77.76 | 37.94 | 143.83 | 255.37 |
| 28 | 46.70 | 21.10 | 233.87 | 312.41 |
| 29 | 73.38 | 30.03 | 161.78 | 237.47 |
| 30 | 68.94 | 25.92 | 169.58 | 222.12 |
| 31 | 55.87 | 17.95 | 172.05 | 273.52 |
| 32 | 55.38 | 7.30 | 200.17 | 286.96 |
| 33 | 53.60 | −8.73 | 207.01 | 290.95 |

As is evident from Tables 67 to 69, the nucleic acid conjugate of the present invention (test substance Nos. 3 to 22, 24, 25, and 27 to 33) reduced the expression of the AT3 gene and decreased the AT3 protein concentration in blood in vivo.

Test Example 7 In Vitro Activity of Nucleic Acid Conjugate Against Human Primary Liver Cell B2M-siRNA (test substance 39) and 260_3'-B2M-siRNA (test substance 40) obtained in Example 15 were each transferred to human primary liver cells (manufactured by Biopredic International, Catalog No. HEP187) by the following method.

Each nucleic acid conjugate diluted with Opti-MEM (Gibco/Thermo Fisher Scientific Inc., Catalog No. 31985) such that the final concentration was 300, 100, 30, 10, 3 or 1 nmol/L was dispensed at 20 µL/well to a 96-well culture plate. Then, human primary liver cells suspended at 1.25× $10^5$ cells/mL in Plating medium (manufactured by Biopredic International, Catalog No. LV0304-2) were inoculated at cells/80 µL/well thereto and cultured at 37° C. for 6 hours under 5% $CO_2$ conditions. Then, the culture supernatant was carefully removed, and Incubation medium (manufactured by Biopredic International, Catalog No. LV0304-2) was added thereto. Untreated cells were inoculated as a negative control group.

The cells harboring each preparation were cultured at 37° C. for 18 hours in a 5% $CO_2$ incubator and washed with ice-cooled phosphate-buffered saline. The recovery of total RNA and the preparation of cDNA through reverse-transcription reaction using the obtained total RNA as a template were performed using SuperPrep Cell Lysis & RT Kit for qPCR (manufactured by Toyobo Co., Ltd., Catalog No. SCQ-201) according to the method described in the instruction attached to the product.

The obtained cDNA was used as a template in PCR reaction using TaqMan® Gene Expression Assays Probe (manufactured by Applied Biosystems, Inc.) as a probe and QuantStudio 12K Flex Real-Time PCR System (manufactured by Applied Biosystems, Inc.) according to the method described in the attached instruction manual to amplify beta-2 microglobulin (hereinafter, referred to as B2M) gene and a constitutively expressed gene D-glyceraldehyde-3-phosphate dehydrogenase (hereinafter, referred to as gapdh) gene. Their respective mRNA amplification levels were measured, and the semi-quantitative value of B2M mRNA was calculated with the amplification level of gapdh mRNA as an internal control. The expression rate of B2M mRNA was determined from the semi-quantitative value of B2M mRNA when the semi-quantitative value of B2M mRNA in the negative control measured in the same way as above was defined as 1. The obtained results about the expression rate of B2M mRNA are shown in Table 70 as an inhibition rate vs. the B2M mRNA expression rate of the negative control.

TABLE 70

| Test substance | Test substance 39(B2M-siRNA) | | | | | |
|---|---|---|---|---|---|---|
| Dose [nmol/L] | 300 | 100 | 30 | 10 | 3 | 1 |
| B2M mRNA level [inhibition rate %] | 37.1 | 34.1 | 23.2 | 20.7 | 9.9 | −6.4 |
| Test substance | Test substance 40(260_3'-B2M-siRNA) | | | | | |
| Dose [nmol/L] | 300 | 100 | 30 | 10 | 3 | 1 |
| B2M mRNA level [inhibition rate %] | 89.3 | 84.0 | 77.2 | 61.9 | 40.0 | 15.8 |

Test Example 8 Evaluation of mRNA Knockdown Activity of Nucleic Acid Conjugate Against Human Monocyte-Derived Macrophage Cell Human CD14-positive monocyte cells (Untouched Frozen NPB-CD14+ Monocytes, manufactured by AllCells, PB011F) were lysed according to the attached protocol using RPMI1640 medium (manufactured by Nacalai Tesque, Inc., 30264-56) containing 10% fetal bovine serum (hereinafter, referred to as 10% FBS RPMI1640 medium) and DNase I Solution (manufactured by StemCell Technologies Inc., 07900).

Then, Recombinant Human GM-CSF Protein CF (manufactured by R&D Systems, Inc., 215-GM-050/CF) (hereinafter, referred to as GM-CSF) was added thereto such that the final concentration was 100 ng/mL. The cells were inoculated at a density of $10^6$ cells/mL to a multi-plate (manufactured by SUMILON/Sumitomo Bakelite Co., Ltd., MS-8196F5) and cultured at 37° C. under 5% $CO_2$ conditions.

Six days after the start of culture, the culture supernatant was removed, and 80 uL of 10% FBS RPMI1640 medium containing 100 ng/mL GM-CSF was added to each well.

The test samples used were nucleic acid conjugate 296_3'-B2M-siRNA (test substance 41) targeting beta-2 microglobulin (hereinafter, referred to as B2M) and HPRT-1, and B2M-siRNA (test substance 42) as a control corresponding to the nucleic acid conjugate. The final concentration of the test sample was set to 3 concentrations: 1 µmol/L, 0.3 µmol/L, and 0.1 µmol/L: The test was conducted at N=3.

The nucleic acid conjugate solution was diluted by the following procedures: a nucleic acid solution prepared with a citrate buffer solution (20 mM citrate (pH 7), 150 mM NaCl) was diluted using Opti-MEM® I Reduced Serum Medium (manufactured by Life Technologies Corp., 31985-070). 20 μL of the diluted nucleic acid solution was added to the cell lysate, while 20 μL of a nucleic acid-free citrate buffer solution/Opti-MEM mixed solution was added to the negative control group, followed by culture at 37° C. under 5% $CO_2$ conditions for 4 days.

A cell lysate containing RNA was prepared using Super-Prep® Cell Lysis & RT Kit for qPCR (manufactured by Toyobo Co., Ltd., SCQ-101), and cDNA was prepared through reverse-transcription reaction using RT Kit for qPCR attached to the kit according to the instruction attached to the kit.

This cDNA was used as a template for PCR reaction, and the Taqman probe method was carried out using QuantStudio 12K Flex Real-Time PCR System (manufactured by Applied Biosystems, Inc.) as follows: in the case of quantifying a knockdown effect on B2M gene, B2M and control HPRT-1 genes were each subjected to PCR reaction. Their respective mRNA amplification levels were measured, and the semi-quantitative value of B2M mRNA was calculated with the amplification level of HPRT-1 mRNA as an internal control.

The B2M gene was measured using TaqMan probe Hs00187842_m1 (manufactured by Applied Biosystems, Inc.) and using TaqMan Gene Expression Master Mix (manufactured by Applied Biosystems, Inc., 4369542) as a reaction reagent according to the attached protocol. The target mRNA level of the nucleic acid was calculated as a relative ratio when the B2M mRNA level in the negative control group (nucleic acid-untransferred group) was defined as 1. Results indicating the relative ratio of the mRNA level by mean±standard deviation are shown in Table 71.

TABLE 71

| Test substance | Test substance 42 (B2M-siRNA) | | | Test substance 41 (296_3'-B2M-siRNA) | | |
|---|---|---|---|---|---|---|
| Dose [μmol/L] | 1 | 0.3 | 0.1 | 1 | 0.3 | 0.1 |
| B2M mRNA level [inhibition rate %] | −1.5 | −16.5 | −0.08 | 40.9 | 34.7 | 29.0 |

These results demonstrated that the nucleic acid conjugate of the present invention (test substance 41) exhibits a significant knockdown effect on human monocyte-derived macrophages, as compared with the control B2M-siRNA (test substance 42).

INDUSTRIAL APPLICABILITY

The nucleic acid conjugate of the present invention can be used for treating various related diseases in vivo by administration to mammals.

Free Test of Sequence Listing

SEQ ID NO: 1 represents the nucleotide sequence of ApoBASO.
SEQ ID NO: 2 represents the nucleotide sequence of AT3-ssRNA.
SEQ ID NO: 3 represents the nucleotide sequence of AT3-asRNA.
SEQ ID NO: 4 represents the nucleotide sequence of B2M-ssRNA.
SEQ ID NO: 5 represents the nucleotide sequence of B2M-asRNA.
SEQ ID NO: 6 represents the nucleotide sequence of CD45ASO.
SEQ ID NO: 7 represents the nucleotide sequence of 3'-dT10.
SEQ ID NO: 8 represents the nucleotide sequence of Hprt1-ssRNA.
SEQ ID NO: 9 represents the nucleotide sequence of Hprt1-asRNA.

The invention claimed is:

1. A nucleic acid conjugate having any structure represented by the following formulas 7-1 to 7-9:

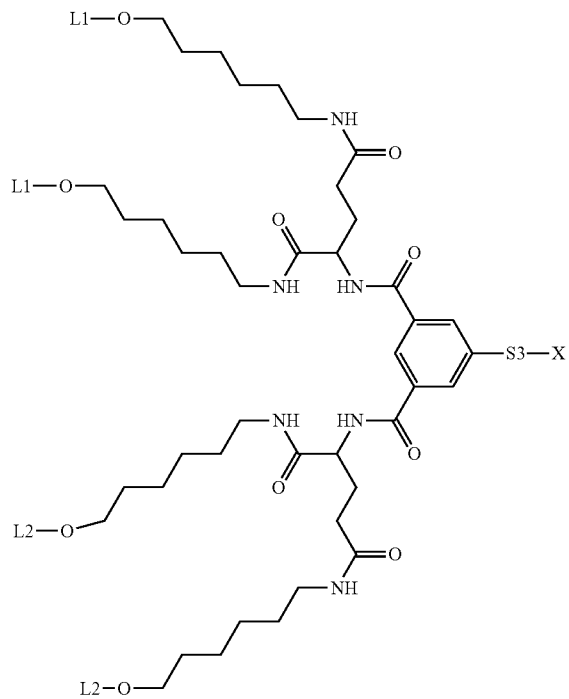

Formula 7-1

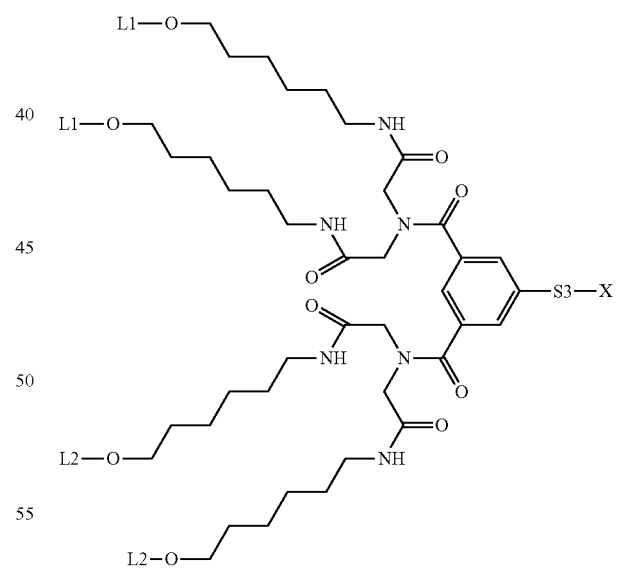

Formula 7-2

-continued

Formula 7-3
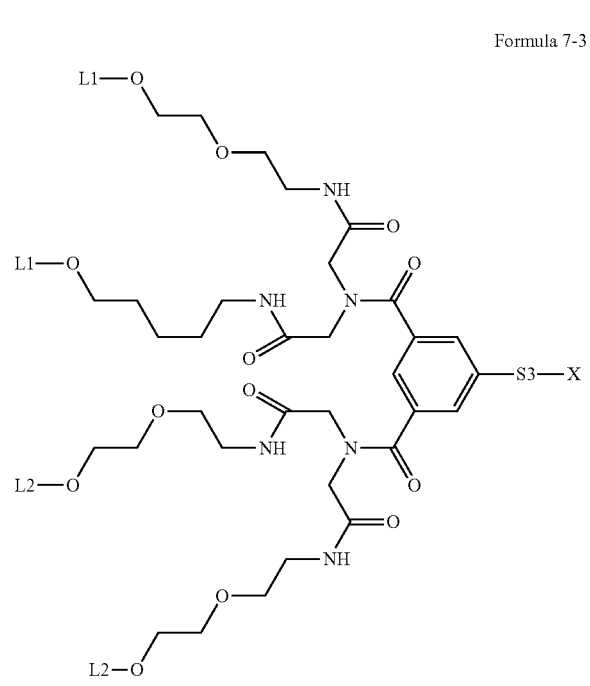
Formula 7-5
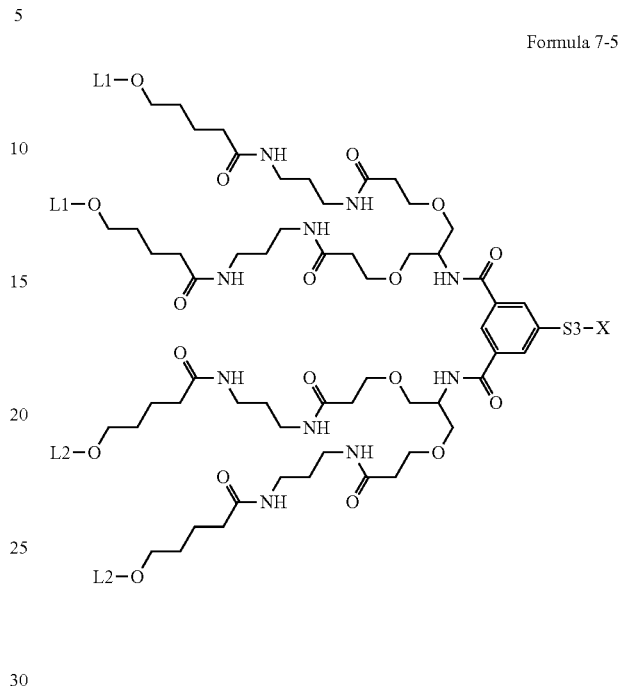
Formula 7-4
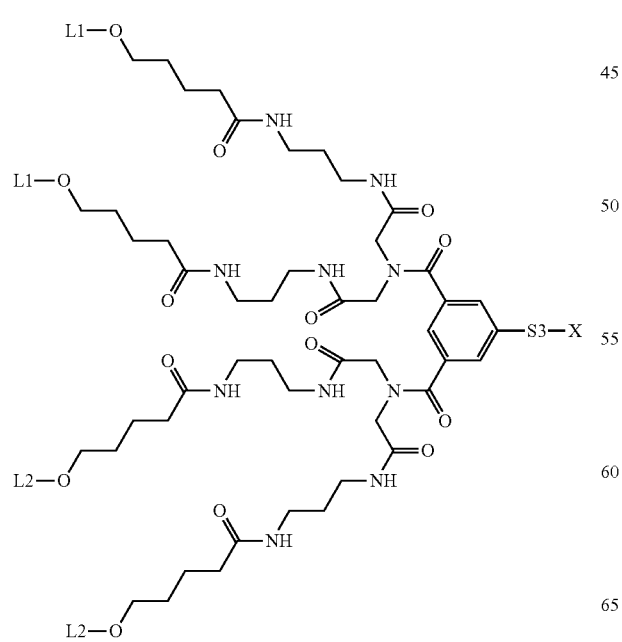
Formula 7-6
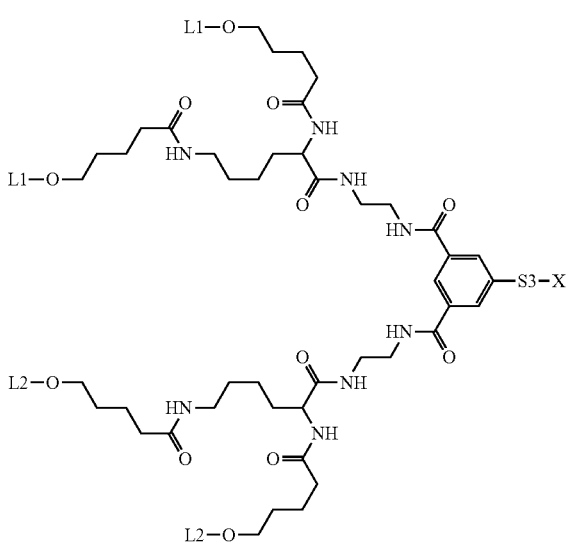

Formula 7-8

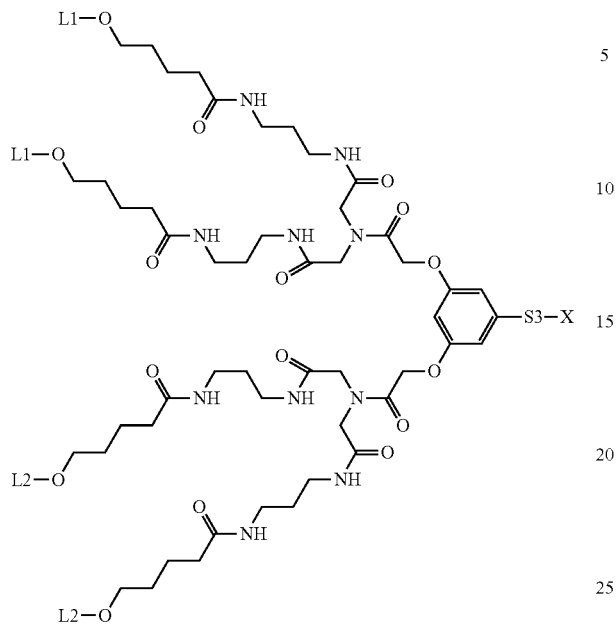

Formula 7-9

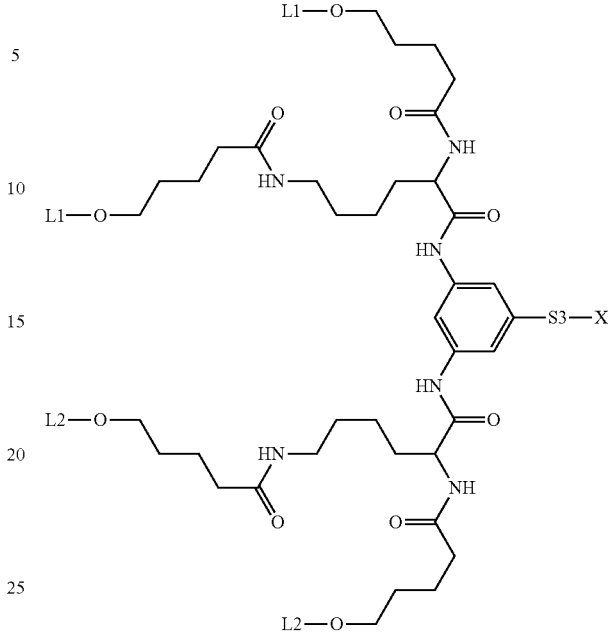

Formula 7-8

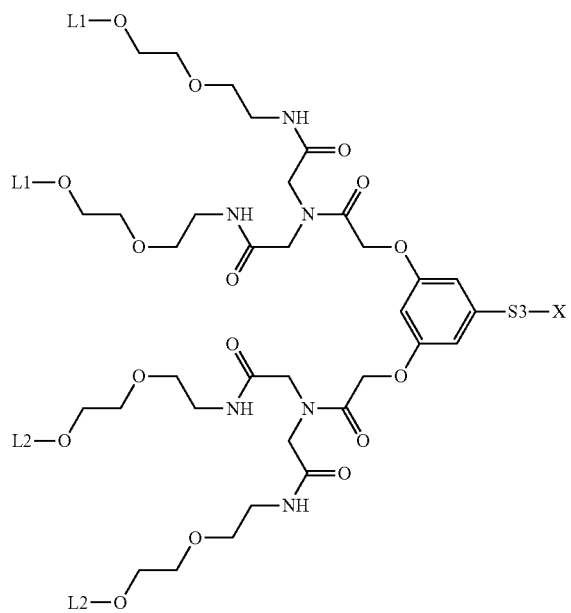

wherein
X is an oligonucleotide,
L1 and L2 are each independently a sugar ligand, and
S3 is a linker.

2. The nucleic acid conjugate according to claim 1, wherein the sugar ligand is mannose or N-acetylgalactosamine.

3. The nucleic acid conjugate according to claim 1, wherein the oligonucleotide comprises a modified nucleotide.

4. A pharmaceutical composition comprising a nucleic acid conjugate according to claim 1.

5. The pharmaceutical composition according to claim 4, wherein the sugar ligand targets a liver cell.

6. The pharmaceutical composition according to claim 4, wherein the pharmaceutical composition is a formulation suitable for intravenous or subcutaneous administration.

7. A method for treating or preventing a disease, comprising administering a nucleic acid conjugate according to claim 1 to a patient in need thereof.

8. A method for treating or preventing a disease, comprising administering a pharmaceutical composition according to claim 4 to a patient in need thereof.

* * * * *

SEQUENCE LISTING

```
<160> NUMBER OF SEQ ID NOS: 9

<210> SEQ ID NO 1
<211> LENGTH: 13
<212> TYPE: DNA
<213> ORGANISM: Artificial Sequence
<220> FEATURE:
<223> OTHER INFORMATION: ApoBASO
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (2)..(2)
<223> OTHER INFORMATION: LNAmC
<220> FEATURE:
<221> NAME/KEY: misc_feature
<222> LOCATION: (2)..(13)
<223> OTHER INFORMATION: 5'-phosphonothioate
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (12)..(12)
<223> OTHER INFORMATION: LNAmC
<220> FEATURE:
<221> NAME/KEY: misc_feature
<222> LOCATION: (13)..(13)
<223> OTHER INFORMATION: LNA
```

<400> SEQUENCE: 1
gnattggtat tna                                                              13

<210> SEQ ID NO 2
<211> LENGTH: 21
<212> TYPE: RNA
<213> ORGANISM: Artificial Sequence
<220> FEATURE:
<223> OTHER INFORMATION: AT3-ssRNA
<220> FEATURE:
<221> NAME/KEY: modified_base
<222> LOCATION: (1)..(1)
<223> OTHER INFORMATION: 2'-deoxy-2'-fluoroguanosine
<220> FEATURE:
<221> NAME/KEY: modified_base
<222> LOCATION: (2)..(2)
<223> OTHER INFORMATION: gm
<220> FEATURE:
<221> NAME/KEY: misc_feature
<222> LOCATION: (2)..(3)
<223> OTHER INFORMATION: 5'-phosphonothioate
<220> FEATURE:
<221> NAME/KEY: modified_base
<222> LOCATION: (3)..(3)
<223> OTHER INFORMATION: 2'-deoxy-2'-fluorouridine
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-deoxy-2'-fluoroadenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: 2'-deoxy-2'-fluorocytidine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(10)
<223> OTHER INFORMATION: 2'-deoxy-2'-fluorocytidine
<220> FEATURE:
<221> NAME/KEY: modified_base
<222> LOCATION: (11)..(11)
<223> OTHER INFORMATION: 2'-deoxy-2'-fluoroadenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-deoxy-2'-fluorouridine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: 2'-deoxy-2'-fluoroadenosine
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)

-continued

```
<223> OTHER INFORMATION: 2'-deoxy-2'-fluorouridine
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: 2'-deoxy-2'-fluorocytidine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: 2'-deoxy-2'-fluoroadenosine

<400> SEQUENCE: 2
gguuaacacc auuuacuuca a                                              21

<210> SEQ ID NO 3
<211> LENGTH: 23
<212> TYPE: RNA
<213> ORGANISM: Artificial Sequence
<220> FEATURE:
<223> OTHER INFORMATION: AT3-asRNA
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: 2'-deoxy-2'-fluorouridine
<220> FEATURE:
<221> NAME/KEY: misc_feature
<222> LOCATION: (2)..(3)
<223> OTHER INFORMATION: 5'-phosphonothioate
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-deoxy-2'-fluoroadenosine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-deoxy-2'-fluoroguanosine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-deoxy-2'-fluoroadenosine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: 2'-deoxy-2'-fluoroadenosine
<220> FEATURE:
<221> NAME/KEY: modified_base
<222> LOCATION: (11)..(11)
<223> OTHER INFORMATION: um
<220> FEATURE:
<221> NAME/KEY: modified_base
```

```
<222> LOCATION: (12)..(13)
<223> OTHER INFORMATION: gm
<220> FEATURE:
<221> NAME/KEY: modified_base
<222> LOCATION: (14)..(14)
<223> OTHER INFORMATION: 2'-deoxy-2'-fluorouridine
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (16)..(16)
<223> OTHER INFORMATION: 2'-deoxy-2'-fluorouridine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-deoxy-2'-fluoroadenosine
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-deoxy-2'-fluorocytidine
<220> FEATURE:
<221> NAME/KEY: modified_base
<222> LOCATION: (21)..(21)
<223> OTHER INFORMATION: cm
<220> FEATURE:
<221> NAME/KEY: modified_base
<222> LOCATION: (22)..(22)
<223> OTHER INFORMATION: 2'-O-methyladenosine
<220> FEATURE:
<221> NAME/KEY: misc_feature
<222> LOCATION: (22)..(23)
<223> OTHER INFORMATION: 5'-phosphonothioate
<220> FEATURE:
<221> NAME/KEY: modified_base
<222> LOCATION: (23)..(23)
<223> OTHER INFORMATION: gm

<400> SEQUENCE: 3
uugaaguaaa ugguguuaac cag                                           23

<210> SEQ ID NO 4
<211> LENGTH: 21
<212> TYPE: RNA
<213> ORGANISM: Artificial Sequence
<220> FEATURE:
<223> OTHER INFORMATION: B2M-ssRNA
<220> FEATURE:
<221> NAME/KEY: modified_base
<222> LOCATION: (1)..(1)
<223> OTHER INFORMATION: 2'-deoxy-2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-deoxy-2'-fluoroguanosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-deoxy-2'-fluorocytidine
<220> FEATURE:
```

```
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-deoxy-2'-fluoroguanosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-deoxy-2'-fluorouridine
<220> FEATURE:
<221> NAME/KEY: modified_base
<222> LOCATION: (10)..(10)
<223> OTHER INFORMATION: cm
<220> FEATURE:
<221> NAME/KEY: modified_base
<222> LOCATION: (11)..(12)
<223> OTHER INFORMATION: 2'-deoxy-2'-fluorouridine
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: 2'-deoxy-2'-fluorocytidine
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: 2'-deoxy-2'-fluoroadenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-deoxy-2'-fluorocytidine
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(20)
<223> OTHER INFORMATION: 2'-deoxy-2'-fluorocytidine
<220> FEATURE:
<221> NAME/KEY: misc_feature
<222> LOCATION: (20)..(21)
<223> OTHER INFORMATION: 5'-phosphonothioate
<220> FEATURE:
<221> NAME/KEY: modified_base
<222> LOCATION: (21)..(21)
<223> OTHER INFORMATION: um

<400> SEQUENCE: 4
aggacugguc uuucuaucuc u                                             21

<210> SEQ ID NO 5
<211> LENGTH: 23
<212> TYPE: RNA
<213> ORGANISM: Artificial Sequence
<220> FEATURE:
<223> OTHER INFORMATION: B2M-asRNA
<220> FEATURE:
<221> NAME/KEY: modified_base
<222> LOCATION: (1)..(1)
<223> OTHER INFORMATION: 2'-deoxy-2'-fluoroadenosine
```

-continued

```
<220> FEATURE:
<221> NAME/KEY: modified_base
<222> LOCATION: (2)..(2)
<223> OTHER INFORMATION: gm
<220> FEATURE:
<221> NAME/KEY: misc_feature
<222> LOCATION: (2)..(3)
<223> OTHER INFORMATION: 5'-phosphonothioate
<220> FEATURE:
<221> NAME/KEY: modified_base
<222> LOCATION: (3)..(3)
<223> OTHER INFORMATION: 2'-deoxy-2'-fluoroadenosine
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: 2'-deoxy-2'-fluoroadenosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-deoxy-2'-fluoroadenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (9)..(9)
<223> OTHER INFORMATION: 2'-deoxy-2'-fluoroadenosine
<220> FEATURE:
<221> NAME/KEY: modified_base
<222> LOCATION: (10)..(11)
<223> OTHER INFORMATION: 2'-O-methyladenosine
<220> FEATURE:
<221> NAME/KEY: modified_base
<222> LOCATION: (12)..(12)
<223> OTHER INFORMATION: 2'-deoxy-2'-fluoroguanosine
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: 2'-deoxy-2'-fluorocytidine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-deoxy-2'-fluoroadenosine
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: 2'-deoxy-2'-fluorouridine
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: 2'-deoxy-2'-fluorocytidine
<220> FEATURE:
<221> NAME/KEY: modified_base
<222> LOCATION: (21)..(21)
```

```
<223> OTHER INFORMATION: um
<220> FEATURE:
<221> NAME/KEY: modified_base
<222> LOCATION: (22)..(22)
<223> OTHER INFORMATION: 2'-deoxy-2'-fluorouridine
<220> FEATURE:
<221> NAME/KEY: misc_feature
<222> LOCATION: (22)..(23)
<223> OTHER INFORMATION: 5'-phosphonothioate
<220> FEATURE:
<221> NAME/KEY: modified_base
<222> LOCATION: (23)..(23)
<223> OTHER INFORMATION: gm

<400> SEQUENCE: 5
agagauagaa agaccagucc uug                                             23

<210> SEQ ID NO 6
<211> LENGTH: 16
<212> TYPE: DNA
<213> ORGANISM: Artificial Sequence
<220> FEATURE:
<223> OTHER INFORMATION: CD45ASO
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (2)..(16)
<223> OTHER INFORMATION: 5'-phosphonothioate
<220> FEATURE:
<221> NAME/KEY: misc_feature
<222> LOCATION: (13)..(16)
<223> OTHER INFORMATION: LNA

<400> SEQUENCE: 6
ccaaatgcca agagtt                                                     16

<210> SEQ ID NO 7
<211> LENGTH: 10
<212> TYPE: DNA
<213> ORGANISM: Artificial Sequence
<220> FEATURE:
<223> OTHER INFORMATION: 3'-dT10
<220> FEATURE:
<221> NAME/KEY: misc_feature
<222> LOCATION: (1)..(1)
<223> OTHER INFORMATION: RNA

<400> SEQUENCE: 7
tttttttttt                                                            10

<210> SEQ ID NO 8
<211> LENGTH: 21
<212> TYPE: RNA
<213> ORGANISM: Artificial Sequence
<220> FEATURE:
<223> OTHER INFORMATION: Hprt1-ssRNA
<220> FEATURE:
<221> NAME/KEY: modified_base
<222> LOCATION: (1)..(1)
<223> OTHER INFORMATION: 2'-deoxy-2'-fluorouridine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: 2'-deoxy-2'-fluorocytidine
<220> FEATURE:
<221> NAME/KEY: modified_base
```

```
<222> LOCATION: (4)..(4)
<223> OTHER INFORMATION: um
<220> FEATURE:
<221> NAME/KEY: modified_base
<222> LOCATION: (5)..(5)
<223> OTHER INFORMATION: 2'-deoxy-2'-fluoroadenosine
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: 2'-deoxy-2'-fluoroguanosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-deoxy-2'-fluorocytidine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: 2'-deoxy-2'-fluoroguanosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: 2'-deoxy-2'-fluoroadenosine
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (15)..(15)
<223> OTHER INFORMATION: 2'-deoxy-2'-fluoroadenosine
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (17)..(17)
<223> OTHER INFORMATION: 2'-deoxy-2'-fluorouridine
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: 2'-deoxy-2'-fluorouridine
<220> FEATURE:
<221> NAME/KEY: modified_base
<222> LOCATION: (20)..(20)
<223> OTHER INFORMATION: 2'-O-methyladenosine
<220> FEATURE:
<221> NAME/KEY: modified_base
<222> LOCATION: (21)..(21)
<223> OTHER INFORMATION: 2'-deoxy-2'-fluorouridine

<400> SEQUENCE: 8
uccuaugacu guagauuuua u                                             21

<210> SEQ ID NO 9
<211> LENGTH: 23
<212> TYPE: RNA
```

```
<213> ORGANISM: Artificial Sequence
<220> FEATURE:
<223> OTHER INFORMATION: Hprt1-asRNA
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(1)
<223> OTHER INFORMATION: 5'-phosphoryl
<220> FEATURE:
<221> NAME/KEY: modified_base
<222> LOCATION: (2)..(2)
<223> OTHER INFORMATION: 2'-deoxy-2'-fluorouridine
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-deoxy-2'-fluoroadenosine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-deoxy-2'-fluoroadenosine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: 2'-deoxy-2'-fluorocytidine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (10)..(10)
<223> OTHER INFORMATION: 2'-deoxy-2'-fluoroadenosine
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: 2'-deoxy-2'-fluoroadenosine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-deoxy-2'-fluorouridine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-deoxy-2'-fluoroadenosine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: 2'-deoxy-2'-fluoroadenosine
```

```
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-deoxy-2'-fluoroguanosine
<220> FEATURE:
<221> NAME/KEY: modified_base
<222> LOCATION: (21)..(21)
<223> OTHER INFORMATION: 2'-O-methyladenosine
<220> FEATURE:
<221> NAME/KEY: modified_base
<222> LOCATION: (22)..(22)
<223> OTHER INFORMATION: 2'-deoxy-2'-fluoroadenosine
<220> FEATURE:
<221> NAME/KEY: misc_feature
<222> LOCATION: (22)..(23)
<223> OTHER INFORMATION: 5'-phosphonothioate
<220> FEATURE:
<221> NAME/KEY: modified_base
<222> LOCATION: (23)..(23)
<223> OTHER INFORMATION: um

<400> SEQUENCE: 9
auaaaaucua cagucauagg aau                                     23
```